(12) United States Patent
Cha et al.

(10) Patent No.: US 11,050,026 B2
(45) Date of Patent: Jun. 29, 2021

(54) SPIRO COMPOUND AND ORGANIC LIGHT-EMITTING ELEMENT COMPRISING SAME

(71) Applicant: LG Chem, Ltd., Seoul (KR)

(72) Inventors: Yongbum Cha, Daejeon (KR); Jin Joo Kim, Daejeon (KR); Sung Kil Hong, Daejeon (KR); Sang Duk Suh, Daejeon (KR)

(73) Assignee: LG Chem, Ltd.

( * ) Notice: Subject to any disclaimer, the term of this patent is extended or adjusted under 35 U.S.C. 154(b) by 522 days.

(21) Appl. No.: 15/577,558

(22) PCT Filed: Nov. 17, 2016

(86) PCT No.: PCT/KR2016/013301
§ 371 (c)(1),
(2) Date: Nov. 28, 2017

(87) PCT Pub. No.: WO2017/086723
PCT Pub. Date: May 26, 2017

(65) Prior Publication Data
US 2018/0175304 A1    Jun. 21, 2018

(30) Foreign Application Priority Data

Nov. 17, 2015    (KR) ........................ 10-2015-0161414

(51) Int. Cl.
| | | |
|---|---|---|
| H01L 51/54 | (2006.01) | |
| H01L 51/00 | (2006.01) | |
| C07D 491/20 | (2006.01) | |
| C07D 495/20 | (2006.01) | |
| C09K 11/06 | (2006.01) | |
| C07F 9/6561 | (2006.01) | |
| C07D 471/06 | (2006.01) | |
| H01L 51/50 | (2006.01) | |
| C07F 7/08 | (2006.01) | |
| C07D 471/10 | (2006.01) | |
| C07F 9/6568 | (2006.01) | |

(52) U.S. Cl.
CPC ........ *H01L 51/0071* (2013.01); *C07D 471/06* (2013.01); *C07D 471/10* (2013.01); *C07D 491/20* (2013.01); *C07D 495/20* (2013.01); *C07F 7/0814* (2013.01); *C07F 7/0816* (2013.01); *C07F 9/6561* (2013.01); *C07F 9/65685* (2013.01); *C09K 11/06* (2013.01); *H01L 51/006* (2013.01); *H01L 51/0052* (2013.01); *H01L 51/0054* (2013.01); *H01L 51/0058* (2013.01); *H01L 51/0059* (2013.01); *H01L 51/0061* (2013.01); *H01L 51/0067* (2013.01); *H01L 51/0094* (2013.01); *H01L 51/50* (2013.01); *C09K 2211/1018* (2013.01); *H01L 51/0072* (2013.01); *H01L 51/0073* (2013.01); *H01L 51/0074* (2013.01); *H01L 51/0085* (2013.01); *H01L 51/5012* (2013.01); *H01L 51/5016* (2013.01); *H01L 51/5056* (2013.01); *H01L 51/5088* (2013.01); *H01L 51/5096* (2013.01)

(58) Field of Classification Search
CPC .. C07D 471/00; C07D 471/06; C07D 471/10; C07D 491/00; C07D 491/10; C07D 495/00; C07D 495/20; C07D 7/0814; C07D 7/0816; C07D 9/6561; C07D 9/6568; C09K 11/06; C09K 2211/00; C09K 2211/10; C09K 2211/1018; H01L 51/0032; H01L 51/0052; H01L 51/0054; H01L 51/0058; H01L 51/0059; H01L 51/006; H01L 51/0061; H01L 51/0067; H01L 51/0071; H01L 51/0072; H01L 51/0073; H01L 51/0074; H01L 51/0085; H01L 51/0094; H01L 51/50; H01L 51/5012; H01L 51/5016; H01L 51/5056; H01L 51/5088; H01L 51/5096
See application file for complete search history.

(56) References Cited

U.S. PATENT DOCUMENTS

| | | | | |
|---|---|---|---|---|
| 2006/0043858 A1* | 3/2006 | Ikeda | .................... | C07C 43/257 |
| | | | | 313/250 |
| 2009/0136779 A1 | 5/2009 | Cheng et al. | | |
| 2011/0278549 A1 | 11/2011 | Kim et al. | | |
| 2014/0316134 A1* | 10/2014 | Stoessel | ............... | C07D 221/20 |
| | | | | 544/180 |
| 2018/0083198 A1 | 3/2018 | Cha et al. | | |

FOREIGN PATENT DOCUMENTS

| | | |
|---|---|---|
| CN | 104293348 A | 1/2015 |
| CN | 104341436 A | 2/2015 |
| CN | 107531723 A | 1/2018 |
| KR | 20000051826 A | 8/2000 |
| KR | 20110113468 A | 10/2011 |
| KR | 20110113469 A | 10/2011 |
| KR | 20110113470 A | 10/2011 |

(Continued)

OTHER PUBLICATIONS

Wee et al. J. Org. Chem. 2009, 74, 8472-8475. (Year: 2009).*
Extended European Search Report including Written Opinion for Application No. EP16866675 dated Jun. 3, 2019.

(Continued)

*Primary Examiner* — Andrew K Bohaty
(74) *Attorney, Agent, or Firm* — Lerner, David, Littenberg, Krumholz & Mentlik, LLP

(57) ABSTRACT

The present specification provides a compound having a spiro structure and an organic light emitting device including the same.

10 Claims, 1 Drawing Sheet

(56) References Cited

FOREIGN PATENT DOCUMENTS

| KR | 20140096372 A | 8/2014 |
| KR | 20150010016 A | 1/2015 |
| WO | 2015009076 A1 | 1/2015 |

OTHER PUBLICATIONS

Shou-Cheng Dong et al: "Spiro-annulated triarylamine-based hosts incorporating dibenzothiophene for highly efficient single-emitting layer white phosphorescent organic light-emitting diodes", Journal of Materials Chemistry C, Jan. 1, 2013 (Jan. 1, 2013), vol . 1 No. 40, p. 6575, XP055192026.
Chinese Search Report for Application No. CN 201680034652.4 dated Jul. 3, 2019, pp. 1-2.
Search report from International Application No. PCT/KR2016/013301, dated Feb. 22, 2017.
Chemical Abstract Compound, STN express. RN 1995084-20-2, Sep. 16, 2016.

\* cited by examiner

[Figure 1]
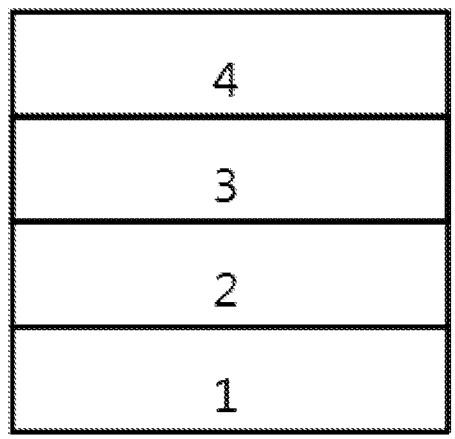
[Figure 2]
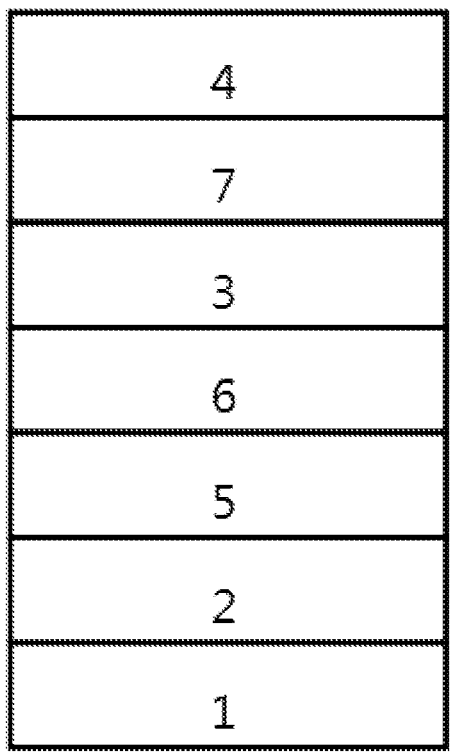

SPIRO COMPOUND AND ORGANIC LIGHT-EMITTING ELEMENT COMPRISING SAME

CROSS-REFERENCE TO RELATED APPLICATIONS

The present application is a national phase entry under 35 U.S.C. § 371 of International Application No. PCT/KR2016/013301 filed Nov. 17, 2016, which claims priority from Korean Patent Application No. 10-2015-0161414 filed Nov. 17, 2015, all of which are incorporated herein by reference.

TECHNICAL FIELD

The present specification relates to a compound having a spiro structure and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826

DETAILED DESCRIPTION OF THE INVENTION

Technical Problem

The present specification describes a compound having a spiro structure and an organic light emitting device including the same.

Technical Solution

An exemplary embodiment of the present specification provides a compound represented by the following Chemical Formula 1:

[Chemical Formula 1]

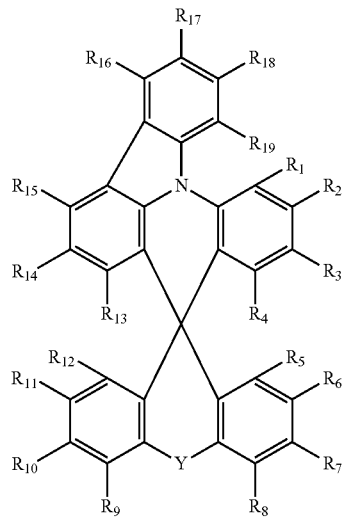

in Chemical Formula 1,

Y is O, S, P(=O)R, PR, CR'R", or SiR'R", and $R_1$ to $R_{19}$, R, R', and R" are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or may be bonded to an adjacent group to form a ring.

Further, an exemplary embodiment of the present specification provides an organic light emitting device including: a first electrode; a second electrode provided to face the first electrode; and an organic material layer having one or more layers disposed between the first electrode and the second electrode, in which one or more layers of the organic material layer include the compound of Chemical Formula 1.

Advantageous Effects

The compound described in the present specification may be used as a material for an organic material layer of an organic light emitting device. The compound according to at least one exemplary embodiment of the present specification may improve the efficiency, achieve low driving voltage and/or improve service life characteristics in the organic light emitting device. In particular, the compound described in the present specification may be used as a material for hole injection, hole transport, hole injection and hole transport, light emission, electron transport, or electron injection.

BRIEF DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 3, an electron transporting layer 7, and a negative electrode 4.

MODE FOR INVENTION

Hereinafter, the present specification will be described in more detail.

Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamino group; an aralkylamino group; a heteroarylamino group; an arylamino group; an arylphosphine group; and a heterocyclic group, or being unsubstituted or substituted with a substituent to which two or more substituents among the substituents exemplified above are linked. For example, "the substituent to which two or more substituents are linked" may be an aryl group substituted with a heteroaryl group.

In the present specification, the number of carbon atoms of a carbonyl group is not particularly limited, but is preferably 1 to 40. Specifically, the carbonyl group may be a compound having the following structures, but is not limited thereto.

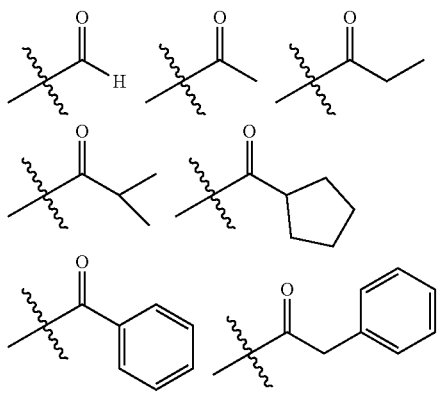

In the present specification, for an ester group, the oxygen of the ester group may be substituted with a straight, branched, or cyclic alkyl group having 1 to 25 carbon atoms, or an aryl group having 6 to 25 carbon atoms. Specifically, the ester group may be a compound having the following structural formulae, but is not limited thereto.

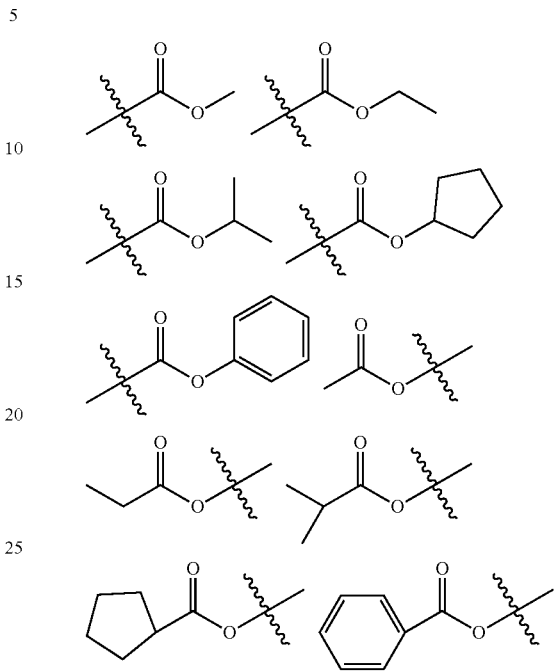

In the present specification, the number of carbon atoms of an imide group is not particularly limited, but is preferably 1 to 25. Specifically, the imide group may be a compound having the following structures, but is not limited thereto.

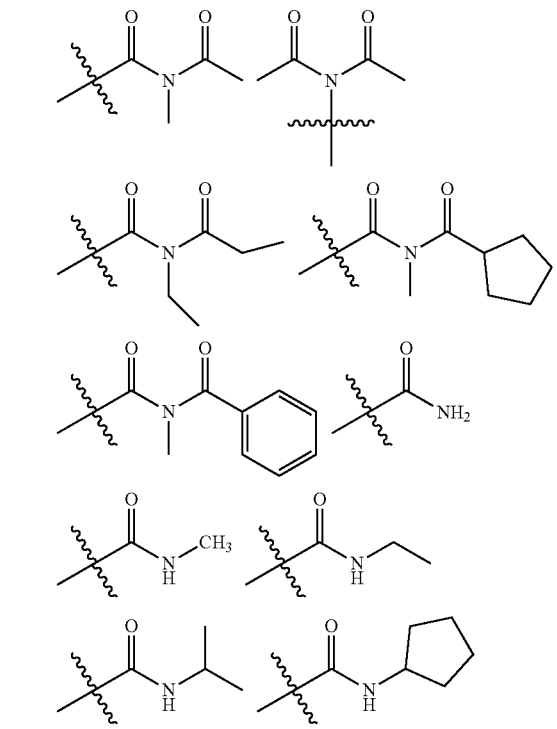

-continued

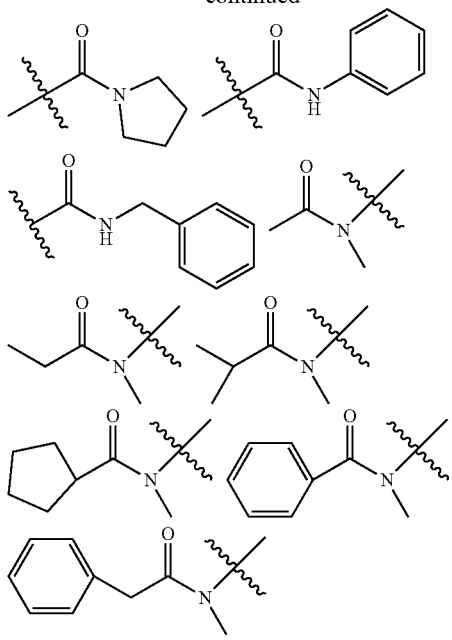

In the present specification, a silyl group may be represented by a chemical formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a chemical formula of —BRR', and R and R' may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, examples of a halogen group include fluorine, chlorine, bromine or iodine.

In the present specification, the alkyl group may be straight or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkenyl group may be straight or branched, and the number of carbon atoms thereof is not particularly limited, but is preferably 2 to 40. According to an exemplary embodiment, the number of carbon atoms of the alkenyl group is 2 to 20. According to yet another exemplary embodiment, the number of carbon atoms of the alkenyl group is 2 to 10. According to still yet another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group is not particularly limited, but has preferably 1 to 40 carbon atoms. According to an exemplary embodiment, the number of carbon atoms of the alkoxy group is 1 to 10. According to another exemplary embodiment, the number of carbon atoms of the alkoxy group is 1 to 6. Specific examples of the alkoxy group include a methoxy group, an ethoxy group, a propoxy group, an isobutyloxy group, a sec-butyloxy group, a pentyloxy group, an iso-amyloxy group, a hexyloxy group, and the like, but are not limited thereto.

In the present specification, the number of carbon atoms of an amino group is not particularly limited, but is preferably 1 to 30. Specific examples of the amino group include a methylamino group, a dimethylamino group, an ethylamino group, a diethylamino group, a phenylamino group, a naphthylamino group, a biphenylamino group, an anthracenylamino group, a 9-methyl-anthracenylamino group, a diphenylamino group, a phenylnaphthylamino group, a ditolylamino group, a phenyltolylamino group, a triphenylamino group, and the like, but are not limited thereto.

In the present specification, examples of an arylamino group include a substituted or unsubstituted monoarylamino group, a substituted or unsubstituted diarylamino group, or a substituted or unsubstituted triarylamino group. The aryl group in the arylamino group may be a monocyclic aryl group, and may be a polycyclic aryl group. The arylamino group including two or more aryl groups may include a monocyclic aryl group, a polycyclic aryl group, or both a monocyclic aryl group and a polycyclic aryl group. Specific examples of the arylamino group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamino group, a phenylnaphthylamino group, a ditolylamino group, a phenyltolylamino group, carbazole, a triphenylamino group, and the like, but are not limited thereto.

In the present specification, examples of a heteroarylamino group include a substituted or unsubstituted monoheteroarylamino group, a substituted or unsubstituted diheteroarylamino group, or a substituted or unsubstituted triheteroarylamino group. The heteroaryl group in the heteroarylamino group may be a monocyclic heterocyclic group, and may be a polycyclic heterocyclic group. The heteroarylamino group including two or more heterocyclic groups may include a monocyclic heterocyclic group, a polycyclic heterocyclic group, or both a monocyclic heterocyclic group and a polycyclic heterocyclic group.

In the present specification, an arylheteroarylamino group means an amino group substituted with an aryl group and a heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a triphenylene group, and the like, but are not limited thereto.

In the present specification, a fluorenyl group may be substituted, and two substituents may be bonded to each other to form a spiro structure.

When the fluorenyl group is substituted, the fluorenyl group may be

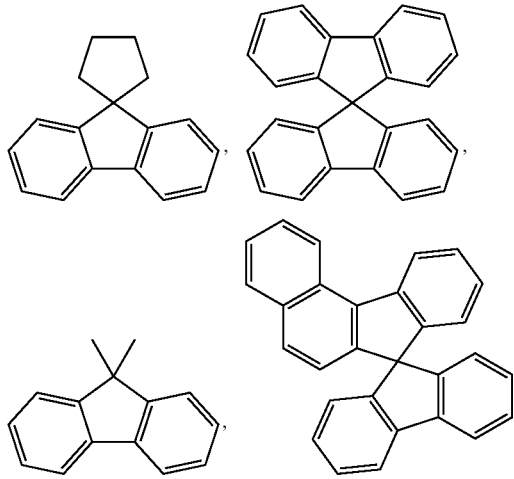

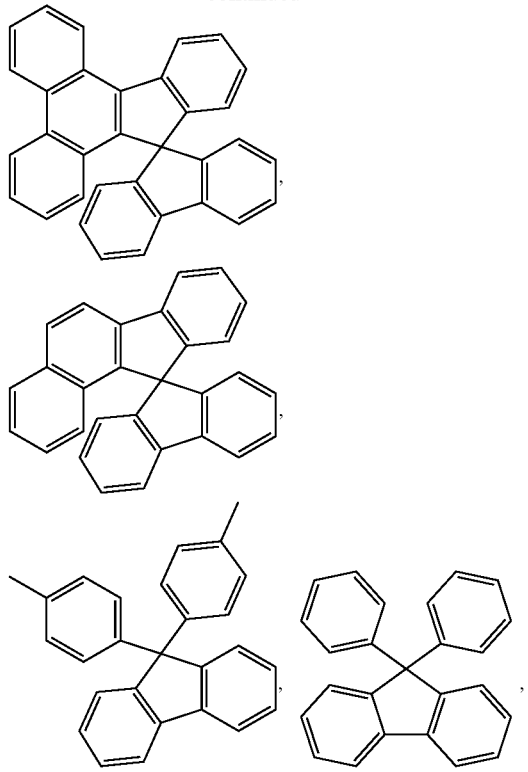

and the like. However, the fluorenyl group is not limited thereto.

In the present specification, a heterocyclic group is a heterocyclic group including one or more of N, O, S, Si, and Se as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the above-described description on the heterocyclic group may be applied to a heteroaryl group except for an aromatic heteroaryl group.

In the present specification, the above-described description on the aryl group may be applied to an aryl group in an aryloxy group, an arylthioxy group, an arylsulfoxy group, an arylphosphine group, an aralkyl group, an aralkylamino group, an aralkenyl group, an alkylaryl group, an arylamino group, and an arylheteroarylamino group.

In the present specification, the above-described description on the alkyl group may be applied to an alkyl group in an alkylthioxy group, an alkylsulfoxy group, an aralkyl group, an aralkylamino group, an alkylaryl group, and an alkylamino group.

In the present specification, the above-described description on the heterocyclic group may be applied to a heteroaryl group in a heteroaryl group, a heteroarylamino group, and an arylheteroarylamino group.

In the present specification, the above-described description on the alkenyl group may be applied to an alkenyl group in an aralkenyl group.

In the present specification, the above-described description on the aryl group may be applied to an arylene except for a divalent arylene group.

In the present specification, the above-described description on the heterocyclic group may be applied to a heteroarylene except for a divalent heteroarylene group.

In the present specification, being bonded to an adjacent group to form a ring means being bonded to an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof. The aliphatic hydrocarbon ring is a ring which is not an aromatic ring, and is a ring composed of only carbon and hydrogen atoms. Examples of the aromatic hydrocarbon ring include benzene, naphthalene, anthracene, and the like, but are not limited thereto. The aliphatic hetero ring is an aliphatic ring including one or more heteroatoms. The aromatic hetero ring is an aromatic ring including one or more heteroatoms. The hetero ring may include O, S, Se, N, or Si as a heteroatom. The aliphatic hydrocarbon ring, the aromatic hydrocarbon ring, the aliphatic hetero ring, and the aromatic hetero ring may be monocyclic or polycyclic.

According to an exemplary embodiment of the present specification, Chemical Formula 1 may be represented by any one of the following Chemical Formulae 2 to 6.

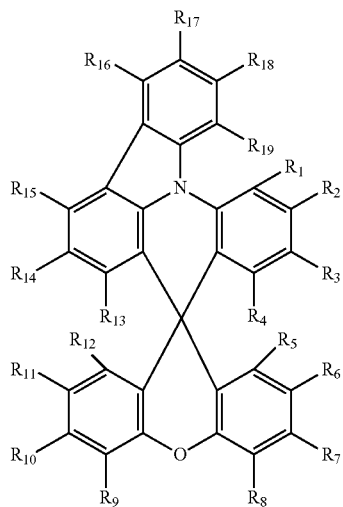

[Chemical Formula 2]

In Chemical Formula 2, R1 to R19 are the same as those defined in Chemical Formula 1.

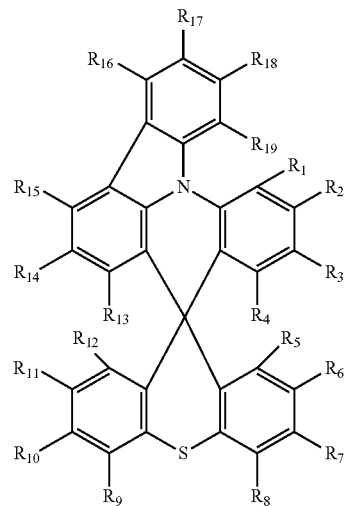

[Chemical Formula 3]

In Chemical Formula 3, $R_1$ to $R_{19}$ are the same as those defined in Chemical Formula 1.

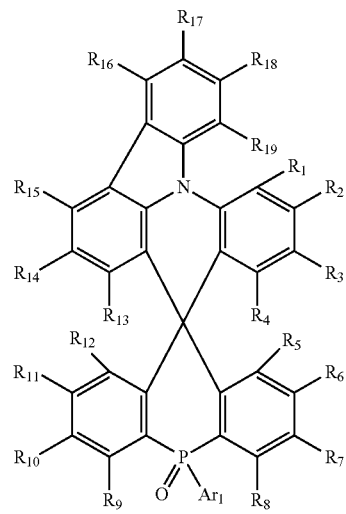

[Chemical Formula 4]

In Chemical Formula 4, $R_1$ to $R_{19}$ are the same as those defined in Chemical Formula 1, and Ar1 is a substituted or unsubstituted aryl group.

[Chemical Formula 5]

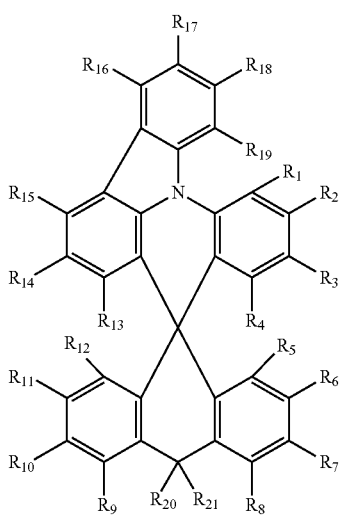

[Chemical Formula 6]

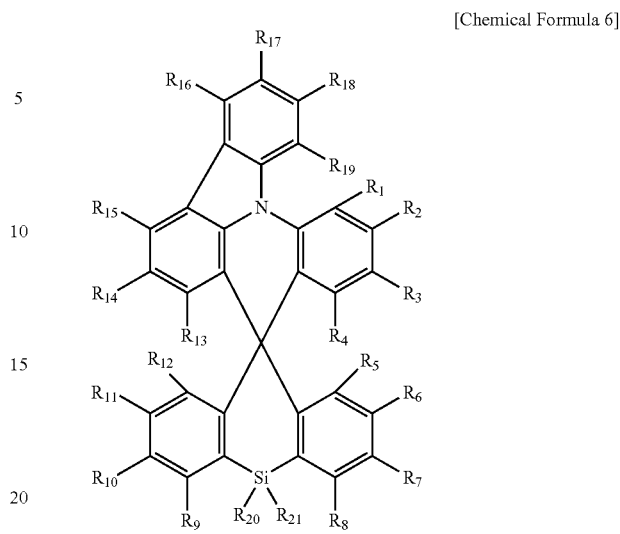

In Chemical Formula 5, $R_1$ to $R_{19}$ are the same as those defined in Chemical Formula 1, and $R_{20}$ and $R_{21}$ are the same as or different from each other, and are each independently a substituted or unsubstituted alkyl group.

According to an exemplary embodiment of the present application, Chemical Formula 5 may be represented by the following Chemical Formula 5-1.

[Chemical Formula 5-1]

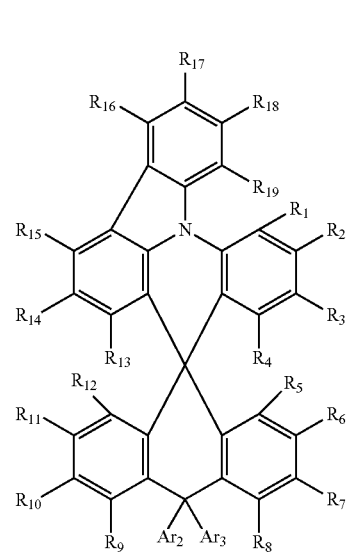

In Chemical Formula 5-1, $R_1$ to $R_{19}$ are the same as those defined in Chemical Formula 1, and $Ar_2$ and $Ar_3$ are a substituted or unsubstituted aryl group.

In Chemical Formula 6, $R_1$ to $R_{19}$ are the same as those defined in Chemical Formula 1, and $R_{20}$ and $R_{21}$ are the same as or different from each other, and are each independently a substituted or unsubstituted alkyl group.

According to an exemplary embodiment of the present invention, one or two or more of $R_1$ to $R_{19}$ is or are bonded to an adjacent group to form a ring.

According to an exemplary embodiment of the present invention, one or two or more of $R_1$ to $R_{19}$ is or are bonded to an adjacent group to form a substituted or unsubstituted aromatic hydrocarbon ring.

According to an exemplary embodiment of the present invention, $R_9$ and $R_{10}$ are bonded to each other to form a substituted or unsubstituted aromatic hydrocarbon ring, or $R_7$ and $R_8$ are bonded to each other to form a substituted or unsubstituted aromatic hydrocarbon ring.

According to an exemplary embodiment of the present invention, $R_9$ and $R_{10}$ are bonded to each other to form a substituted or unsubstituted aromatic hydrocarbon ring, and R7 and R8 are bonded to each other to form a substituted or unsubstituted aromatic hydrocarbon ring.

According to an exemplary embodiment of the present invention, one or two or more of $R_1$ to $R_{19}$ is or are bonded to an adjacent group to form a substituted or unsubstituted benzene ring.

According to an exemplary embodiment of the present invention, $R_9$ and $R_{10}$ are bonded to each other to form a substituted or unsubstituted benzene ring, or $R_7$ and $R_8$ are bonded to each other to form a substituted or unsubstituted benzene ring.

According to an exemplary embodiment of the present invention, $R_9$ and $R_{10}$ are bonded to each other to form a substituted or unsubstituted benzene ring, and $R_7$ and $R_8$ are bonded to each other to form a substituted or unsubstituted benzene ring.

According to an exemplary embodiment of the present specification, Chemical Formula 1 may be represented by the following Chemical Formula 7 or 8.

[Chemical Formula 7]

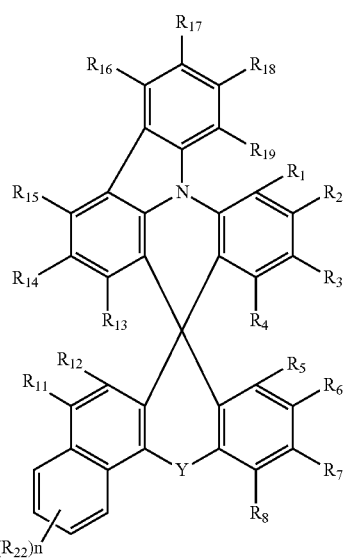

In Chemical Formula 7, $R_1$ to $R_8$, $R_{11}$ to $R_{19}$, and Y are the same as those defined in Chemical Formula 1, $R_{22}$ is the same as the definitions of $R_1$ to $R_{19}$ of Chemical Formula 1, n is an integer from 0 to 4, and when n is 2 or more, $R_{22}$'s are the same as or different from each other.

[Chemical Formula 8]

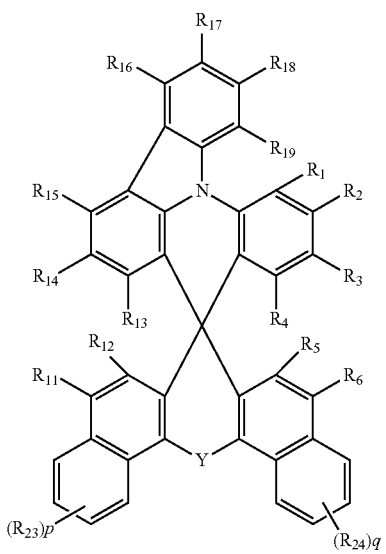

In Chemical Formula 8, $R_1$ to $R_6$, $R_{11}$ to $R_{19}$, and Y are the same as those defined in Chemical Formula 1, $R_{23}$ and $R_{24}$ are the same as or different from each other, and are the same as the definitions of $R_1$ to $R_{19}$ of Chemical Formula 1, p and q are each an integer from 0 to 4, and when p and q are each 2 or more, structures in the parenthesis are the same as or different from each other.

According to an exemplary embodiment of the present invention, at least one of $R_1$ to $R_{19}$ in Chemical Formulae 1 to 6 is a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or is bonded to an adjacent group to form a ring, and the others are hydrogen or deuterium. When $R_1$ to R19 are substituted, the substituent is deuterium, a halogen group, a nitrile group, a silyl group, an alkyl group, an alkylamino group, an aralkylamino group, a heteroarylamino group, an arylamino group, an arylheteroarylamino group, an arylphosphine group, a phosphine oxide group, an aryl group, or a heterocyclic group.

According to an exemplary embodiment of the present invention, at least one of $R_1$ to $R_{19}$ in Chemical Formulae 1 to 6 is a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or is bonded to an adjacent group to form a ring, and the others are hydrogen or deuterium.

According to an exemplary embodiment of the present invention, at least one of $R_1$ to $R_{19}$ in Chemical Formula 1 to 6 is a substituted or unsubstituted aryl group; a substituted or unsubstituted heterocyclic group; a substituted or unsubstituted arylamino group; or a substituted or unsubstituted arylphosphine group.

According to an exemplary embodiment of the present invention, at least one of $R_1$ to $R_{19}$ in Chemical Formulae 1 to 6 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded. The group to which two or more groups are bonded may be a group to which two or more substituents exemplified above are bonded, for example, a heteroaryl group substituted with an aryl group, an aryl group substituted with a heteroaryl group, an aryl group substituted with an arylamino group, an aryl group substituted with an arylphosphine group, and the like, and is not limited to these examples.

According to an exemplary embodiment of the present invention, at least one of $R_1$ to $R_{19}$ in Chemical Formulae 1 to 6 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or a substituent of Group A.

[Group A]

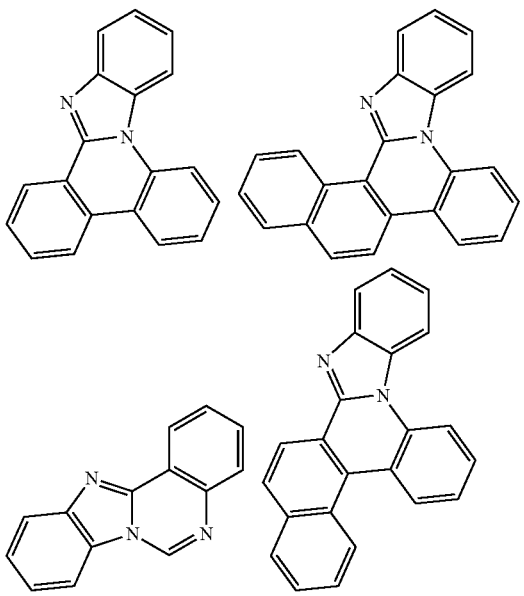

In the structural formulae, any one carbon is a linking moiety for forming a monovalent group, and the other carbons are a group to which one or two or more groups of hydrogen or a substituent, for example, a halogen group, a nitrile group, an alkyl group, a silyl group, an arylamino group, an arylphosphine group, an aryl group, and a heteroaryl group is or are bonded.

According to an exemplary embodiment of the present invention, $R_1$ to $R_8$, $R_{11}$ to $R_{19}$, and $R_{22}$ in Chemical Formula 7 are hydrogen or deuterium.

According to an exemplary embodiment of the present invention, $R_1$ to $R_8$, $R_{11}$ to $R_{19}$, and $R_{22}$ in Chemical Formula 7 are hydrogen.

According to an exemplary embodiment of the present invention, at least one of $R_1$ to $R_8$, $R_{11}$ to $R_{19}$, and $R_{22}$ in Chemical Formula 7 is a substituted or unsubstituted aryl group; a substituted or unsubstituted heterocyclic group; or a substituted or unsubstituted arylamino group.

According to an exemplary embodiment of the present invention, at least one of $R_1$ to $R_8$, $R_{11}$ to $R_{19}$, and $R_{22}$ in Chemical Formula 7 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, at least one of $R_1$ to $R_8$, $R_{11}$ to $R_{19}$, and $R_{22}$ in Chemical Formula 7 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group is phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_1$ to $R_6$, $R_{11}$ to $R_{19}$, $R_{23}$, and $R_{24}$ in Chemical Formula 8 are hydrogen or deuterium.

According to an exemplary embodiment of the present invention, $R_1$ to $R_6$, $R_{11}$ to $R_{19}$, $R_{23}$, and $R_{24}$ in Chemical Formula 8 are hydrogen.

According to an exemplary embodiment of the present invention, at least one of $R_1$ to $R_6$, $R_{11}$ to $R_{19}$, $R_{23}$, and $R_{24}$ in Chemical Formula 8 is a substituted or unsubstituted aryl group; a substituted or unsubstituted heterocyclic group; or a substituted or unsubstituted arylamino group.

According to an exemplary embodiment of the present invention, at least one of $R_1$ to $R_6$, $R_{11}$ to $R_{19}$, $R_{23}$, and $R_{24}$ in Chemical Formula 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, at least one of $R_1$ to $R_6$, $R_{11}$ to $R_{19}$, $R_{23}$, and $R_{24}$ in Chemical Formula 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, at least one of $R_5$ to $R_8$ in Chemical Formulae 1 to 6 is a substituted or unsubstituted aryl group; a substituted or unsubstituted heterocyclic group; or a substituted or unsubstituted arylamino group.

According to an exemplary embodiment of the present invention, at least one of $R_5$ to $R_8$ in Chemical Formulae 1 to 6 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, at least one of $R_5$ to $R_8$ in Chemical Formulae 1 to 6 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_6$ in Chemical Formulae 1 to 8 is a substituted or unsubstituted aryl group; a substituted or unsubstituted heterocyclic group; or a substituted or unsubstituted arylamino group.

According to an exemplary embodiment of the present invention, $R_6$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, $R_6$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_8$ in Chemical Formulae 1 to 8 is a substituted or unsubstituted aryl group; a substituted or unsubstituted heterocyclic group; or a substituted or unsubstituted arylamino group.

According to an exemplary embodiment of the present invention, $R_8$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, $R_8$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, at least one of $R_5$ to $R_8$ and at least one of R9 to R12 in Chemical Formulae 1 to 6 are a substituted or unsubstituted aryl group; a substituted or unsubstituted heterocyclic group; or a substituted or unsubstituted arylamino group.

According to an exemplary embodiment of the present invention, at least one of $R_5$ to $R_8$ and at least one of $R_9$ to $R_{12}$ in Chemical Formulae 1 to 6 are an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, at least one of $R_5$ to $R_8$ and at least one of $R_9$ to $R_{12}$ in Chemical Formulae 1 to 6 are an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_6$ and $R_{11}$ in Chemical Formulae 1 to 8 are a substituted or unsubstituted aryl group; a substituted or unsubstituted heterocyclic group; or a substituted or unsubstituted arylamino group.

According to an exemplary embodiment of the present invention, $R_6$ and $R_{11}$ in Chemical Formulae 1 to 8 are an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, $R_6$ and $R_{11}$ in Chemical Formulae 1 to 8 are an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_6$ and $R_{11}$ in Chemical Formulae 1 to 8 are hydrogen or an aryl group, for example, a phenyl group, a biphenylyl group, and a naphthyl group.

According to an exemplary embodiment of the present invention, $R_6$ and $R_{11}$ in Chemical Formulae 1 to 8 are hydrogen or a phenyl group.

According to an exemplary embodiment of the present invention, $R_{14}$ in Chemical Formulae 1 to 8 is a substituted or unsubstituted aryl group; a substituted or unsubstituted heterocyclic group; or a substituted or unsubstituted arylamino group.

According to an exemplary embodiment of the present invention, $R_{14}$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, $R_{14}$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_{14}$ in Chemical Formulae 1 to 8 are hydrogen or an aryl group, for example, a phenyl group, a biphenylyl group, and a naphthyl group.

According to an exemplary embodiment of the present invention, $R_{14}$ in Chemical Formulae 1 to 8 is hydrogen or a phenyl group.

According to an exemplary embodiment of the present invention, $R_{17}$ in Chemical Formulae 1 to 8 is a substituted or unsubstituted aryl group; a substituted or unsubstituted heterocyclic group; or a substituted or unsubstituted arylamino group.

According to an exemplary embodiment of the present invention, $R_{17}$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, $R_{17}$ in Chemical Formulae 1 to 8 is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_{17}$ in Chemical Formulae 1 to 8 are hydrogen or an aryl group, for example, a phenyl group, a biphenylyl group, and a naphthyl group.

According to an exemplary embodiment of the present invention, $R_{17}$ in Chemical Formulae 1 to 8 is hydrogen or a phenyl group.

According to an exemplary embodiment of the present invention, $R_{14}$ and $R_{17}$ in Chemical Formulae 1 to 8 are a substituted or unsubstituted aryl group; a substituted or unsubstituted heterocyclic group; or a substituted or unsubstituted arylamino group.

According to an exemplary embodiment of the present invention, $R_{14}$ and $R_{17}$ in Chemical Formulae 1 to 8 are an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded.

According to an exemplary embodiment of the present invention, $R_{14}$ and $R_{17}$ in Chemical Formulae 1 to 8 are an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded, and here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or triphenylsilyl, the aryl group and aryl are phenyl, biphenylyl, terphenylyl, naphthyl, phenanthrenyl, or fluorenyl, and the heteroaryl group is pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or the substituent of Group A.

According to an exemplary embodiment of the present invention, $R_{14}$ and $R_{17}$ in Chemical Formulae 1 to 8 are hydrogen or an aryl group, for example, a phenyl group, a biphenylyl group, and a naphthyl group.

According to an exemplary embodiment of the present invention, $R_{14}$ and $R_{17}$ in Chemical Formulae 1 to 8 are hydrogen or a phenyl group.

According to an exemplary embodiment of the present invention, $R_{20}$ and $R_{21}$ in Chemical Formula 5 is a straight or branched alkyl group having 1 to 6 carbon atoms, for example, methyl.

According to an exemplary embodiment of the present invention, $Ar_1$ to $Ar_3$ in Chemical Formulae 4 and 6 are the same as or different from each other, and are each independently an aryl group having 6 to 20 carbon atoms, for example, a phenyl group.

According to an exemplary embodiment of the present invention, at least one of $R_1$ to $R_{19}$ is selected from the following chemical formulae.

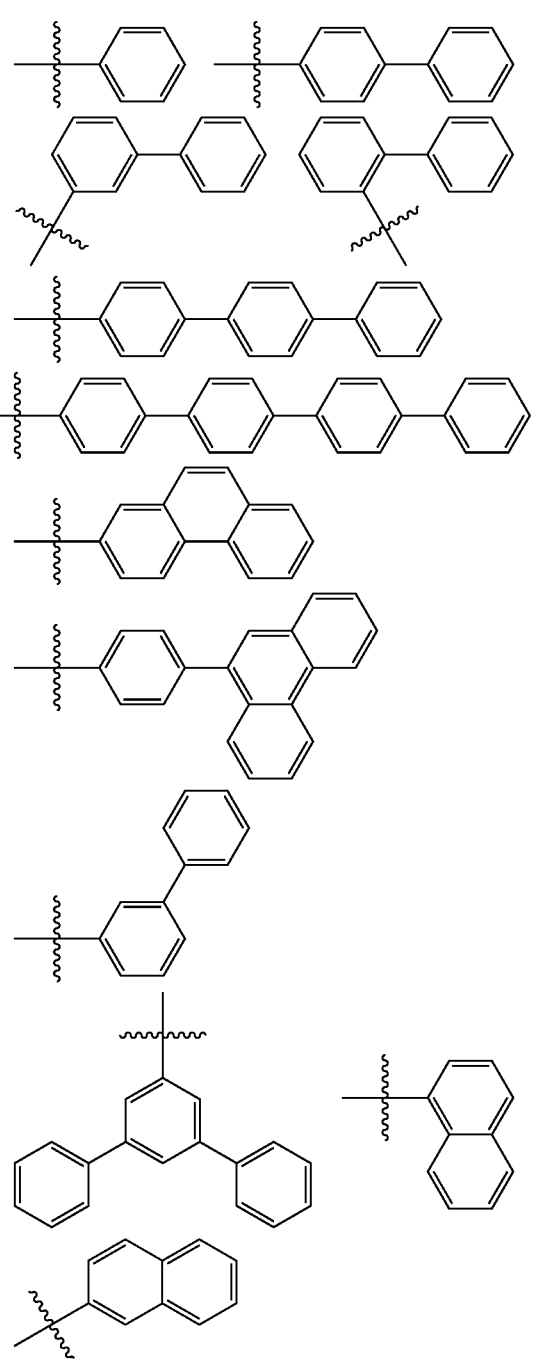

-continued
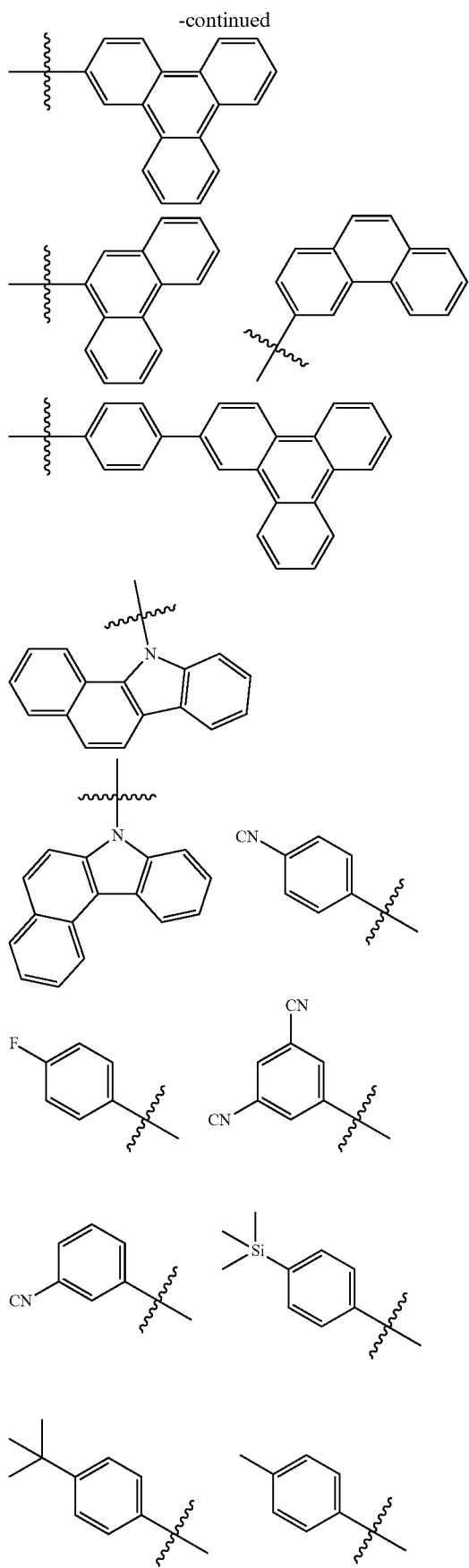
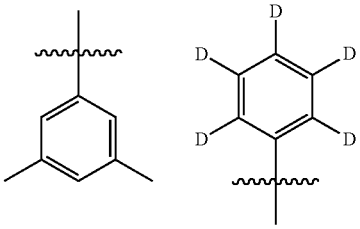
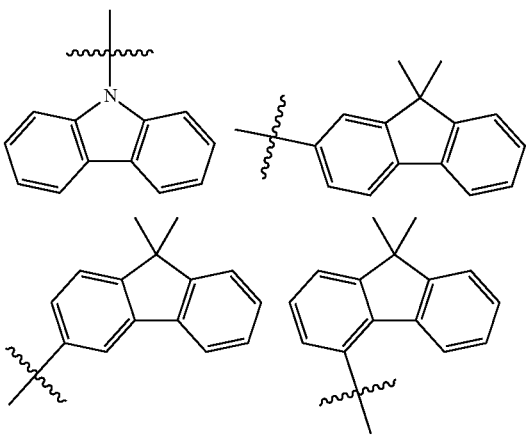
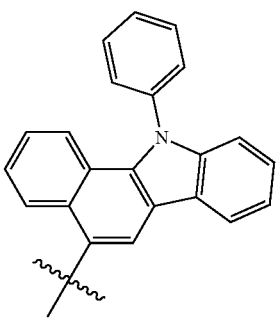
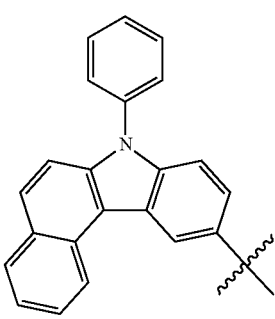
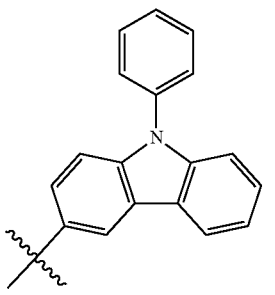

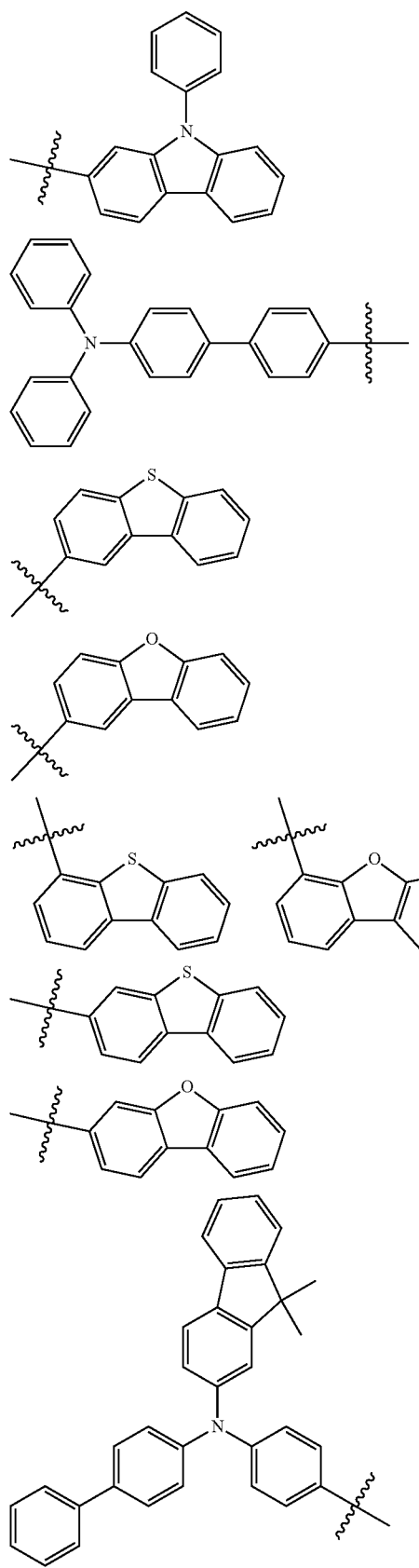
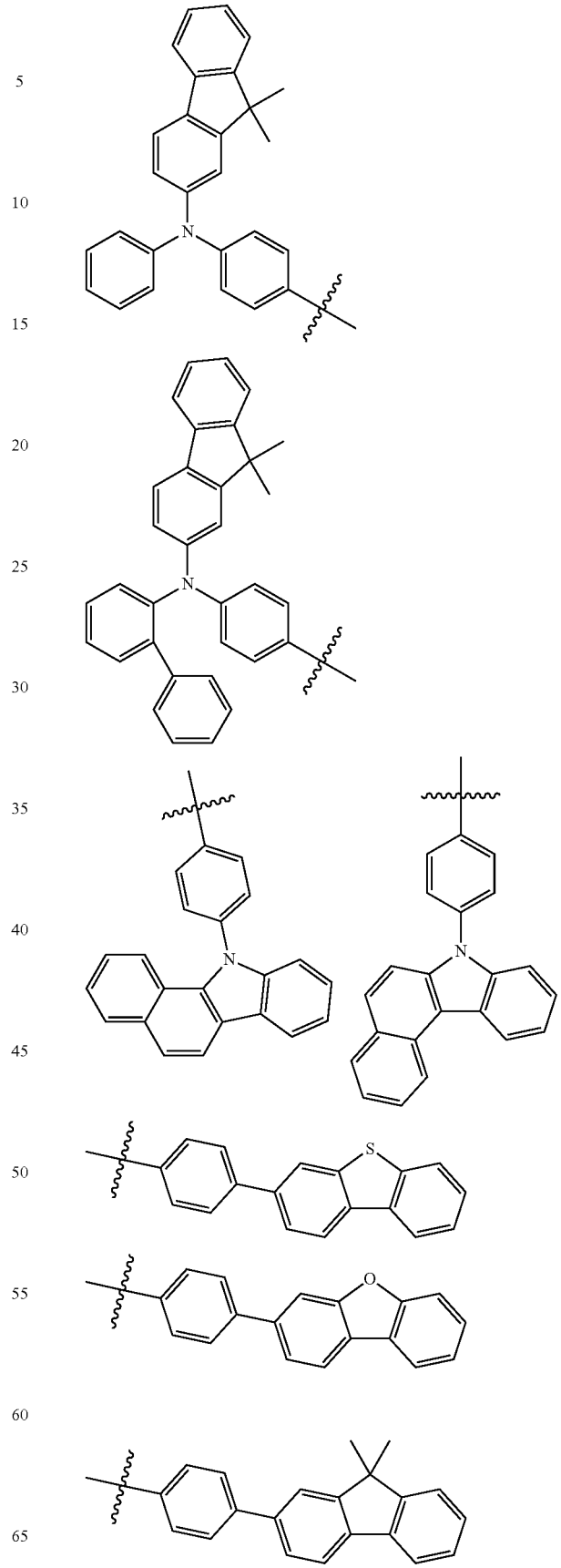

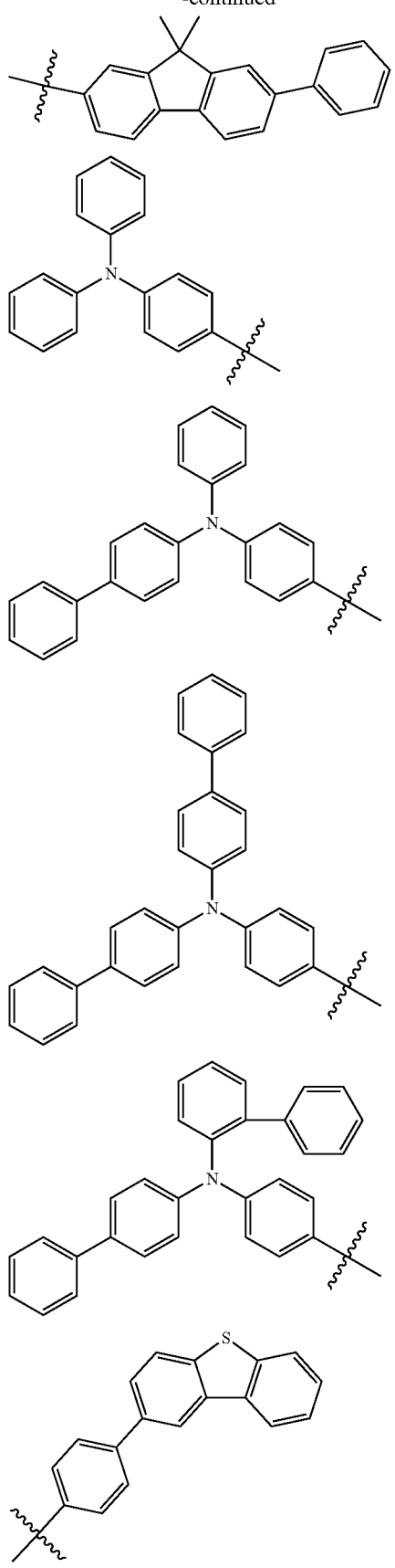
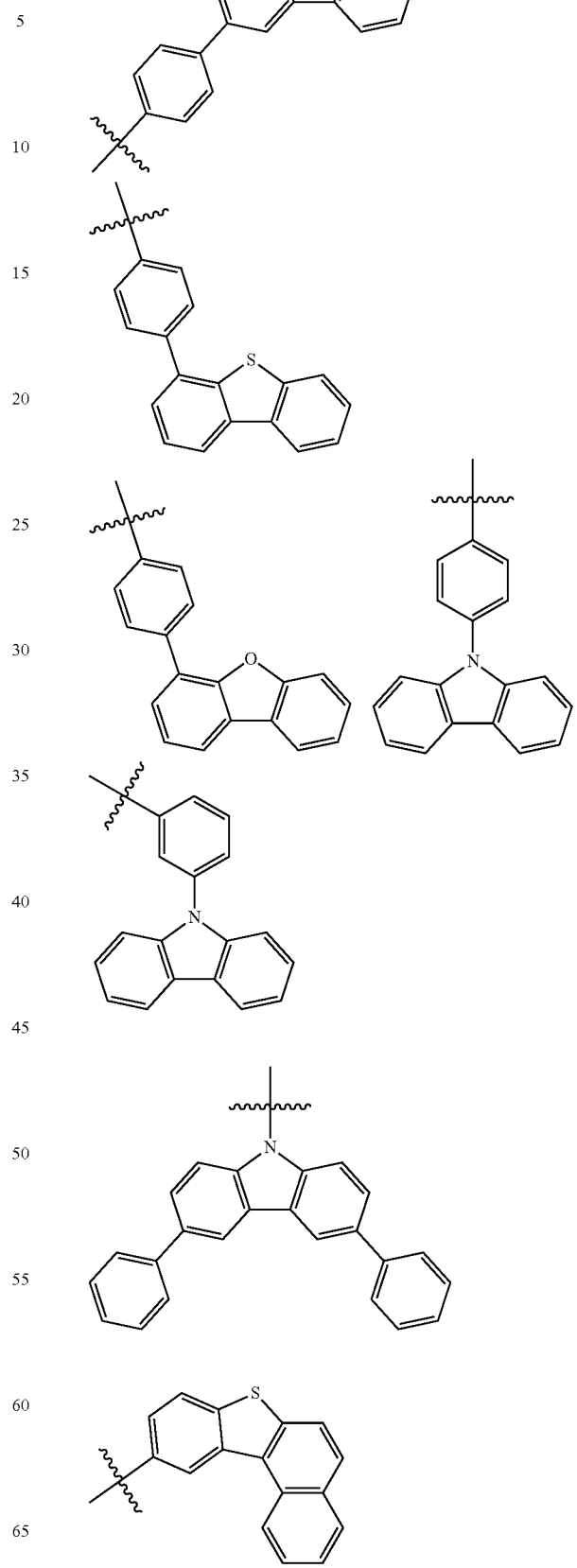

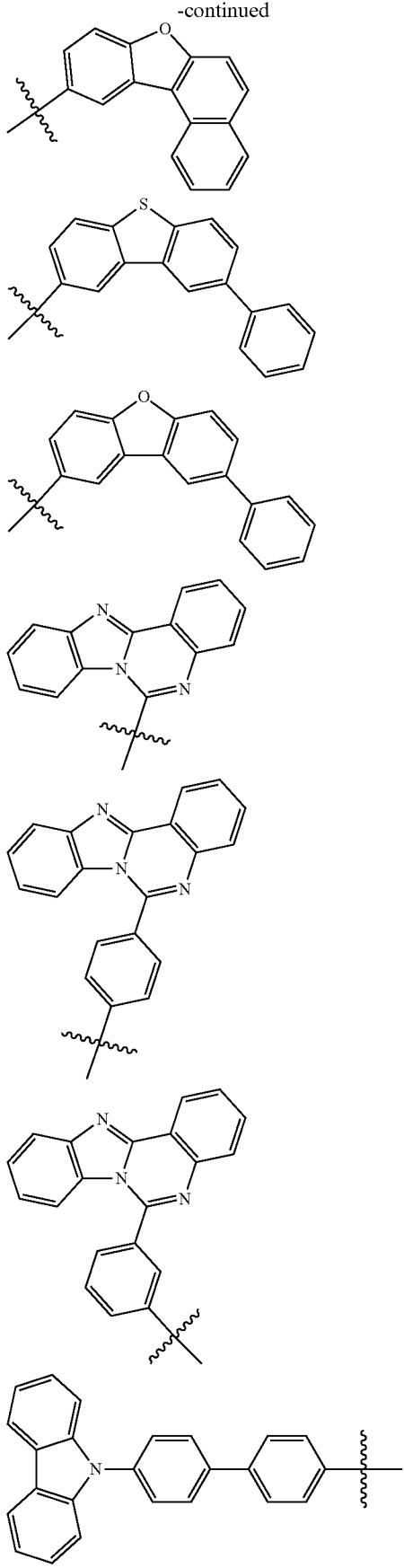
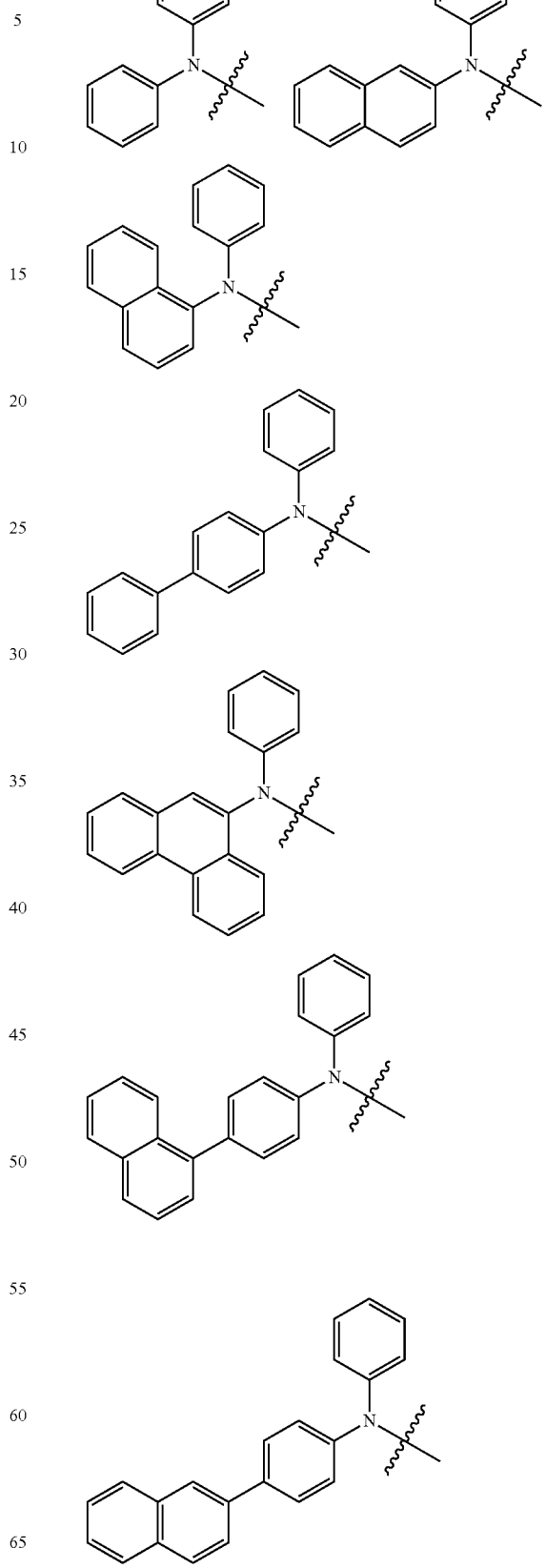

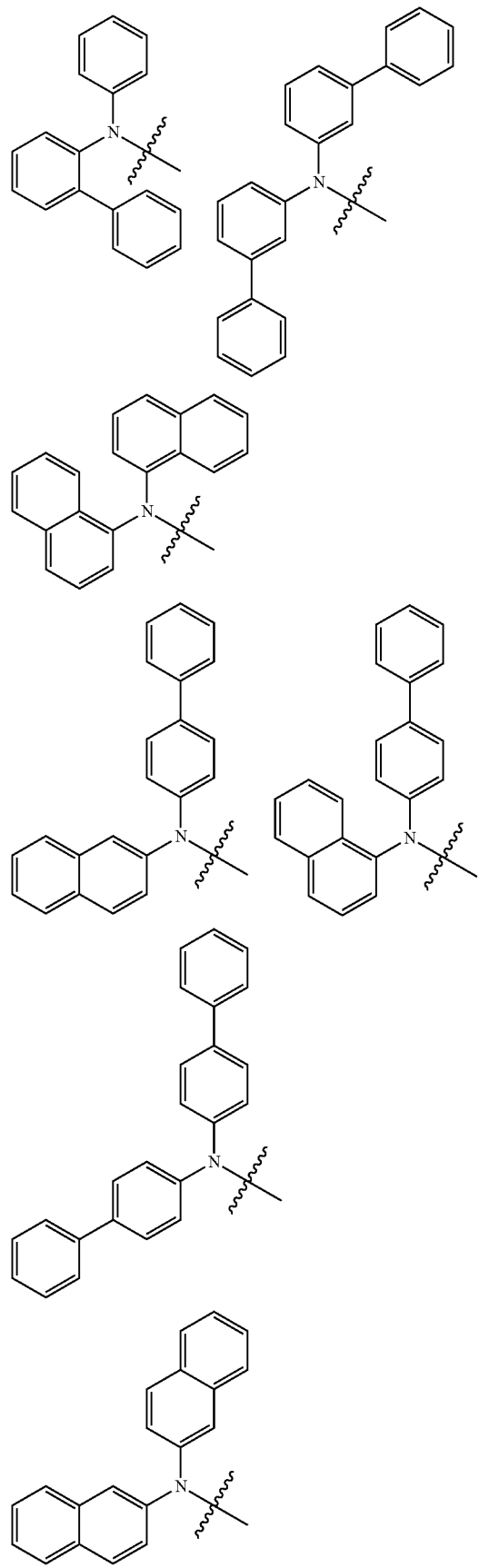
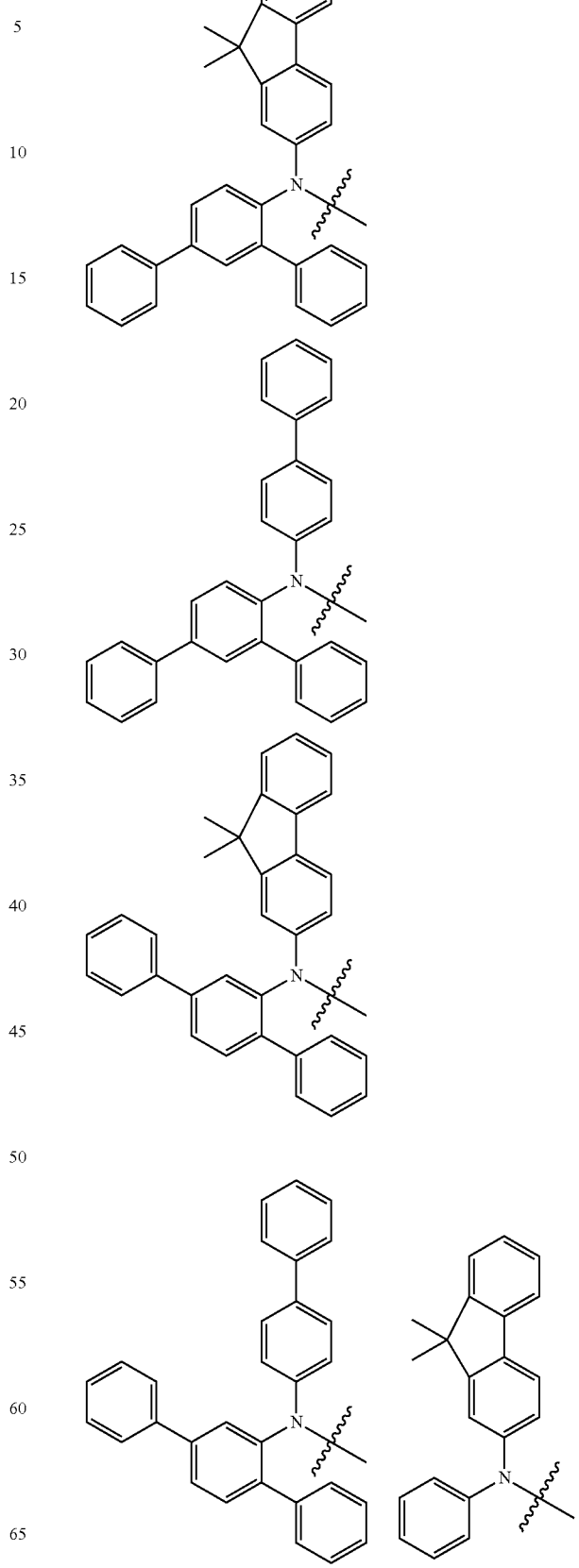

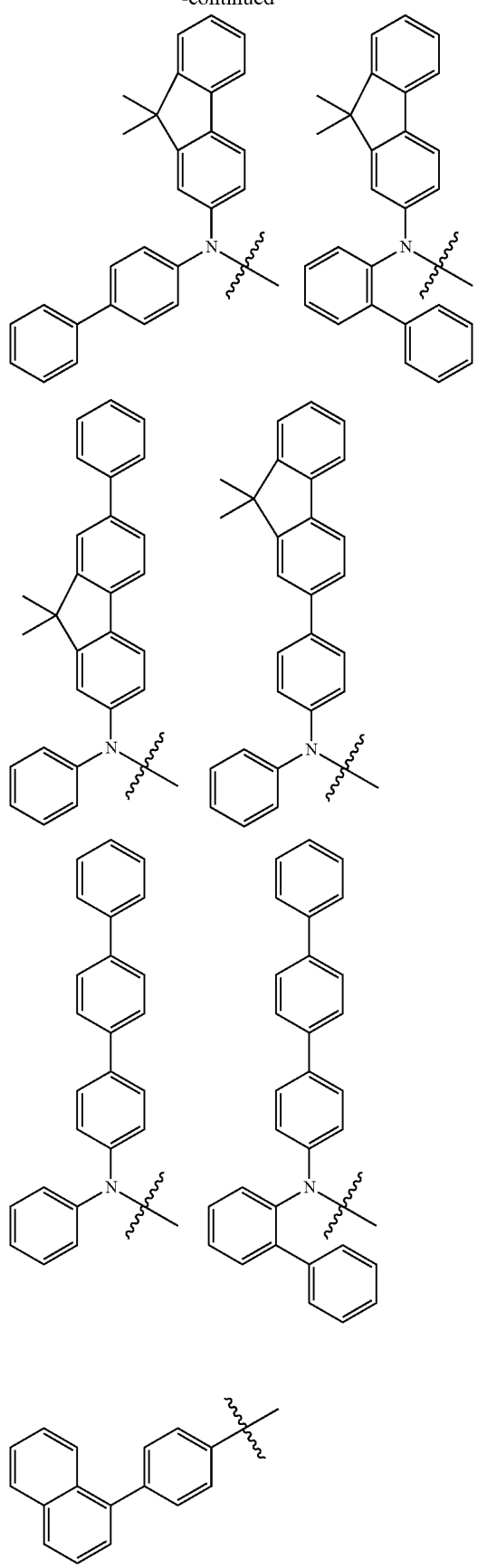
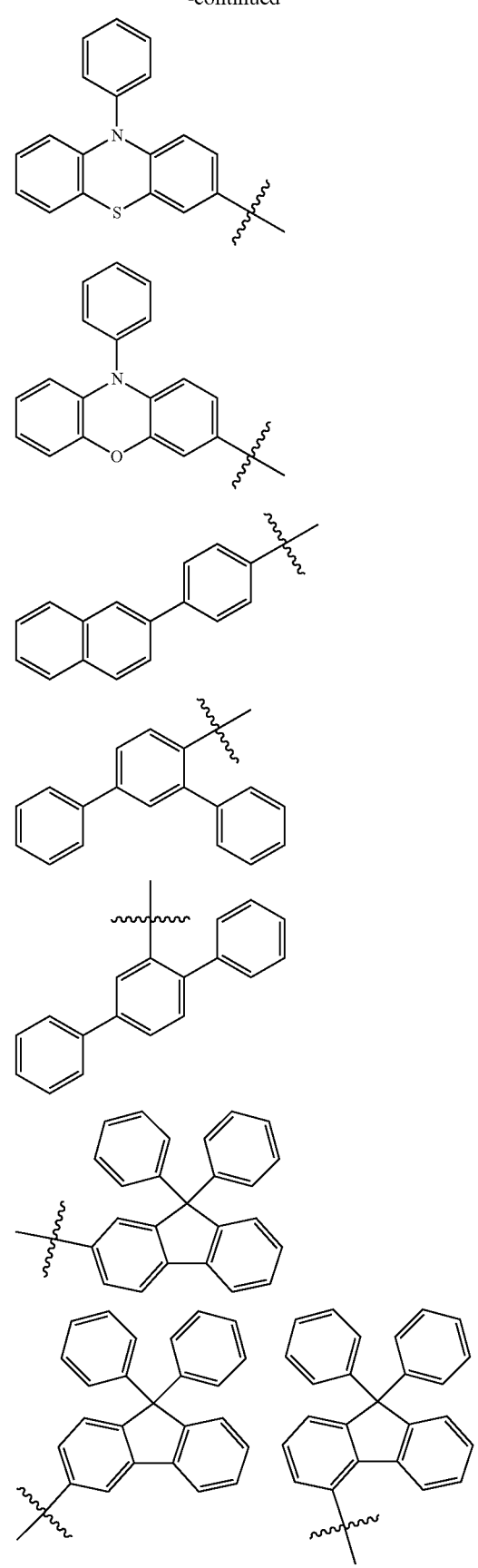
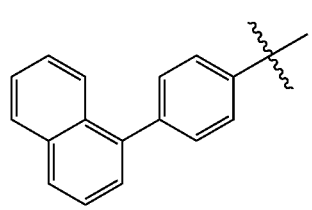

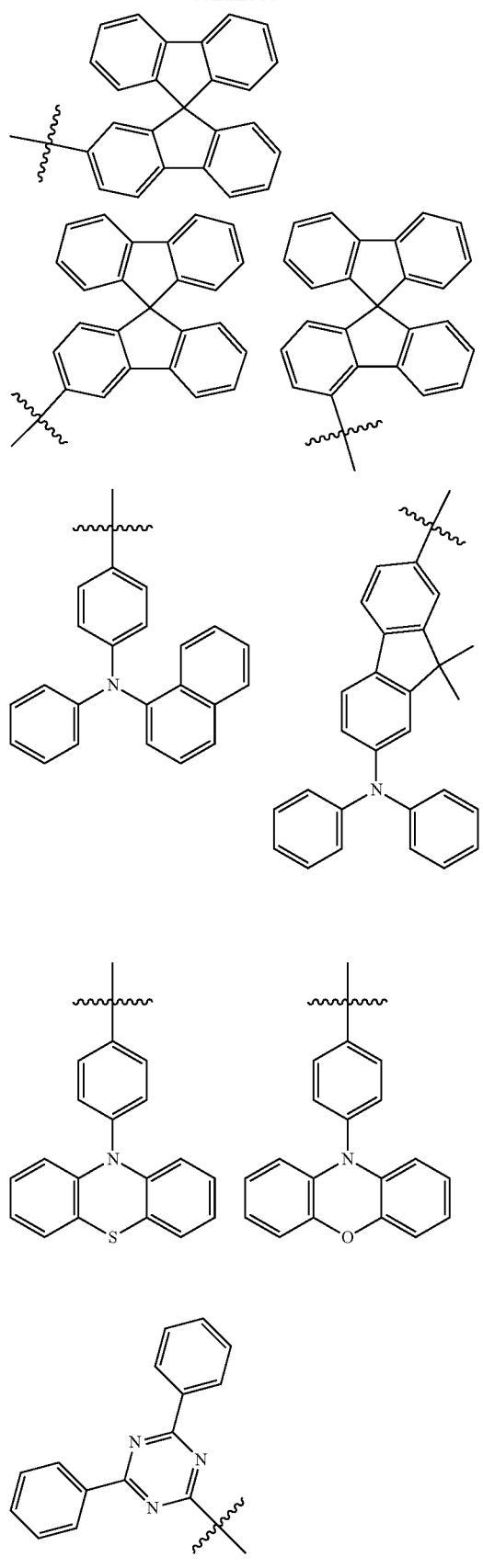

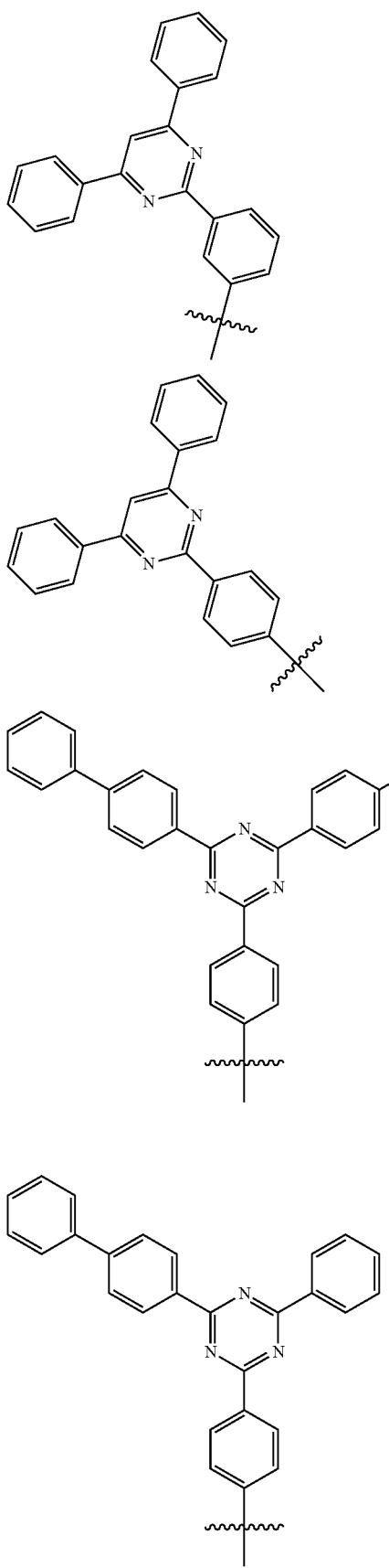
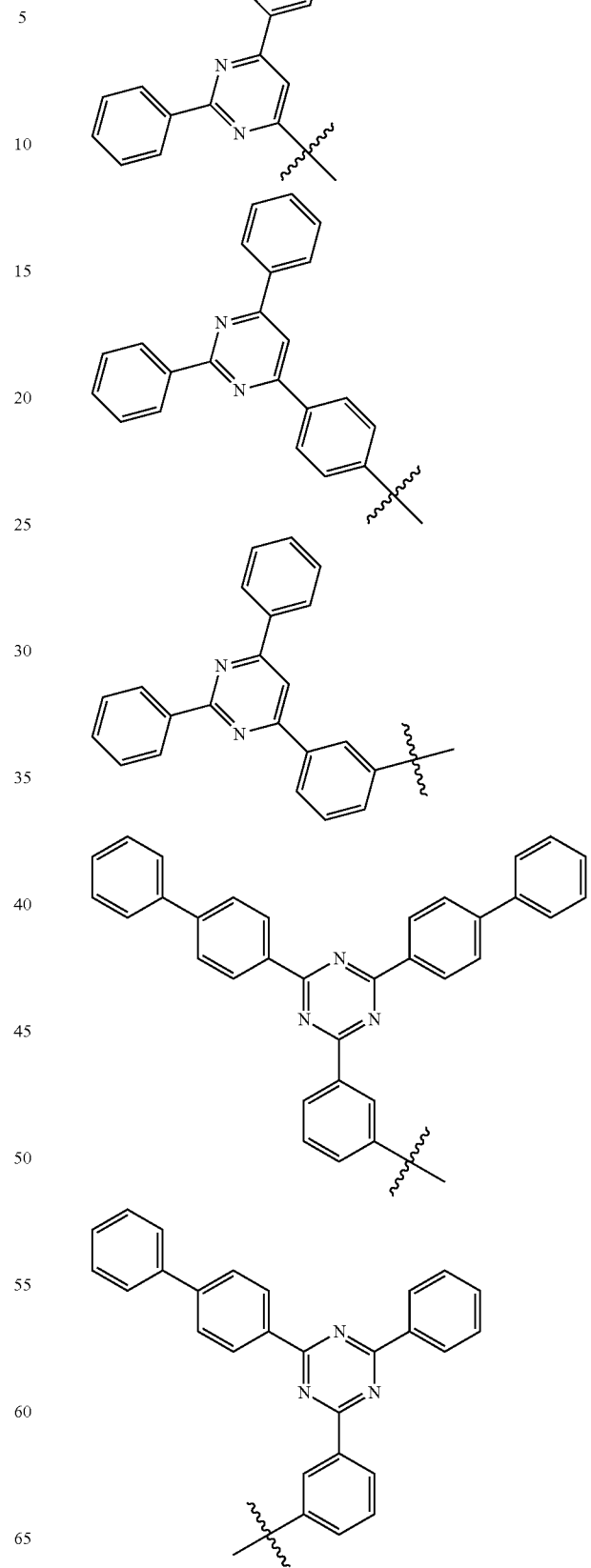

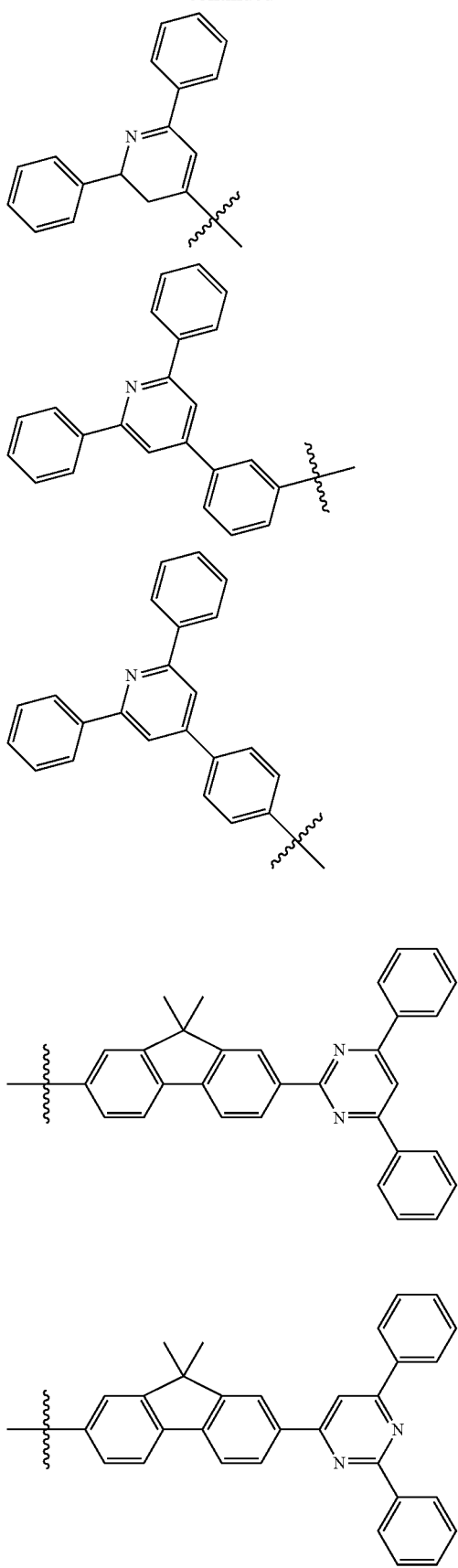
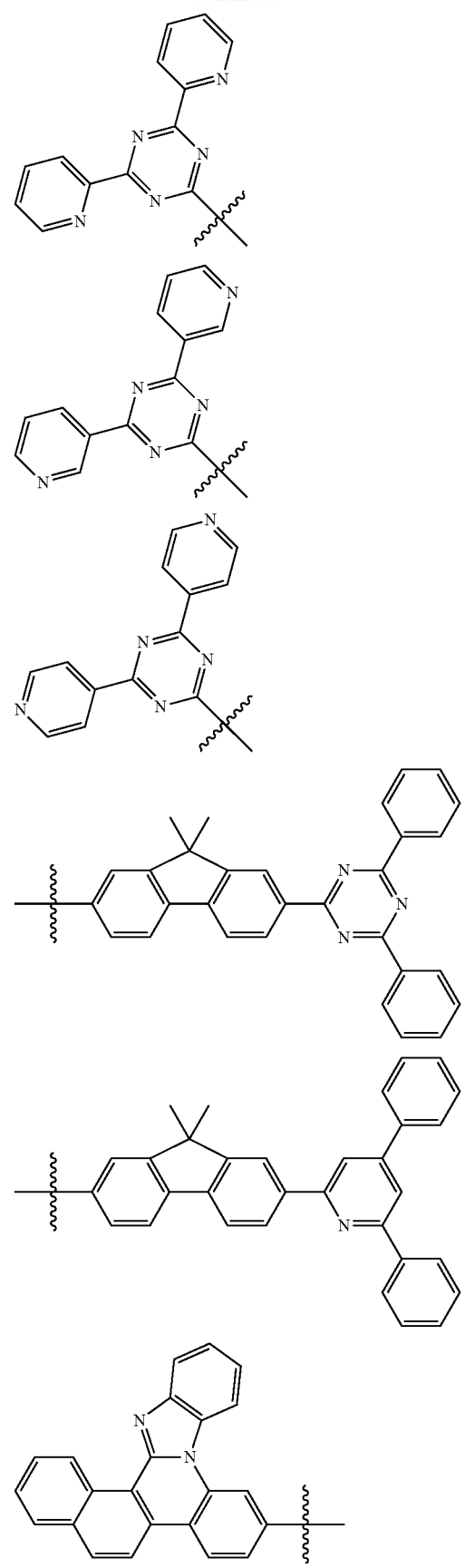

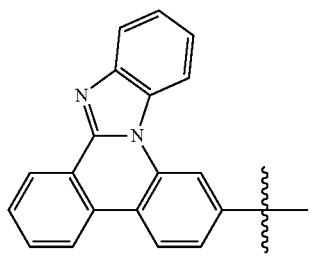
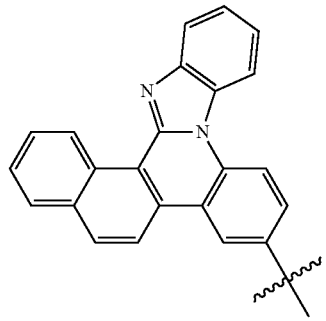
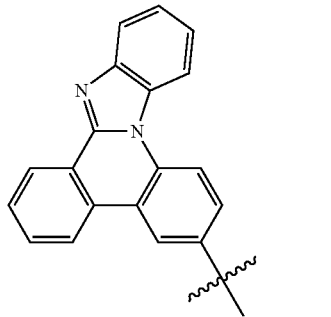
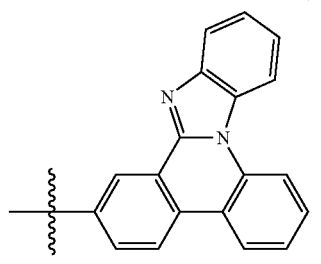
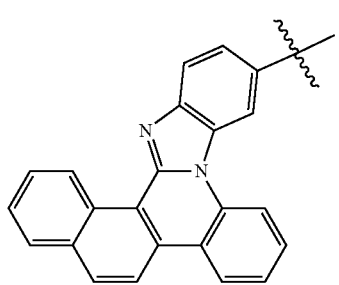
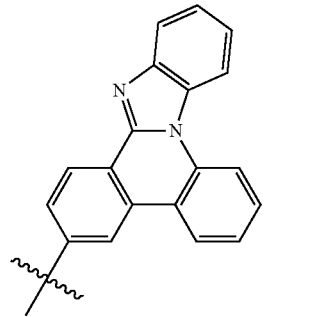
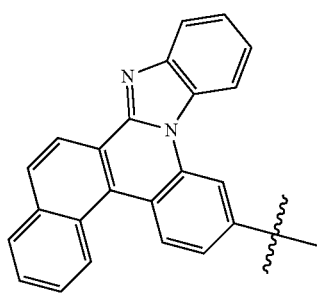
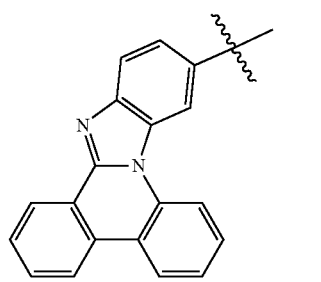
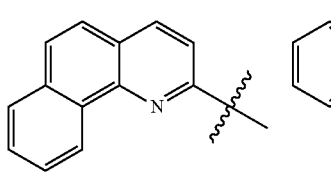
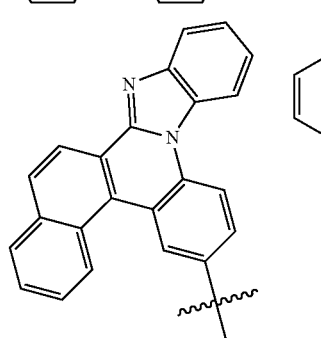
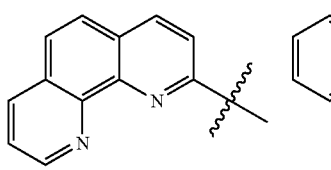
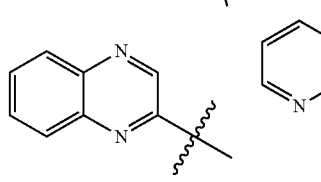

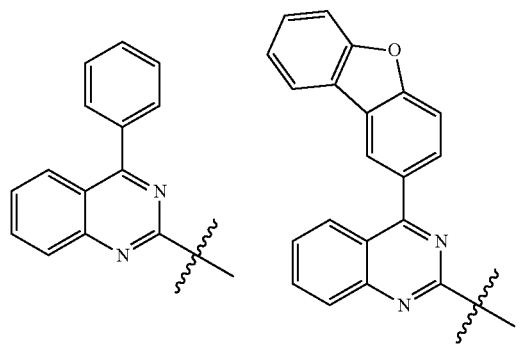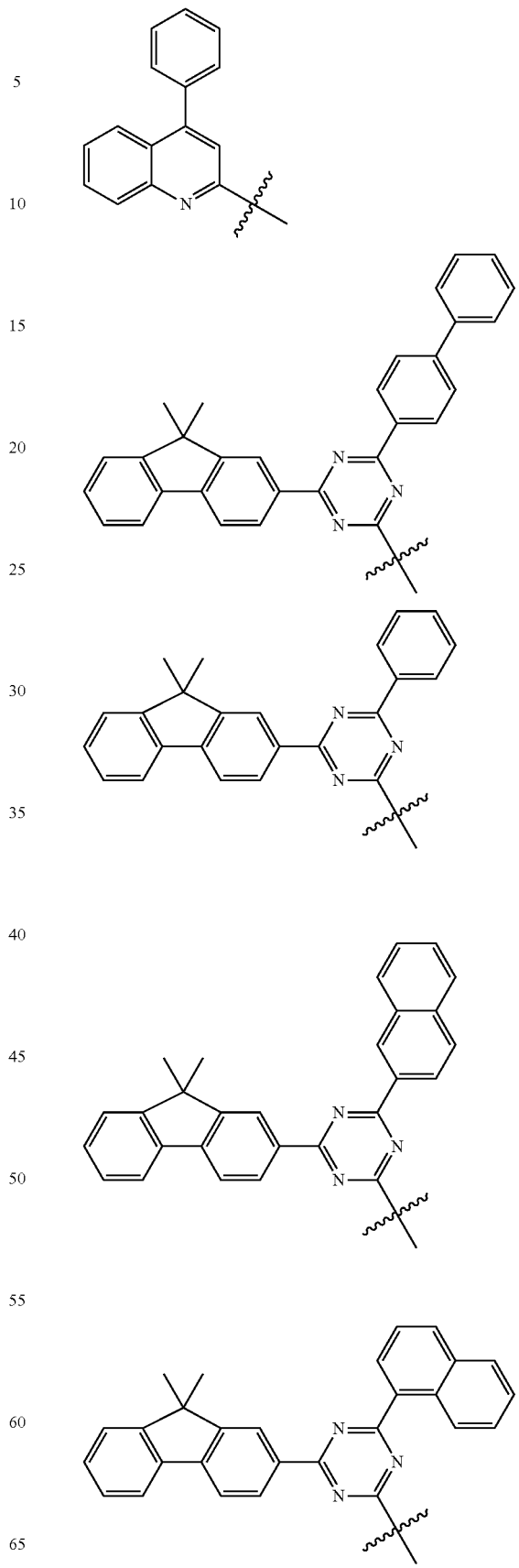

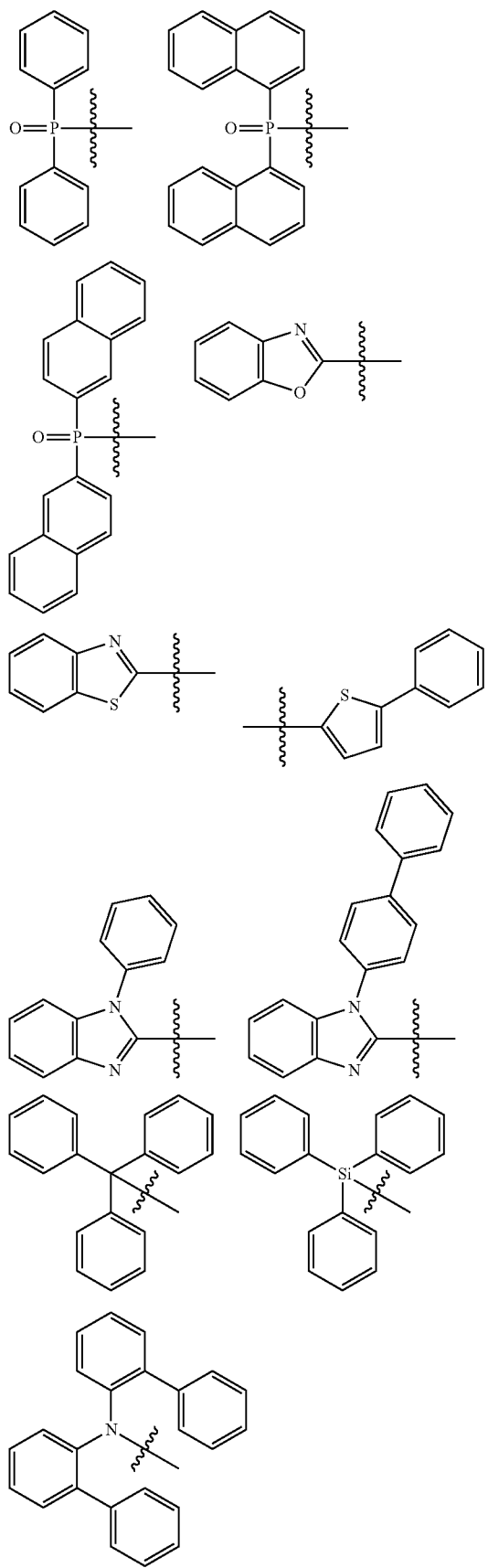
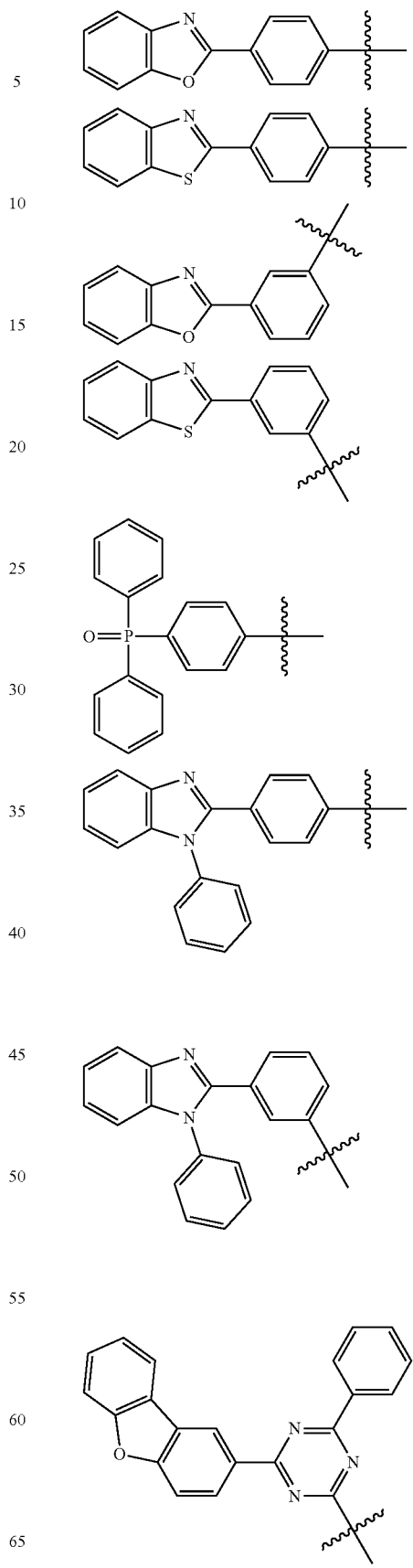

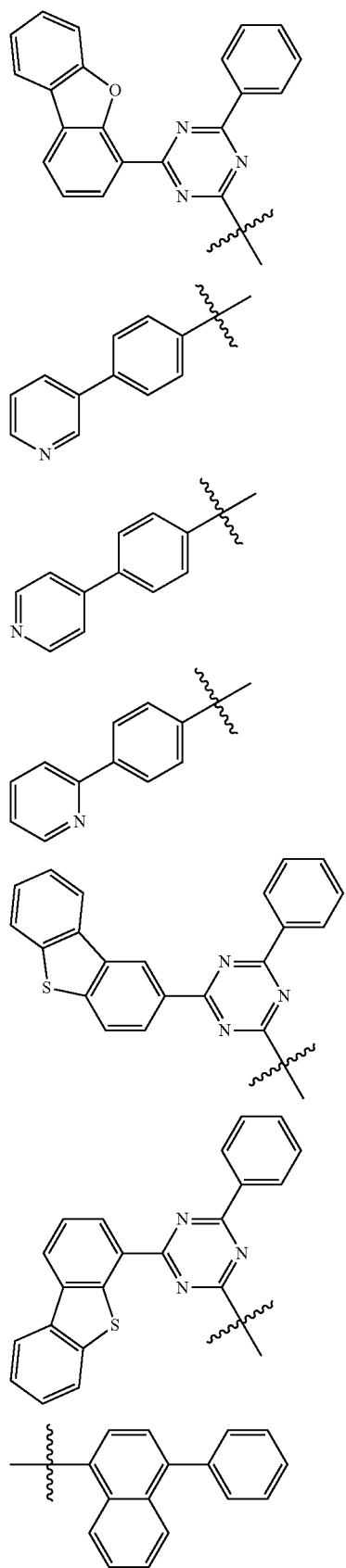
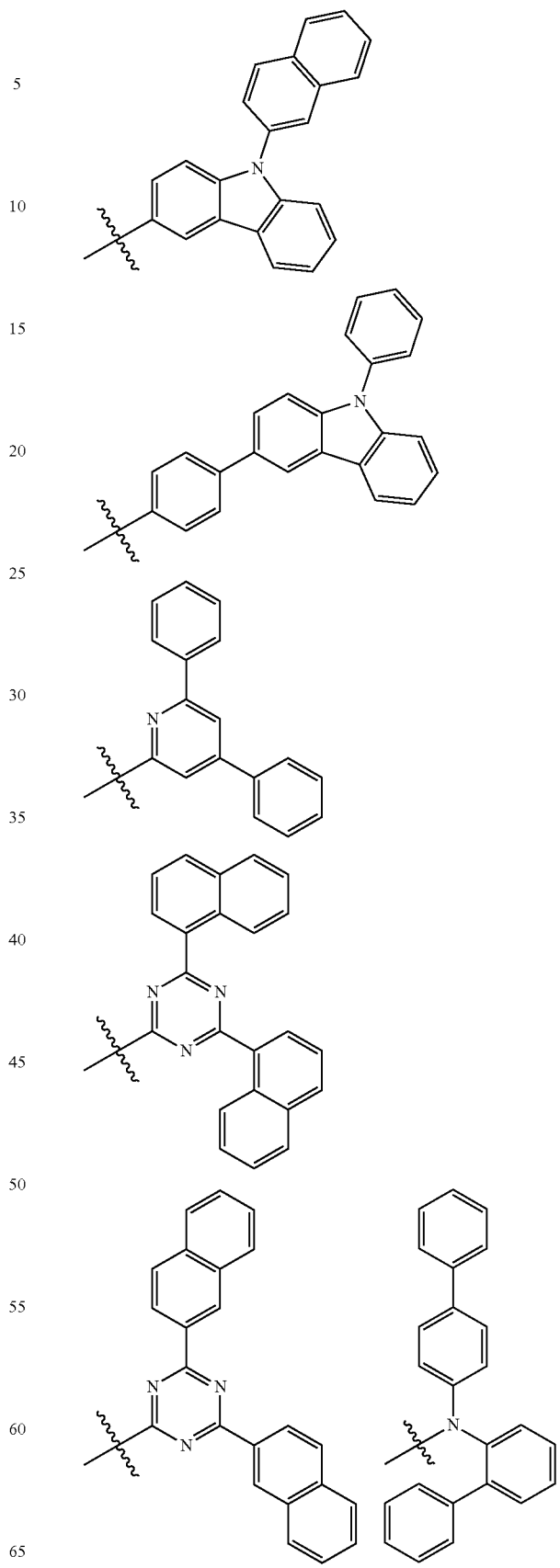

-continued
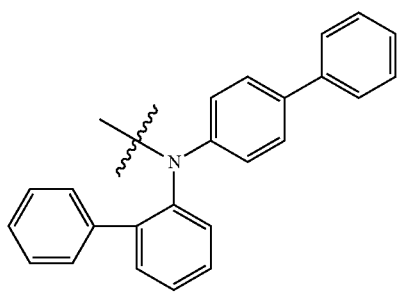
According to an exemplary embodiment of the present invention, the compound of Chemical Formula 1 may be any one selected from the following compounds.
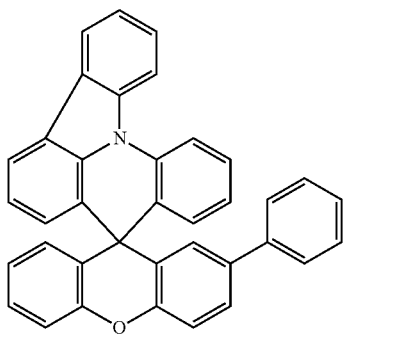
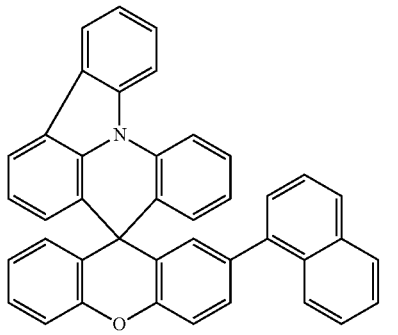
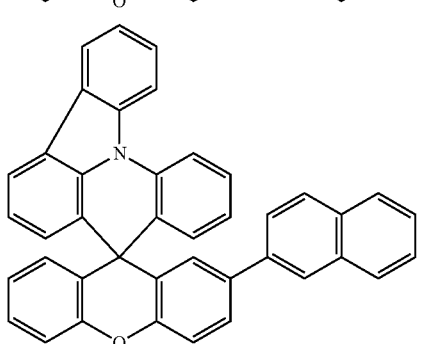
-continued
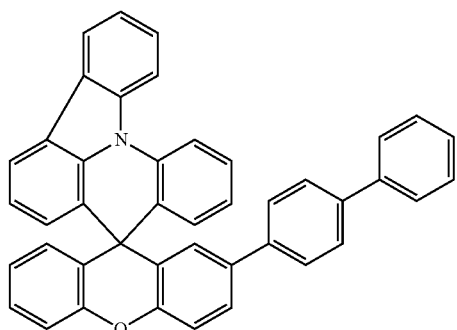
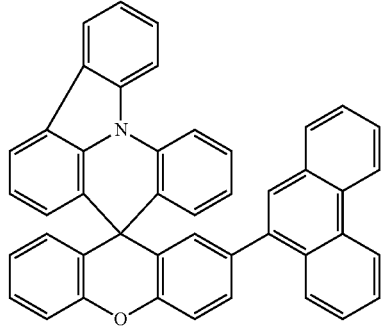
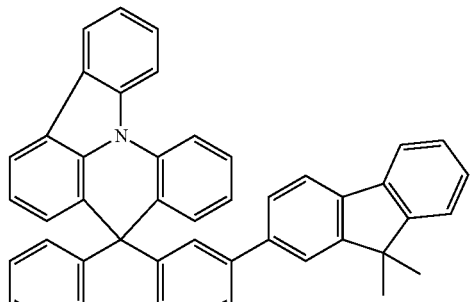
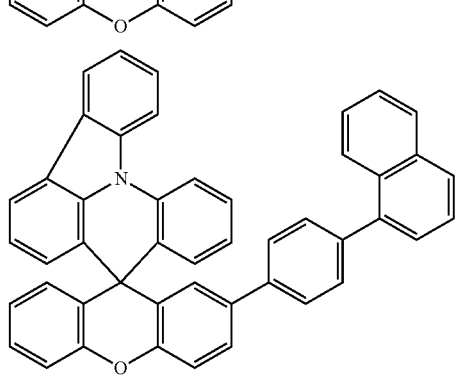
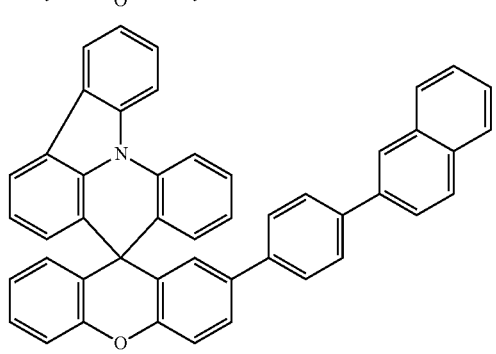

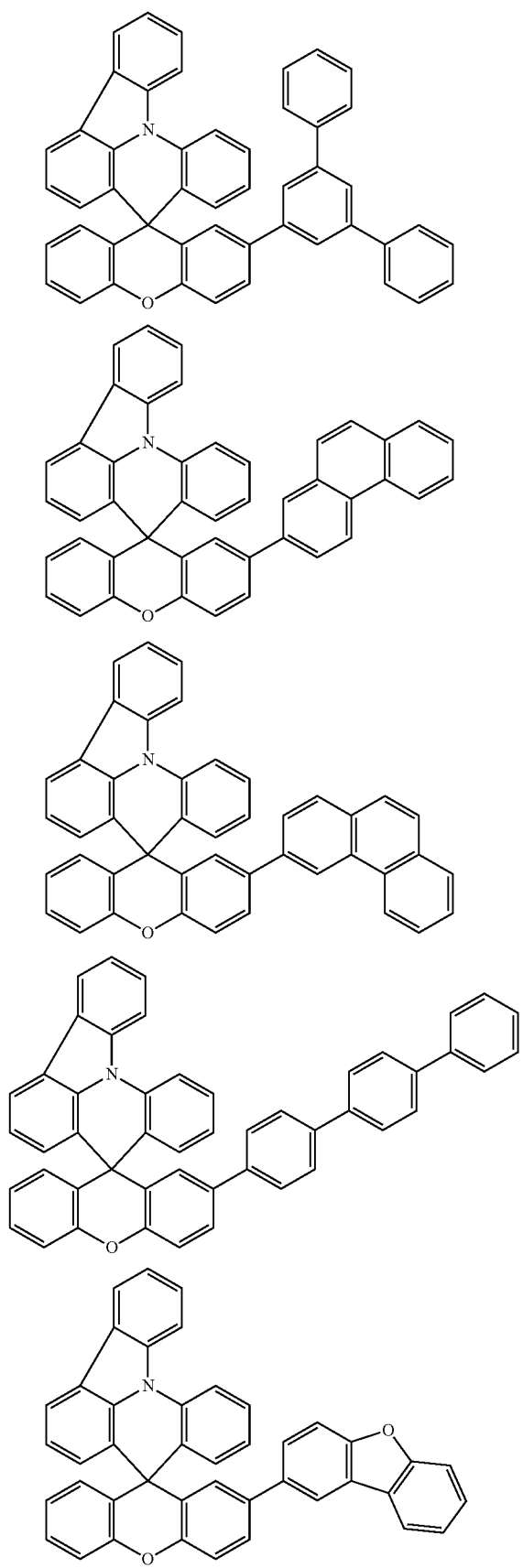
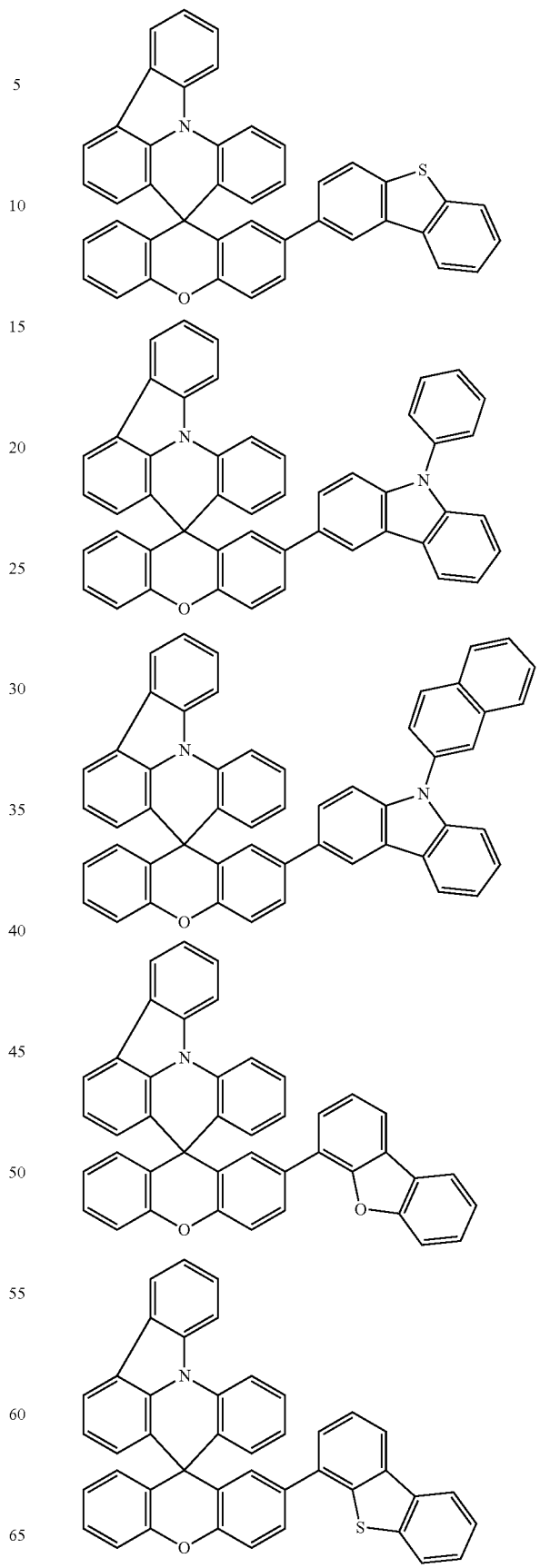

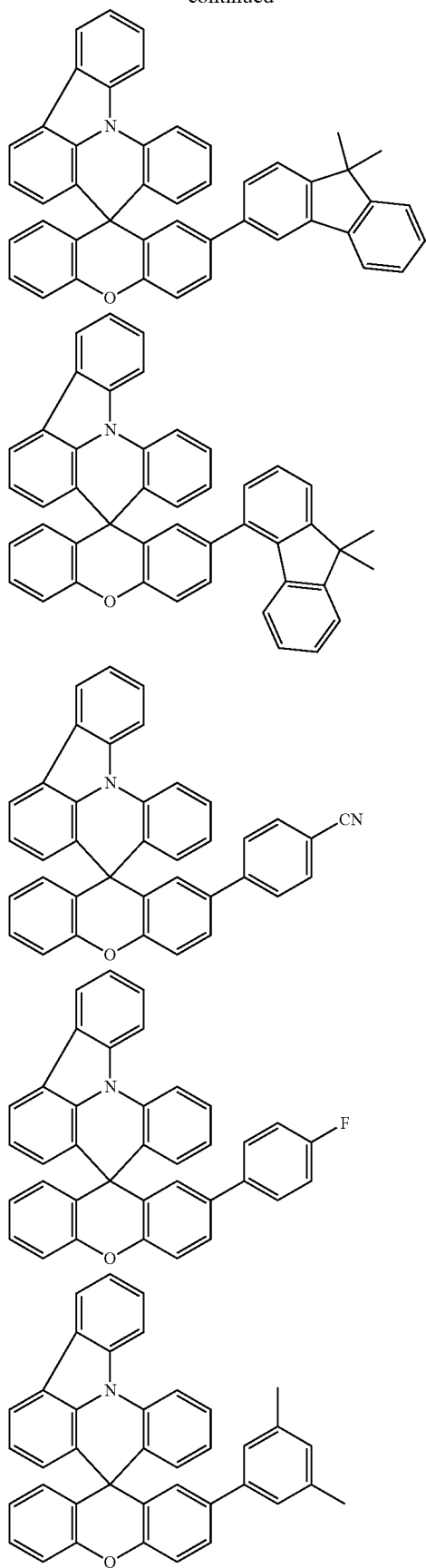
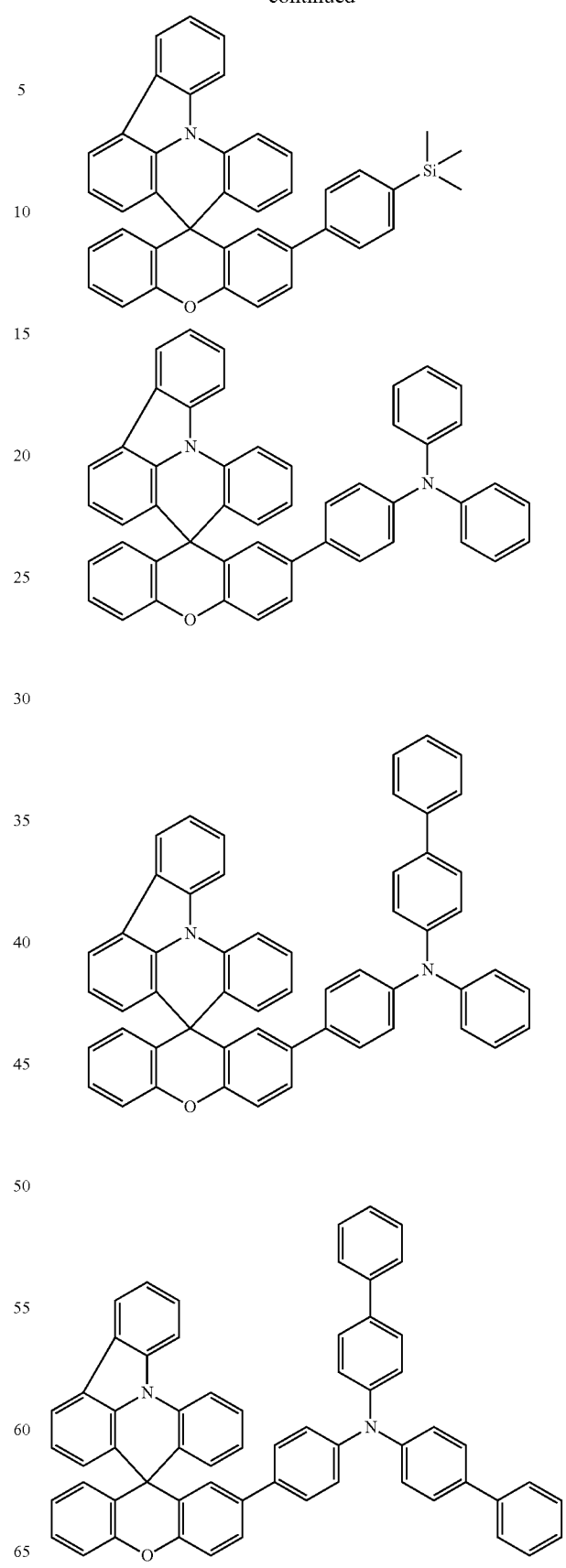

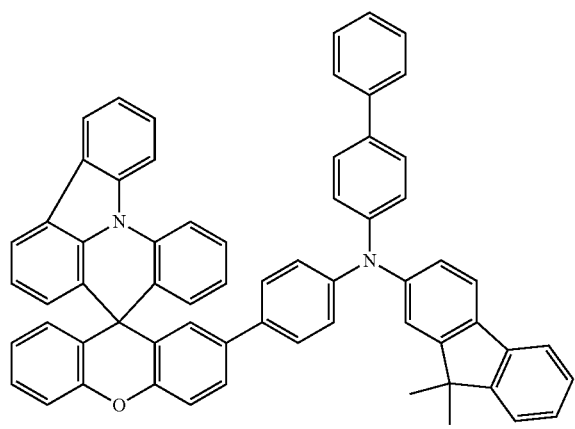
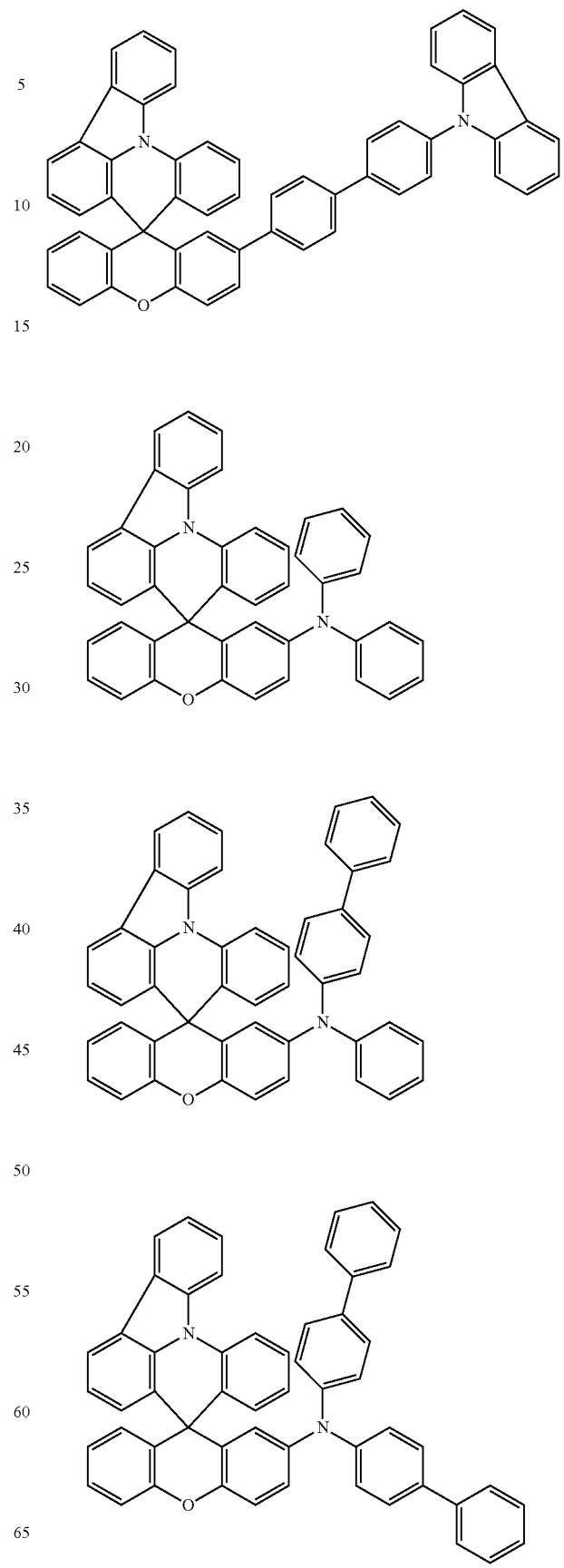

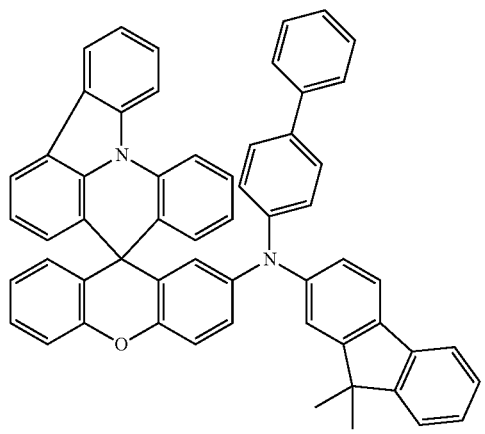
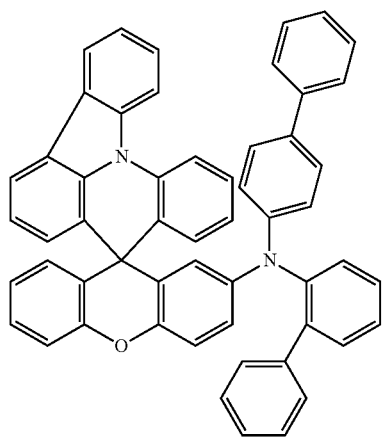
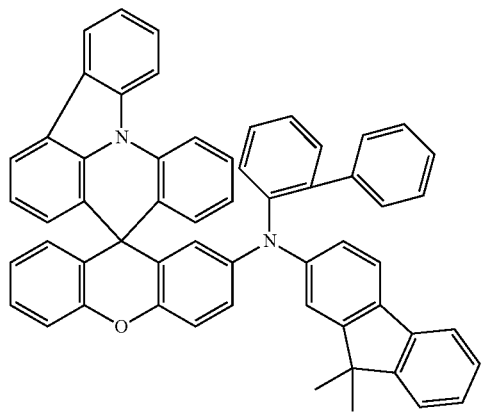
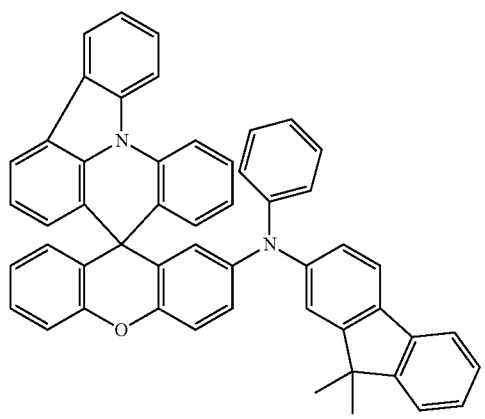
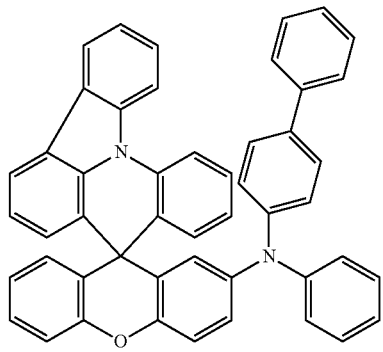
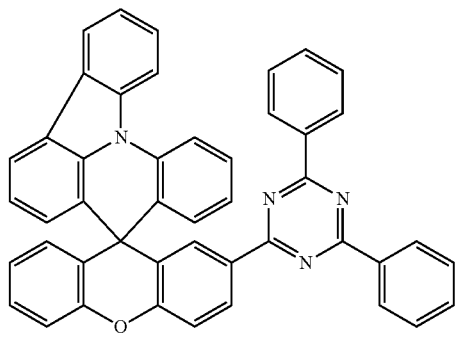
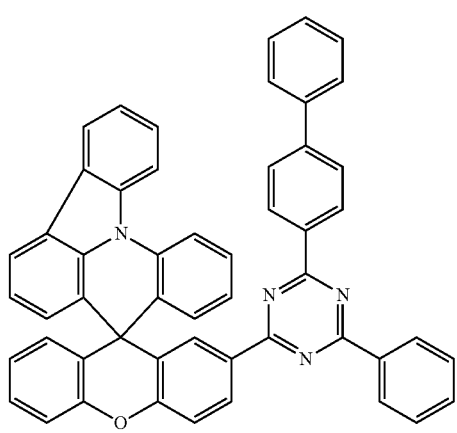
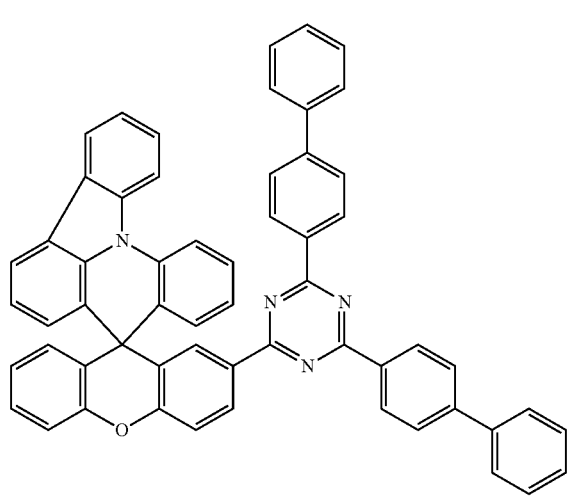

61
-continued
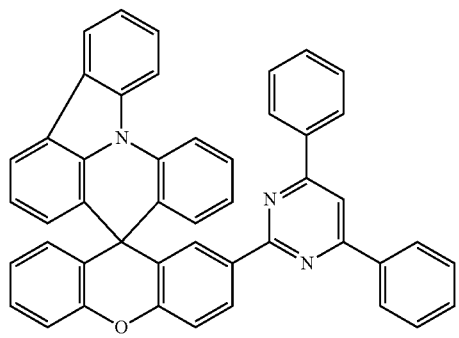
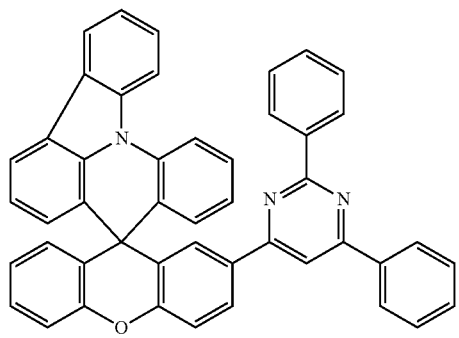
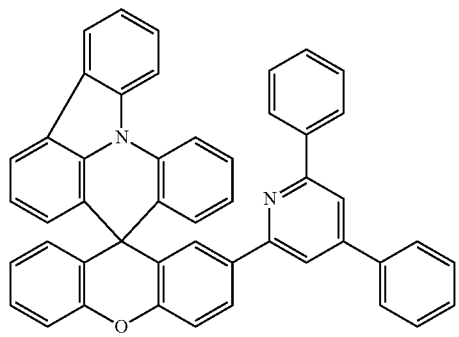
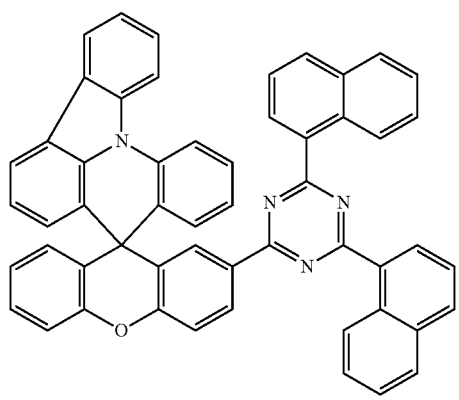
62
-continued
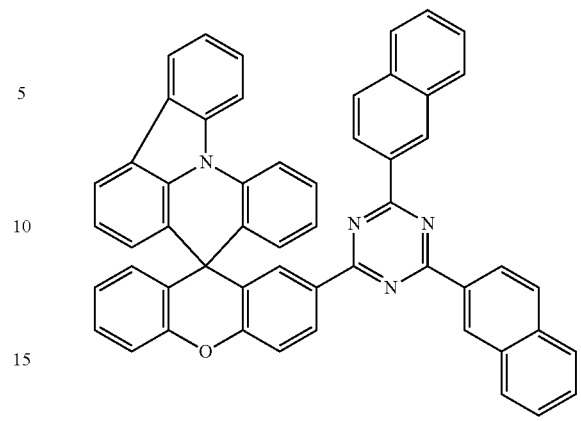
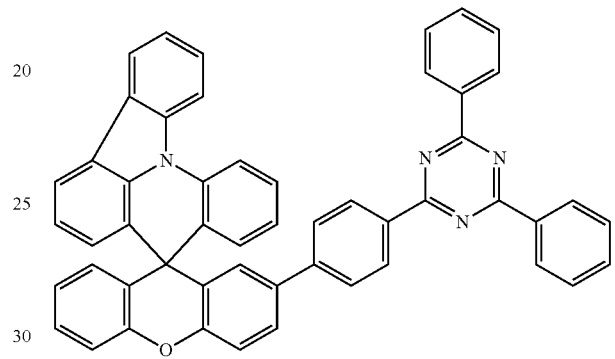
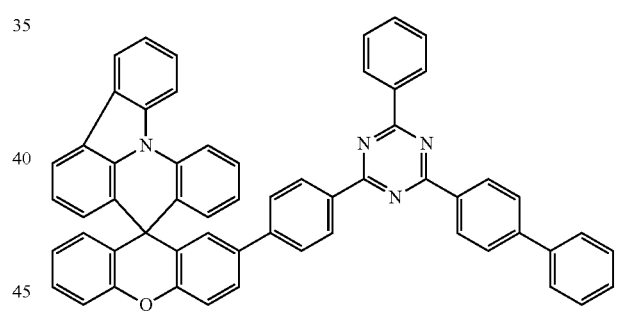
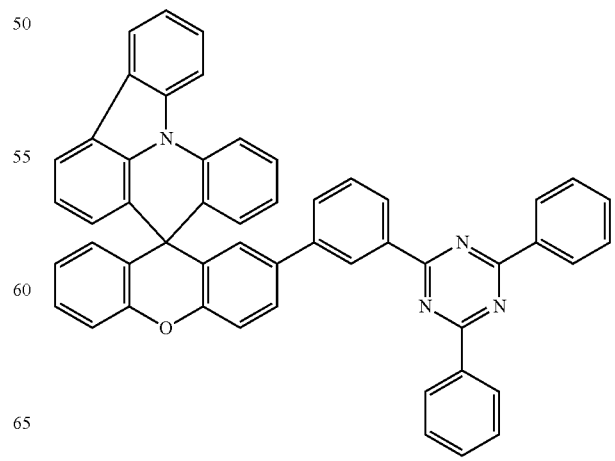

-continued
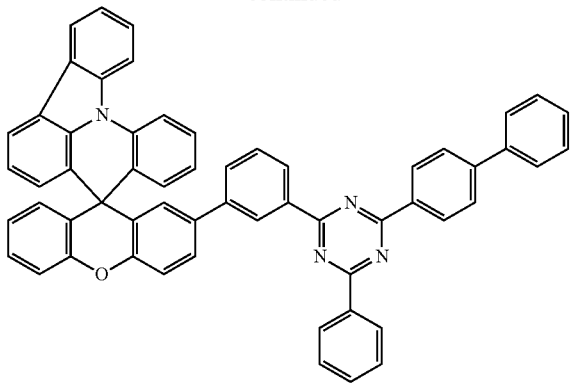
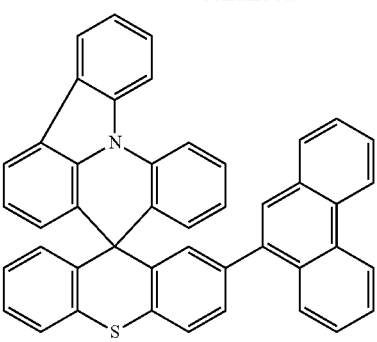
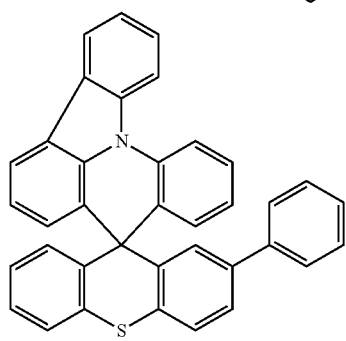
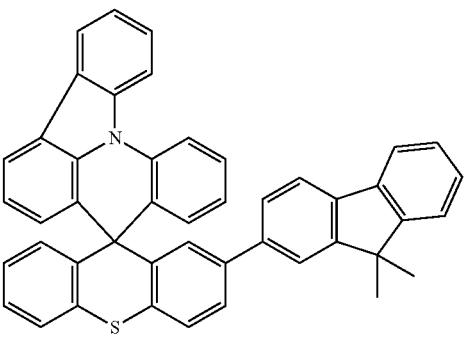
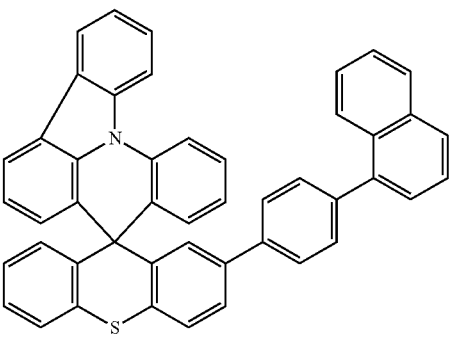
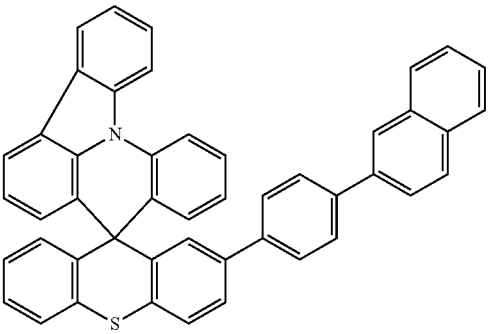
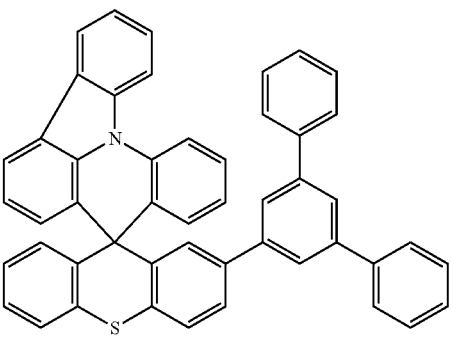

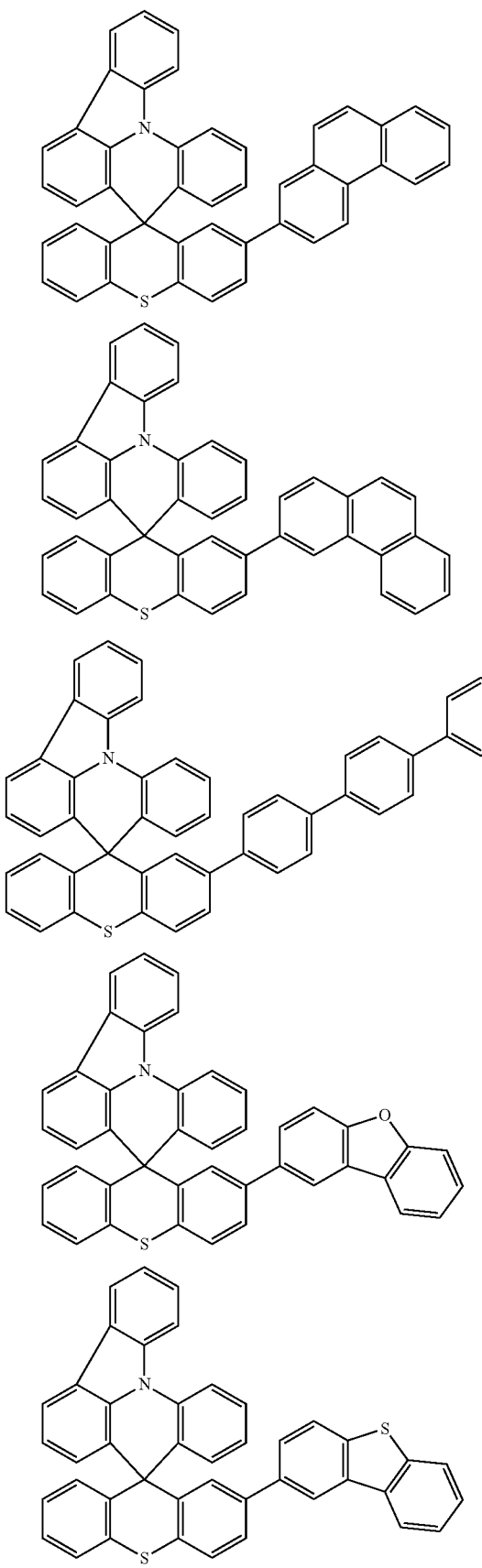
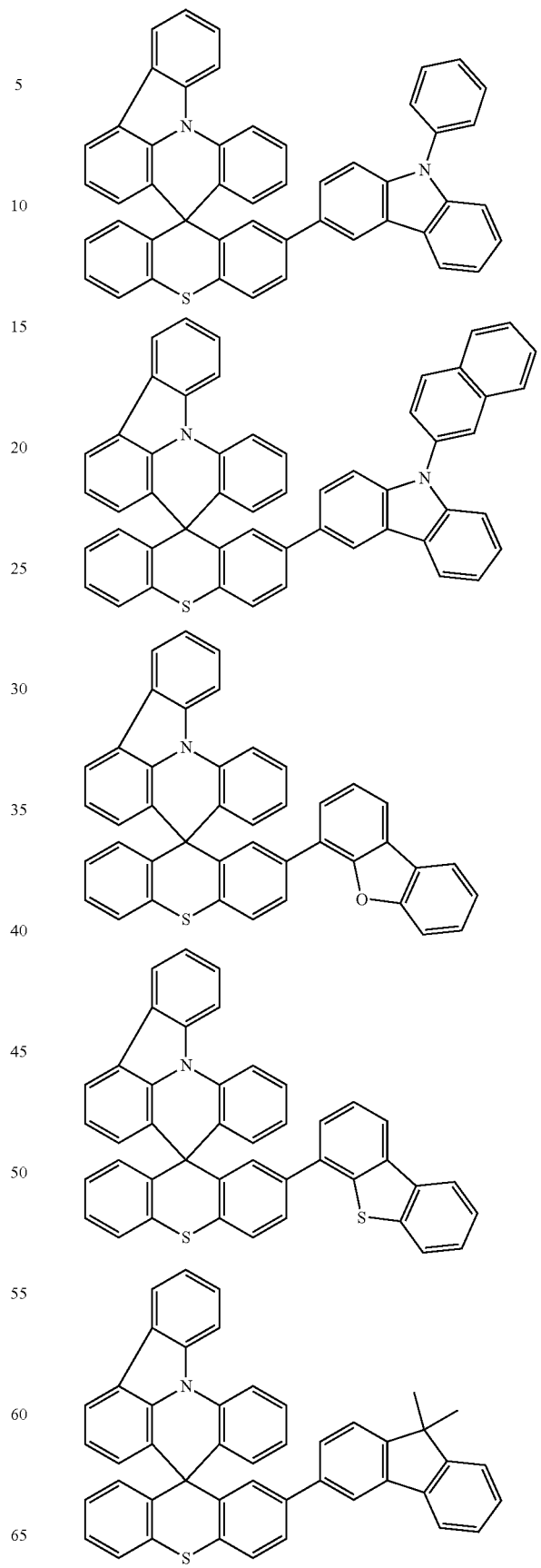

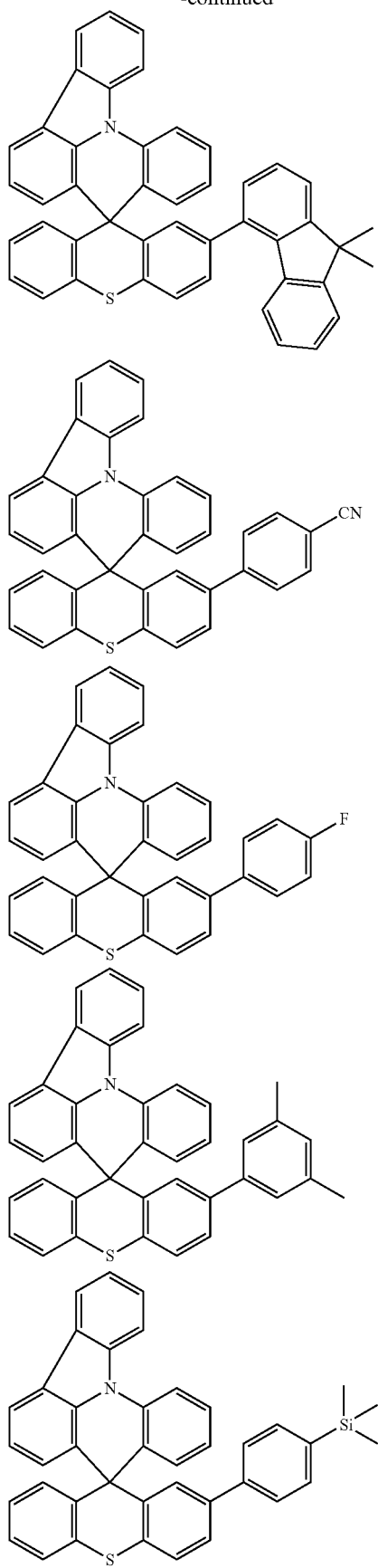
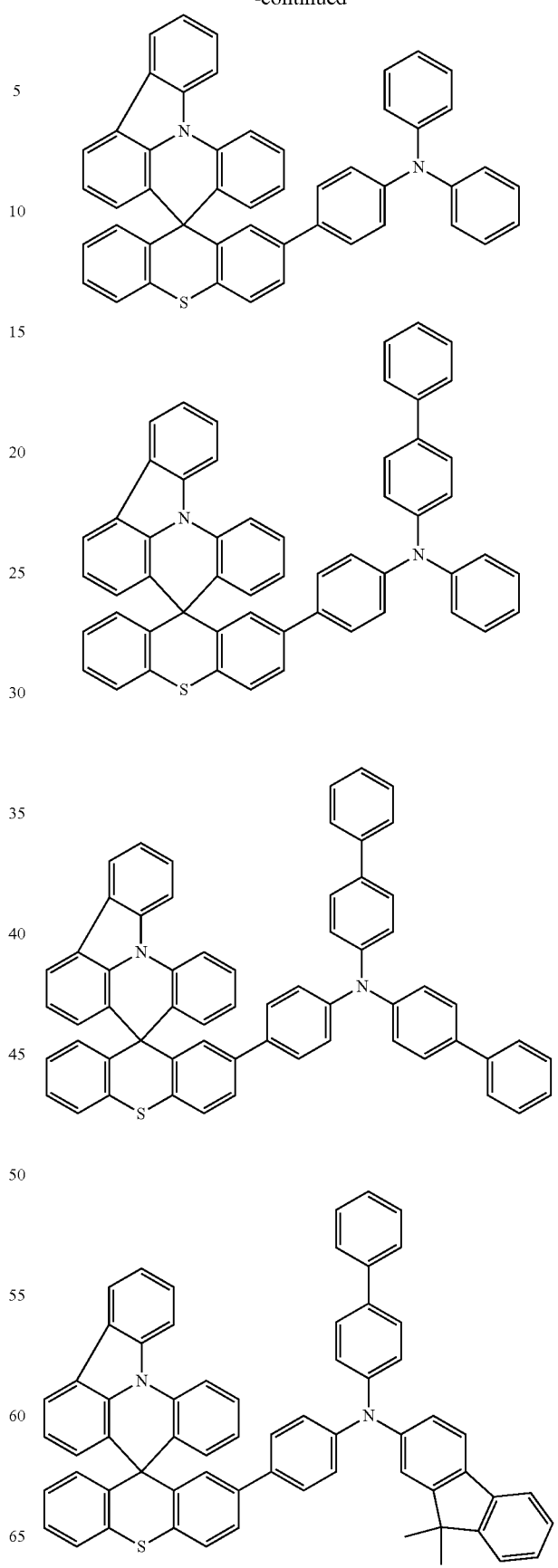

69
-continued
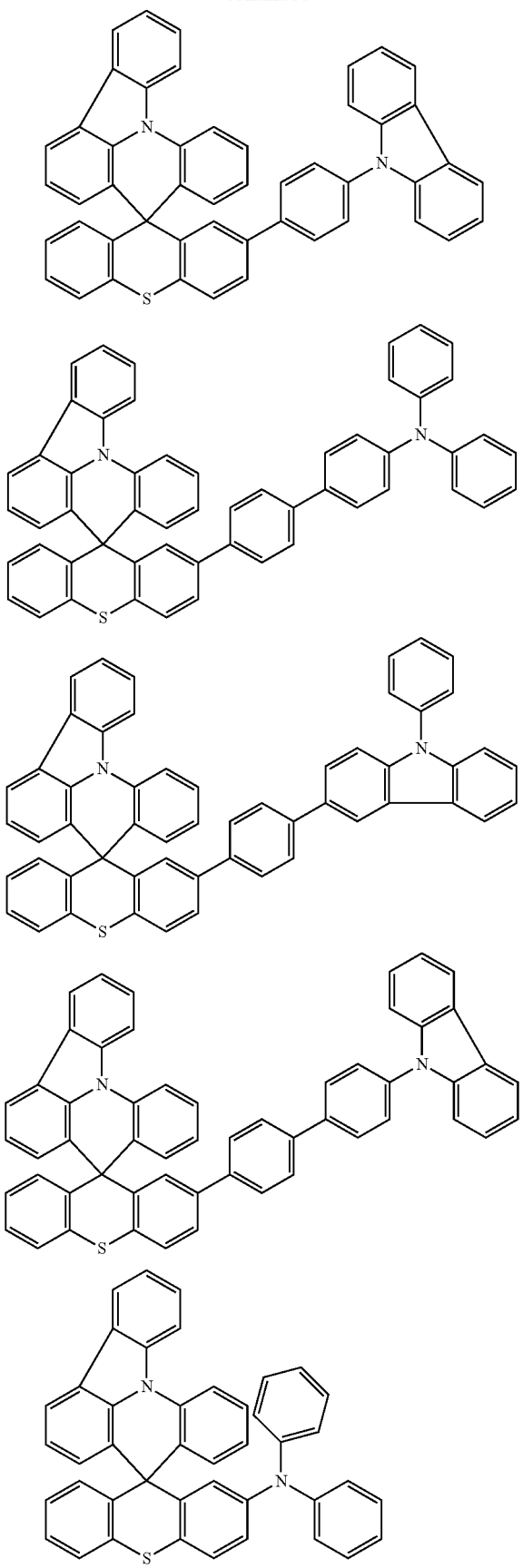
70
-continued
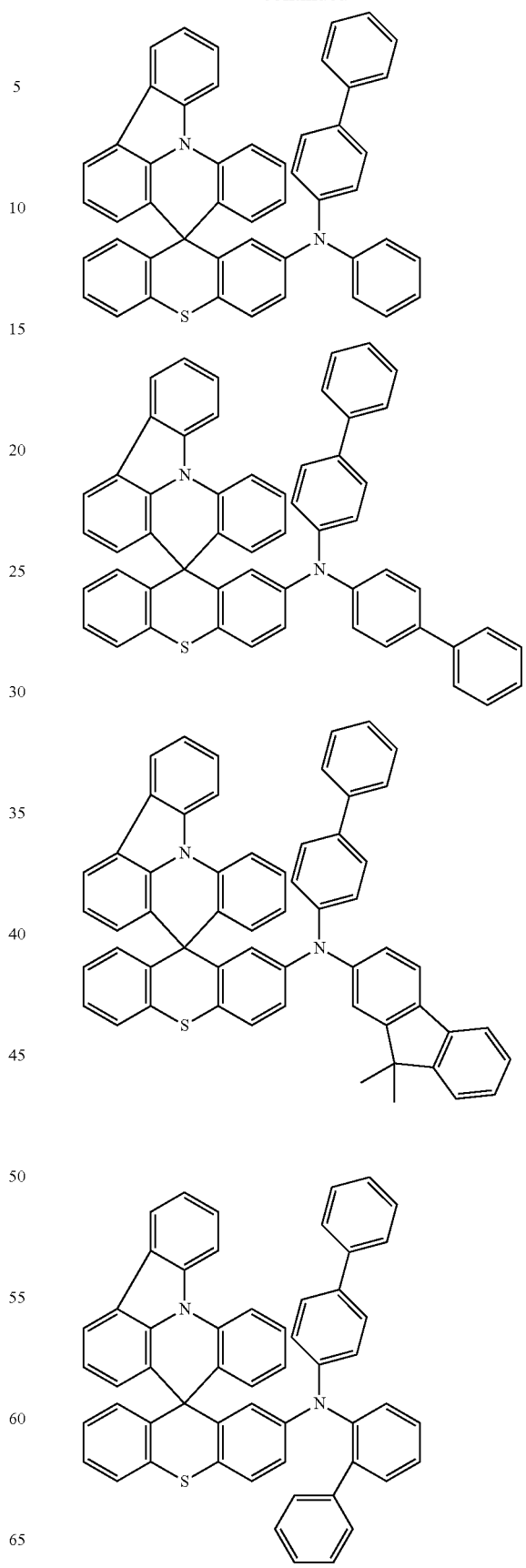

71
-continued
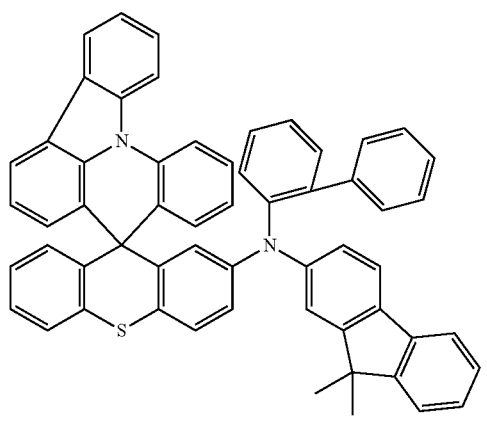
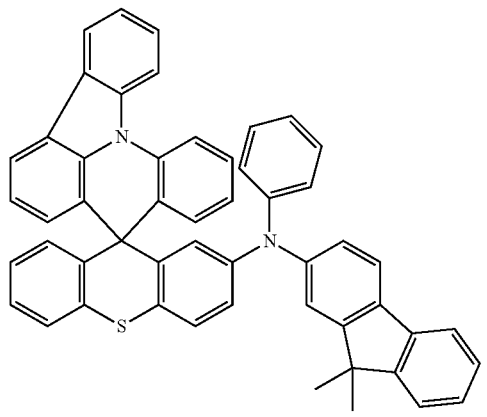
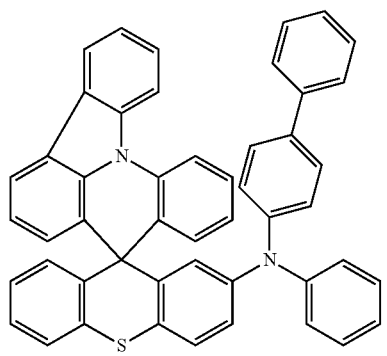
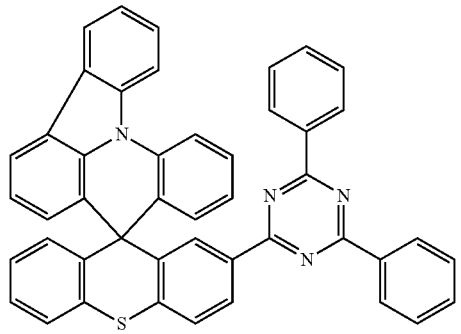
72
-continued
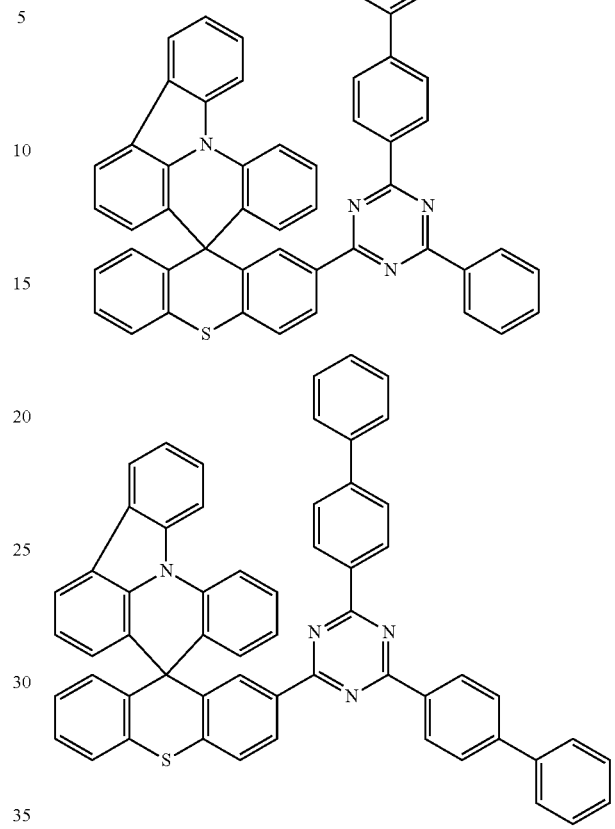
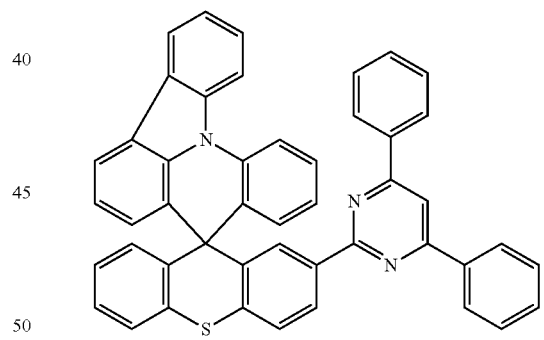
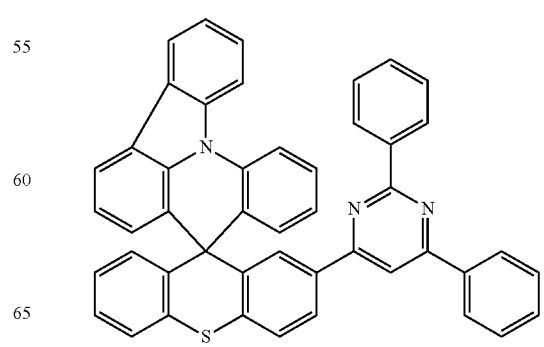

73
-continued
74
-continued
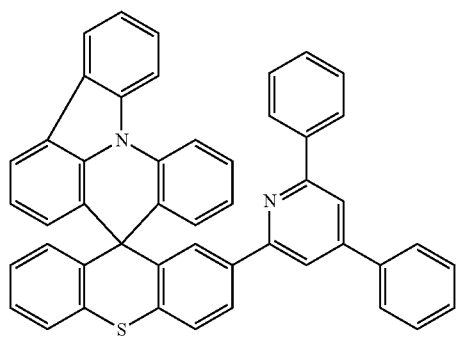
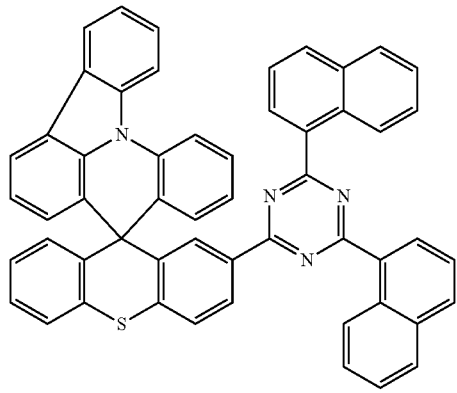
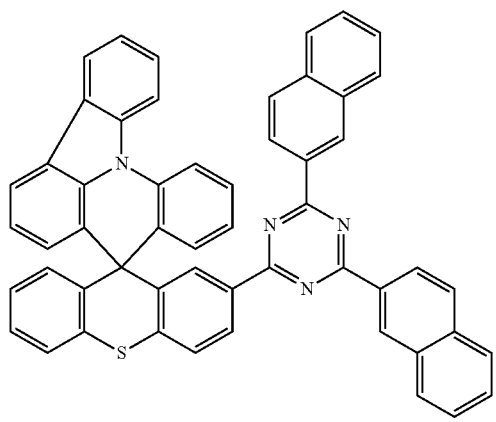
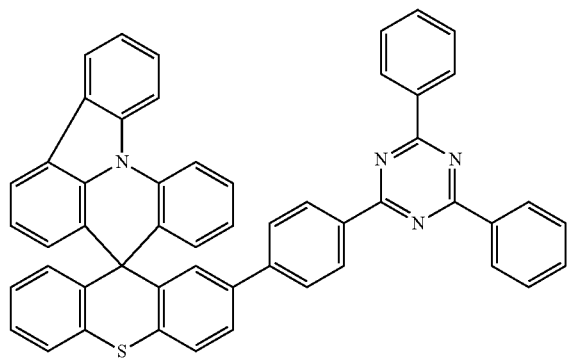
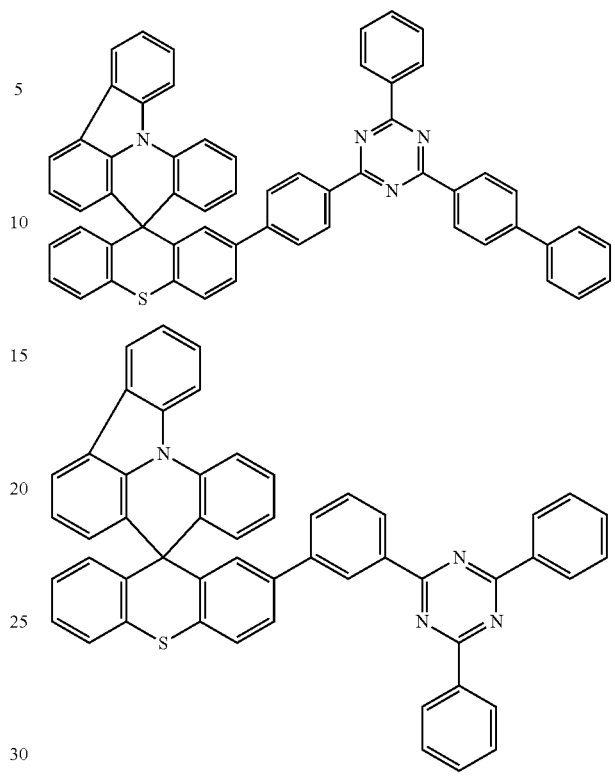
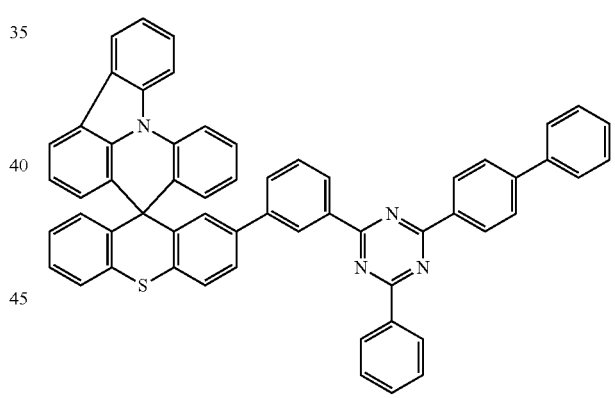
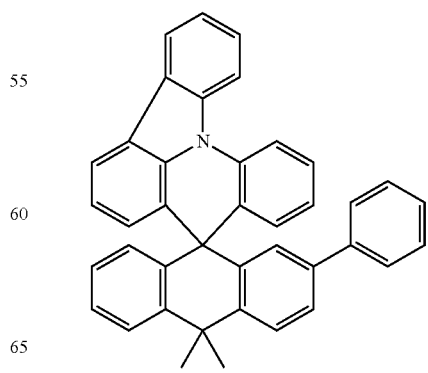

75
-continued
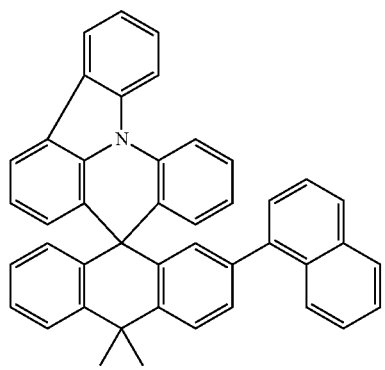
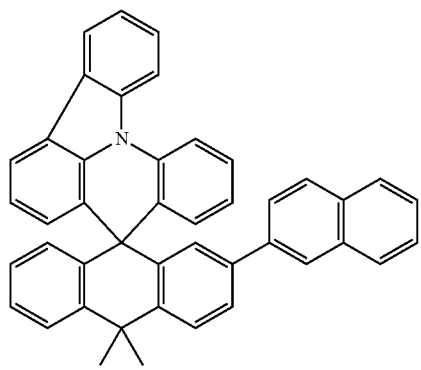
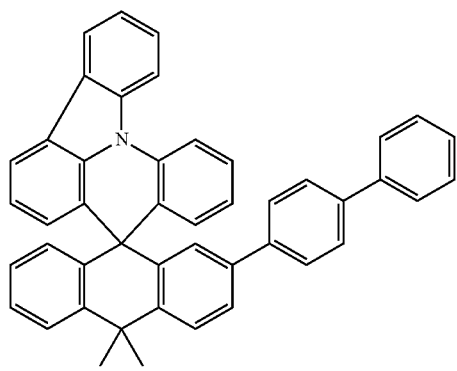
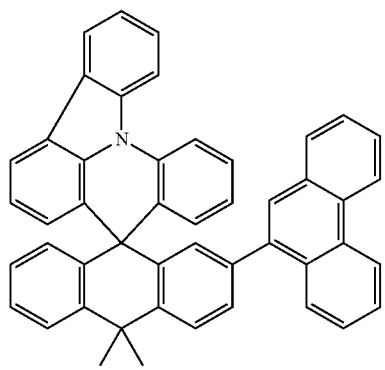
76
-continued
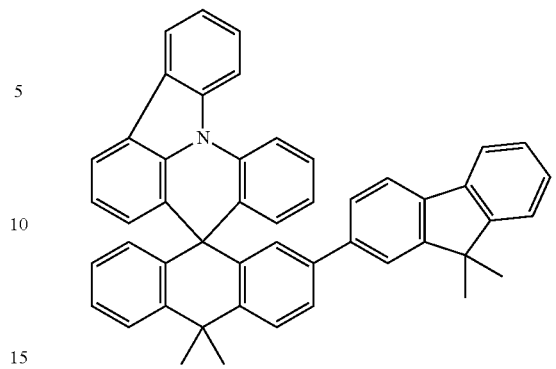
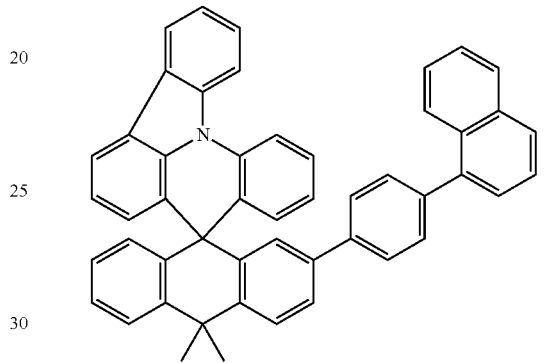
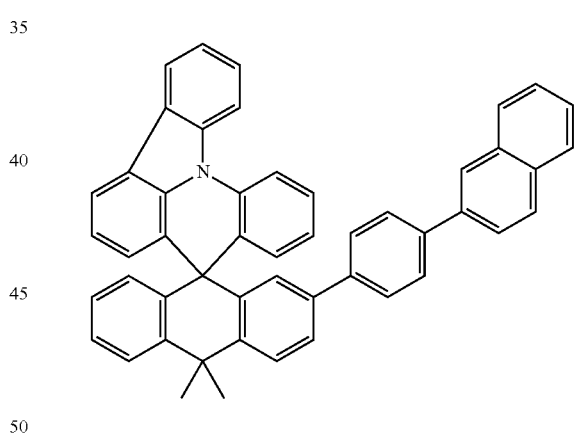
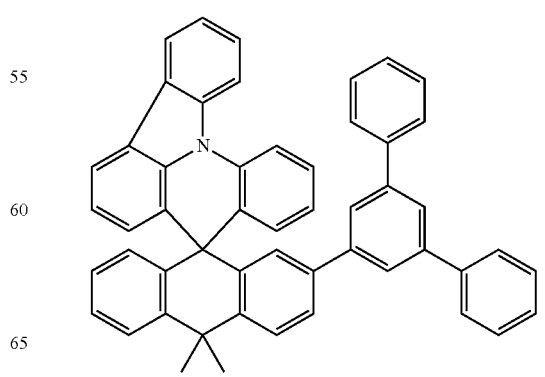

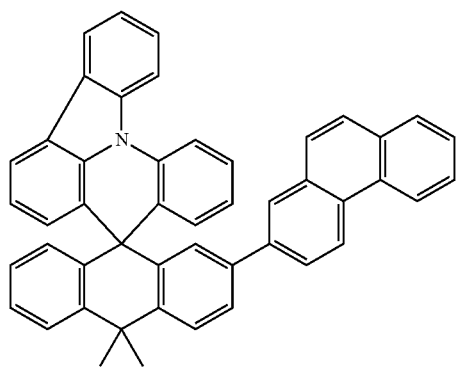
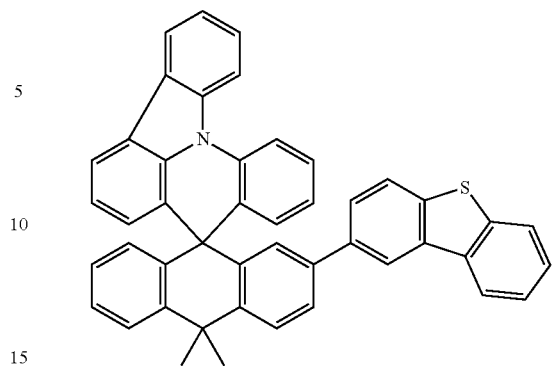
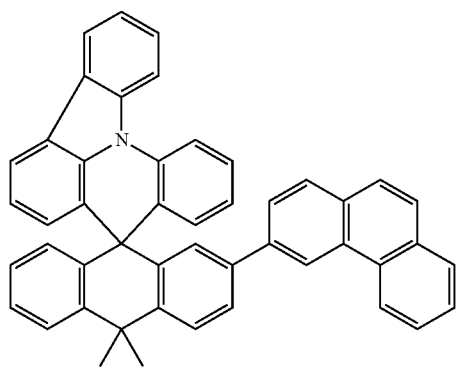
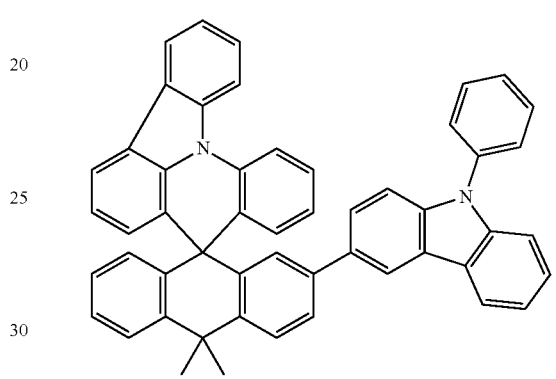
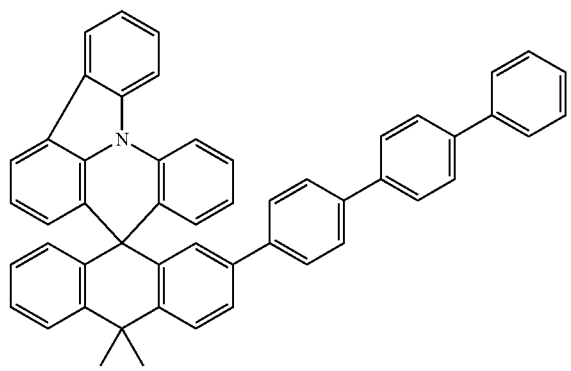
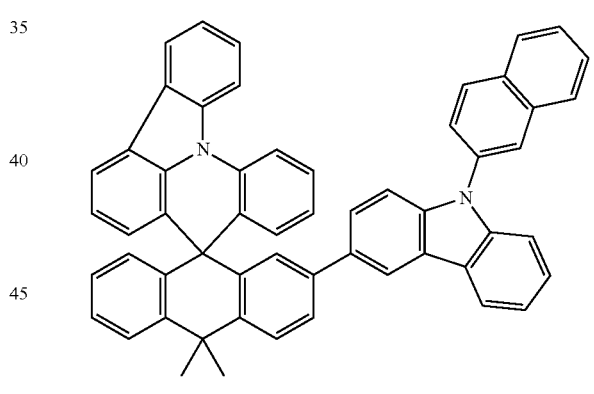
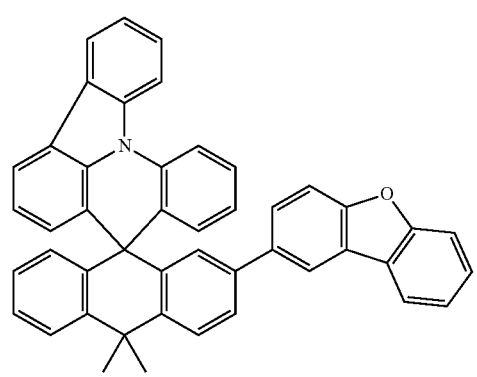
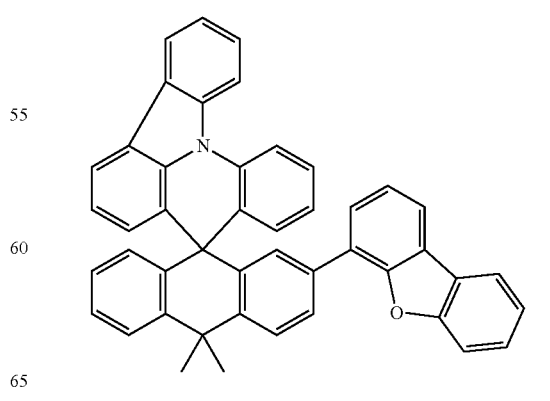

| 79 -continued | 80 -continued |
|---|---|
| 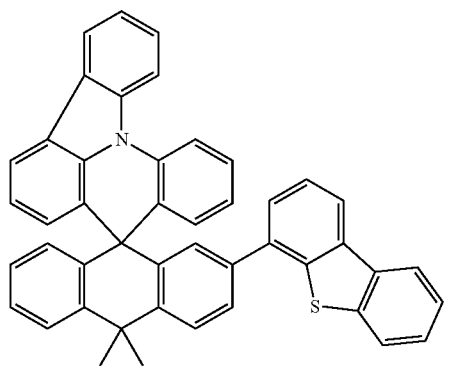 | 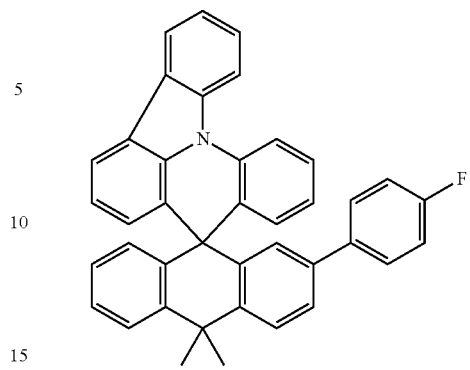 |
| 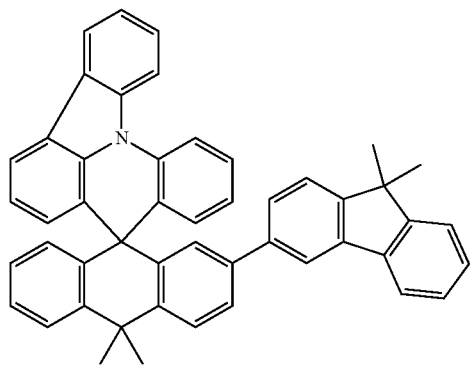 | 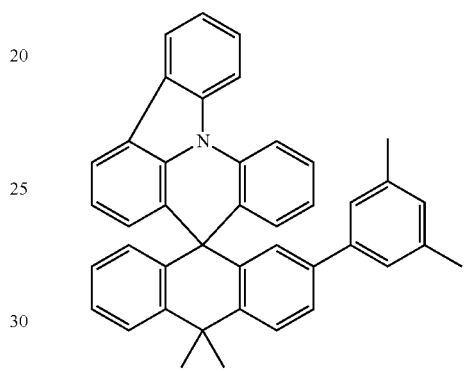 |
| 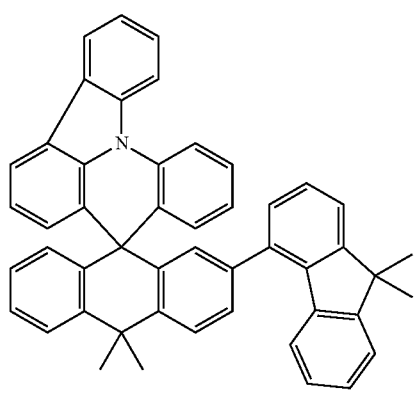 | 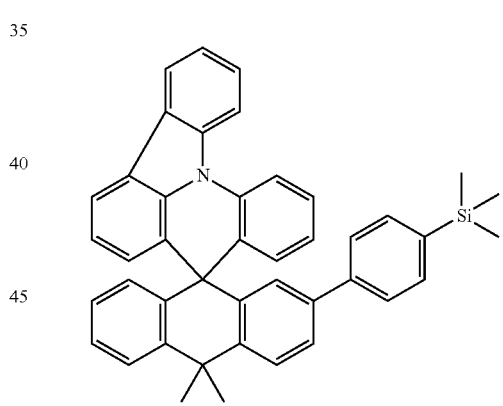 |
| 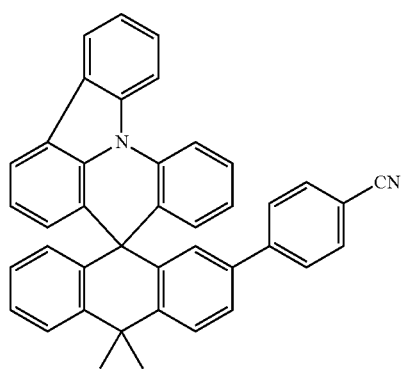 | 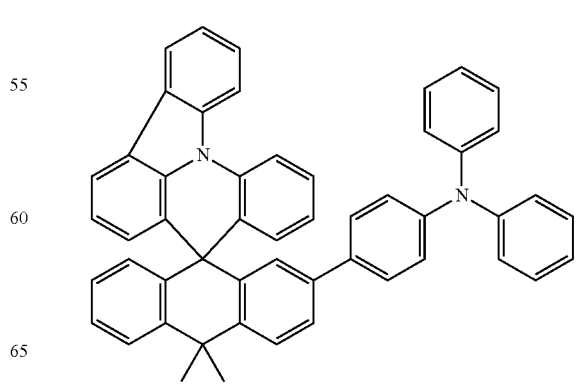 |

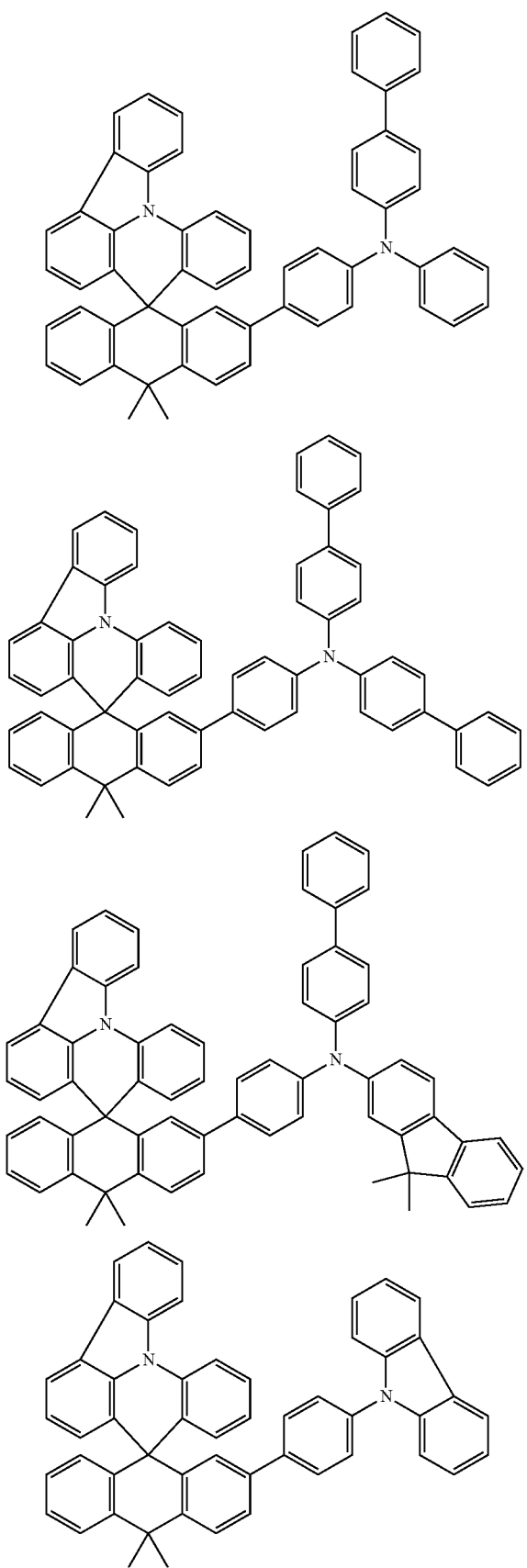
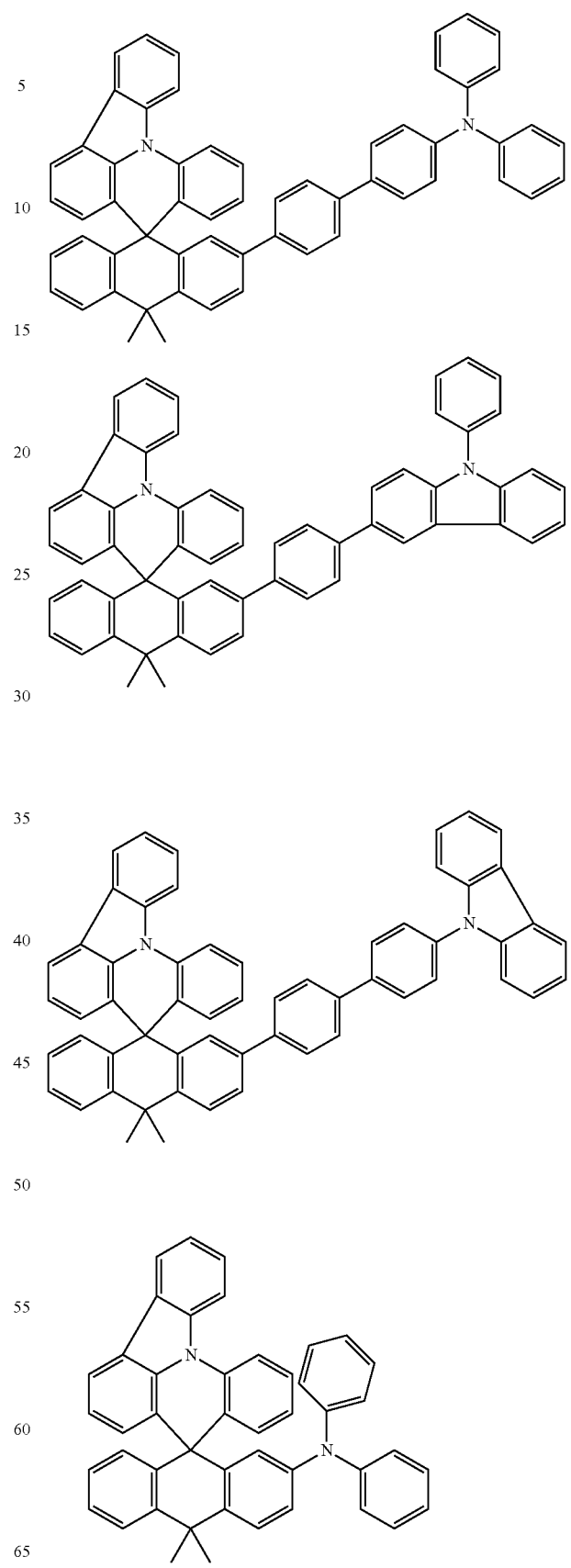

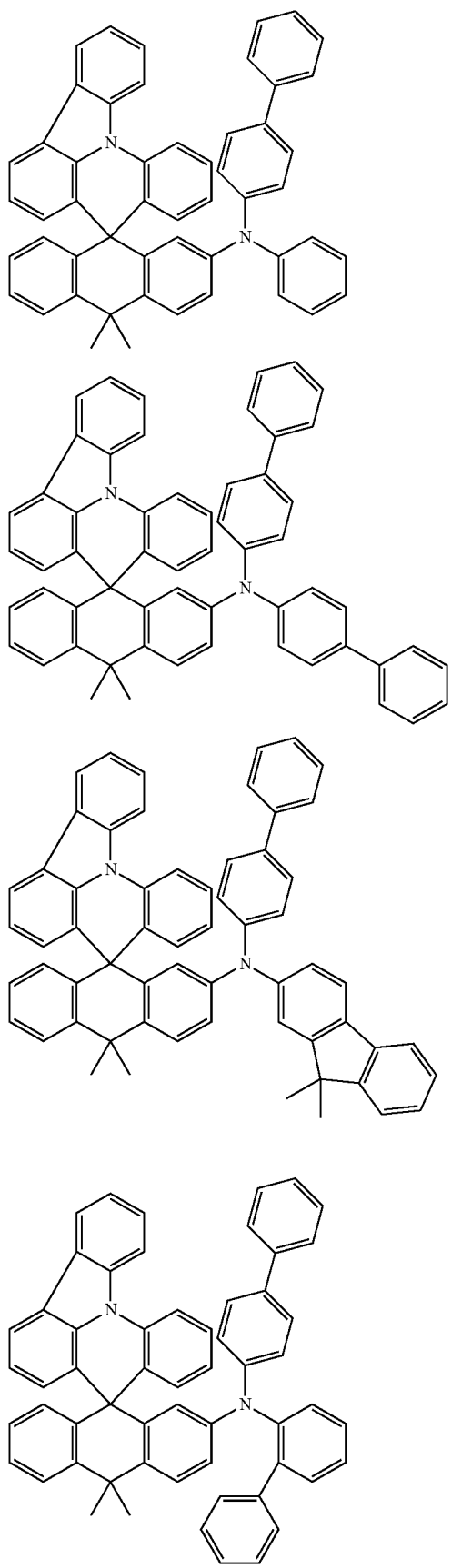
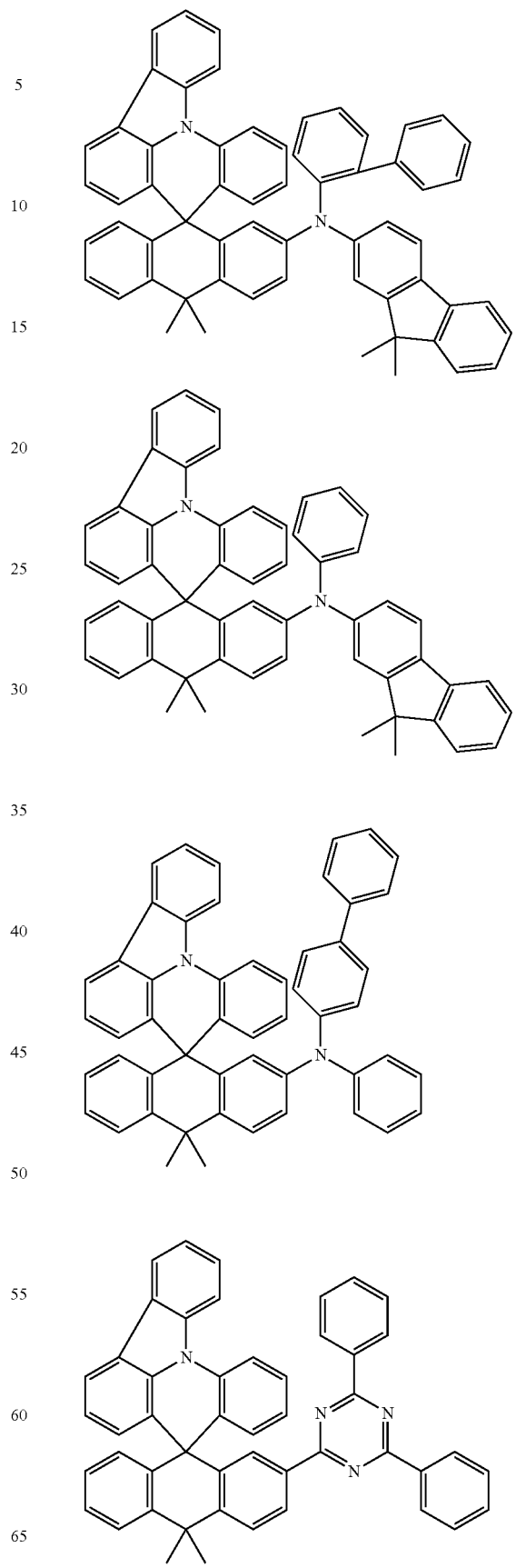

85
-continued
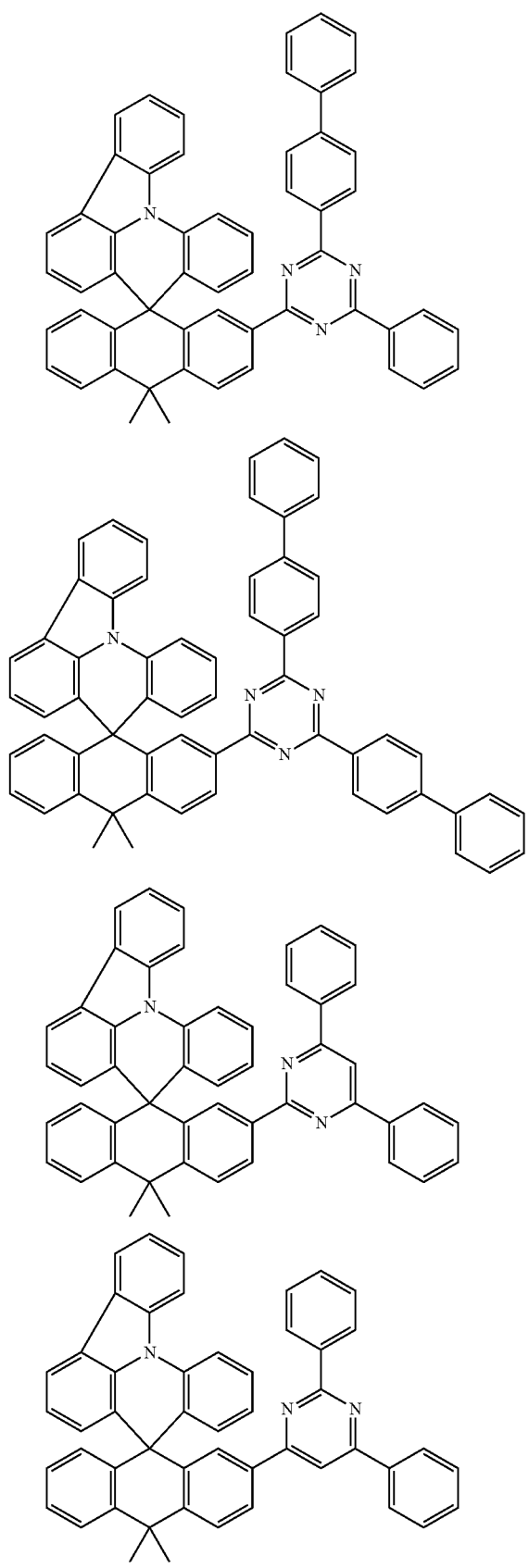
86
-continued
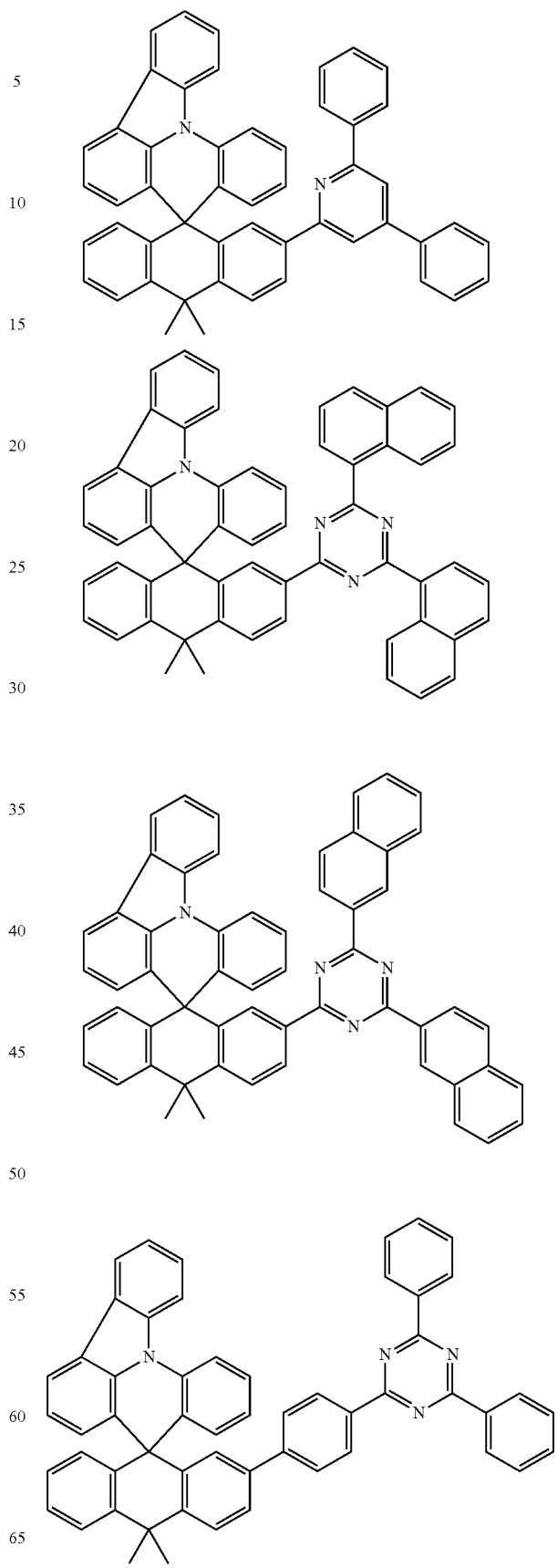

87
-continued
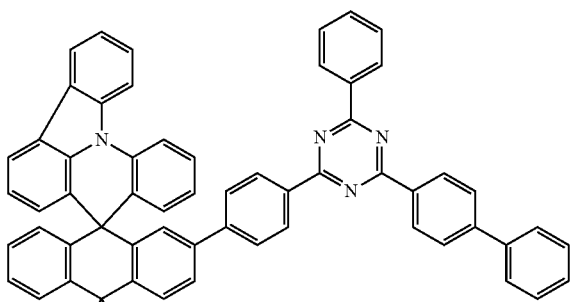
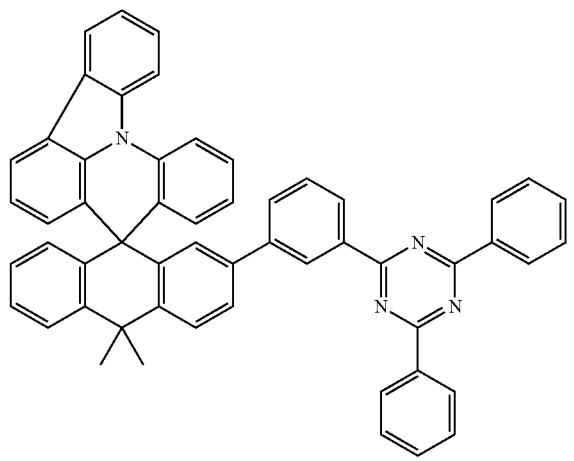
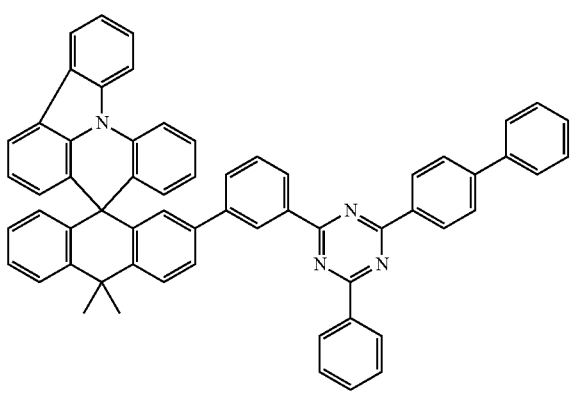
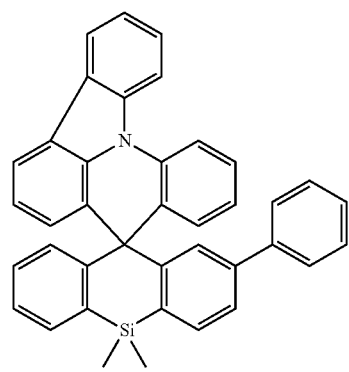
88
-continued
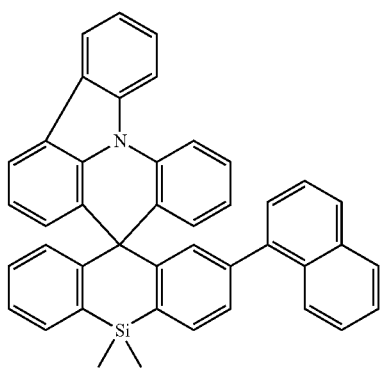
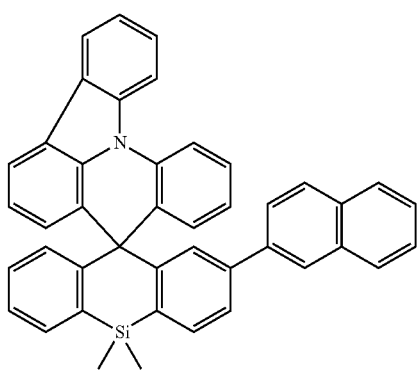
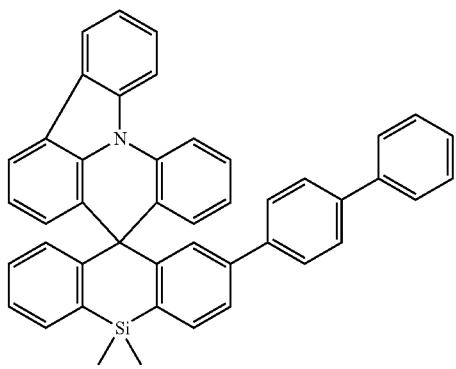
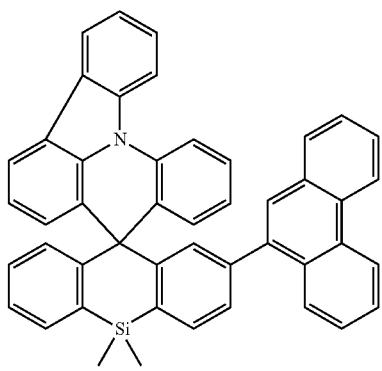

89
-continued
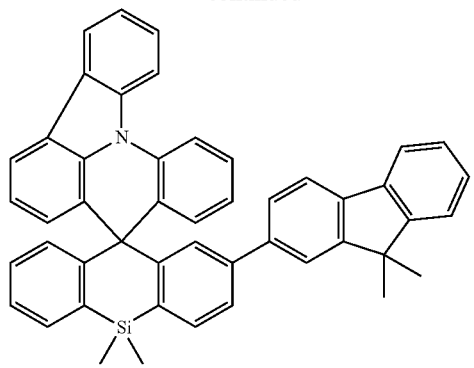
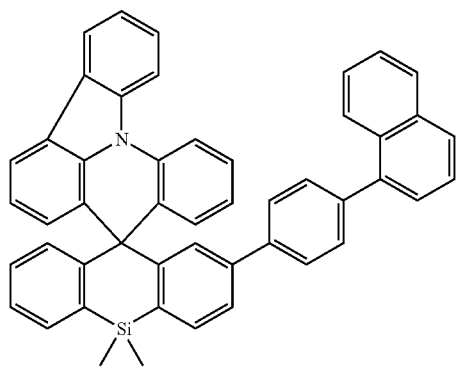
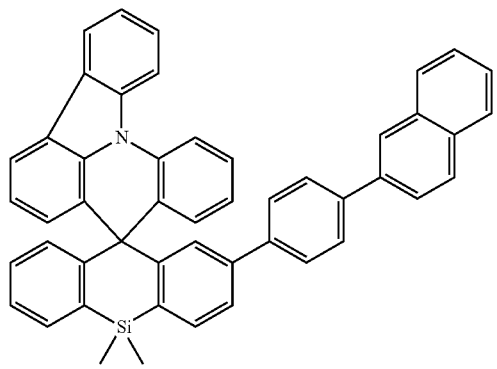
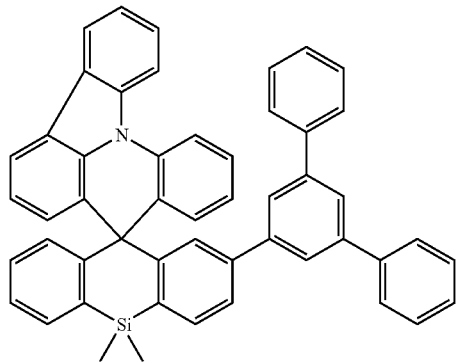
90
-continued
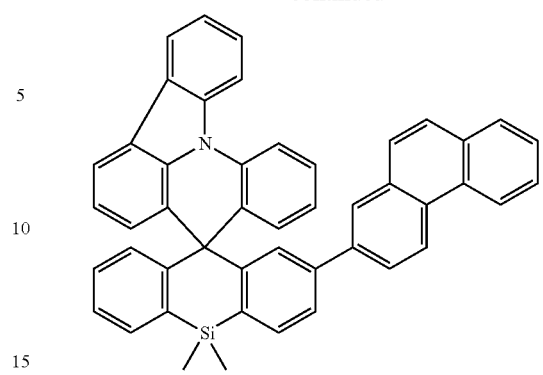
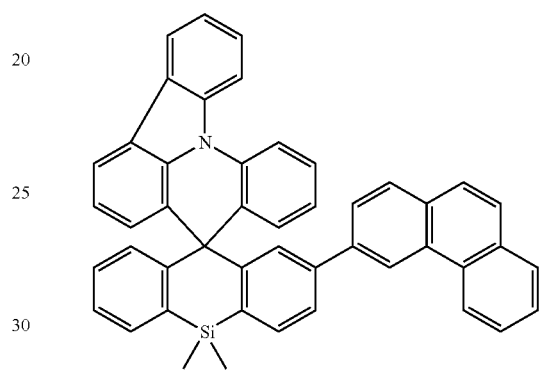
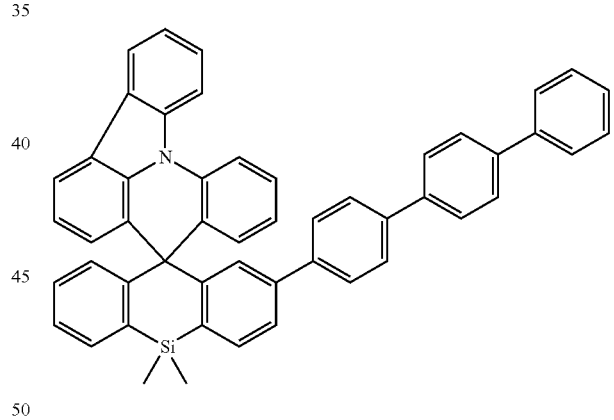
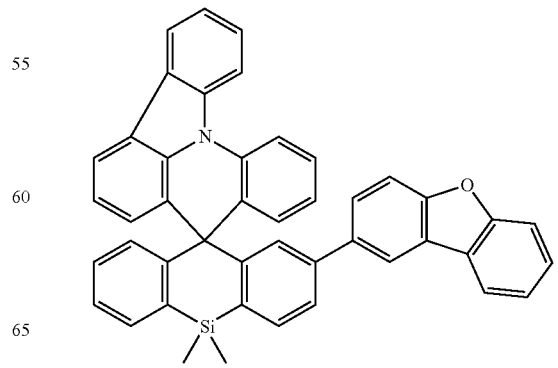

91
-continued
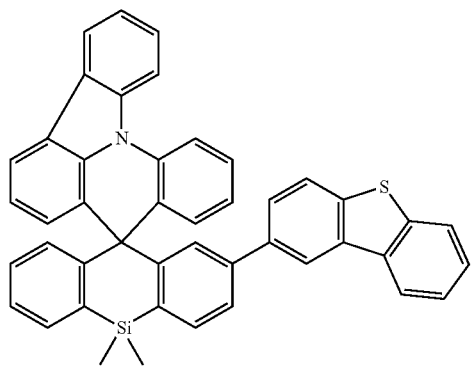
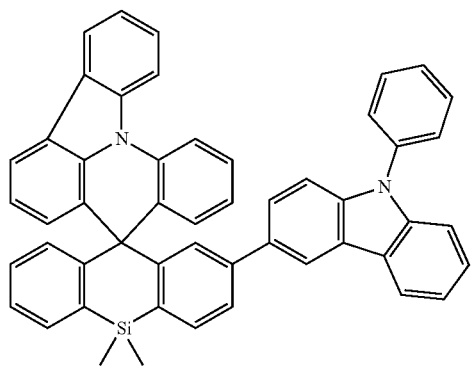
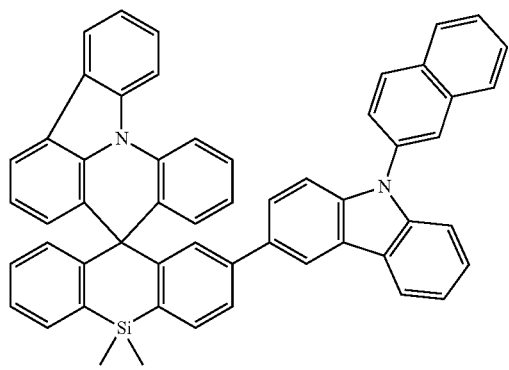
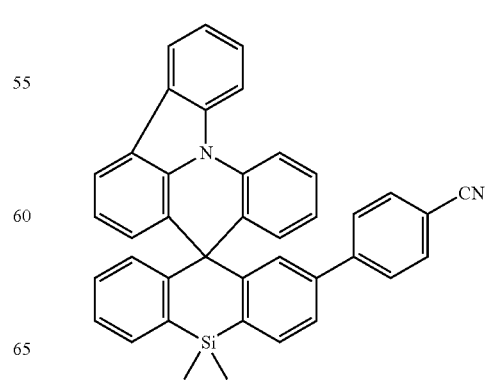
92
-continued
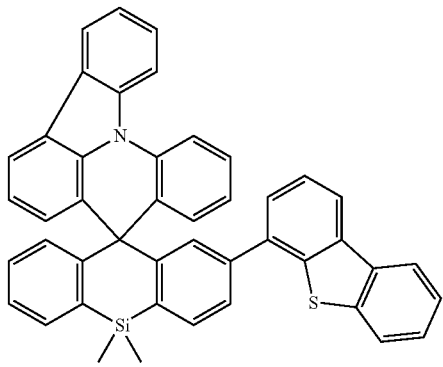
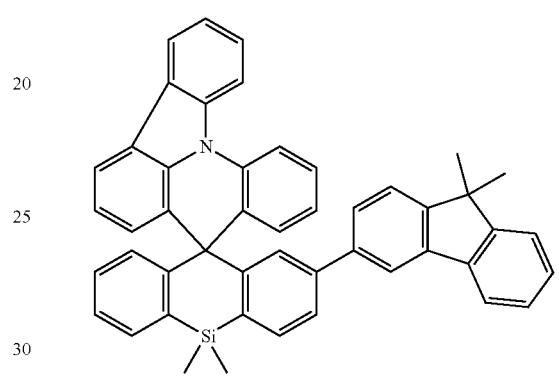
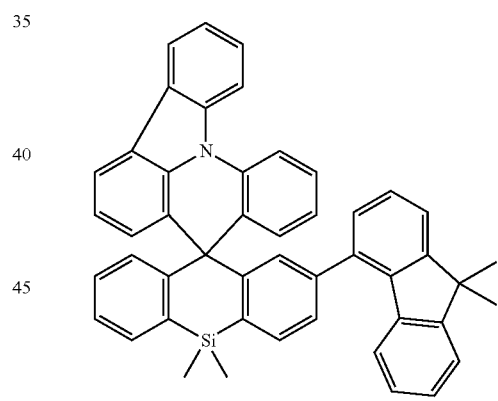

93
-continued
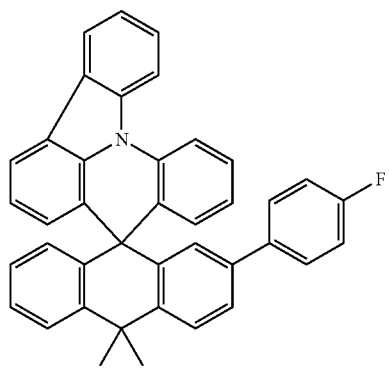
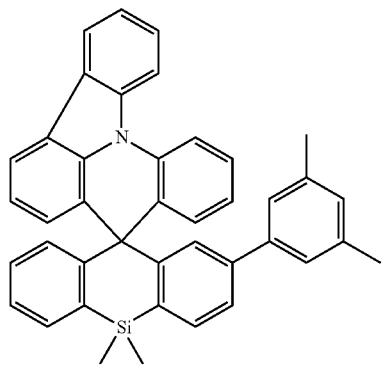
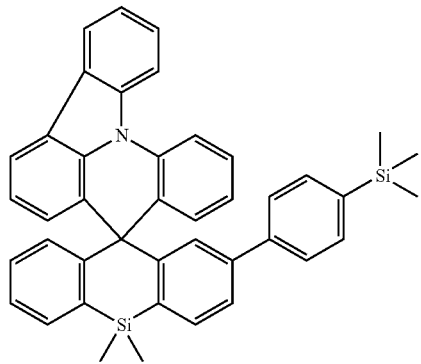
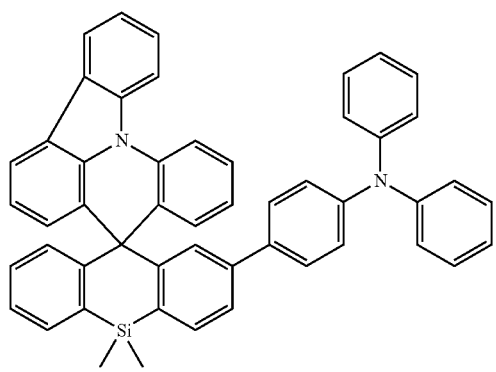
94
-continued
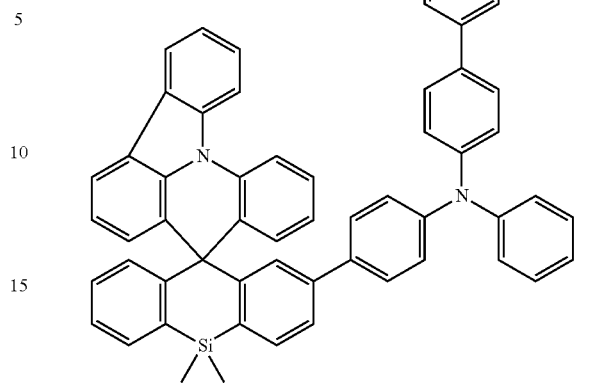
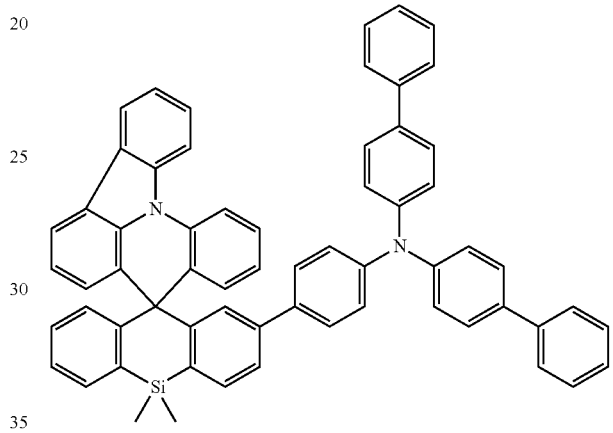
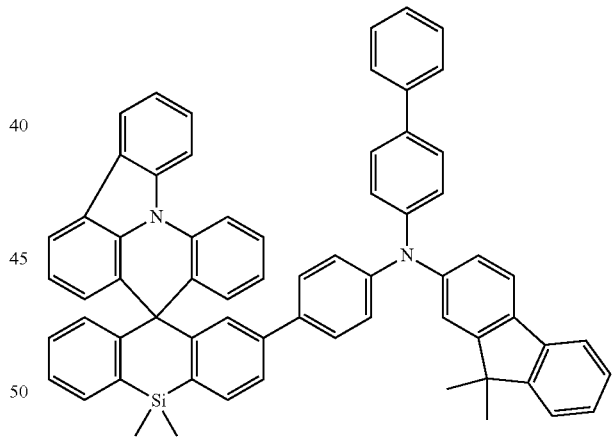
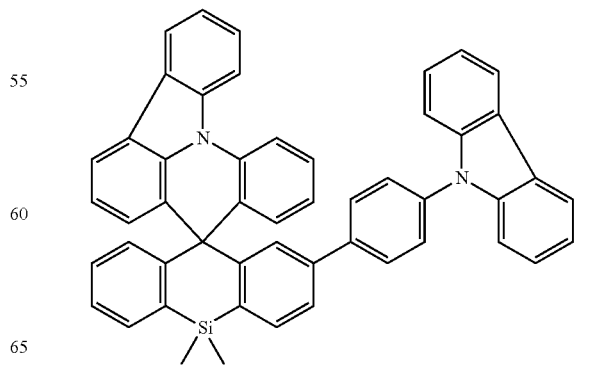

95
-continued
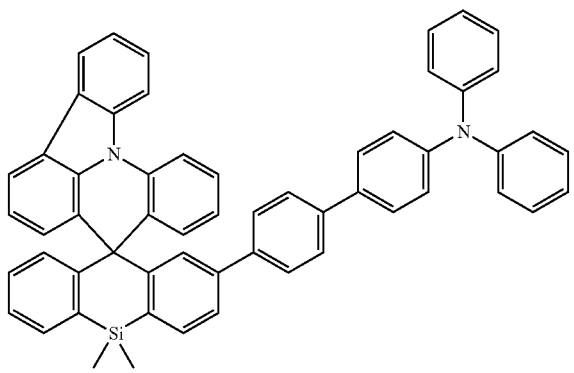
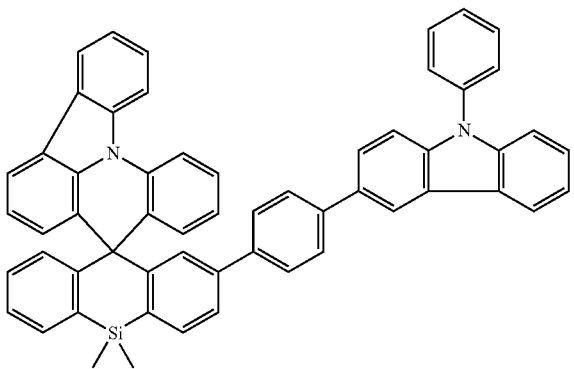
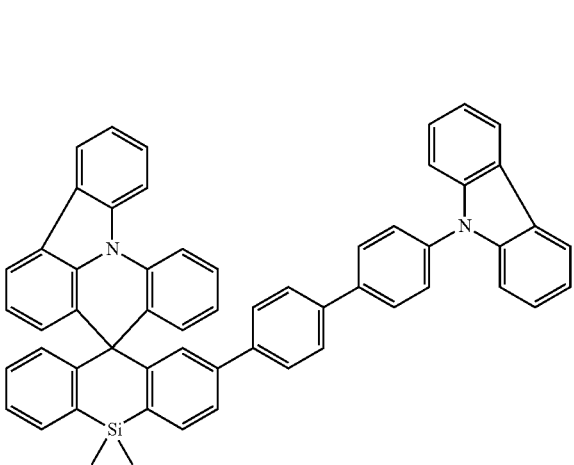
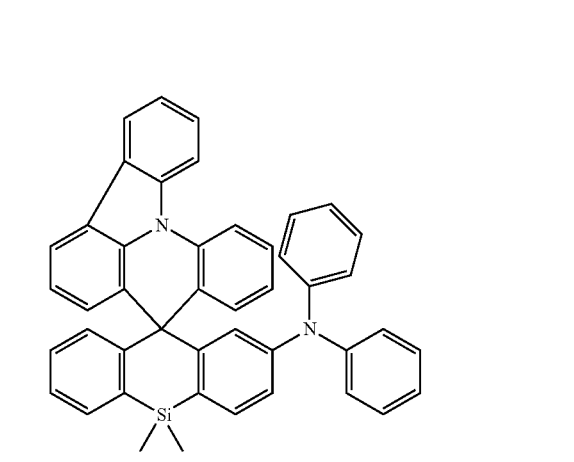
96
-continued
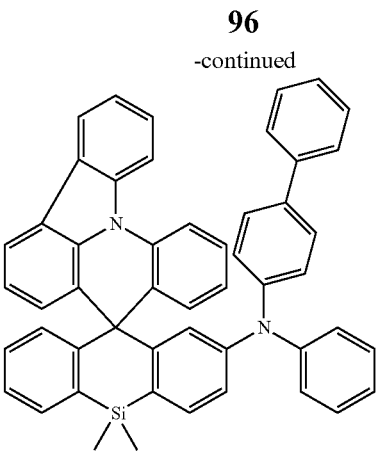
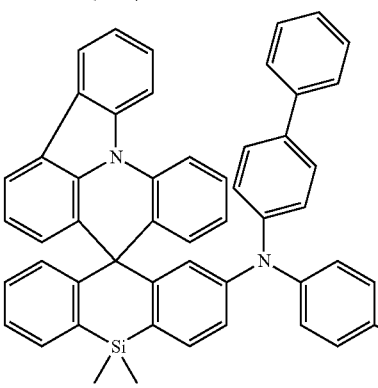
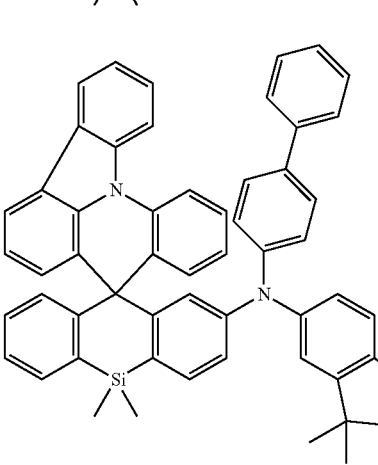
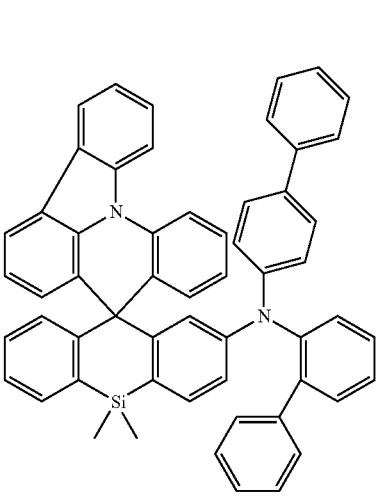

97
-continued
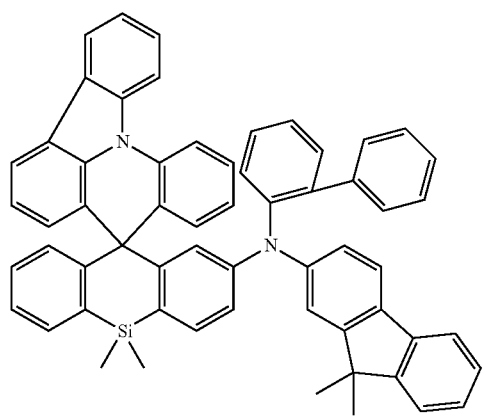
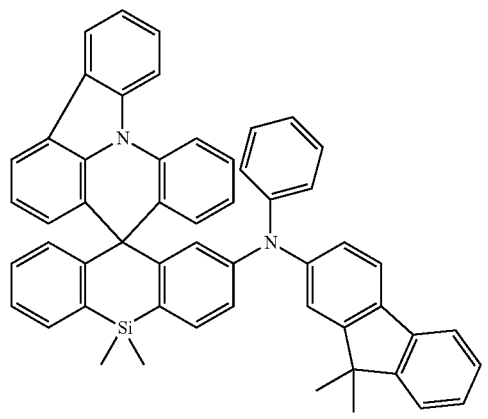
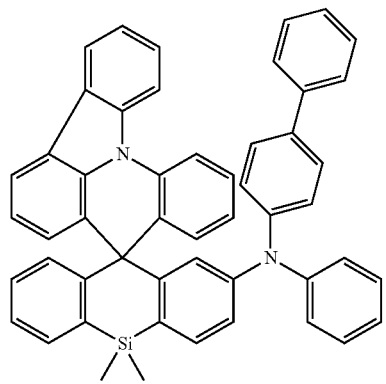
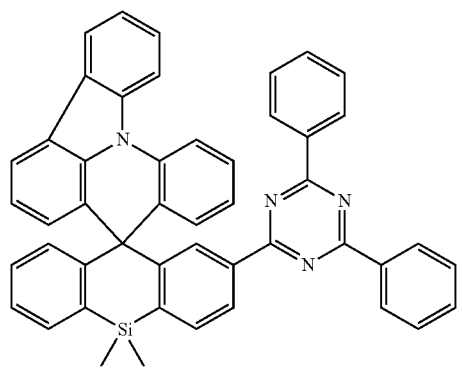
98
-continued
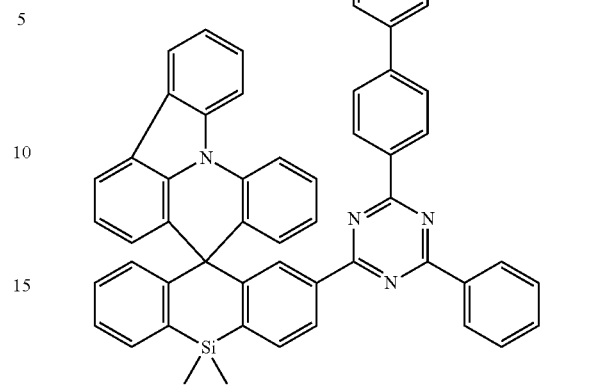
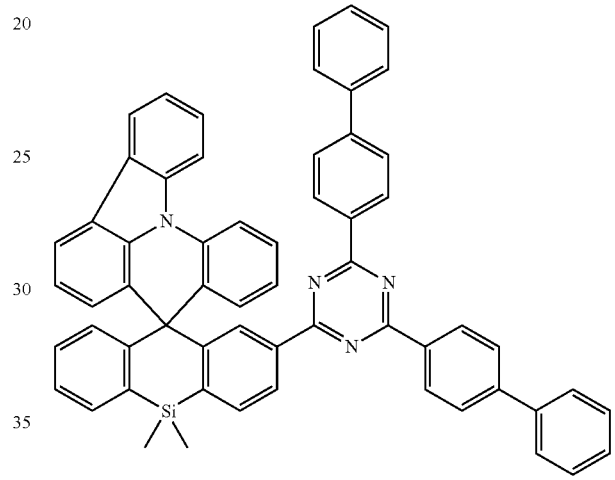
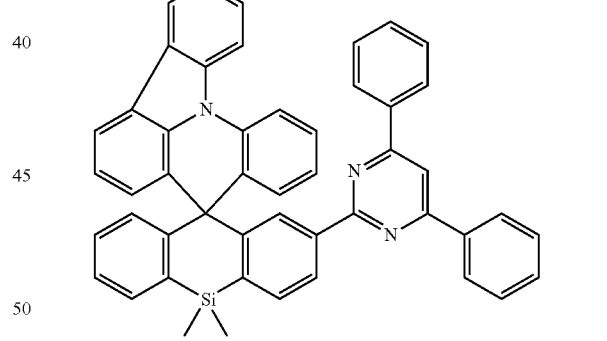
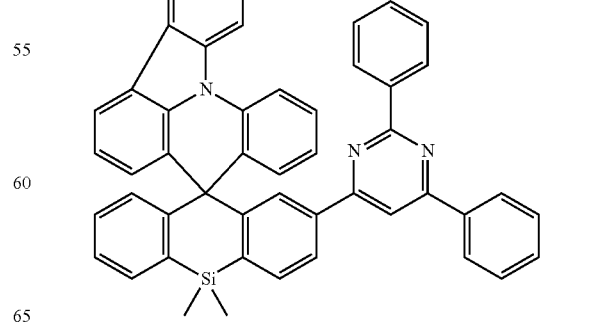

99
-continued
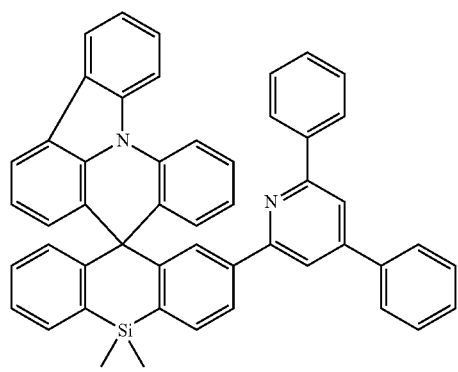
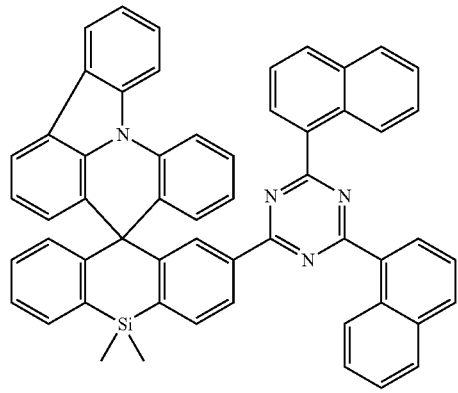
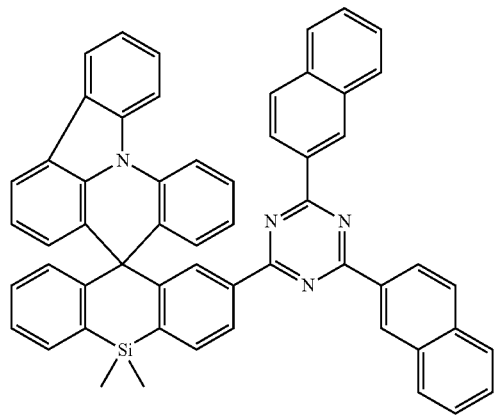
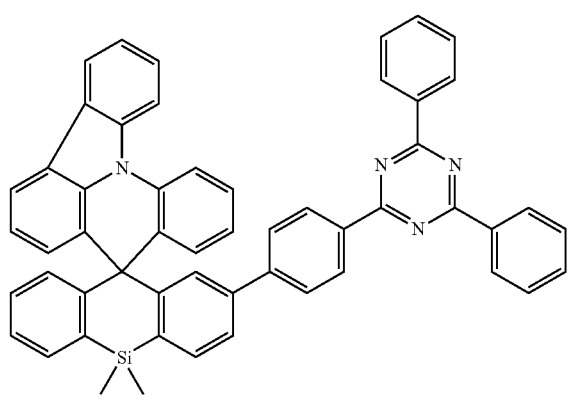
100
-continued
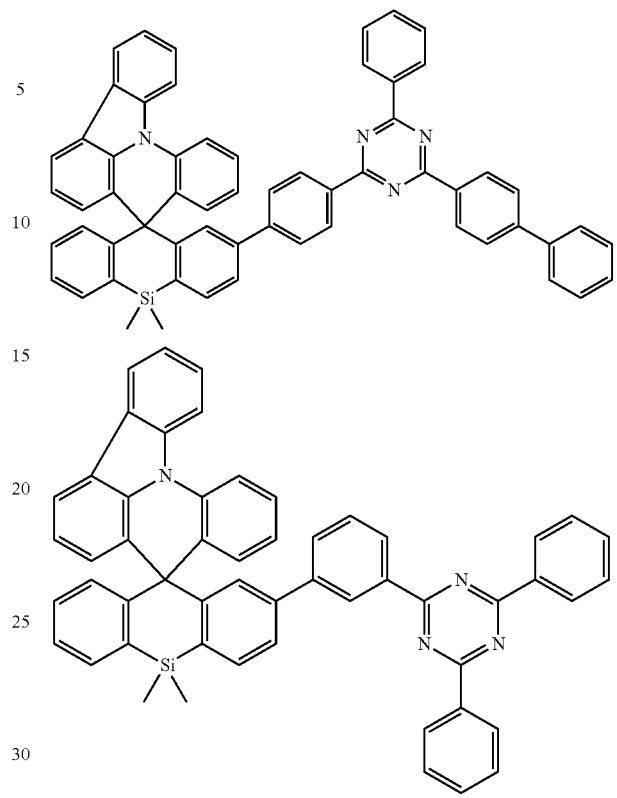
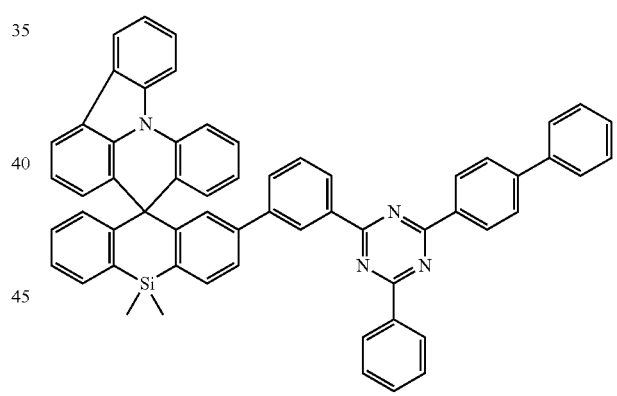
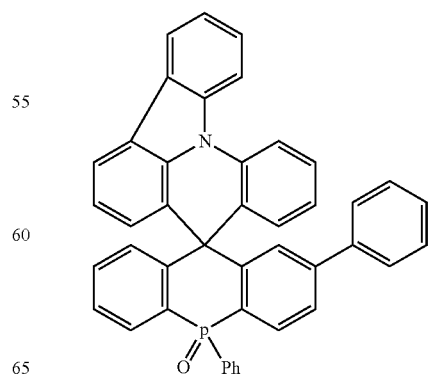

101
-continued
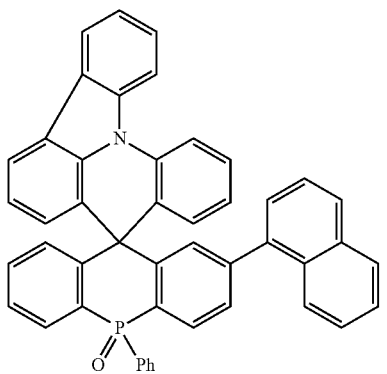
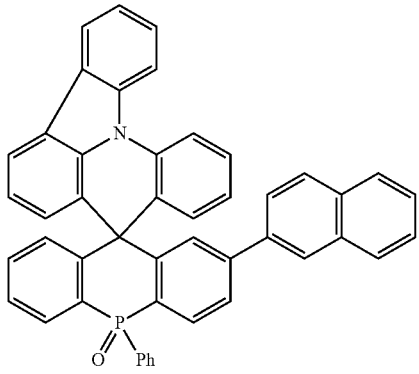
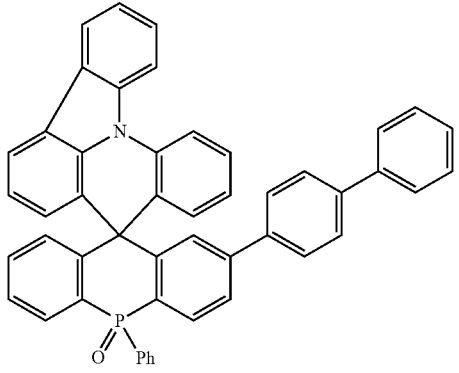
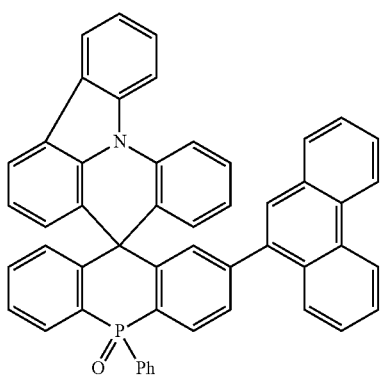
102
-continued
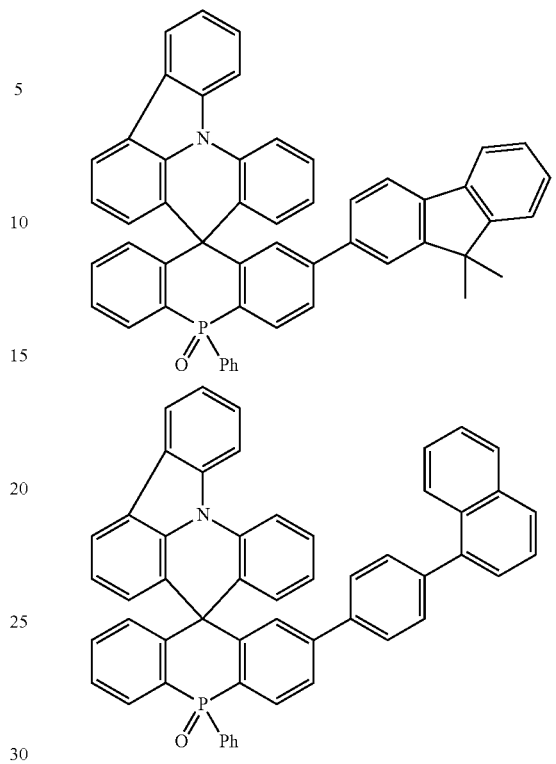
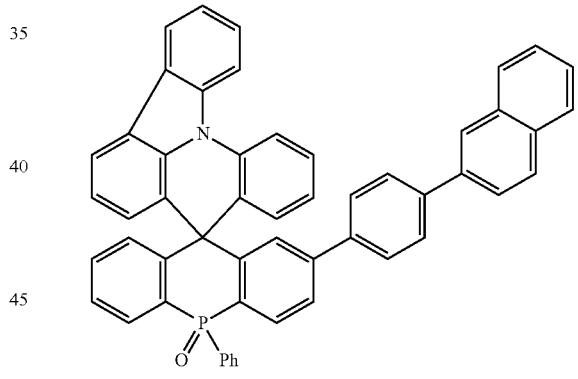
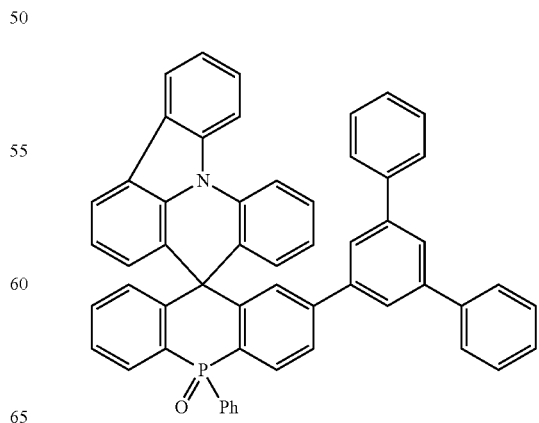

103
-continued
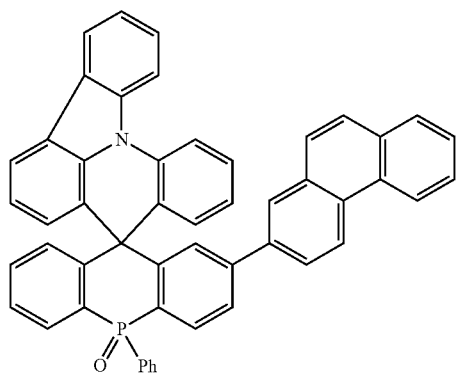
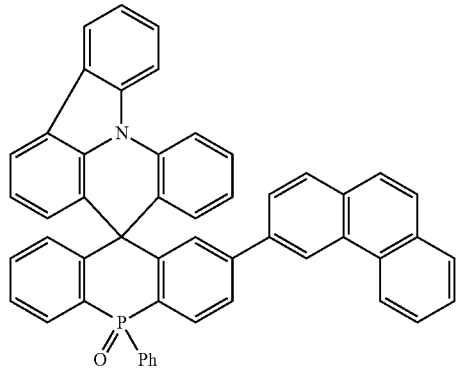
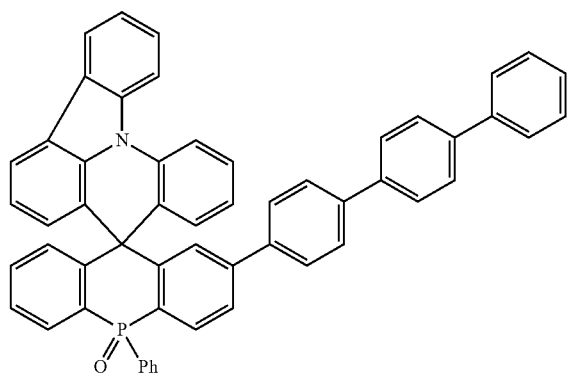
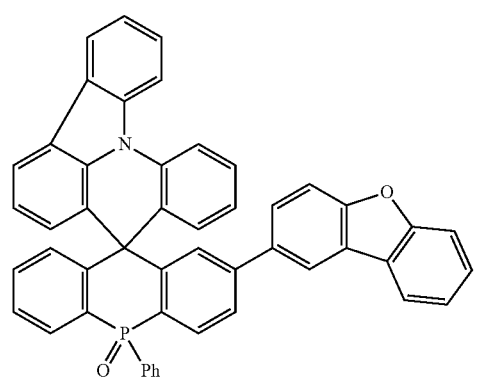
104
-continued
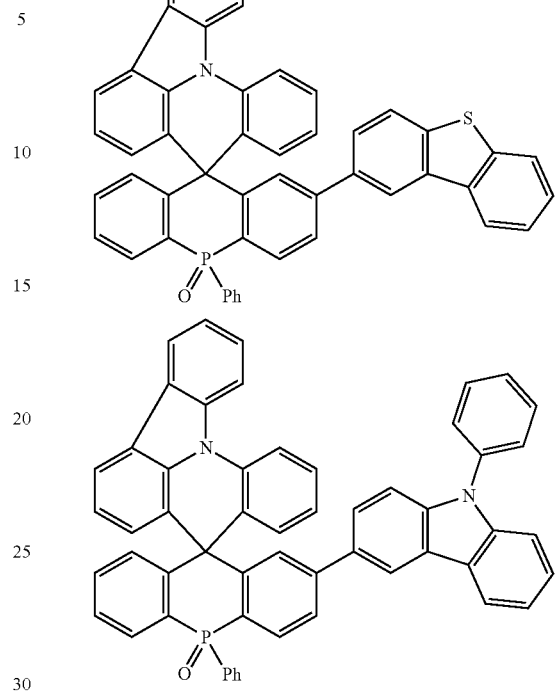
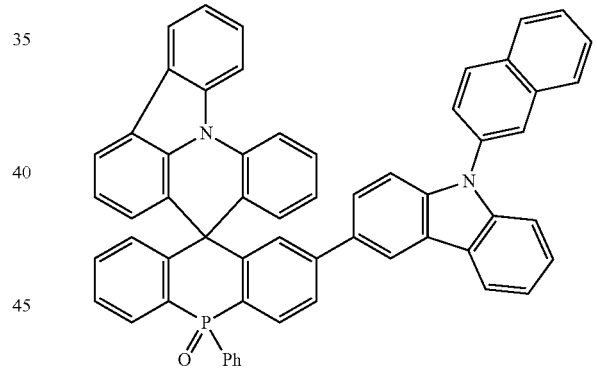
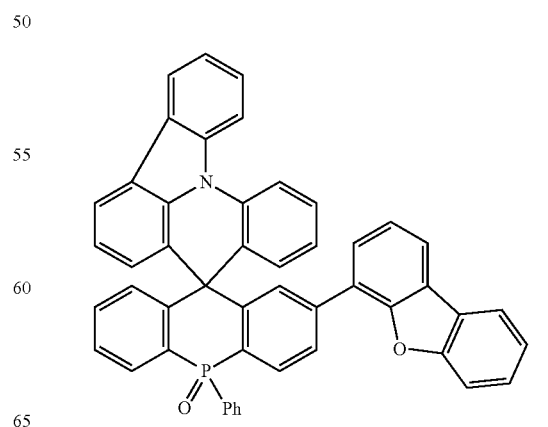

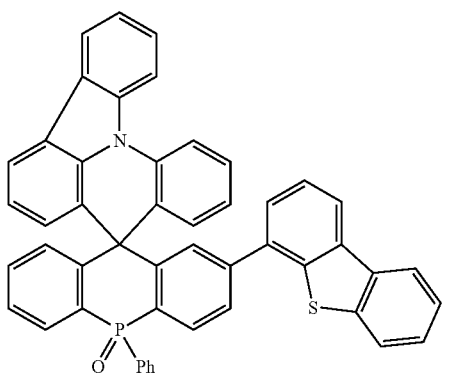
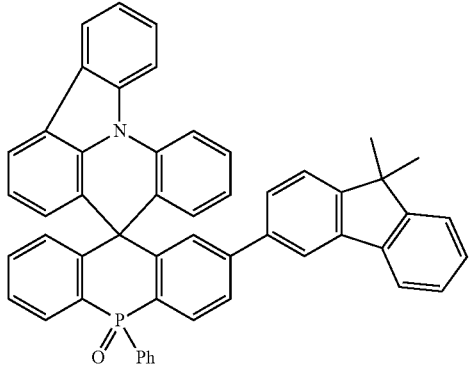
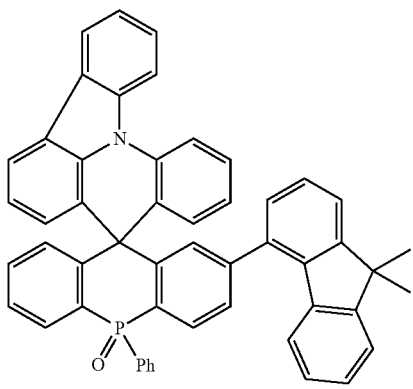
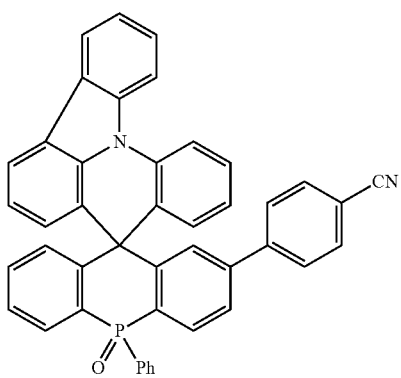
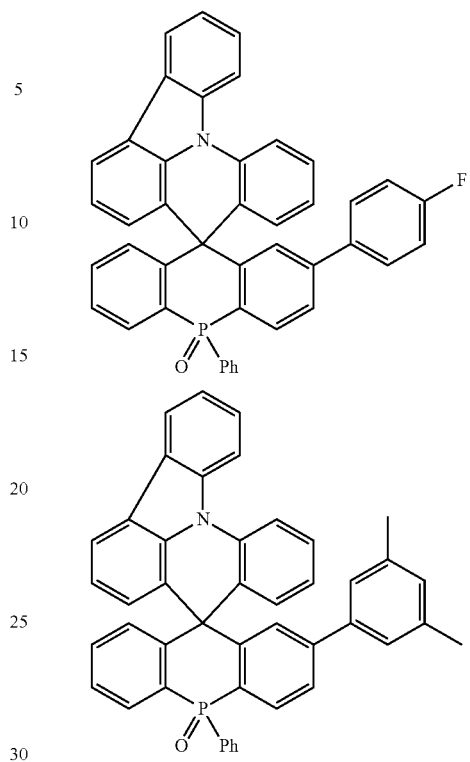
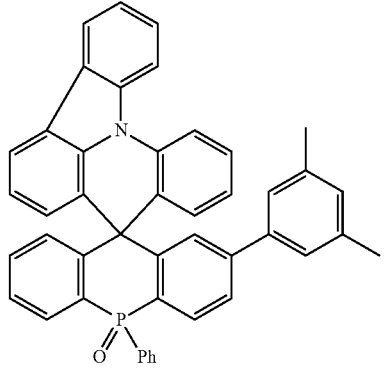
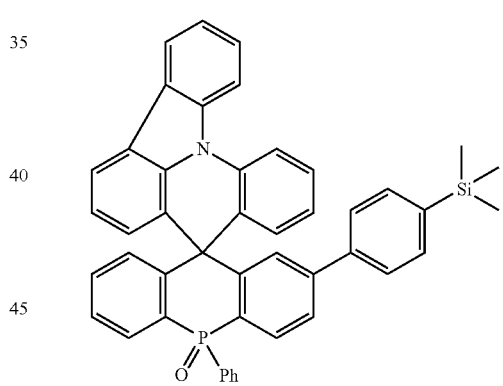
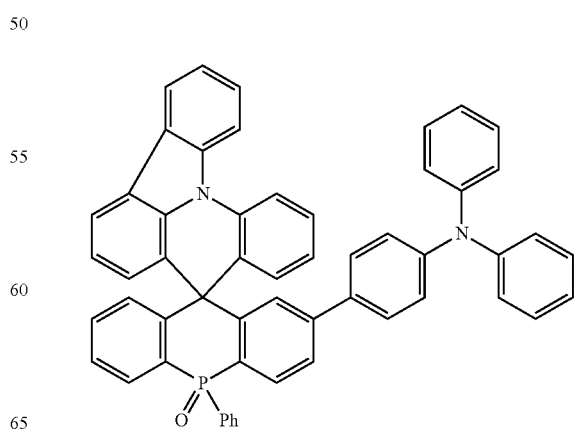

107
-continued
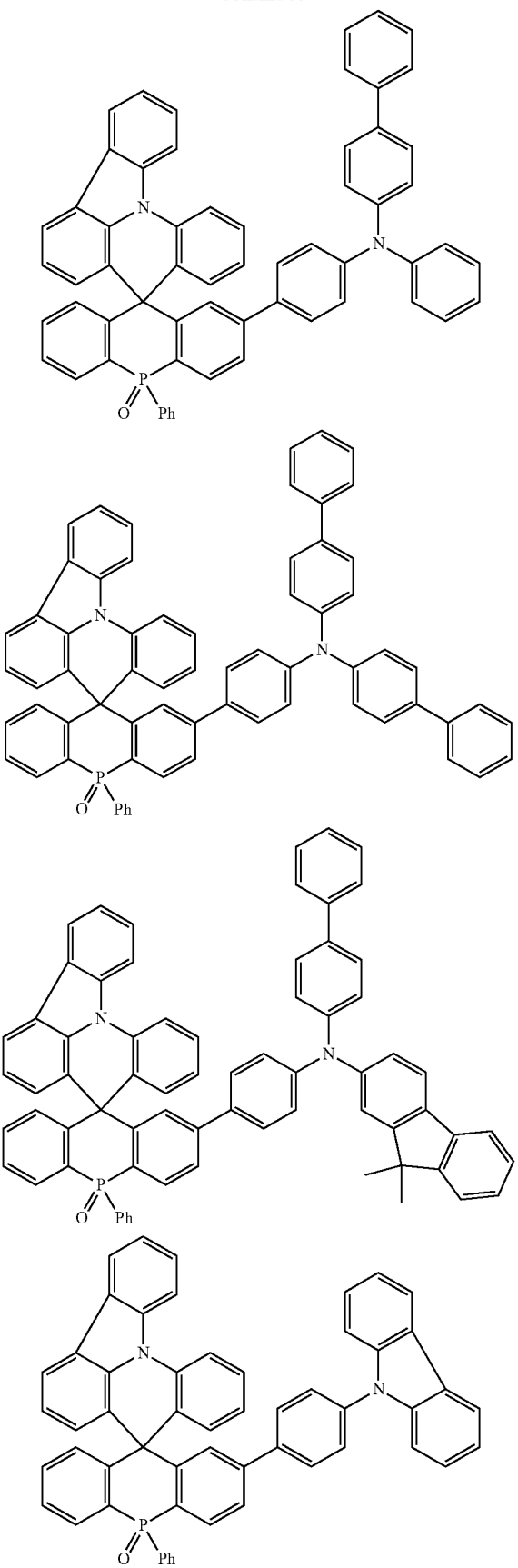
108
-continued
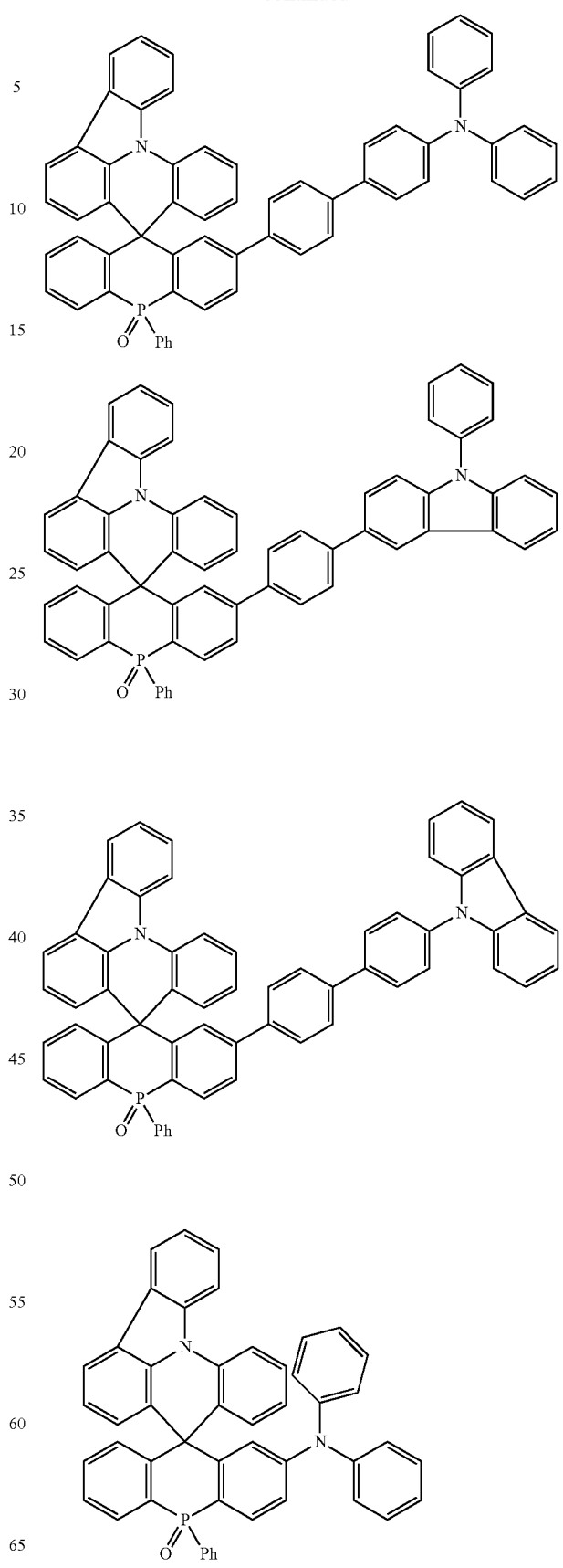

109
-continued
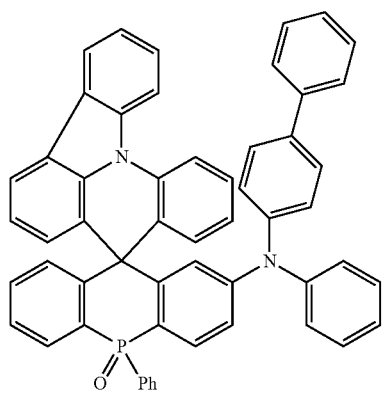
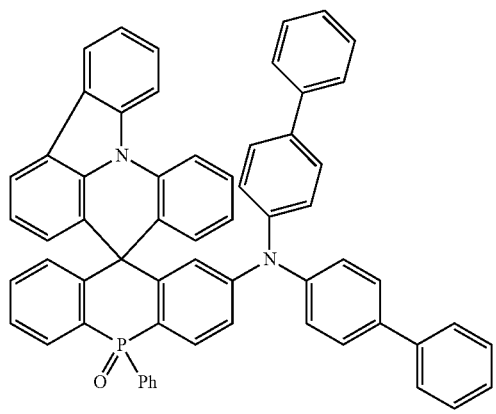
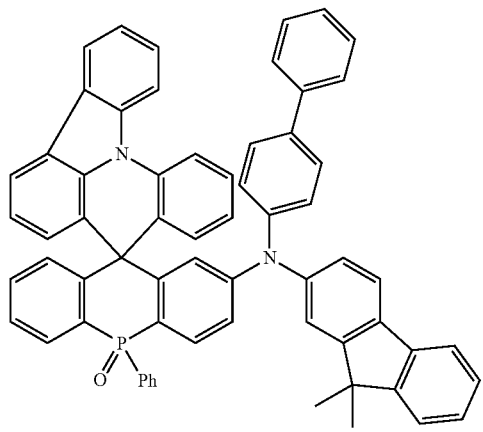
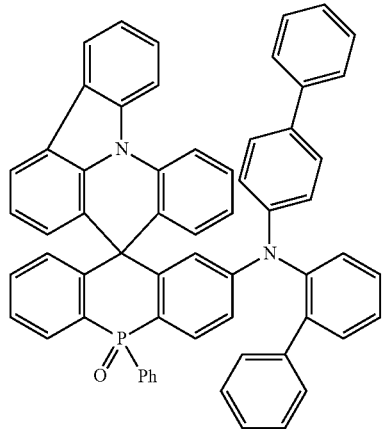
110
-continued
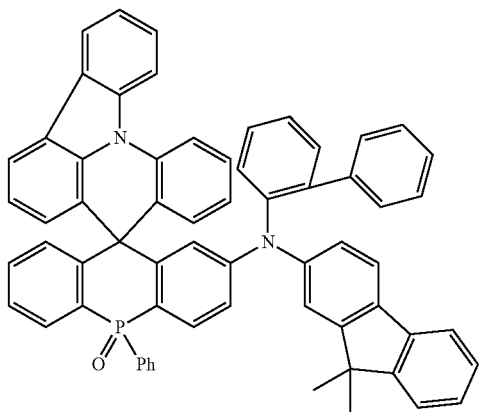
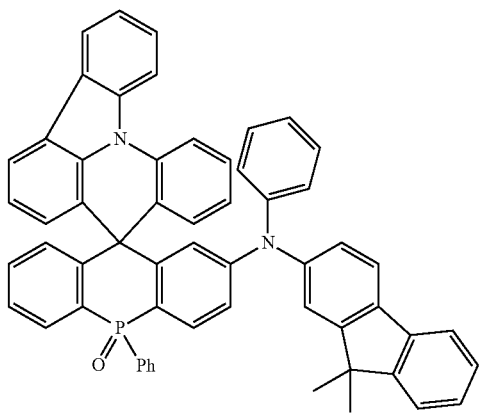
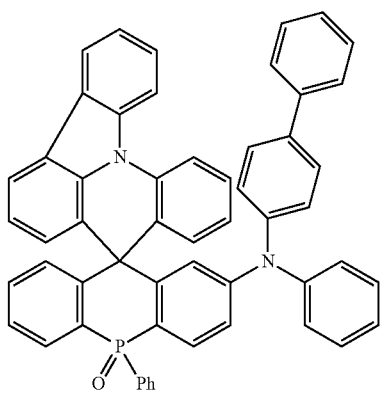
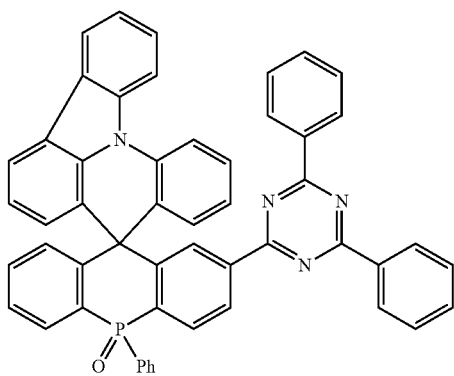

111
-continued
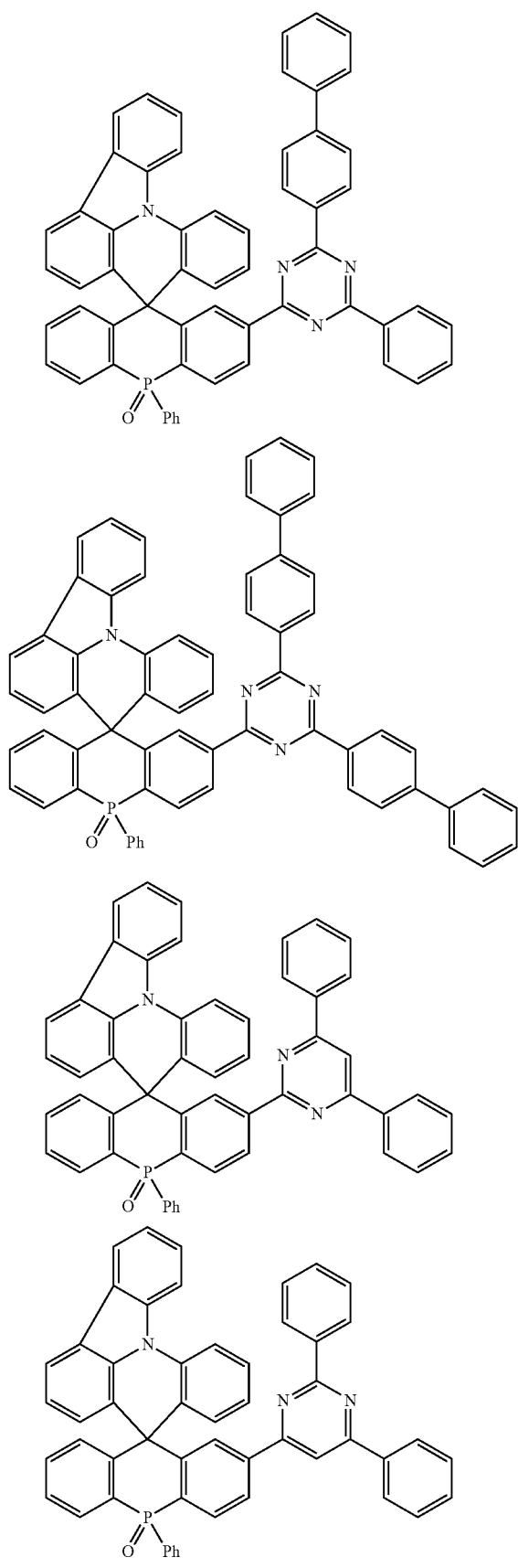
112
-continued
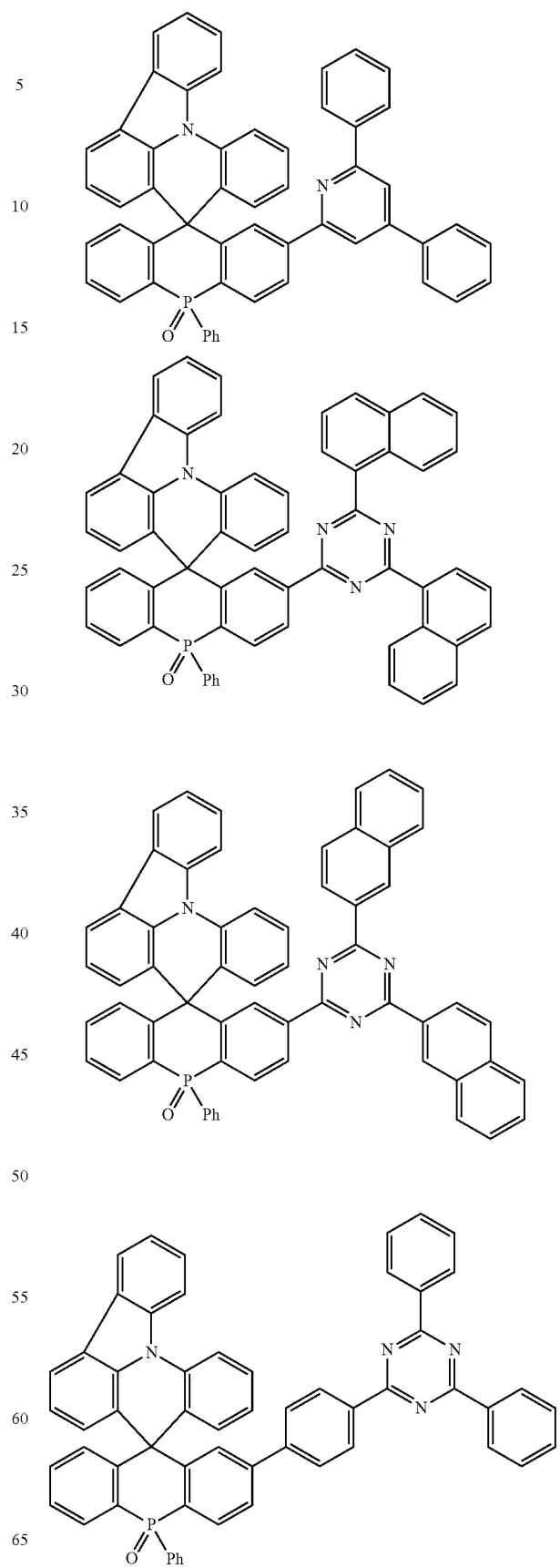

113
-continued
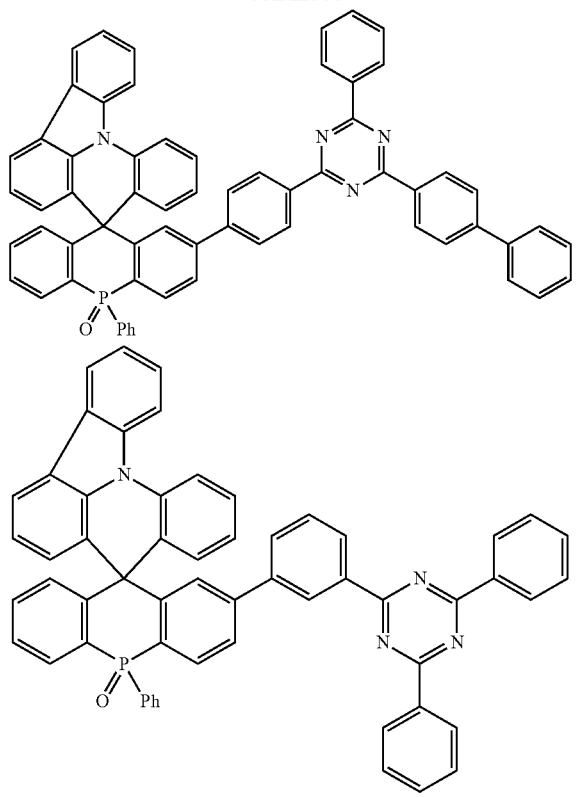
114
-continued
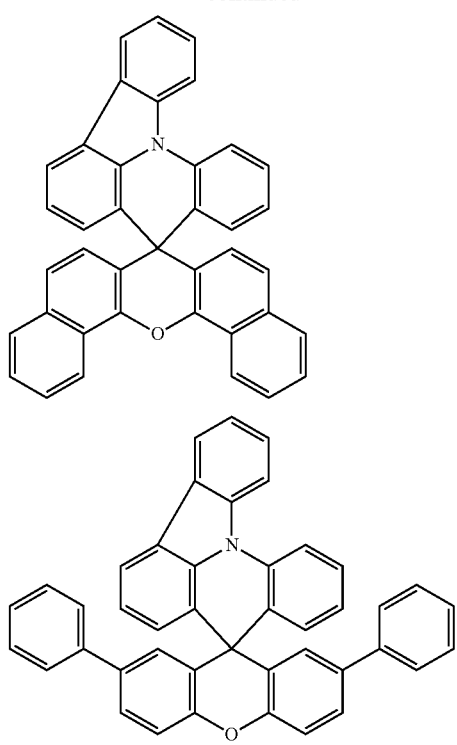
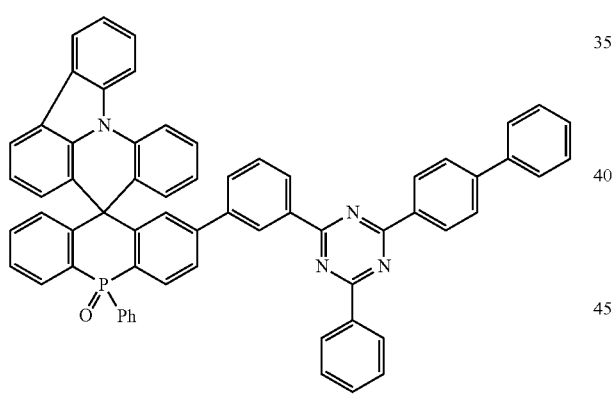
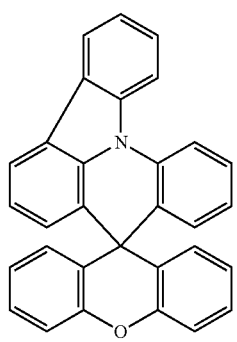
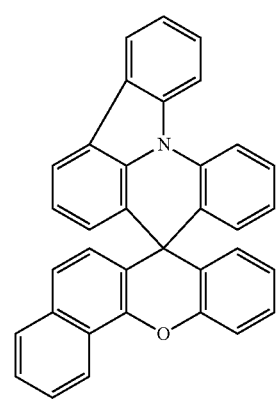
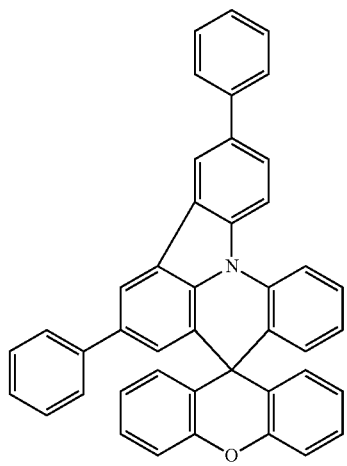

115
-continued
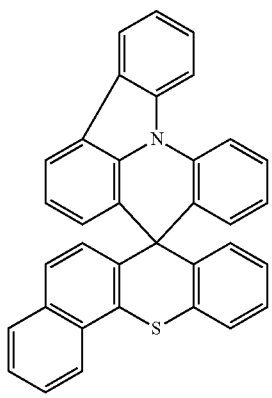
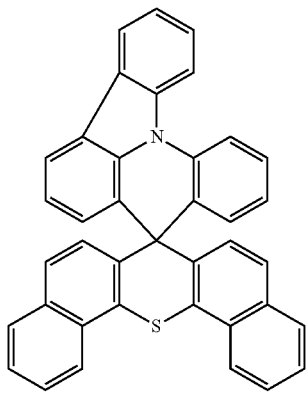
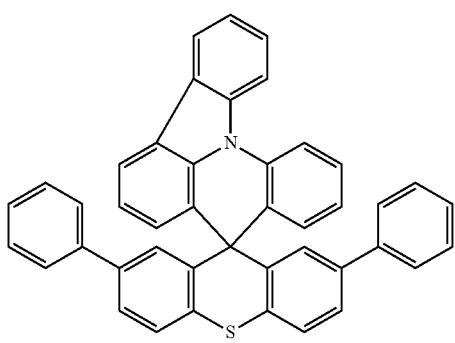
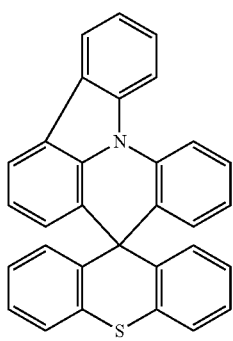
116
-continued
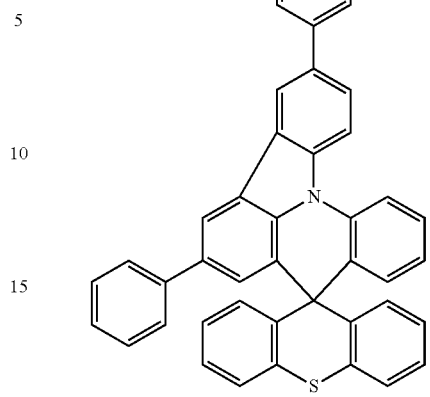
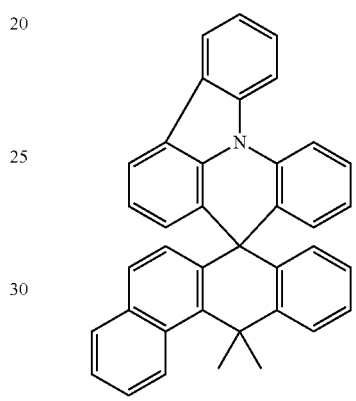
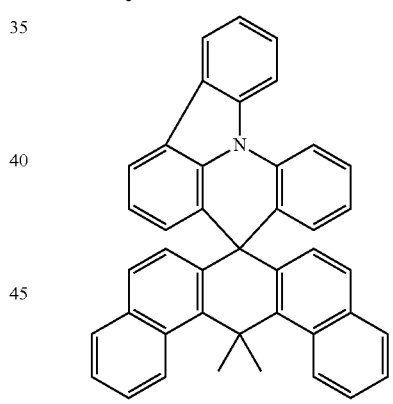

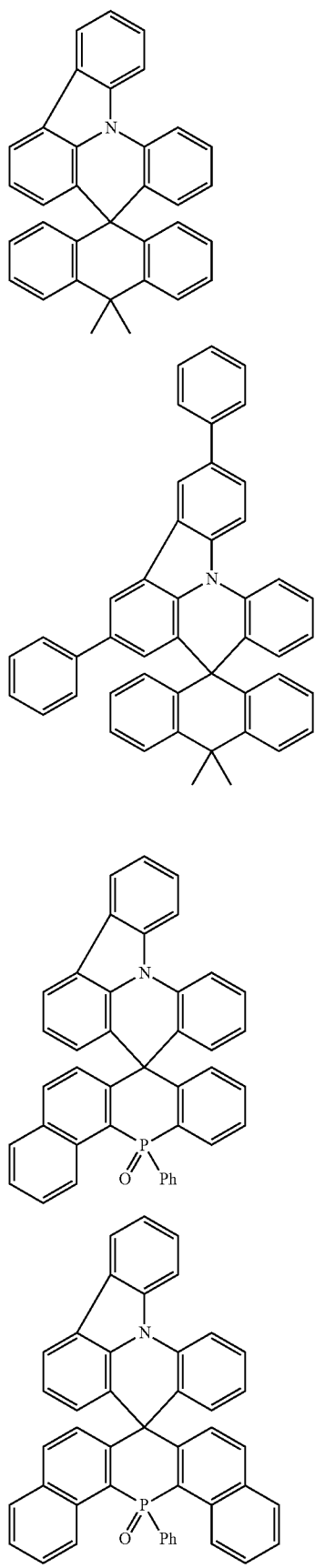
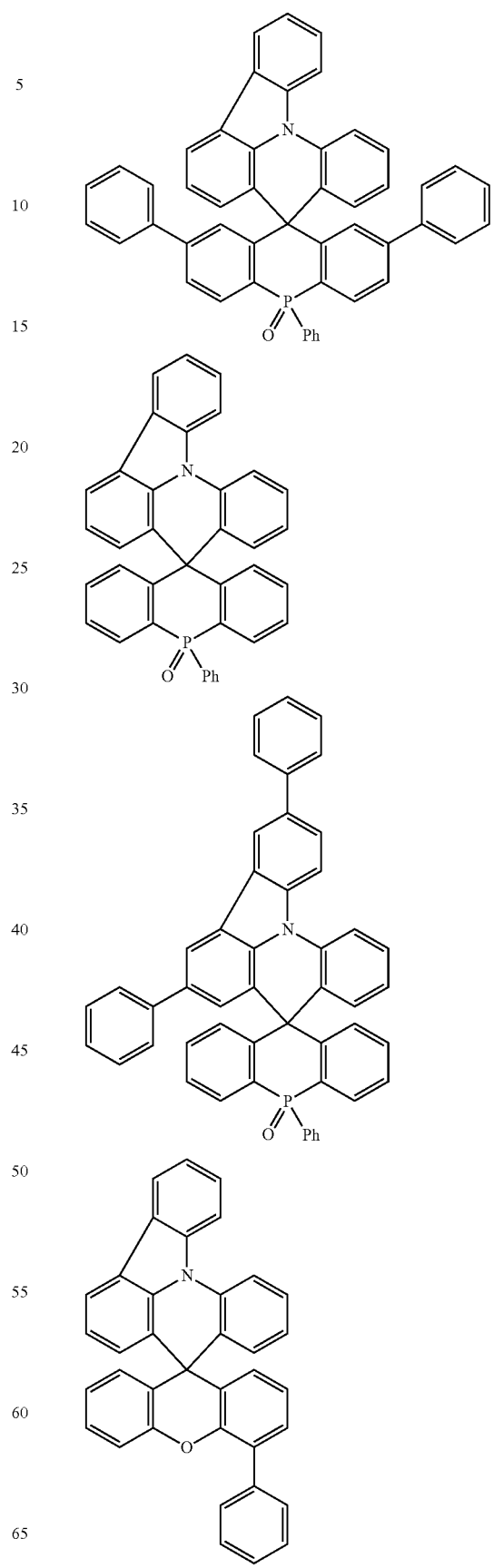

119
-continued
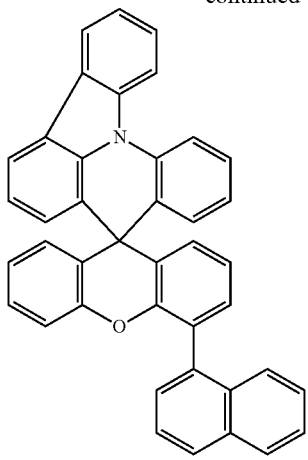
120
-continued
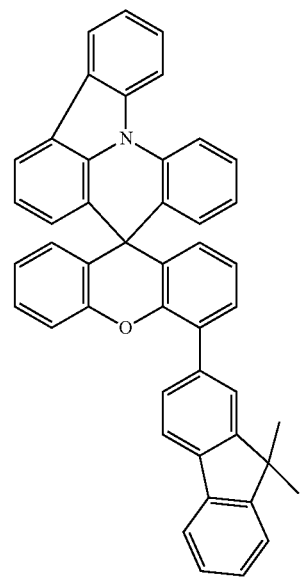
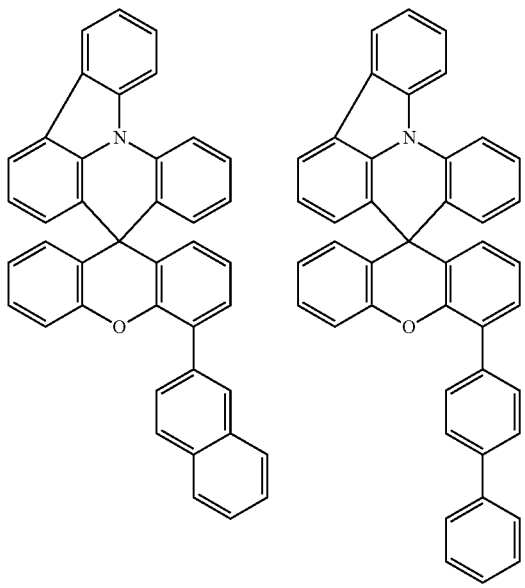
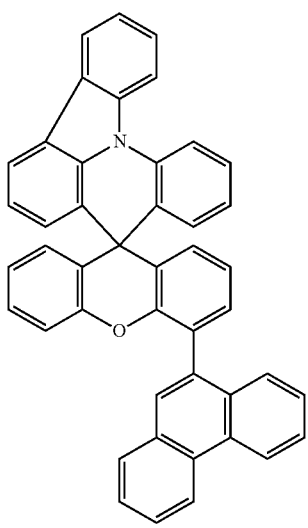
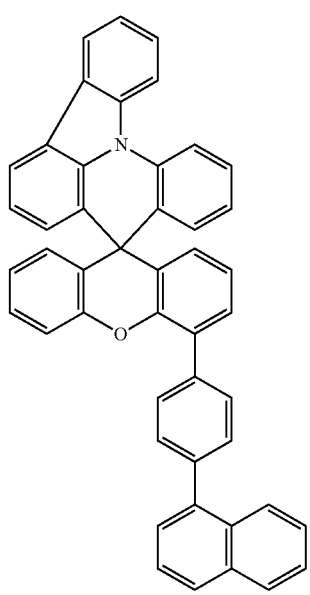

121
-continued
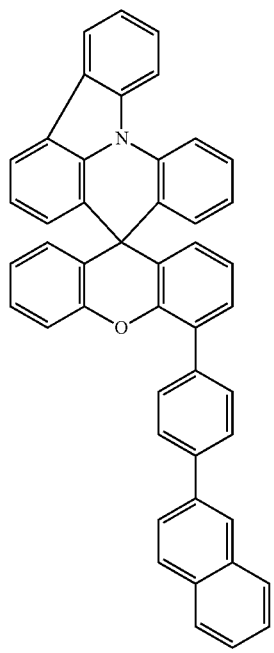
122
-continued
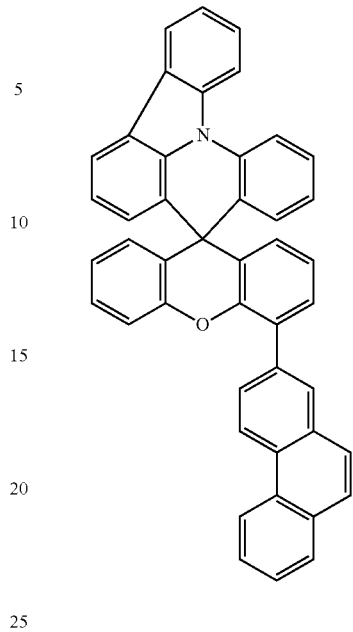
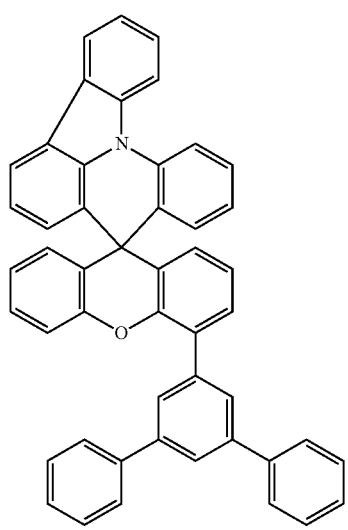
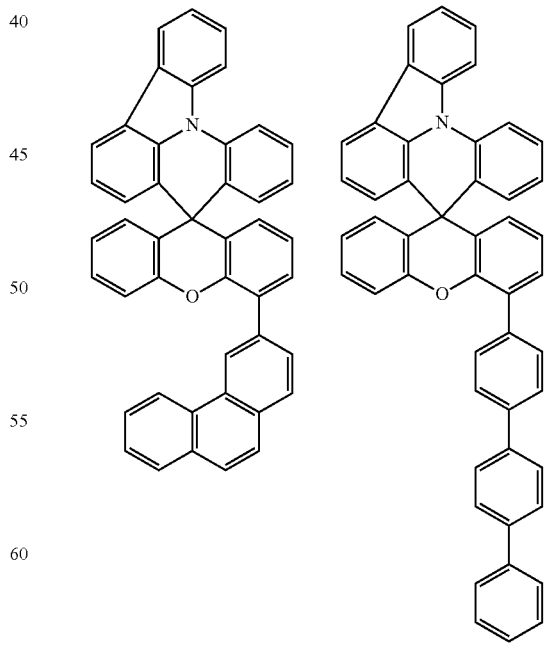

123
-continued
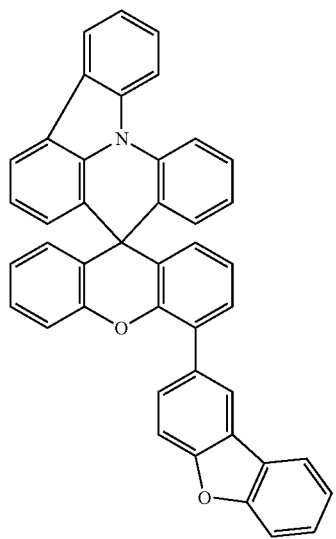
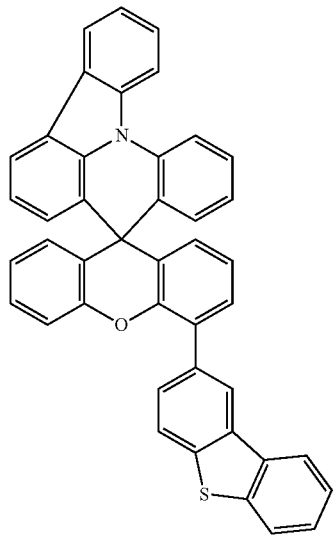
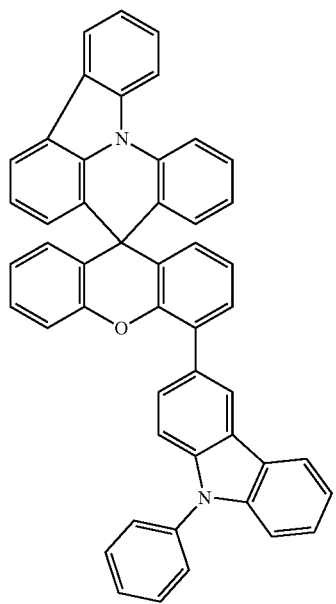
124
-continued
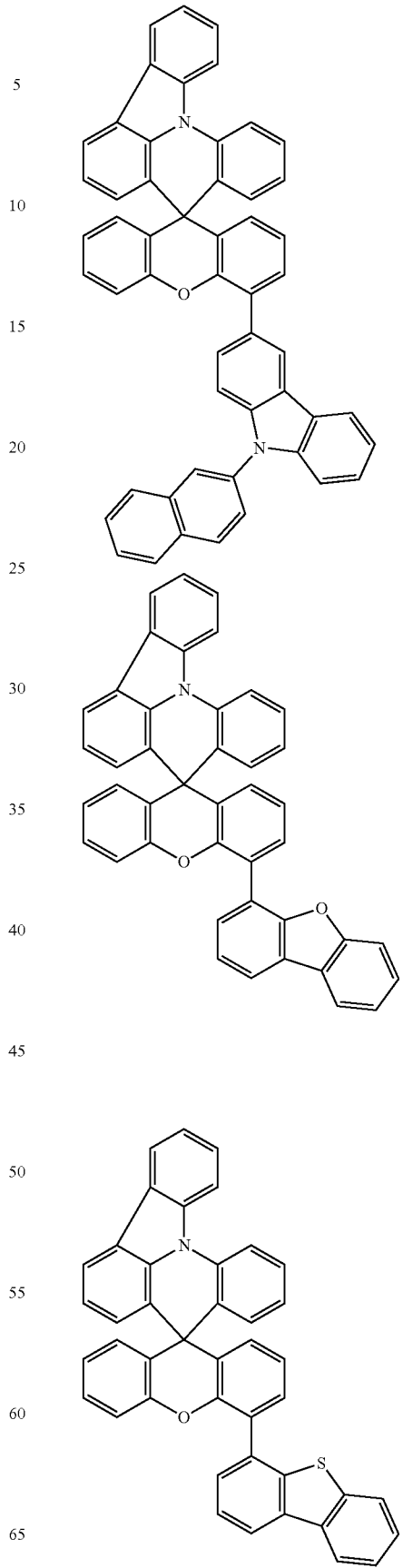

125
-continued
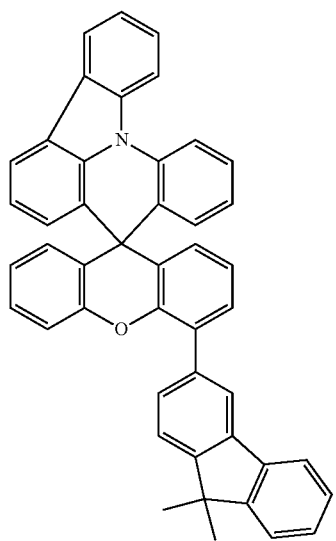
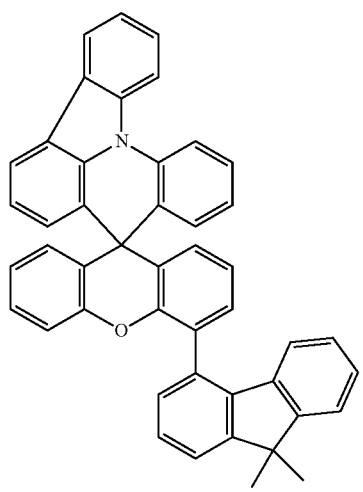
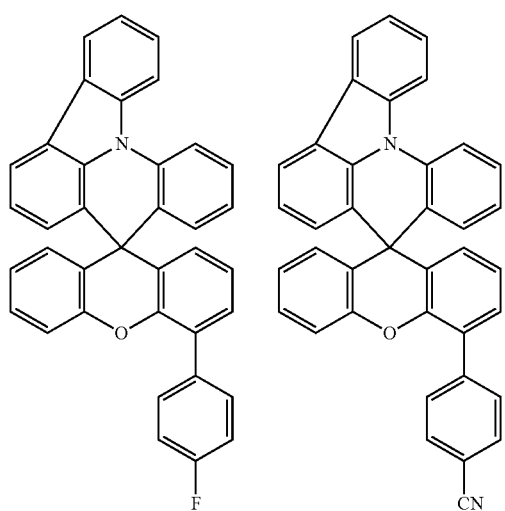
126
-continued
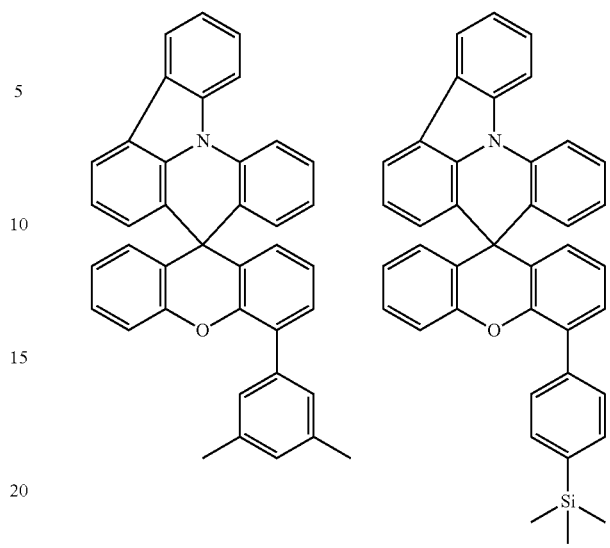
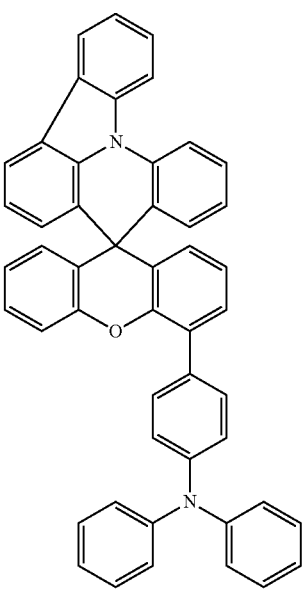

127
-continued
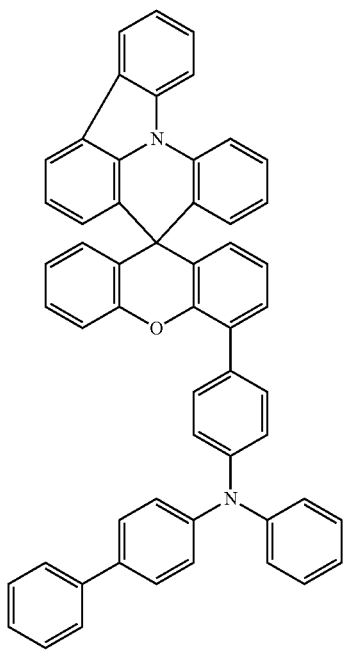
128
-continued
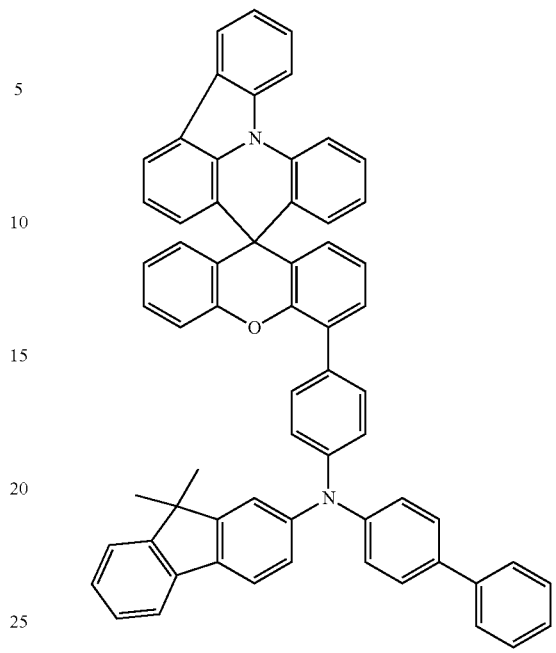
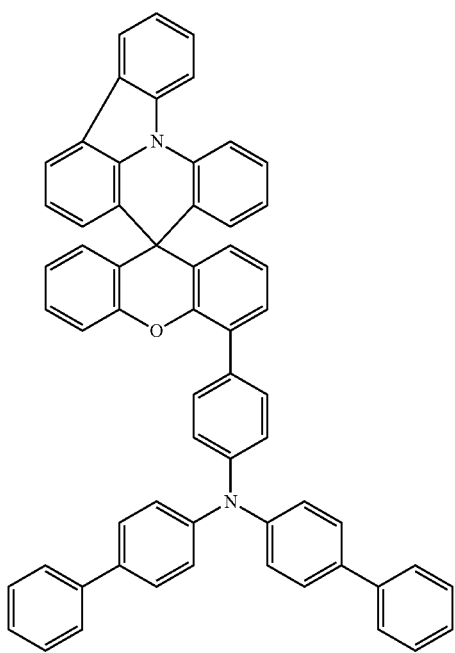
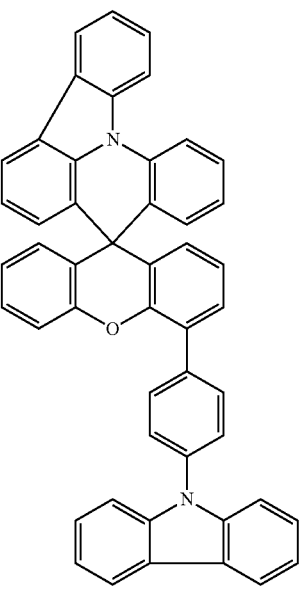

129
-continued
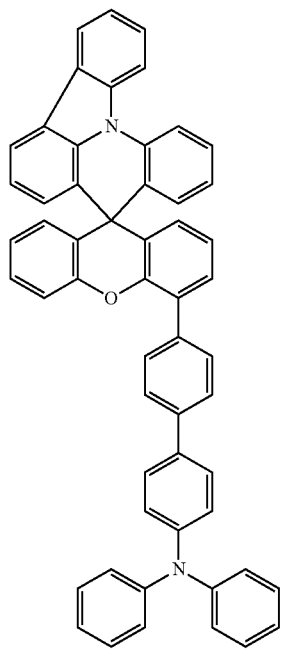
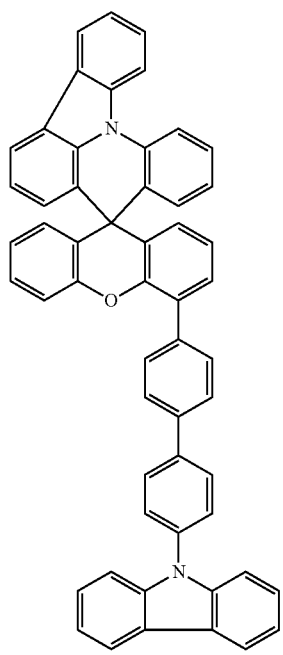
130
-continued
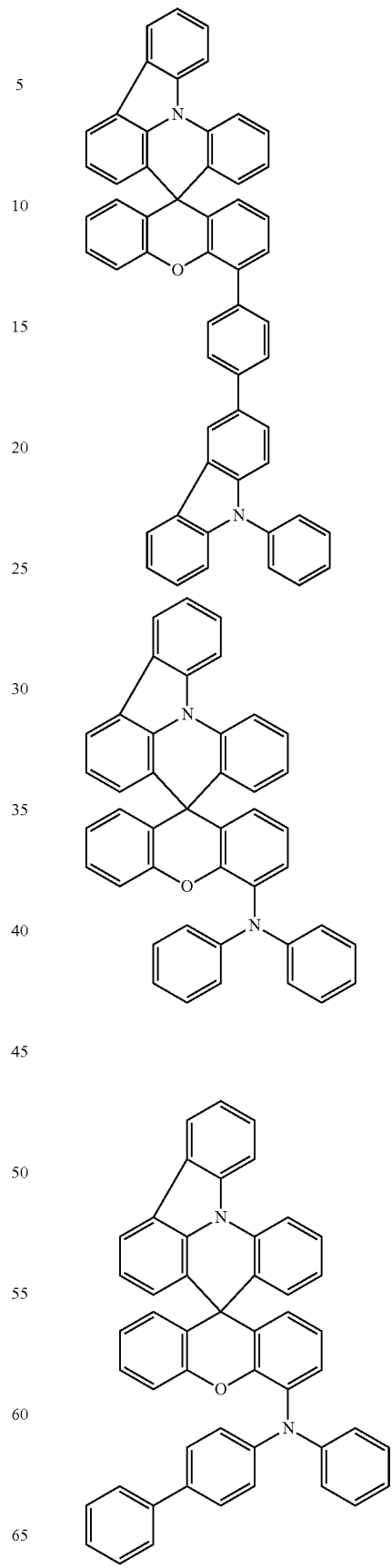

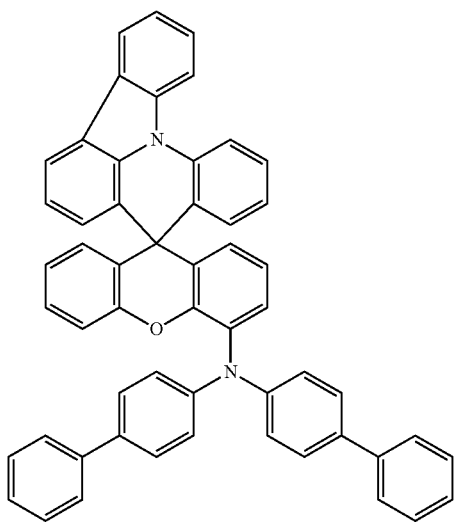
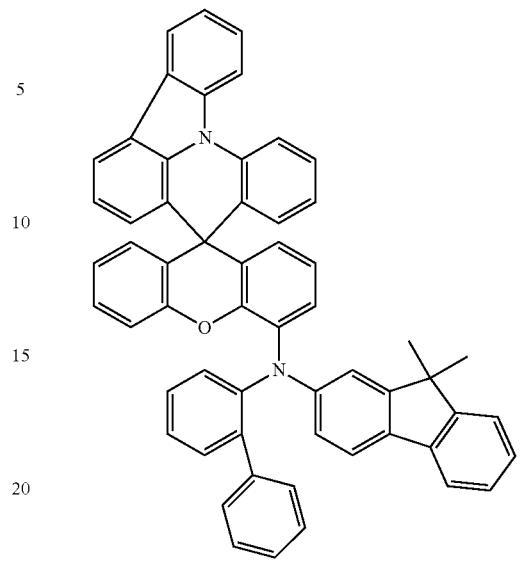
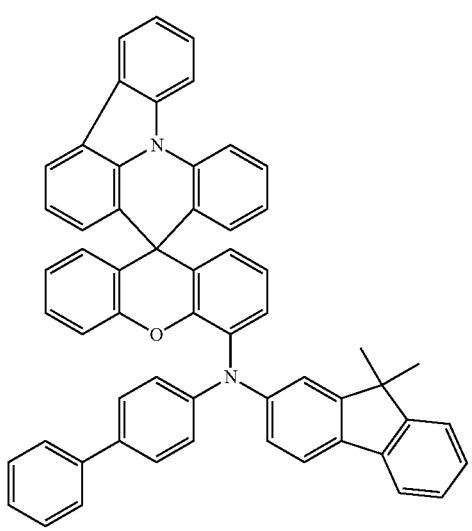
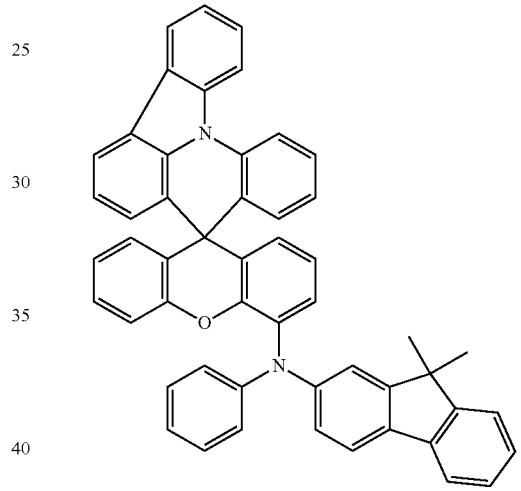
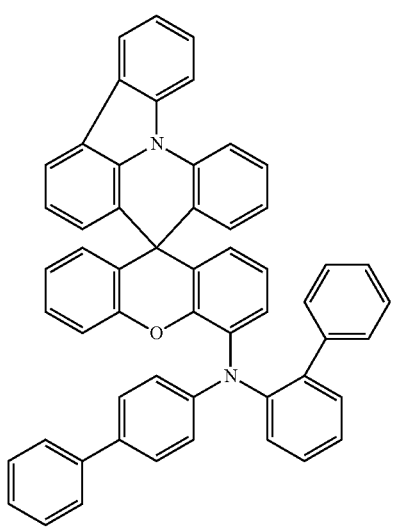
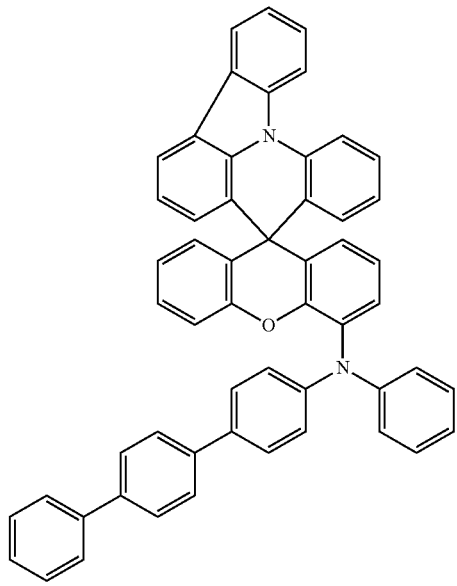

133
-continued
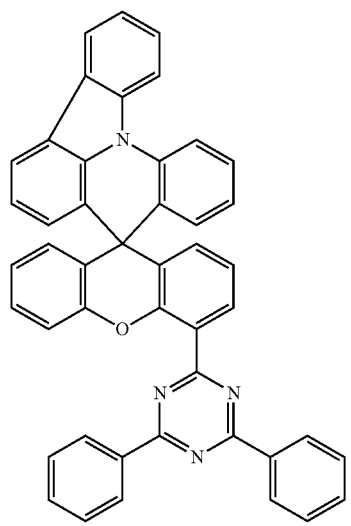
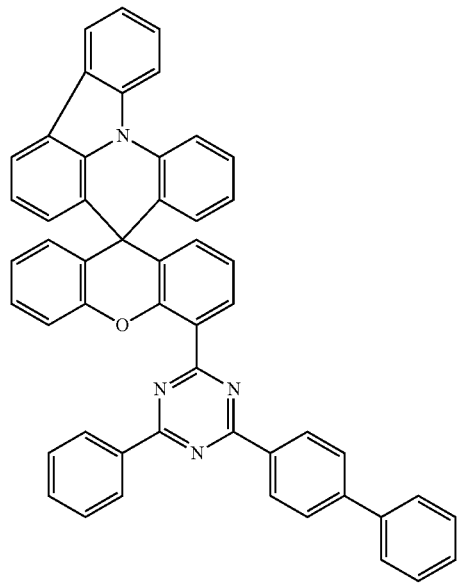
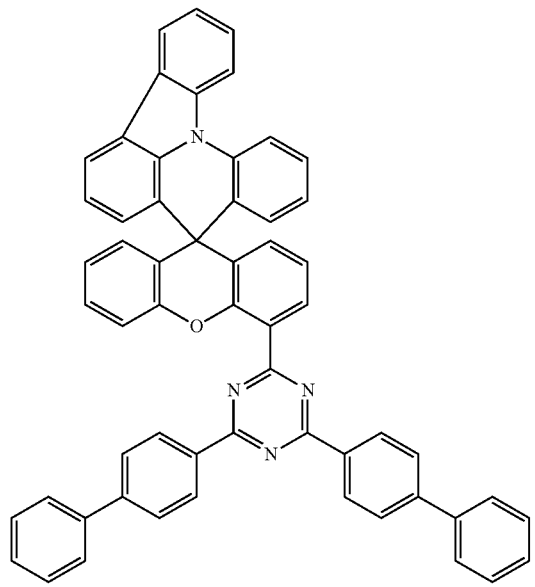
134
-continued
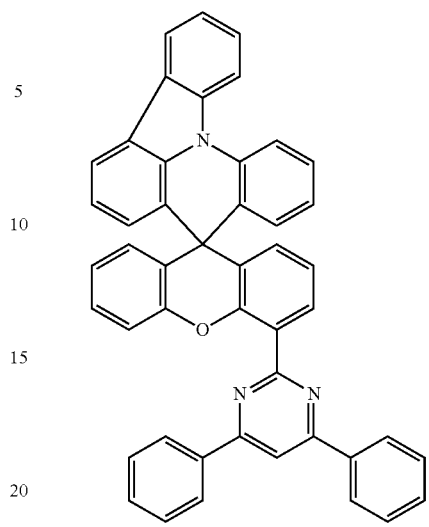
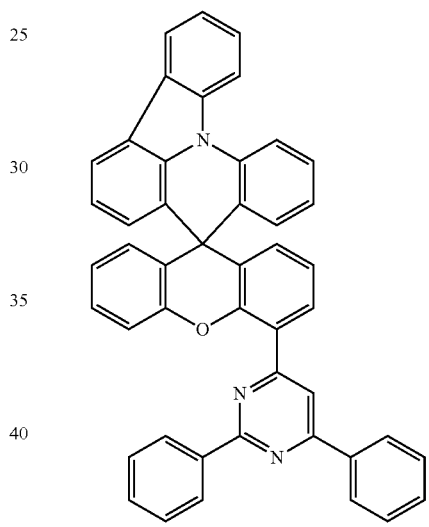
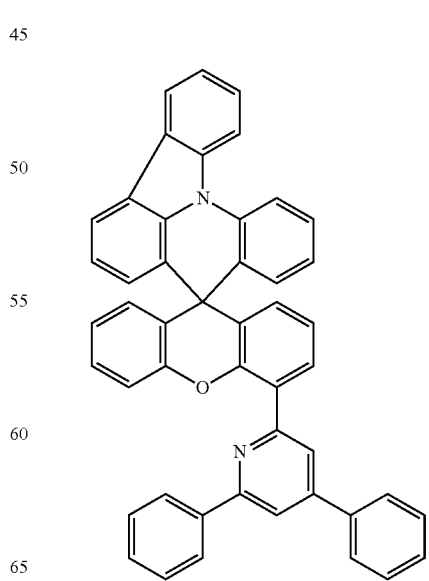

135
-continued
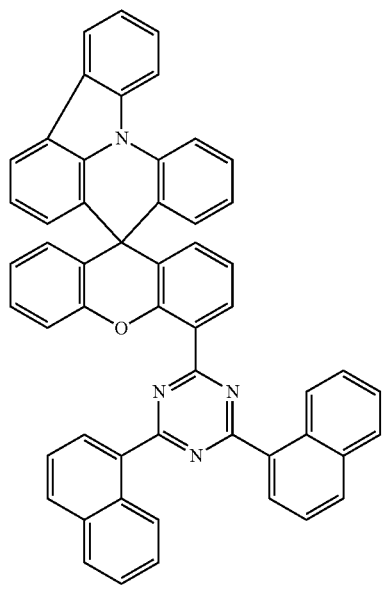
136
-continued
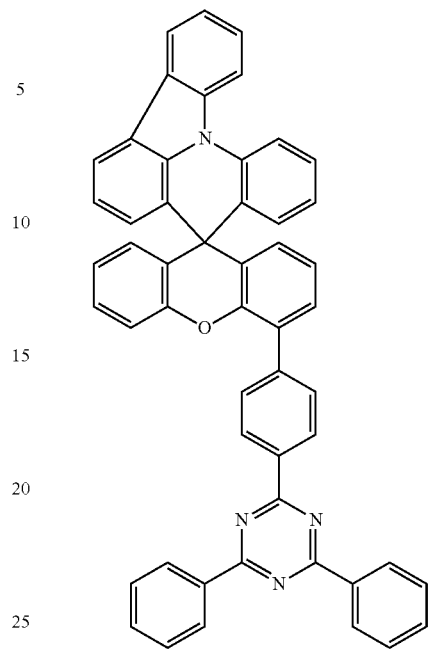
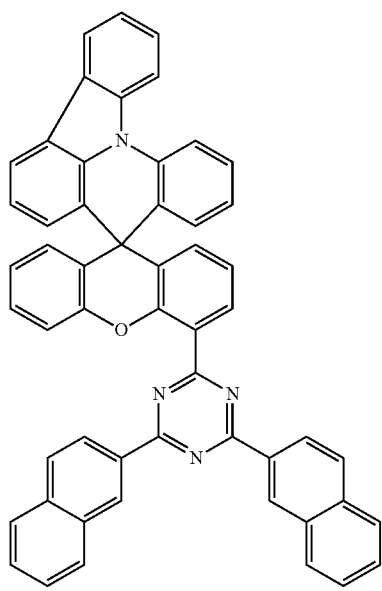
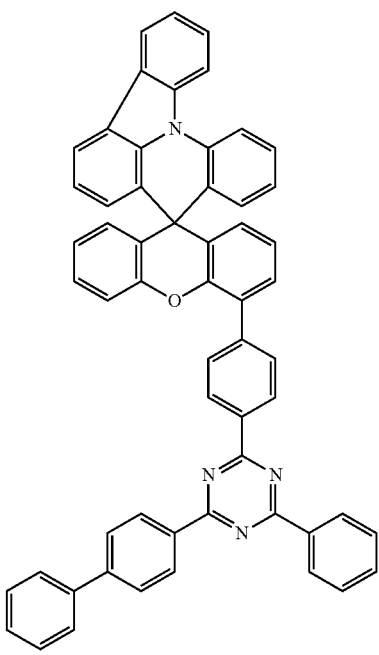

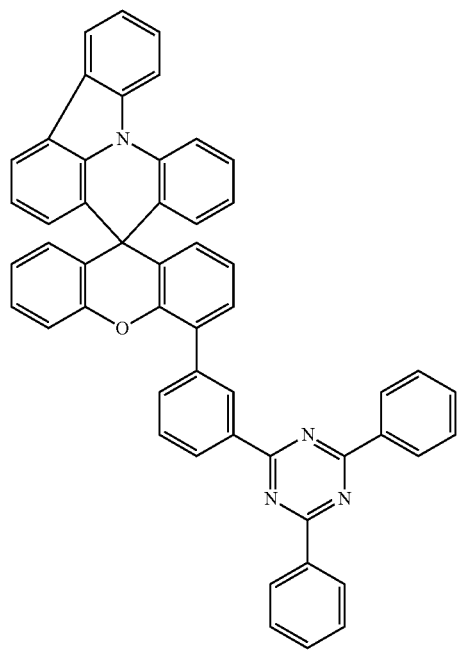
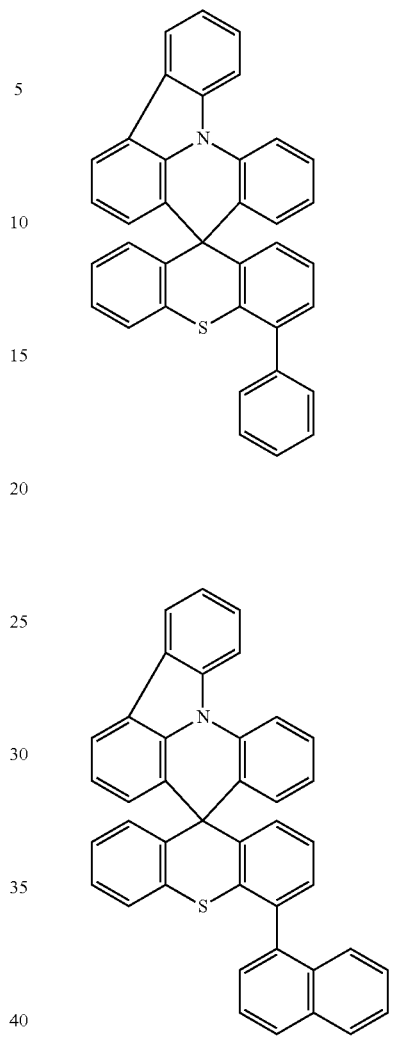
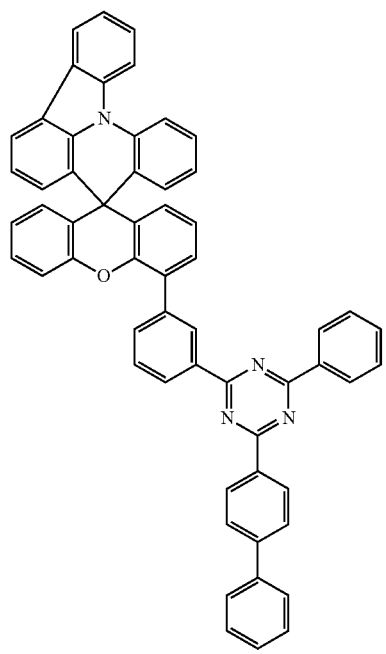
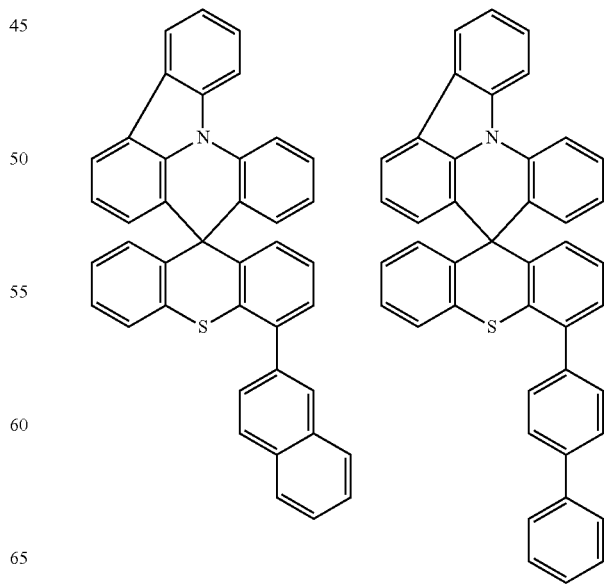

139
-continued
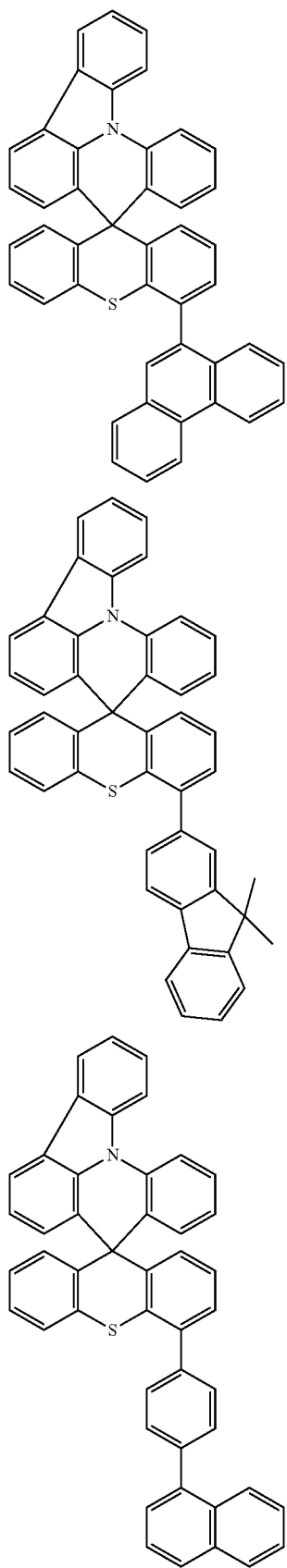
140
-continued
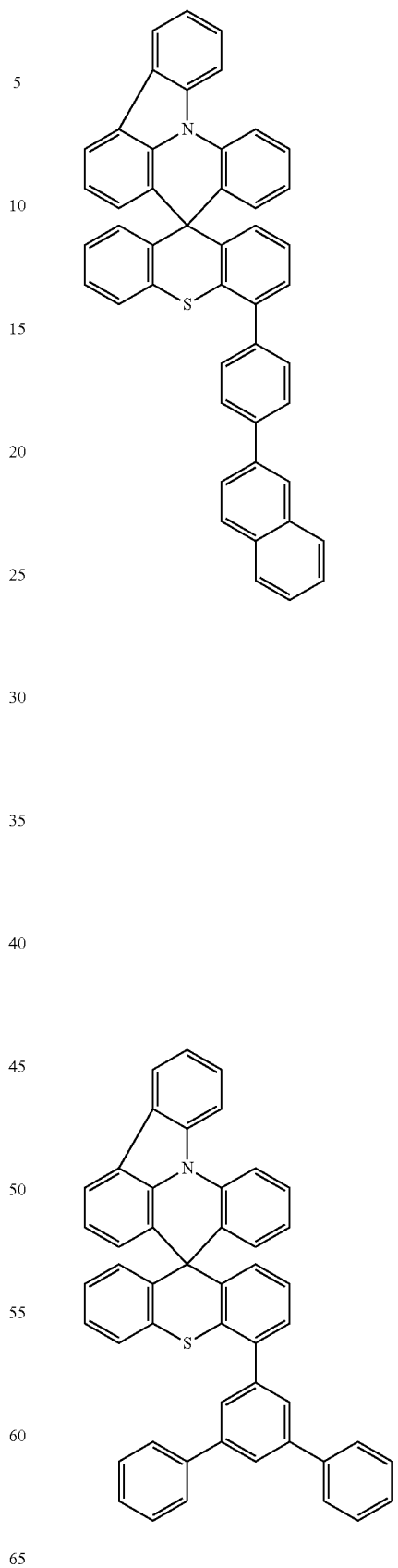

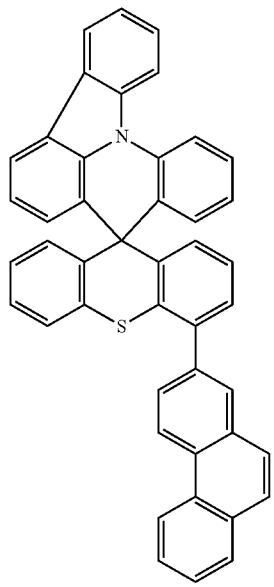
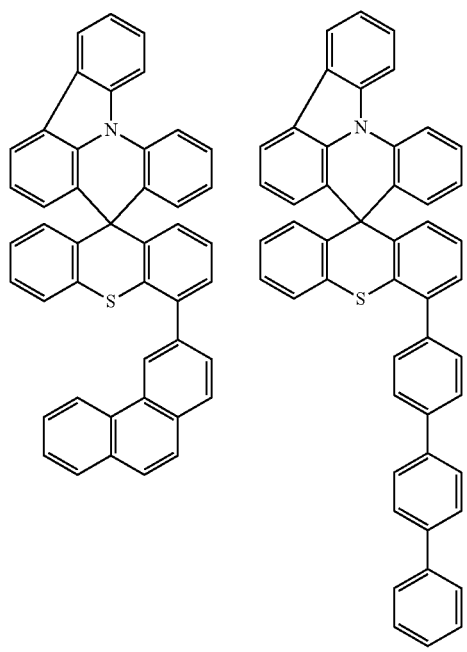
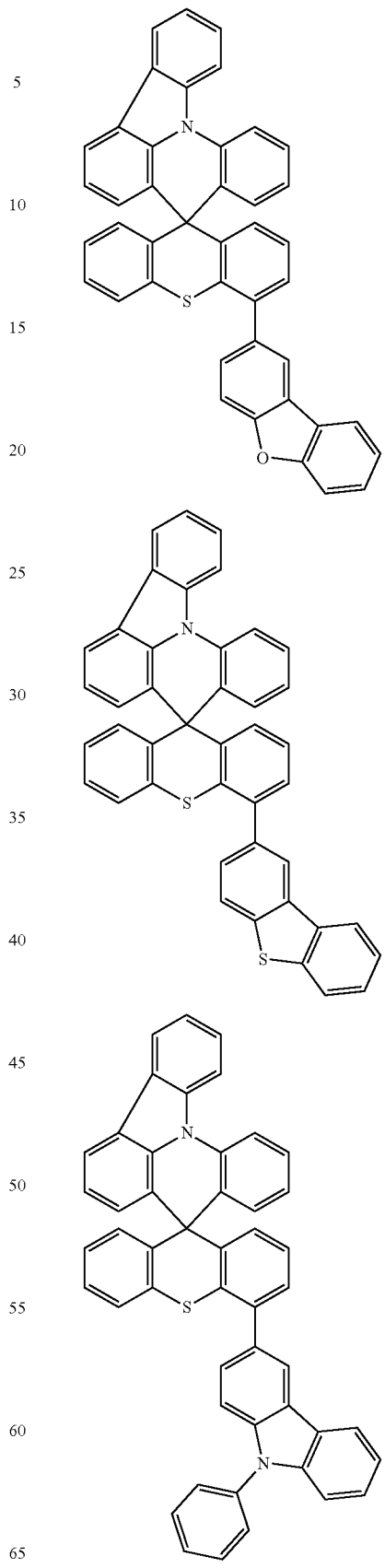

143
-continued
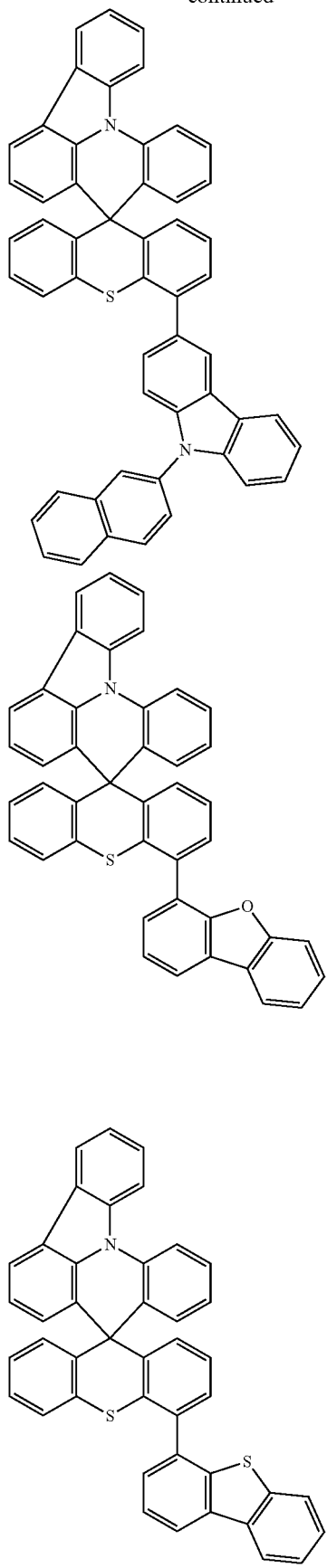
144
-continued
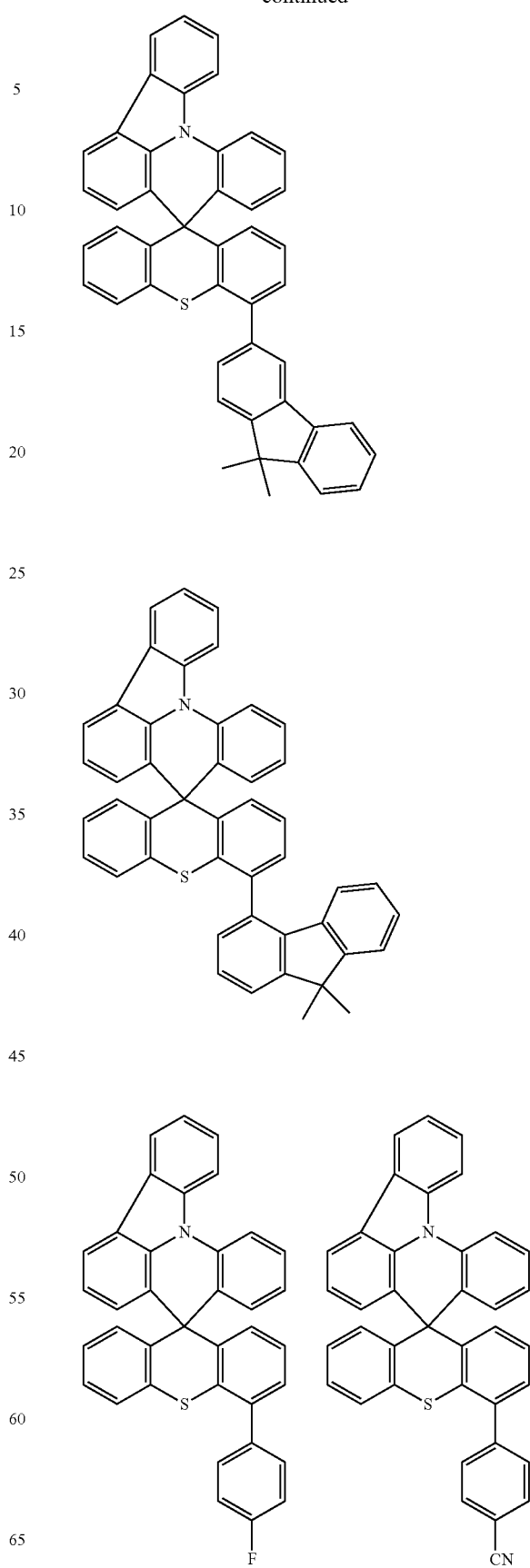

145
-continued
146
-continued
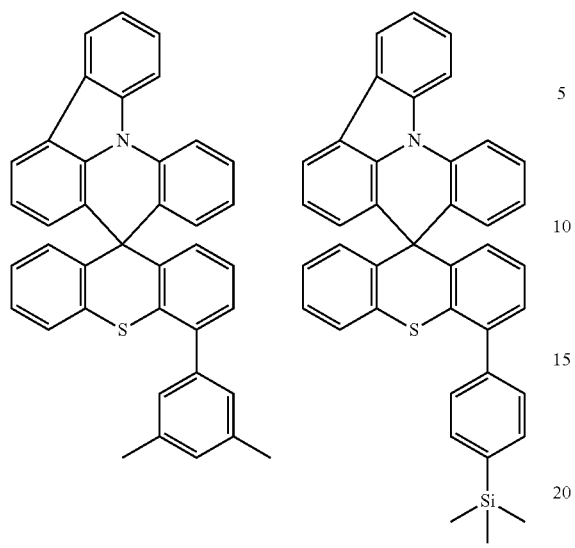
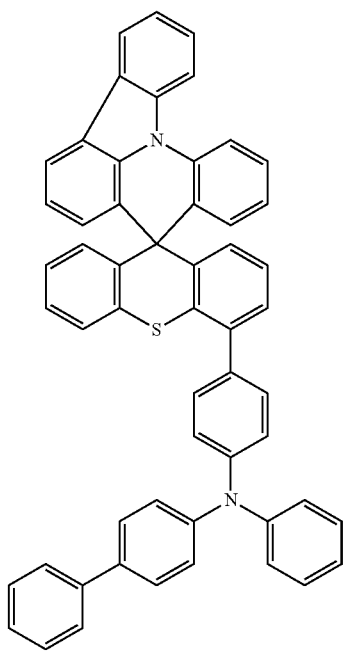
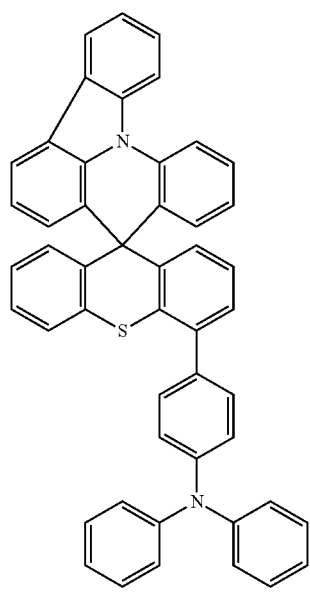
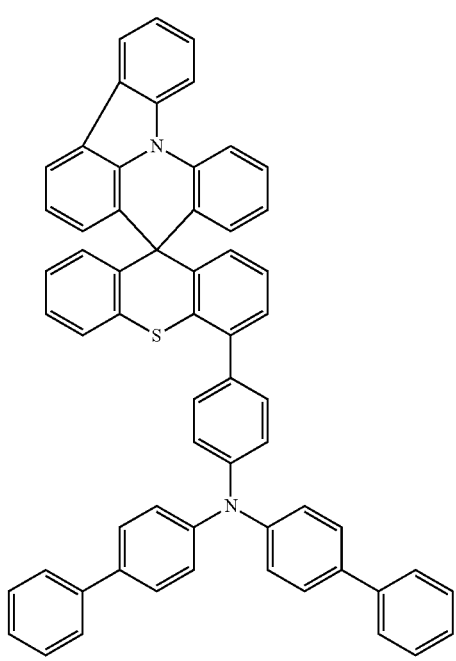

147
-continued
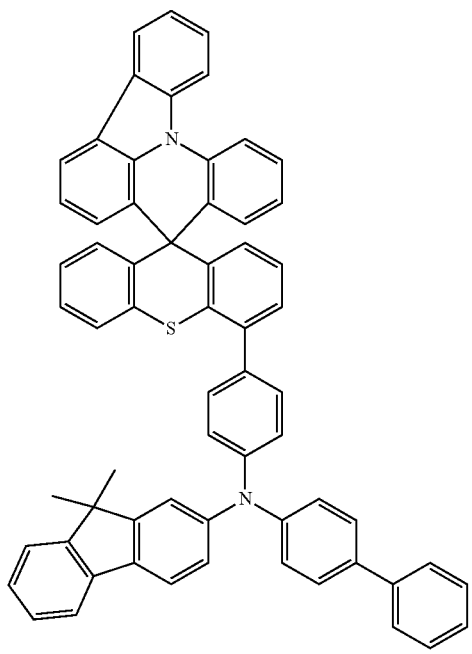
148
-continued
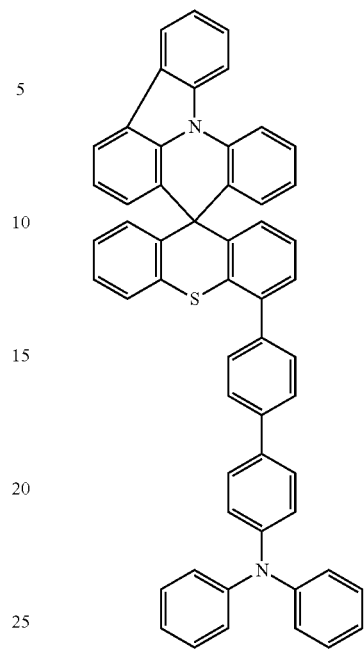
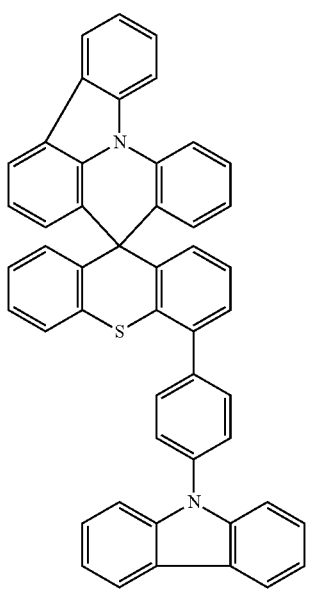
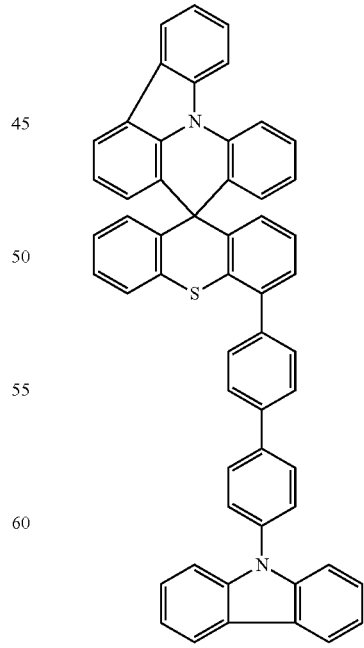

149
-continued
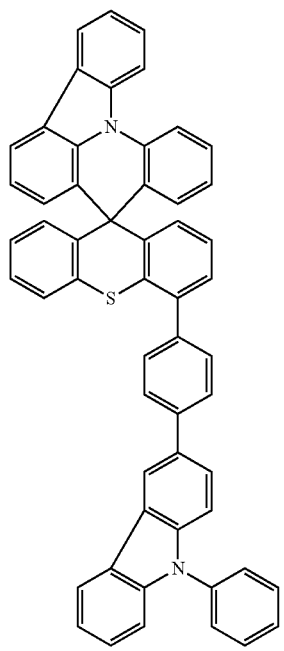
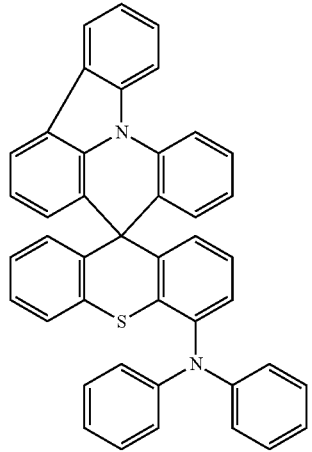
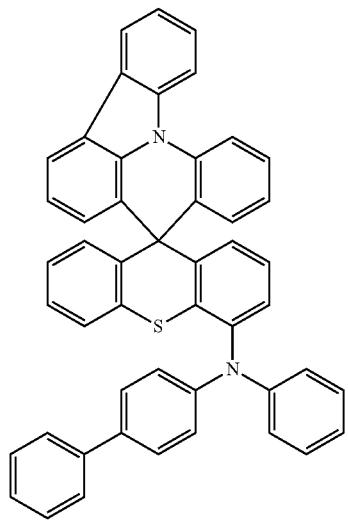
150
-continued
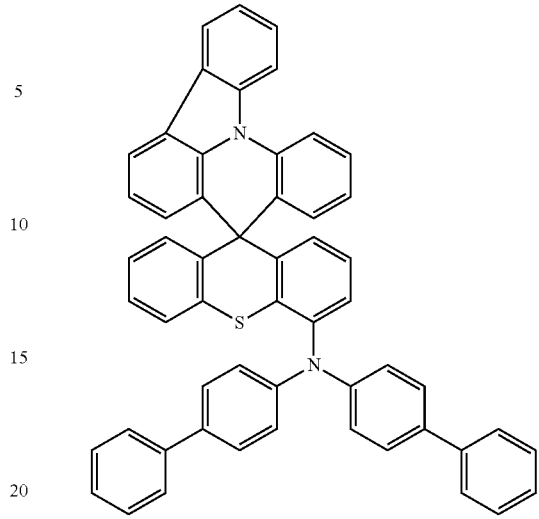
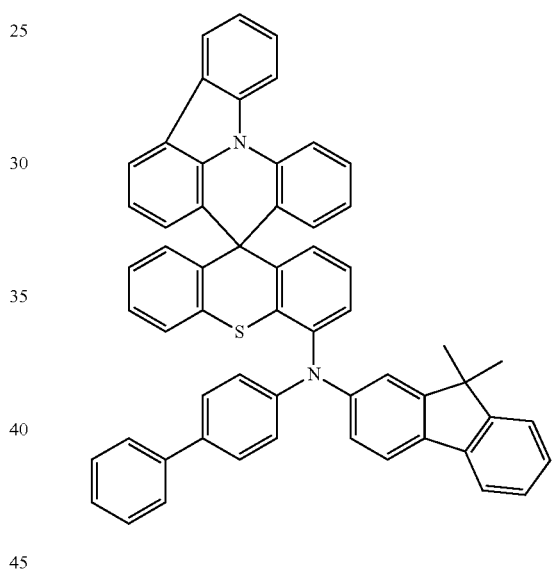
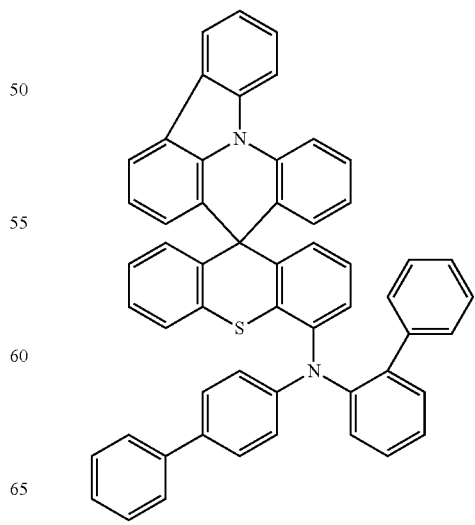

151
-continued
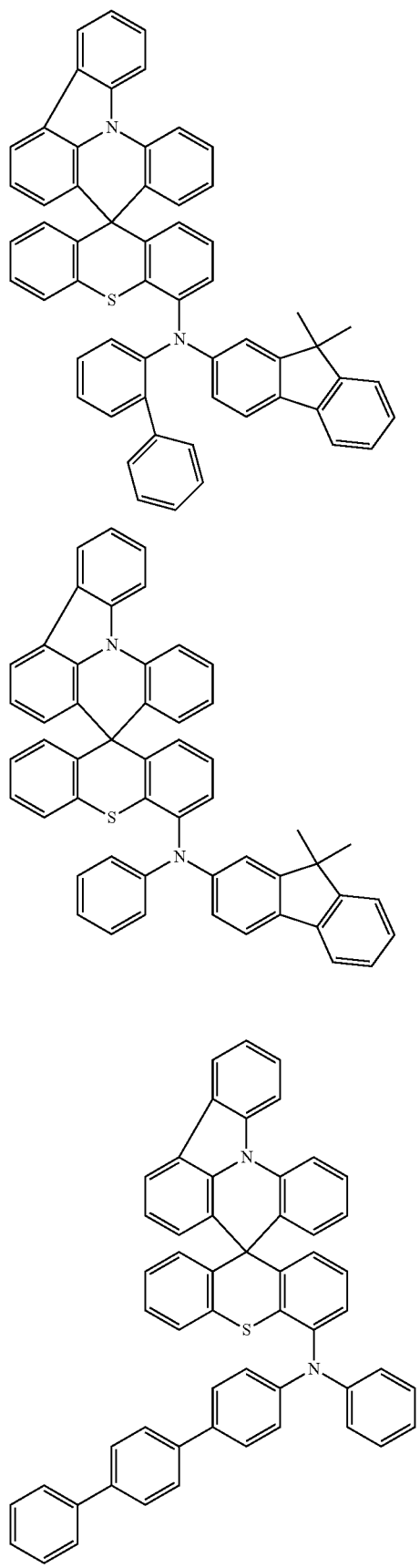
152
-continued
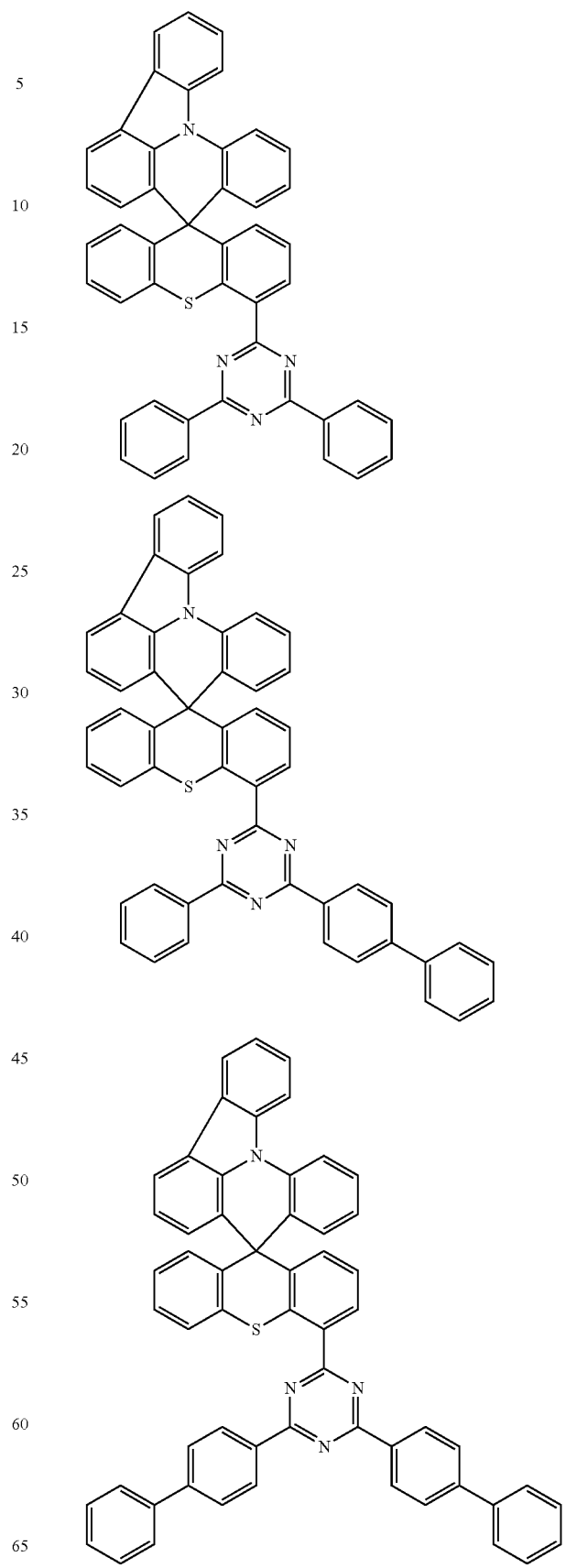

153
-continued
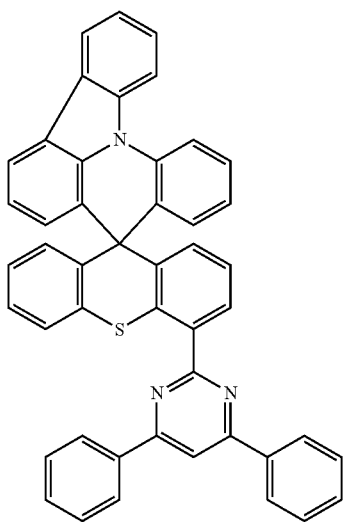
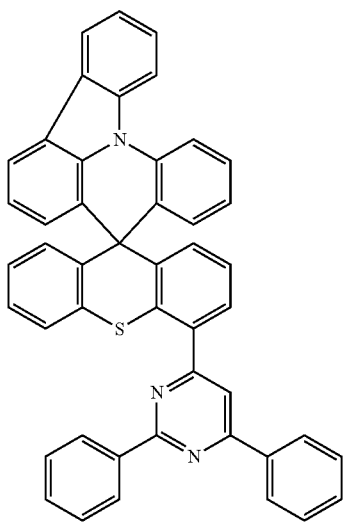
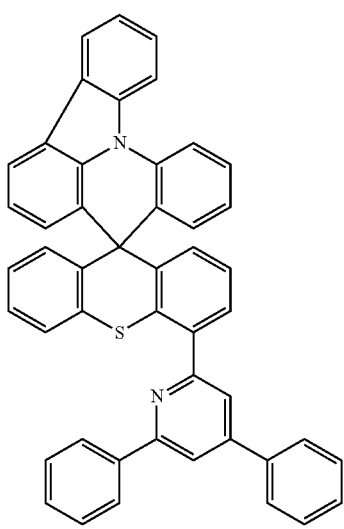
154
-continued
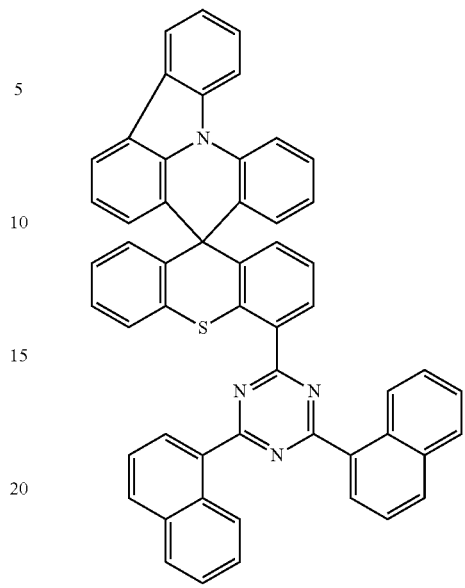

155
-continued
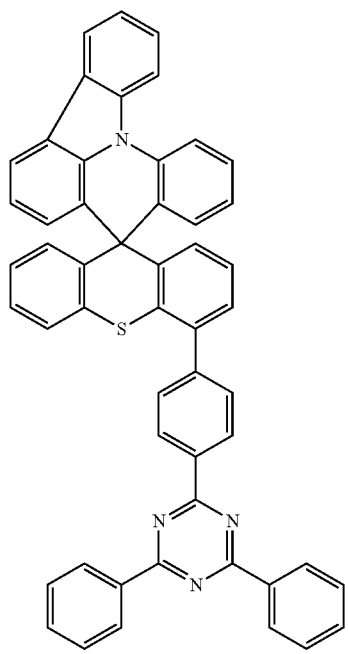
156
-continued
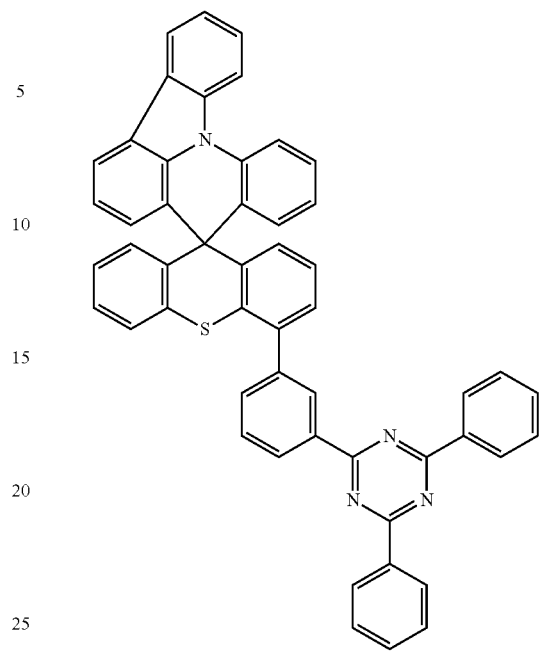
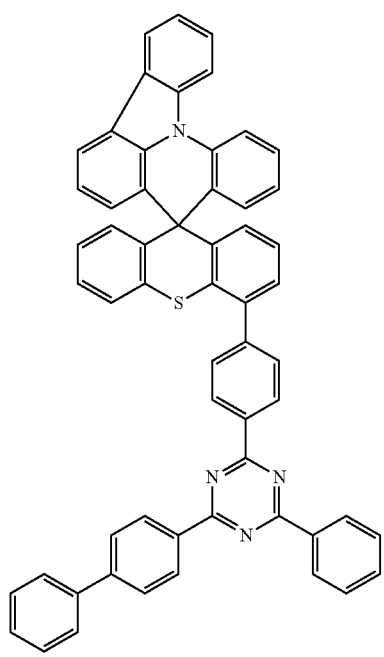
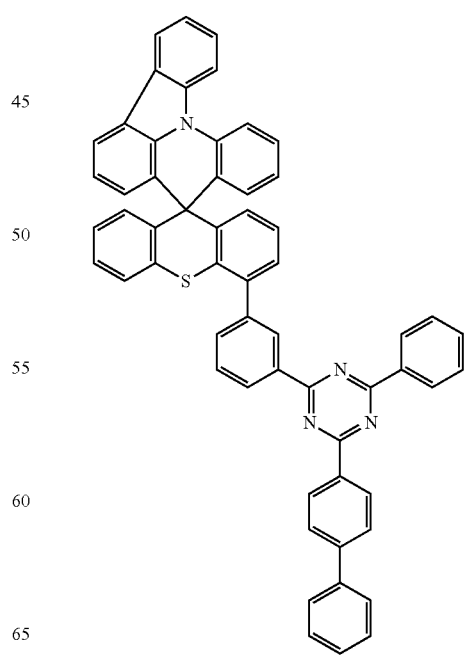

157
-continued
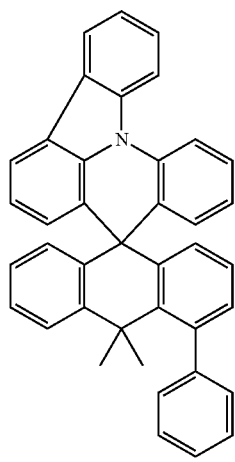
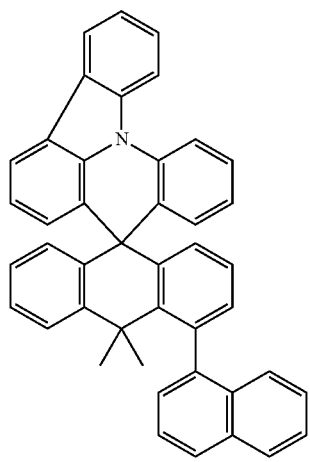
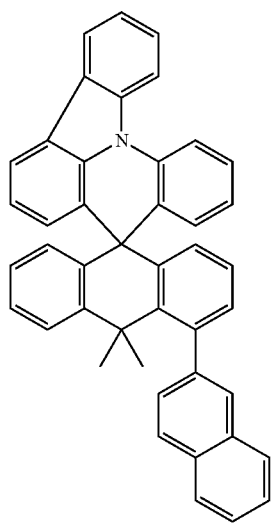
158
-continued
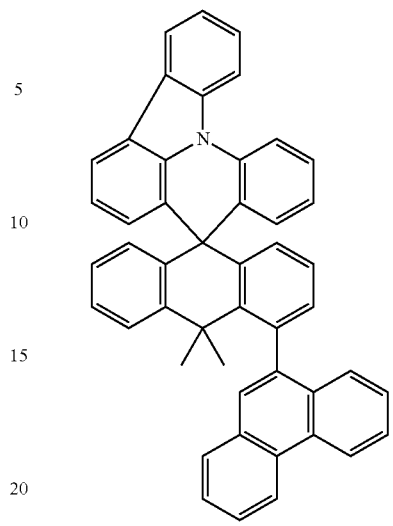
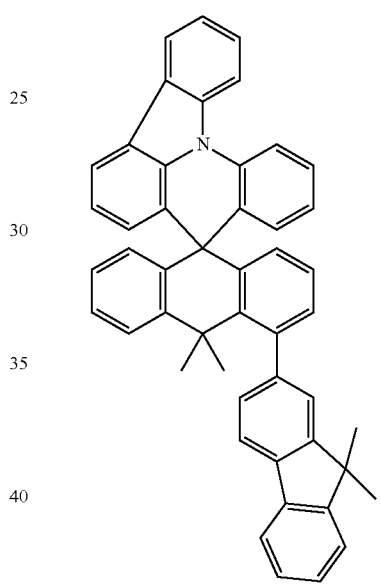
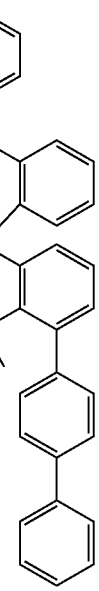

159
-continued
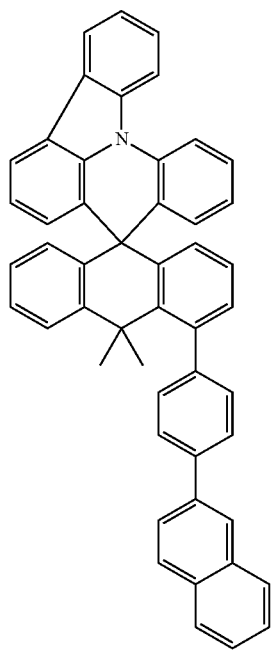
160
-continued
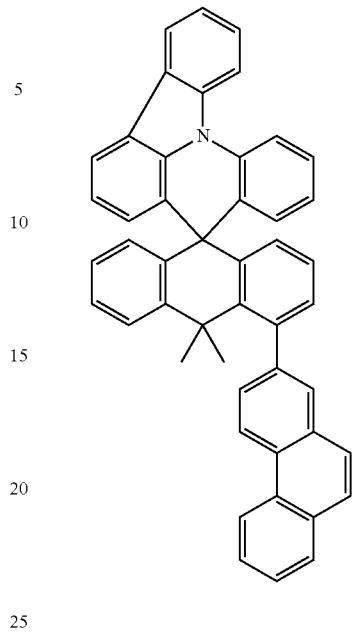
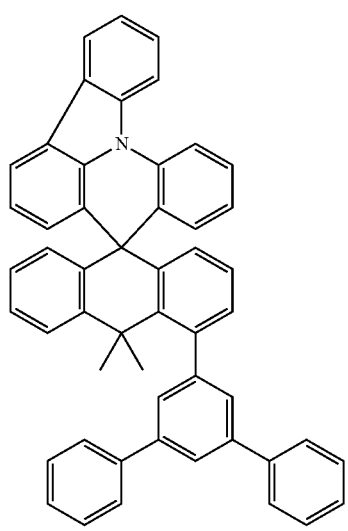
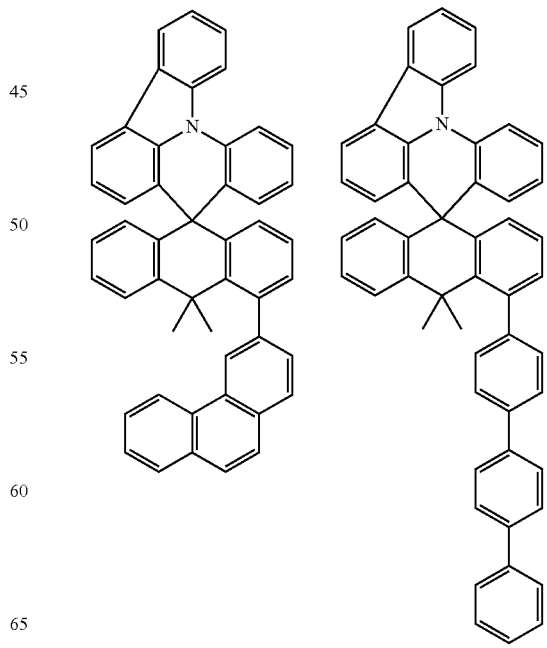

161
-continued
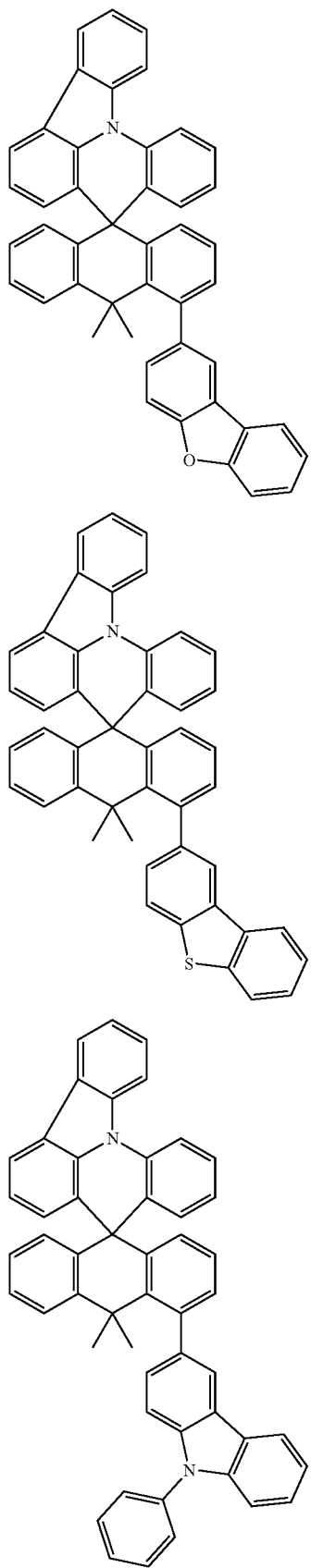
162
-continued
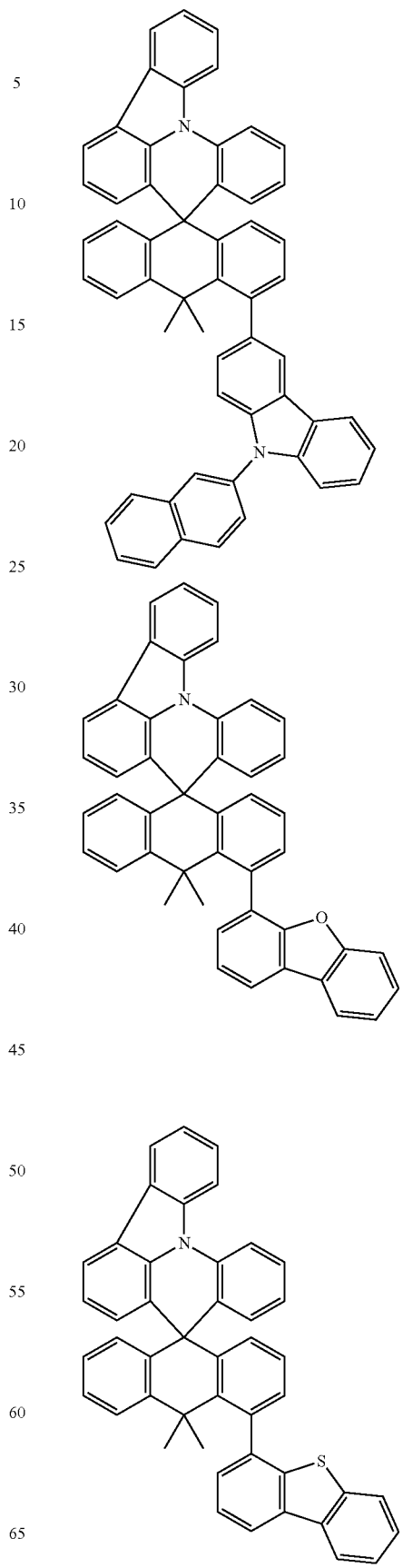

163
-continued
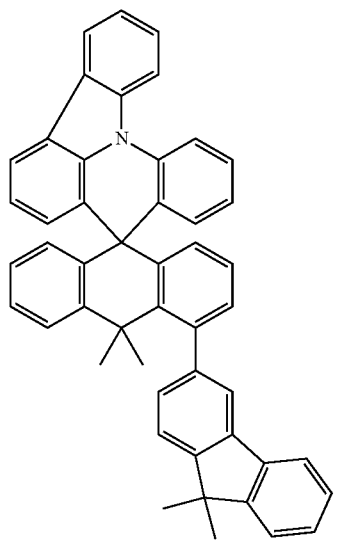
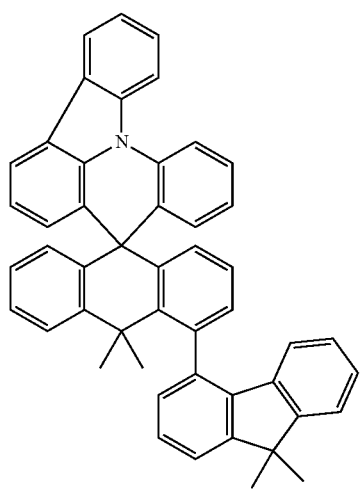
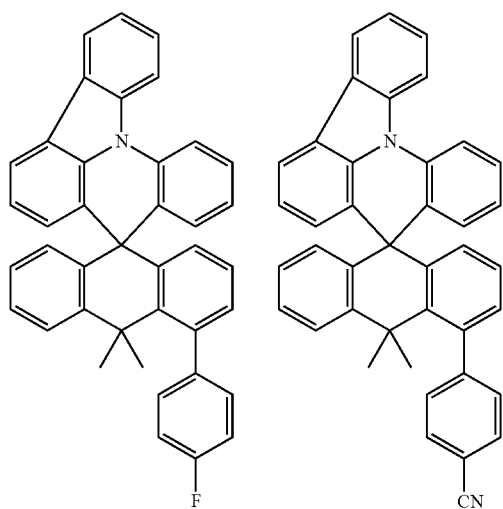
164
-continued
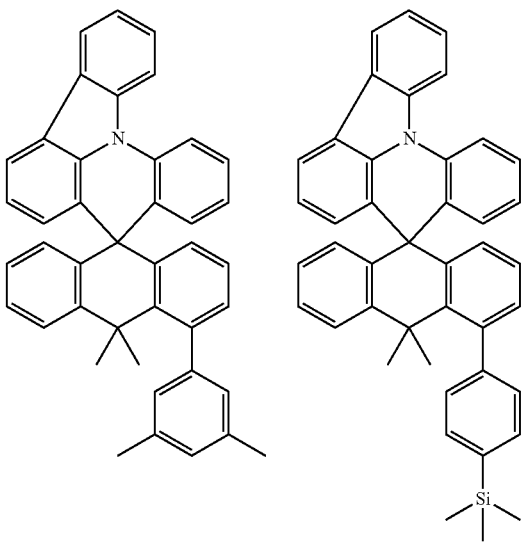
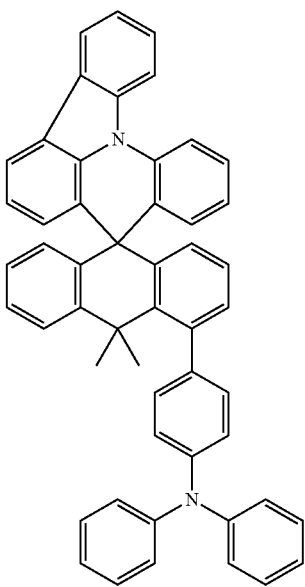

165
-continued
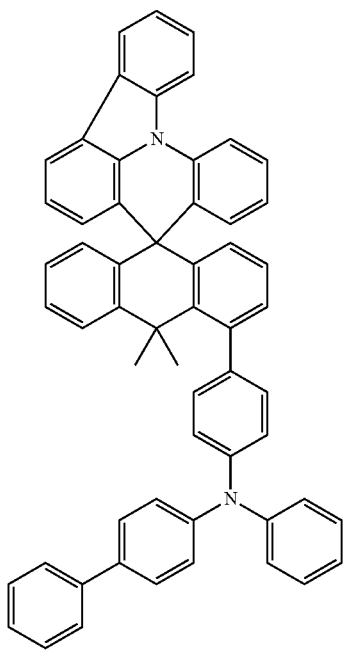
166
-continued
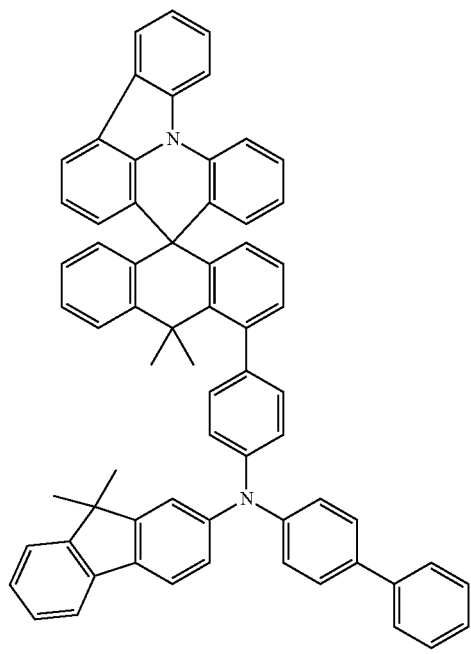
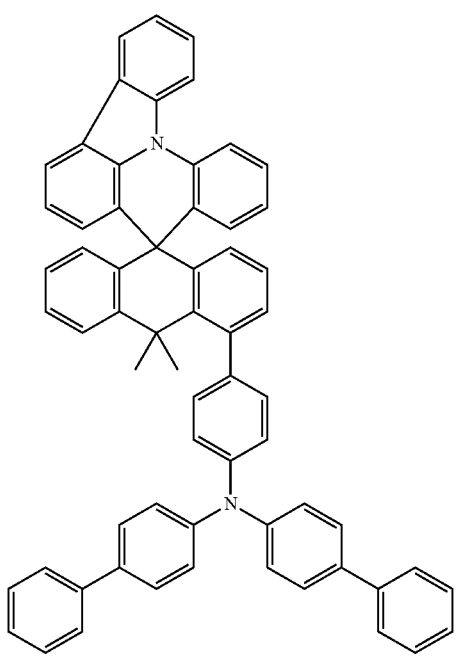
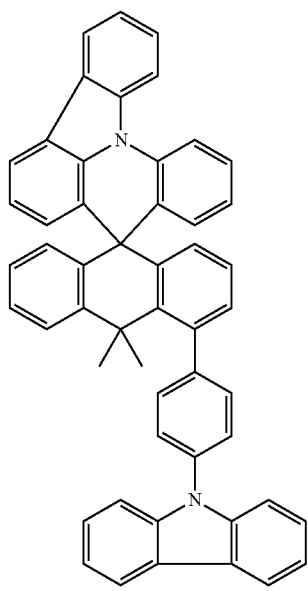

167
-continued
168
-continued
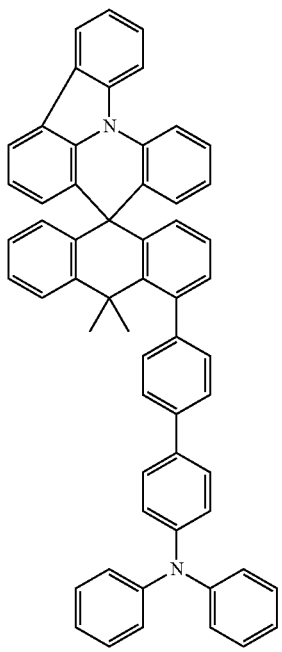
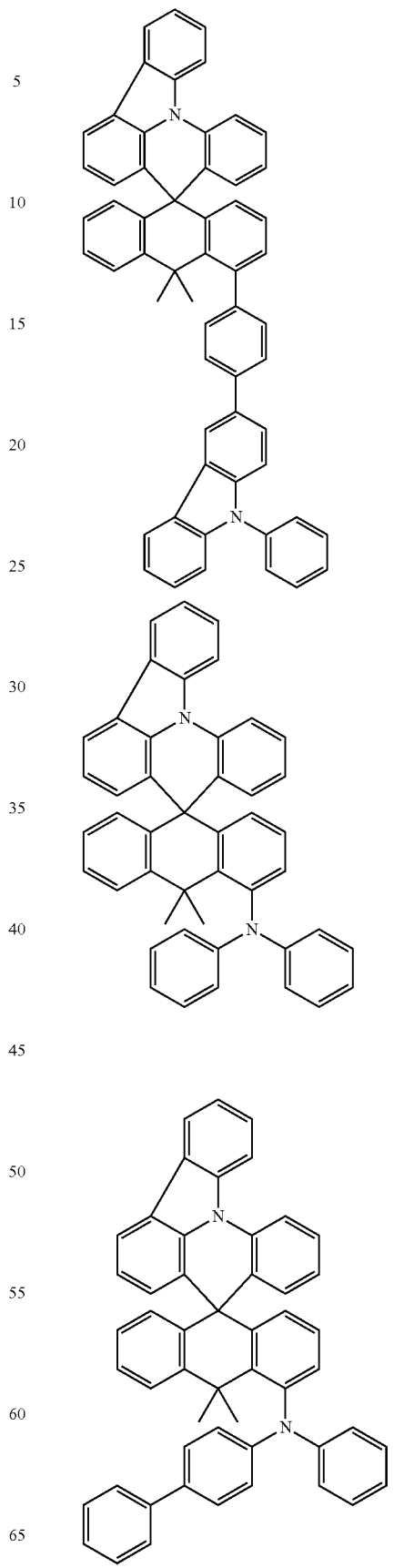

169
-continued
170
-continued
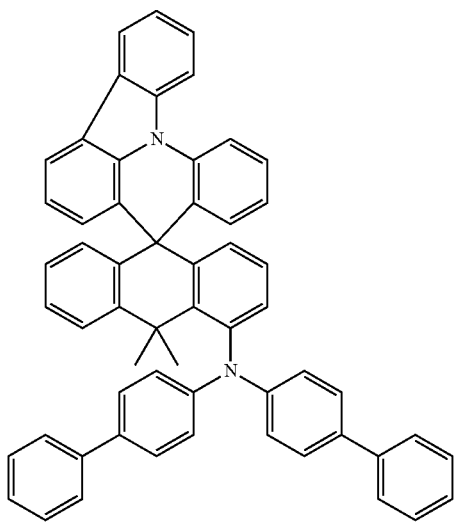
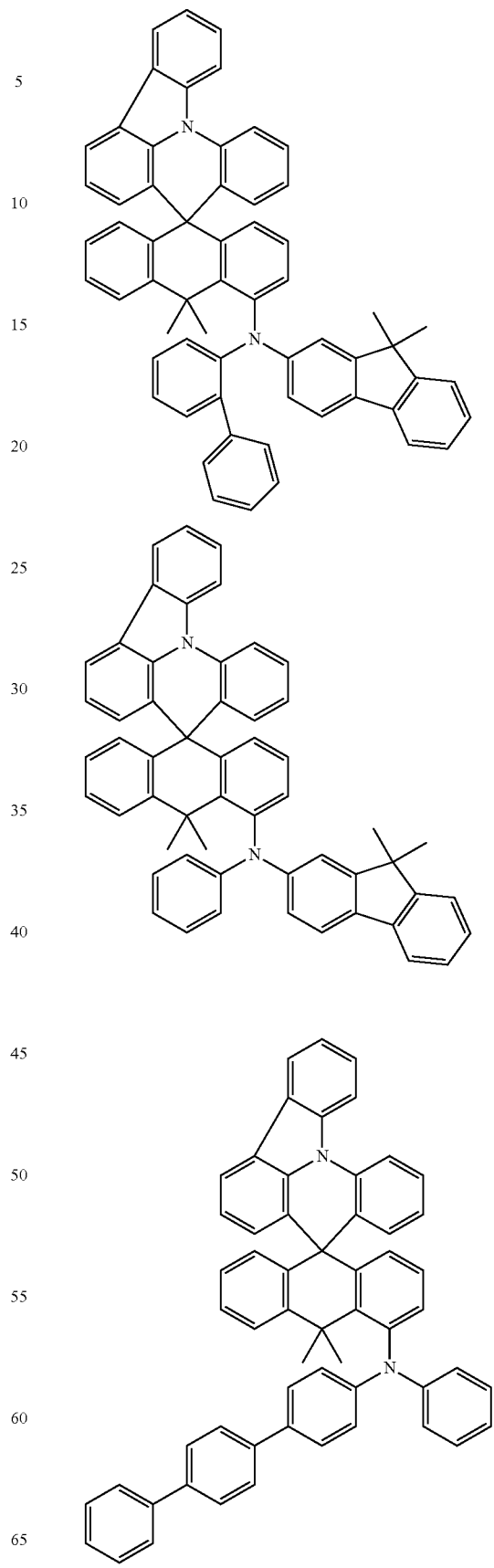

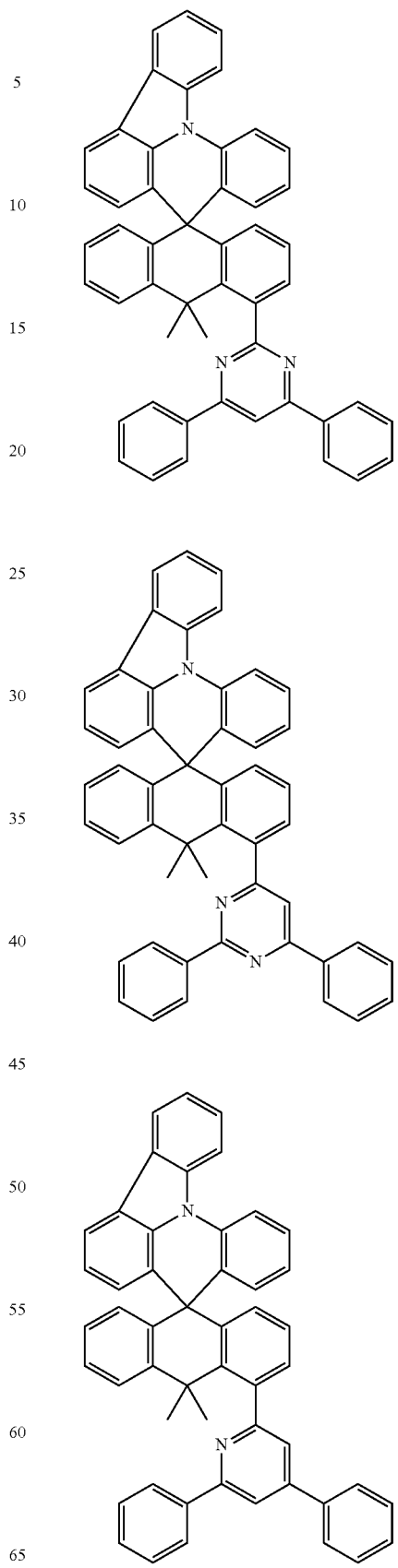

173
-continued
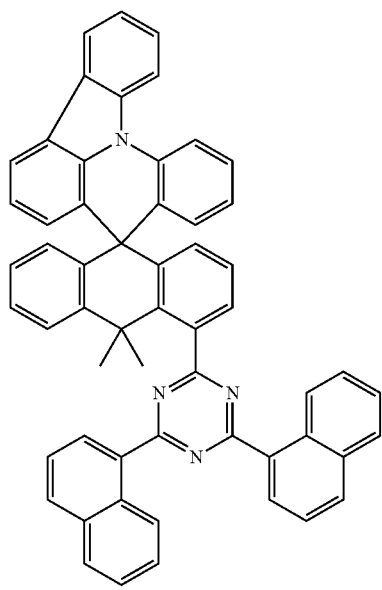
174
-continued
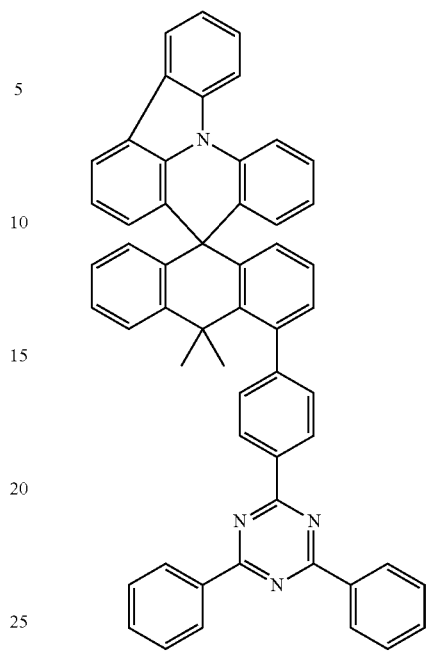
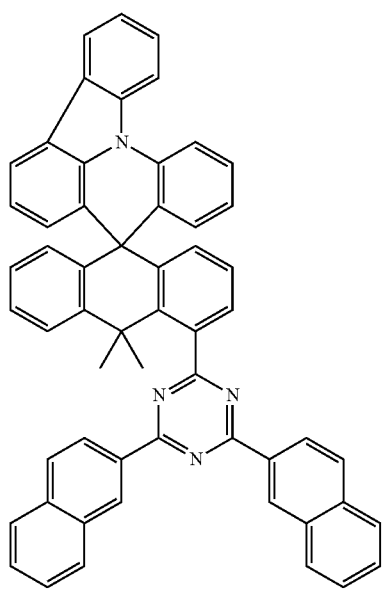
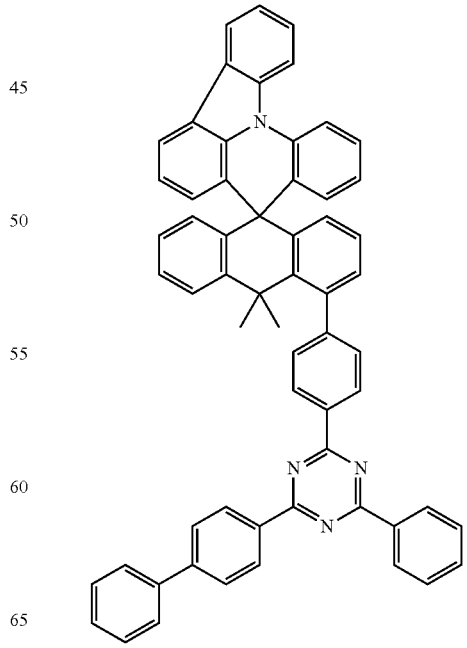

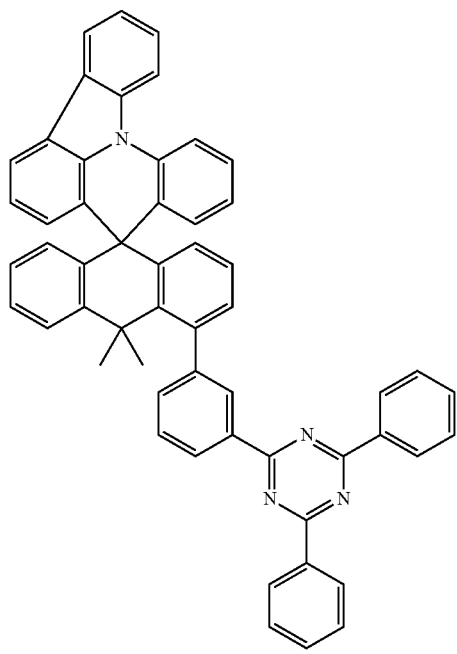
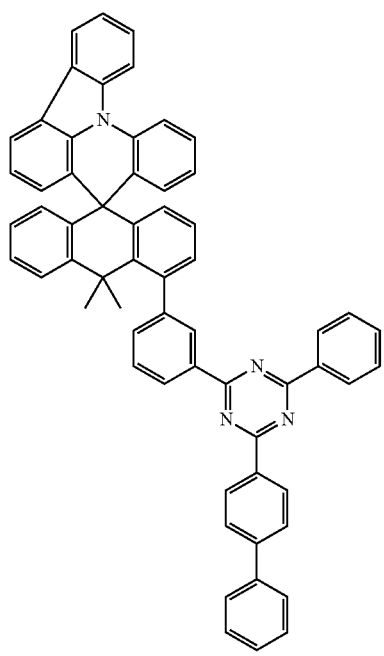
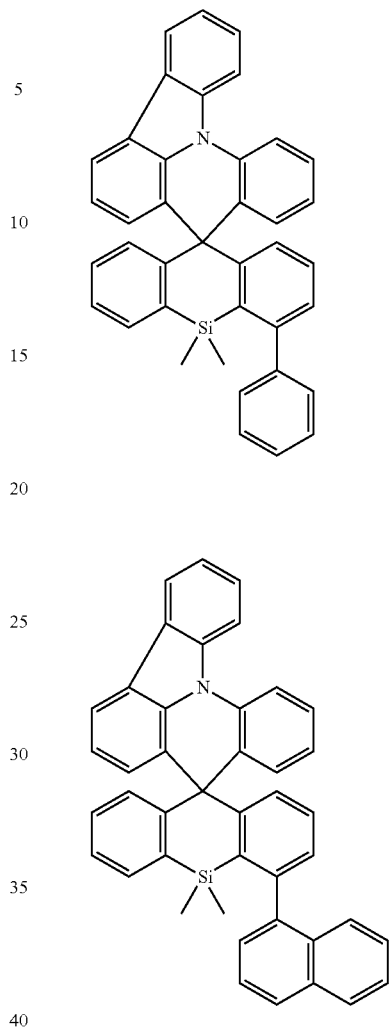
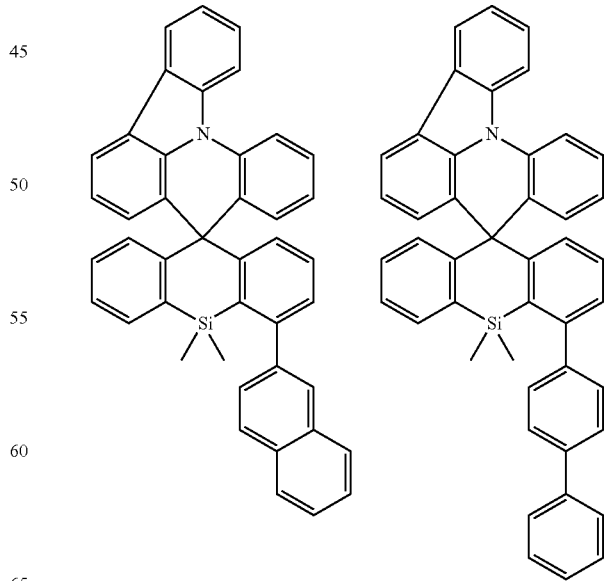

177
-continued
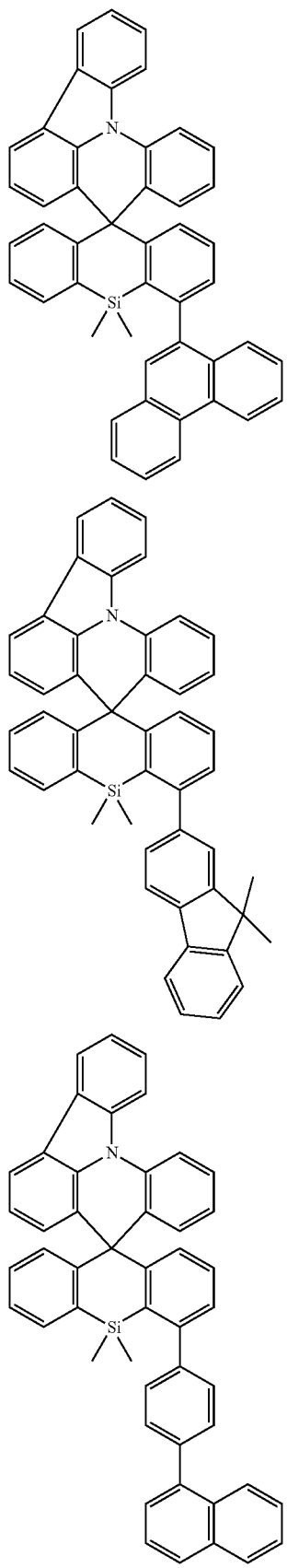
178
-continued
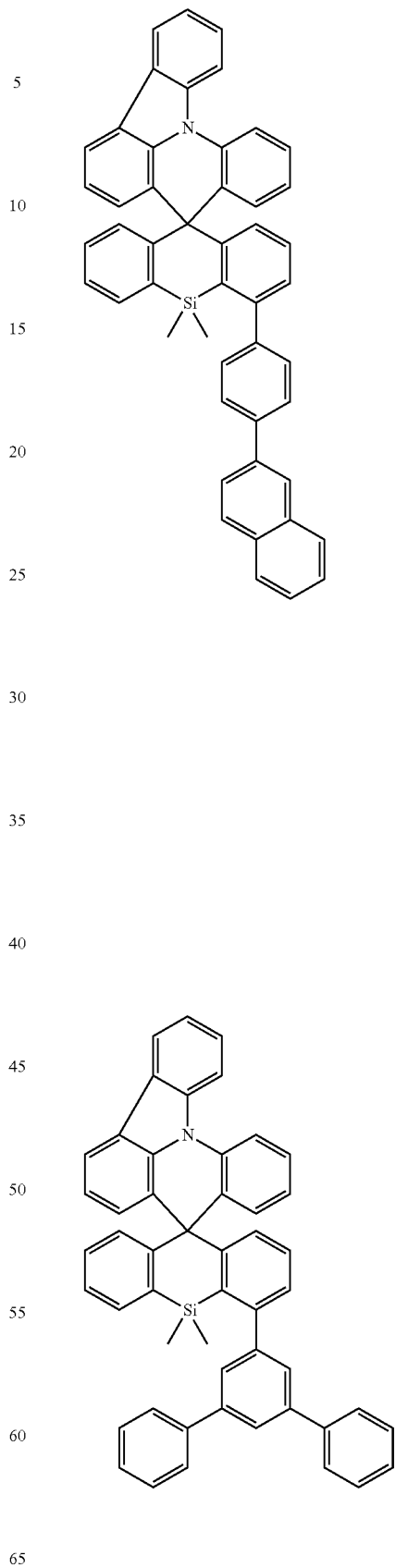

179
-continued
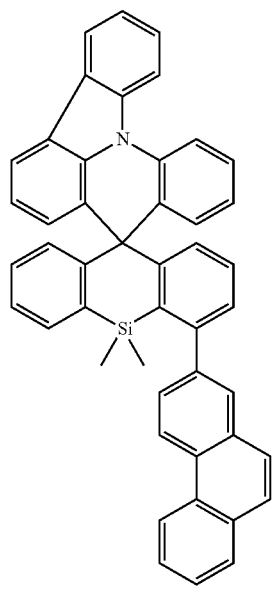
180
-continued
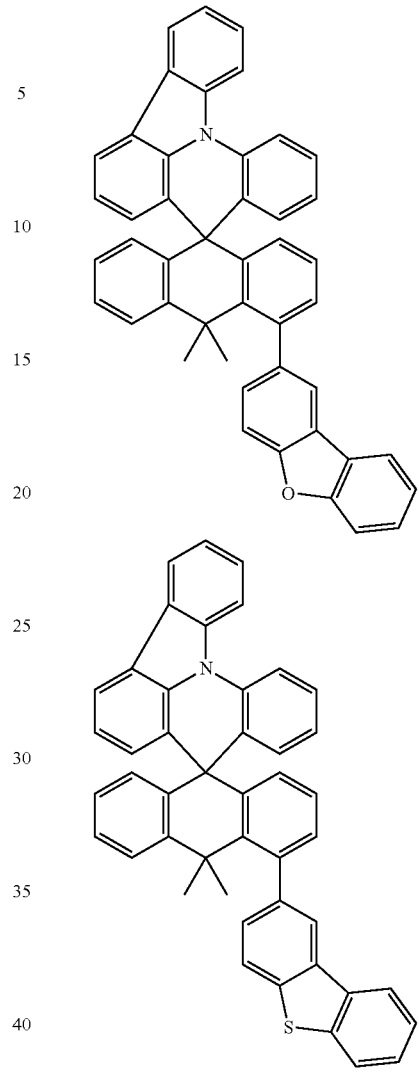
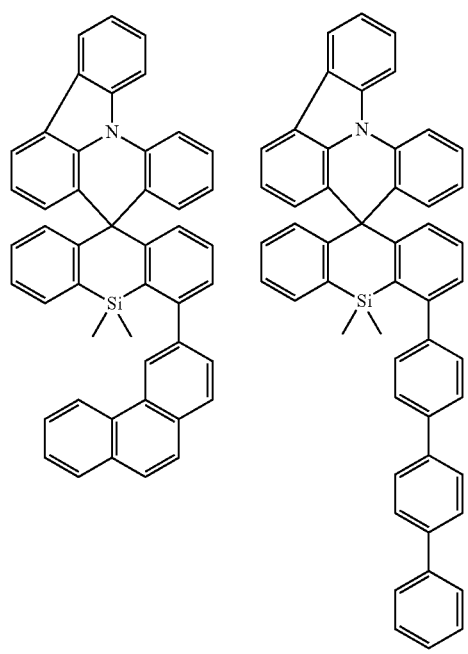
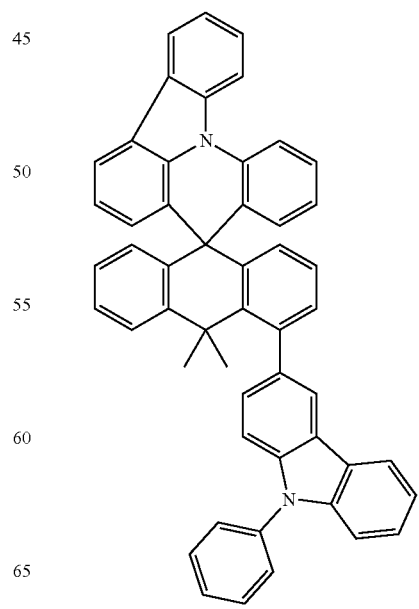

181
-continued
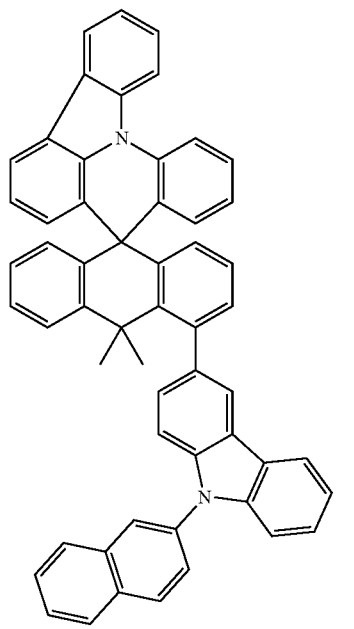
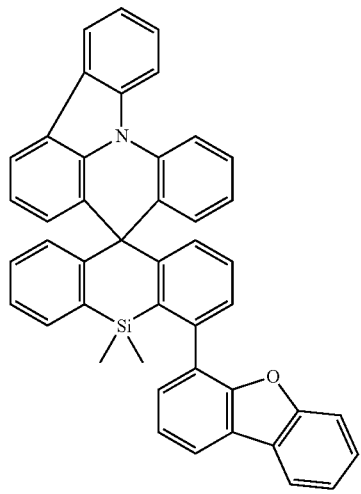
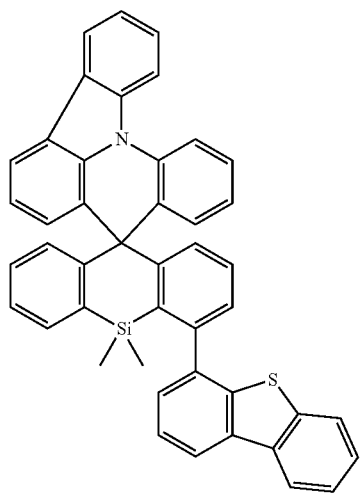
182
-continued
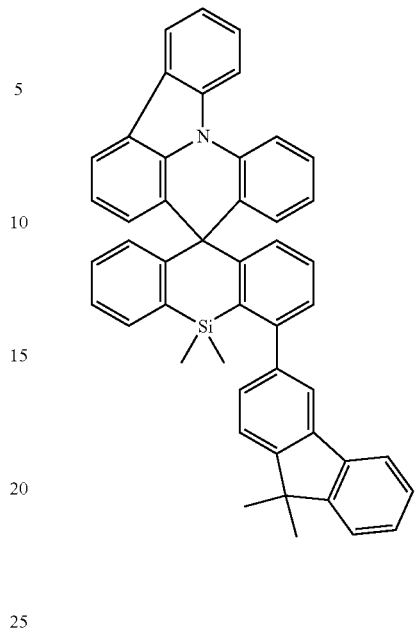
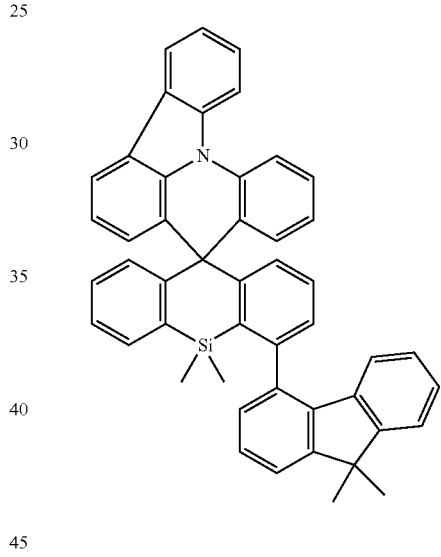
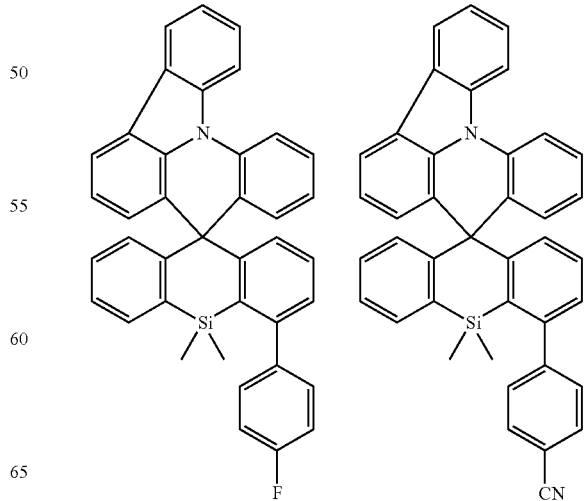

183
-continued
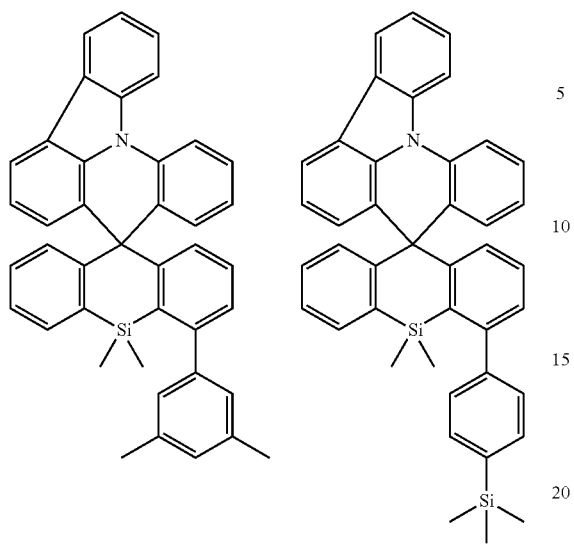
184
-continued
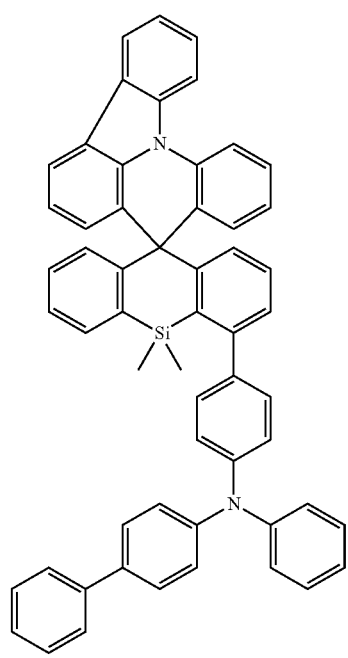
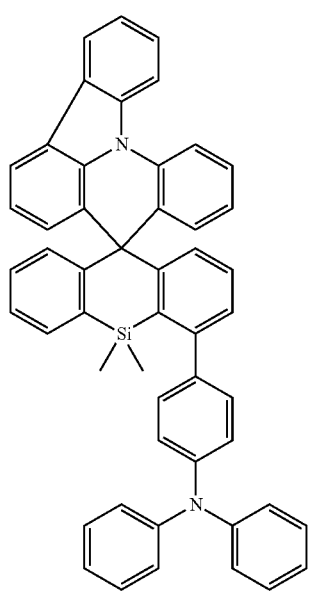
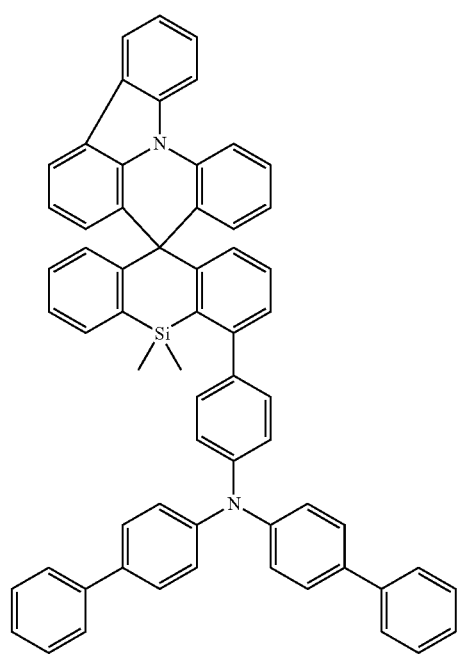

185
-continued
186
-continued
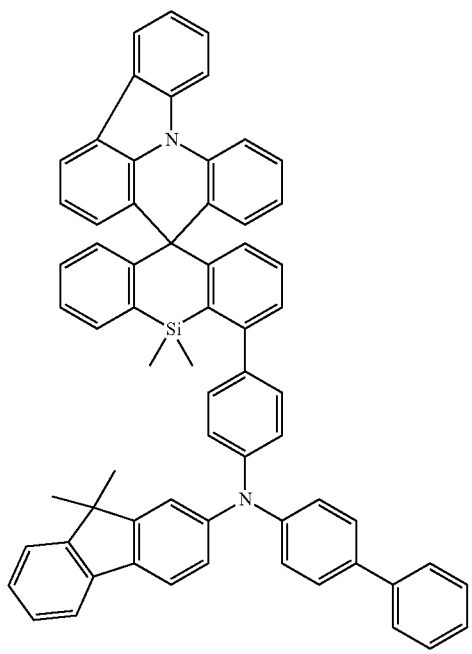
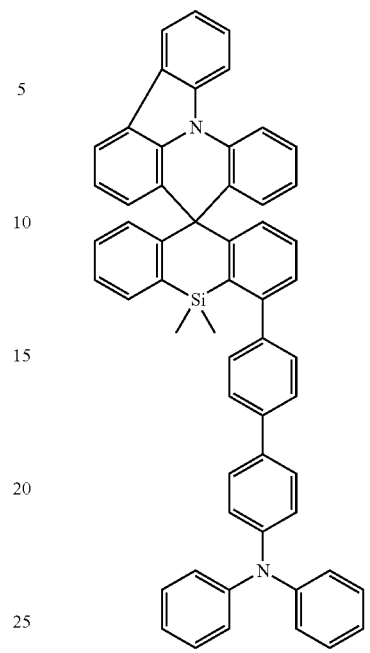

187
-continued
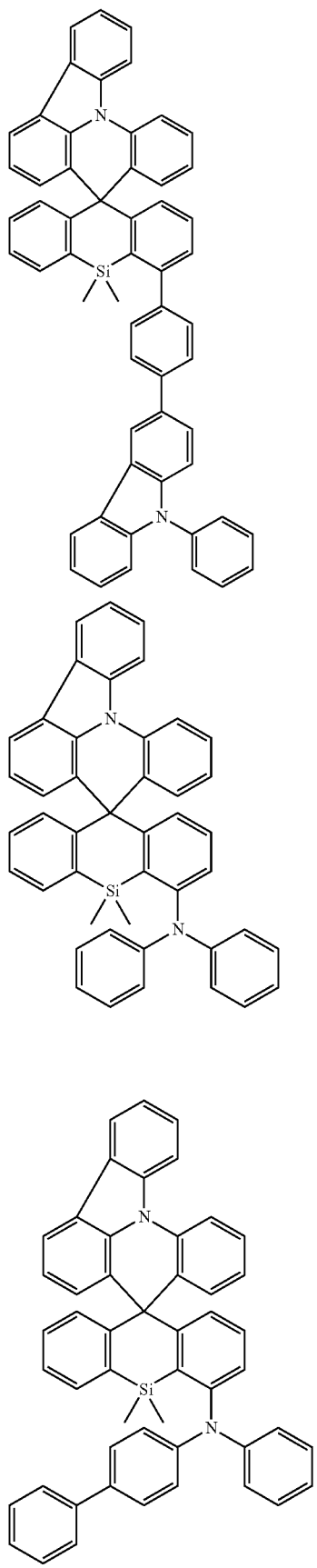
188
-continued
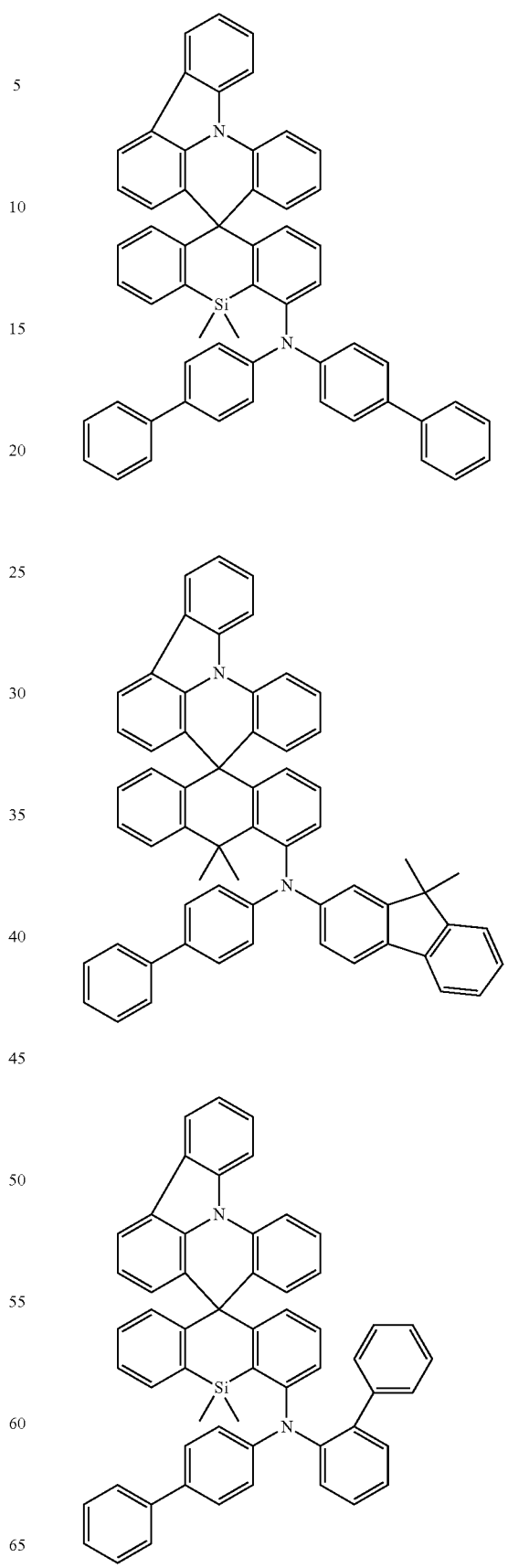

189
-continued
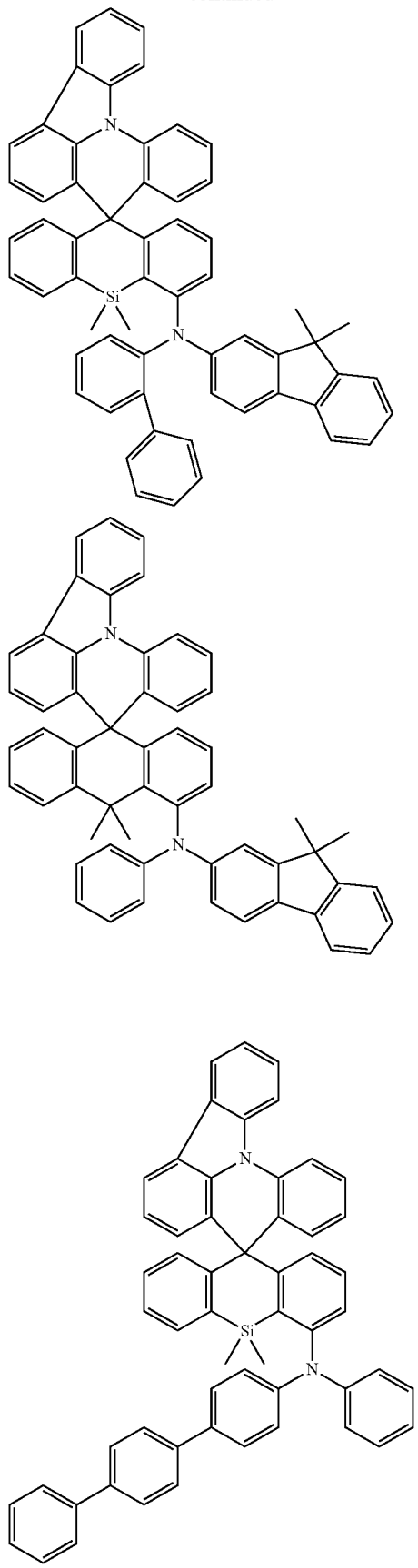
190
-continued
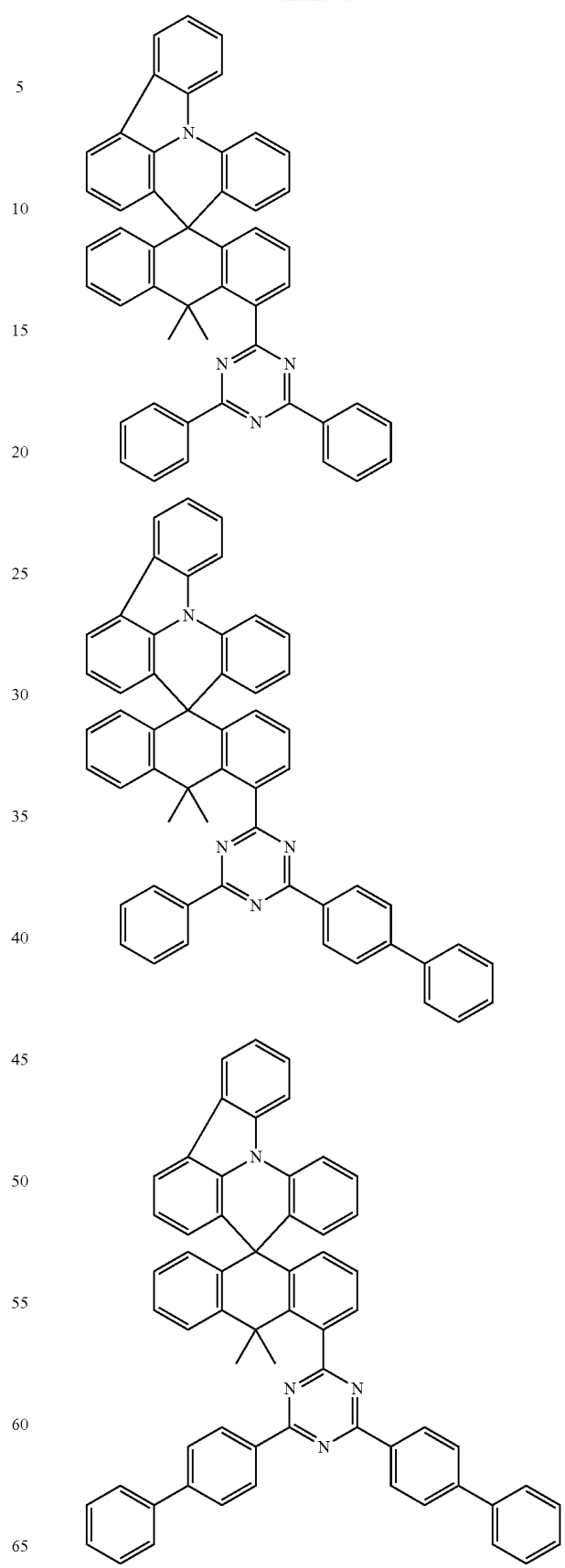

191
-continued
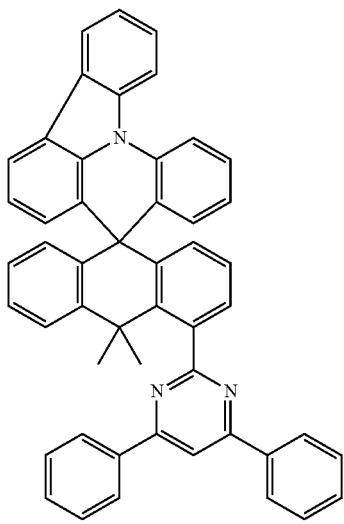
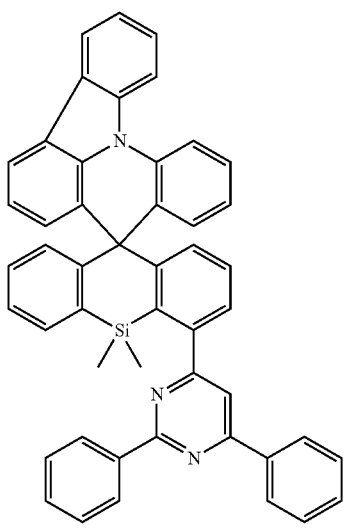
192
-continued
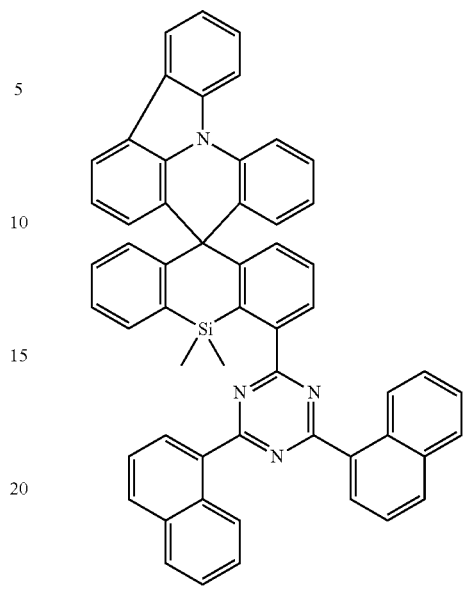
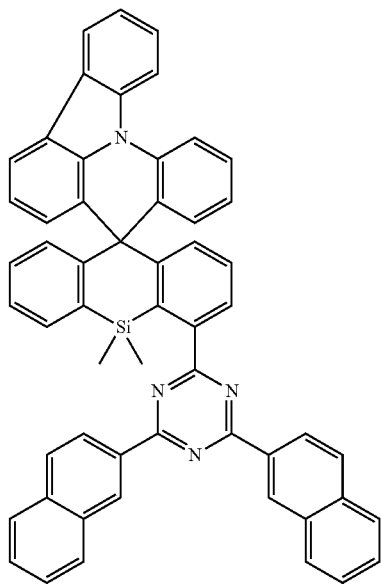

193
-continued
194
-continued
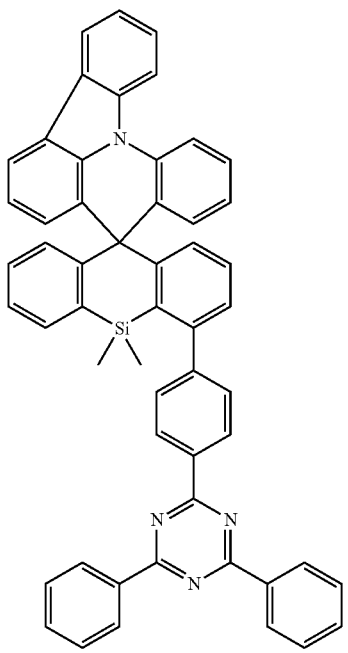
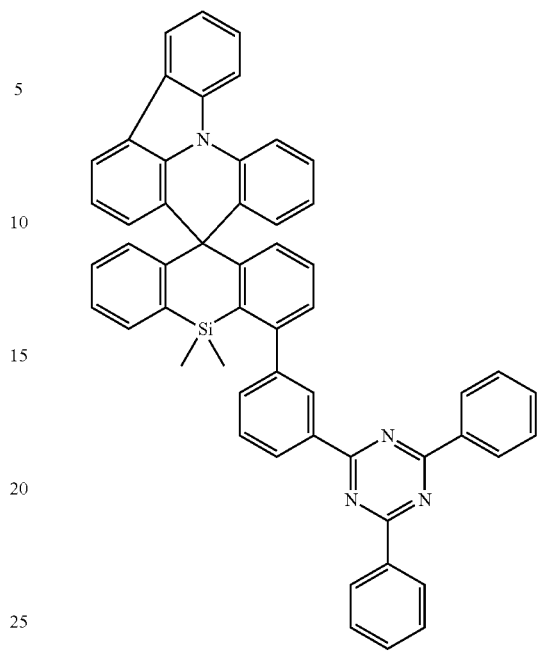
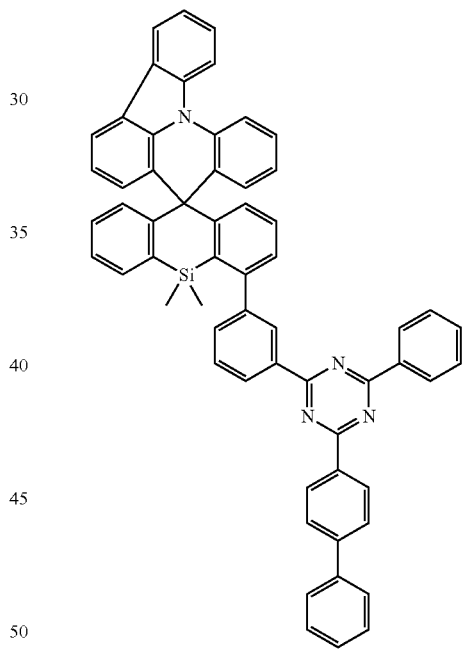
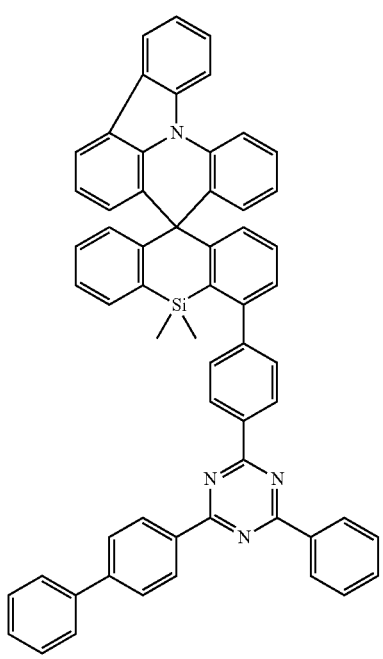
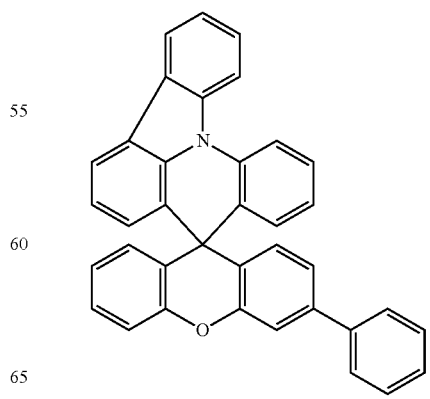

-continued
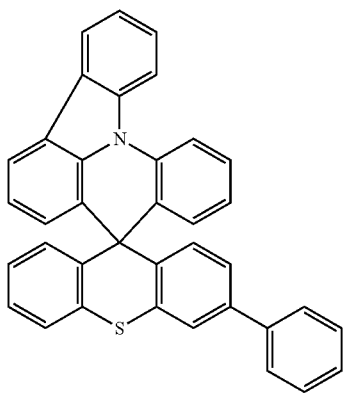
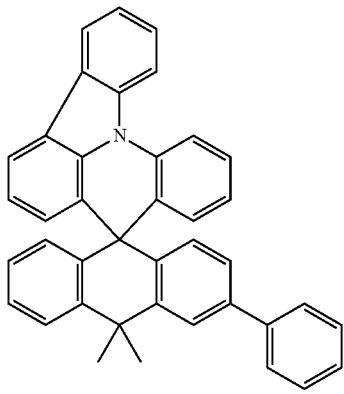
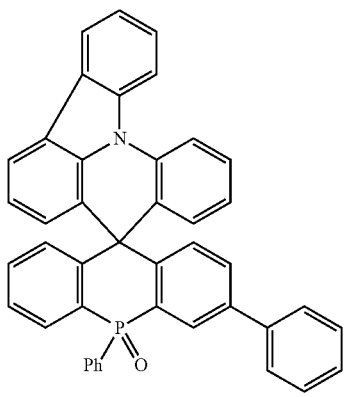
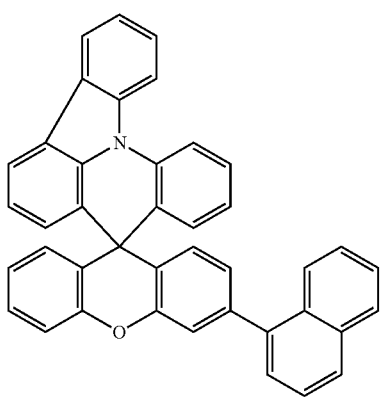
-continued
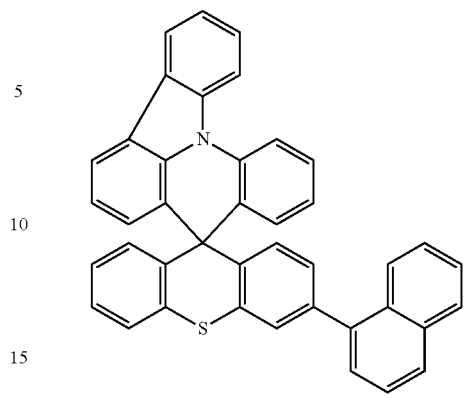
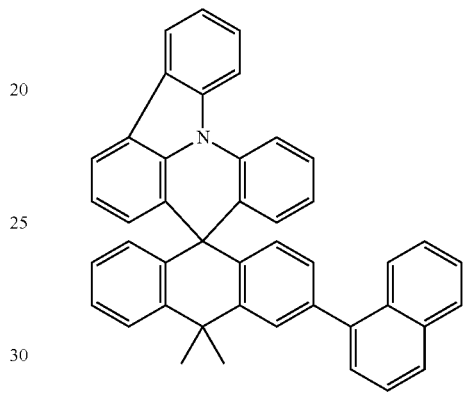
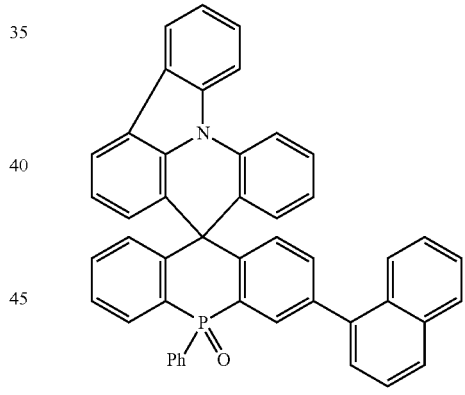
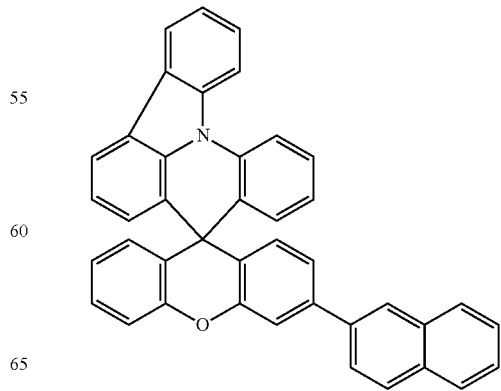

197
-continued
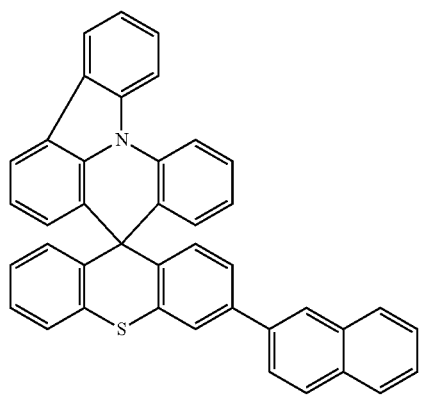
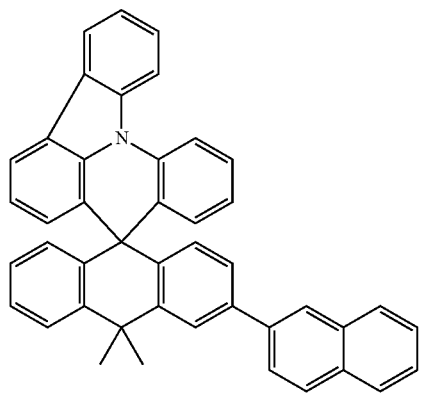
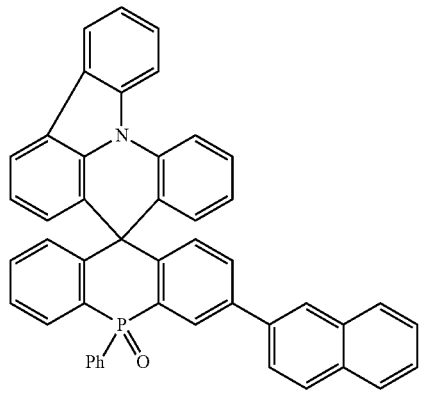
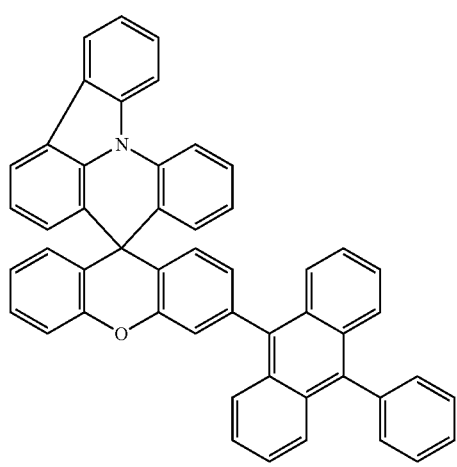
198
-continued
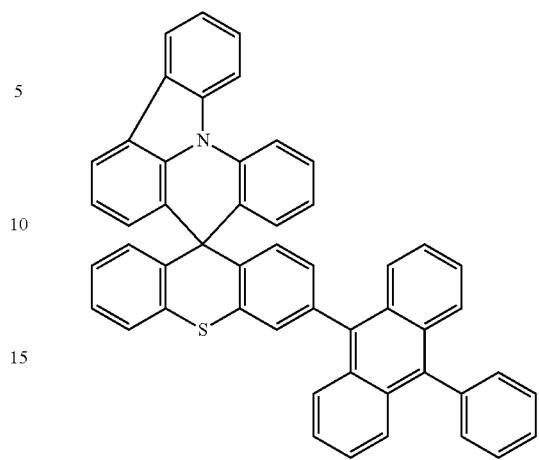
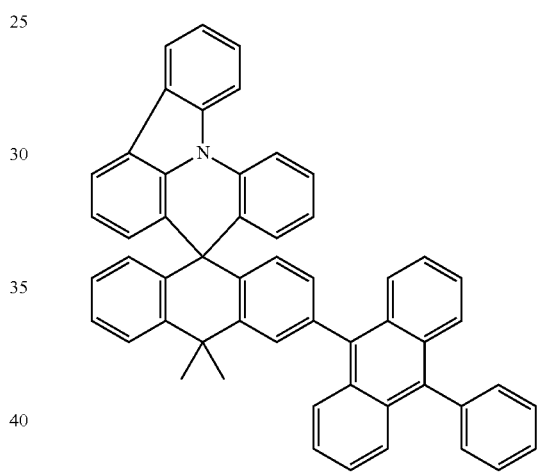

199
-continued
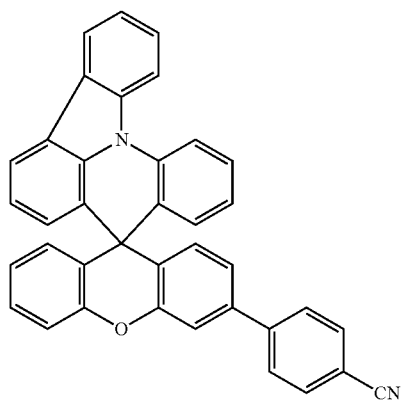
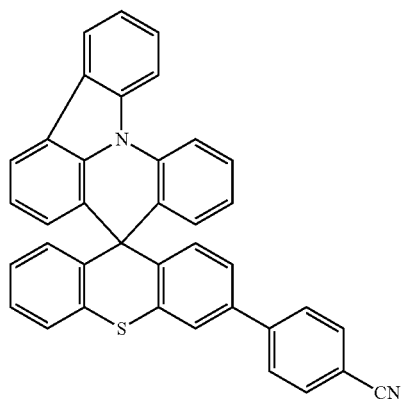
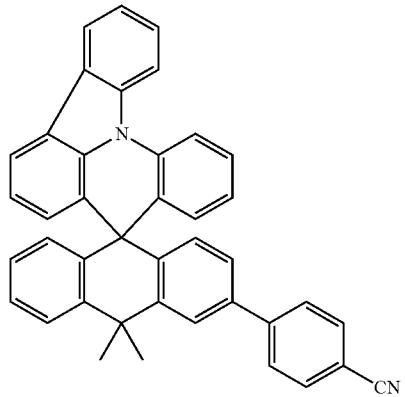
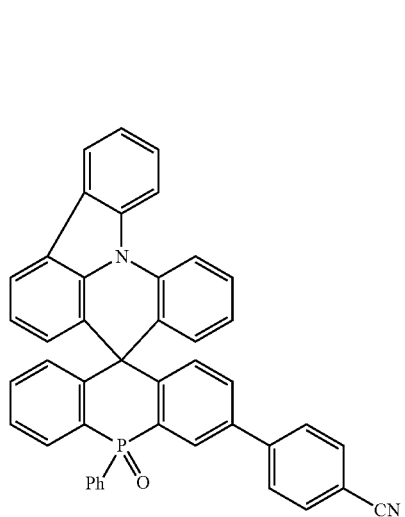
200
-continued
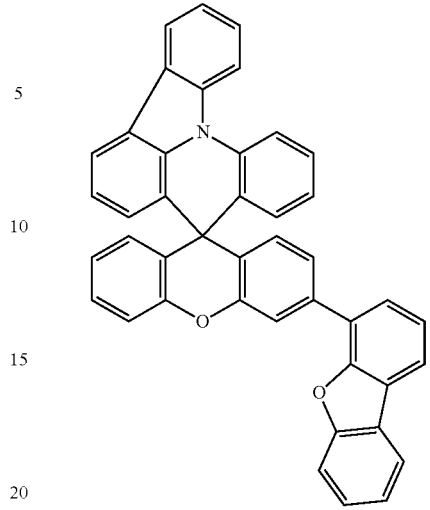
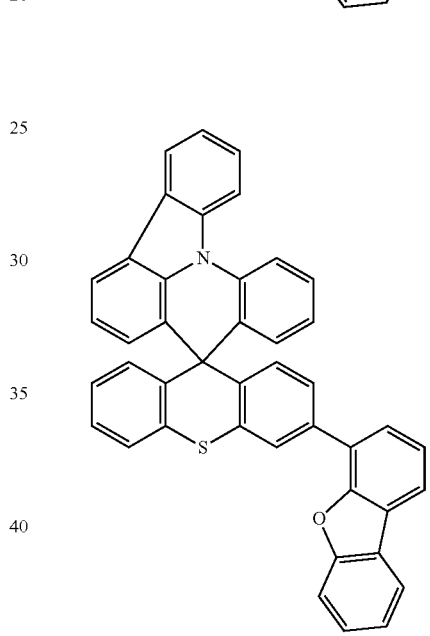
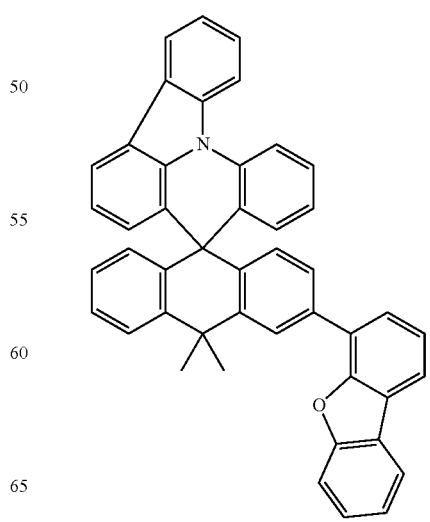

201
-continued
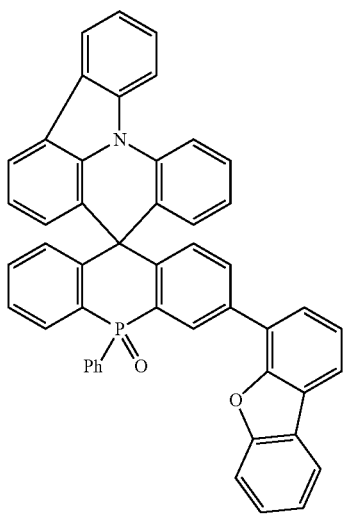
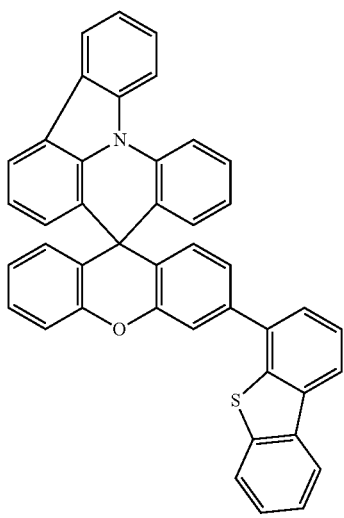
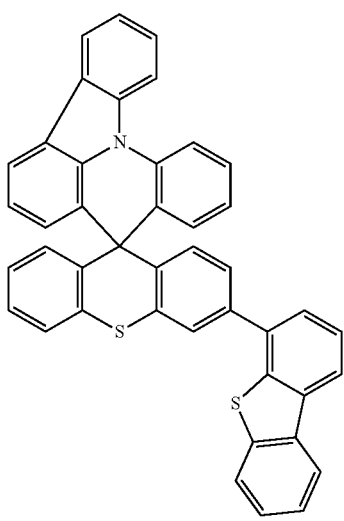
202
-continued
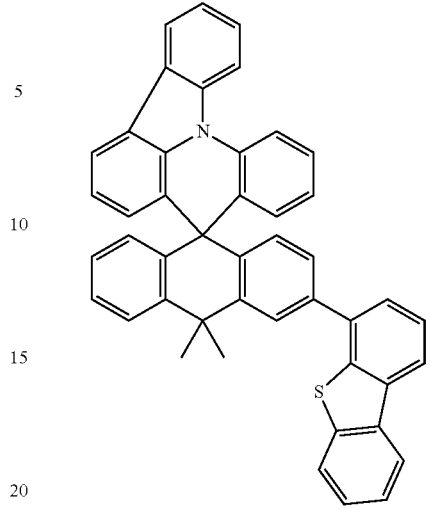
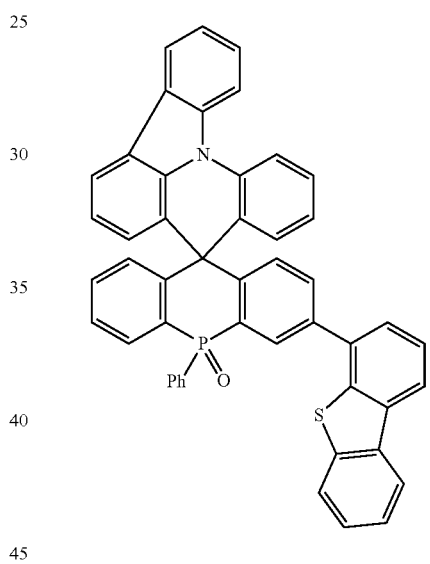
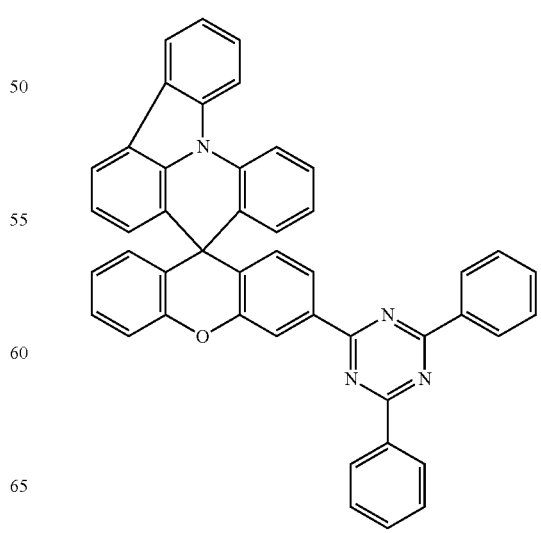

203
-continued
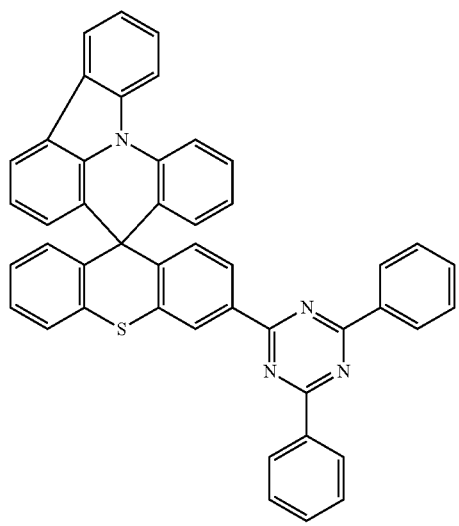
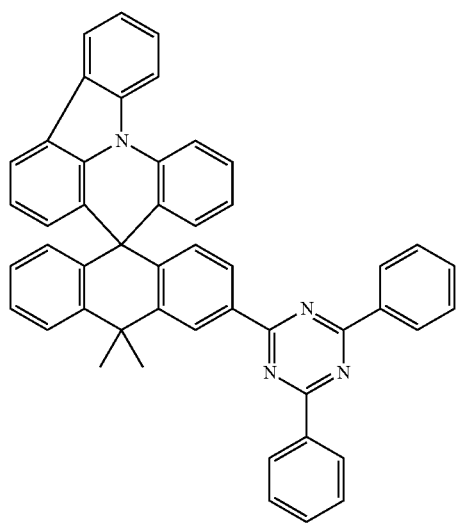
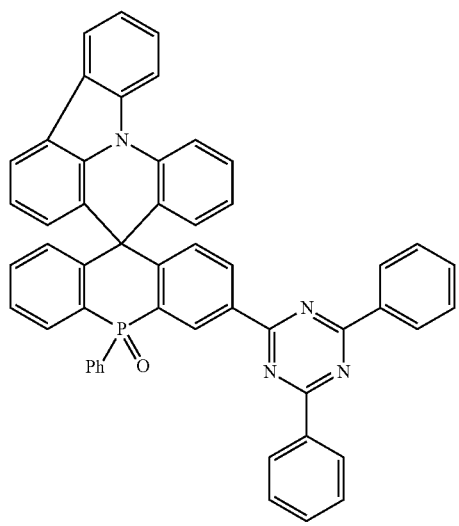
204
-continued
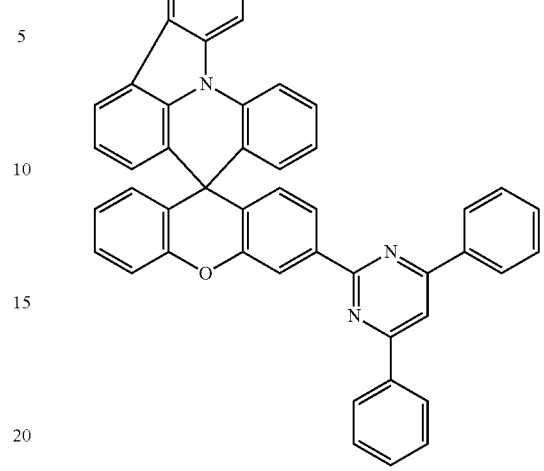
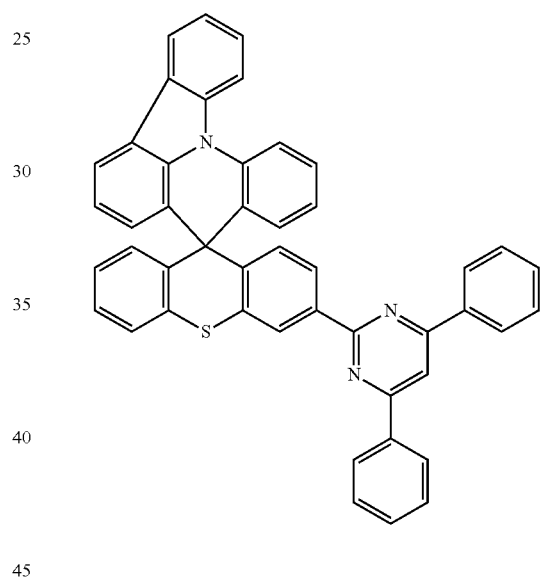
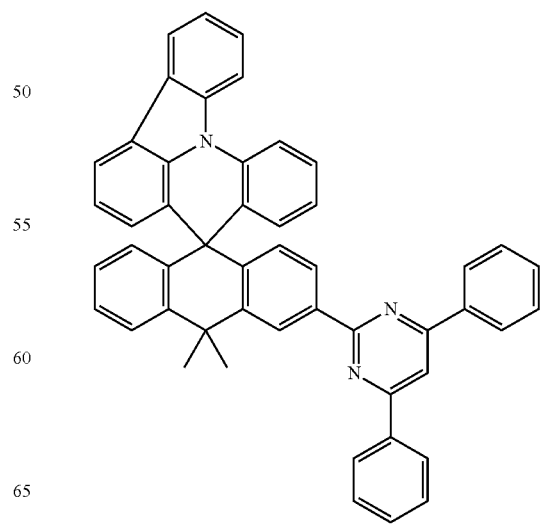

205
-continued
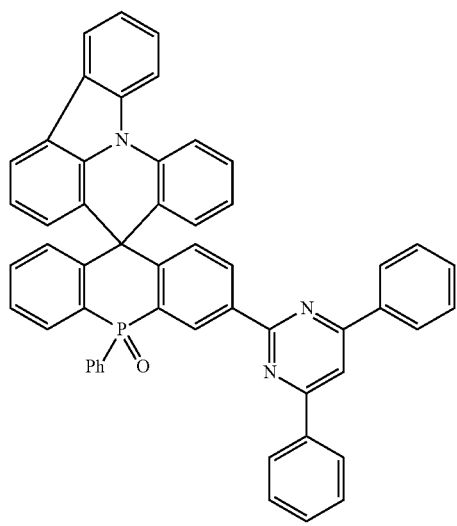
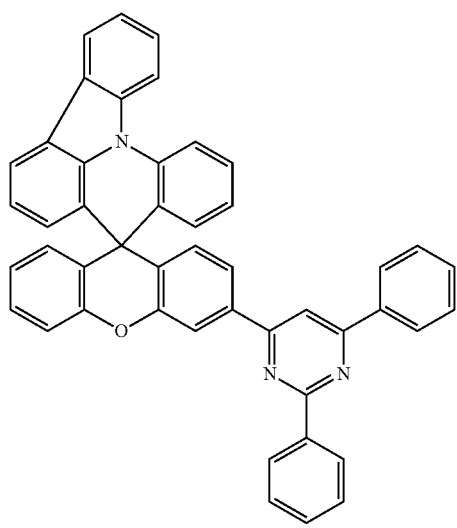
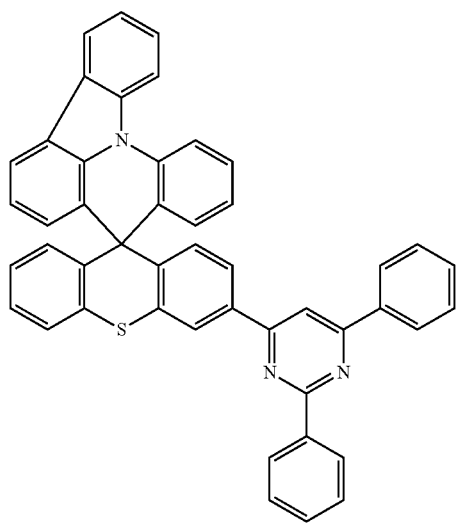
206
-continued
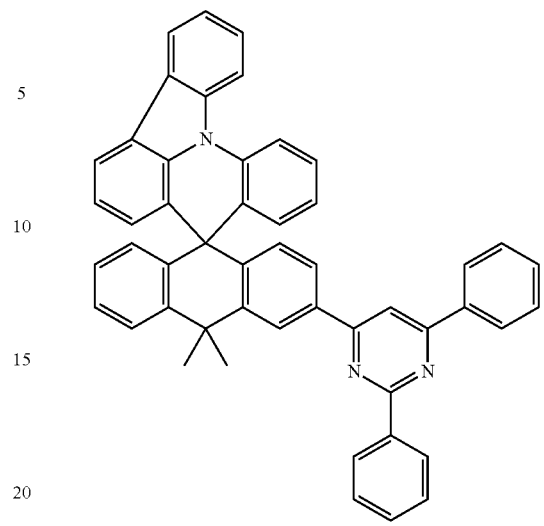
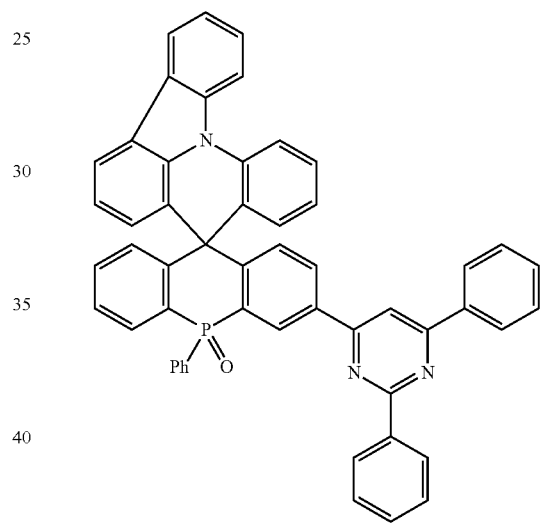
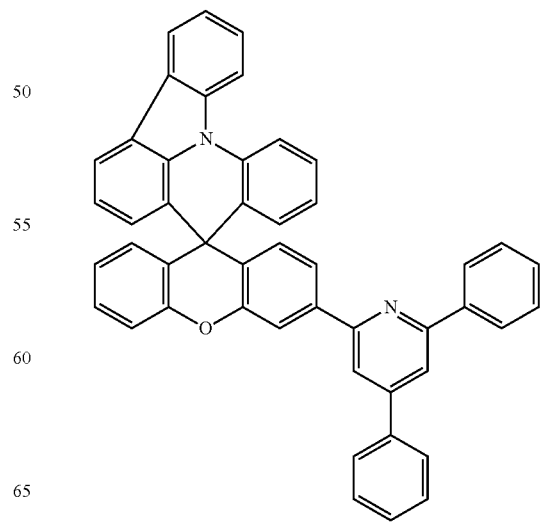

207
-continued
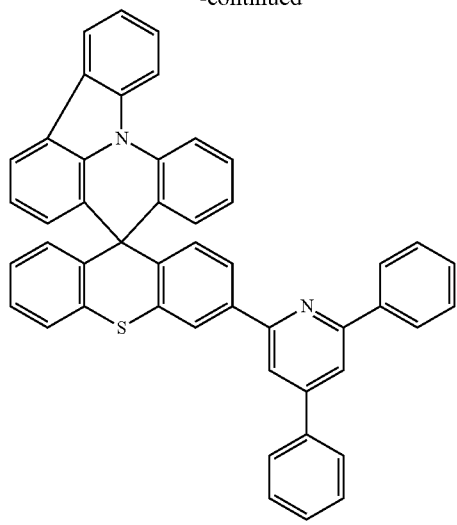
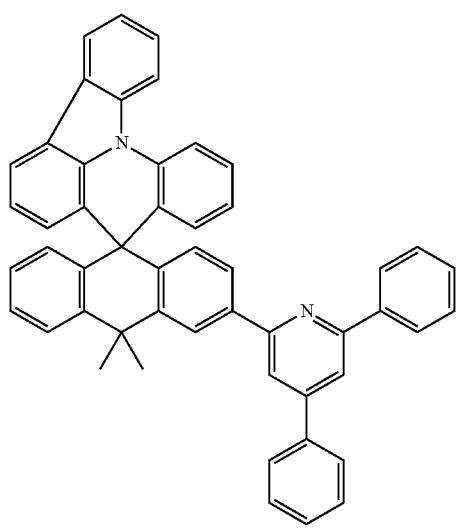
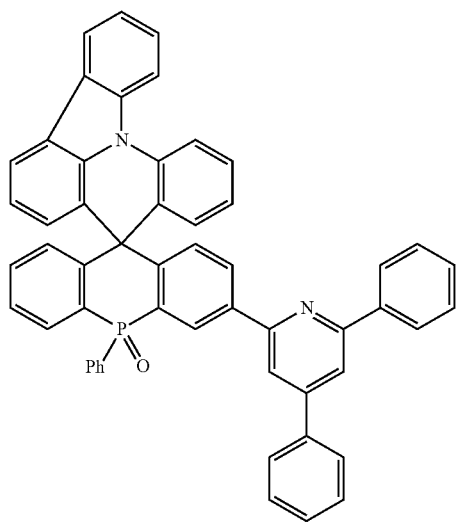
208
-continued
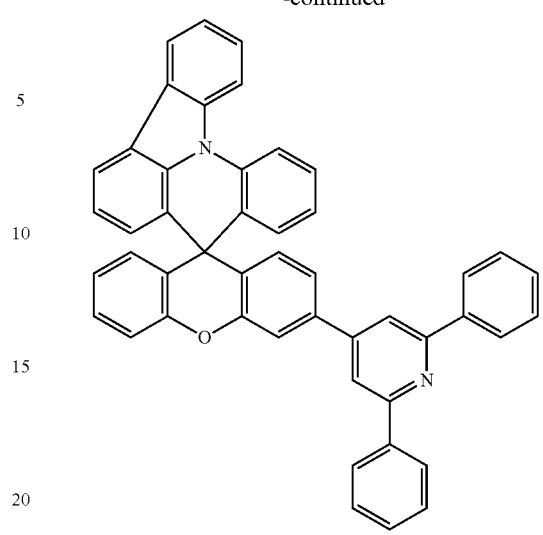
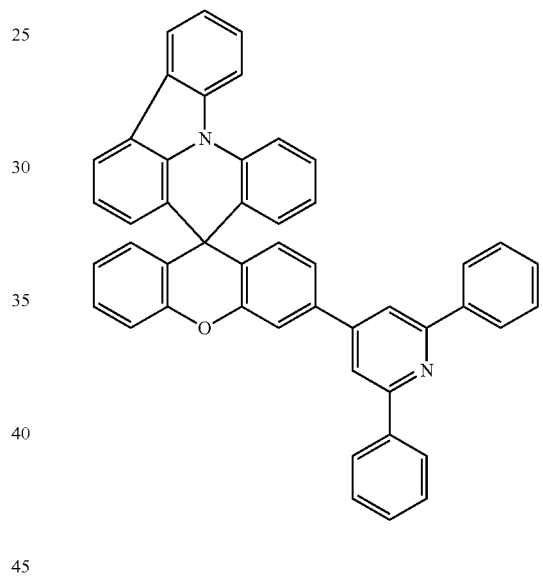
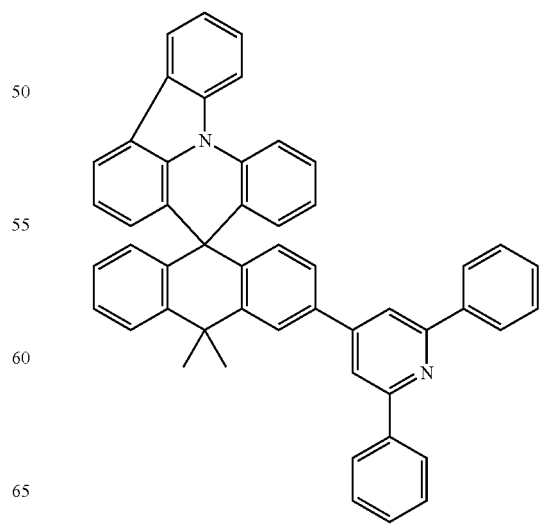

209
-continued
210
-continued
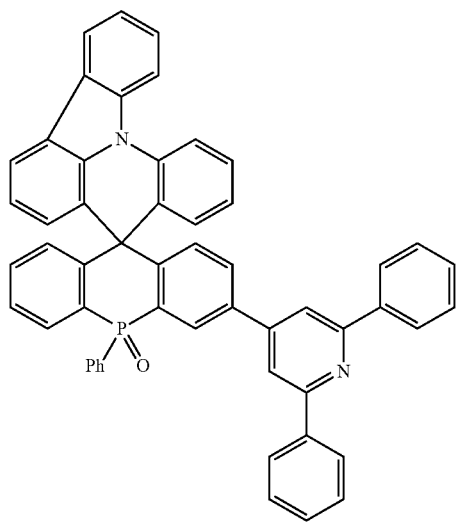
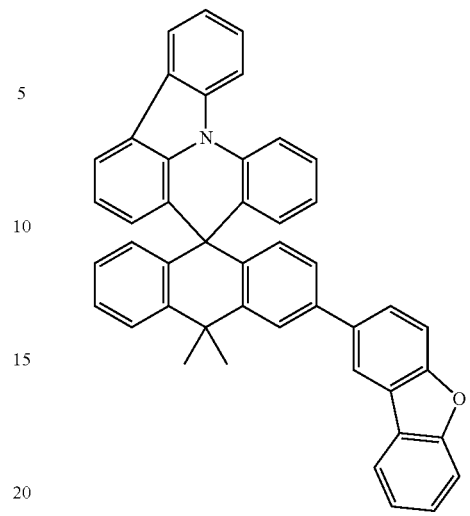
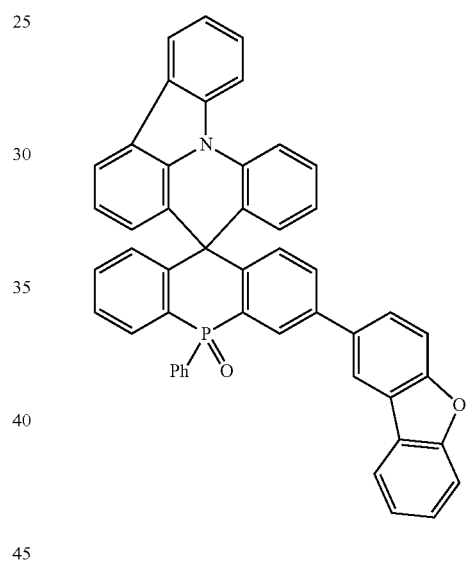
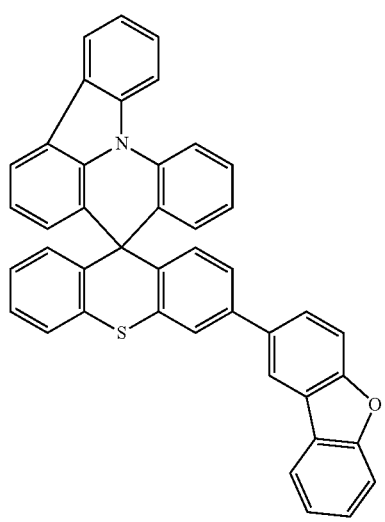
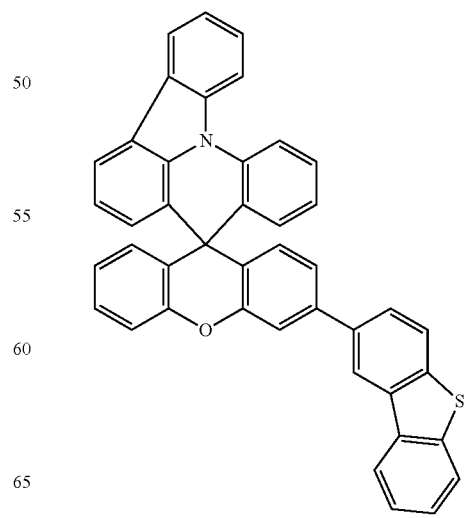

211
-continued
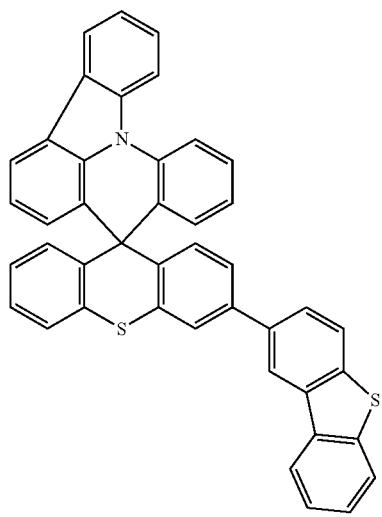
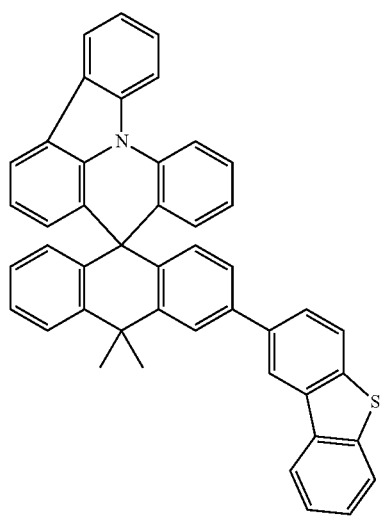
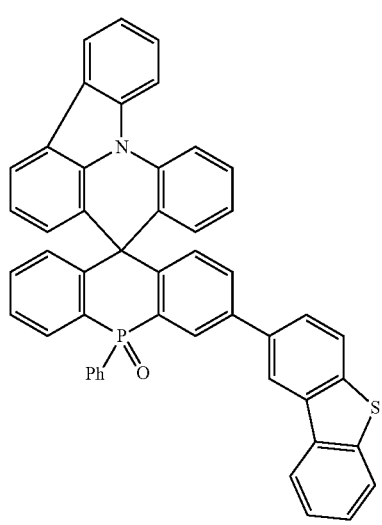
212
-continued
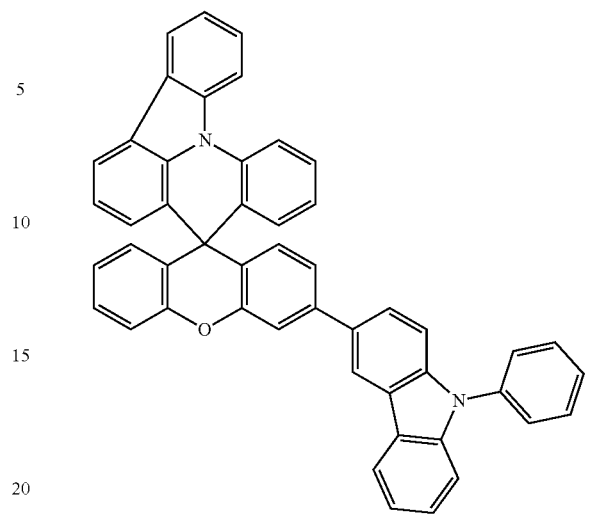
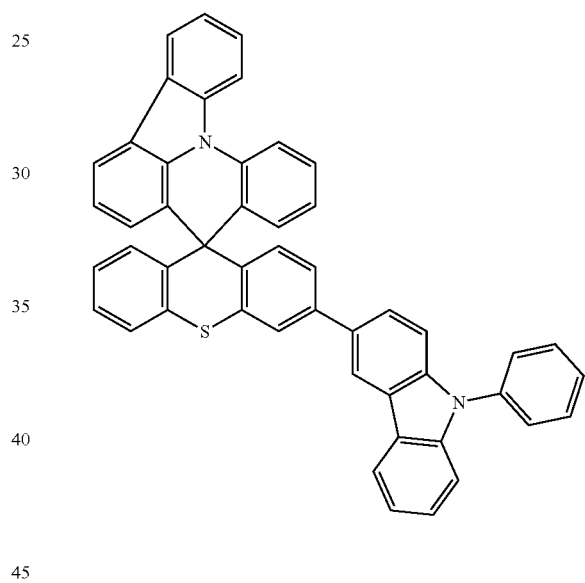

213
-continued
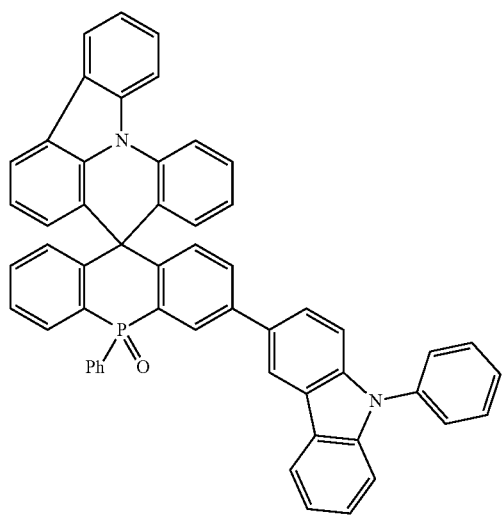
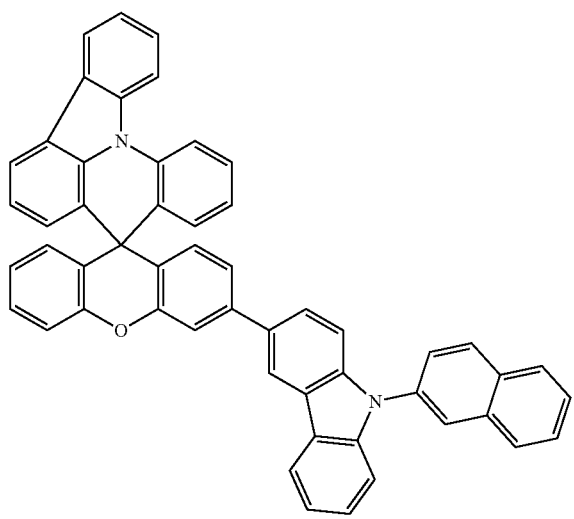
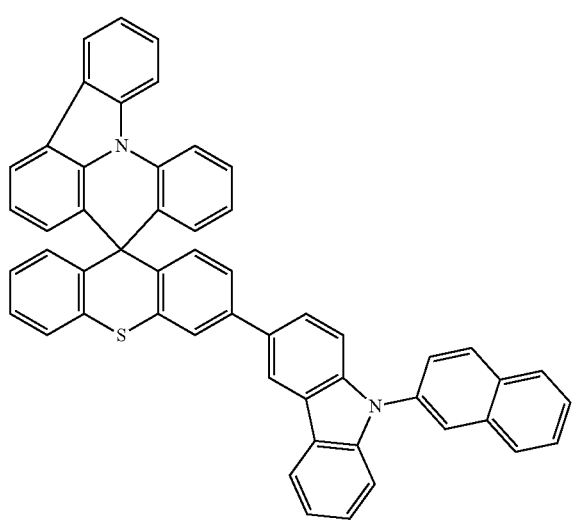
214
-continued
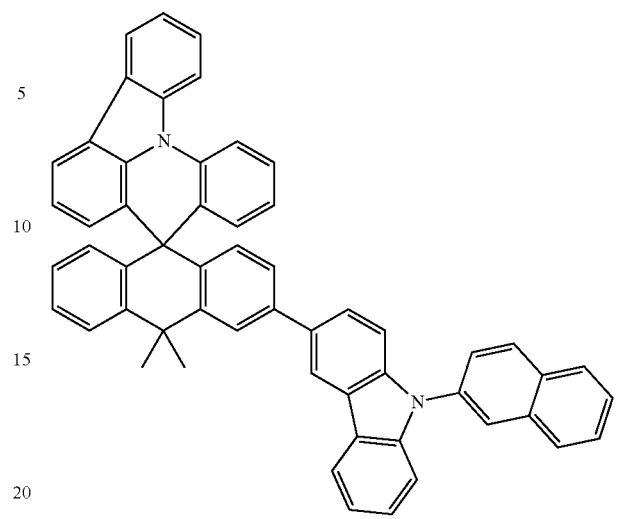
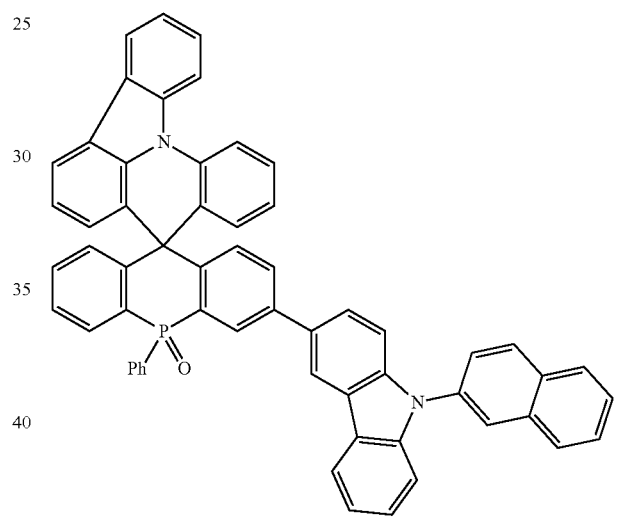
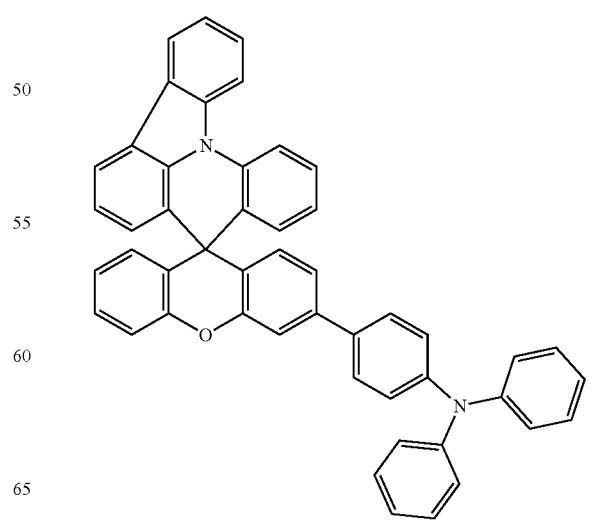

215
-continued
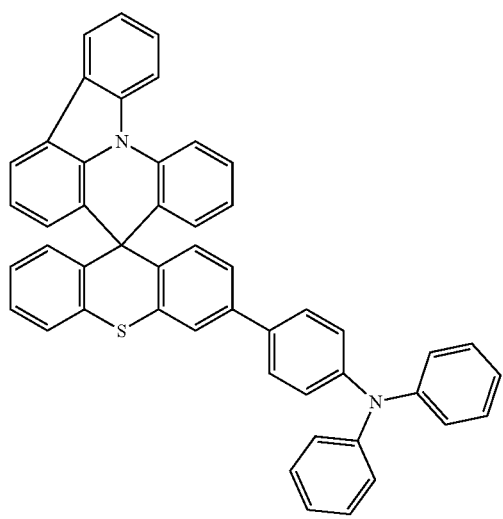
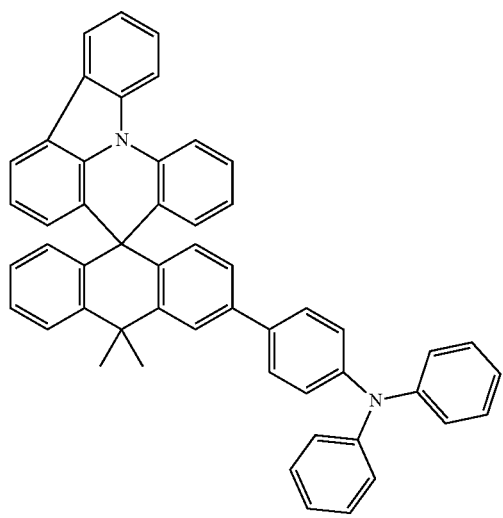
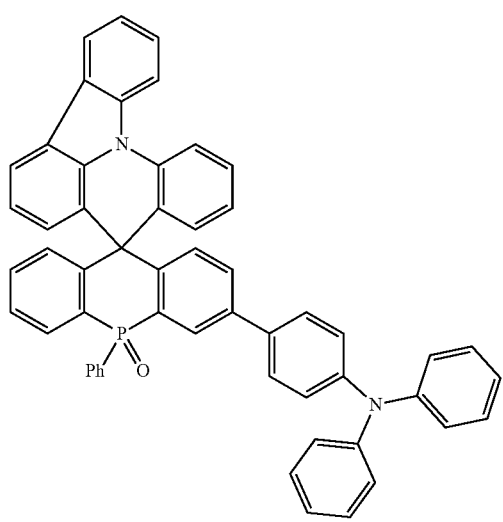
216
-continued
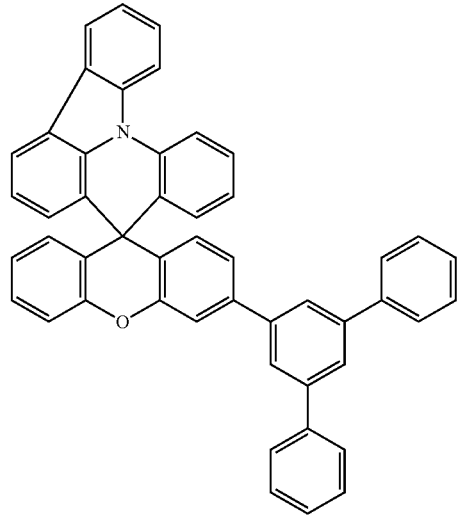
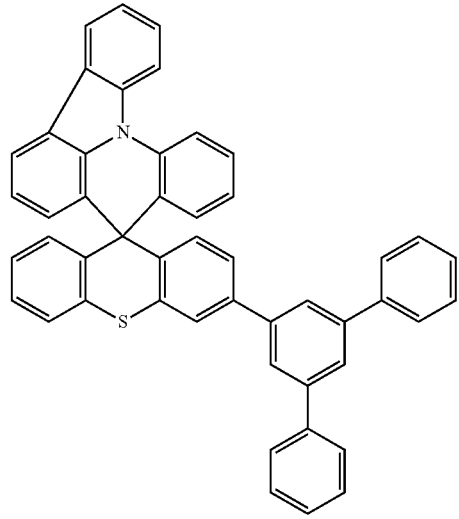
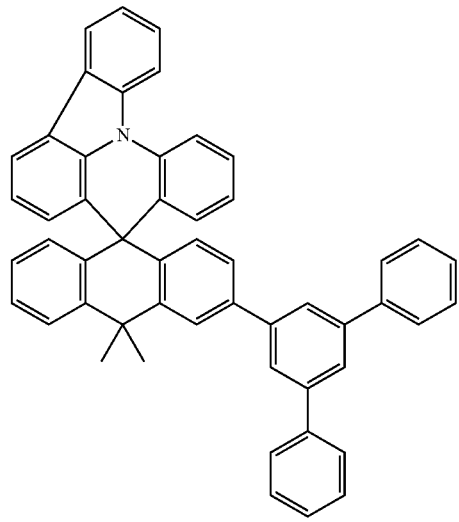

217
-continued
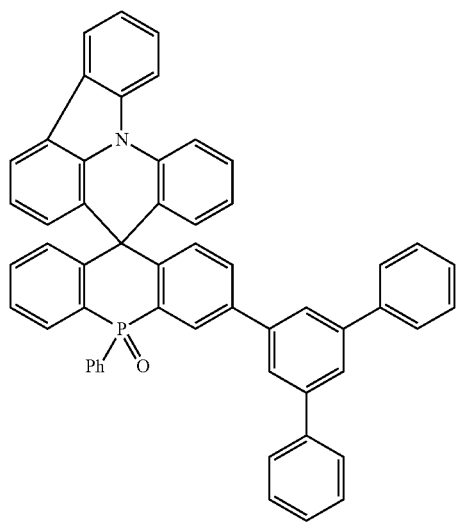
218
-continued
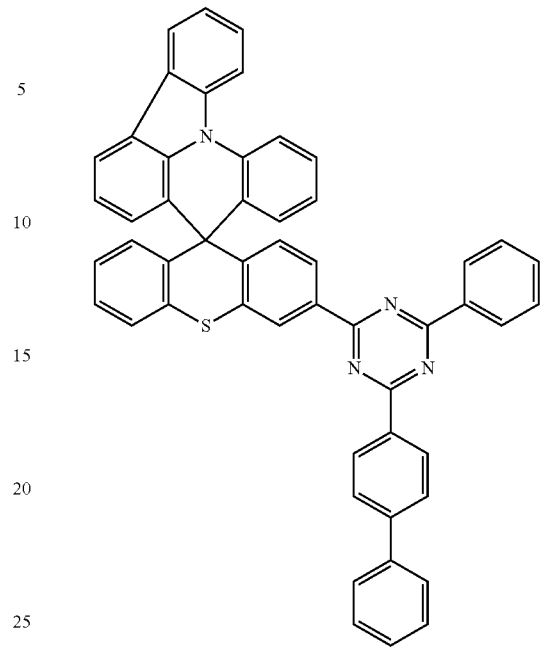
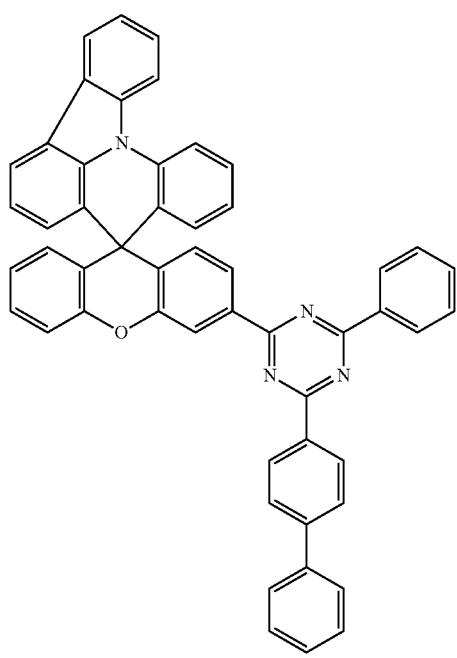
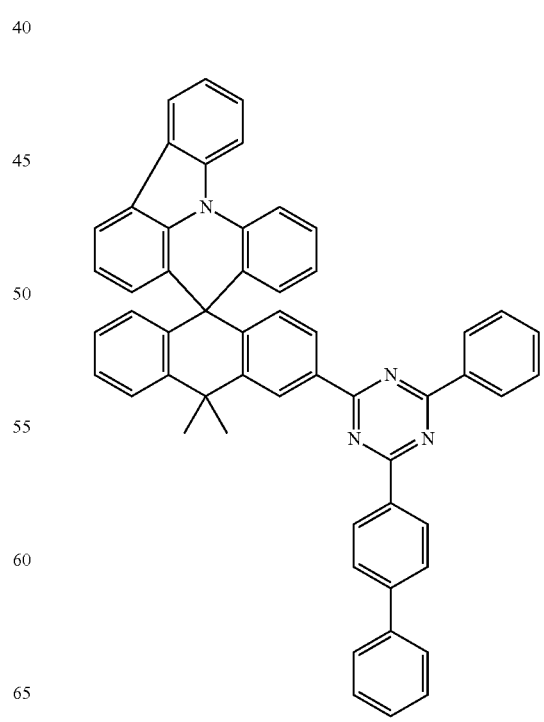

219
-continued
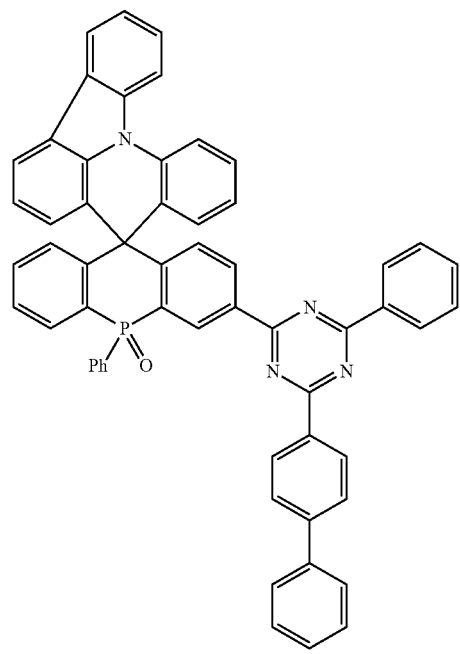
220
-continued
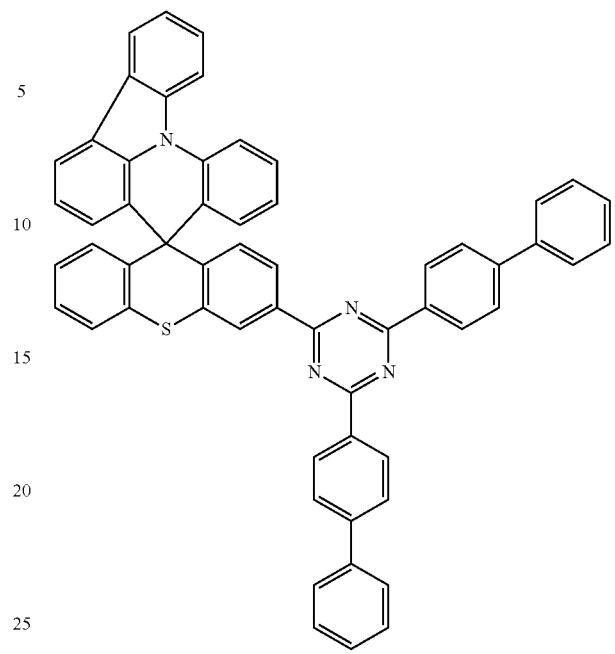
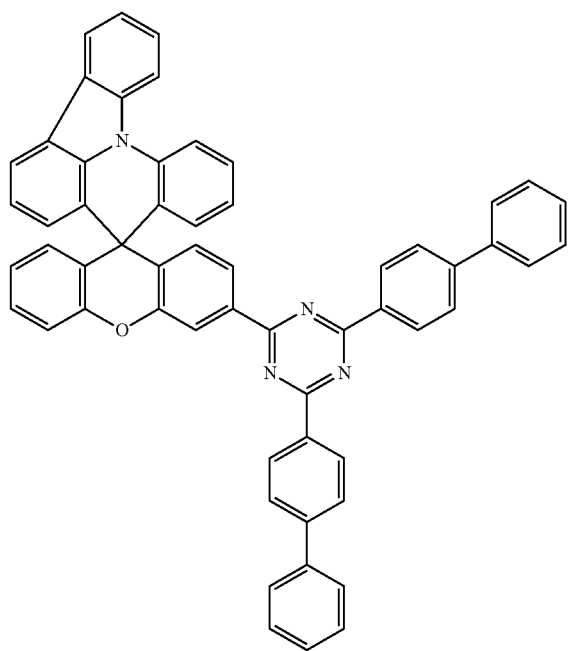

221
-continued
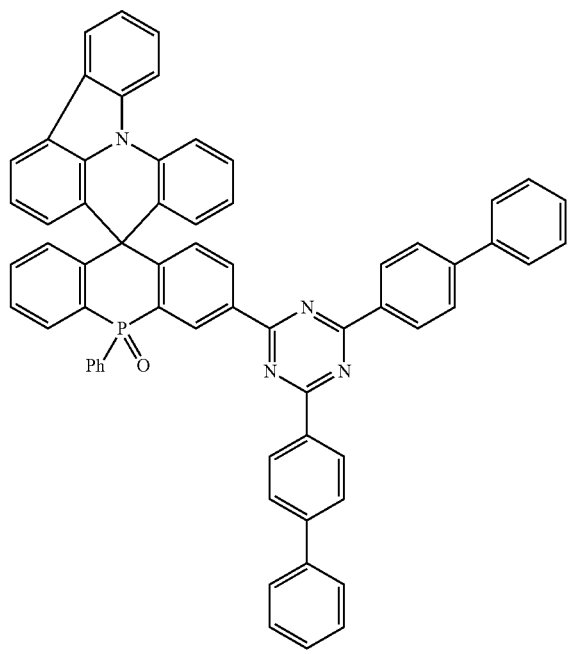
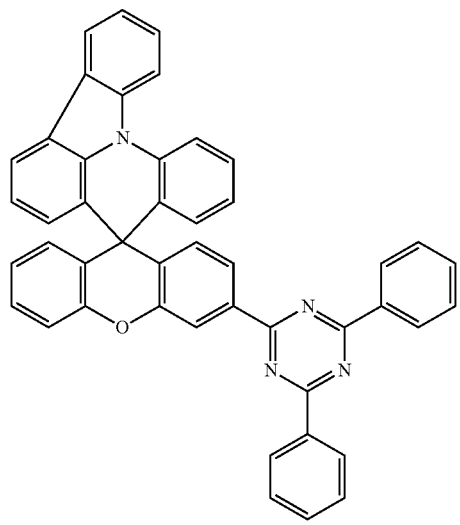
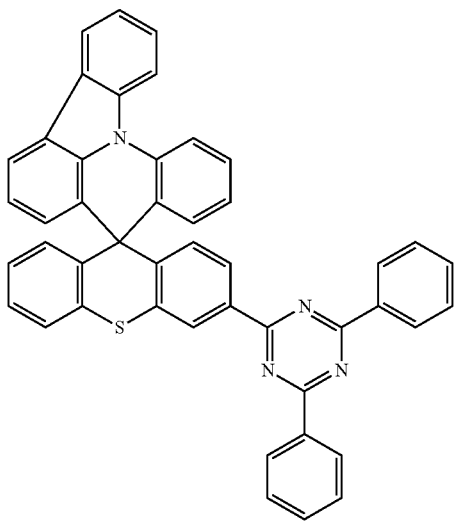
222
-continued
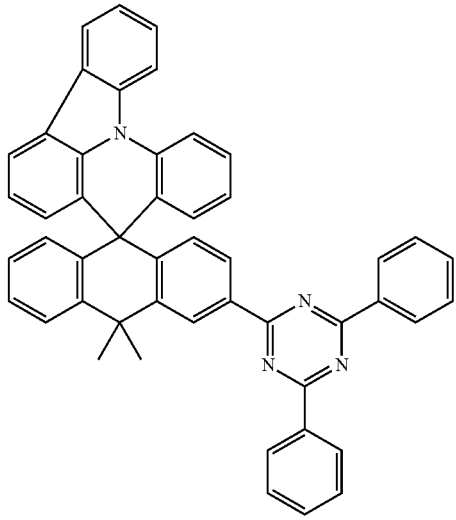
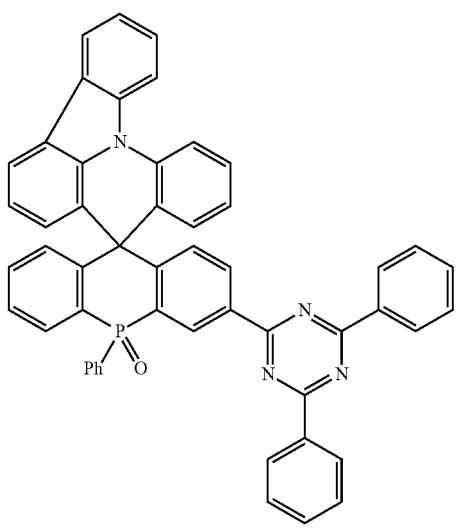
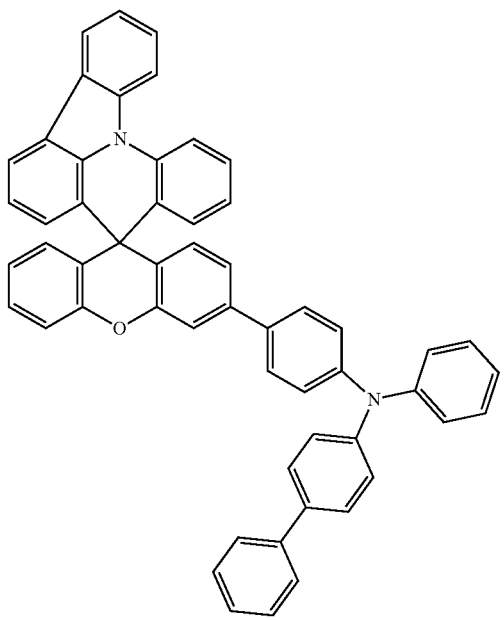

223
-continued
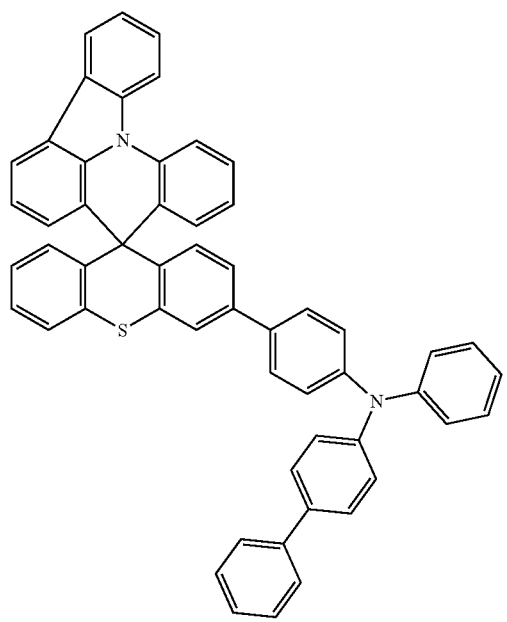
224
-continued
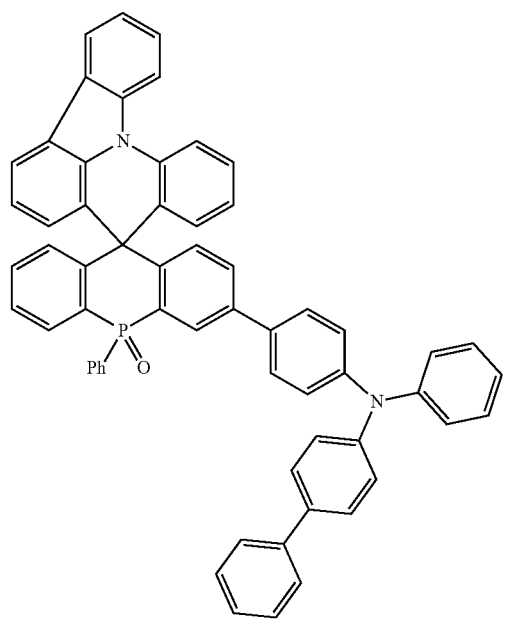
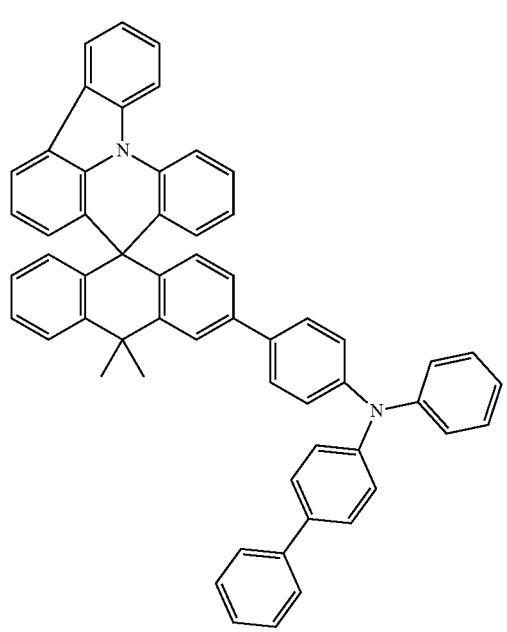
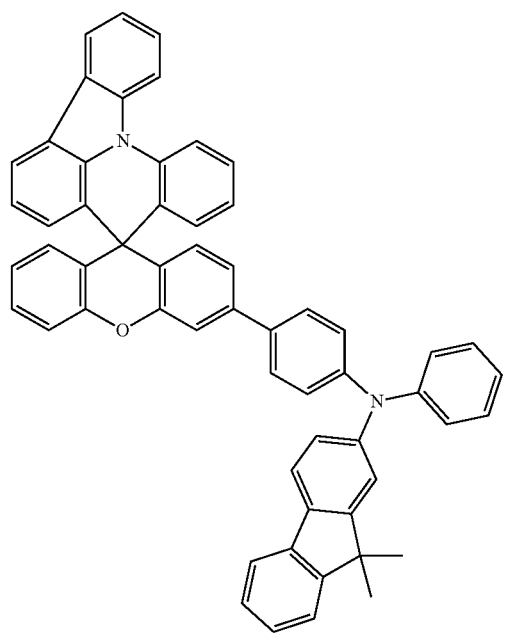

225
-continued
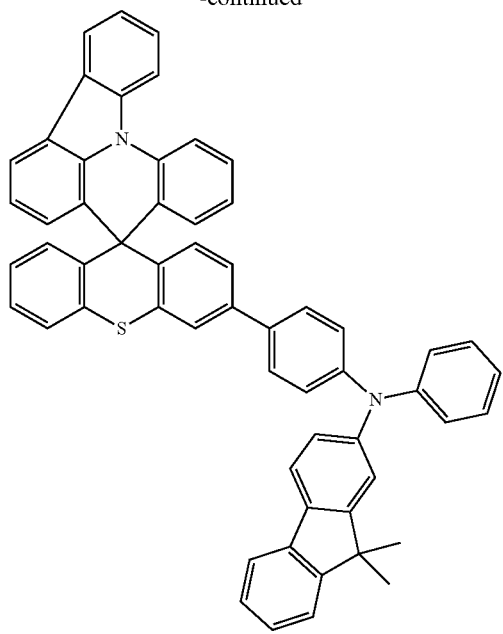
226
-continued
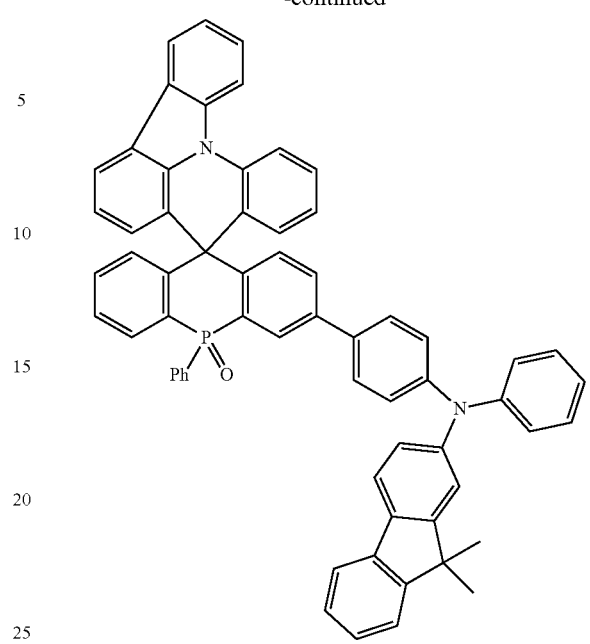
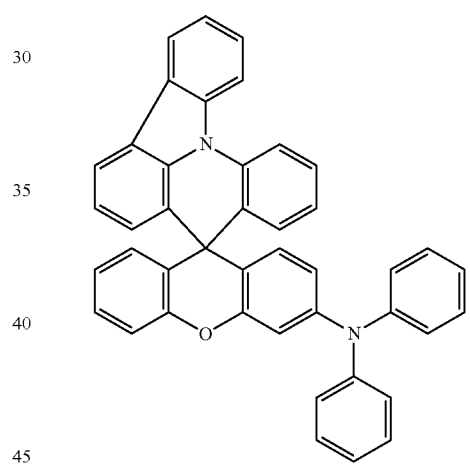
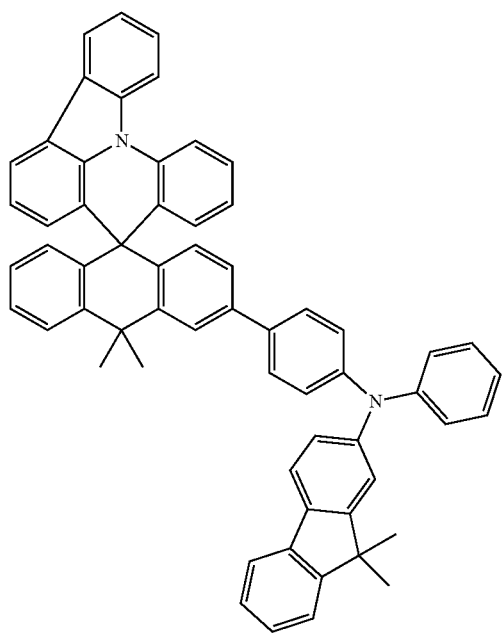
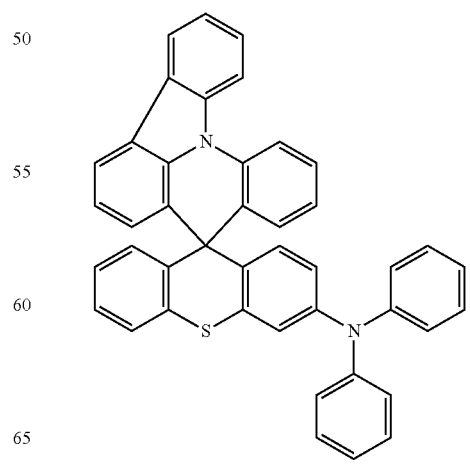

227
-continued
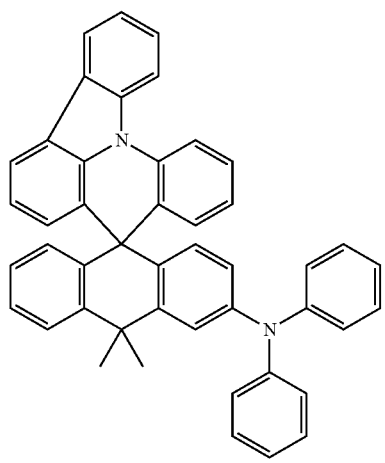
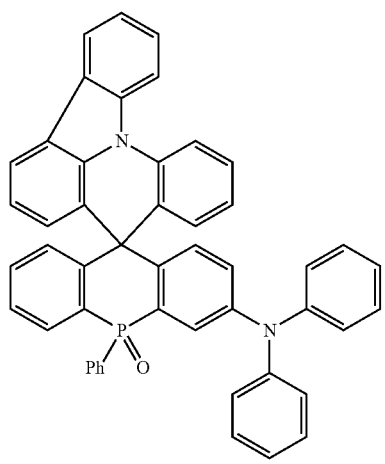
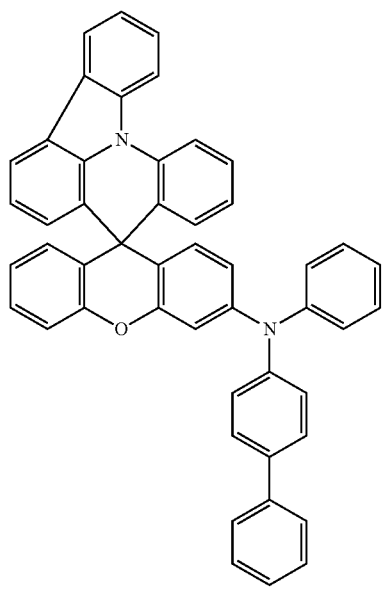
228
-continued
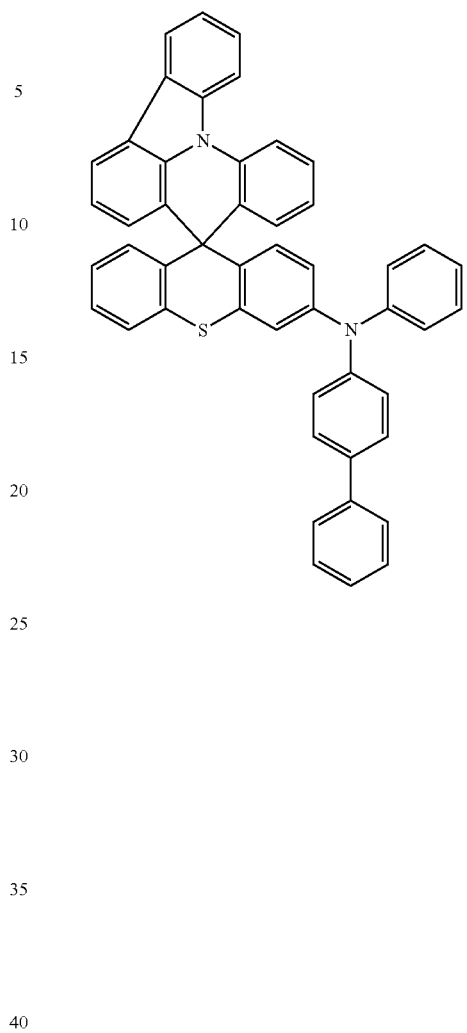
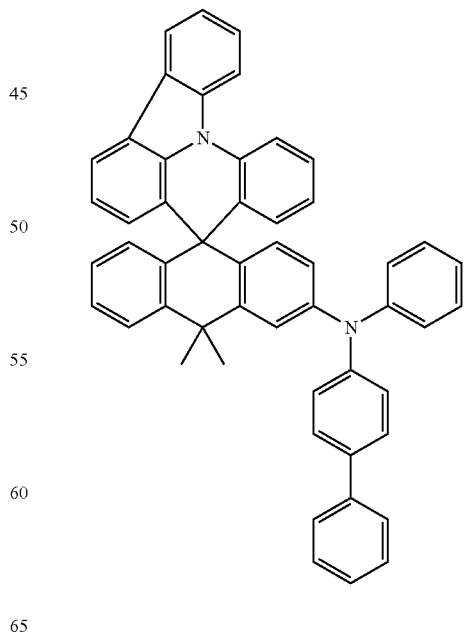

229
-continued
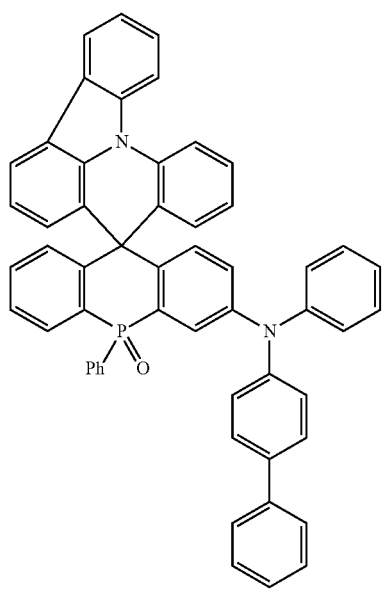
230
-continued
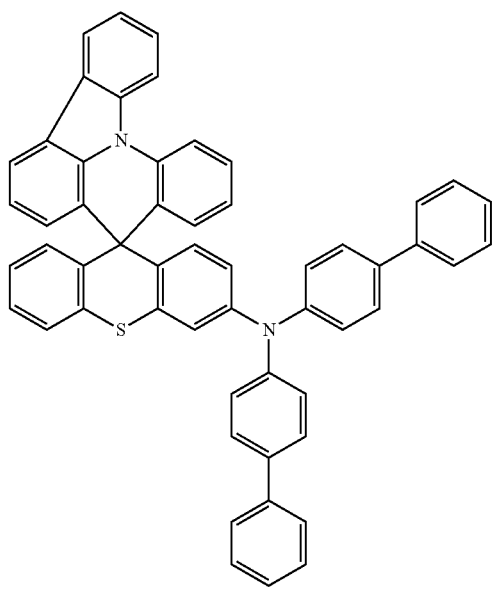
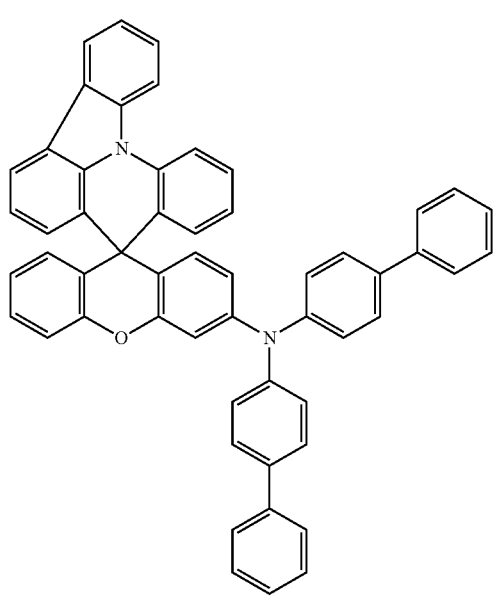

231
-continued
232
-continued
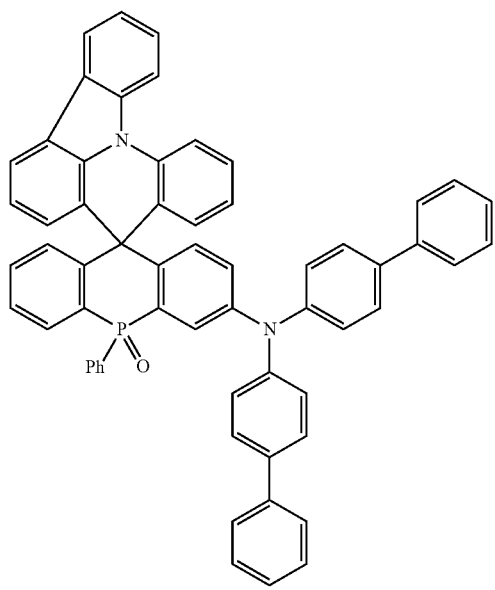
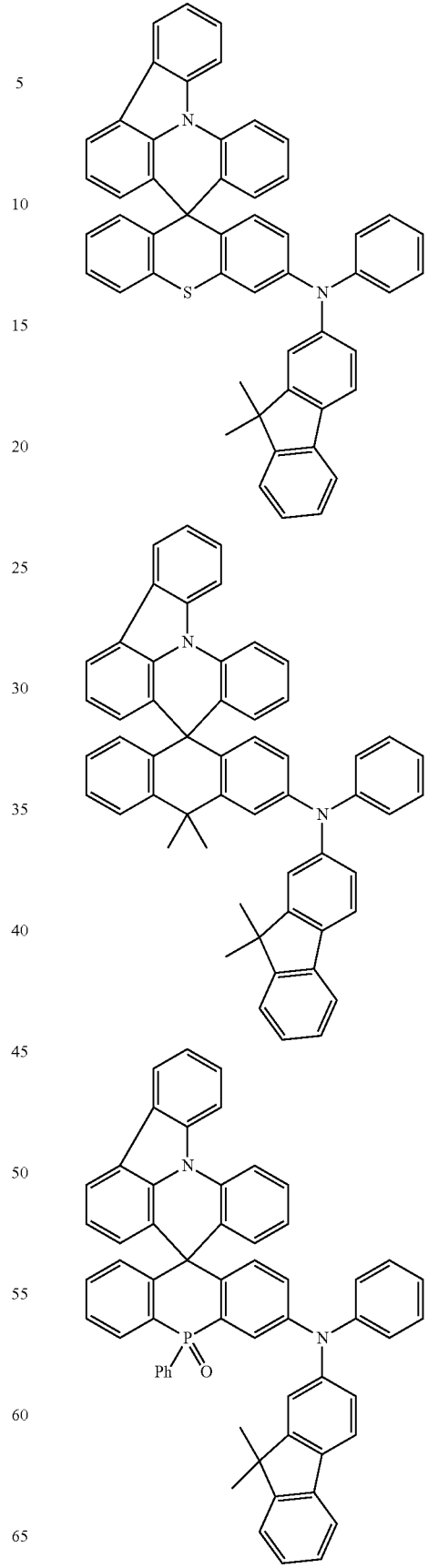
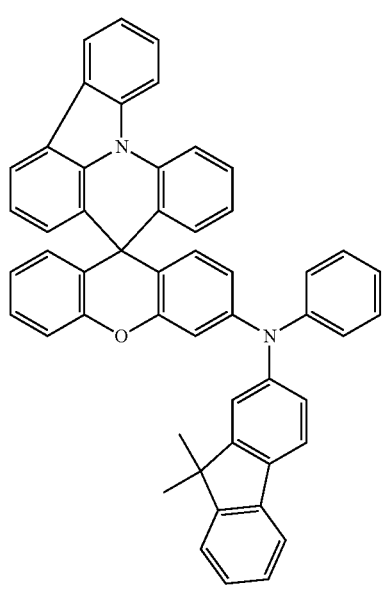

233
-continued
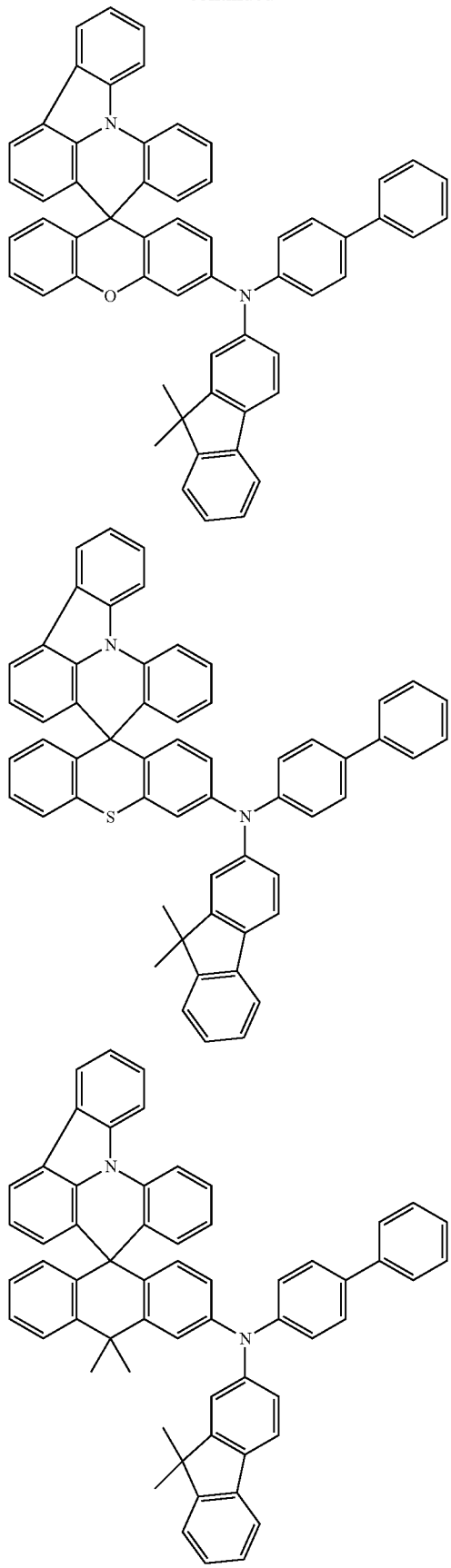
234
-continued
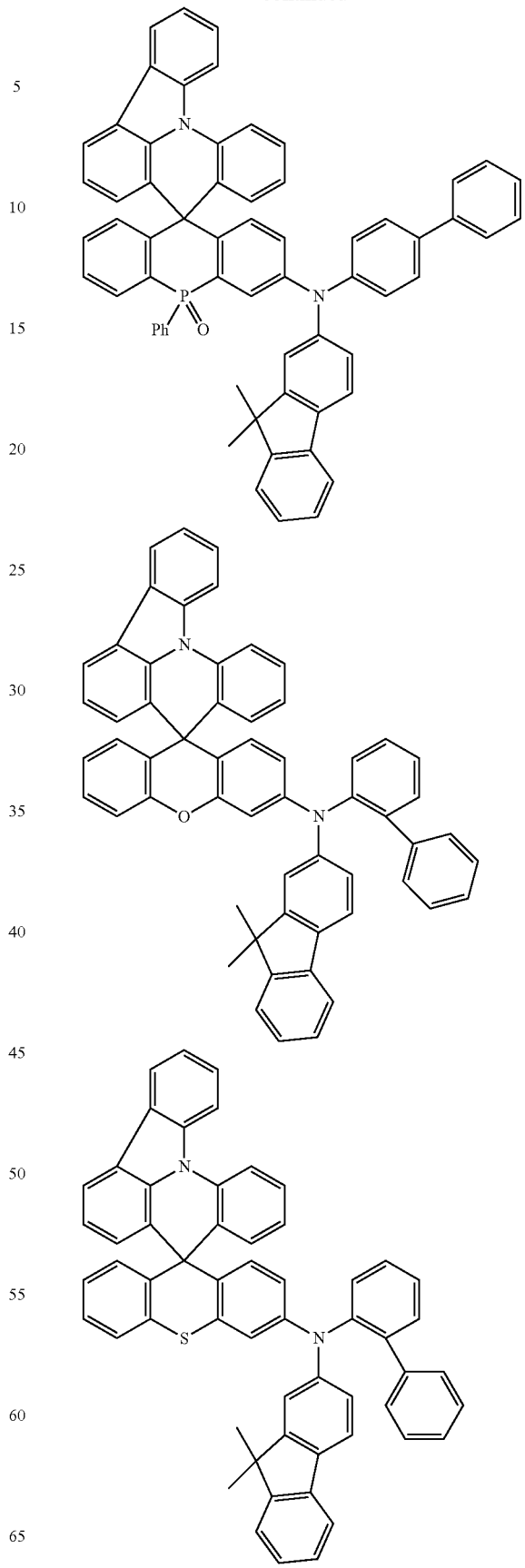

235
-continued
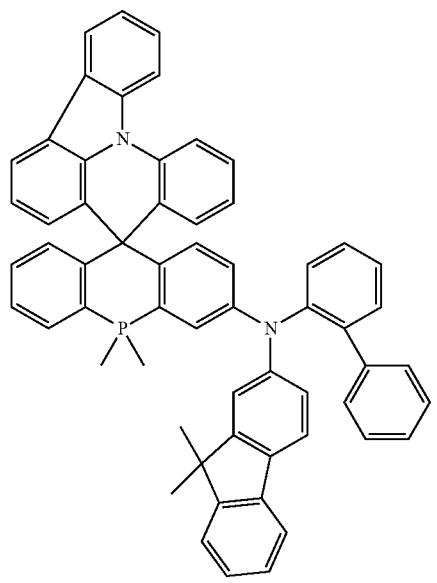
236
-continued
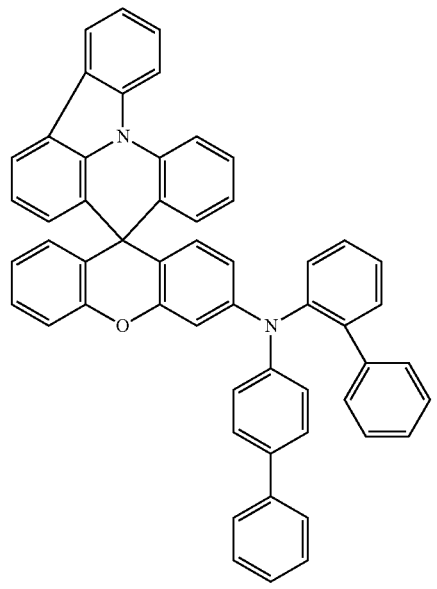
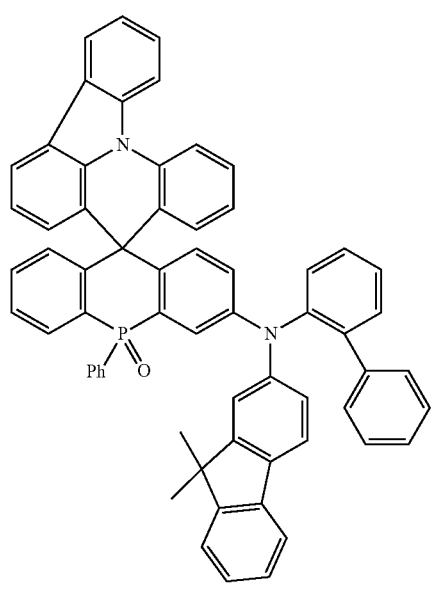

237
-continued
238
-continued
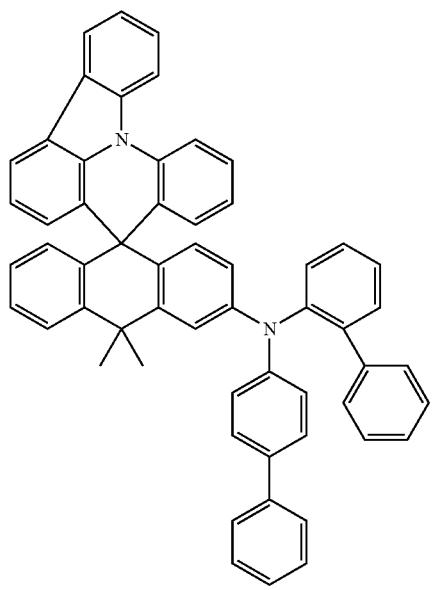
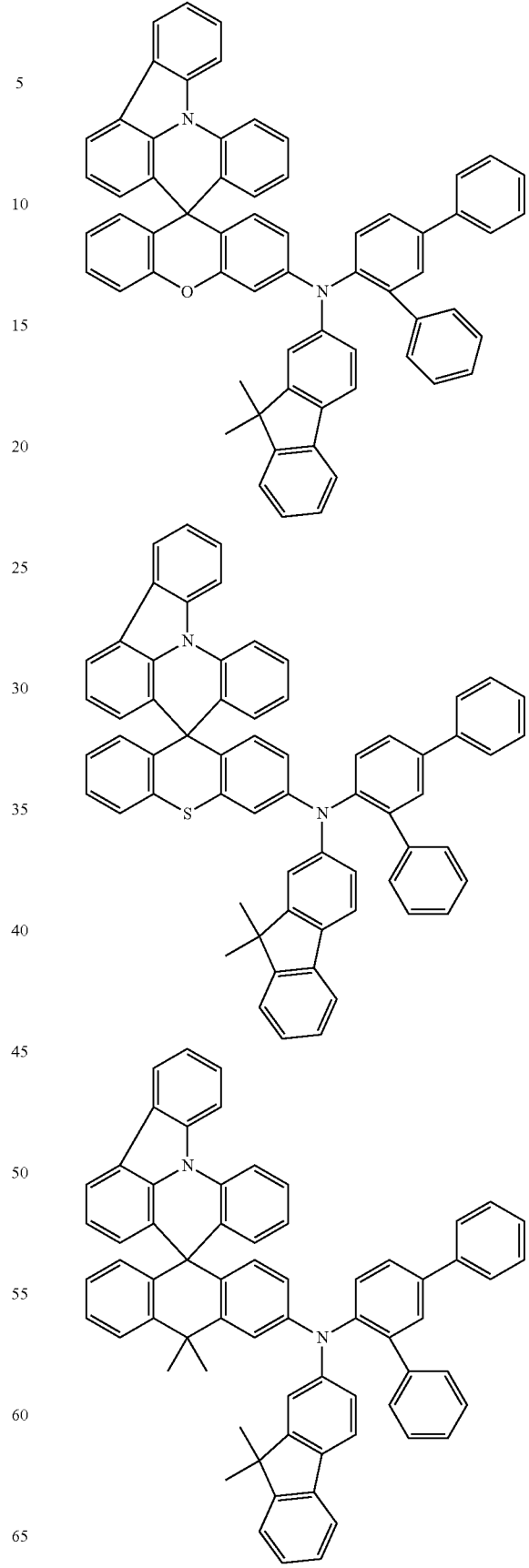
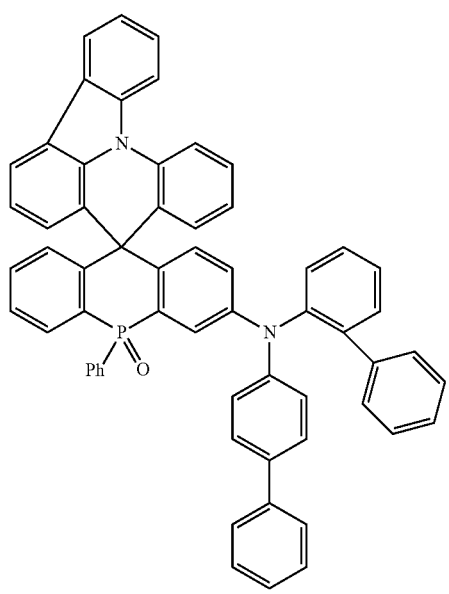

239
-continued
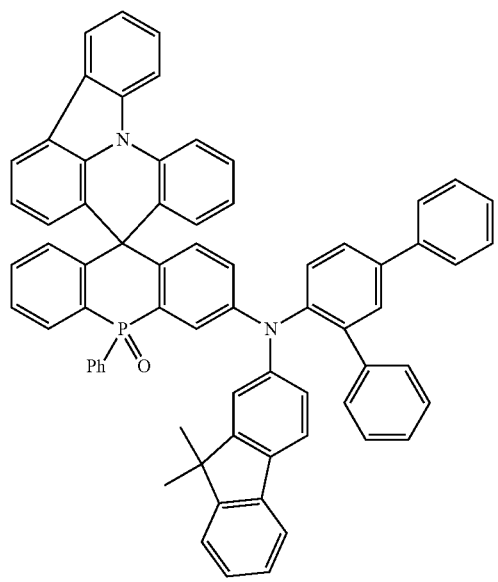
240
-continued
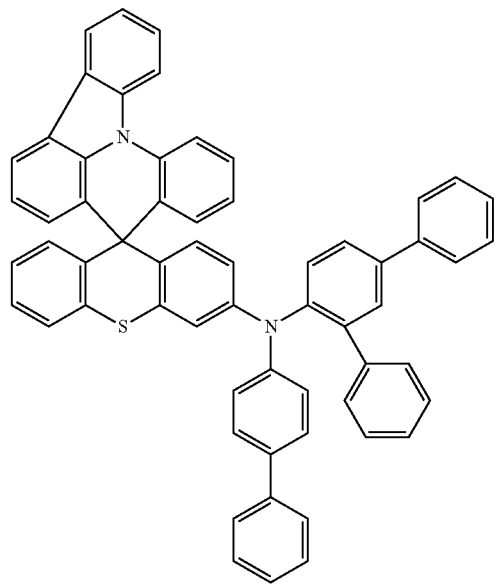
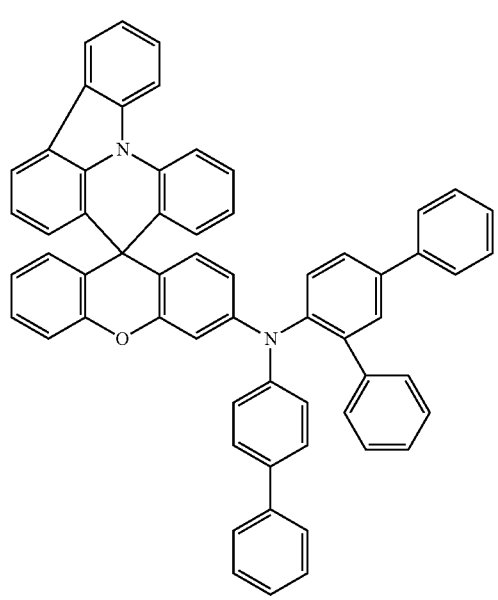
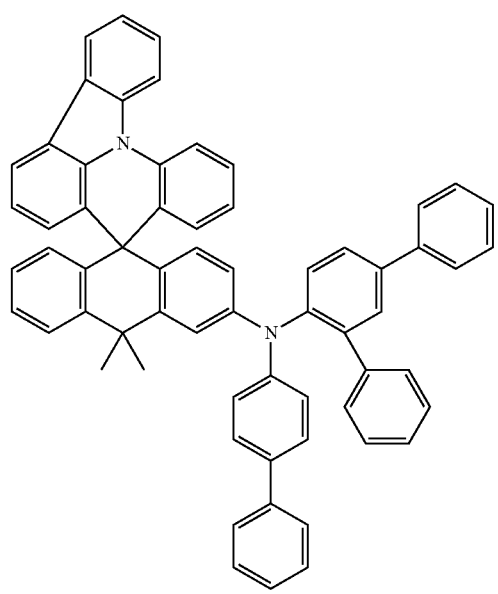

241
-continued
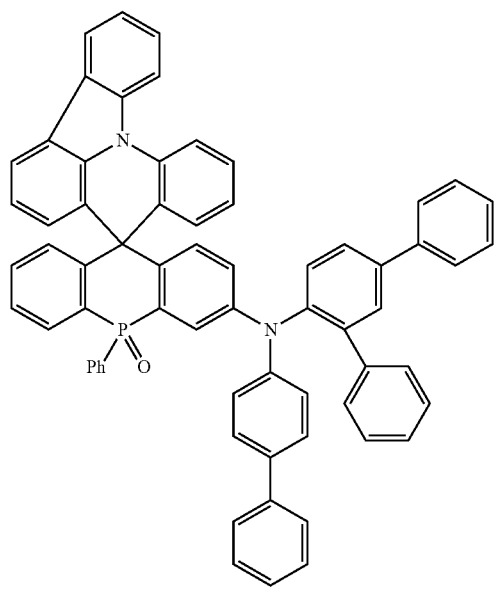
242
-continued
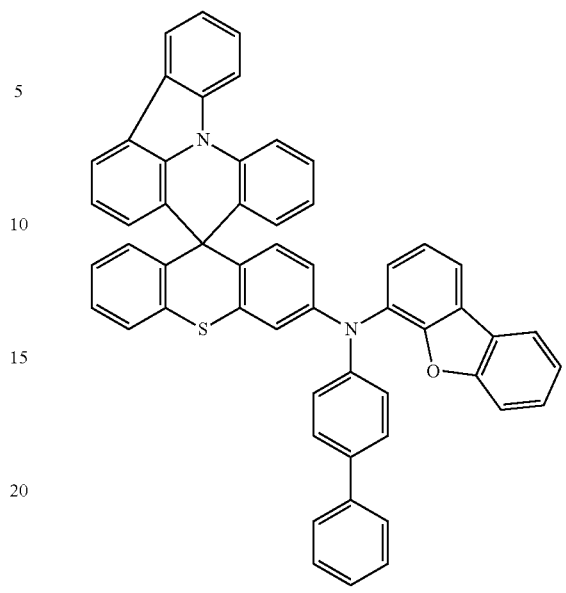
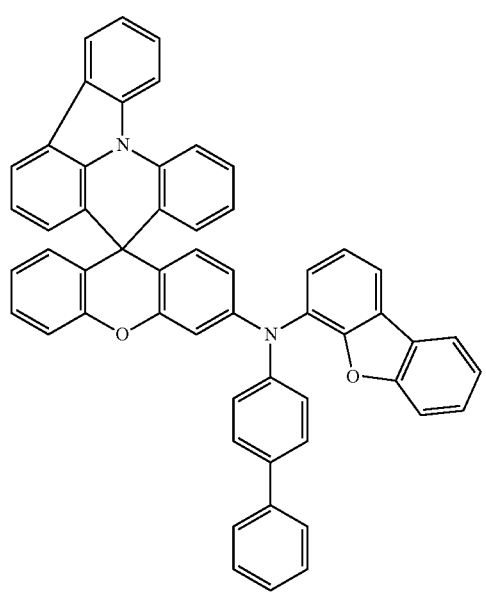
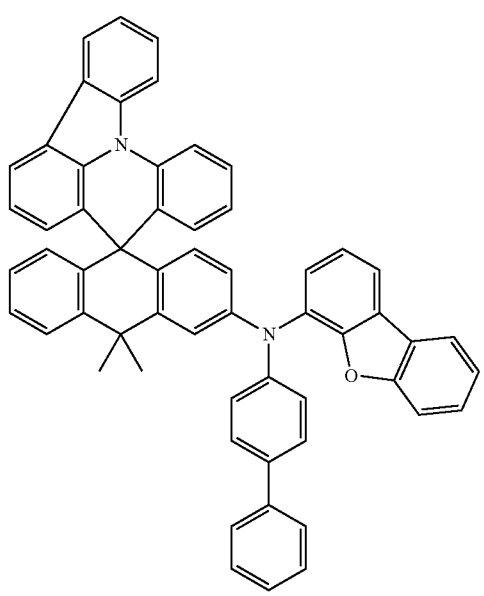

243
-continued
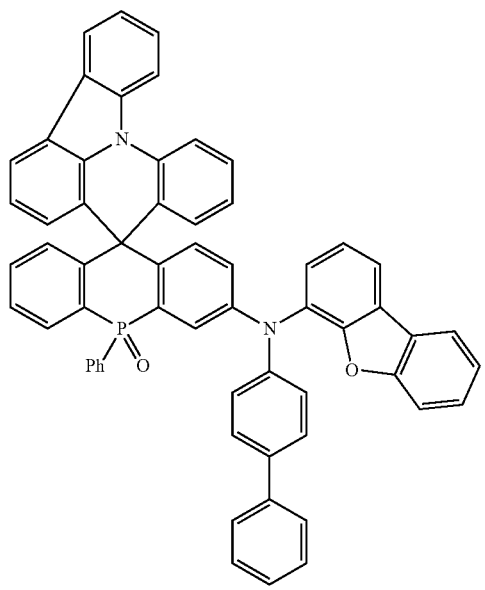
244
-continued
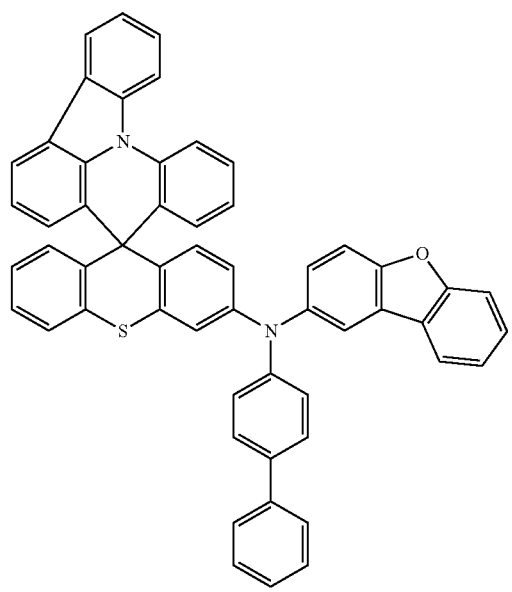
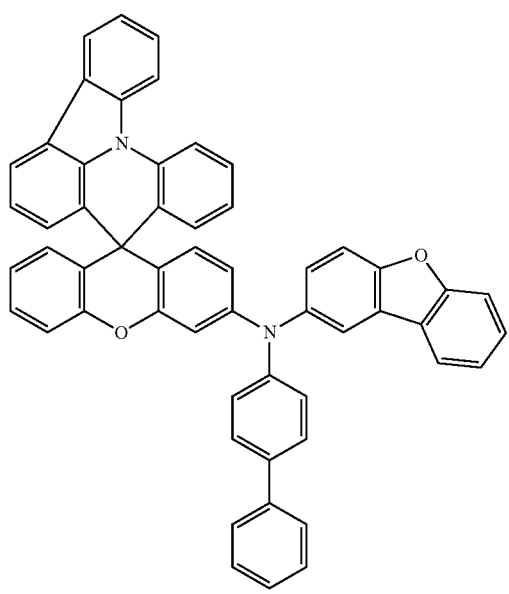
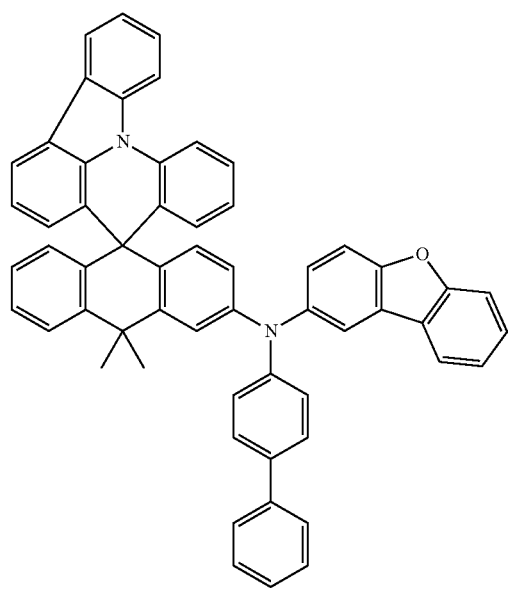

245
-continued
246
-continued
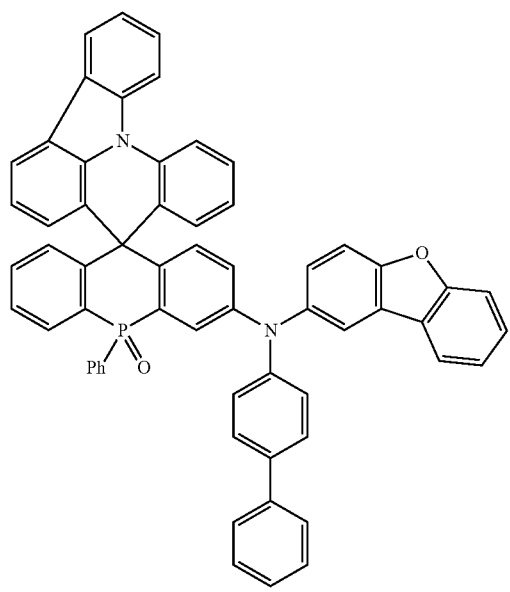
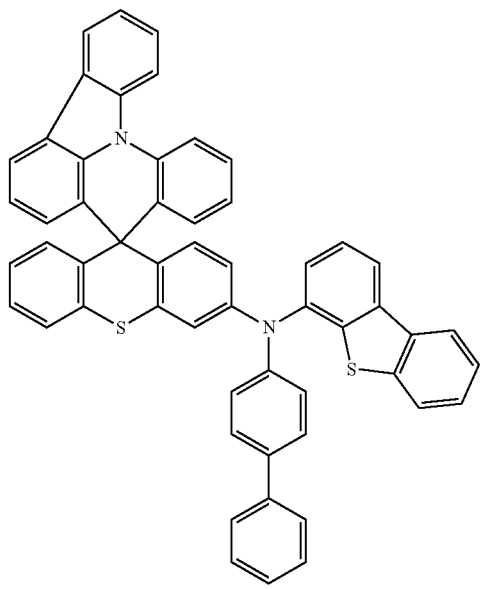
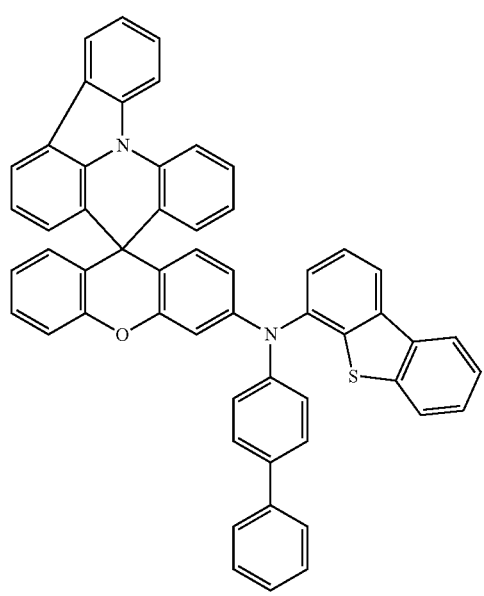

247
-continued
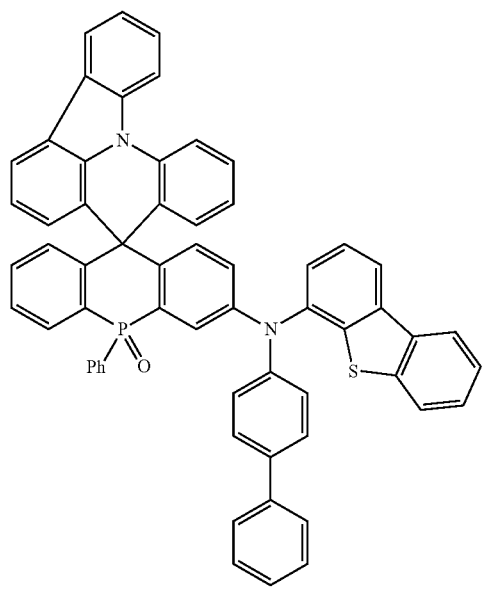
248
-continued
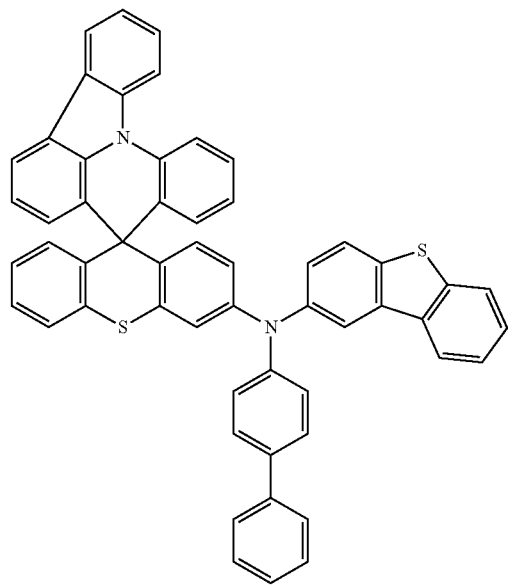
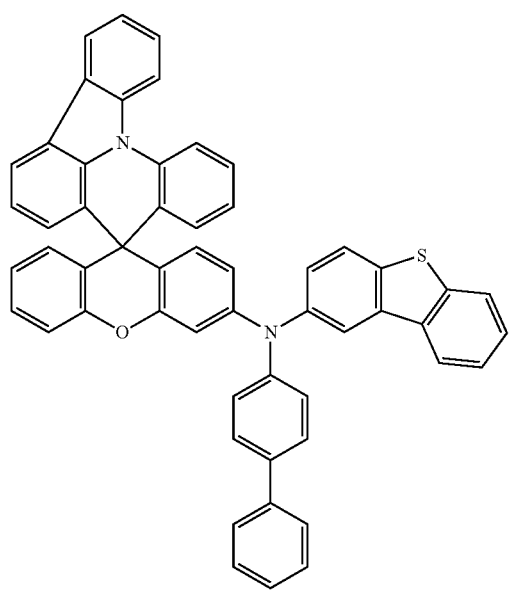
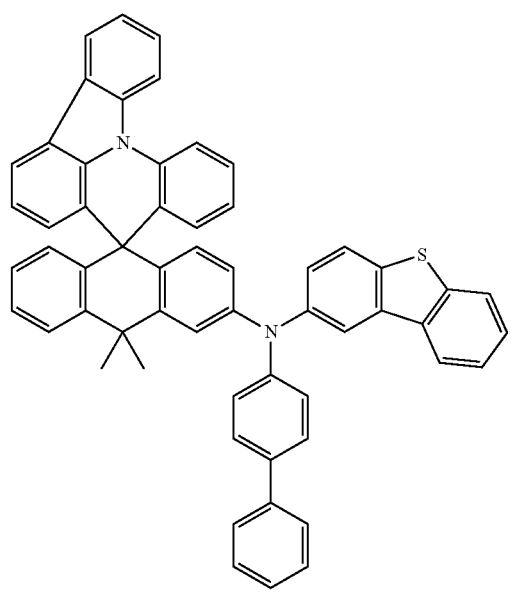

249
-continued
250
-continued
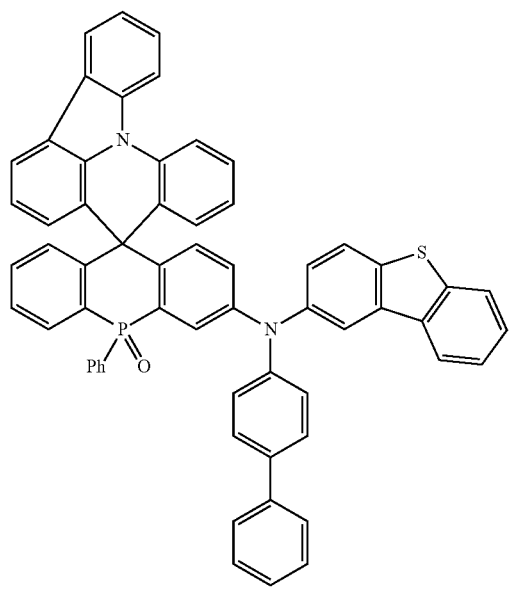
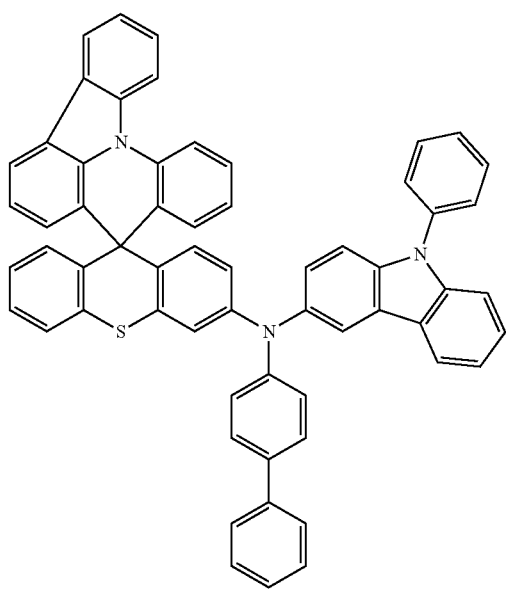

251
-continued
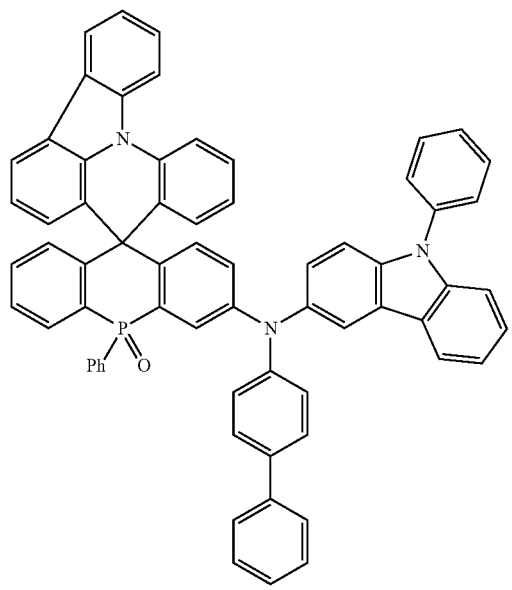
252
-continued
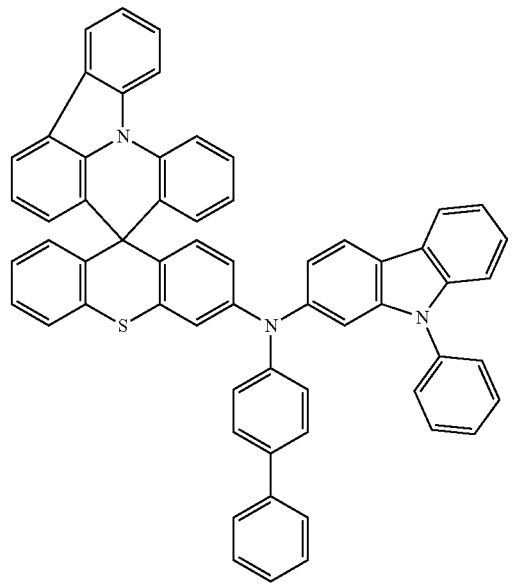
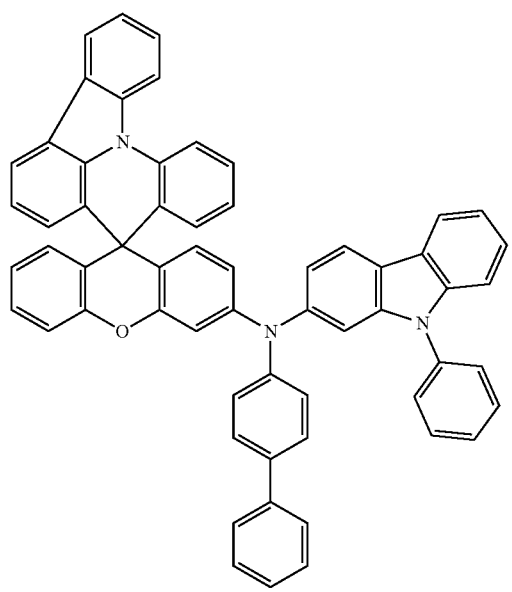
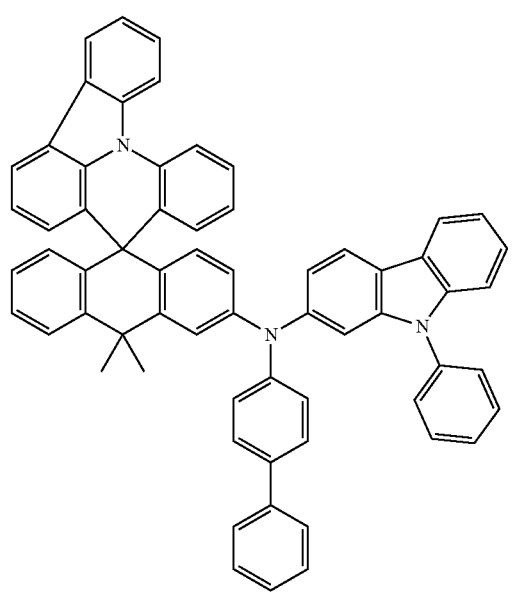

253
-continued
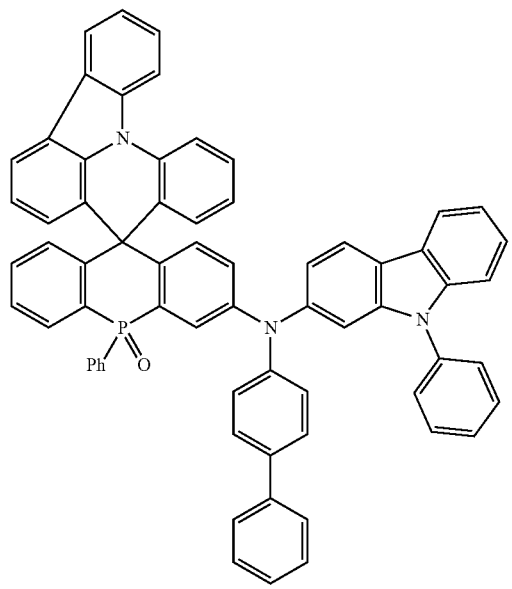
254
-continued
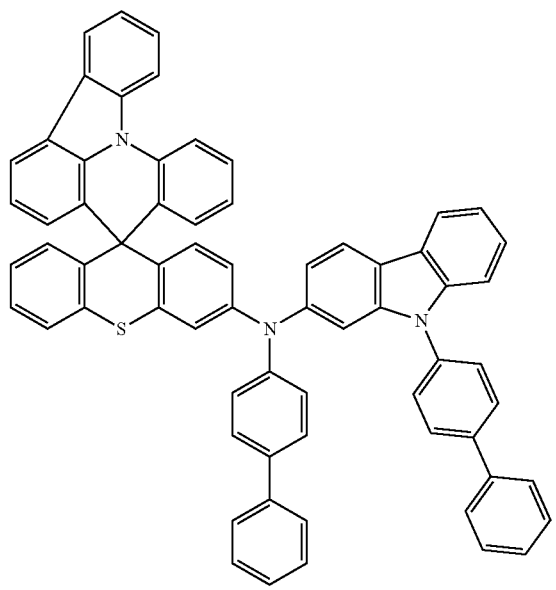
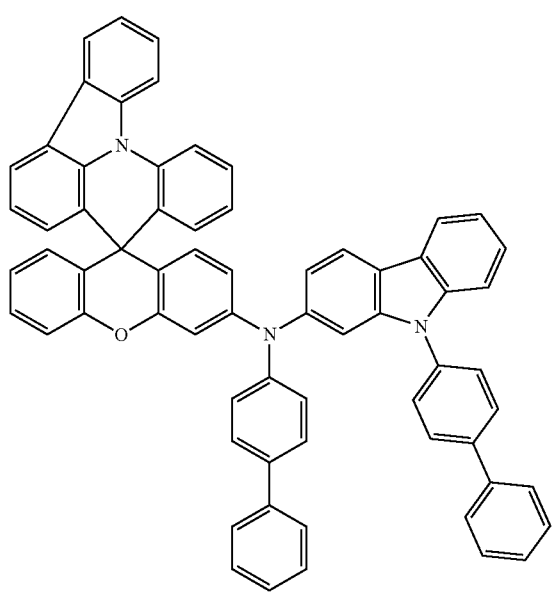
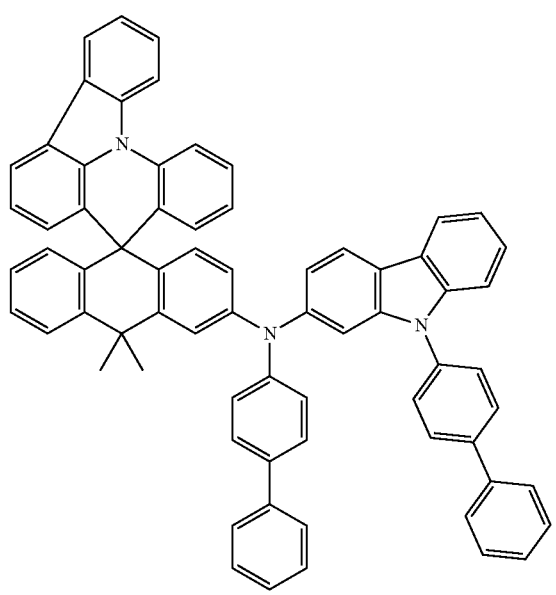

255
-continued
256
-continued
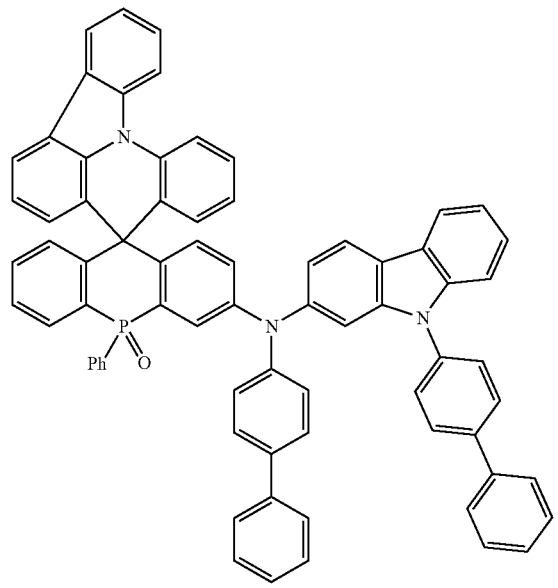
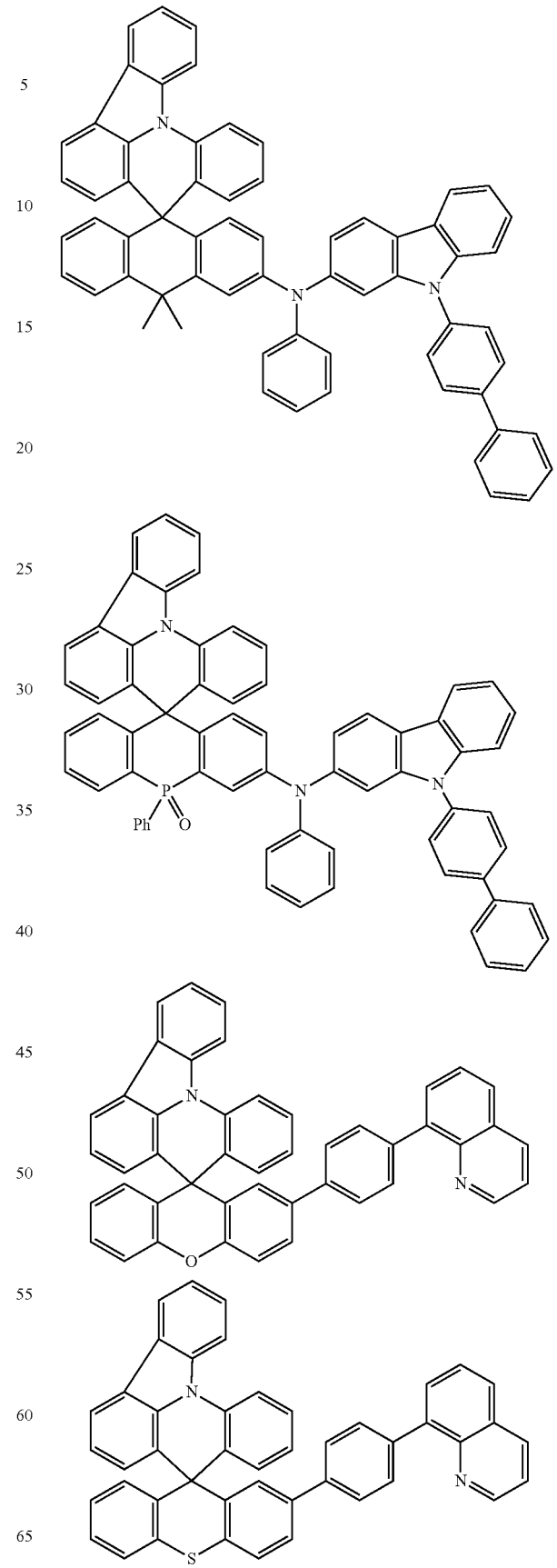

257
-continued
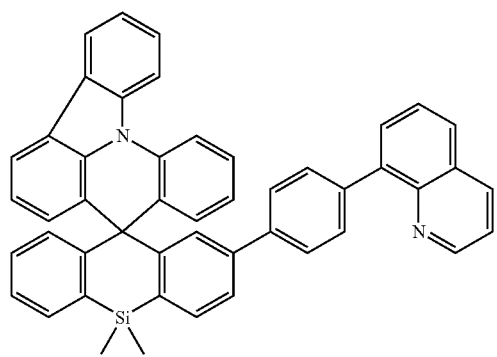
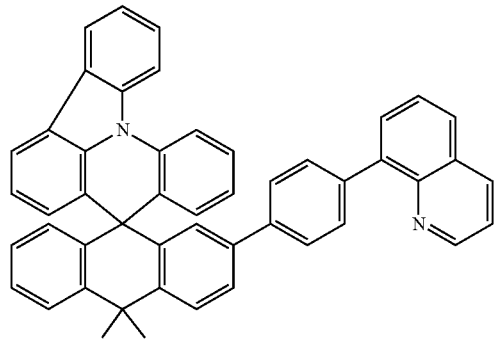
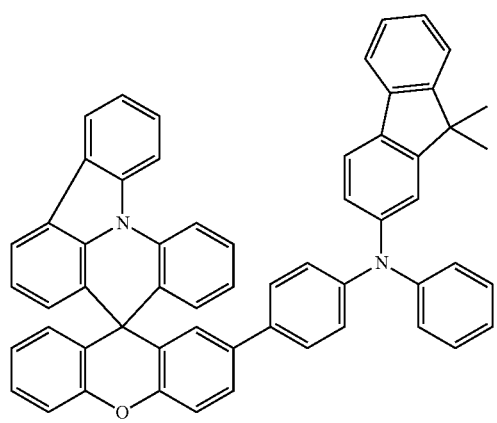
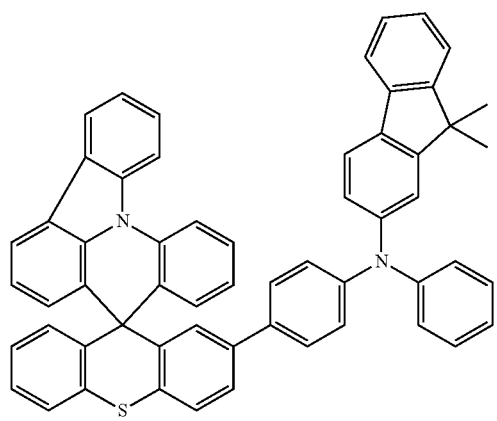
258
-continued
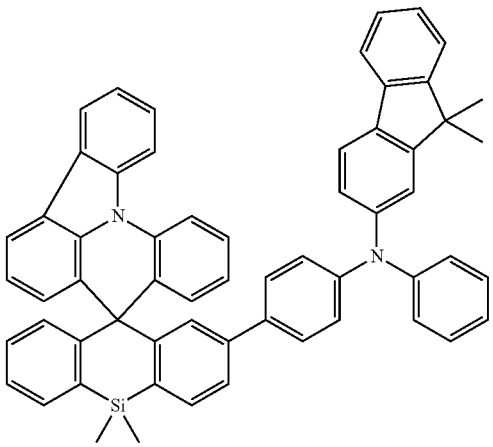
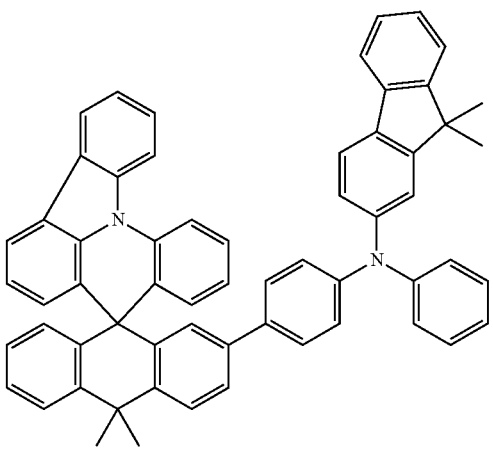
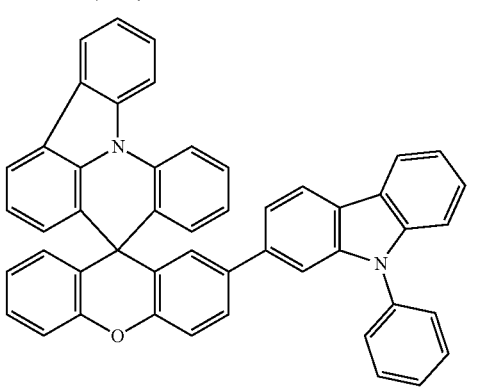
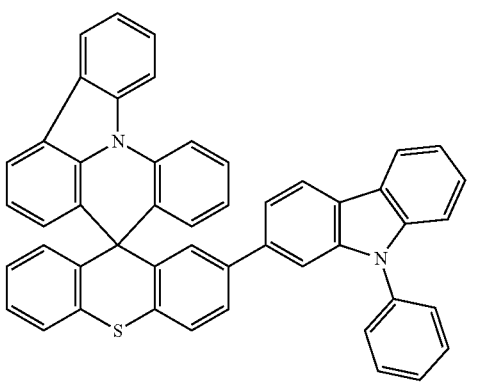

259
-continued
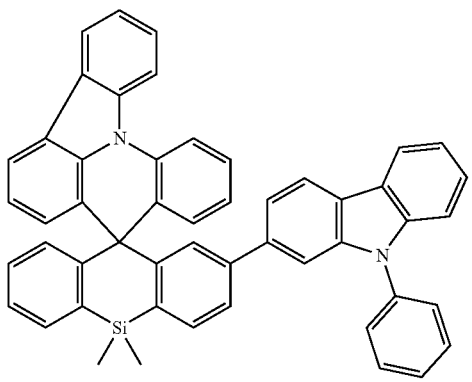
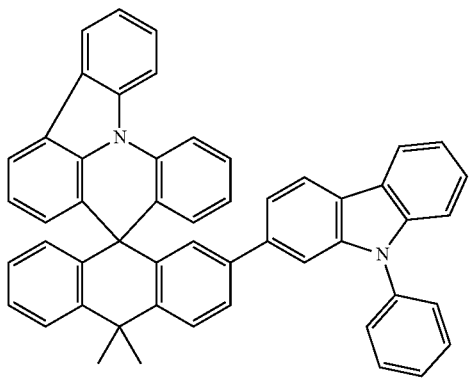
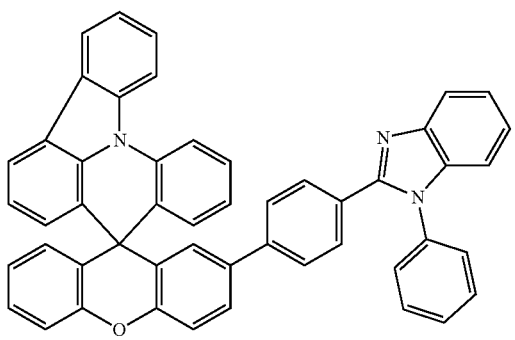
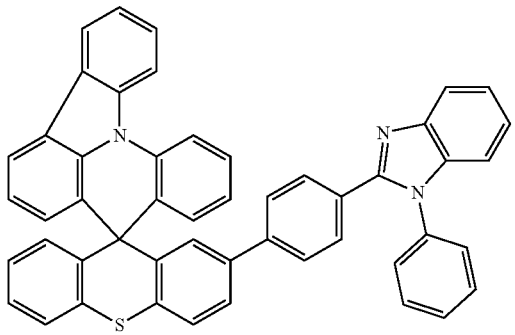
260
-continued
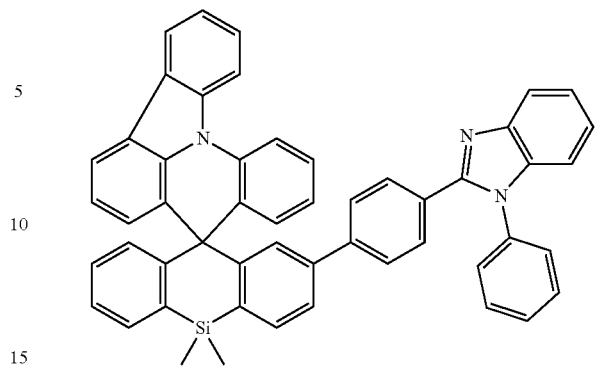
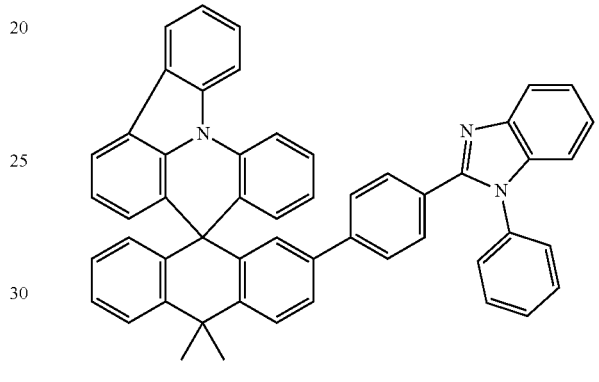
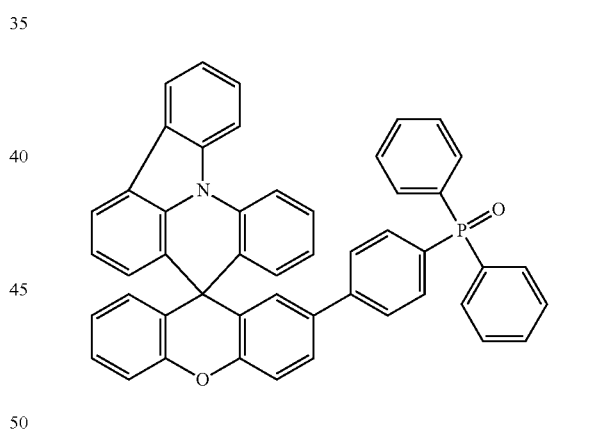
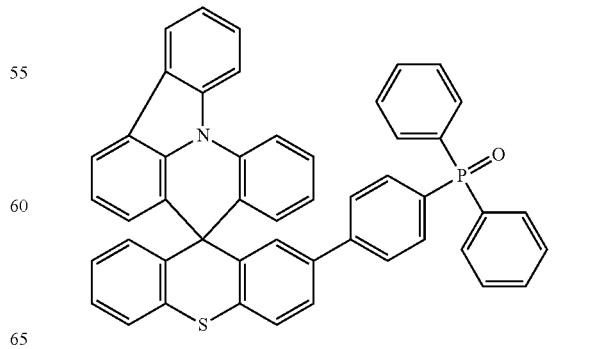

261
-continued
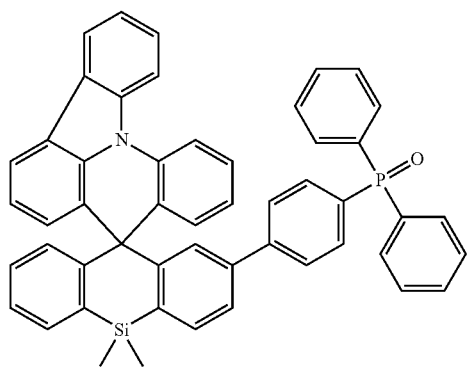
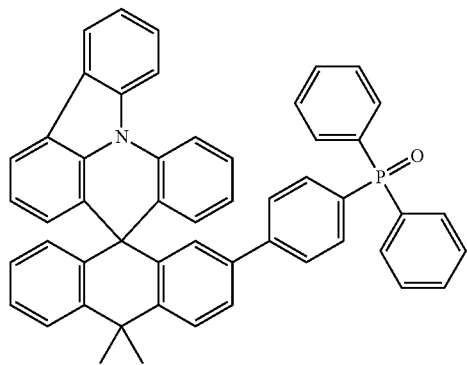
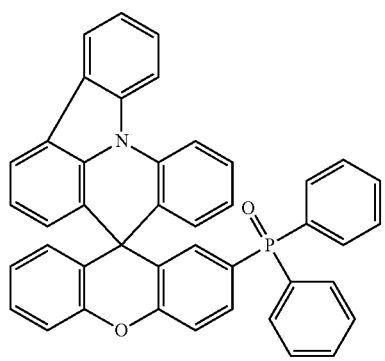
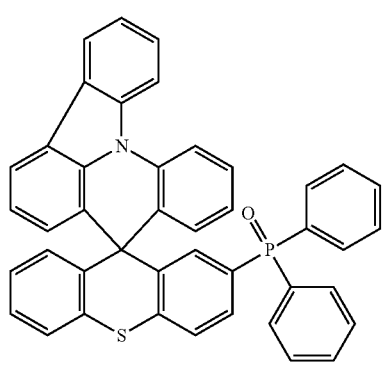
262
-continued
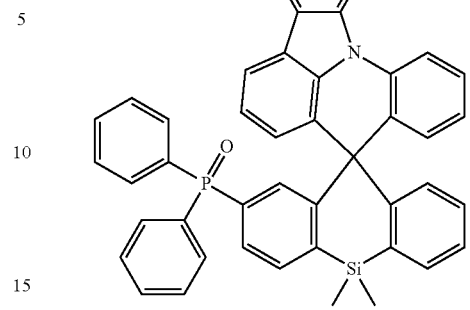
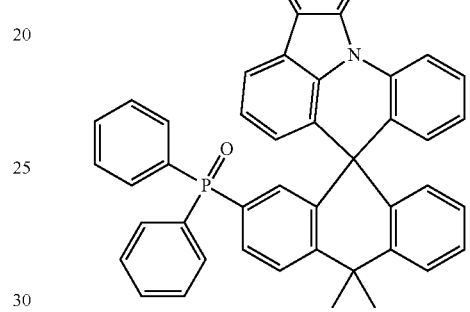
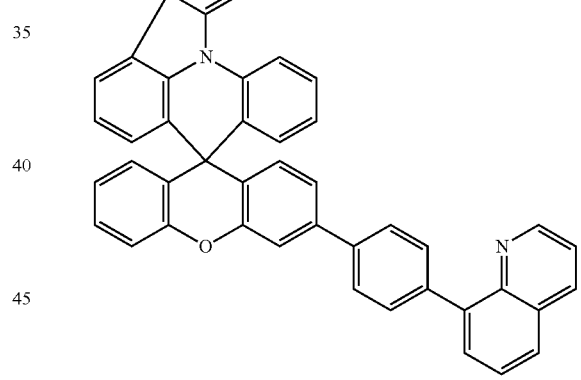
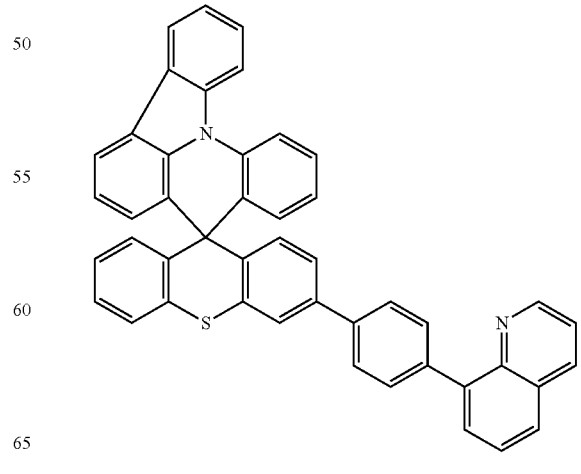

263
-continued
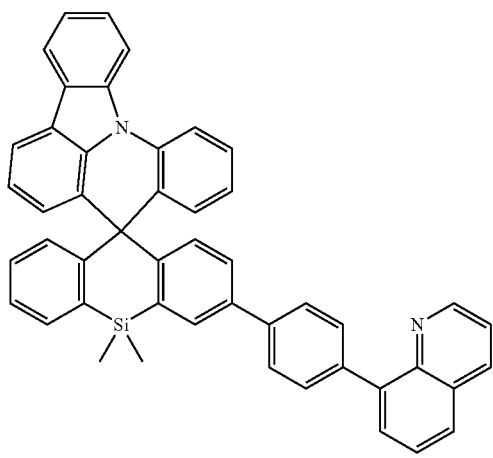
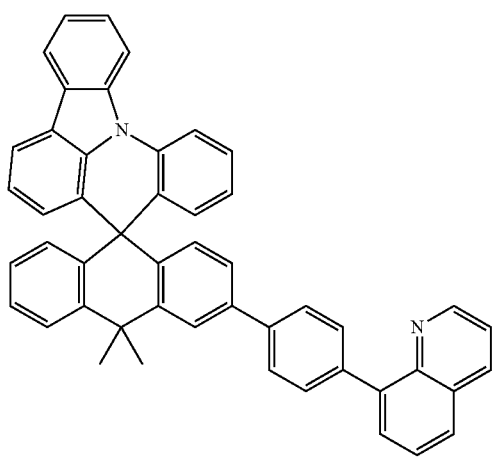
264
-continued
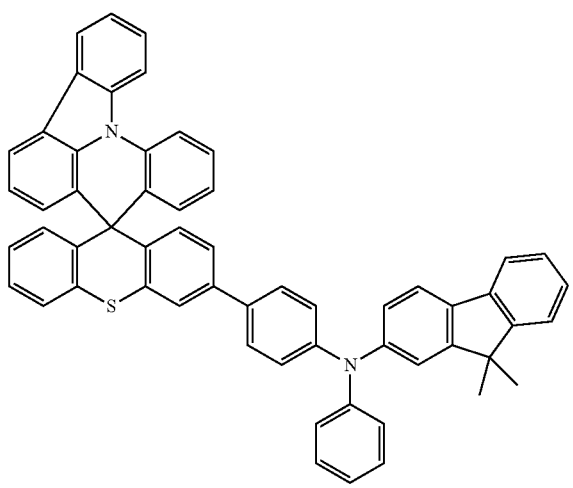
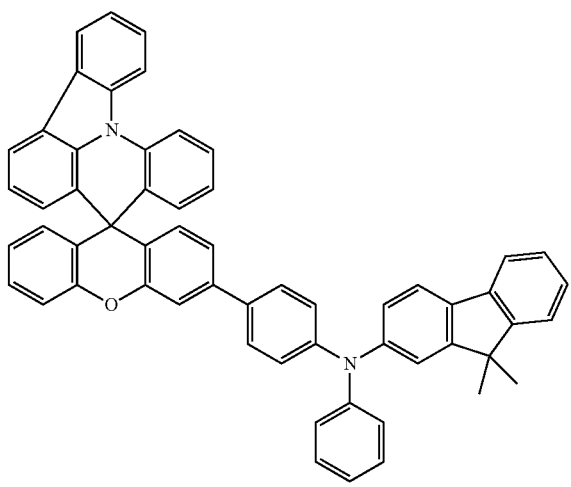
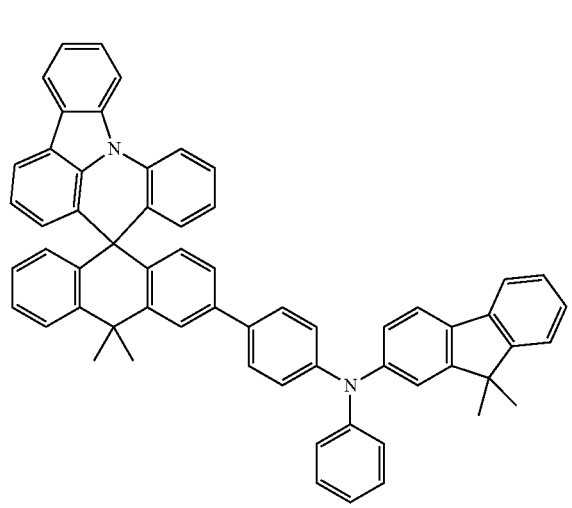

265
-continued
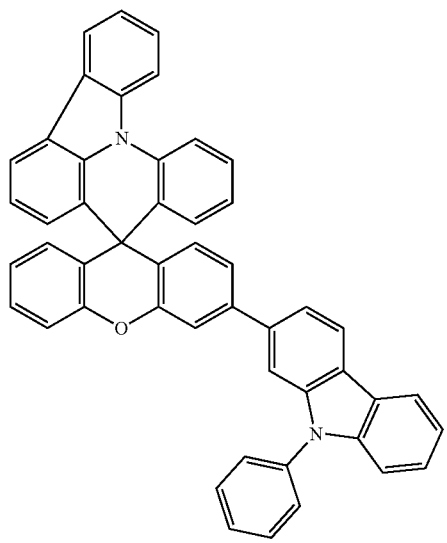
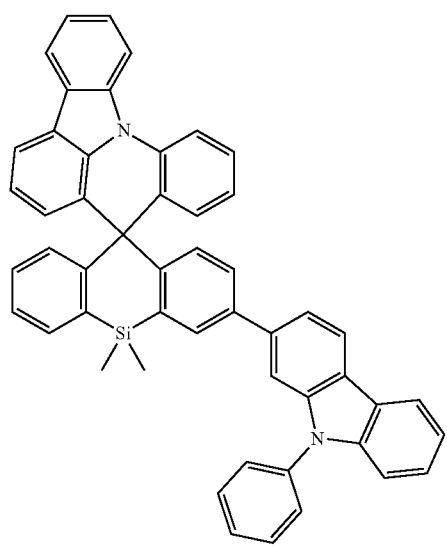
266
-continued
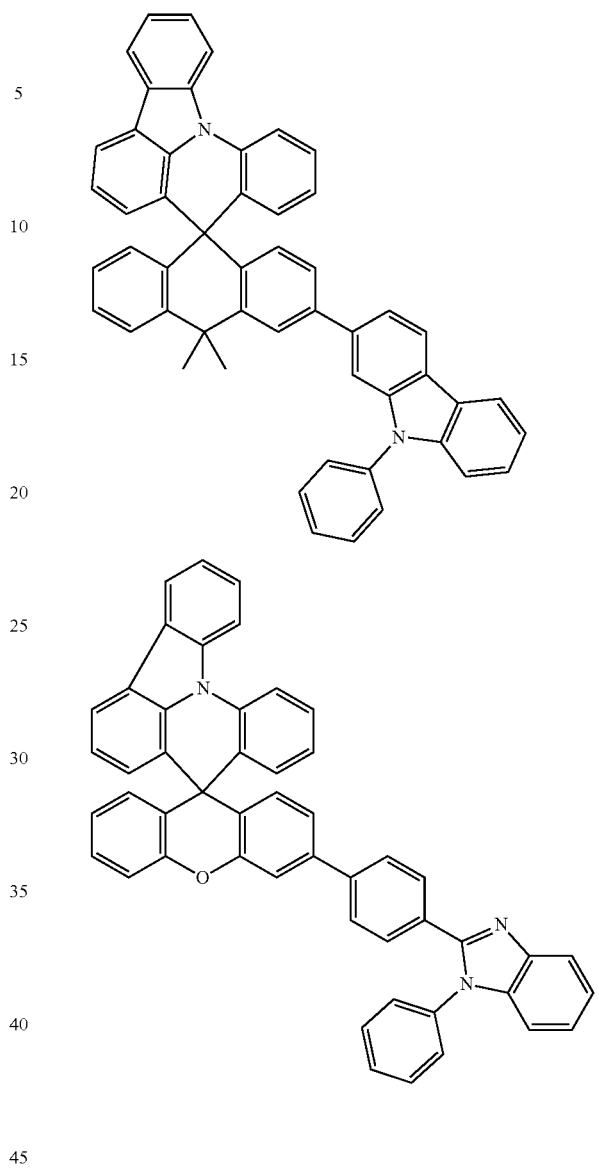

267
-continued
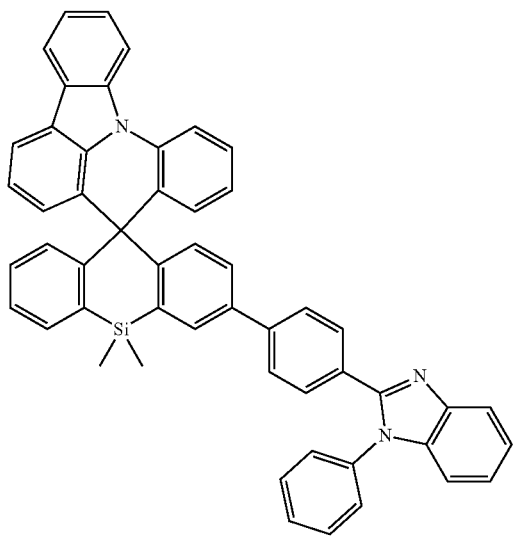
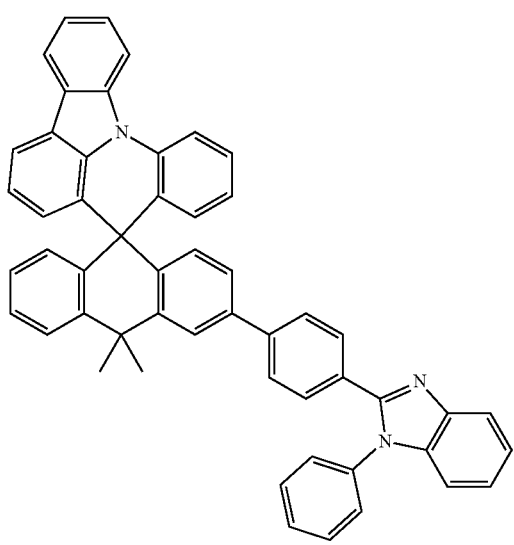
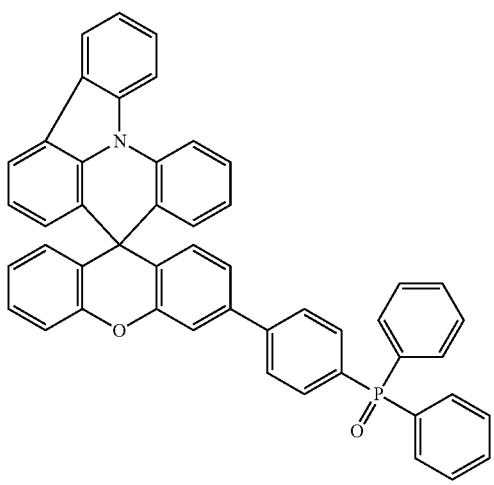
268
-continued
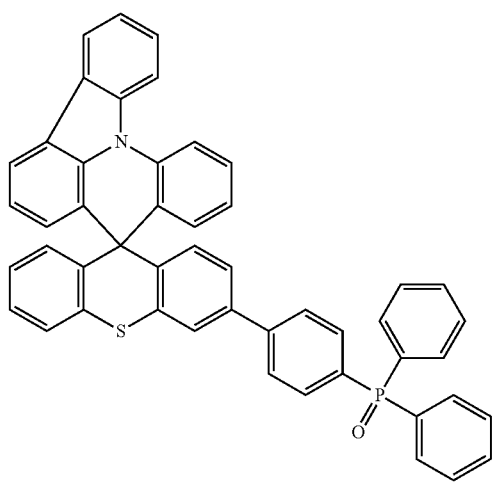
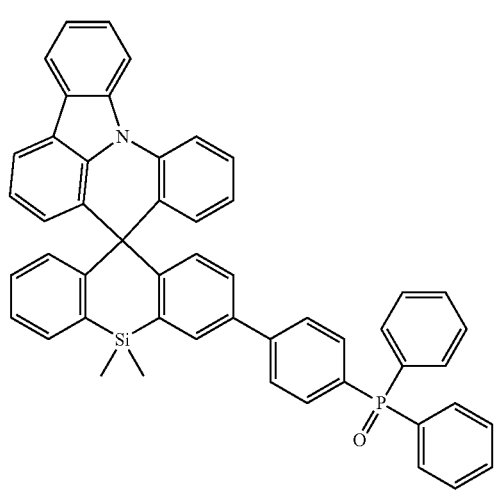
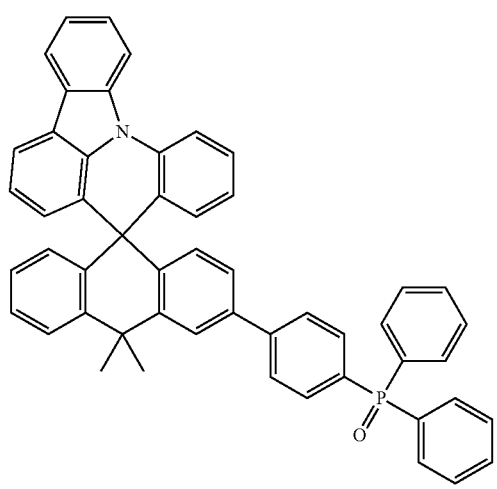

269
-continued
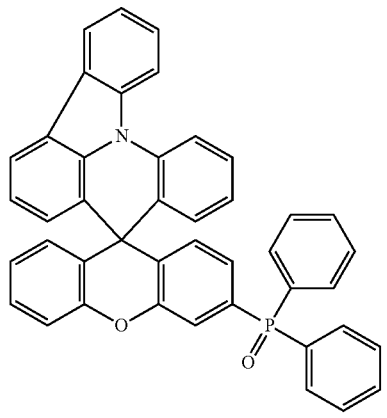
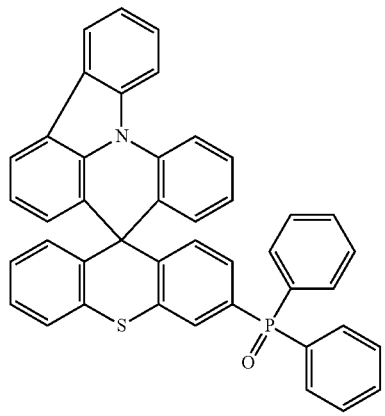
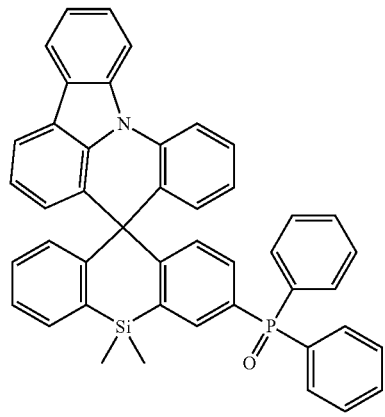
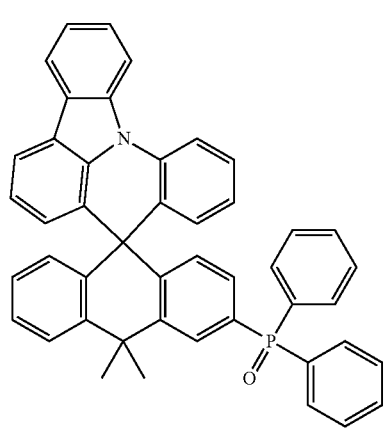
270
-continued
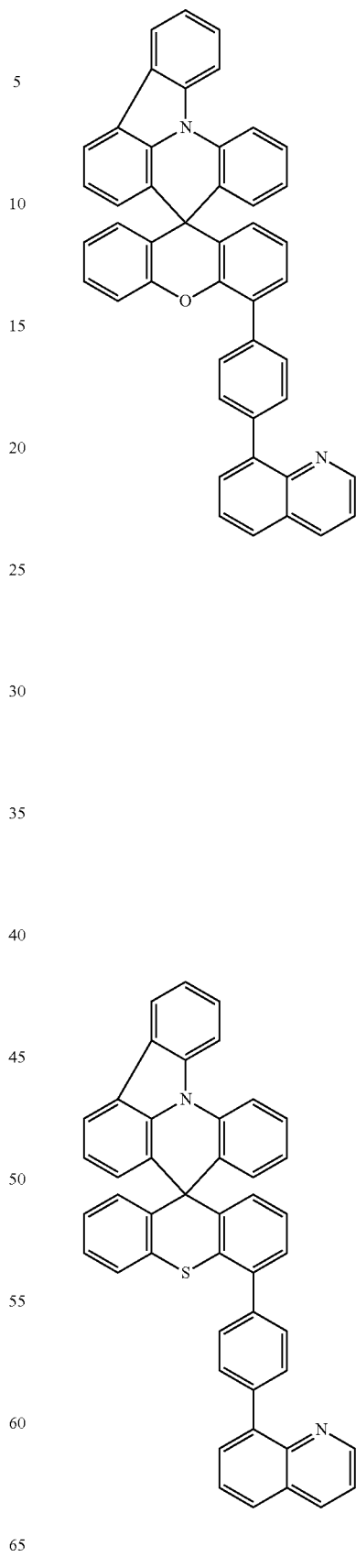

271
-continued
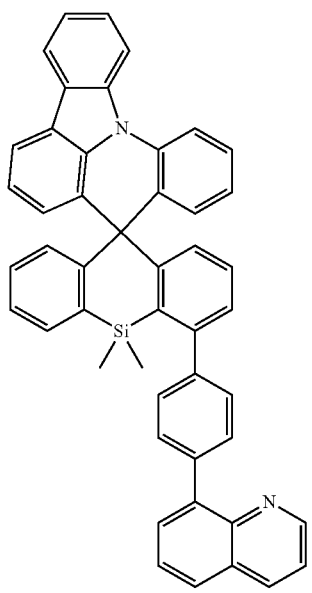
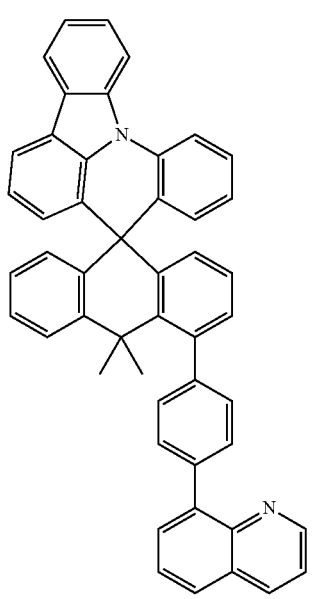
272
-continued
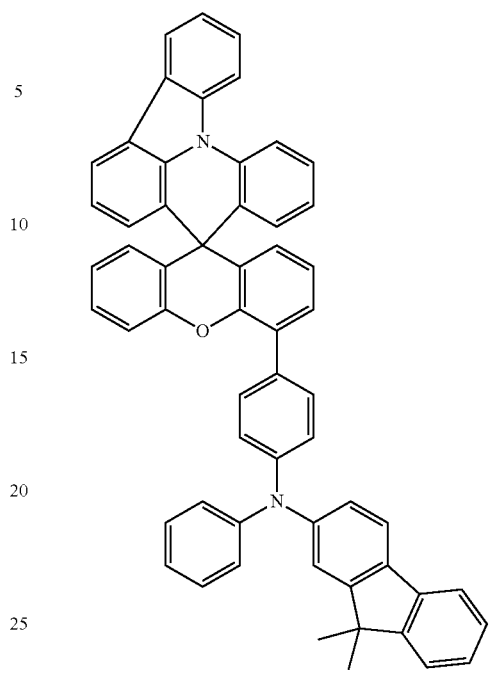
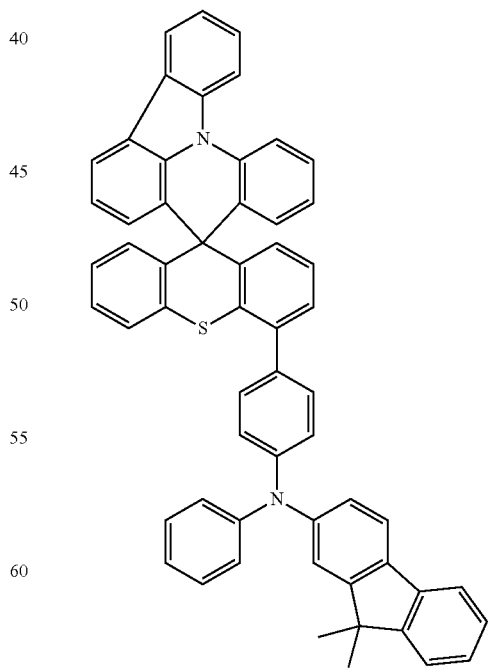

273
-continued
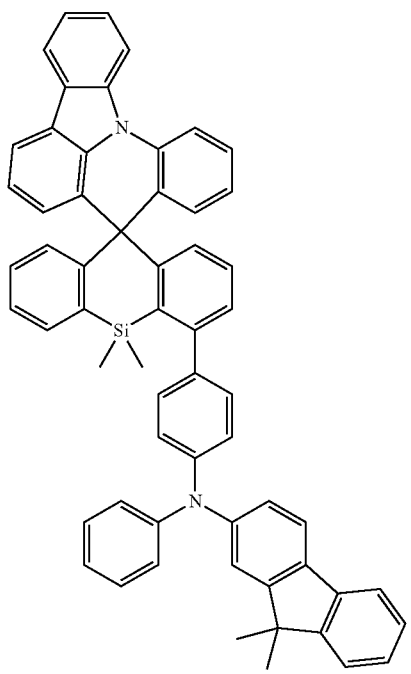
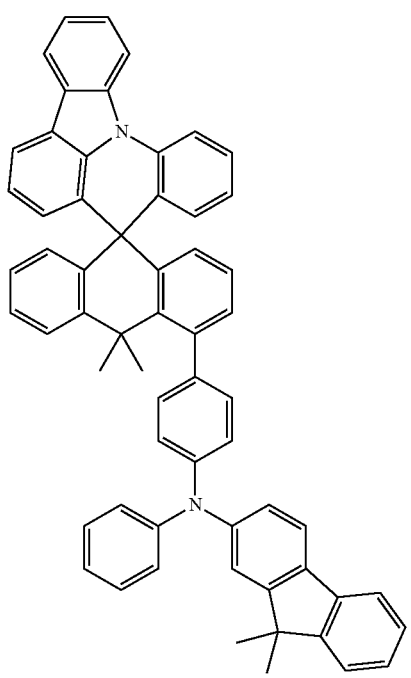
274
-continued
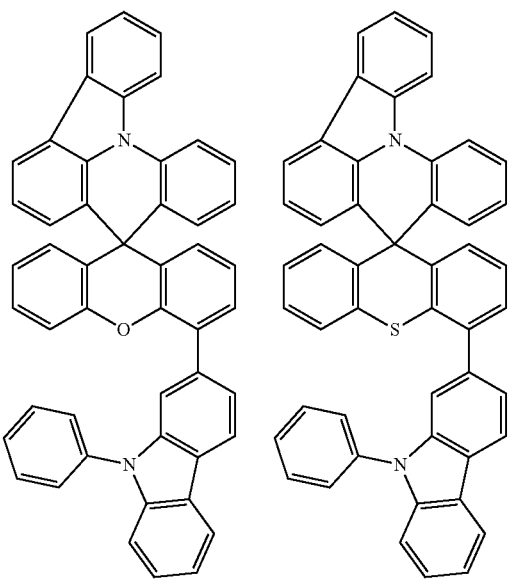
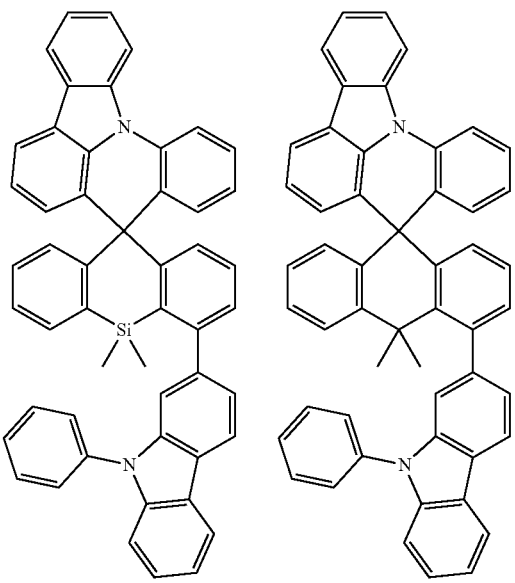

275
-continued
276
-continued
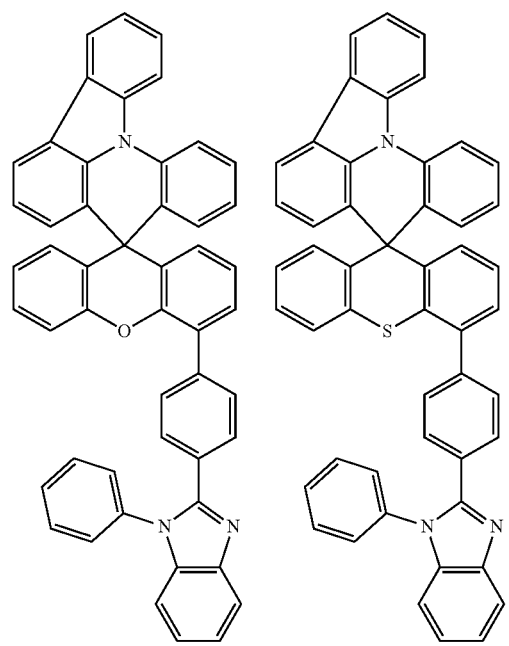
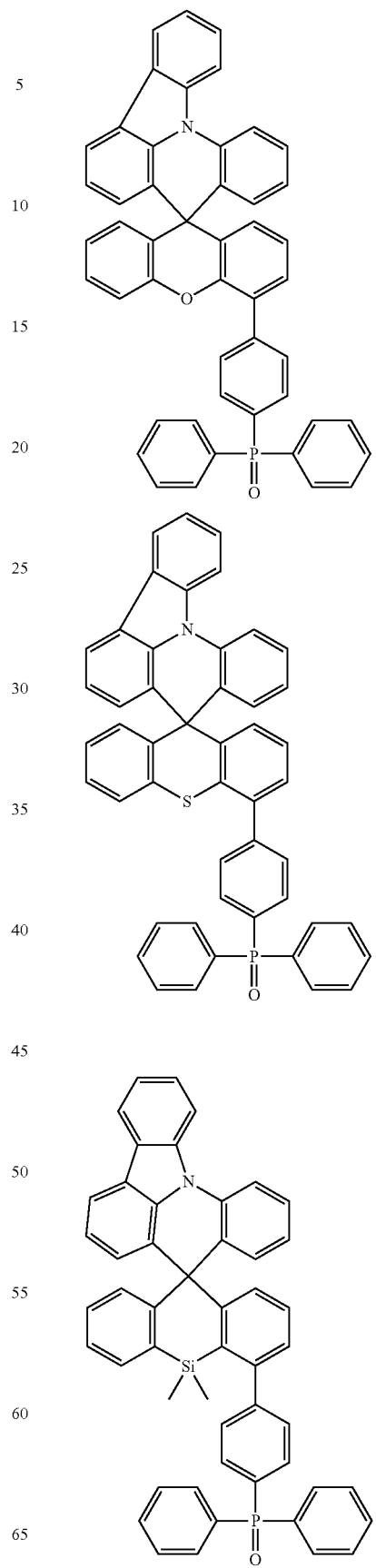

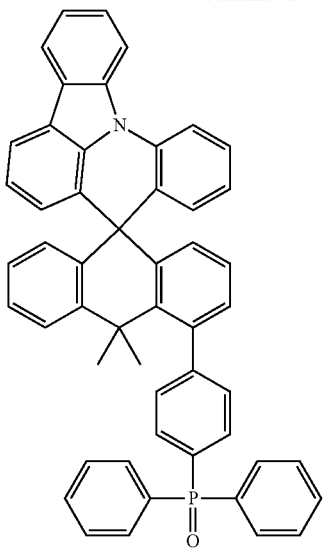
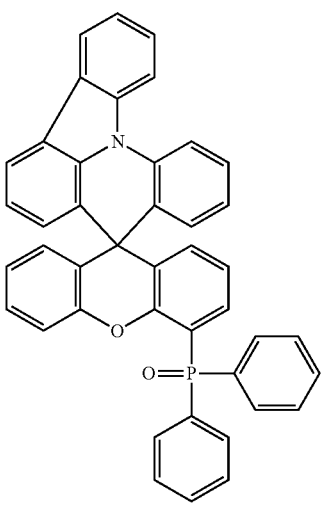
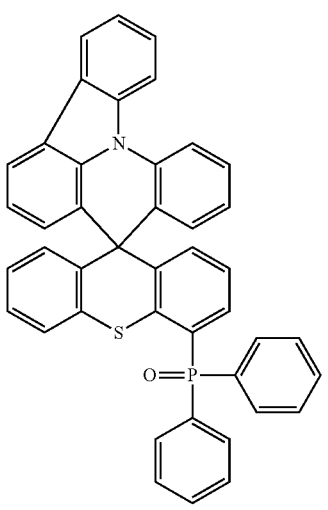
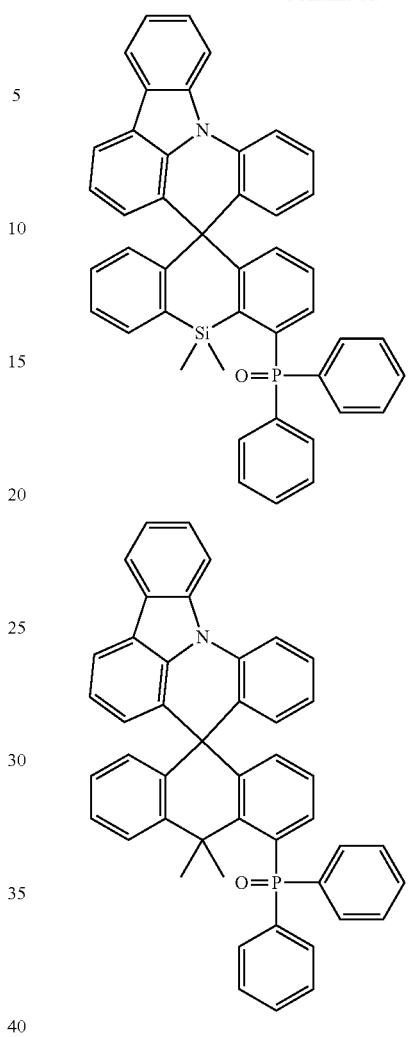

The compound represented by Chemical Formula 1 may be prepared based on the Preparation Examples to be described below. For example, a core structure may be prepared as in the following Reaction Formula 1, and then a substituent may be introduced as in Reaction Formulae 2 to 4. The following Chemical Formulae 1 to 4 relate to an example in which a specific substituent is introduced, but the person skilled in the art may not introduce a substituent by using the technology known in the art, if necessary, and when introducing a substituent, the person skilled in the art may perform the introduction by changing the kind or number of substituents. Further, the person skilled in the art may perform the introduction by changing samples, reaction conditions, or starting materials of the following Reaction Formulae 1 to 4 using the technology known in the art.

[Reaction Formula 1]

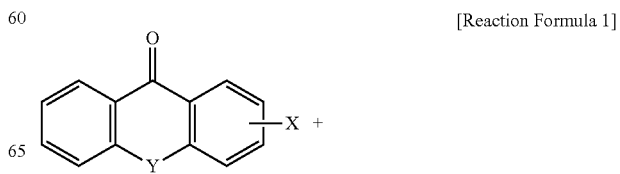

-continued

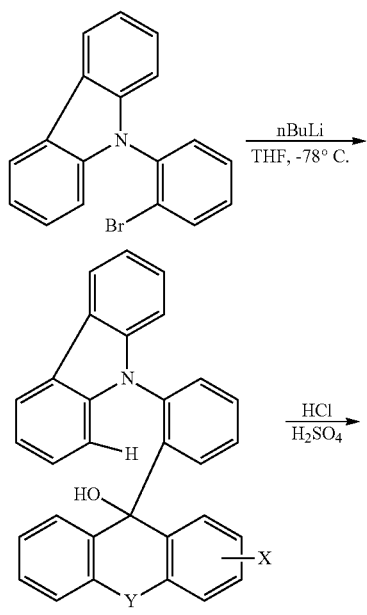

X = I, Br, Cl
Y = O, S, Si(R'), P(R'), P(=O)R', CR'R''

In Reaction Formula 1, Y is the same as that defined in Chemical Formula 1.

[Reaction Formula 2]

-continued

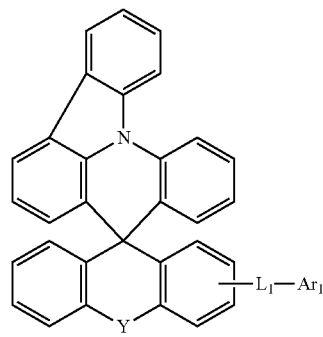

In Reaction Formula 2, Y is the same as that defined in Chemical Formula 1, X is the same as that defined in Reaction Formula 1, $L_1$ is a direct bond, a substituted or unsubstituted arylene group or a substituted or unsubstituted heteroarylene group, and Ar1 is a substituted or unsubstituted aryl group or a substituted or unsubstituted heteroaryl group.

[Reaction Formula 3]

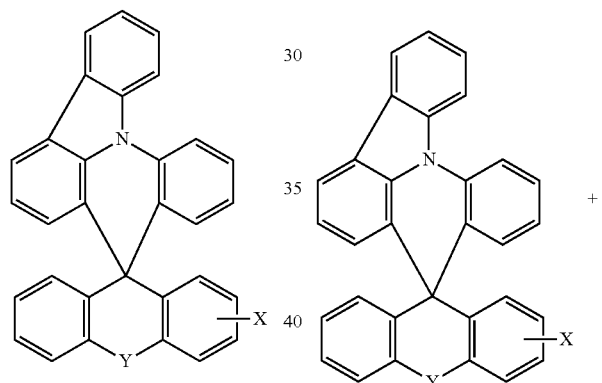

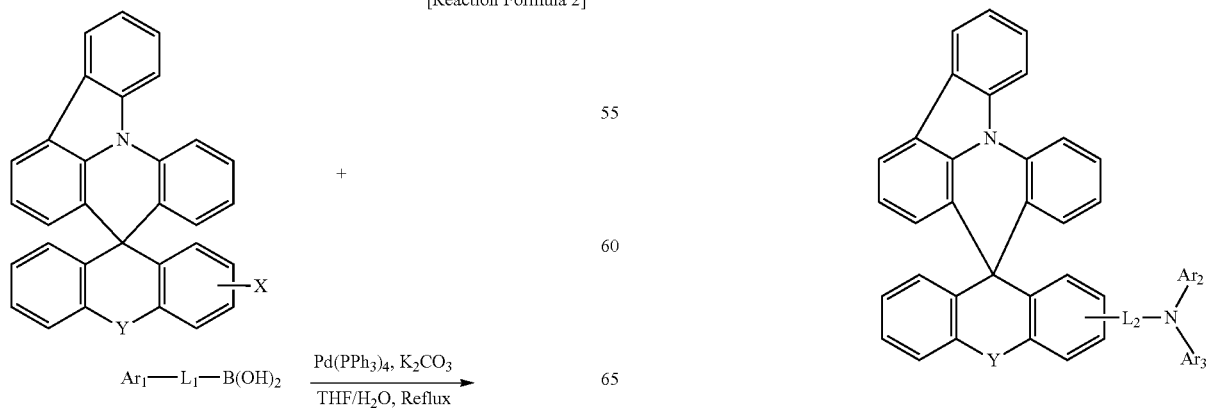

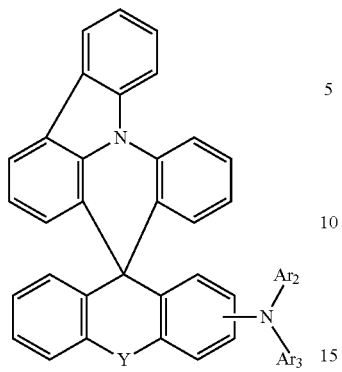

In Reaction Formula 3, Y is the same as that defined in Chemical Formula 1, X is the same as that defined in Reaction Formula 1, $L_2$ is a direct bond, a substituted or unsubstituted arylene group or a substituted or unsubstituted heteroarylene group, and $Ar_2$ and $Ar_3$ are a substituted or unsubstituted aryl group or a substituted or unsubstituted heteroaryl group.

[Reaction Formula 4]

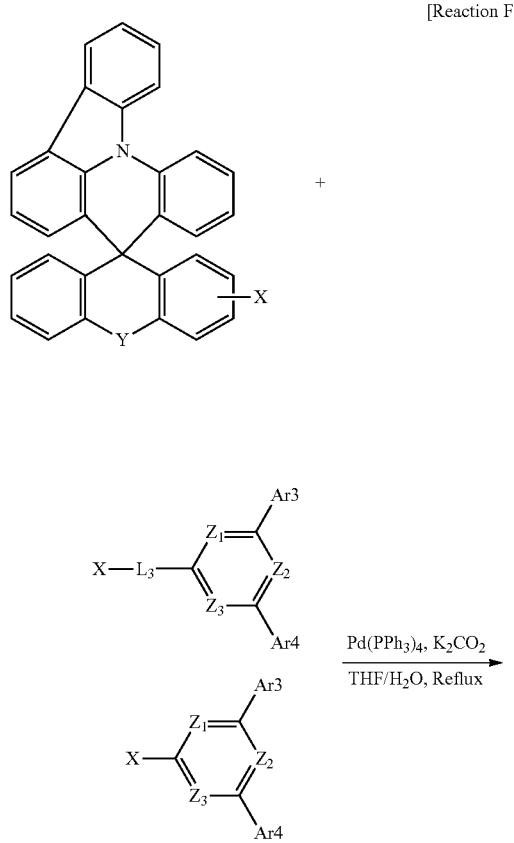

X = I, Br, Cl
Z = CH or N

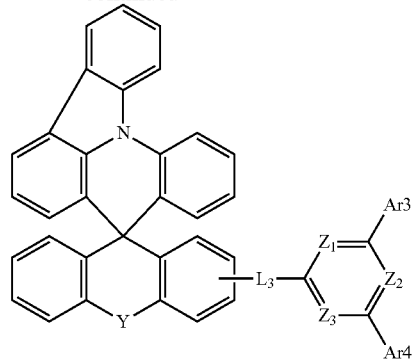

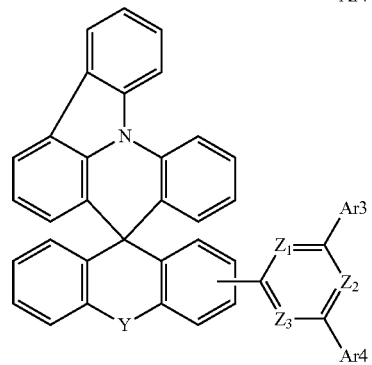

In Reaction Formula 4, Y is the same as that defined in Chemical Formula 1, X is the same as that defined in Reaction Formula 1, $L_3$ is a direct bond, a substituted or unsubstituted arylene group or a substituted or unsubstituted heteroarylene group, and $Ar_3$ and $Ar_4$ are a substituted or unsubstituted aryl group or a substituted or unsubstituted heteroaryl group.

Furthermore, the present specification provides an organic light emitting device including the compound represented by Chemical Formula 1.

An exemplary embodiment of the present specification provides an organic light emitting device including: a first electrode; a second electrode provided to face the first electrode; and an organic material layer having one or more layers disposed between the first electrode and the second electrode, in which one or more layers of the organic material layer include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transporting layer, or a layer which simultaneously injects and transports holes, and the hole injection layer, the hole transporting layer, or the layer which simultaneously injects and transports holes includes the compound of Chemical Formula 1.

In another exemplary embodiment, the organic material layer includes a light emitting layer, and the light emitting layer includes the compound of Chemical Formula 1.

In an exemplary embodiment of the present specification, the light emitting layer includes the compound of Chemical Formula 1 and further includes a light emitting dopant.

In another exemplary embodiment, the light emitting dopant includes a fluorescent dopant or a phosphorescent dopant.

In still another exemplary embodiment, the phosphorescent dopant includes an iridium-based phosphorescent dopant.

In yet another exemplary embodiment, the phosphorescent dopant material includes $Ir(ppy)_3$ or $(piq)_2Ir(acac)$.

In an exemplary embodiment of the present specification, the organic material layer includes an electron transporting layer or an electron injection layer, and the electron transporting layer or the electron injection layer includes the compound of Chemical Formula 1.

In an exemplary embodiment of the present specification, the organic material layer includes an electron blocking layer, and the electron blocking layer includes the compound of Chemical Formula 1.

In an exemplary embodiment of the present specification, the electron transporting layer, the electron injection layer, or the layer which simultaneously transports and injects electrons includes the compound of Chemical Formula 1.

In another exemplary embodiment, the organic material layer includes a light emitting layer and an electron transporting layer, and the electron transporting layer includes the compound of Chemical Formula 1.

An exemplary embodiment of the present specification provides an organic light emitting device including: a first electrode; a second electrode provided to face the first electrode; a light emitting layer disposed between the first electrode and the second electrode; and an organic material layer having two or more layers disposed between the light emitting layer and the first electrode, or between the light emitting layer and the second electrode, in which at least one of the organic material layer having two or more layers includes the heterocyclic compound. In one exemplary embodiment, as the organic material layer having two or more layers, two or more may be selected from the group consisting of an electron transporting layer, an electron injection layer, a layer which simultaneously transports and injects electrons, and a hole blocking layer.

In an exemplary embodiment of the present specification, the organic material layer includes an electron transporting layer having two or more layers, and at least one of the electron transporting layer having two or more layers includes the heterocyclic compound. Specifically, in an exemplary embodiment of the present specification, the heterocyclic compound may also be included in one layer of the electron transporting layer having two or more layers, and may be included in each of the electron transporting layer having two or more layers.

In addition, in an exemplary embodiment of the present specification, when the heterocyclic compound is included in each of the electron transporting layer having two or more layers, the other materials except for the heterocyclic compound may be the same as or different from each other.

In another exemplary embodiment, the organic light emitting device may be an organic light emitting device having a structure (normal type) in which a positive electrode, an organic material layer having one or more layers, and a negative electrode are sequentially stacked on a substrate.

In still another exemplary embodiment, the organic light emitting device may be an organic light emitting device having a reverse-direction structure (inverted type) in which a negative electrode, an organic material layer having one or more layers, and a positive electrode are sequentially stacked on a substrate.

For example, the structure of the organic light emitting device according to an exemplary embodiment of the present specification is exemplified in FIGS. 1 and 2.

FIG. 1 illustrates an example of an organic light emitting device composed of a substrate 1, a positive electrode 2, a light emitting layer 3, and a negative electrode 4. In the structure as described above, the compound may be included in the light emitting layer.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4. In the structure as described above, the compound may be included in one or more layers of the hole injection layer, the hole transporting layer, the light emitting layer, and the electron transporting layer.

According to an exemplary embodiment of the present specification, the organic material layer includes the light emitting layer, and the light emitting layer includes a compound represented by the following Chemical Formula 1-A.

[Chemical Formula 1-A]

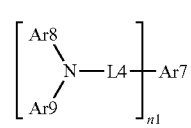

In Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Arg are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may be bonded to each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L4 is a direct bond.

According to an exemplary embodiment of the present specification, n1 is 2.

In an exemplary embodiment of the present specification, Ar7 is a divalent pyrene group which is unsubstituted or substituted with deuterium, a methyl group, an ethyl group, or a tert-butyl group.

According to an exemplary embodiment of the present specification, Ar8 and Ar9 are the same as or different from each other, and are each independently a substituted or unsubstituted aryl group having 6 to 30 carbon atoms.

According to an exemplary embodiment of the present specification, Ar8 and Ar9 are the same as or different from each other, and are each independently an aryl group which is unsubstituted or substituted with a germanium group substituted with an alkyl group.

According to an exemplary embodiment of the present specification, Ar8 and Ar9 are the same as or different from each other, and are each independently an aryl group which is unsubstituted or substituted with a trimethylgermanium group.

According to an exemplary embodiment of the present specification, Ar8 and Ar9 are the same as or different from each other, and are each independently a substituted or unsubstituted phenyl group.

According to an exemplary embodiment of the present specification, Ar8 and Arg are a phenyl group which is unsubstituted or substituted with a trimethylgermanium group.

According to an exemplary embodiment of the present specification, Chemical Formula 1-A is represented by the following compound.

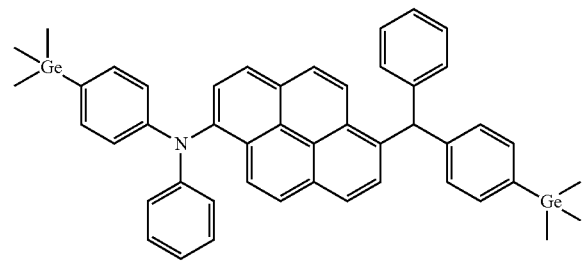

According to an exemplary embodiment of the present specification, the organic material layer includes a light emitting layer, and the light emitting layer includes a compound represented by the following Chemical Formula 2-A.

[Chemical Formula 2-A]

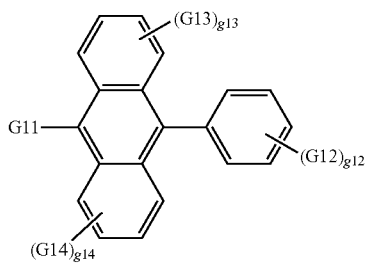

In Chemical Formula 2-A,

G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

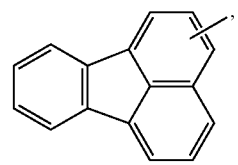

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer from 1 to 5, g13 and g14 are each an integer from 1 to 4, and when g12 to g14 are each 2 or more, two or more structures in the parenthesis are the same as or different from each other.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, G11 is a 1-naphthyl group.

According to an exemplary embodiment of the present specification, G12 is a 2-naphthyl group.

According to an exemplary embodiment of the present specification, G13 and G14 are hydrogen.

According to an exemplary embodiment of the present specification, Chemical Formula 2-A is represented by the following compound.

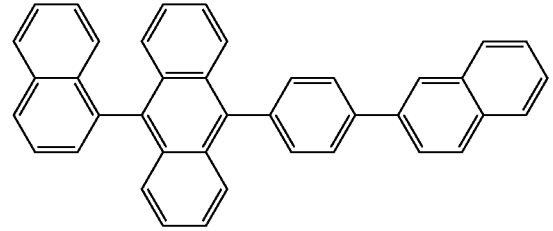 [SMILES: c1ccc2cc(-c3ccc(-c4c5ccccc5c(-c5cccc6ccccc56)c5ccccc45)cc3)ccc2c1]

The organic light emitting device of the present specification may be manufactured by the materials and methods known in the art, except that one or more layers of the organic material layer include the compound of the present specification, that is, the compound of Chemical Formula 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layer include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, materials having a large work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene] (PEDOT), polypyrrole, and polyaniline, and the like, but are not limited thereto.

As the negative electrode material, materials having a small work function are usually preferred so as to facilitate the injection of electrons into an organic material layer. Specific examples of the negative electrode material which may be in the present invention include: a metal such as magnesium, calcium, sodium, potassium, titanium, indium, yttrium, lithium, gadolinium, aluminum, silver, tin, and lead, or an alloy thereof; a multi-layer structured material such as LiF/Al or LiO$_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is preferably a material which may receive holes and electrons transported from a hole transporting layer and an electron transporting layer, respectively, and combine the holes and the electrons to emit light in a visible ray region, and has good quantum efficiency to fluorescence or phosphorescence. Specific examples thereof include: 8-hydroxy-quinoline-aluminum complex (Alq$_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material is a material which accepts electrons from an electron injection layer and transports the electrons to a light emitting layer, and an electron transporting material is suitably a material having high electron mobility which may proficiently accept electrons from a negative electrode and may transfer the electrons to a light emitting layer. Specific examples thereof include: Al complexes of 8-hydroxyquinoline; complexes including Alq3; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the materials to be used.

In an exemplary embodiment of the present specification, the compound of Chemical Formula 1 may be included in an organic solar cell or an organic transistor in addition to an organic light emitting device.

The preparation of the compound represented by Chemical Formula 1 and the organic light emitting device including the same will be specifically described in the following Examples. However, the following Examples are provided for exemplifying the present specification, and the scope of the present specification is not limited thereby.

Synthesis Example 1

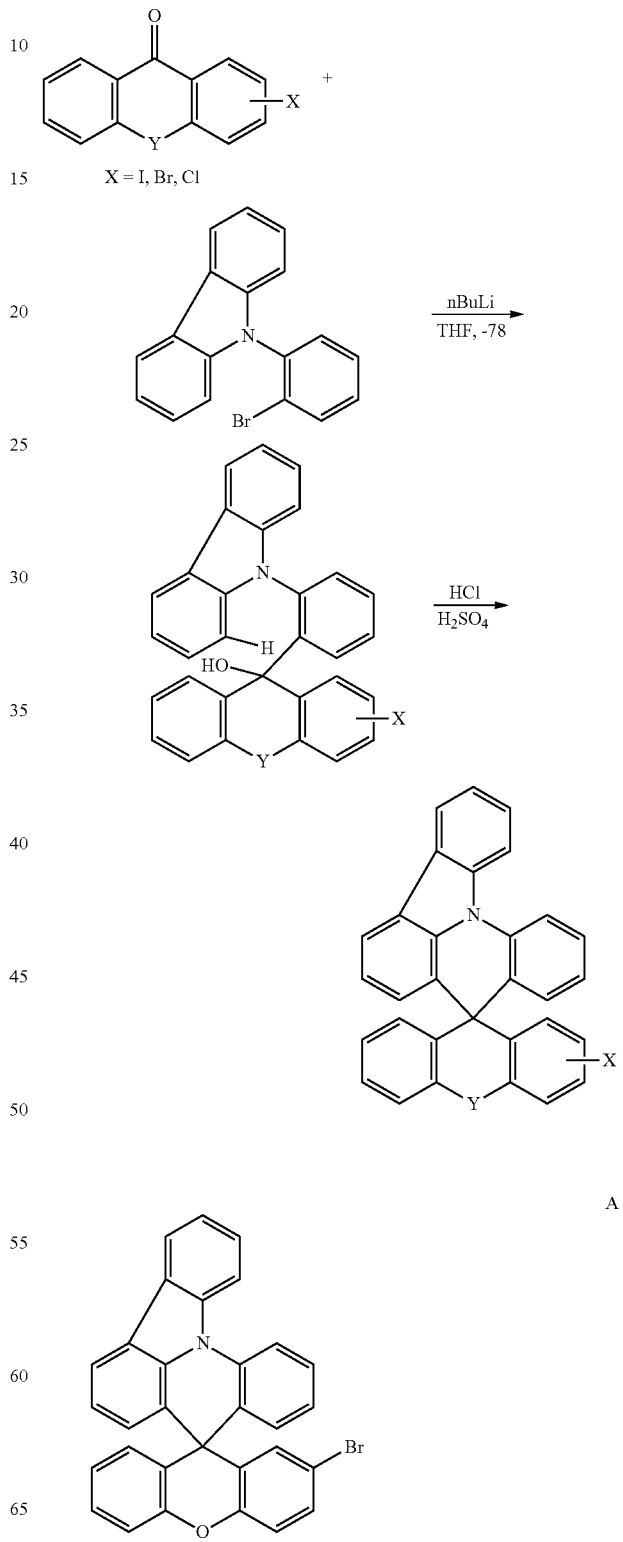

B
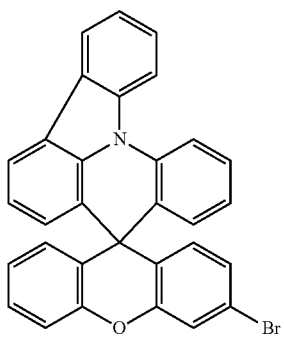
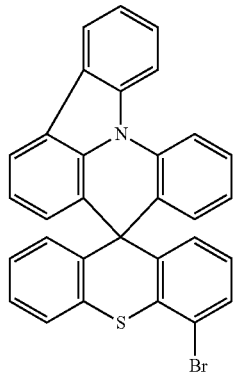
C
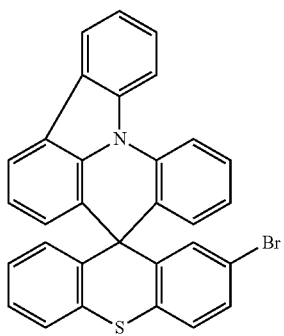
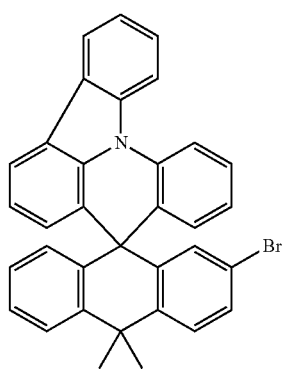
D
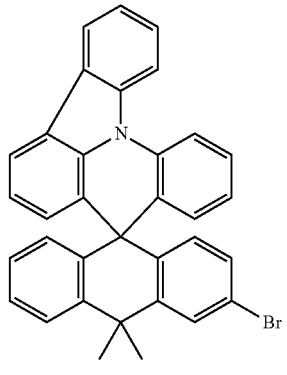
E
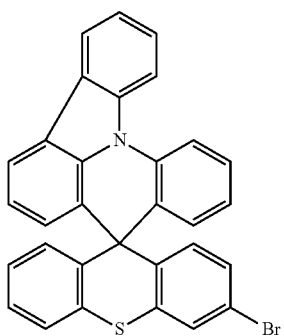
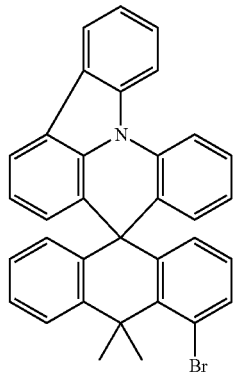

293
-continued
J
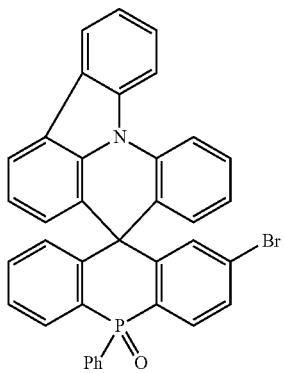
K
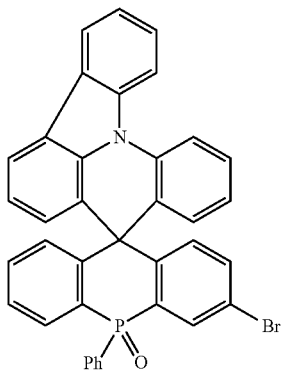
L
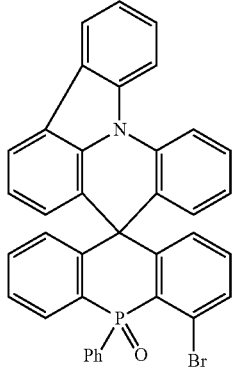
Y = O, S, Si(R'), P(R'), P(=O)R', CR'R"
Synthesis Example 2
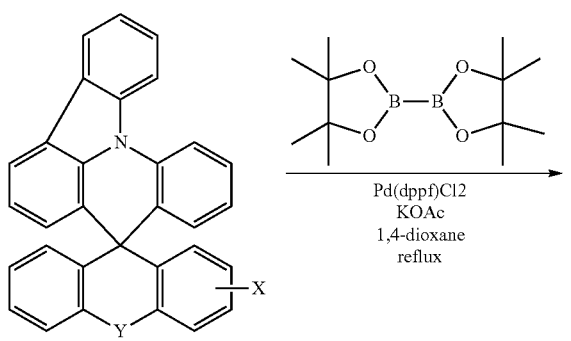
294
-continued
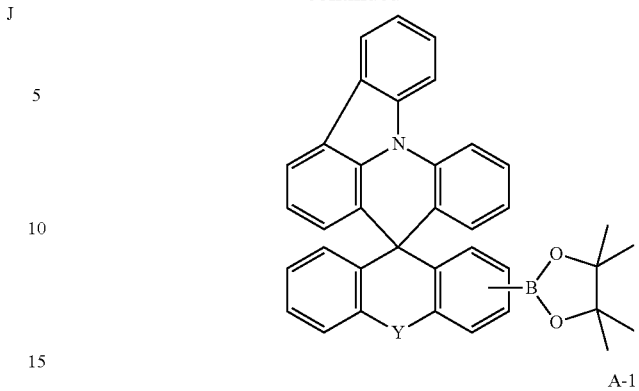
A-1
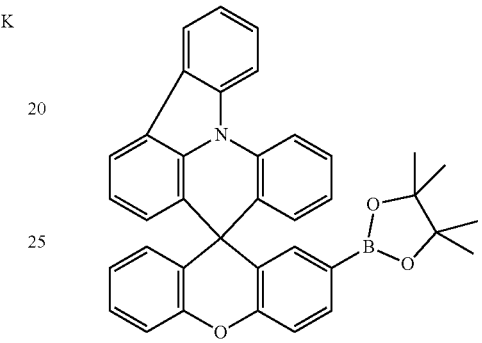
B-1
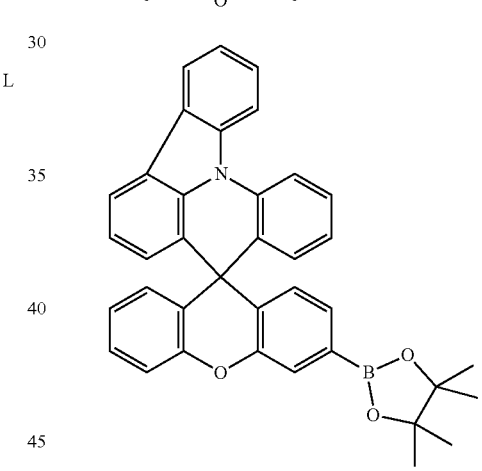
C-1
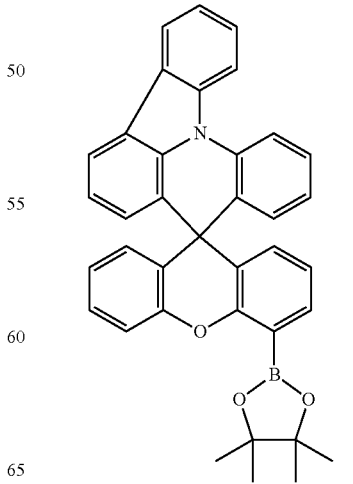

D-1
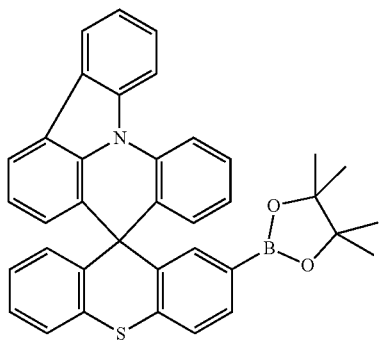
E-1
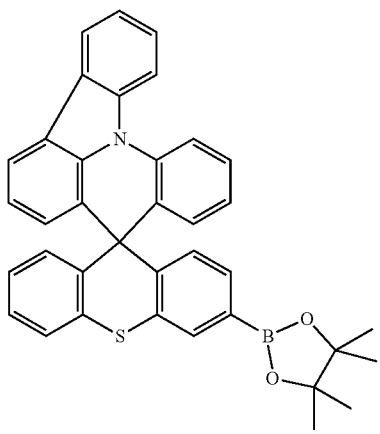
F-1
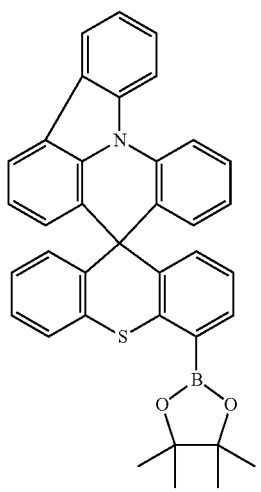
G-1
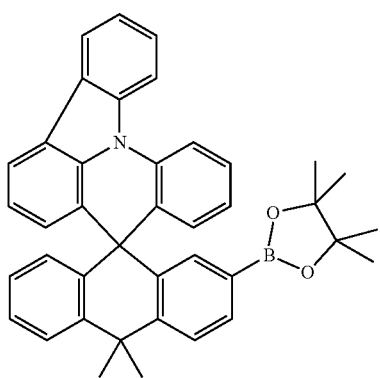
H-1
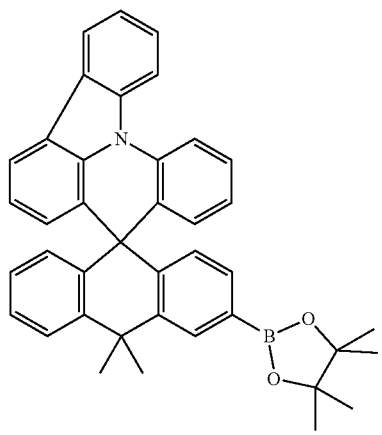
I-1
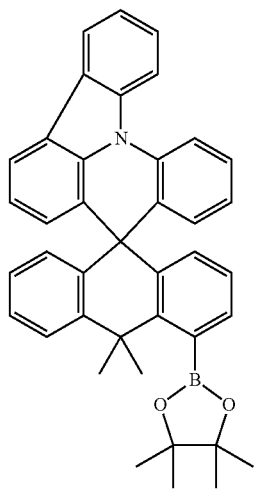
J-1

K-1

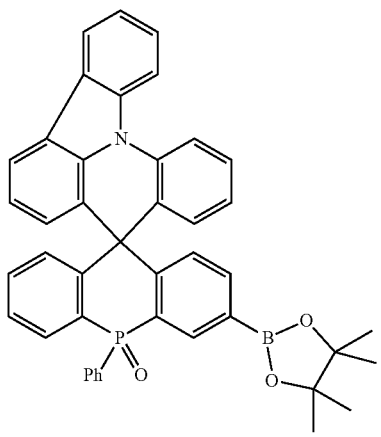

L-1

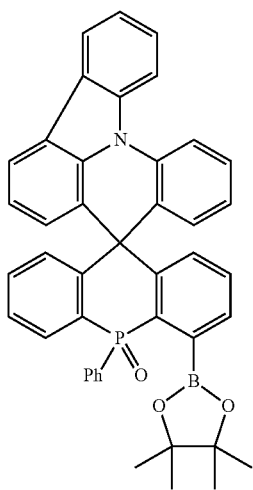

Preparation Example 1

1) Synthesis of Compound of the Following Compound 1

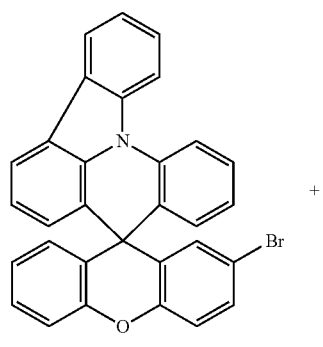

[Compound A]

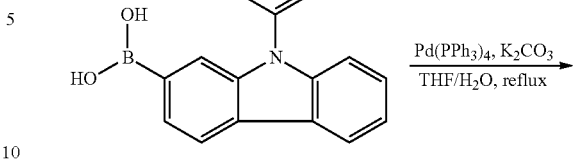

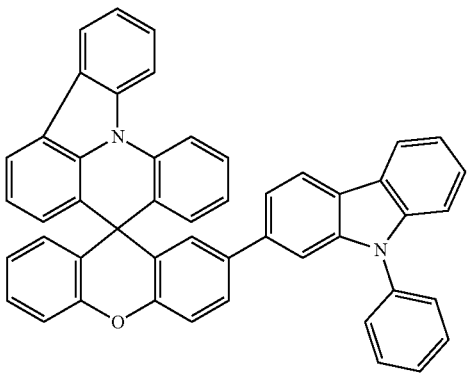

[Compound 1]

Compound A (10.0 g, 20.00 mmol) and (9-phenyl-9H-carbazol-2-yl)boronic acid (5.90 g, 20.57 mmol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.62 g, 0.54 mmol) was put thereinto, and then the resulting mixture was heated and stirred for 3 hours. The temperature was lowered to normal temperature, the aqueous layer was removed, and the residue was dried over anhydrous magnesium sulfate, and then concentrated under reduced pressure, and recrystallized with 230 ml of ethyl acetate to prepare Compound 1 (10.55 g, yield: 80%).

MS[M+H]$^+$=663

Preparation Example 2

1) Synthesis of Compound of the Following Compound 2

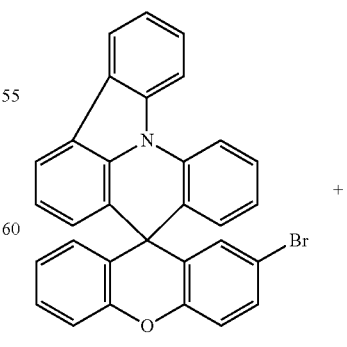

[Compound A]

299
-continued

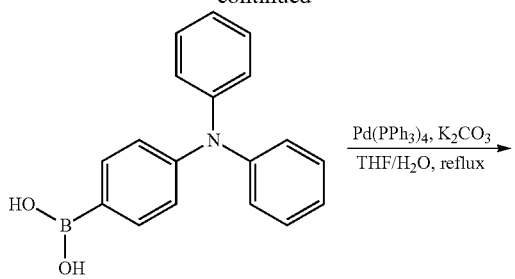

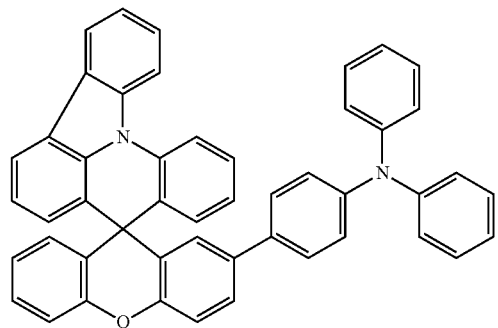

[Compound 2]

Compound A (10.0 g, 20.62 mmol) and (4-(diphenylamino)phenyl)boronic acid (6.51 g, 22.68 mmol) were completely dissolved in 240 ml of tetrahydrofuran in a 500-ml round bottom flask under a nitrogen atmosphere, and then a 2 M aqueous potassium carbonate solution (120 ml) was added thereto, tetrakis-(triphenylphosphine)palladium (0.69 g, 0.61 mmol) was put thereinto, and then the resulting mixture was heated and stirred for 2 hours. The temperature was lowered to normal temperature, the aqueous layer was removed, and the residue was dried over anhydrous magnesium sulfate, and then concentrated under reduced pressure, and recrystallized with 230 ml of ethyl acetate to prepare Compound 2 (10.18 g, yield: 76%).

MS[M+H]=665

Preparation Example 3

1) Synthesis of Compound of the Following Compound 3

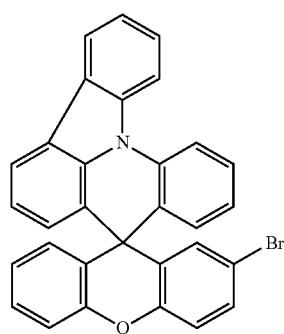

A
[Compound A]

300
-continued

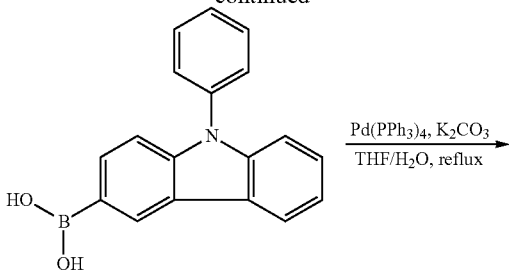

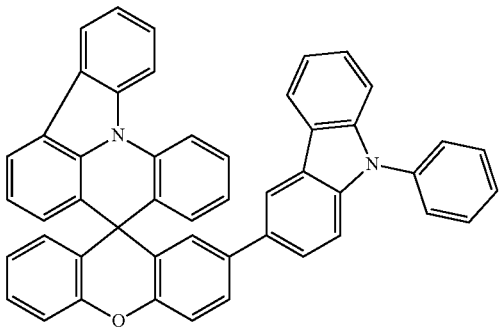

[Compound 3]

Compound A (10.0 g, 20.00 mmol) and (9-phenyl-9H-carbazol-2-yl)boronic acid (5.90 g, 20.57 mmol) were completely dissolved in 360 ml of tetrahydrofuran in a 500-ml round bottom flask under a nitrogen atmosphere, and then a 2 M aqueous potassium carbonate solution (180 ml) was added thereto, tetrakis-(triphenylphosphine)palladium (0.62 g, 0.54 mmol) was put thereinto, and then the resulting mixture was heated and stirred for 5 hours. The temperature was lowered to normal temperature, the aqueous layer was removed, and the residue was dried over anhydrous magnesium sulfate, and then concentrated under reduced pressure, and recrystallized with 280 ml of ethyl acetate to prepare Compound 3 (11.46 g, yield: 86%).

MS[M+H]$^+$=663

Preparation Example 4

1) Synthesis of Compound of the Following Compound 4

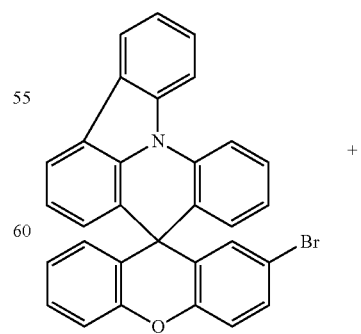

A
[Compound A]

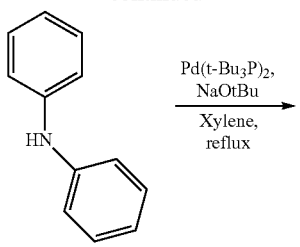

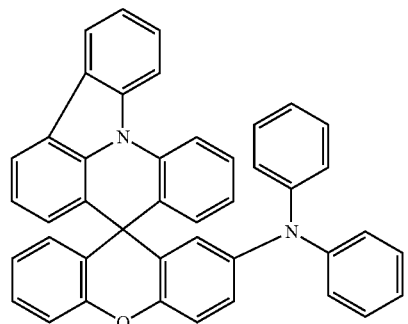

[Compound 4]

Compound A (10.0 g, 20.00 mmol) and diphenylamine (3.55 g, 21.00 mmol) were completely dissolved in 160 ml of xylene in a 500-ml round bottom flask under a nitrogen atmosphere, and then sodium tert-butoxide (2.30 g, 24.00 mol) was added thereto, bis(tri-tert-butylphosphine) palladium(0) (0.10 g, 0.20 mmol) was put thereinto, and then the resulting mixture was heated and stirred for 1 hour. The temperature was lowered to normal temperature, the mixture was filtered to remove the base, and then xylene was concentrated under reduced pressure, and the residue was subjected to column chromatography at a ratio of tetrahydrofuran:hexane=1:25 to prepare Compound 4 (8.41 g, yield: 71%).

MS[M+H]$^+$=589

Preparation Example 5

1) Synthesis of Compound of the Following Compound 5

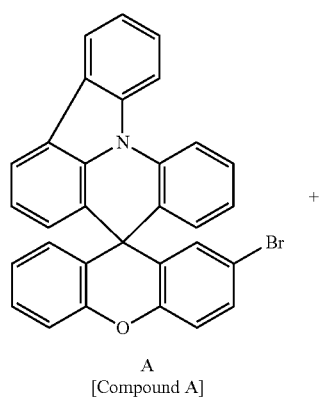

[Compound A]

+

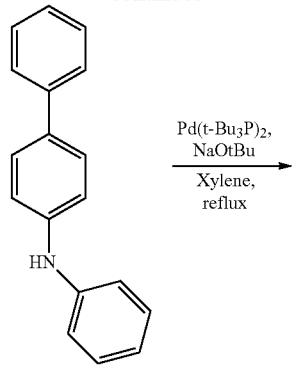

[Compound 5]

Compound A (10.0 g, 20.00 mmol) and N-phenyl-[1,1'-biphenyl]-4-amine (5.15 g, 21.00 mmol) were completely dissolved in 200 ml of xylene in a 500-ml round bottom flask under a nitrogen atmosphere, and then sodium tert-butoxide (2.30 g, 24.00 mol) was added thereto, bis(tri-tert-butylphosphine) palladium(0) (0.10 g, 0.20 mmol) was put thereinto, and then the resulting mixture was heated and stirred for 3 hours. The temperature was lowered to normal temperature, the mixture was filtered to remove the base, and then xylene was concentrated under reduced pressure, and the residue was subjected to column chromatography at a ratio of tetrahydrofuran:hexane=1:20 to prepare Compound 5 (10.98 g, yield: 83%).

MS[M+H]$^+$=665

Preparation Example 6

1) Synthesis of Compound of the Following Compound 6

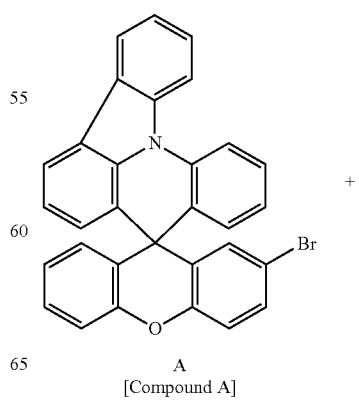

[Compound A]

+

303

-continued

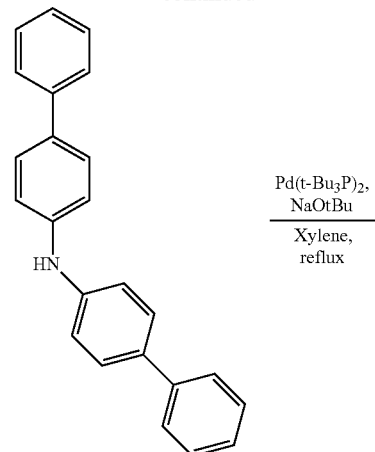

Preparation Example 7

1) Synthesis of Compound of the Following Compound 7

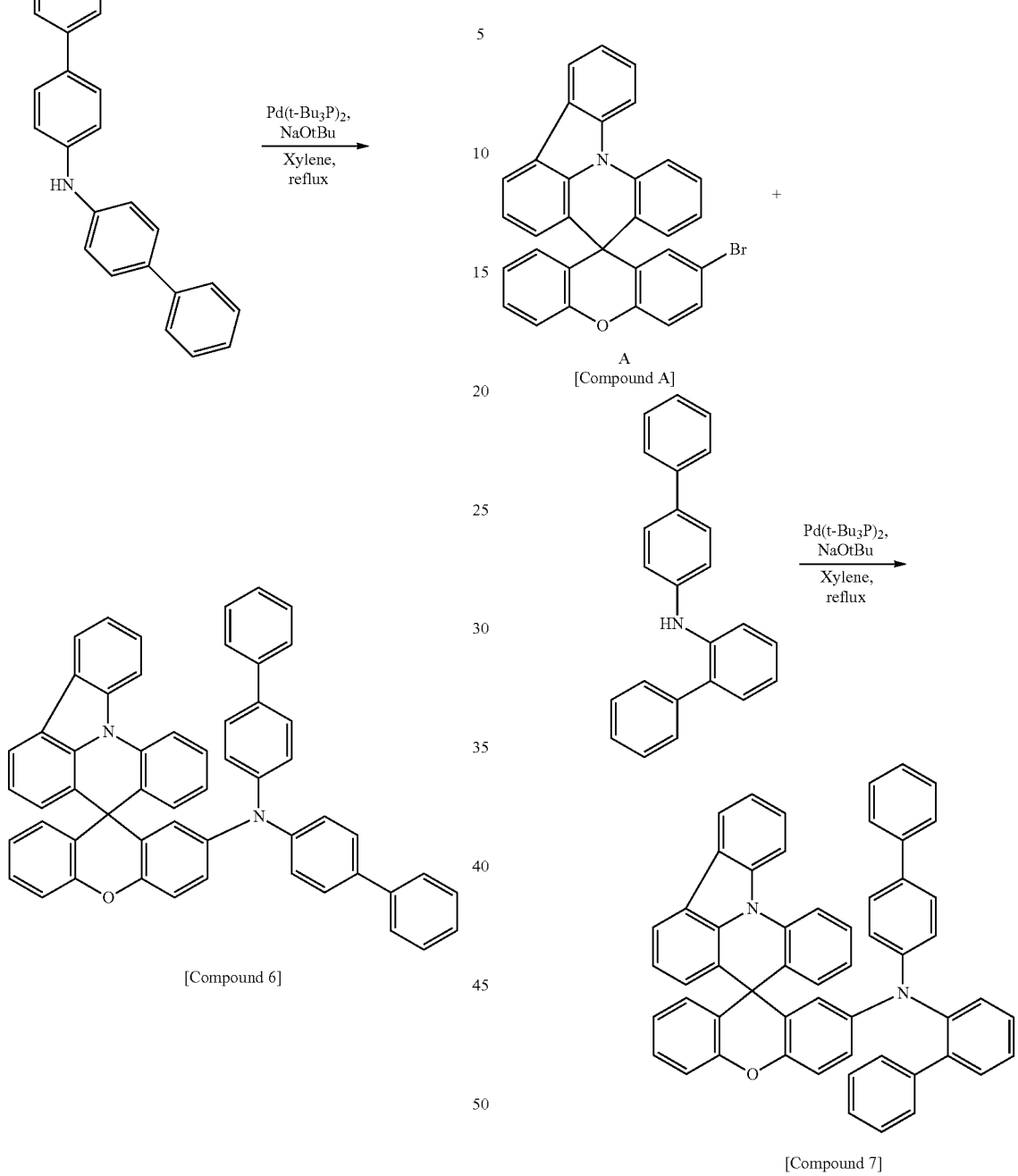

Compound A (10.0 g, 20.00 mmol) and di([1,1'-biphenyl]-4-yl)amine (6.74 g, 21.00 mmol) were completely dissolved in 320 ml of xylene in a 500-ml round bottom flask under a nitrogen atmosphere, and then sodium tert-butoxide (2.30 g, 24.00 mol) was added thereto, bis(tri-tert-butylphosphine) palladium(0) (0.10 g, 0.20 mmol) was put thereinto, and then the resulting mixture was heated and stirred for 5 hours. The temperature was lowered to normal temperature, the mixture was filtered to remove the base, and then xylene was concentrated under reduced pressure, and the residue was recrystallized with 300 ml of ethyl acetate to prepare Compound 6 (12.05 g, yield: 81%).

MS[M+H]$^+$=741

Compound A (10.0 g, 20.00 mmol) and di([1,1'-biphenyl]-4-yl)amine (6.74 g, 21.00 mmol) were completely dissolved in 305 ml of xylene in a 500-ml round bottom flask under a nitrogen atmosphere, and then sodium tert-butoxide (2.30 g, 24.00 mol) was added thereto, bis(tri-tert-butylphosphine) palladium(0) (0.10 g, 0.20 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 200 ml of ethyl acetate to prepare Compound 7 (8.45 g, yield: 57%).

MS[M+H]$^+$=741

Preparation Example 8

1) Synthesis of Compound of the Following Compound 8

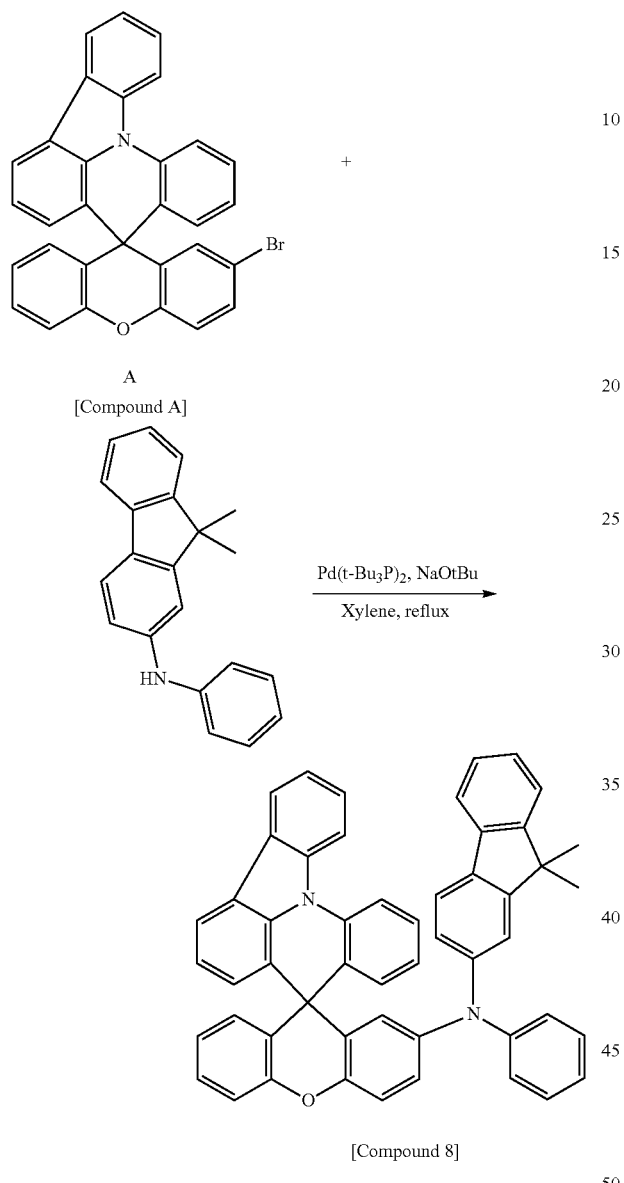

[Compound 8]

Compound A (10.0 g, 20.00 mmol) and 9,9-dimethyl-N-phenyl-9H-fluoren-2-amine (5.99 g, 21.00 mmol) were completely dissolved in 220 ml of xylene in a 500-ml round bottom flask under a nitrogen atmosphere, and then sodium tert-butoxide (2.30 g, 24.00 mol) was added thereto, bis(tri-tert-butylphosphine) palladium(0) (0.11 g, 0.21 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 150 ml of ethyl acetate to prepare Compound 8 (9.62 g, yield: 68%).

MS[M+H]$^+$=705

Preparation Example 9

1) Synthesis of Compound of the Following Compound 9

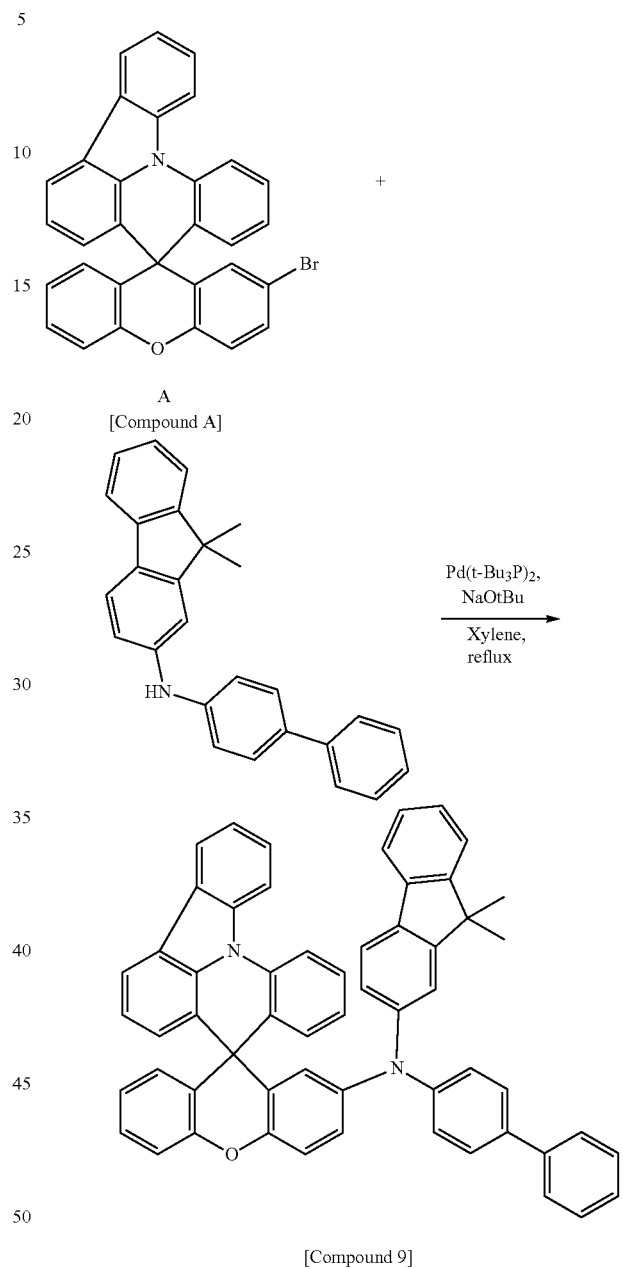

[Compound 9]

Compound A (10.0 g, 20.00 mmol) and N-([1,1'-biphenyl]-4-yl)-9,9-dimethyl-9H-fluoren-2-amine (7.58 g, 22.68 mmol) were completely dissolved in 290 ml of xylene in a 500-ml round bottom flask under a nitrogen atmosphere, and then sodium tert-butoxide (2.30 g, 24.00 mol) was added thereto, bis(tri-tert-butylphosphine) palladium(0) (0.10 g, 0.20 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 240 ml of ethyl acetate to prepare Compound 9 (13.87 g, yield: 89%).

MS[M+H]$^+$=781

307

Preparation Example 10

1) Synthesis of Compound of the Following Compound 10

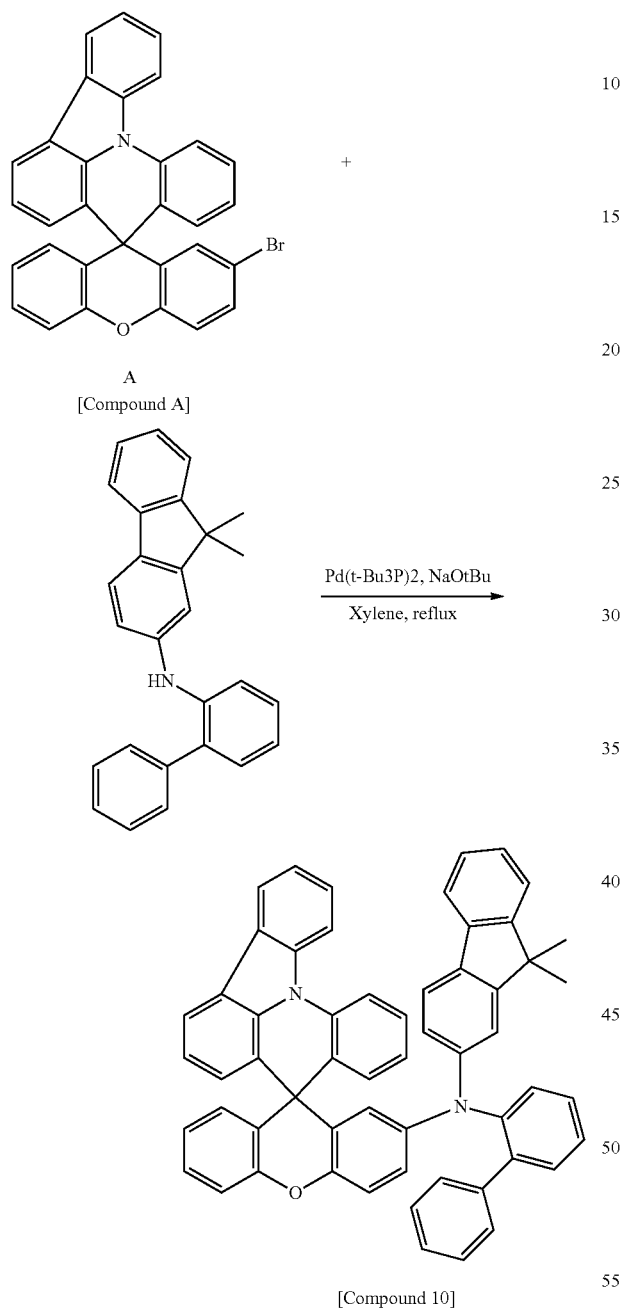

308 remove the base, and then xylene was concentrated under reduced pressure, and the residue was recrystallized with 200 ml of ethyl acetate to prepare Compound 10 (11.12 g, yield: 71%).

MS[M+H]$^+$=781

Preparation Example 11

1) Synthesis of Compound of the Following Compound 11

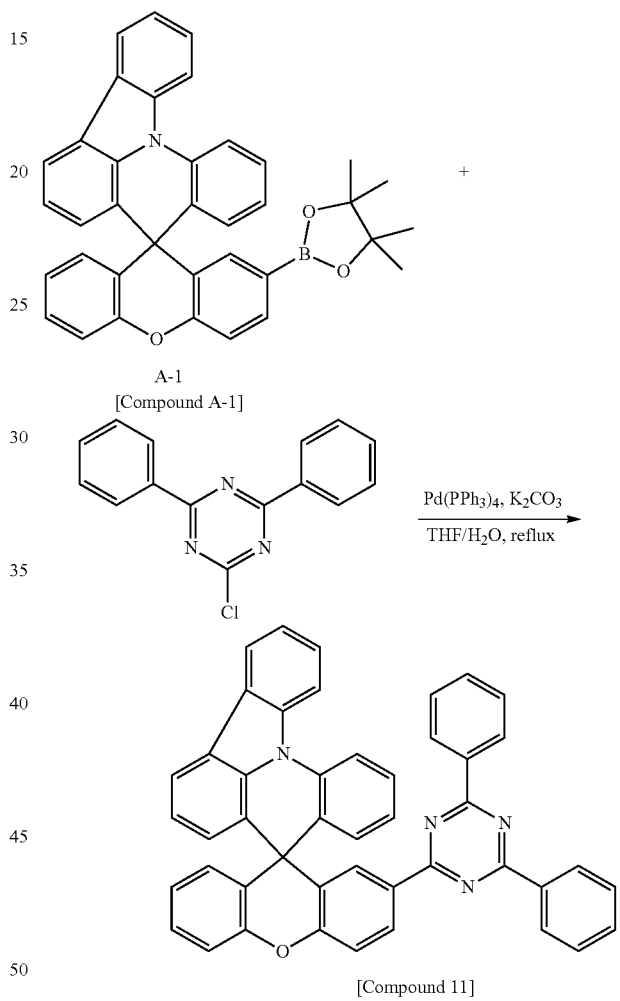

Compound A (10.0 g, 20.00 mmol) and N-([1,1'-biphenyl]-4-yl)-2,2-dimethyl-9H-fluoren-2-amine (7.58 g, 22.68 mmol) were completely dissolved in 290 ml of xylene in a 500-ml round bottom flask under a nitrogen atmosphere, and then sodium tert-butoxide (2.30 g, 24.00 mol) was added thereto, bis(tri-tert-butylphosphine) palladium(0) (0.10 g, 0.20 mmol) was put thereinto, and then the resulting mixture was heated and stirred for 2 hours. The temperature was lowered to normal temperature, the mixture was filtered to Compound A-1 (10.0 g, 18.28 mmol) and 2-chloro-4,6-diphenyl-1,3,5-triazine (4.24 g, 15.90 mol) were completely dissolved in 200 ml of tetrahydrofuran in a 500-ml round bottom flask under a nitrogen atmosphere, and then a 2 M aqueous potassium carbonate solution (100 ml) was added thereto, tetrakis-(triphenylphosphine)palladium (0.69 g, 0.60 mmol) was put thereinto, and then the resulting mixture was heated and stirred for 6 hours. The temperature was lowered to normal temperature, the aqueous layer was removed, and the residue was dried over anhydrous magnesium sulfate, and then concentrated under reduced pressure, and recrystallized with 280 ml of ethyl acetate to prepare Compound 11 (9.84 g, yield: 82%).

MS[M+H]+=653

Preparation Example 12

1) Synthesis of Compound of the Following Compound 12

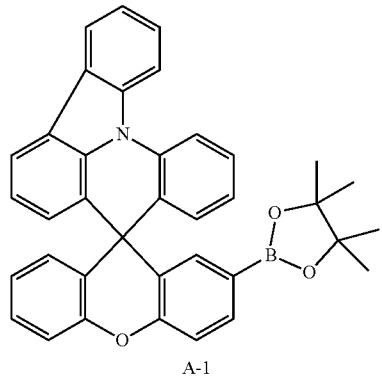
[Compound A-1]

+

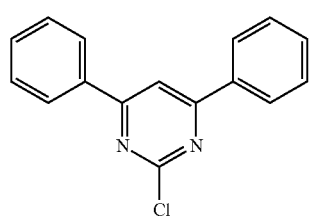

Pd(PPh₃)₄, K₂CO₃
―――――――――→
THF/H₂O, reflux

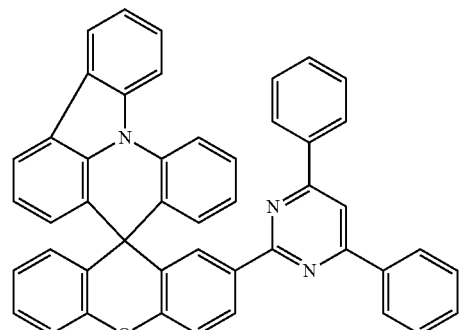
[Compound 12]

Compound A-1 (10.0 g, 18.28 mmol) and 2-chloro-4,6-diphenylpyrimidine (4.24 g, 15.90 mol) were completely dissolved in 220 ml of tetrahydrofuran in a 500-ml round bottom flask under a nitrogen atmosphere, and then a 2 M aqueous potassium carbonate solution (110 ml) was added thereto, tetrakis-(triphenylphosphine)palladium (0.58 g, 0.51 mmol) was put thereinto, and then the resulting mixture was heated and stirred for 3 hours. The temperature was lowered to normal temperature, the aqueous layer was removed, and the residue was dried over anhydrous magnesium sulfate, and then concentrated under reduced pressure, and recrystallized with 240 ml of ethyl acetate to prepare Compound 12 (8.46 g, yield: 71%).

MS[M+H]⁺=652

Preparation Example 13

1) Synthesis of Compound of the Following Compound 13

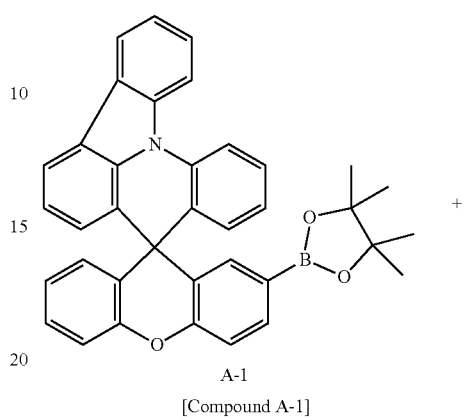
[Compound A-1]

+

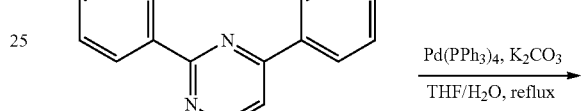

Pd(PPh₃)₄, K₂CO₃
―――――――――→
THF/H₂O, reflux

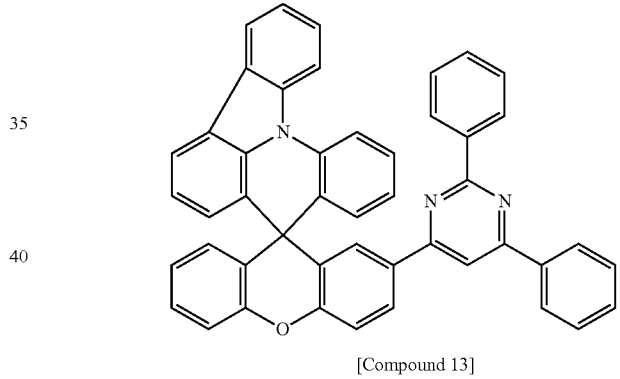
[Compound 13]

Compound A-1 (10.0 g, 18.28 mmol) and 2-chloro-4,6-diphenylpyrimidine (4.24 g, 15.90 mol) were completely dissolved in 220 ml of tetrahydrofuran in a 500-ml round bottom flask under a nitrogen atmosphere, and then a 2 M aqueous potassium carbonate solution (110 ml) was added thereto, tetrakis-(triphenylphosphine)palladium (0.58 g, 0.51 mmol) was put thereinto, and then the resulting mixture was heated and stirred for 3 hours. The temperature was lowered to normal temperature, the aqueous layer was removed, and the residue was dried over anhydrous magnesium sulfate, and then concentrated under reduced pressure, and recrystallized with 240 ml of ethyl acetate to prepare Compound 13 (8.89 g, yield: 74%).

MS[M+H]⁺=652

Preparation Example 14

1) Synthesis of Compound of the Following Compound 14

311

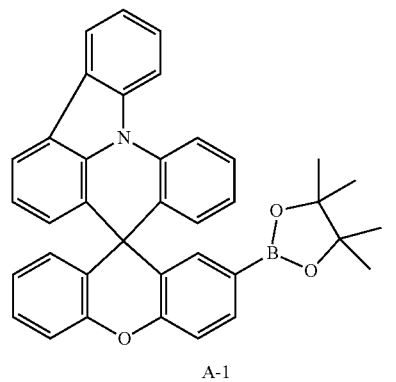

[Compound A-1]

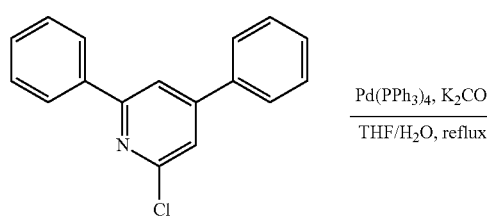

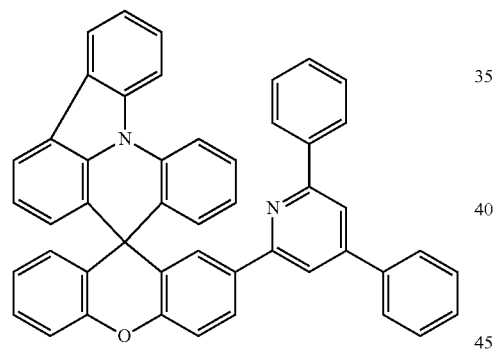

[Compound 14]

Compound A-1 (10.0 g, 18.28 mmol) and 2-chloro-4,6-diphenylpyridine (4.24 g, 15.90 mol) were completely dissolved in 180 ml of tetrahydrofuran in a 500-ml round bottom flask under a nitrogen atmosphere, and then a 2 M aqueous potassium carbonate solution (90 ml) was added thereto, tetrakis-(triphenylphosphine)palladium (0.58 g, 0.51 mmol) was put thereinto, and then the resulting mixture was heated and stirred for 3 hours. The temperature was lowered to normal temperature, the aqueous layer was removed, and the residue was dried over anhydrous magnesium sulfate, and then concentrated under reduced pressure, and recrystallized with 190 ml of ethyl acetate to prepare Compound 14 (7.45 g, yield: 62%).

MS[M+H]$^+$=651

Preparation Example 15

1) Synthesis of Compound of the Following Compound 15

312

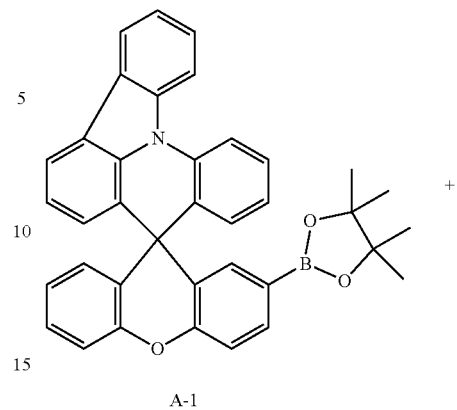

[Compound A-1]

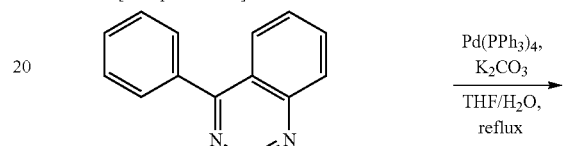

[Compound 15]

Compound A-1 (10.0 g, 18.28 mmol) and 2-chloro-4-phenylquinazoline (3.83 g, 15.90 mol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.58 g, 0.51 mmol) was put thereinto, and then the resulting mixture was heated and stirred for 6 hours. The temperature was lowered to normal temperature, the aqueous layer was removed, and the residue was dried over anhydrous magnesium sulfate, and then concentrated under reduced pressure, and recrystallized with 300 ml of ethyl acetate to prepare Compound 15 (7.23 g, yield: 63%).

MS[M+H]$^+$=626

Preparation Example 16

1) Synthesis of Compound of the Following Compound 16

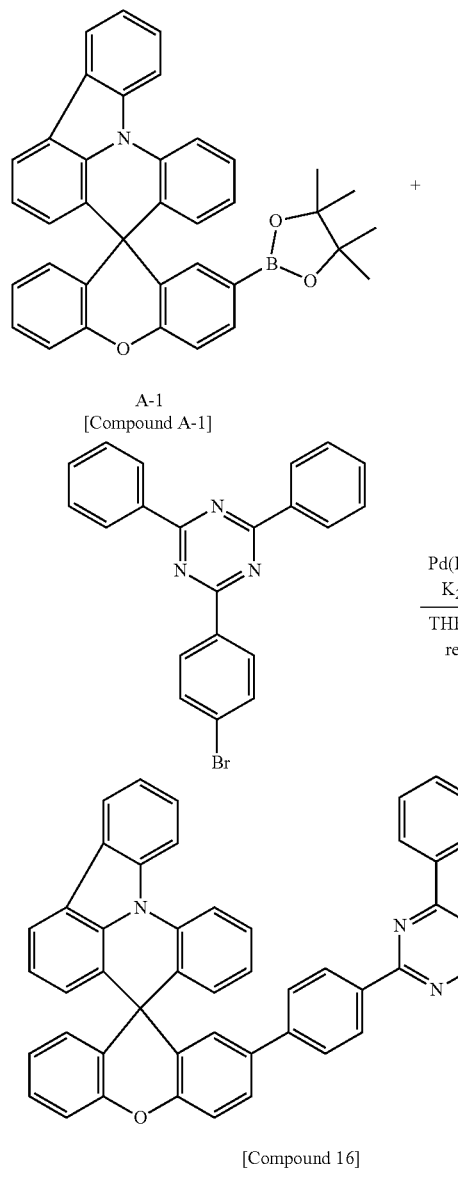

[Compound 16]

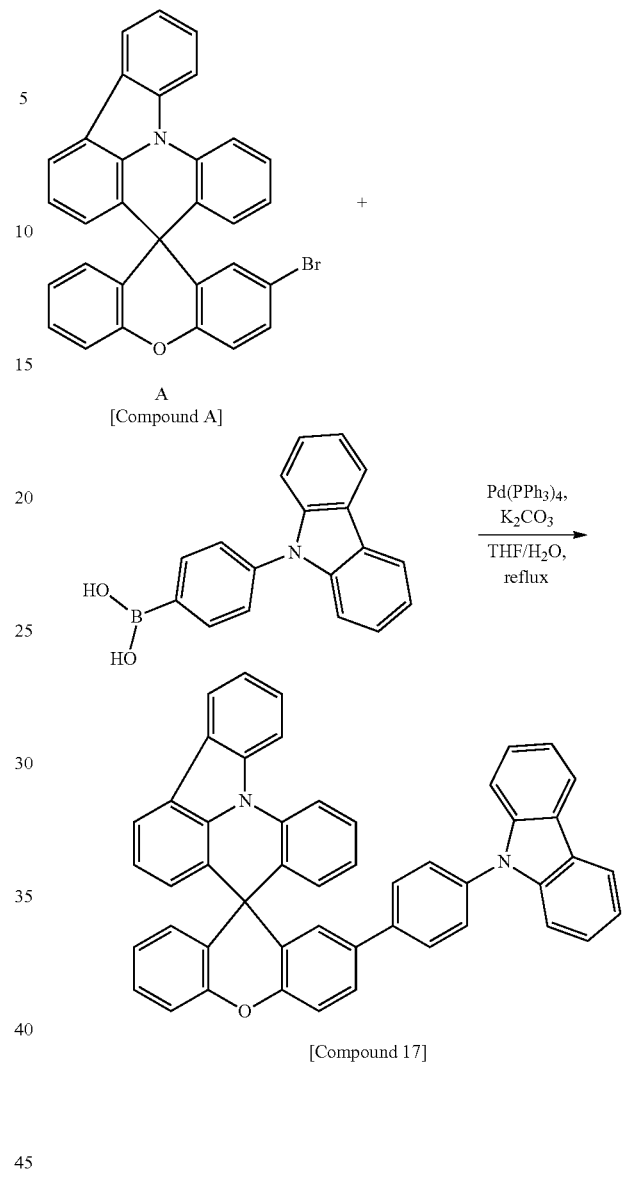

[Compound 17]

Compound A-1 (10.0 g, 18.28 mmol) and 2-(4-bromophenyl)-4,6-diphenyl-1,3,5-triazine (6.17 g, 15.90 mol) were completely dissolved in 220 ml of tetrahydrofuran in a 500-ml round bottom flask under a nitrogen atmosphere, and then a 2 M aqueous potassium carbonate solution (110 ml) was added thereto, tetrakis-(triphenylphosphine)palladium (0.69 g, 0.60 mmol) was put thereinto, and then the resulting mixture was heated and stirred for 8 hours. The temperature was lowered to normal temperature, the aqueous layer was removed, and the residue was dried over anhydrous magnesium sulfate, and then concentrated under reduced pressure, and recrystallized with 380 ml of ethyl acetate to prepare Compound 16 (11.85 g, yield: 89%).

MS[M+H]$^+$=729

Preparation Example 17

1) Synthesis of Compound of the Following Compound 17

Compound A (10.0 g, 20.00 mmol) and 4-(9H-carbazol-9-yl)phenyl)boronic acid (5.90 g, 20.57 mmol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.62 g, 0.54 mmol) was put thereinto, and then the resulting mixture was heated and stirred for 3 hours. The temperature was lowered to normal temperature, the aqueous layer was removed, and the residue was dried over anhydrous magnesium sulfate, and then concentrated under reduced pressure, and recrystallized with 230 ml of ethyl acetate to prepare Compound 17 (10.55 g, yield: 80%).

MS[M+H]$^+$=663

Preparation Example 18

1) Synthesis of Compound of the Following Compound 18

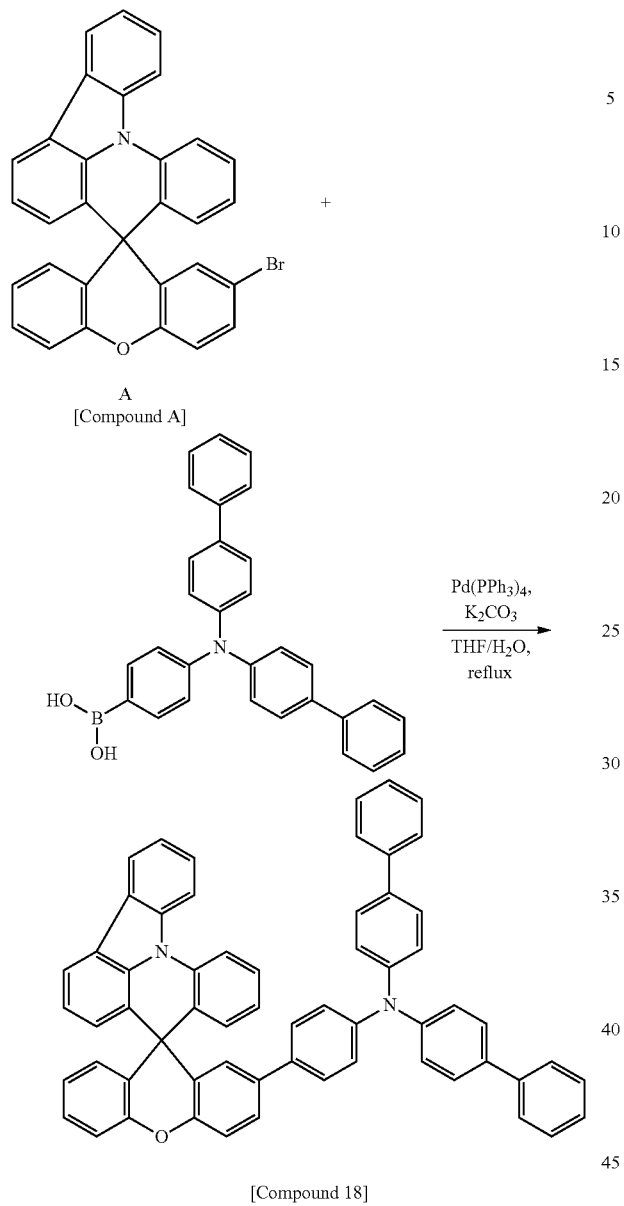

[Compound 18]

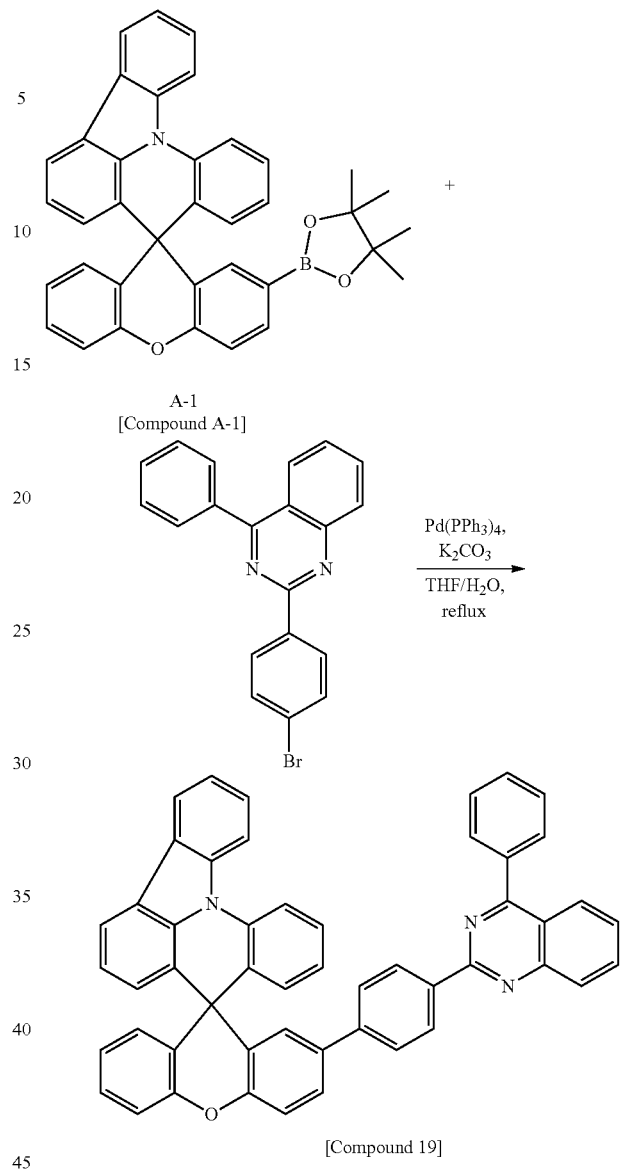

[Compound 19]

Compound A (10.0 g, 20.62 mmol) and (4-(diphenylamino)phenyl)boronic acid (10.00 g, 22.68 mmol) were completely dissolved in 240 ml of tetrahydrofuran in a 500-ml round bottom flask under a nitrogen atmosphere, and then a 2 M aqueous potassium carbonate solution (120 ml) was added thereto, tetrakis-(triphenylphosphine)palladium (0.69 g, 0.61 mmol) was put thereinto, and then the resulting mixture was heated and stirred for 3 hours. The temperature was lowered to normal temperature, the aqueous layer was removed, and the residue was dried over anhydrous magnesium sulfate, and then concentrated under reduced pressure, and recrystallized with 230 ml of ethyl acetate to prepare Compound 18 (12.66 g, yield: 85%).

MS[M+H]$^+$=818

Preparation Example 19

1) Synthesis of Compound of the Following Compound 19

Compound A-1 (10.0 g, 18.28 mmol) and 2-(4-bromophenyl)-4-phenylquinazoline (5.74 g, 15.90 mol) were completely dissolved in 320 ml of tetrahydrofuran in a 500-ml round bottom flask under a nitrogen atmosphere, and then a 2 M aqueous potassium carbonate solution (160 ml) was added thereto, tetrakis-(triphenylphosphine)palladium (0.58 g, 0.51 mmol) was put thereinto, and then the resulting mixture was heated and stirred for 9 hours. The temperature was lowered to normal temperature, the aqueous layer was removed, and the residue was dried over anhydrous magnesium sulfate, and then concentrated under reduced pressure, and recrystallized with 350 ml of ethyl acetate to prepare Compound 19 (10.22 g, yield: 81%).

MS[M+H]$^+$=702

Preparation Example 20

1) Synthesis of Compounds of the Following Compounds 20 to 38

20
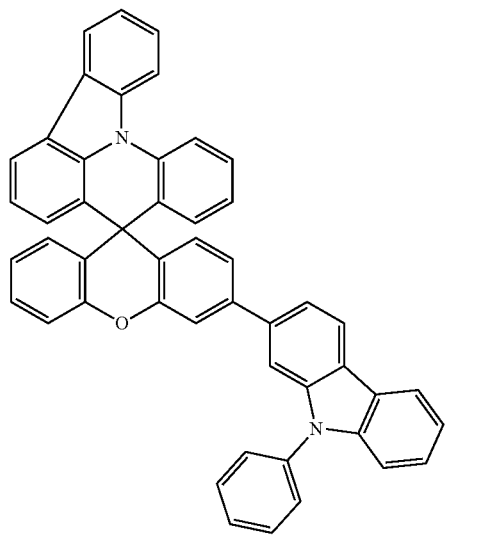
21
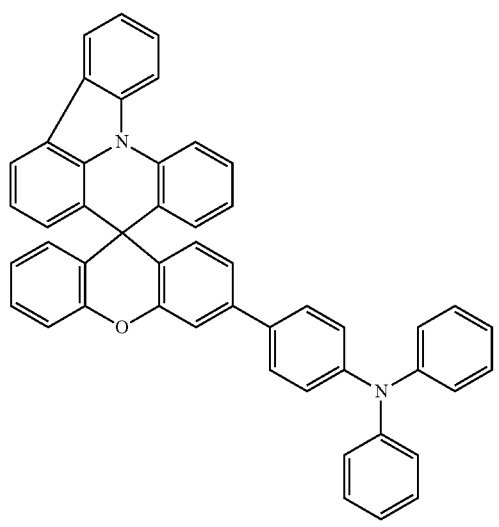
22
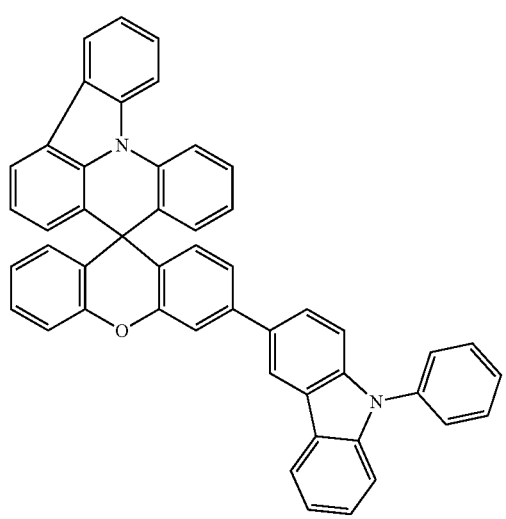
23
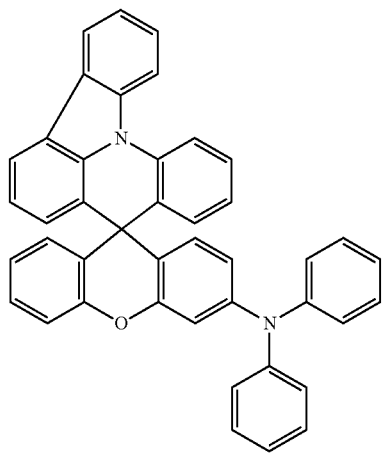
24
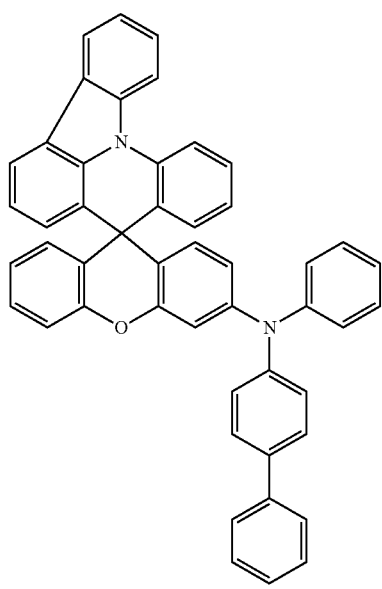
25
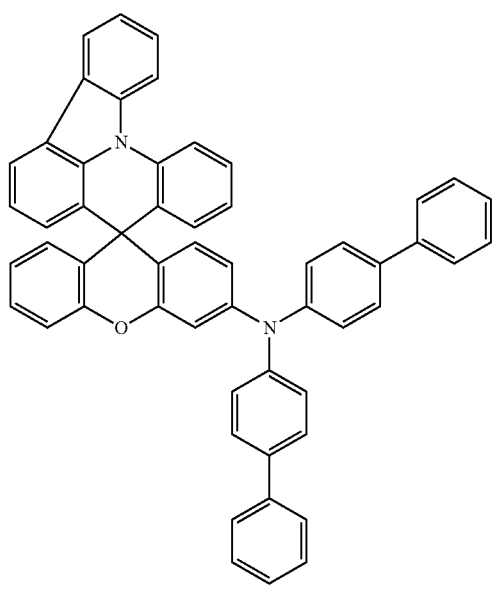

26
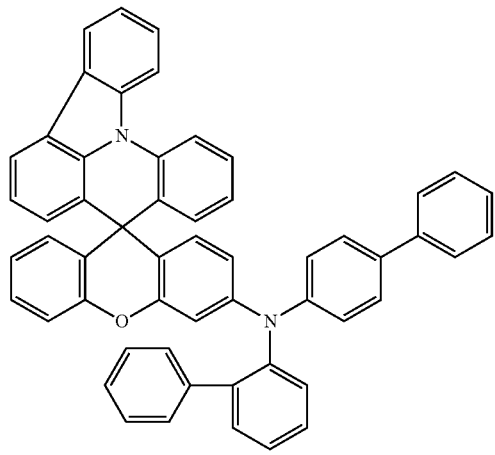
27
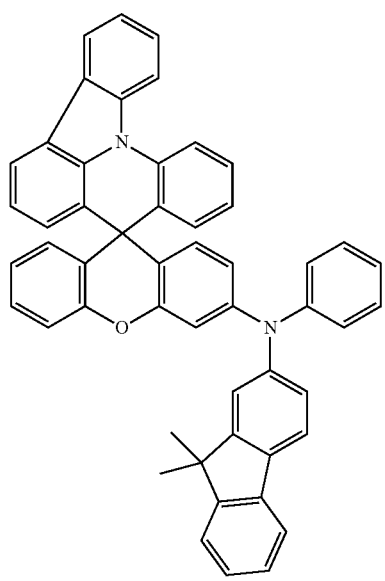
28
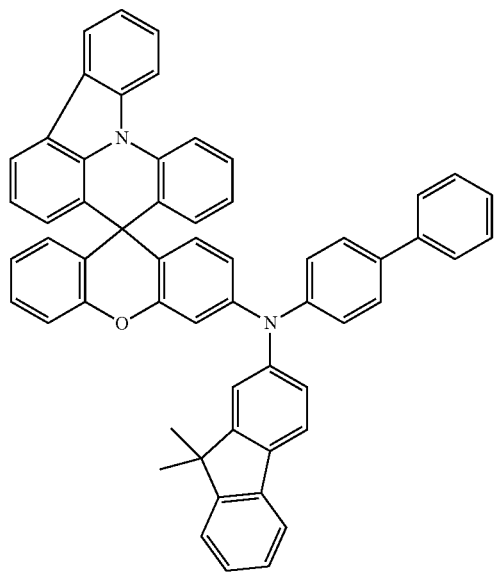
29
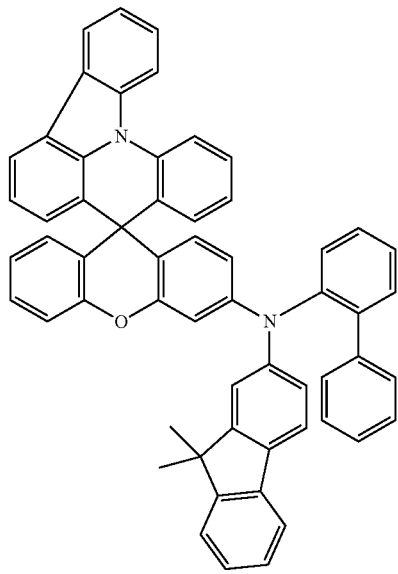
30
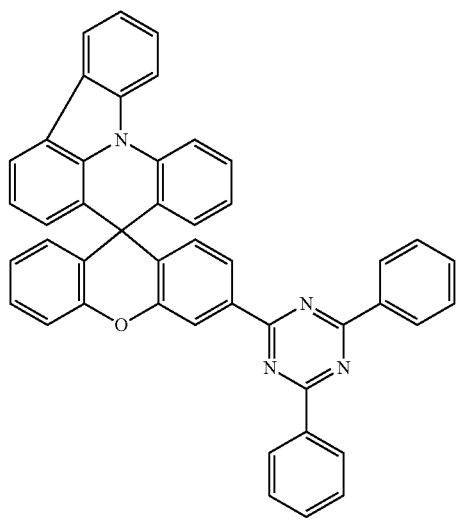
31
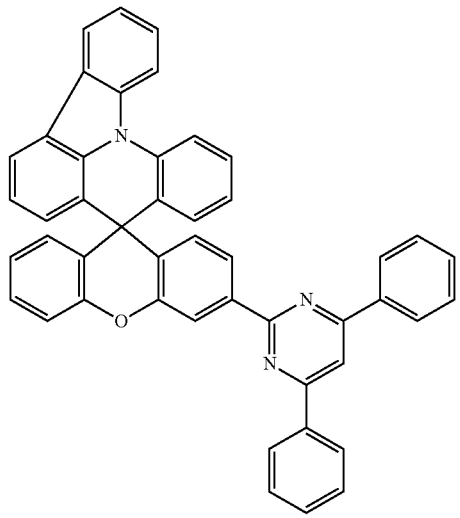

321
-continued
32
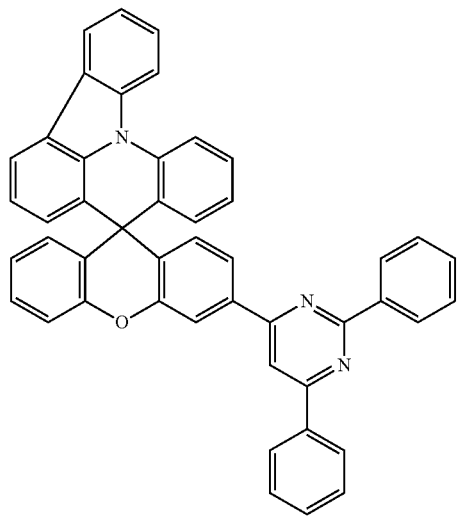
33
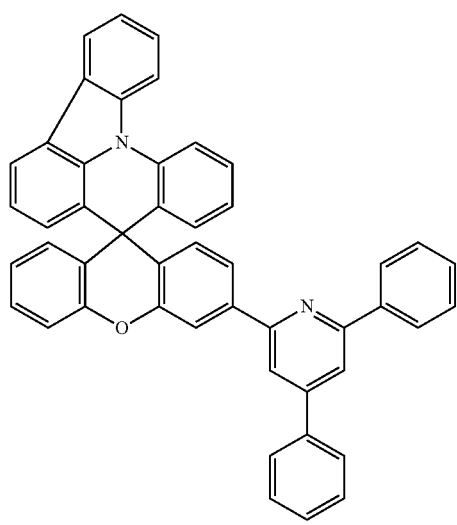
34
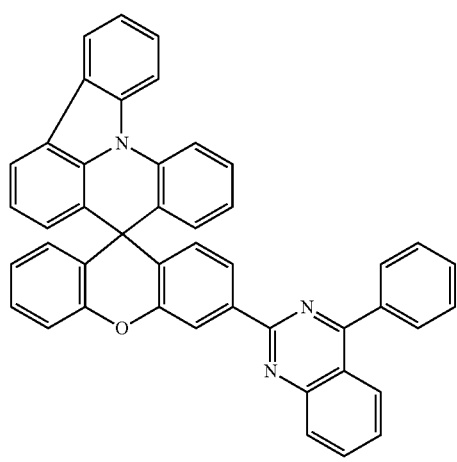
322
-continued
35
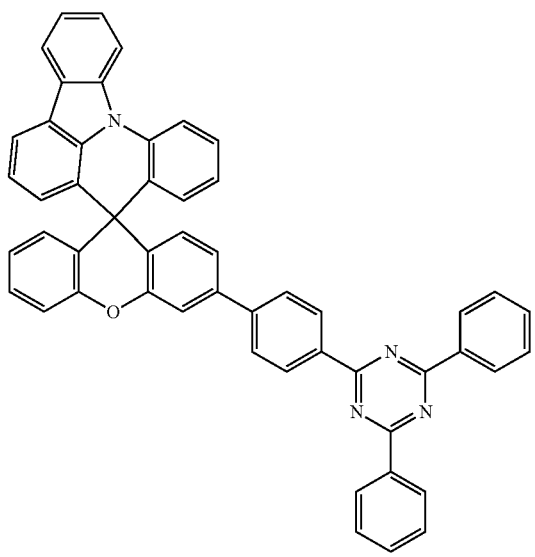
36
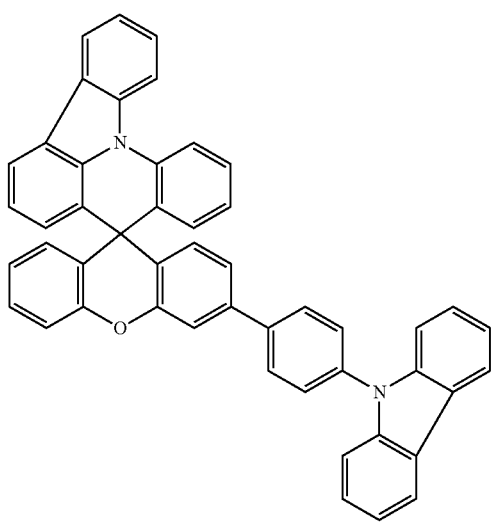

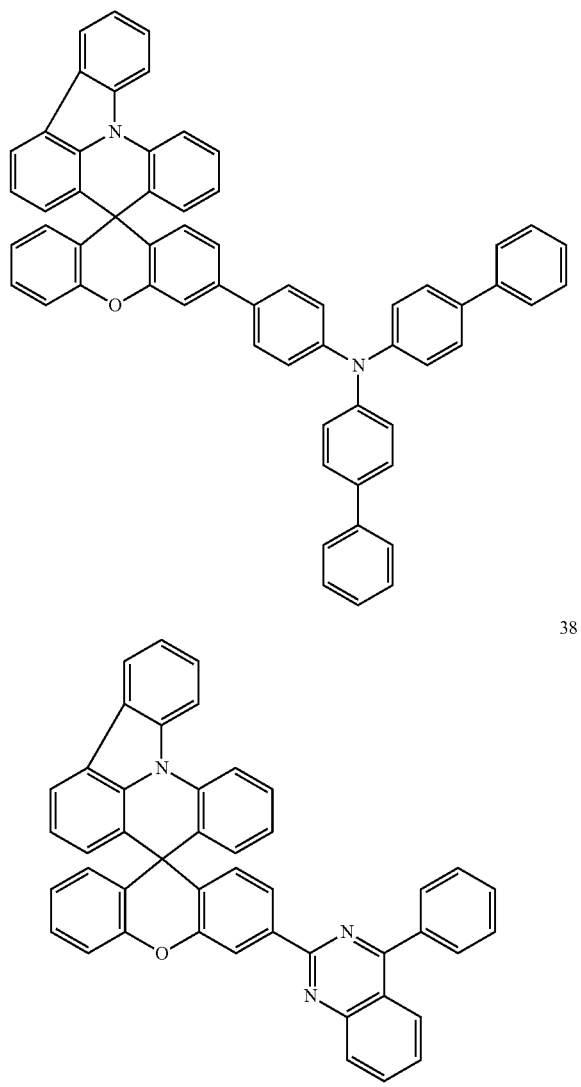

Compounds 20 to 38 were prepared in the same manner as in the method of preparing Compounds 1 to 19, except that Compound B and Compound B-1 were used instead of Compound A and Compound A-1, respectively, as starting materials in Preparation Examples 1 to 19. The MS[M+H]$^+$ values of Compounds 20 to 38 are shown in the following Table 1.

TABLE 1

| Compound No. | MS[M + H]$^+$ |
|---|---|
| 20 | 663 |
| 21 | 665 |
| 22 | 663 |
| 23 | 589 |
| 24 | 665 |
| 25 | 741 |
| 26 | 741 |
| 27 | 731 |
| 28 | 781 |
| 29 | 781 |
| 30 | 653 |
| 31 | 652 |
| 32 | 652 |

TABLE 1-continued

| Compound No. | MS[M + H]$^+$ |
|---|---|
| 33 | 651 |
| 34 | 626 |
| 35 | 729 |
| 36 | 663 |
| 37 | 817 |
| 38 | 626 |

Preparation Example 21

1) Synthesis of Compounds of the Following Compounds 39 to 57

325
-continued
41
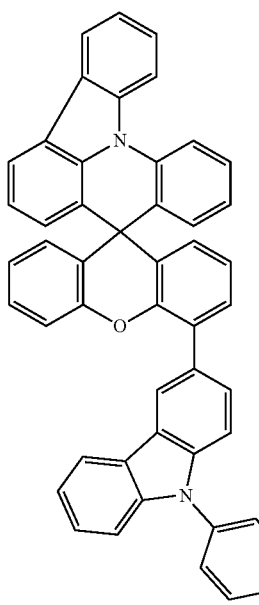
42
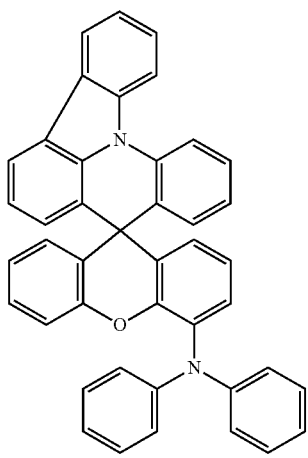
43
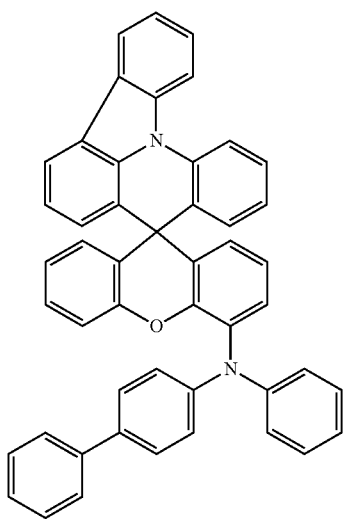
326
-continued
44
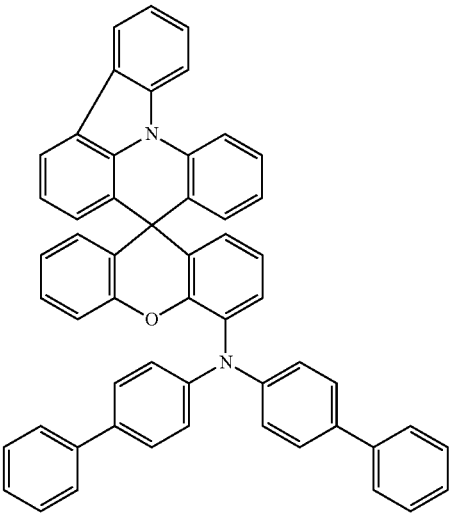
45
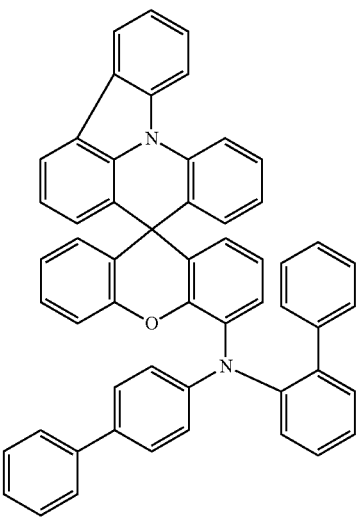
46
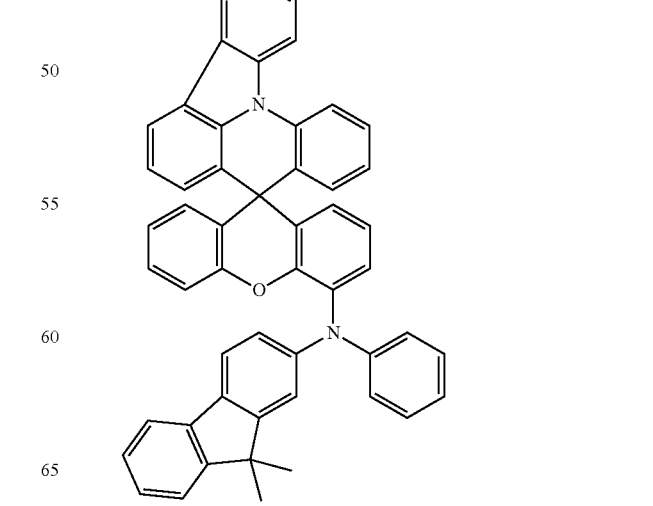

327
-continued
47
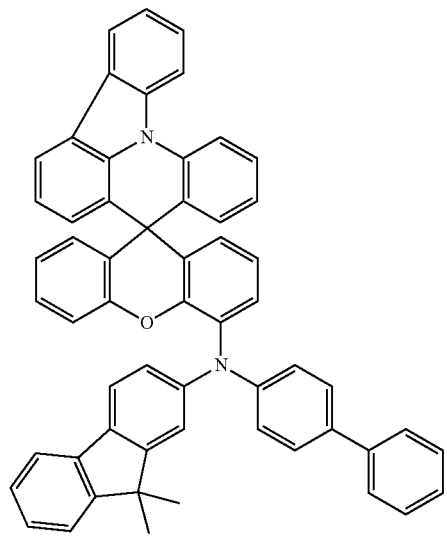
48
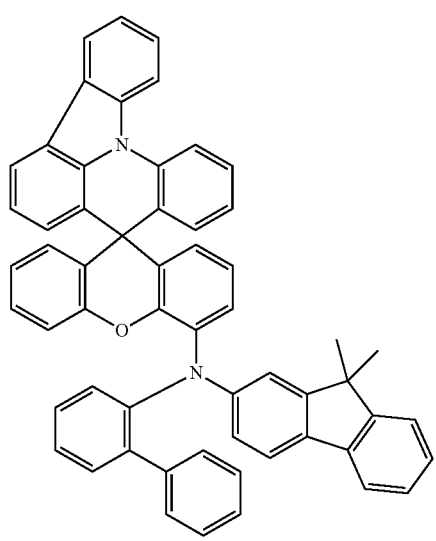
49
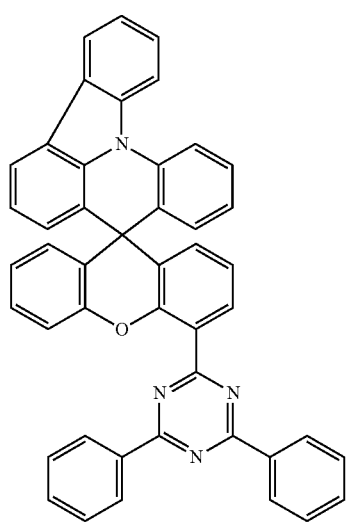
328
-continued
50
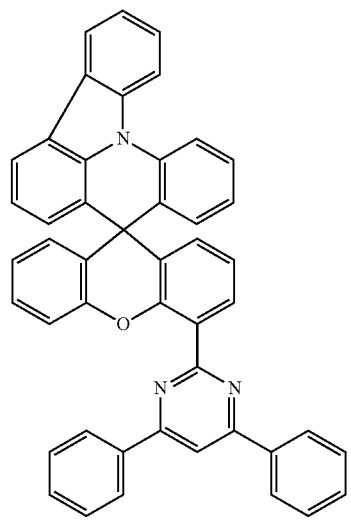
51
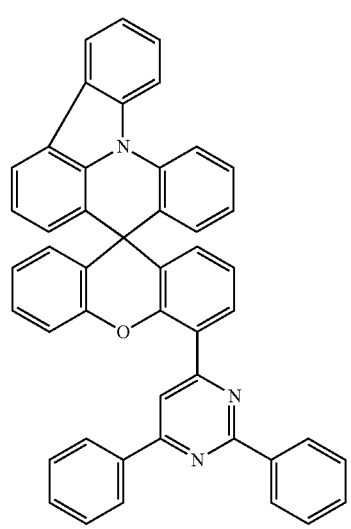
52
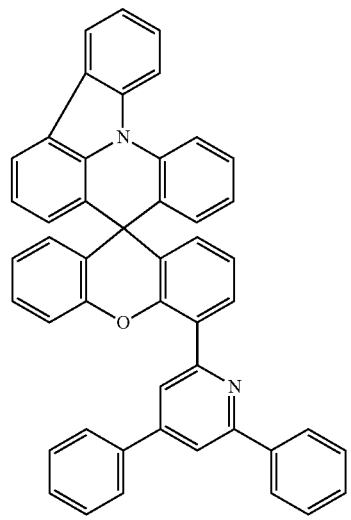

329
-continued
53
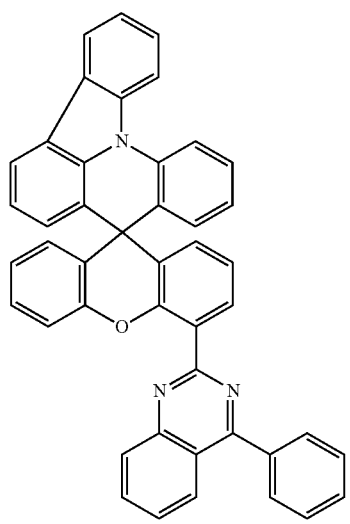
54
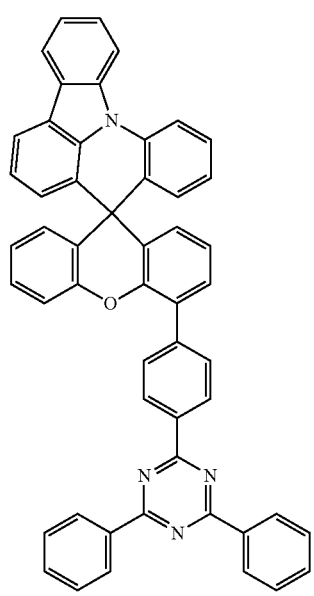
330
-continued
55
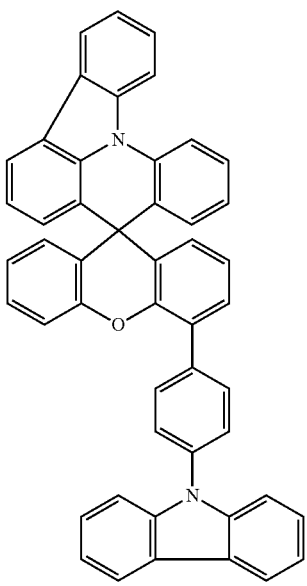
56
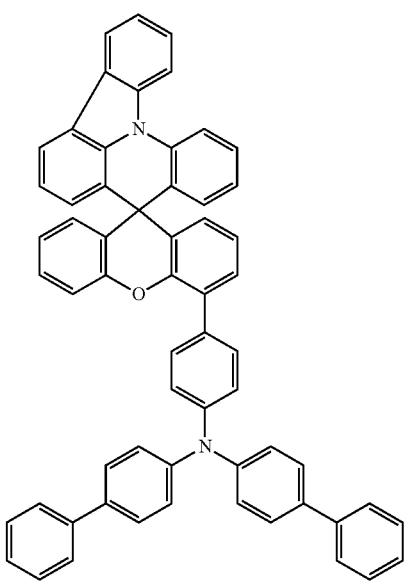

57

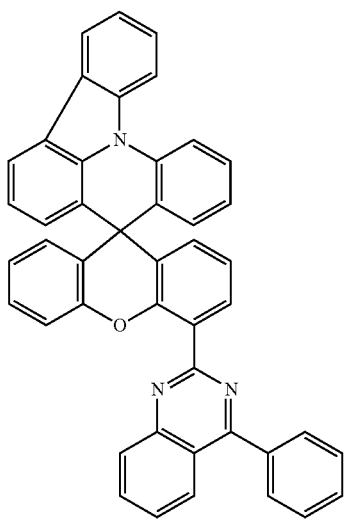

Compounds 39 to 57 were prepared in the same manner as in the method of preparing Compounds 1 to 19, except that Compound C and Compound C-1 were used instead of Compound A and Compound A-1, respectively, as starting materials in Preparation Examples 1 to 19. The MS[M+H]$^+$ values of Compounds 39 to 57 are shown in the following Table 2.

TABLE 2

| Compound No. | MS[M + H]$^+$ |
|---|---|
| 39 | 663 |
| 40 | 665 |
| 41 | 663 |
| 42 | 589 |
| 43 | 665 |
| 44 | 741 |
| 45 | 741 |
| 46 | 731 |
| 47 | 781 |
| 48 | 781 |
| 49 | 653 |
| 50 | 652 |
| 51 | 652 |
| 52 | 651 |
| 53 | 626 |
| 54 | 729 |
| 55 | 663 |
| 56 | 817 |
| 57 | 626 |

Preparation Example 22

1) Synthesis of Compounds of the Following Compounds 58 to 76

58

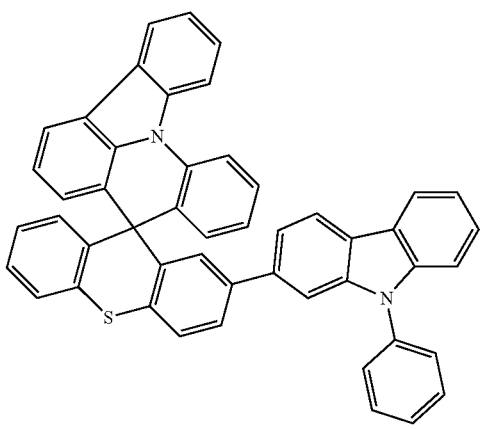

59

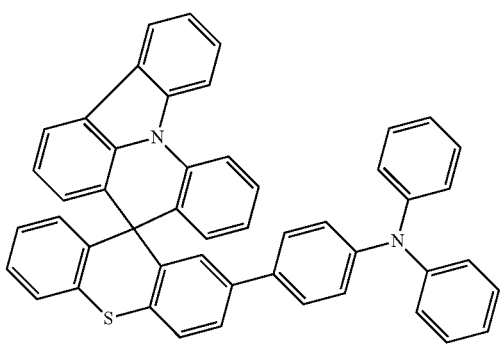

60

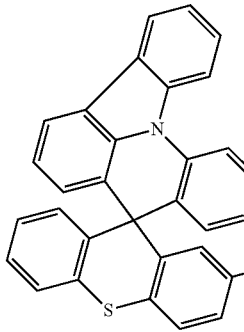

61

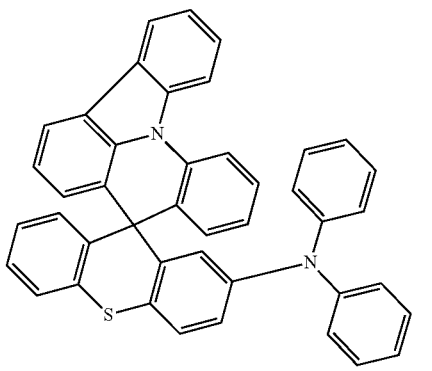

62
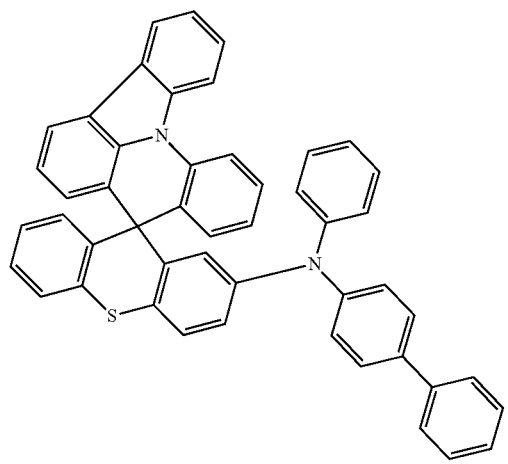
63
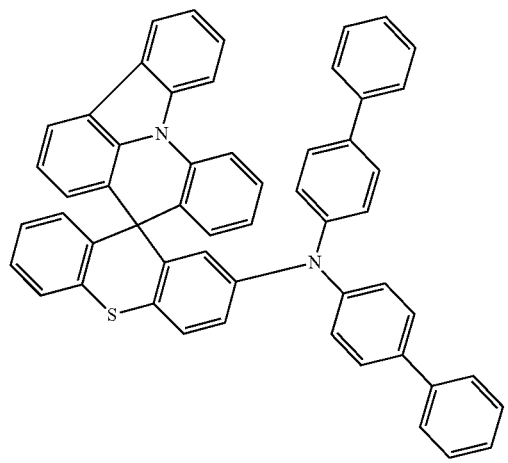
64
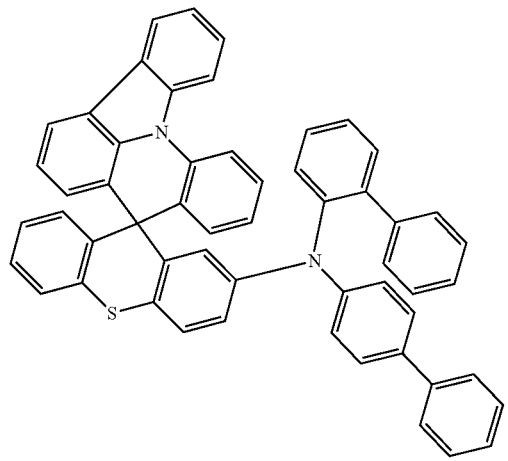
65
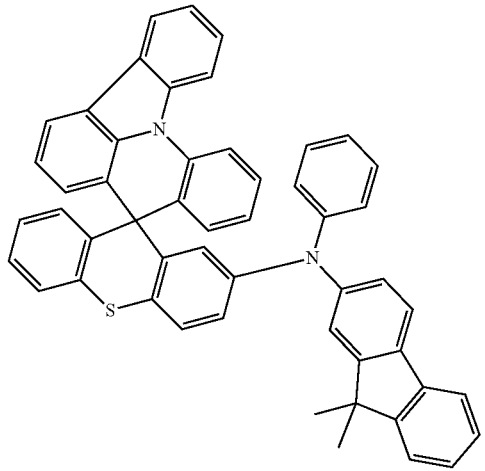
66
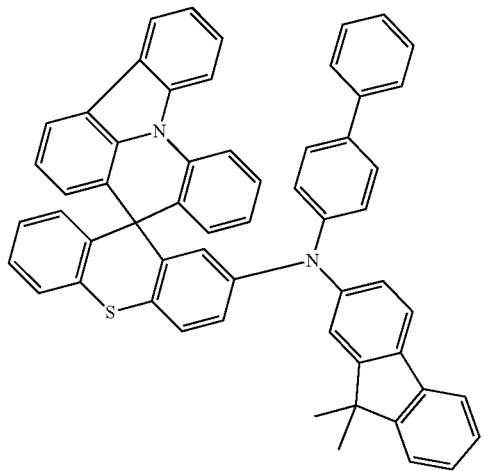
67
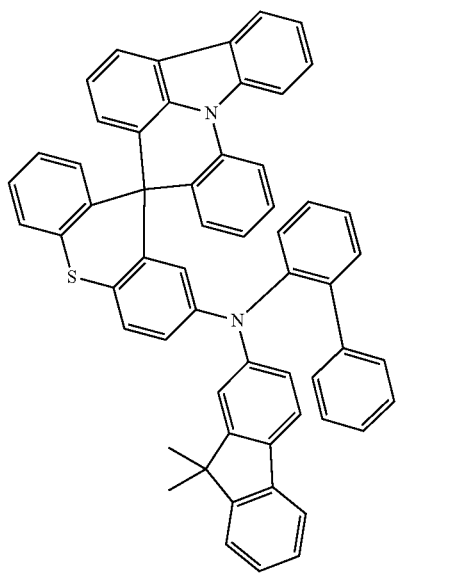

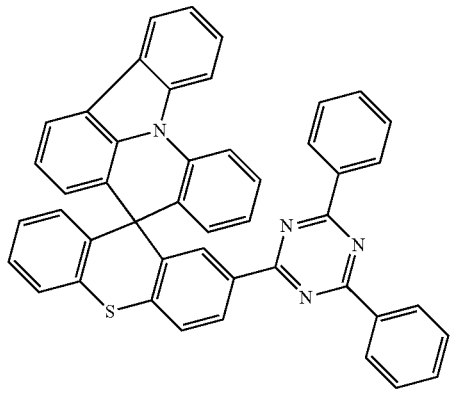
68
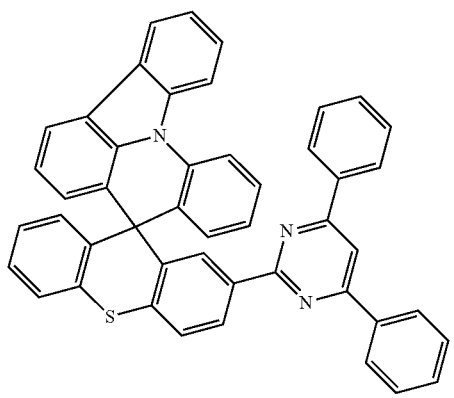
69
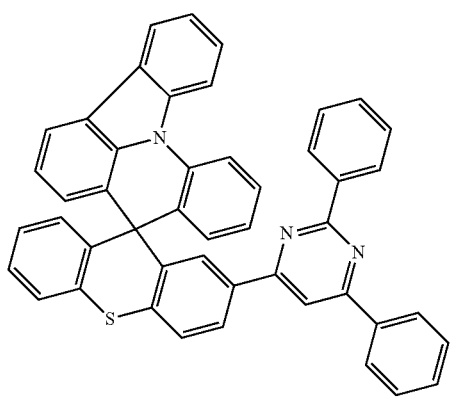
70
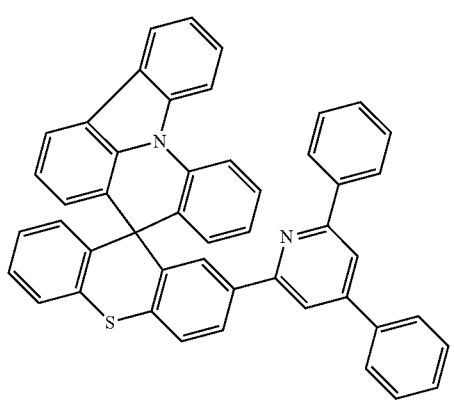
71
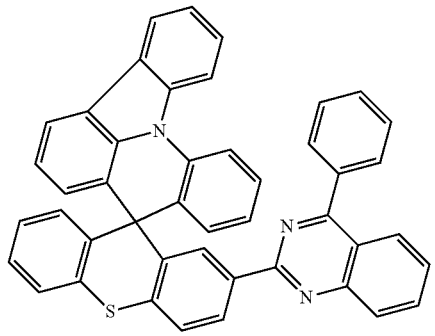
72
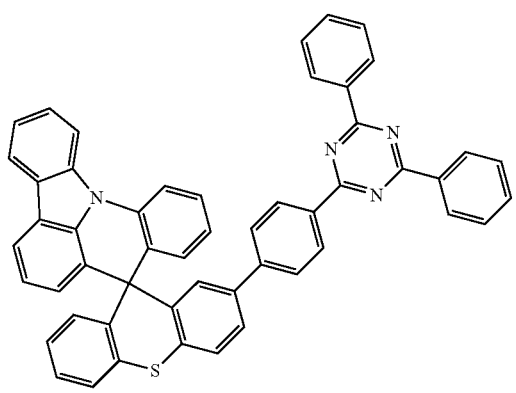
73
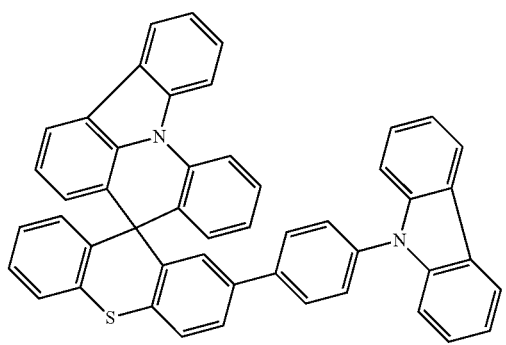
74
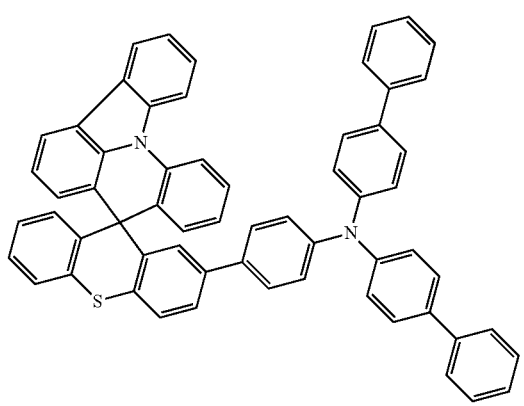
75

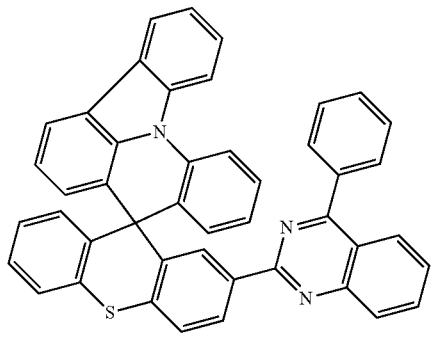

76

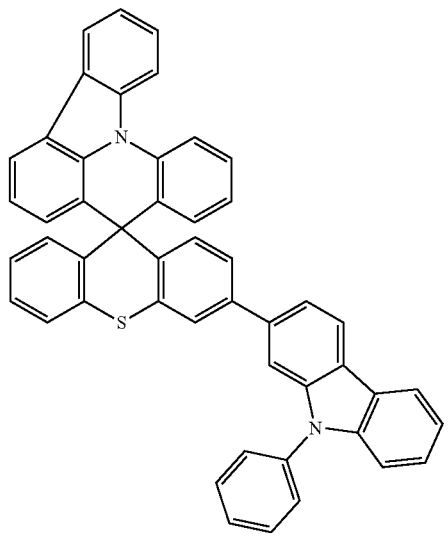

77

Compounds 58 to 76 were prepared in the same manner as in the method of preparing Compounds 1 to 19, except that Compound D and Compound D-1 were used instead of Compound A and Compound A-1, respectively, as starting materials in Preparation Examples 1 to 19. The MS[M+H]$^+$ values of Compounds 58 to 76 are shown in the following Table 3.

TABLE 3

| Compound No. | MS[M + H]$^+$ |
|---|---|
| 58 | 679 |
| 59 | 681 |
| 60 | 679 |
| 61 | 605 |
| 62 | 681 |
| 63 | 757 |
| 64 | 757 |
| 65 | 747 |
| 66 | 797 |
| 67 | 797 |
| 68 | 669 |
| 69 | 668 |
| 70 | 668 |
| 71 | 667 |
| 72 | 642 |
| 73 | 745 |
| 74 | 679 |
| 75 | 833 |
| 76 | 642 |

Preparation Example 23

1) Synthesis of Compounds of the Following Compounds 77 to 95

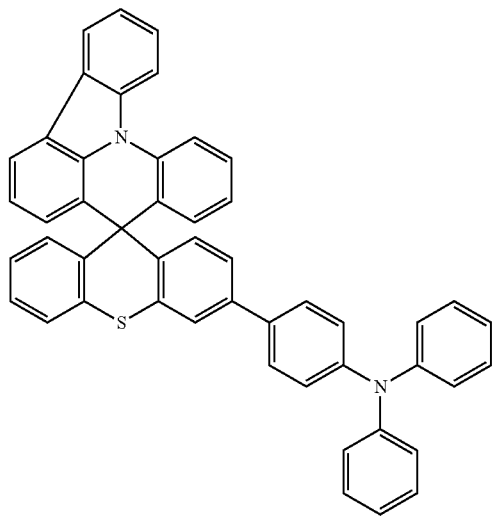

78

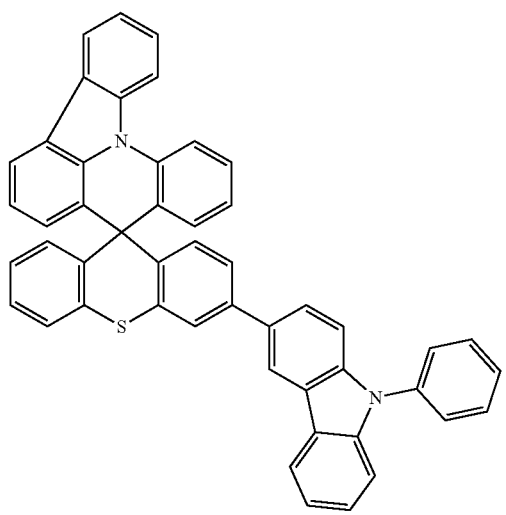

79

339
-continued
80
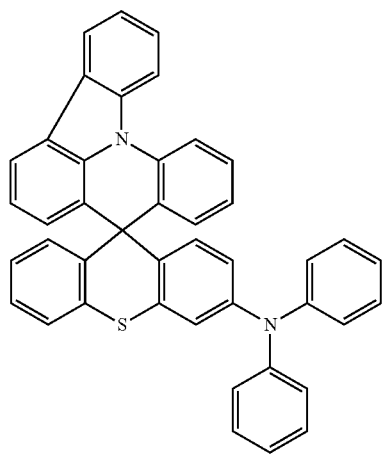
81
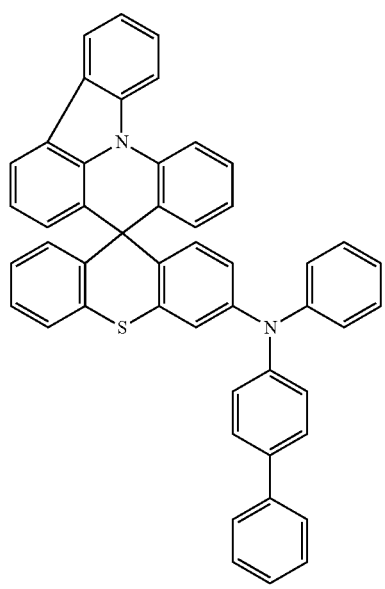
82
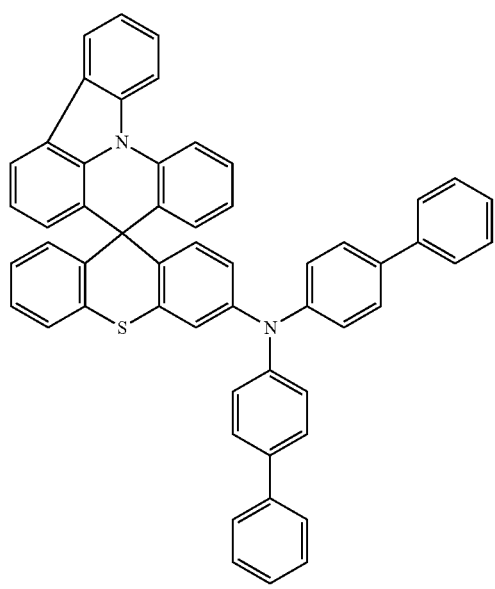
340
-continued
83
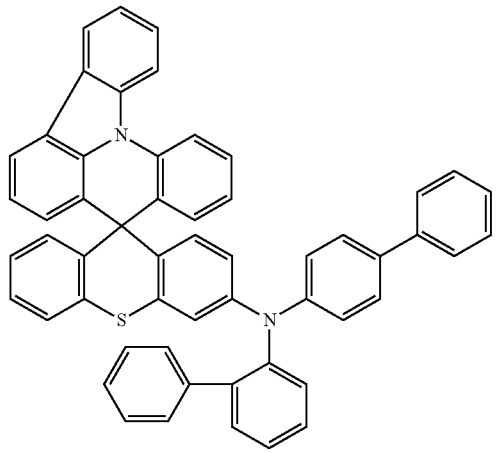
84
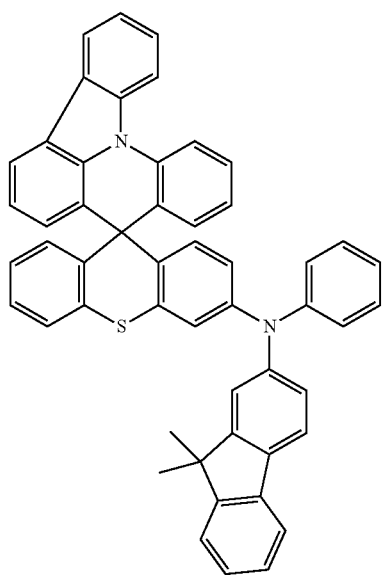
85
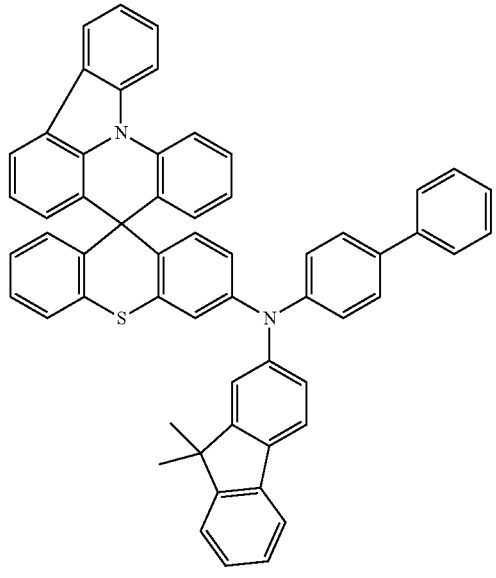

86
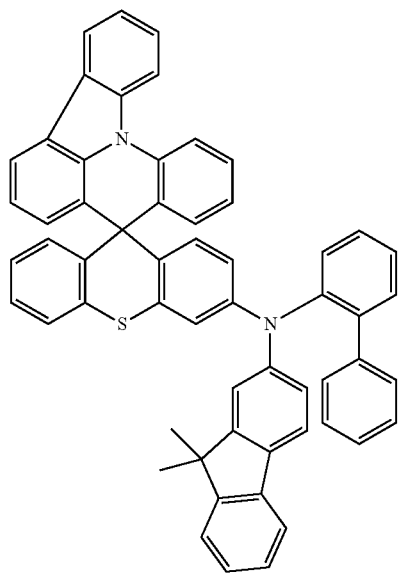
87
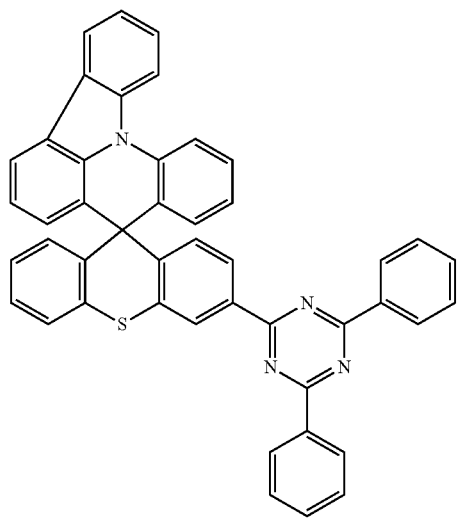
88
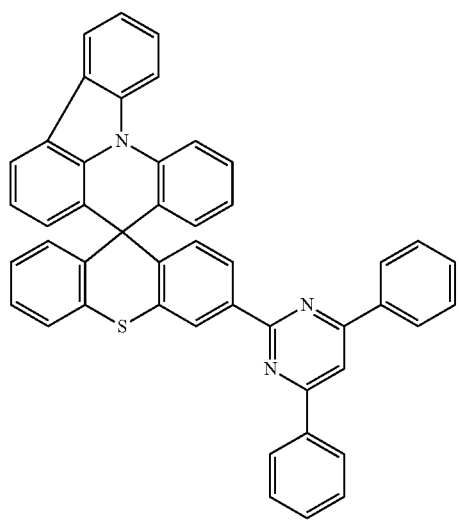
89
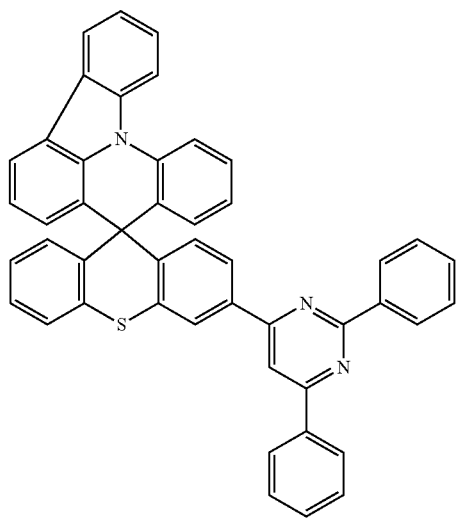
90
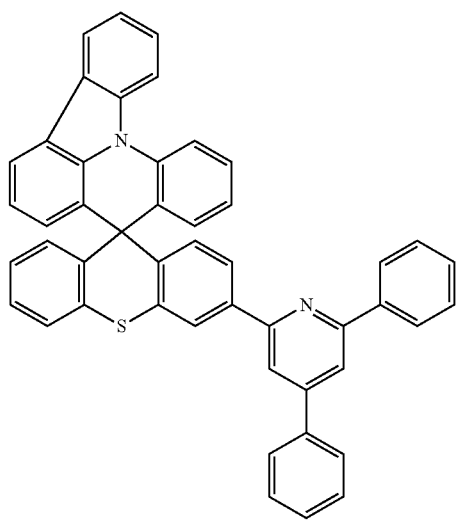
91
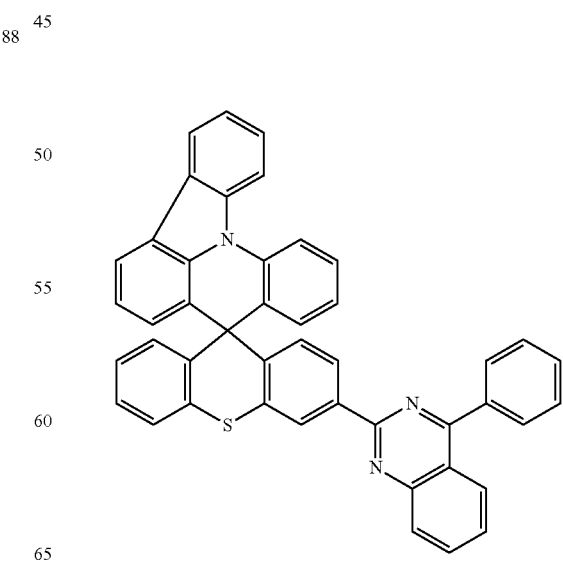

92
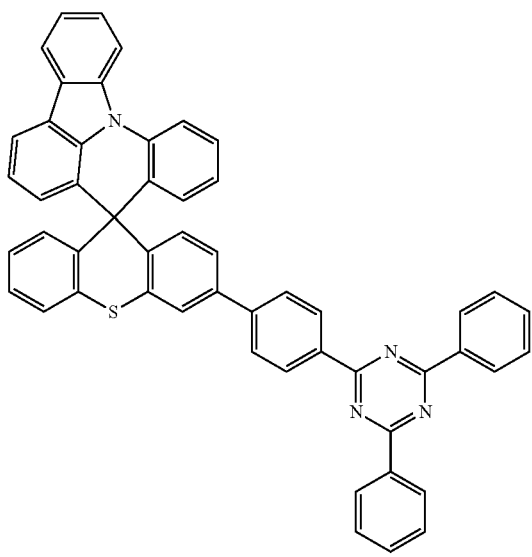
94
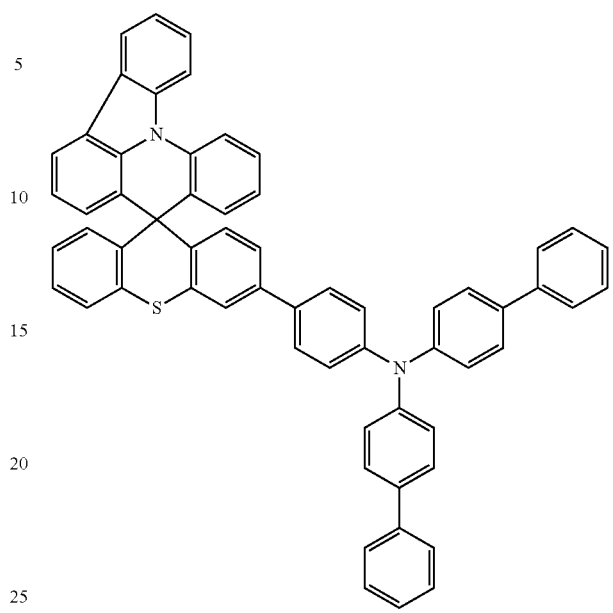
95
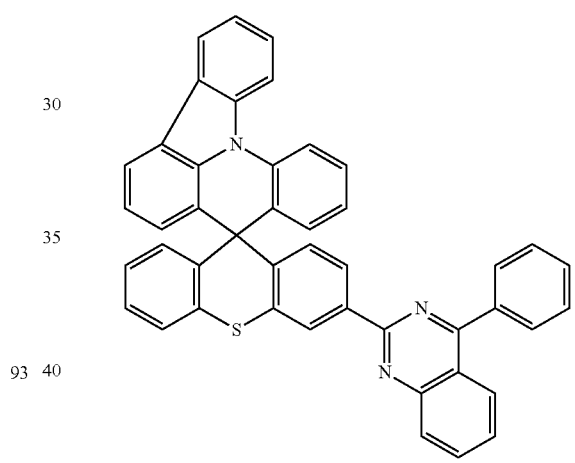
93
Compounds 77 to 95 were prepared in the same manner as in the method of preparing Compounds 1 to 19, except that Compound E and Compound E-1 were used instead of Compound A and Compound A-1, respectively, as starting materials in Preparation Examples 1 to 19. The MS[M+H]$^+$ values of Compounds 77 to 95 are shown in the following Table 4.
TABLE 4
| Compound No. | MS[M + H]$^+$ |
|---|---|
| 77 | 679 |
| 78 | 681 |
| 79 | 679 |
| 80 | 605 |
| 81 | 681 |
| 82 | 757 |
| 83 | 757 |
| 84 | 747 |
| 85 | 797 |
| 86 | 797 |
| 87 | 669 |
| 88 | 668 |
| 89 | 668 |

TABLE 4-continued
| Compound No. | MS[M + H]+ |
|---|---|
| 90 | 667 |
| 91 | 642 |
| 92 | 745 |
| 93 | 679 |
| 94 | 833 |
| 95 | 642 |
Preparation Example 24
1) Synthesis of Compounds of the Following Compounds 96 to 114
96
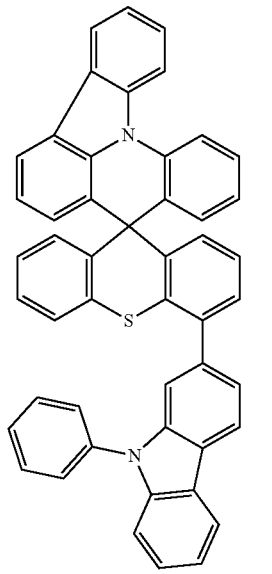
97
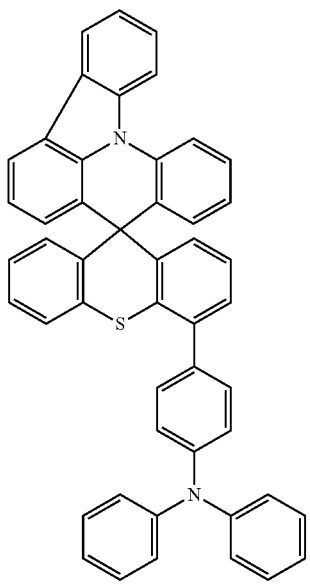
98
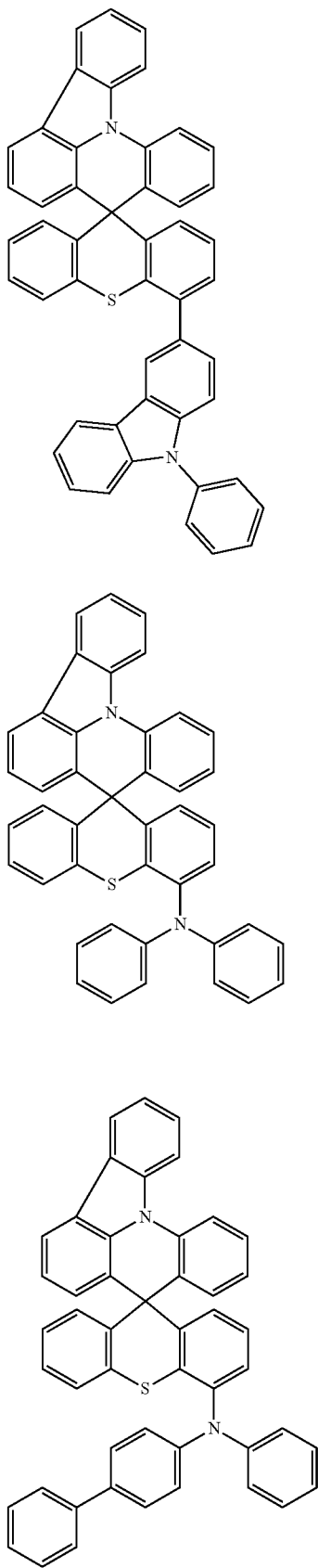
99
100

101
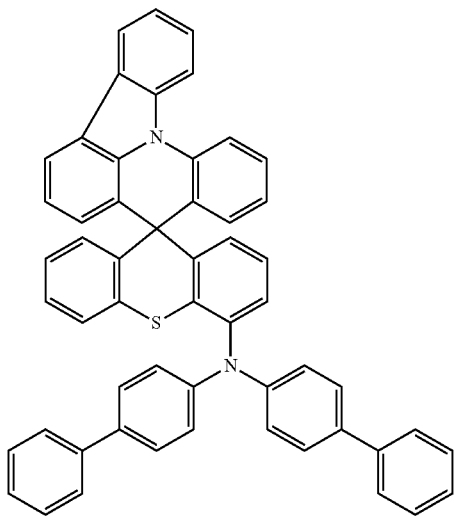
102
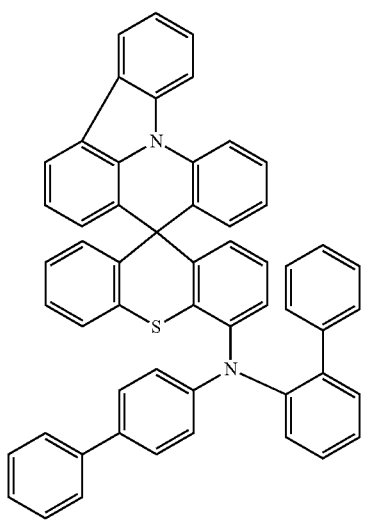
103
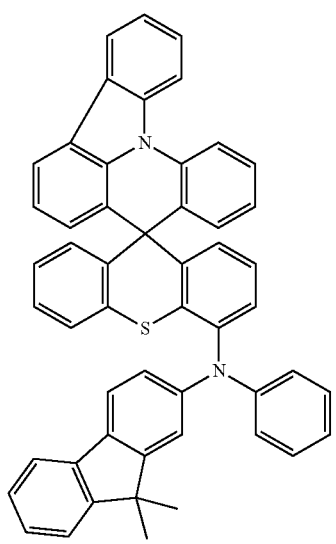
104
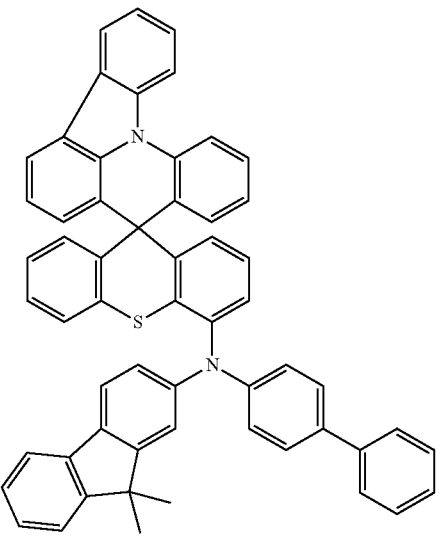
105
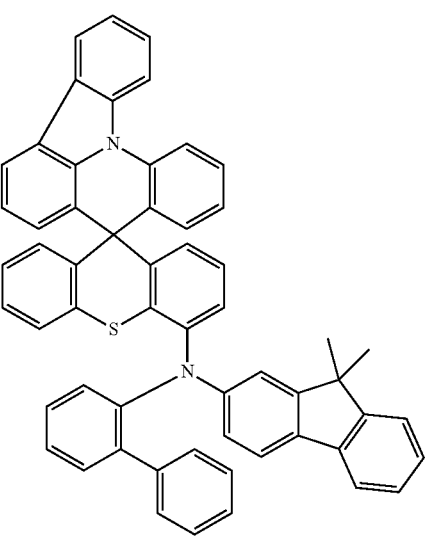
106
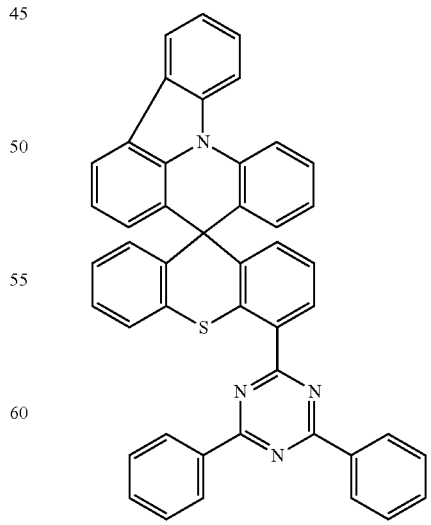

349
-continued
107
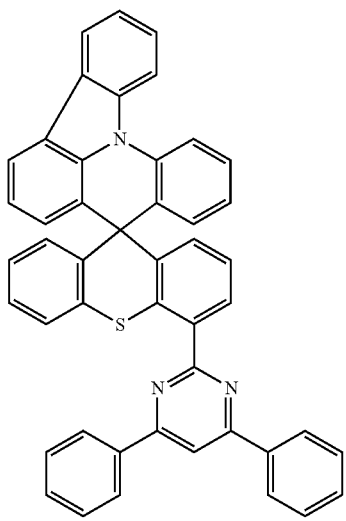
108
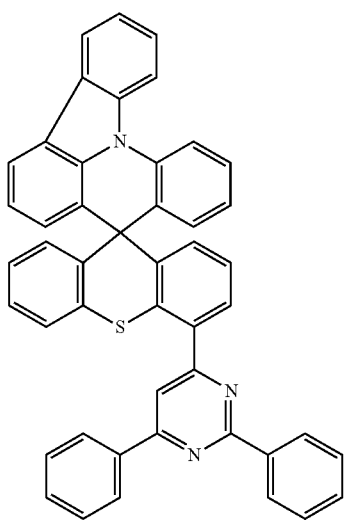
109
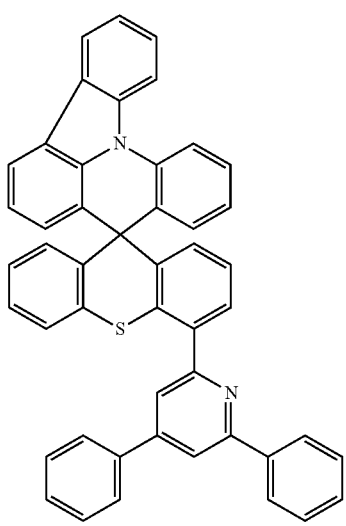
350
-continued
110
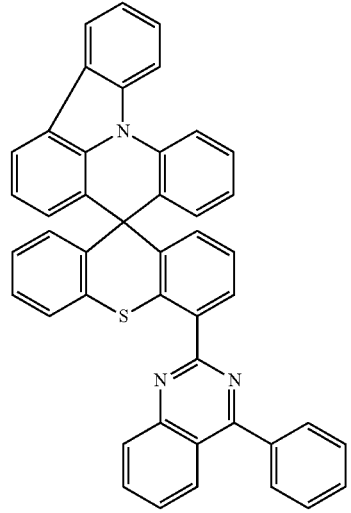
111
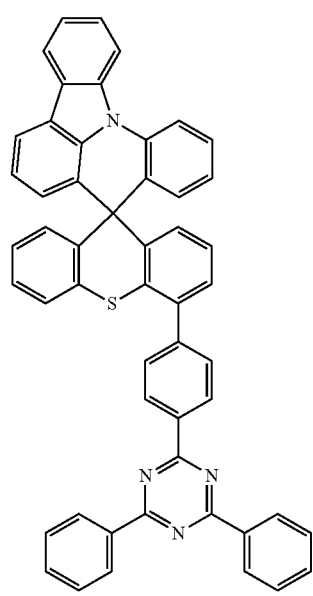

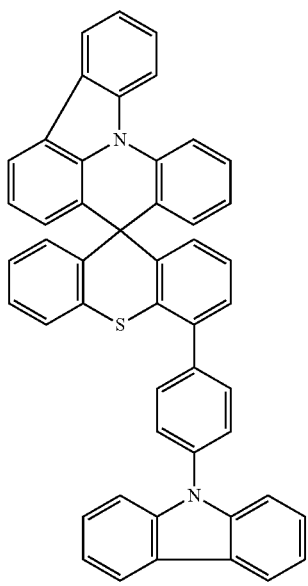

112

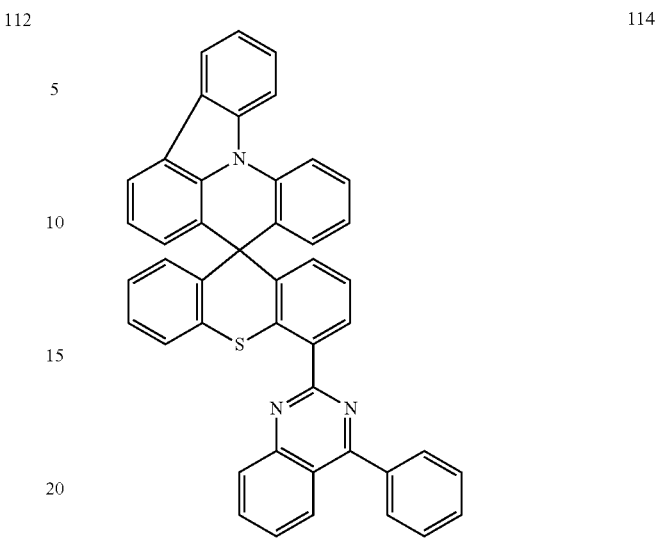

114

Compounds 96 to 114 were prepared in the same manner as in the method of preparing Compounds 1 to 19, except that Compound F and Compound F-1 were used instead of Compound A and Compound A-1, respectively, as starting materials in Preparation Examples 1 to 19. The MS[M+H]$^+$ values of Compounds 96 to 114 are shown in the following Table 5.

TABLE 5

| Compound No. | MS[M + H]$^+$ |
|---|---|
| 96 | 679 |
| 97 | 681 |
| 98 | 679 |
| 99 | 605 |
| 100 | 681 |
| 101 | 757 |
| 102 | 757 |
| 103 | 747 |
| 104 | 797 |
| 105 | 797 |
| 106 | 669 |
| 107 | 668 |
| 108 | 668 |
| 109 | 667 |
| 110 | 642 |
| 111 | 745 |
| 112 | 679 |
| 113 | 833 |
| 114 | 642 |

113

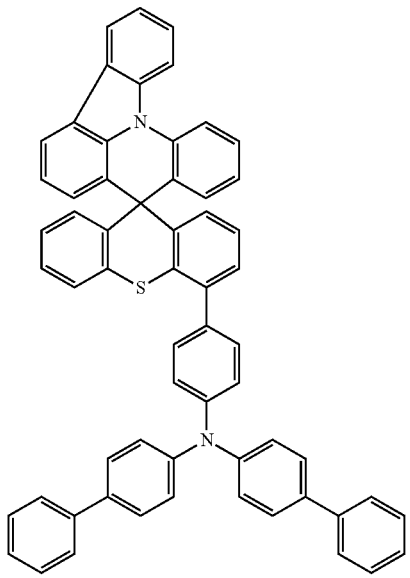

Preparation Example 25

1) Synthesis of Compound of the Following Compound 115

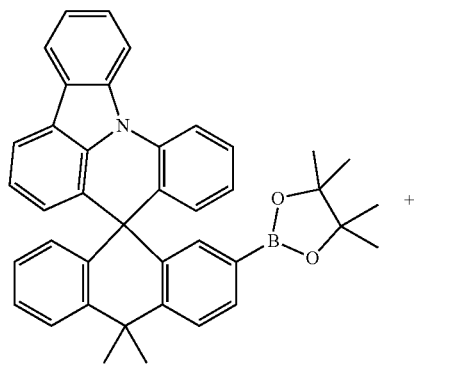

G-1
[Compound G-1]

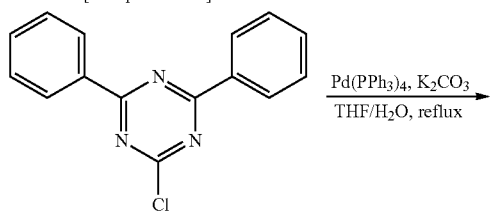

Pd(PPh₃)₄, K₂CO₃
THF/H₂O, reflux

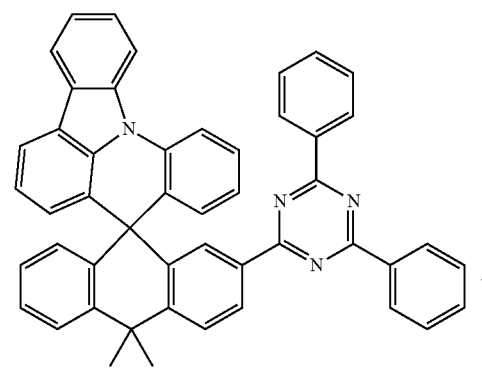

[Compound 115]

Compound G-1 (10.0 g, 17.88 mmol) and 2-chloro-4,6-diphenyl-1,3,5-triazine (4.24 g, 16.20 mol) were completely dissolved in 200 ml of tetrahydrofuran in a 500-ml round bottom flask under a nitrogen atmosphere, and then a 2 M aqueous potassium carbonate solution (100 ml) was added thereto, tetrakis-(triphenylphosphine)palladium (0.69 g, 0.60 mmol) was put thereinto, and then the resulting mixture was heated and stirred for 4 hours. The temperature was lowered to normal temperature, the aqueous layer was removed, and the residue was dried over anhydrous magnesium sulfate, and then concentrated under reduced pressure, and recrystallized with 230 ml of ethyl acetate to prepare Compound 115 (9.72 g, yield: 83%).

MS[M+H]⁺=679

Preparation Example 26

1) Synthesis of Compound of the Following Compound 116

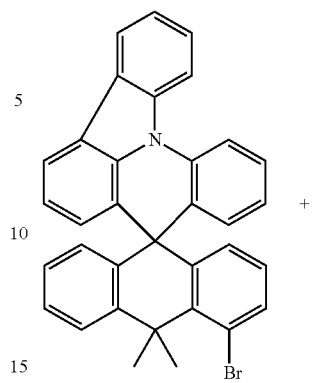

I
[Compound I]

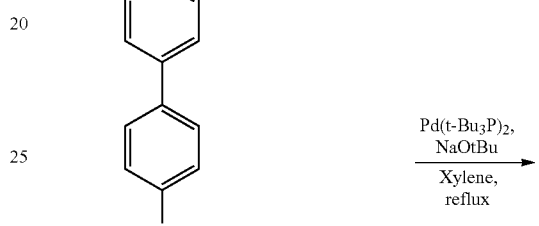

Pd(t-Bu₃P)₂,
NaOtBu
Xylene,
reflux

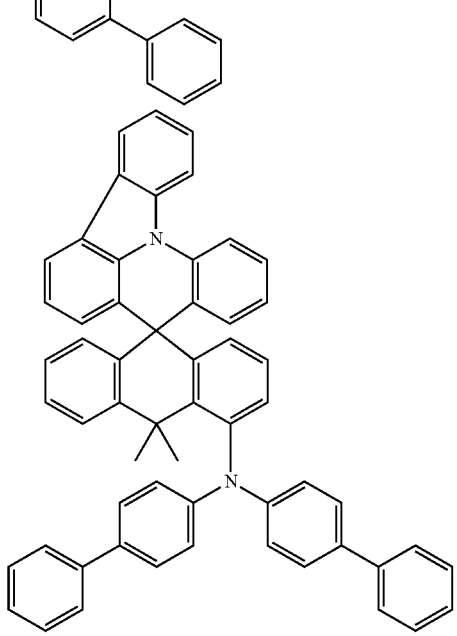

[Compound 116]

Compound I (10.0 g, 19.84 mmol) and di([1,1'-biphenyl]-4-yl)amine (6.74 g, 20.78 mmol) were completely dissolved in 290 ml of xylene in a 500-ml round bottom flask under a nitrogen atmosphere, and then sodium tert-butoxide (2.30 g, 24.00 mol) was added thereto, bis(tri-tert-butylphosphine)palladium(0) (0.10 g, 0.20 mmol) was put thereinto, and then the resulting mixture was heated and stirred for 2 hours. The temperature was lowered to normal temperature, the mixture was filtered to remove the base, and then xylene was concentrated under reduced pressure, and the residue was recrystallized with 280 ml of ethyl acetate to prepare Compound 116 (11.32 g, yield: 78%).

MS[M+H]$^+$=769

Preparation Example 27

1) Synthesis of Compound of the Following Compound 117

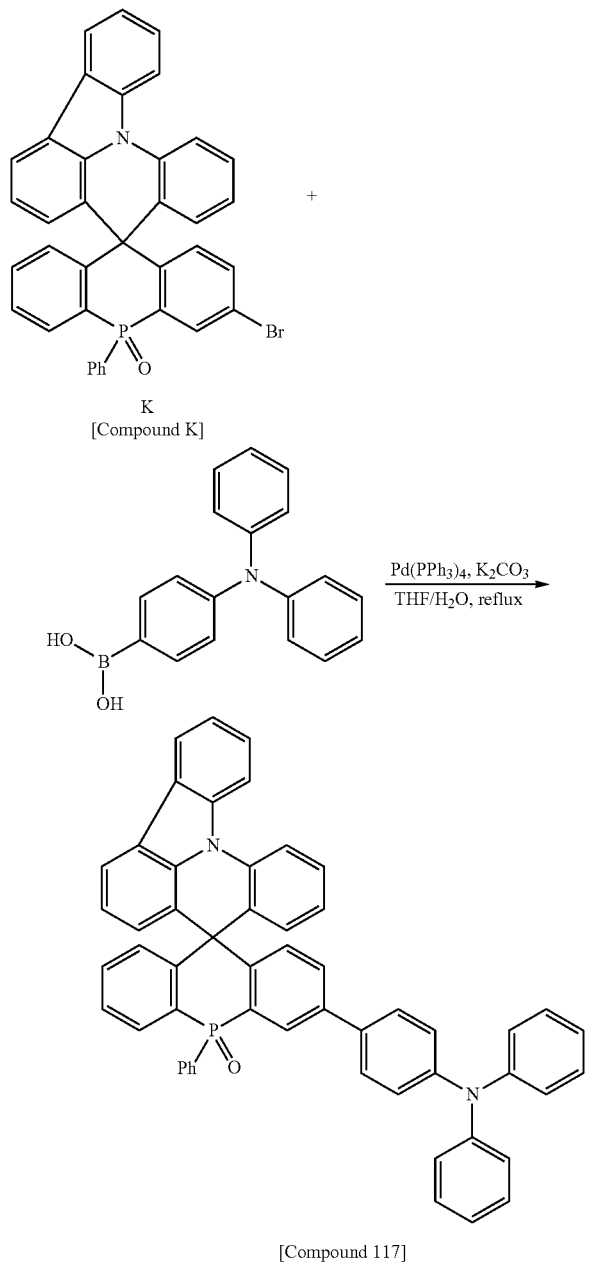

[Compound K]

[Compound 117]

Compound K (10.0 g, 19.84 mmol) and (4-(diphenylamino)phenyl)boronic acid (6.51 g, 20.95 mmol) were completely dissolved in 220 ml of tetrahydrofuran in a 500-ml round bottom flask under a nitrogen atmosphere, and then a 2 M aqueous potassium carbonate solution (110 ml) was added thereto, tetrakis-(triphenylphosphine)palladium (0.69 g, 0.61 mmol) was put thereinto, and then the resulting mixture was heated and stirred for 2 hours. The temperature was lowered to normal temperature, the aqueous layer was removed, and the residue was dried over anhydrous magnesium sulfate, and then concentrated under reduced pressure, and recrystallized with 180 ml of ethyl acetate to prepare Compound 117 (9.88 g, yield: 77%).

MS[M+H]$^+$=773

Experimental Example 1-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

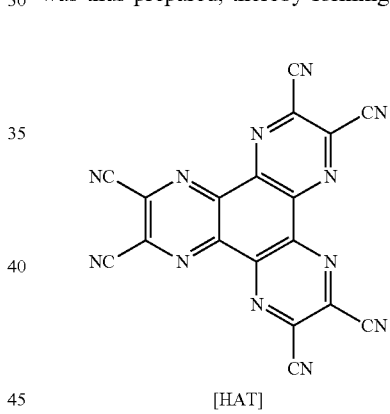

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transporting layer.

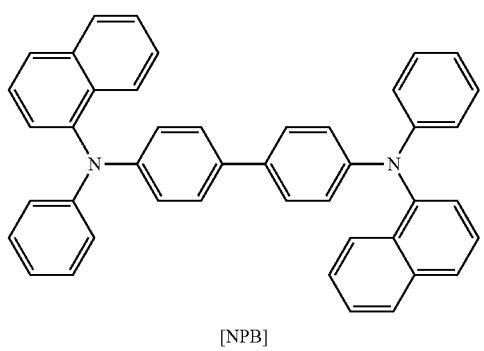

[NPB]

Subsequently, the following Compound 1 was vacuum deposited to have a film thickness of 100 Å on the hole transporting layer, thereby forming an electron blocking layer.

[Compound 1]

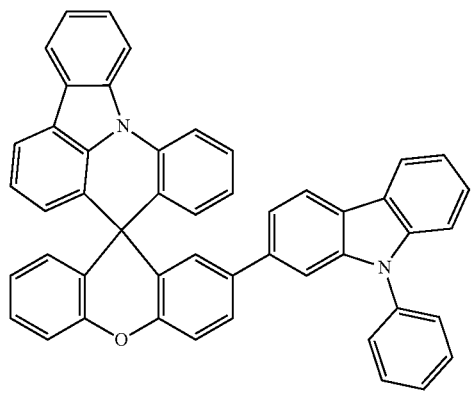

Subsequently, the following BH and BD were vacuum deposited at a weight ratio of 25:1 to have a film thickness of 300 Å on the electron blocking layer, thereby forming a light emitting layer.

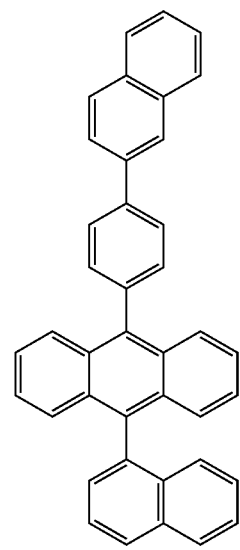

[BH]

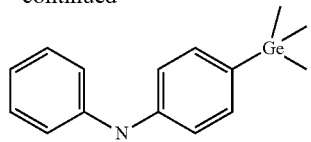
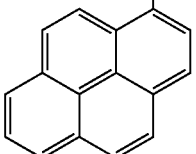
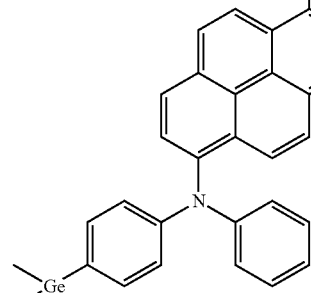

[BD]

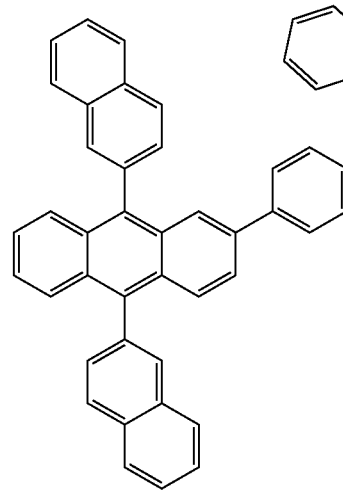
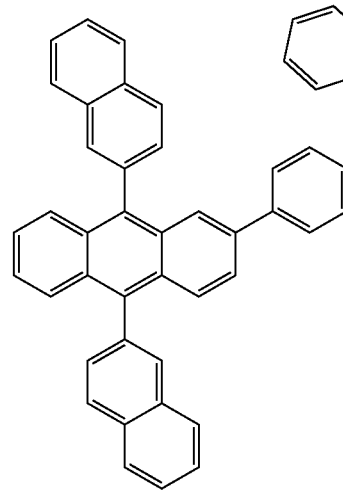
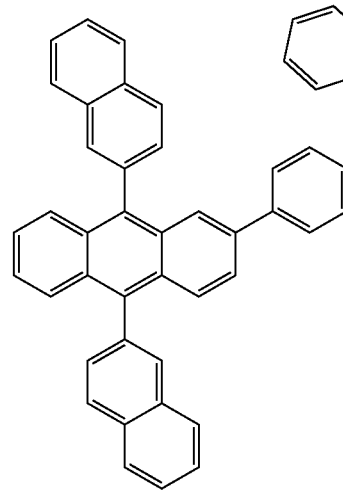
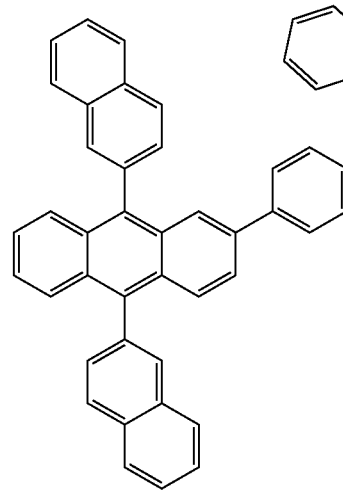
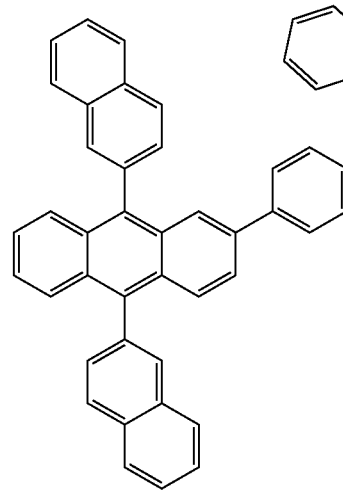

[ET1]

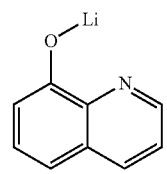

[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Experimental Example 1-2

An organic light emitting device was manufactured in the same manner as in Experimental Example 1-1, except that Compound 2 was used instead of Compound 1 in Experimental Example 1-1.

Experimental Example 1-3

An organic light emitting device was manufactured in the same manner as in Experimental Example 1-1, except that Compound 3 was used instead of Compound 1 in Experimental Example 1-1.

Experimental Example 1-4

An organic light emitting device was manufactured in the same manner as in Experimental Example 1-1, except that Compound 4 was used instead of Compound 1 in Experimental Example 1-1.

Experimental Example 1-5

An organic light emitting device was manufactured in the same manner as in Experimental Example 1-1, except that Compound 5 was used instead of Compound 1 in Experimental Example 1-1.

Experimental Example 1-6

An organic light emitting device was manufactured in the same manner as in Experimental Example 1-1, except that Compound 6 was used instead of Compound 1 in Experimental Example 1-1.

Experimental Example 1-7

An organic light emitting device was manufactured in the same manner as in Experimental Example 1-1, except that Compound 7 was used instead of Compound 1 in Experimental Example 1-1.

Experimental Example 1-8

An organic light emitting device was manufactured in the same manner as in Experimental Example 1-1, except that Compound 8 was used instead of Compound 1 in Experimental Example 1-1.

Experimental Example 1-9

An organic light emitting device was manufactured in the same manner as in Experimental Example 1-1, except that Compound 9 was used instead of Compound 1 in Experimental Example 1-1.

Experimental Example 1-10

An organic light emitting device was manufactured in the same manner as in Experimental Example 1-1, except that Compound 10 was used instead of Compound 1 in Experimental Example 1-1.

Experimental Example 1-11

An organic light emitting device was manufactured in the same manner as in Experimental Example 1-1, except that Compound 17 was used instead of Compound 1 in Experimental Example 1-1.

Experimental Example 1-12

An organic light emitting device was manufactured in the same manner as in Experimental Example 1-1, except that Compound 18 was used instead of Compound 1 in Experimental Example 1-1.

Experimental Example 1-13

An organic light emitting device was manufactured in the same manner as in Experimental Example 1-1, except that Compound 20 was used instead of Compound 1 in Experimental Example 1-1.

Experimental Example 1-14

An organic light emitting device was manufactured in the same manner as in Experimental Example 1-1, except that Compound 21 was used instead of Compound 1 in Experimental Example 1-1.

Experimental Example 1-15

An organic light emitting device was manufactured in the same manner as in Experimental Example 1-1, except that Compound 22 was used instead of Compound 1 in Experimental Example 1-1.

Experimental Example 1-16

An organic light emitting device was manufactured in the same manner as in Experimental Example 1-1, except that Compound 23 was used instead of Compound 1 in Experimental Example 1-1.

Experimental Example 1-17

An organic light emitting device was manufactured in the same manner as in Experimental Example 1-1, except that Compound 24 was used instead of Compound 1 in Experimental Example 1-1.

Experimental Example 1-18

An organic light emitting device was manufactured in the same manner as in Experimental Example 1-1, except that Compound 25 was used instead of Compound 1 in Experimental Example 1-1.

Experimental Example 1-19

An organic light emitting device was manufactured in the same manner as in Experimental Example 1-1, except that Compound 26 was used instead of Compound 1 in Experimental Example 1-1.

Experimental Example 1-20

An organic light emitting device was manufactured in the same manner as in Experimental Example 1-1, except that Compound 27 was used instead of Compound 1 in Experimental Example 1-1.

Experimental Example 1-21

An organic light emitting device was manufactured in the same manner as in Experimental Example 1-1, except that Compound 28 was used instead of Compound 1 in Experimental Example 1-1.

Experimental Example 1-22

An organic light emitting device was manufactured in the same manner as in Experimental Example 1-1, except that Compound 29 was used instead of Compound 1 in Experimental Example 1-1.

Experimental Example 1-23

An organic light emitting device was manufactured in the same manner as in Experimental Example 1-1, except that Compound 36 was used instead of Compound 1 in Experimental Example 1-1.

Experimental Example 1-24

An organic light emitting device was manufactured in the same manner as in Experimental Example 1-1, except that Compound 37 was used instead of Compound 1 in Experimental Example 1-1.

Experimental Example 1-25

An organic light emitting device was manufactured in the same manner as in Experimental Example 1-1, except that Compound 40 was used instead of Compound 1 in Experimental Example 1-1.

Experimental Example 1-26

An organic light emitting device was manufactured in the same manner as in Experimental Example 1-1, except that Compound 44 was used instead of Compound 1 in Experimental Example 1-1.

Experimental Example 1-27

An organic light emitting device was manufactured in the same manner as in Experimental Example 1-1, except that Compound 47 was used instead of Compound 1 in Experimental Example 1-1.

Experimental Example 1-28

An organic light emitting device was manufactured in the same manner as in Experimental Example 1-1, except that Compound 56 was used instead of Compound 1 in Experimental Example 1-1.

Experimental Example 1-29

An organic light emitting device was manufactured in the same manner as in Experimental Example 1-1, except that Compound 59 was used instead of Compound 1 in Experimental Example 1-1.

Experimental Example 1-30

An organic light emitting device was manufactured in the same manner as in Experimental Example 1-1, except that Compound 63 was used instead of Compound 1 in Experimental Example 1-1.

Experimental Example 1-31

An organic light emitting device was manufactured in the same manner as in Experimental Example 1-1, except that Compound 66 was used instead of Compound 1 in Experimental Example 1-1.

Experimental Example 1-32

An organic light emitting device was manufactured in the same manner as in Experimental Example 1-1, except that Compound 75 was used instead of Compound 1 in Experimental Example 1-1.

Experimental Example 1-33

An organic light emitting device was manufactured in the same manner as in Experimental Example 1-1, except that Compound 78 was used instead of Compound 1 in Experimental Example 1-1.

Experimental Example 1-34

An organic light emitting device was manufactured in the same manner as in Experimental Example 1-1, except that Compound 82 was used instead of Compound 1 in Experimental Example 1-1.

Experimental Example 1-35

An organic light emitting device was manufactured in the same manner as in Experimental Example 1-1, except that Compound 85 was used instead of Compound 1 in Experimental Example 1-1.

Experimental Example 1-36

An organic light emitting device was manufactured in the same manner as in Experimental Example 1-1, except that Compound 94 was used instead of Compound 1 in Experimental Example 1-1.

Experimental Example 1-37

An organic light emitting device was manufactured in the same manner as in Experimental Example 1-1, except that Compound 97 was used instead of Compound 1 in Experimental Example 1-1.

Experimental Example 1-38

An organic light emitting device was manufactured in the same manner as in Experimental Example 1-1, except that Compound 101 was used instead of Compound 1 in Experimental Example 1-1.

Experimental Example 1-39

An organic light emitting device was manufactured in the same manner as in Experimental Example 1-1, except that Compound 104 was used instead of Compound 1 in Experimental Example 1-1.

Experimental Example 1-40

An organic light emitting device was manufactured in the same manner as in Experimental Example 1-1, except that Compound 113 was used instead of Compound 1 in Experimental Example 1-1.

Experimental Example 1-41

An organic light emitting device was manufactured in the same manner as in Experimental Example 1-1, except that Compound 116 was used instead of Compound 1 in Experimental Example 1-1.

Experimental Example 1-42

An organic light emitting device was manufactured in the same manner as in Experimental Example 1-1, except that Compound 117 was used instead of Compound 1 in Experimental Example 1-1.

Comparative Example 1-1

An organic light emitting device was manufactured in the same manner as in Experimental Example 1-1, except that EB 1 was used instead of Compound 1 in Experimental Example 1-1.

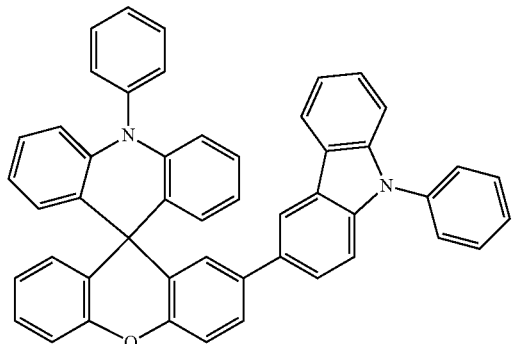

[EB 1]

Comparative Example 1-2

An organic light emitting device was manufactured in the same manner as in Experimental Example 1-1, except that EB 2 was used instead of Compound 1 in Experimental Example 1-1.

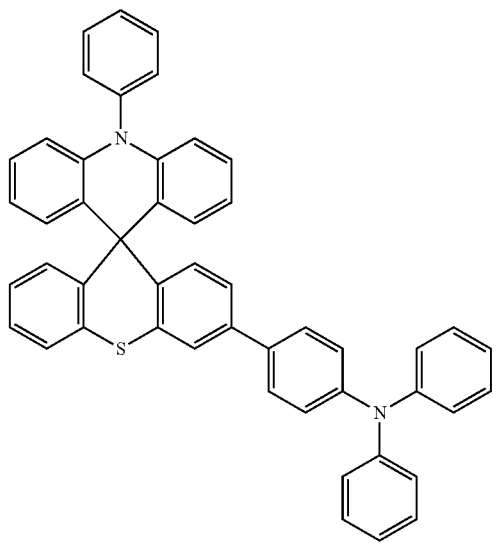

[EB 2]

Comparative Example 1-3

An organic light emitting device was manufactured in the same manner as in Experimental Example 1-1, except that EB 3 was used instead of Compound 1 in Experimental Example 1-1.

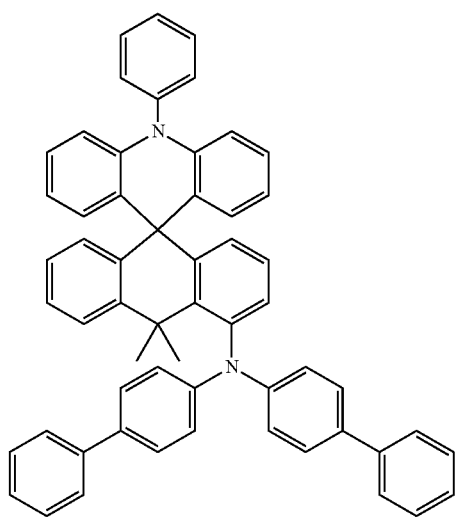

[EB 3]

When current was applied to the organic light emitting devices manufactured in Experimental Examples 1-1 to 1-42 and Comparative Examples 1-1 to 1-3, the results of Table 6 were obtained.

TABLE 6

| | Compound (Electron blocking layer) | Voltage (V@10 mA/ cm$^2$) | Efficiency (cd/A@10 mA/ cm$^2$) | Color coordinate (x, y) |
|---|---|---|---|---|
| Experimental Example 1-1 | Compound 1 | 3.81 | 5.20 | (0.139, 0.125) |
| Experimental Example 1-2 | Compound 2 | 3.73 | 5.35 | (0.138, 0.126) |
| Experimental Example 1-3 | Compound 3 | 3.55 | 5.79 | (0.138, 0.127) |
| Experimental Example 1-4 | Compound 4 | 3.56 | 5.57 | (0.137, 0.125) |
| Experimental Example 1-5 | Compound 5 | 3.58 | 5.78 | (0.136, 0.125) |
| Experimental Example 1-6 | Compound 6 | 3.57 | 5.61 | (0.136, 0.127) |
| Experimental Example 1-7 | Compound 7 | 3.59 | 5.63 | (0.136, 0.125) |
| Experimental Example 1-8 | Compound 8 | 3.50 | 5.65 | (0.137, 0.125) |
| Experimental Example 1-9 | Compound 9 | 3.61 | 5.54 | (0.138, 0.125) |
| Experimental Example 1-10 | Compound 10 | 3.65 | 5.63 | (0.136, 0.125) |
| Experimental Example 1-11 | Compound 17 | 3.64 | 5.51 | (0.137, 0.125) |
| Experimental Example 1-12 | Compound 18 | 3.66 | 5.41 | (0.136, 0.125) |
| Experimental Example 1-13 | Compound 20 | 3.79 | 5.55 | (0.138, 0.126) |
| Experimental Example 1-14 | Compound 21 | 3.75 | 5.74 | (0.137, 0.125) |
| Experimental Example 1-15 | Compound 22 | 3.70 | 5.46 | (0.136, 0.127) |
| Experimental Example 1-16 | Compound 23 | 3.71 | 5.78 | (0.135, 0.127) |
| Experimental Example 1-17 | Compound 24 | 3.52 | 5.67 | (0.138, 0.127) |
| Experimental Example 1-18 | Compound 25 | 3.63 | 5.55 | (0.137, 0.125) |
| Experimental Example 1-19 | Compound 26 | 3.85 | 5.50 | (0.139, 0.125) |
| Experimental Example 1-20 | Compound 27 | 3.72 | 5.35 | (0.138, 0.126) |
| Experimental Example 1-21 | Compound 28 | 3.57 | 5.79 | (0.138, 0.127) |
| Experimental Example 1-22 | Compound 29 | 3.58 | 5.67 | (0.137, 0.125) |
| Experimental Example 1-23 | Compound 36 | 3.54 | 5.61 | (0.136, 0.125) |
| Experimental Example 1-24 | Compound 37 | 3.53 | 5.73 | (0.136, 0.127) |
| Experimental Example 1-25 | Compound 40 | 3.54 | 5.65 | (0.136, 0.125) |
| Experimental Example 1-26 | Compound 44 | 3.63 | 5.54 | (0.137, 0.125) |
| Experimental Example 1-27 | Compound 47 | 3.65 | 5.43 | (0.138, 0.125) |
| Experimental Example 1-28 | Compound 56 | 3.63 | 5.51 | (0.136, 0.125) |
| Experimental Example 1-29 | Compound 59 | 3.64 | 5.51 | (0.137, 0.125) |
| Experimental Example 1-30 | Compound 63 | 3.57 | 5.55 | (0.136, 0.125) |
| Experimental Example 1-31 | Compound 66 | 3.77 | 5.54 | (0.138, 0.126) |
| Experimental Example 1-32 | Compound 75 | 3.70 | 5.46 | (0.137, 0.125) |
| Experimental Example 1-33 | Compound 78 | 3.71 | 5.58 | (0.136, 0.127) |
| Experimental Example 1-34 | Compound 82 | 3.71 | 5.58 | (0.135, 0.127) |
| Experimental Example 1-35 | Compound 85 | 3.54 | 5.67 | (0.138, 0.127) |
| Experimental Example 1-36 | Compound 94 | 3.63 | 5.55 | (0.137, 0.125) |
| Experimental Example 1-37 | Compound 97 | 3.65 | 5.41 | (0.136, 0.125) |
| Experimental Example 1-38 | Compound 101 | 3.72 | 5.55 | (0.138, 0.126) |
| Experimental Example 1-39 | Compound 104 | 3.77 | 5.54 | (0.137, 0.125) |
| Experimental Example 1-40 | Compound 113 | 3.70 | 5.46 | (0.136, 0.127) |
| Experimental Example 1-41 | Compound 116 | 3.71 | 5.58 | (0.135, 0.127) |
| Experimental Example 1-42 | Compound 117 | 3.54 | 5.67 | (0.138, 0.127) |
| Comparative Example 1-1 | EB 1 | 4.26 | 4.72 | (0.138, 0.127) |
| Comparative Example 1-2 | EB 2 | 4.45 | 4.58 | (0.139, 0.125) |
| Comparative Example 1-3 | EB 3 | 4.64 | 4.21 | (0.139, 0.126) |

As observed in Table 6, it can be seen that the compounds in Experimental Examples 1-1 to 1-42 exhibit lower voltage and higher efficiency characteristics than those in Comparative Examples 1-1 to 1-3, in which a substituent is linked to a material having a core similar to that of the compound of the present invention as an electron blocking layer in the organic light emitting device.

It could be confirmed that the compound derivatives of the Chemical Formulae according to the present invention have excellent electron blocking capability and thus exhibit low voltage and high efficiency characteristics, and may be applied to an organic light emitting device.

Experimental Example 2-1

The compounds prepared in the Synthesis Examples were subjected to high-purity sublimation purification by a typically known method, and then green organic light emitting devices were manufactured by the following method.

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

An organic light emitting device was manufactured by configuring a light emitting device in the order of m-MTDATA (60 nm)/TCTA (80 nm)/Compound 10+10% Ir(ppy)$_3$ (300 nm)/BCP (10 nm)/Alq$_3$ (30 nm)/LiF (1 nm)/Al (200 nm) on the thus prepared ITO transparent electrode by using Compound 10 as a host.

The structures of m-MTDATA, TCTA, Ir(ppy)$_3$, and BCP are as follows.

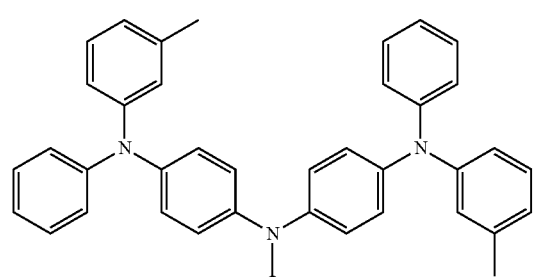

[m-MTDATA]

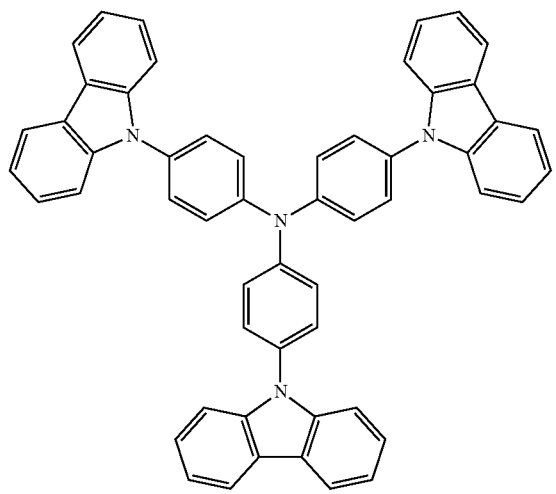

[TCTA]

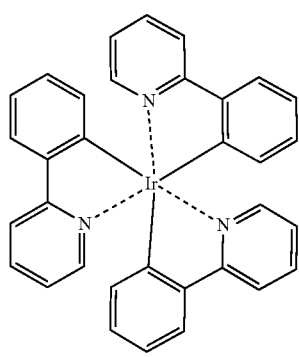

[Ir(ppy)₃]

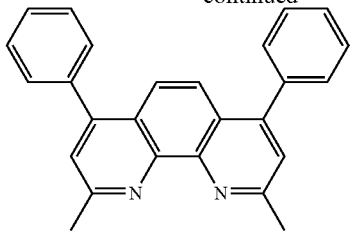

[BCP]

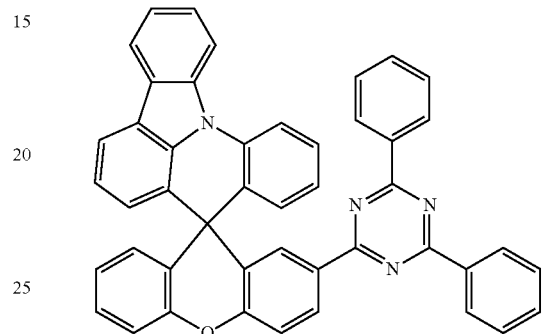

[Compound 11]

Experimental Example 2-2

An organic light emitting device was manufactured in the same manner as in Experimental Example 2-1, except that Compound 12 was used instead of Compound 11 in Experimental Example 2-1.

Experimental Example 2-3

An organic light emitting device was manufactured in the same manner as in Experimental Example 2-1, except that Compound 13 was used instead of Compound 11 in Experimental Example 2-1.

Experimental Example 2-4

An organic light emitting device was manufactured in the same manner as in Experimental Example 2-1, except that Compound 14 was used instead of Compound 11 in Experimental Example 2-1.

Experimental Example 2-5

An organic light emitting device was manufactured in the same manner as in Experimental Example 2-1, except that Compound 16 was used instead of Compound 11 in Experimental Example 2-1.

Experimental Example 2-6

An organic light emitting device was manufactured in the same manner as in Experimental Example 2-1, except that Compound 30 was used instead of Compound 11 in Experimental Example 2-1.

Experimental Example 2-7

An organic light emitting device was manufactured in the same manner as in Experimental Example 2-1, except that Compound 31 was used instead of Compound 11 in Experimental Example 2-1.

Experimental Example 2-8

An organic light emitting device was manufactured in the same manner as in Experimental Example 2-1, except that Compound 32 was used instead of Compound 11 in Experimental Example 2-1.

Experimental Example 2-9

An organic light emitting device was manufactured in the same manner as in Experimental Example 2-1, except that Compound 33 was used instead of Compound 11 in Experimental Example 2-1.

Experimental Example 2-10

An organic light emitting device was manufactured in the same manner as in Experimental Example 2-1, except that Compound 35 was used instead of Compound 11 in Experimental Example 2-1.

Experimental Example 2-11

An organic light emitting device was manufactured in the same manner as in Experimental Example 2-1, except that Compound 49 was used instead of Compound 11 in Experimental Example 2-1.

Experimental Example 2-12

An organic light emitting device was manufactured in the same manner as in Experimental Example 2-1, except that Compound 50 was used instead of Compound 11 in Experimental Example 2-1.

Experimental Example 2-13

An organic light emitting device was manufactured in the same manner as in Experimental Example 2-1, except that Compound 51 was used instead of Compound 11 in Experimental Example 2-1.

Experimental Example 2-14

An organic light emitting device was manufactured in the same manner as in Experimental Example 2-1, except that Compound 52 was used instead of Compound 11 in Experimental Example 2-1.

Experimental Example 2-15

An organic light emitting device was manufactured in the same manner as in Experimental Example 2-1, except that Compound 54 was used instead of Compound 11 in Experimental Example 2-1.

Experimental Example 2-16

An organic light emitting device was manufactured in the same manner as in Experimental Example 2-1, except that Compound 68 was used instead of Compound 11 in Experimental Example 2-1.

Experimental Example 2-17

An organic light emitting device was manufactured in the same manner as in Experimental Example 2-1, except that Compound 69 was used instead of Compound 11 in Experimental Example 2-1.

Experimental Example 2-18

An organic light emitting device was manufactured in the same manner as in Experimental Example 2-1, except that Compound 70 was used instead of Compound 11 in Experimental Example 2-1.

Experimental Example 2-19

An organic light emitting device was manufactured in the same manner as in Experimental Example 2-1, except that Compound 71 was used instead of Compound 11 in Experimental Example 2-1.

Experimental Example 2-20

An organic light emitting device was manufactured in the same manner as in Experimental Example 2-1, except that Compound 73 was used instead of Compound 11 in Experimental Example 2-1.

Experimental Example 2-21

An organic light emitting device was manufactured in the same manner as in Experimental Example 2-1, except that Compound 87 was used instead of Compound 11 in Experimental Example 2-1.

Experimental Example 2-22

An organic light emitting device was manufactured in the same manner as in Experimental Example 2-1, except that Compound 88 was used instead of Compound 11 in Experimental Example 2-1.

Experimental Example 2-23

An organic light emitting device was manufactured in the same manner as in Experimental Example 2-1, except that Compound 89 was used instead of Compound 11 in Experimental Example 2-1.

Experimental Example 2-24

An organic light emitting device was manufactured in the same manner as in Experimental Example 2-1, except that Compound 90 was used instead of Compound 11 in Experimental Example 2-1.

Experimental Example 2-25

An organic light emitting device was manufactured in the same manner as in Experimental Example 2-1, except that Compound 92 was used instead of Compound 11 in Experimental Example 2-1.

Experimental Example 2-26

An organic light emitting device was manufactured in the same manner as in Experimental Example 2-1, except that Compound 106 was used instead of Compound 11 in Experimental Example 2-1.

Experimental Example 2-27

An organic light emitting device was manufactured in the same manner as in Experimental Example 2-1, except that Compound 107 was used instead of Compound 11 in Experimental Example 2-1.

Experimental Example 2-28

An organic light emitting device was manufactured in the same manner as in Experimental Example 2-1, except that Compound 108 was used instead of Compound 11 in Experimental Example 2-1.

Experimental Example 2-29

An organic light emitting device was manufactured in the same manner as in Experimental Example 2-1, except that Compound 109 was used instead of Compound 11 in Experimental Example 2-1.

Experimental Example 2-30

An organic light emitting device was manufactured in the same manner as in Experimental Example 2-1, except that Compound 111 was used instead of Compound 11 in Experimental Example 2-1.

Comparative Example 2-1

An organic light emitting device was manufactured in the same manner as in Experimental Example 2-1, except that GH 1 was used instead of Compound 11 in Experimental Example 2-1.

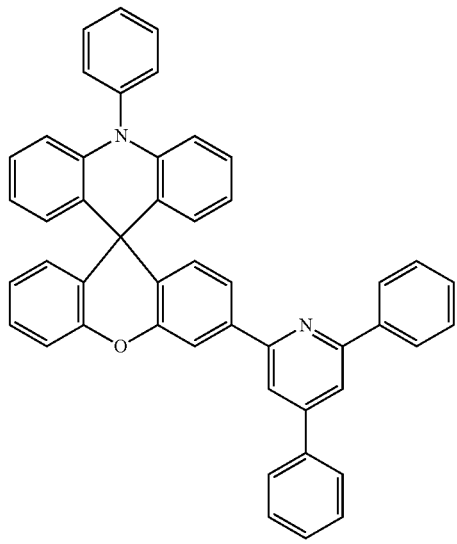

[GH 1]

Comparative Example 2-2

An organic light emitting device was manufactured in the same manner as in Experimental Example 2-1, except that GH 2 was used instead of Compound 11 in Experimental Example 2-1.

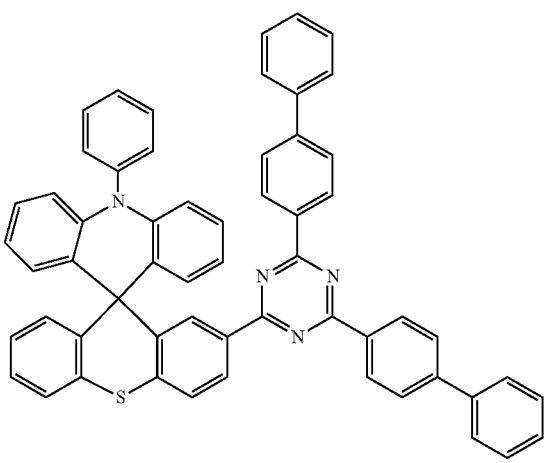

[GH 2]

Comparative Example 2-3

An organic light emitting device was manufactured in the same manner as in Experimental Example 2-1, except that GH 3 was used instead of Compound 11 in Experimental Example 2-1.

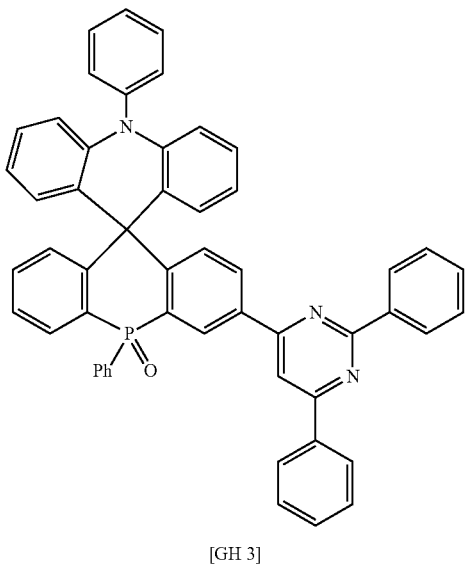 [SMILES: O=P1(c2ccccc2)c2ccccc2C2(c3ccccc3N(c3ccccc3)c3ccccc32)c2ccc(-c3cc(-c4ccccc4)nc(-c4ccccc4)n3)cc21]

[GH 3]

When current was applied to the organic light emitting devices manufactured in Experimental Examples 2-1 to 2-30 and Comparative Examples 2-1 to 2-3, the results of Table 7 were obtained.

TABLE 7

| Compound (Host) | Voltage (V@10 mA/cm$^2$) | Efficiency (cd/A@10 mA/cm$^2$) | EL peak (nm) |
|---|---|---|---|
| Experimental Example 2-1 | Compound 11 | 5.28 | 46.93 | 517 |
| Experimental Example 2-2 | Compound 12 | 5.36 | 45.24 | 516 |
| Experimental Example 2-3 | Compound 13 | 5.25 | 46.79 | 518 |
| Experimental Example 2-4 | Compound 14 | 5.39 | 45.15 | 517 |
| Experimental Example 2-5 | Compound 16 | 5.38 | 45.31 | 515 |
| Experimental Example 2-6 | Compound 30 | 5.23 | 46.63 | 516 |
| Experimental Example 2-7 | Compound 31 | 5.39 | 45.62 | 516 |
| Experimental Example 2-8 | Compound 32 | 5.37 | 45.64 | 517 |
| Experimental Example 2-9 | Compound 33 | 5.34 | 45.68 | 518 |
| Experimental Example 2-10 | Compound 35 | 5.28 | 46.83 | 517 |
| Experimental Example 2-11 | Compound 49 | 5.25 | 46.93 | 517 |
| Experimental Example 2-12 | Compound 50 | 5.32 | 45.24 | 516 |
| Experimental Example 2-13 | Compound 51 | 5.20 | 46.79 | 518 |
| Experimental Example 2-14 | Compound 52 | 5.36 | 45.15 | 517 |
| Experimental Example 2-15 | Compound 54 | 5.37 | 45.31 | 515 |
| Experimental Example 2-16 | Compound 68 | 5.28 | 46.63 | 516 |
| Experimental Example 2-17 | Compound 69 | 5.39 | 45.62 | 516 |
| Experimental Example 2-18 | Compound 70 | 5.38 | 45.64 | 517 |
| Experimental Example 2-19 | Compound 71 | 5.34 | 45.68 | 518 |
| Experimental Example 2-20 | Compound 73 | 5.23 | 46.83 | 517 |
| Experimental Example 2-21 | Compound 87 | 5.28 | 46.93 | 517 |
| Experimental Example 2-22 | Compound 88 | 5.36 | 45.24 | 516 |
| Experimental Example 2-23 | Compound 89 | 5.20 | 46.79 | 518 |
| Experimental Example 2-24 | Compound 90 | 5.31 | 45.15 | 517 |
| Experimental Example 2-25 | Compound 92 | 5.23 | 46.31 | 515 |
| Experimental Example 2-26 | Compound 106 | 5.38 | 45.63 | 516 |
| Experimental Example 2-27 | Compound 107 | 5.29 | 46.62 | 516 |
| Experimental Example 2-28 | Compound 108 | 5.26 | 46.64 | 517 |
| Experimental Example 2-29 | Compound 109 | 5.35 | 45.68 | 518 |
| Experimental Example 2-30 | Compound 111 | 5.21 | 46.83 | 517 |
| Comparative Example 2-1 | GH 1 | 7.01 | 35.45 | 517 |
| Comparative Example 2-2 | GH 2 | 6.51 | 38.08 | 518 |
| Comparative Example 2-3 | GH 3 | 6.65 | 37.11 | 517 |

As a result of the experiment, it could be confirmed that the green organic light emitting devices of Experimental Examples 2-1 to 2-30 in which the compound represented by Chemical Formula 1 according to the present invention was used as a host material of the green light emitting layer exhibited better performances in terms of current efficiency and driving voltage than the green organic light emitting devices of Comparative Examples 2-1 to 2-3 in which a substituent is linked to a material having a core similar to that of the compound of the present invention.

Experimental Example 3-1

The compounds synthesized in the Preparation Examples were subjected to high-purity sublimation purification in a typically known method, and then red organic light emitting devices were manufactured by the following method.

An ITO glass was patterned and then washed, such that the light emitting area of the ITO glass became 2 mm×2 mm. After the substrate was mounted in a vacuum chamber, the base pressure was set to 1×10$^{-6}$ torr, and then layers were sequentially formed on the ITO by using DNTPD (700 Å) and α-NPB (300 Å). Subsequently, a light emitting layer was formed by using Compound 15 as a host (90 wt %), and co-depositing the following (piq)2Ir(acac) (10 wt %) (300 Å) as a dopant, films were additionally formed in the order of Alq$_3$ (350 Å), LiF (5 Å), and Al (1,000 Å), and measurements were made at 0.4 mA.

The structures of DNTPD, α-NPB, (piq)2Ir(acac), and Alq3 are as follows.

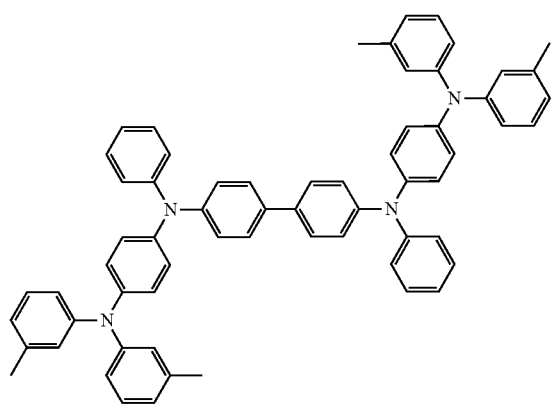

[DNTPD]

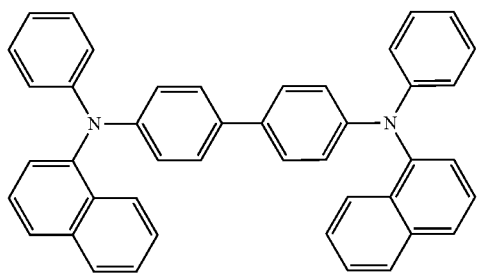

[α-NPB]

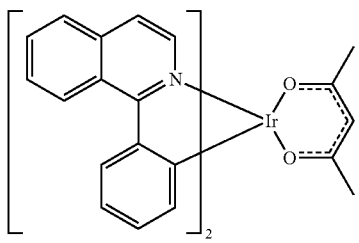

[(piq)₂Ir(acac)]

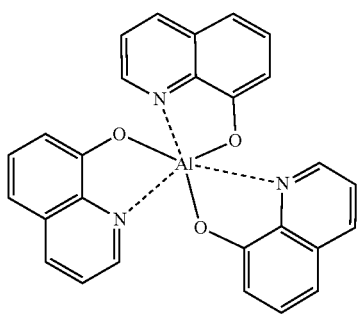

[Alq₃]

-continued

[Compound 15]

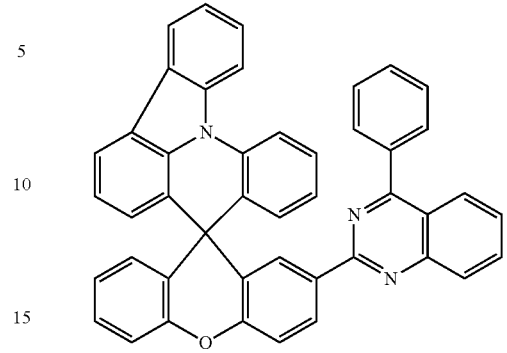

Experimental Example 3-2

An organic light emitting device was manufactured in the same manner as in Experimental Example 3-1, except that Compound 19 was used instead of Compound 15 in Experimental Example 3-1.

Experimental Example 3-3

An organic light emitting device was manufactured in the same manner as in Experimental Example 3-1, except that Compound 34 was used instead of Compound 15 in Experimental Example 3-1.

Experimental Example 3-4

An organic light emitting device was manufactured in the same manner as in Experimental Example 3-1, except that Compound 38 was used instead of Compound 15 in Experimental Example 3-1.

Experimental Example 3-5

An organic light emitting device was manufactured in the same manner as in Experimental Example 3-1, except that Compound 53 was used instead of Compound 15 in Experimental Example 3-1.

Experimental Example 3-6

An organic light emitting device was manufactured in the same manner as in Experimental Example 3-1, except that Compound 57 was used instead of Compound 15 in Experimental Example 3-1.

Experimental Example 3-7

An organic light emitting device was manufactured in the same manner as in Experimental Example 3-1, except that Compound 72 was used instead of Compound 15 in Experimental Example 3-1.

Experimental Example 3-8

An organic light emitting device was manufactured in the same manner as in Experimental Example 3-1, except that Compound 76 was used instead of Compound 15 in Experimental Example 3-1.

Experimental Example 3-9

An organic light emitting device was manufactured in the same manner as in Experimental Example 3-1, except that Compound 91 was used instead of Compound 15 in Experimental Example 3-1.

Experimental Example 3-10

An organic light emitting device was manufactured in the same manner as in Experimental Example 3-1, except that Compound 95 was used instead of Compound 15 in Experimental Example 3-1.

Experimental Example 3-11

An organic light emitting device was manufactured in the same manner as in Experimental Example 3-1, except that Compound 110 was used instead of Compound 15 in Experimental Example 3-1.

Experimental Example 3-12

An organic light emitting device was manufactured in the same manner as in Experimental Example 3-1, except that Compound 114 was used instead of Compound 15 in Experimental Example 3-1.

Comparative Example 3-1

An organic light emitting device was manufactured in the same manner as in Experimental Example 3-1, except that the following Compound RH 15 (CBP) was used instead of Compound 15 in Experimental Example 3-1.

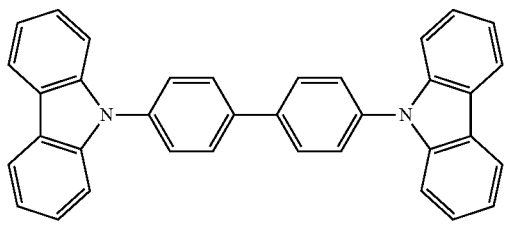

[RH 1]

Comparative Example 3-2

An organic light emitting device was manufactured in the same manner as in Experimental Example 3-1, except that the following Compound RH 2 was used instead of Compound 15 in Experimental Example 3-1.

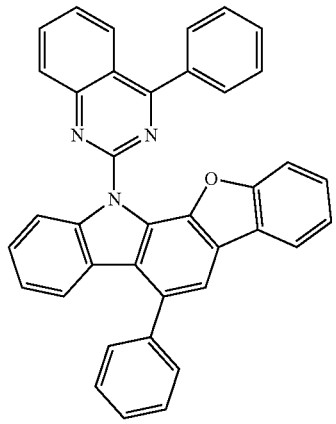

[RH 2]

Comparative Example 3-3

An organic light emitting device was manufactured in the same manner as in Experimental Example 3-1, except that the following Compound RH 3 was used instead of Compound 15 in Experimental Example 3-1.

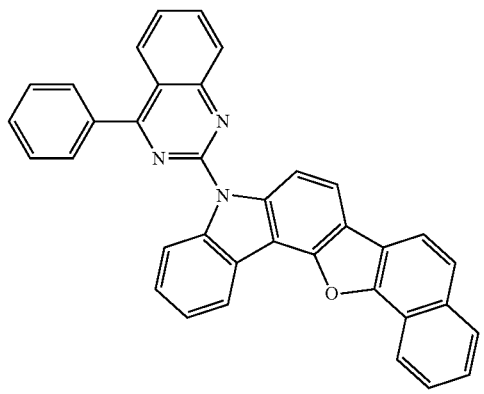

[RH 3]

For the organic light emitting devices manufactured according to Experimental Examples 3-1 to 3-12 and Comparative Examples 3-1 to 3-3, the voltages, current densities, luminances, color coordinates, and service lives were measured, and the results are shown in the following Table 8. T95 means the time taken for the luminance to be reduced to 95% of the initial luminance (5,000 nit).

TABLE 8

| Classification | Host | Voltage (V) | Luminance (cd/m$^2$) | Color coordinate (x, y) | T95 (hr) |
|---|---|---|---|---|---|
| Experimental Example 3-1 | Compound 15 | 4.1 | 1950 | (0.670, 0.329) | 415 |
| Experimental Example 3-2 | Compound 19 | 4.2 | 1850 | (0.674, 0.325) | 425 |
| Experimental Example 3-3 | Compound 34 | 4.3 | 1700 | (0.672, 0.327) | 440 |
| Experimental Example 3-4 | Compound 38 | 4.3 | 1740 | (0.673, 0.335) | 435 |

TABLE 8-continued

| Classification | Host | Voltage (V) | Luminance (cd/m²) | Color coordinate (x, y) | T95 (hr) |
|---|---|---|---|---|---|
| Experimental Example 3-5 | Compound 53 | 4.2 | 1890 | (0.675, 0.333) | 435 |
| Experimental Example 3-6 | Compound 57 | 4.5 | 1510 | (0.670, 0.339) | 440 |
| Experimental Example 3-7 | Compound 72 | 4.2 | 1870 | (0.671, 0.338) | 425 |
| Experimental Example 3-8 | Compound 76 | 4.4 | 1660 | (0.668, 0.329) | 475 |
| Experimental Example 3-9 | Compound 91 | 4.3 | 1750 | (0.673, 0.325) | 455 |
| Experimental Example 3-10 | Compound 95 | 4.5 | 1560 | (0.671, 0.323) | 485 |
| Experimental Example 3-11 | Compound 110 | 4.2 | 1850 | (0.672, 0.324) | 425 |
| Experimental Example 3-12 | Compound 114 | 4.1 | 1960 | (0.670, 0.325) | 435 |
| Comparative Example 3-1 | RH 1 | 5.6 | 1300 | (0.670, 0.325) | 265 |
| Comparative Example 3-2 | RH 2 | 5.8 | 1250 | (0.671, 0.327) | 275 |
| Comparative Example 3-3 | RH 3 | 6.2 | 1150 | (0.674, 0.329) | 295 |

As a result of the experiment, it could be confirmed that the red organic light emitting devices of Experimental Examples 3-1 to 3-12 in which the compound according to the present invention was used as a host material for a light emitting layer exhibited better performances in terms of current efficiency, driving voltage, and service life than the organic light emitting devices of Comparative Examples 3-1 to 3-3 in which a substituent is linked to a material having a core similar to that of the compound of the present invention.

Although the preferred exemplary embodiments (an electron blocking layer, a green light emitting device, and a red light emitting device) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Electron transporting layer

The invention claimed is:

1. An organic light emitting device comprising:
a first electrode;
a second electrode provided to face the first electrode; and
an organic material layer having one or more layers disposed between the first electrode and the second electrode,
wherein the one or more layers of the organic material layer comprise an electron blocking layer or a light emitting layer, and the electron blocking layer or the light emitting layer comprises a compound represented by the following Chemical Formula 1:

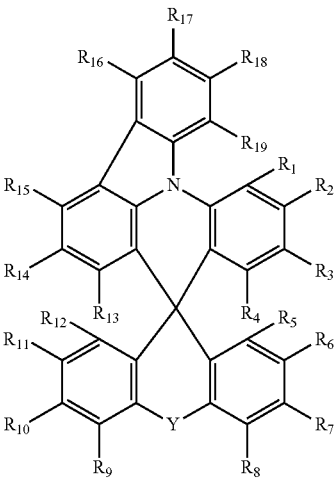

[Chemical Formula 1]

in Chemical Formula 1,

Y is O, S, P(=O)R, or CR'R", $R_1$ to $R_5$, and $R_9$ to $R_{19}$ are hydrogen or deuterium, and $R_6$ to $R_8$, R, R', and R" are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, wherein at least one of $R_6$ to $R_8$ is a substituted or unsubstituted aryl group; a substituted or unsubstituted heterocyclic group; or a substituted or unsubstituted arylamino group.

2. The organic light emitting device of claim 1, wherein Chemical Formula 1 is represented by one of the following Chemical Formulae 2 to 5:

[Chemical Formula 2]

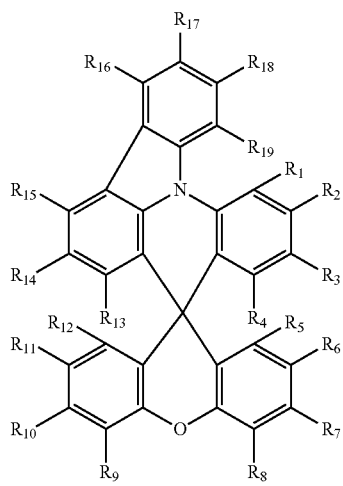

in Chemical Formula 2, $R_1$ to $R_{19}$ are the same as those defined in Chemical Formula 1,

[Chemical Formula 3]

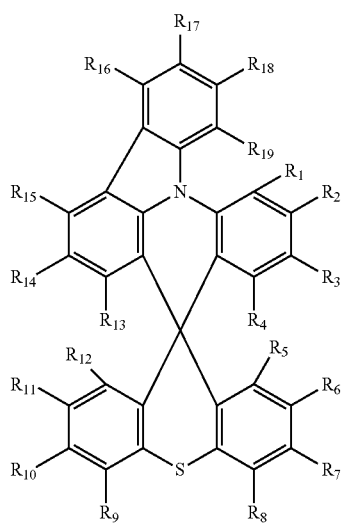

in Chemical Formula 3, $R_1$ to $R_{19}$ are the same as those defined in Chemical Formula 1,

[Chemical Formula 4]

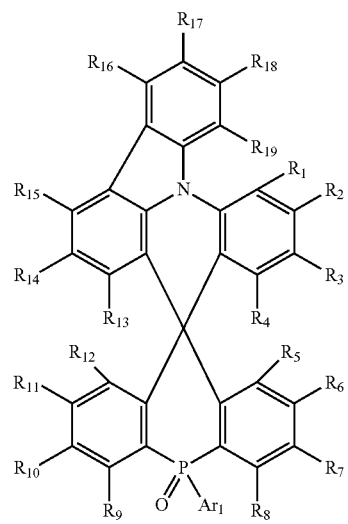

in Chemical Formula 4, $R_1$ to $R_{19}$ are the same as those defined in Chemical Formula 1, and $Ar_1$ is a substituted or unsubstituted aryl group, and

[Chemical Formula 5]

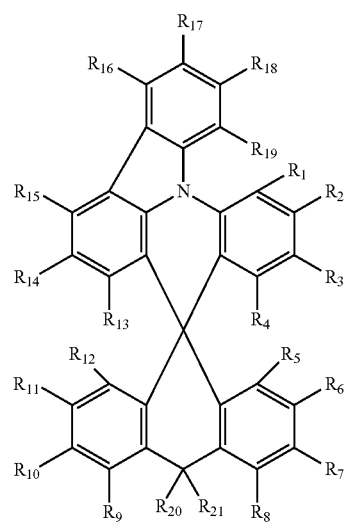

in Chemical Formula 5, $R_1$ to $R_{19}$ are the same as those defined in Chemical Formula 1, and $R_{20}$ and $R_{21}$ are the same as or different from each other, and are each independently a substituted or unsubstituted alkyl group.

3. The organic light emitting device of claim 1, wherein $R_6$ or $R_8$ is a substituted or unsubstituted aryl group; a substituted or unsubstituted heterocyclic group; or a substituted or unsubstituted arylamino group.

4. The organic light emitting device of claim 1, wherein at least one of $R_6$ to $R_8$ is selected from the following structural formulae:

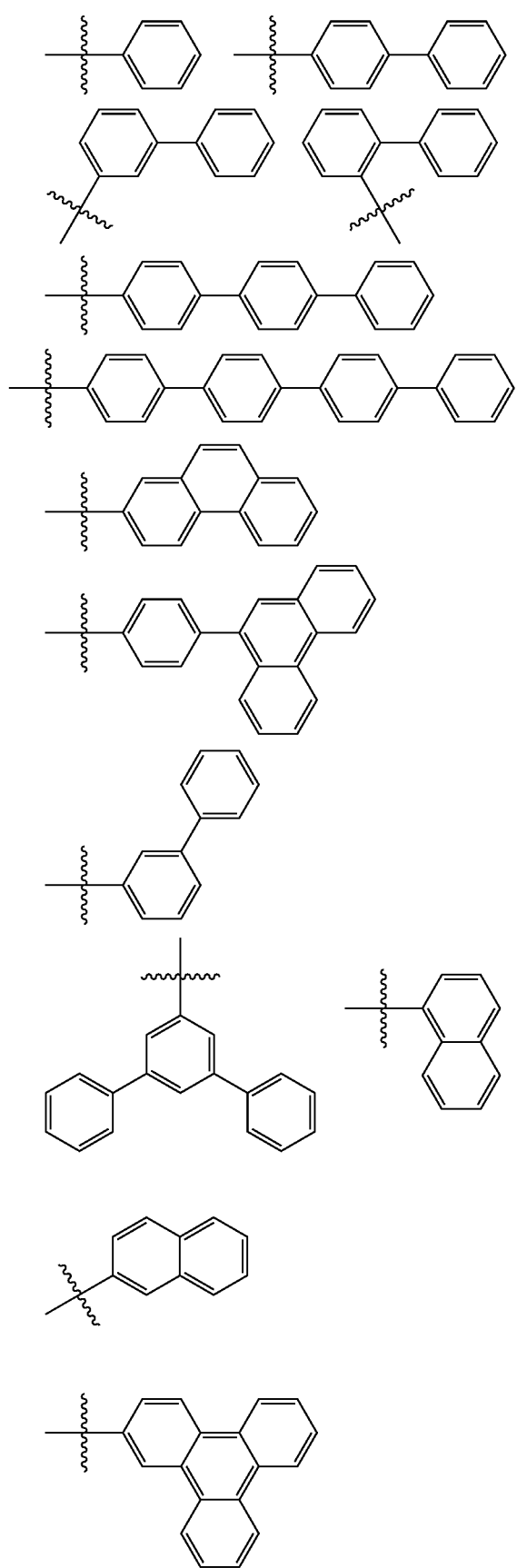
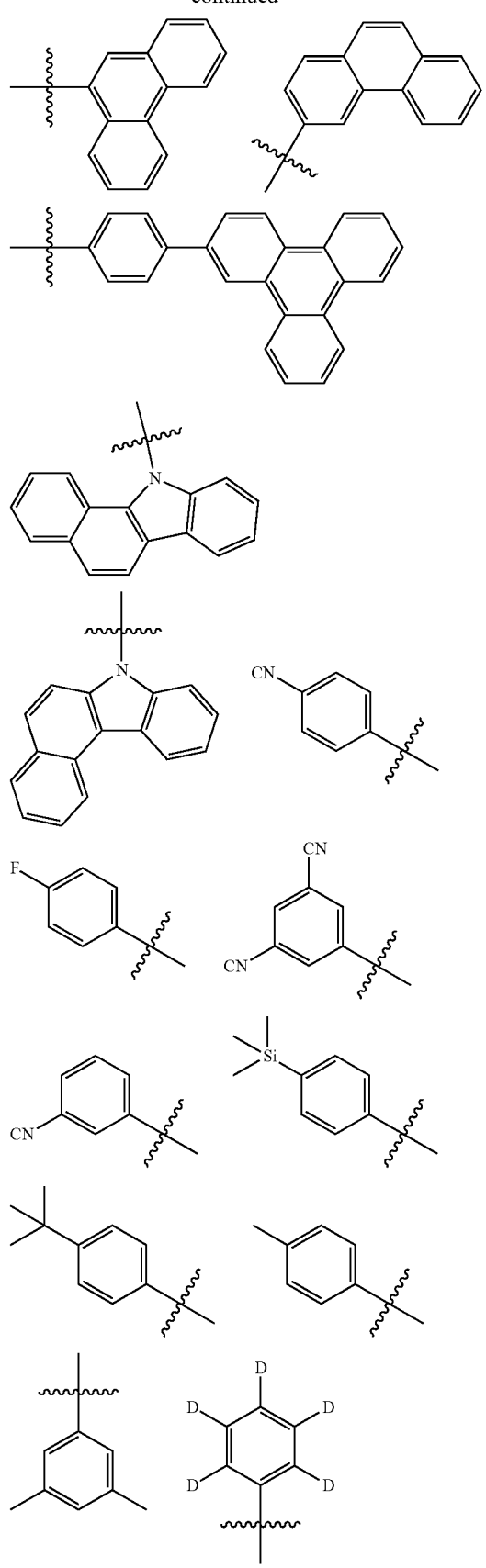

385
-continued
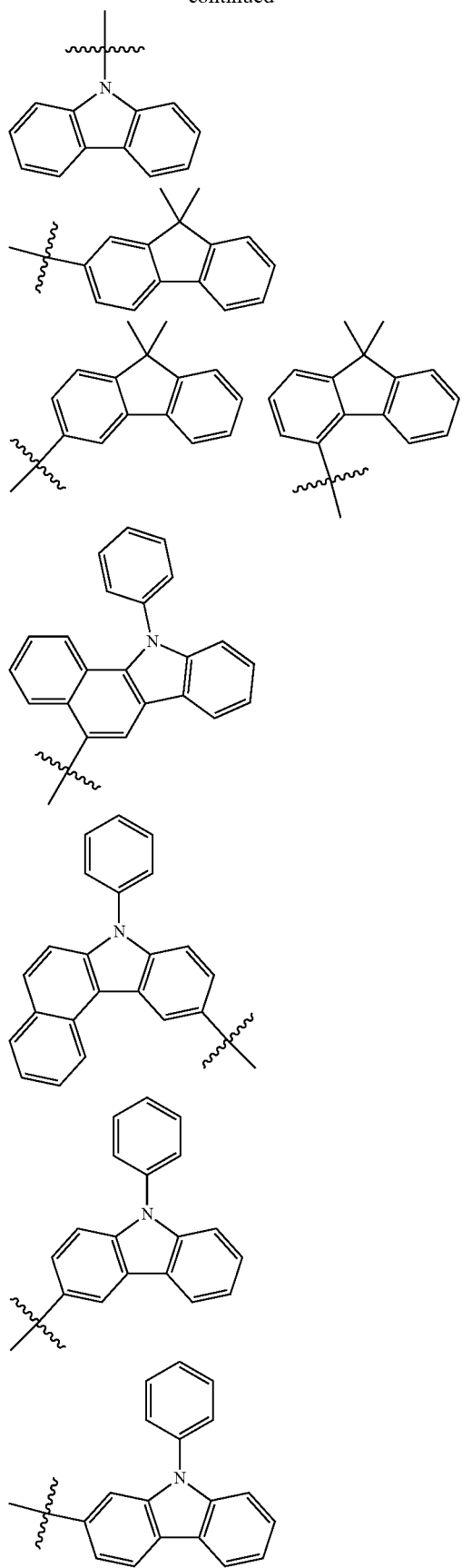
386
-continued
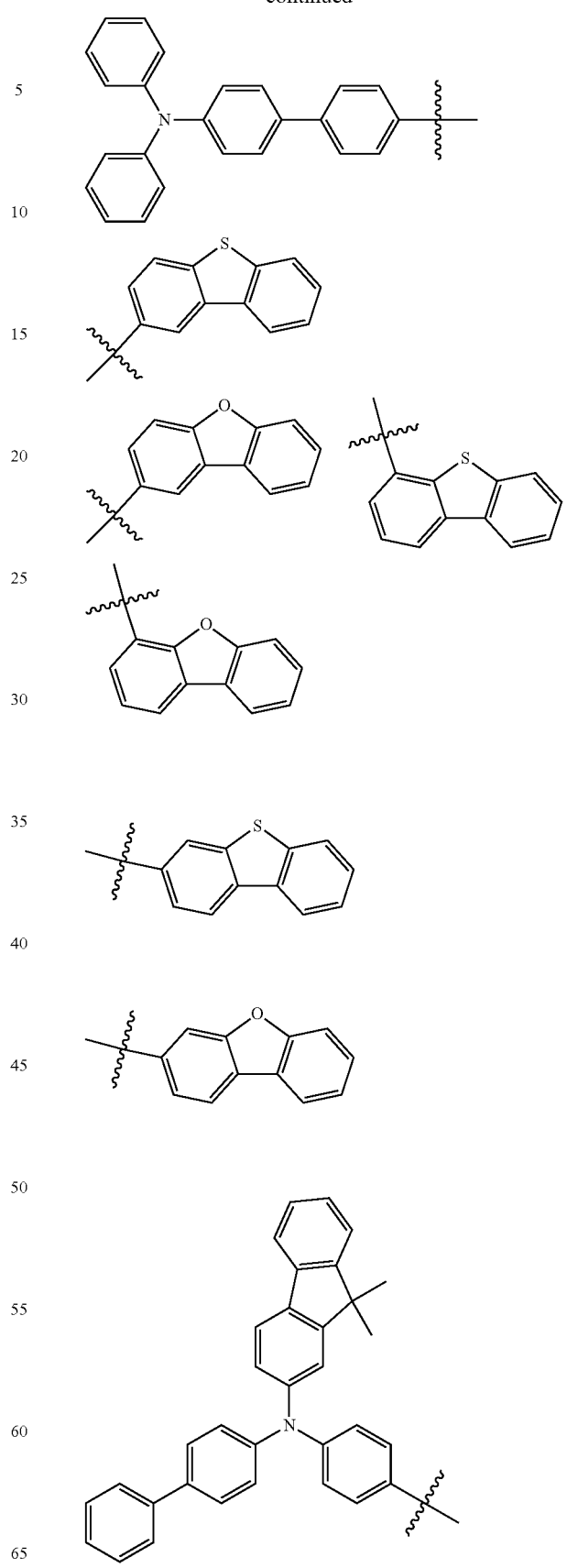

387
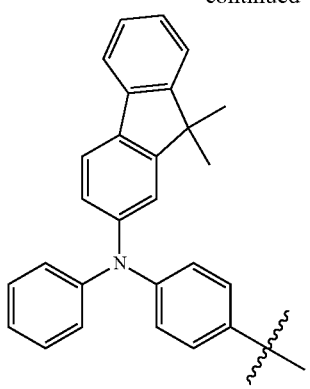
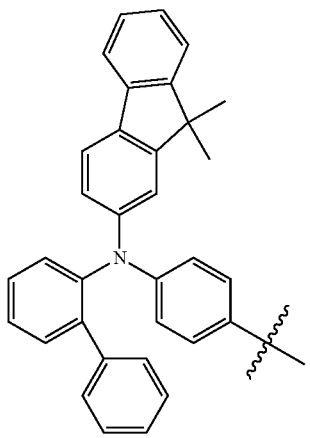
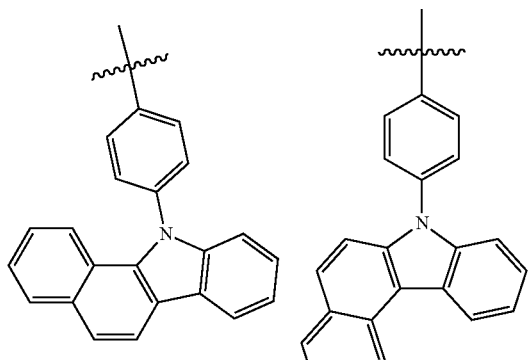
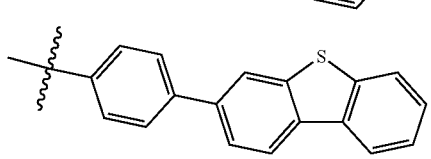
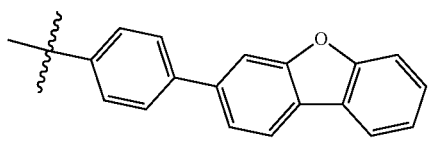
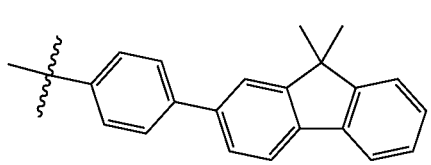
388
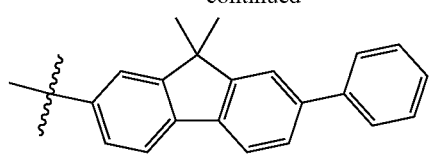
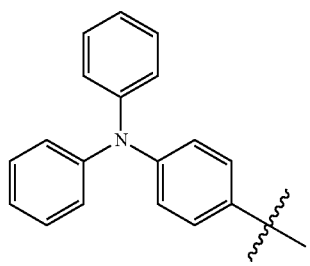
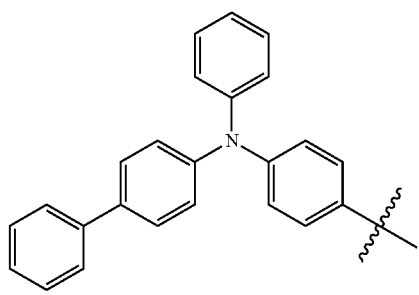
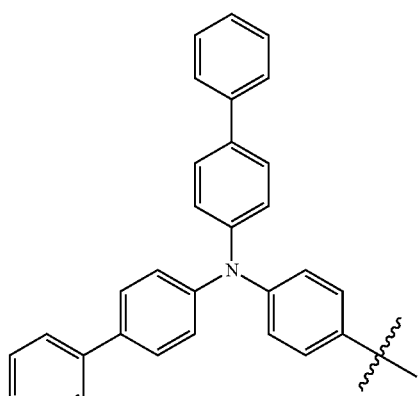
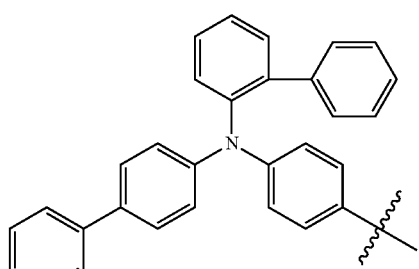
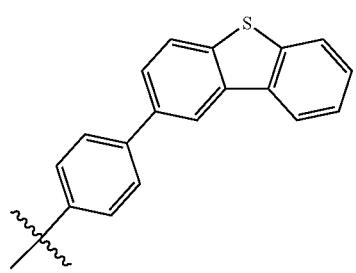

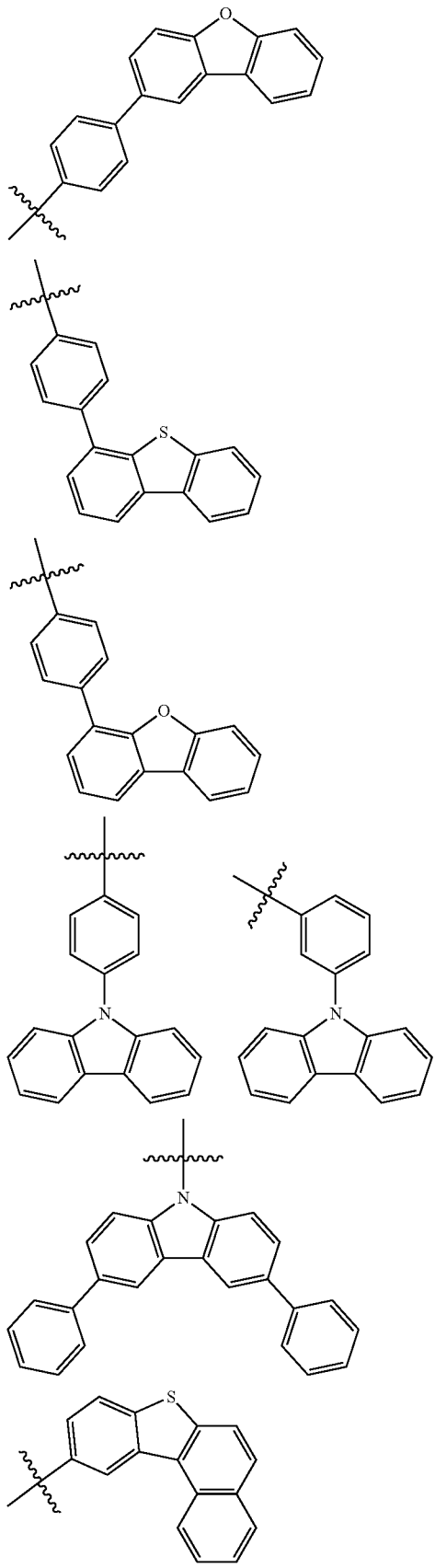
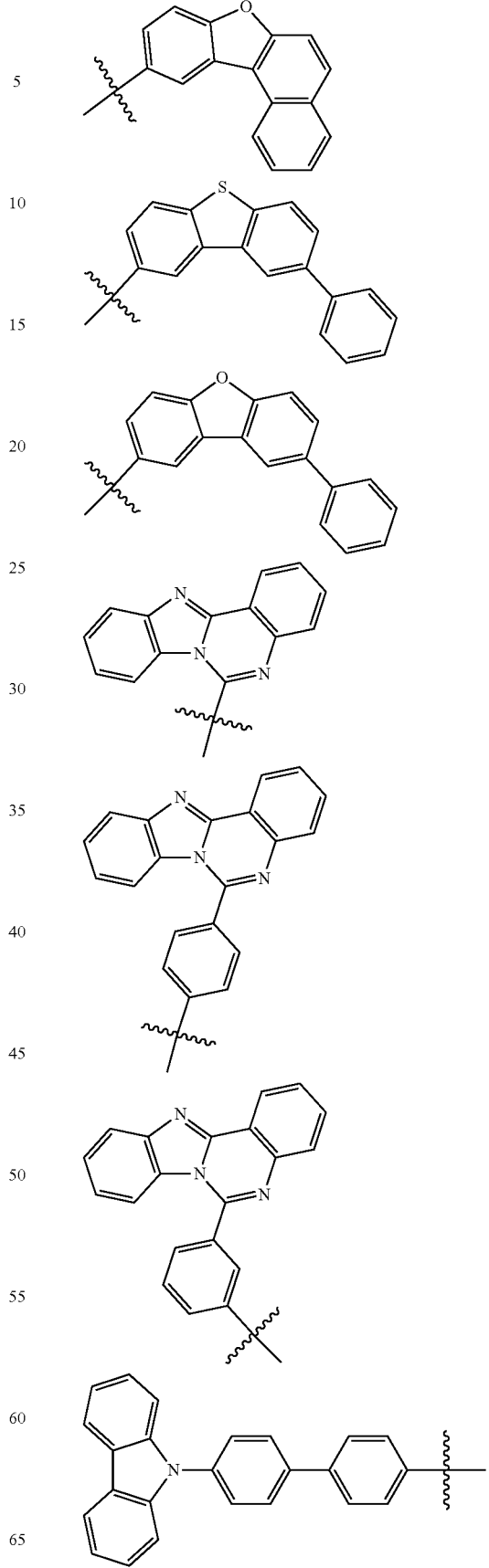

391
-continued
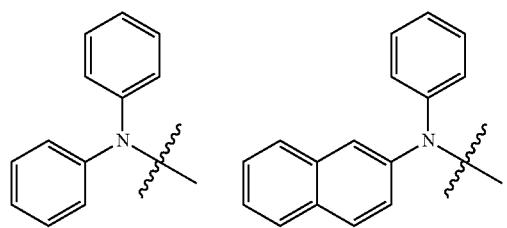
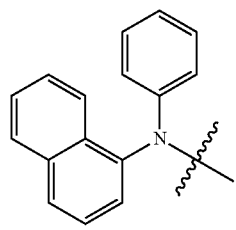
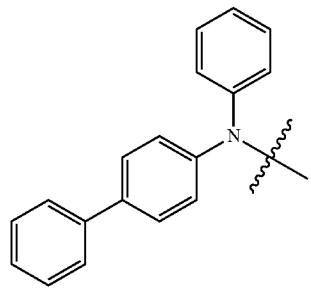
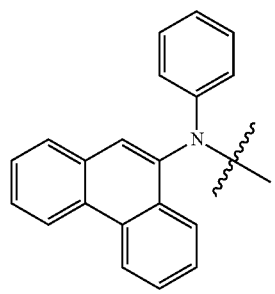
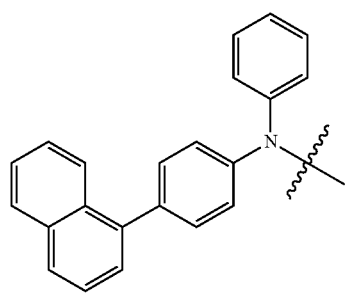
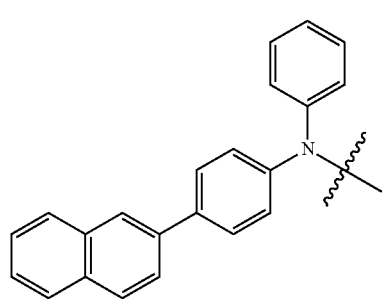
392
-continued
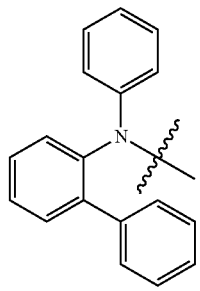
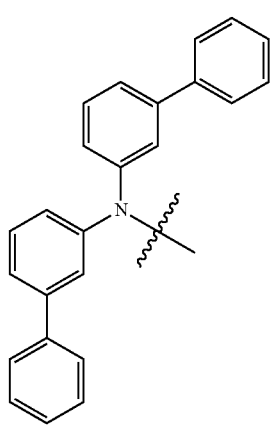
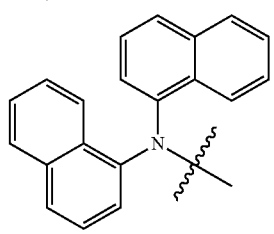
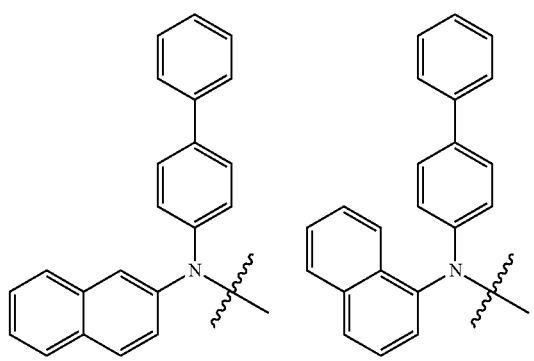
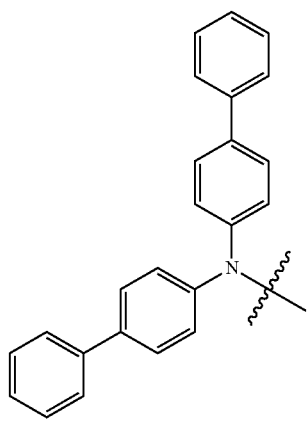

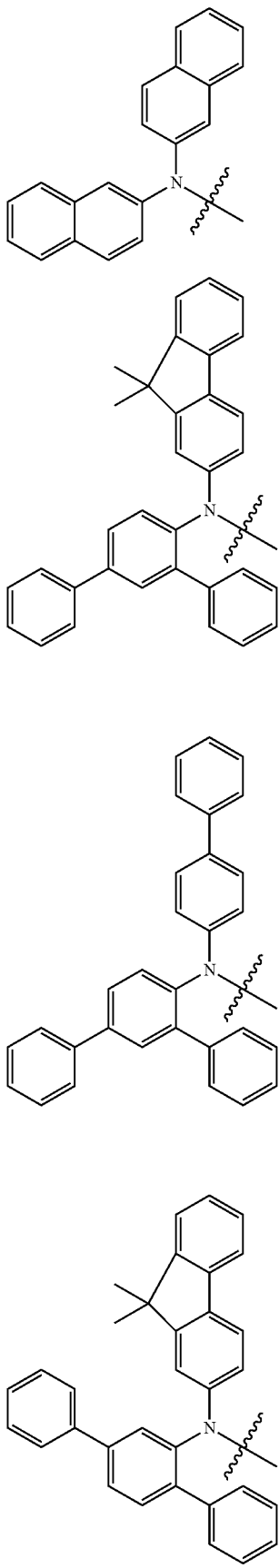
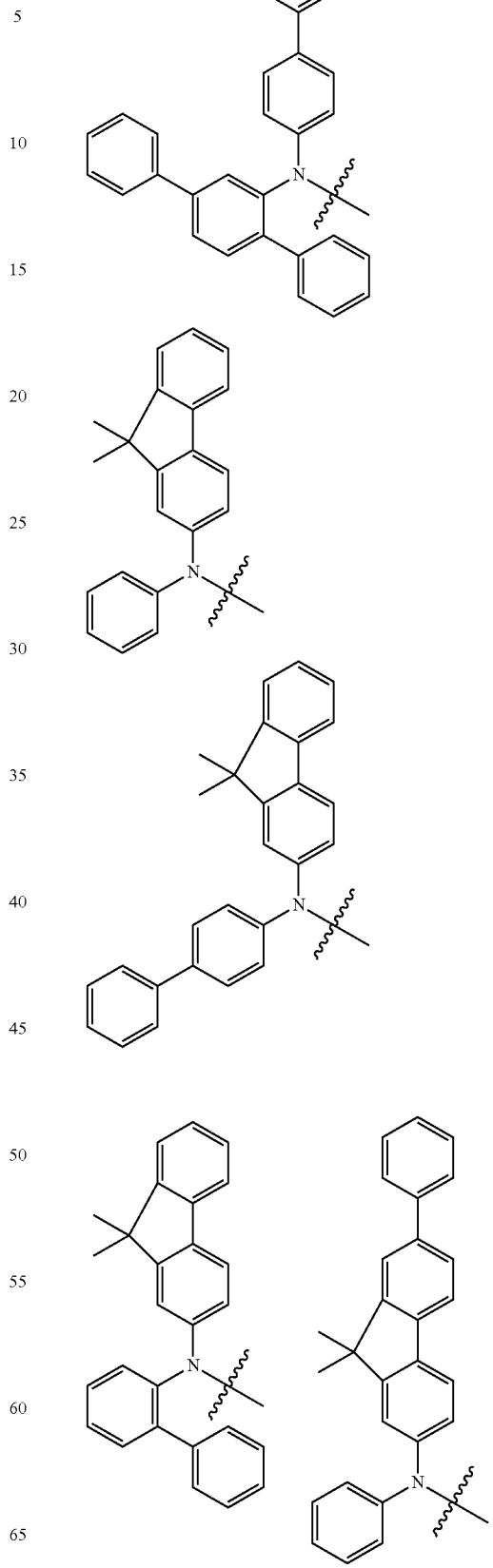

395
-continued
396
-continued
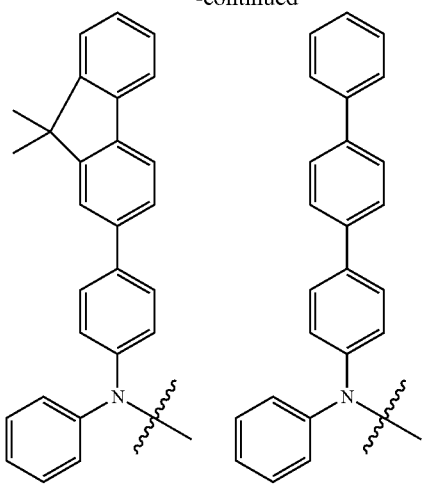
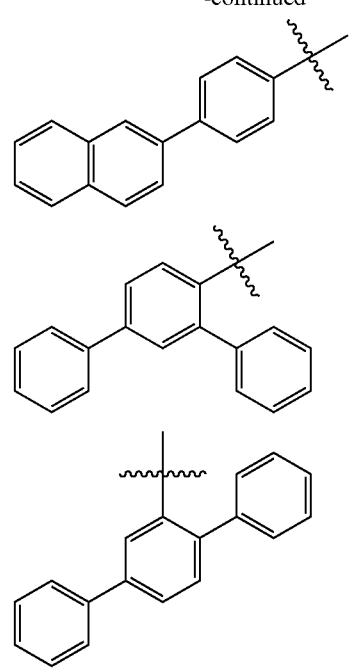
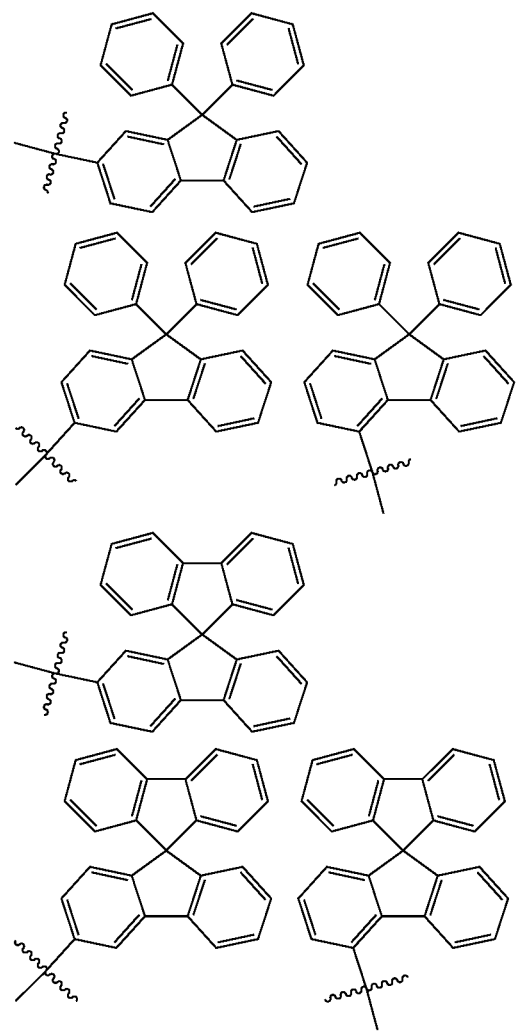
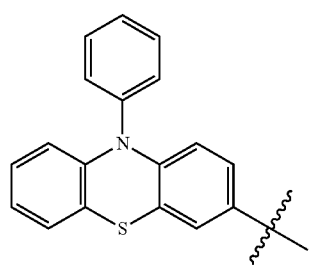
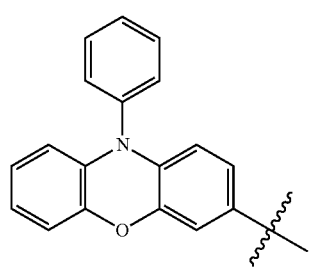

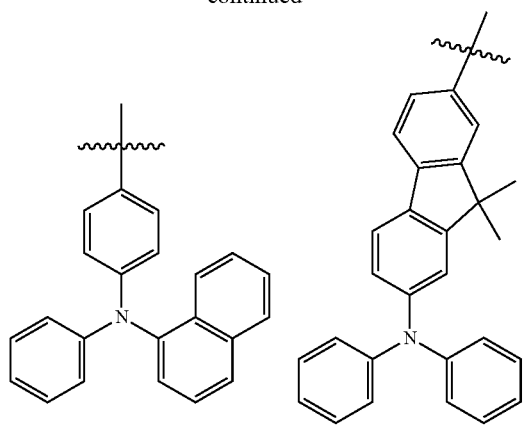
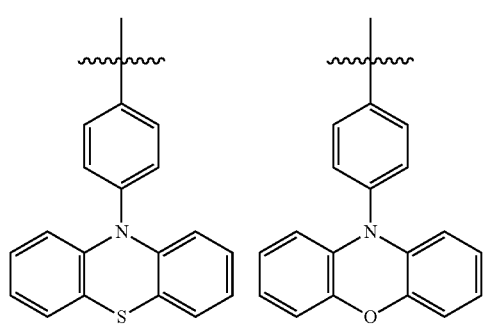
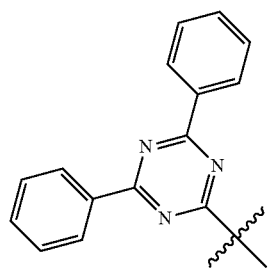
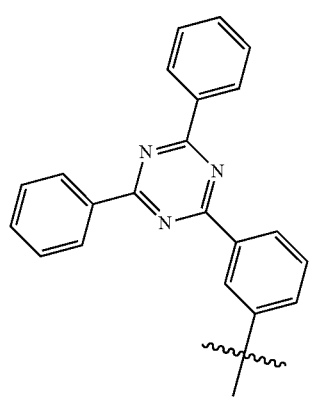
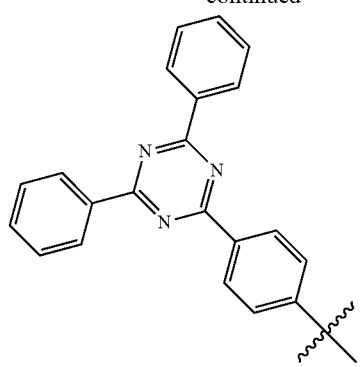
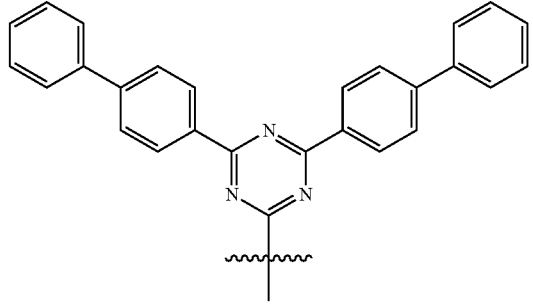
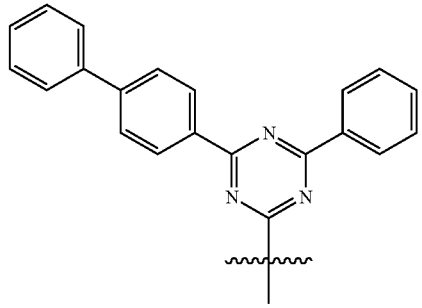
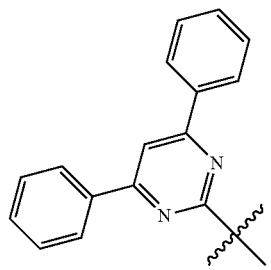
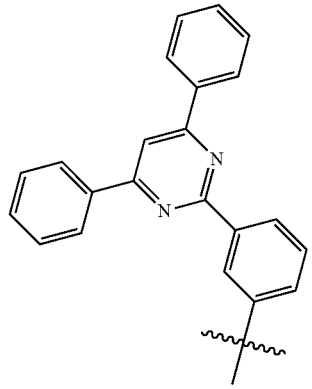

399
-continued
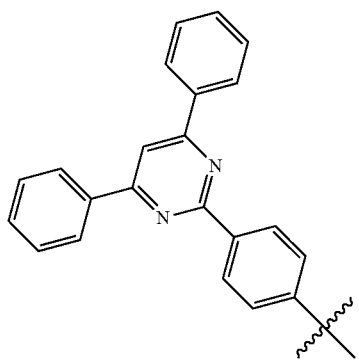
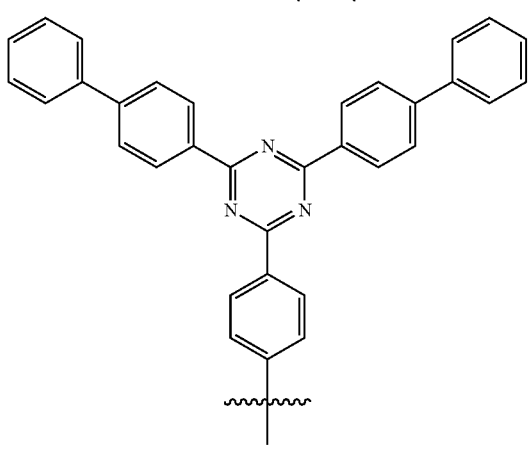
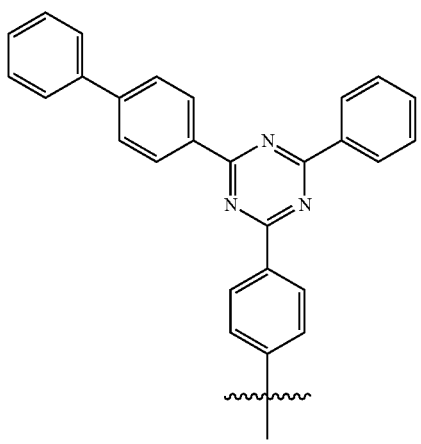
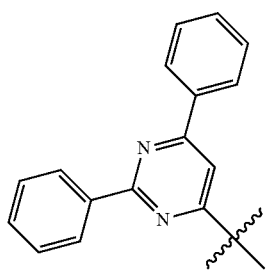
400
-continued
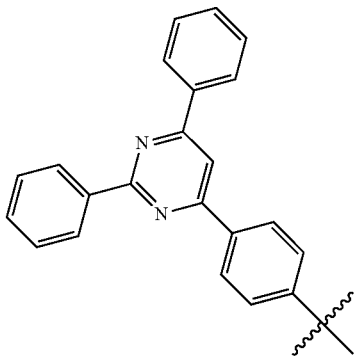
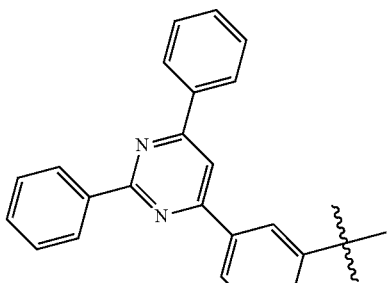
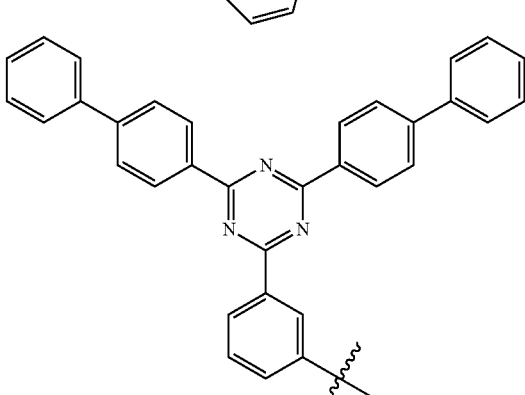
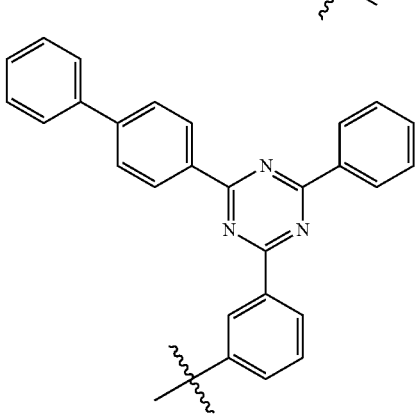
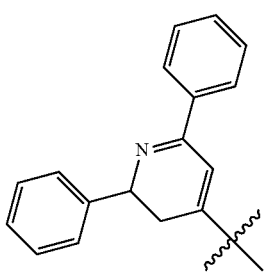

401
-continued
402
-continued
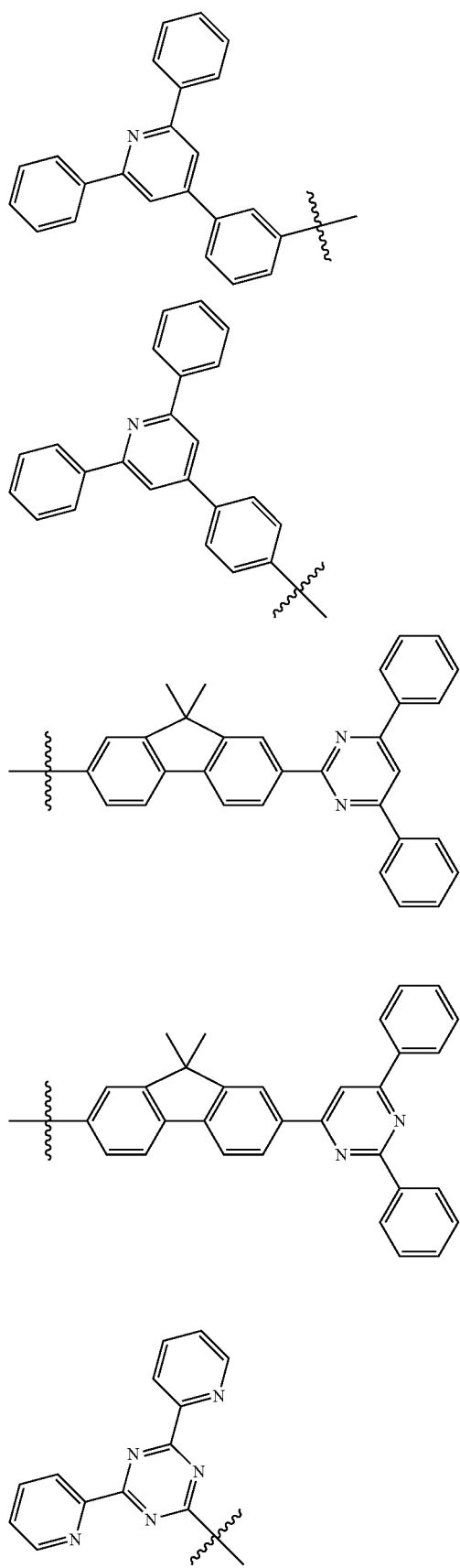
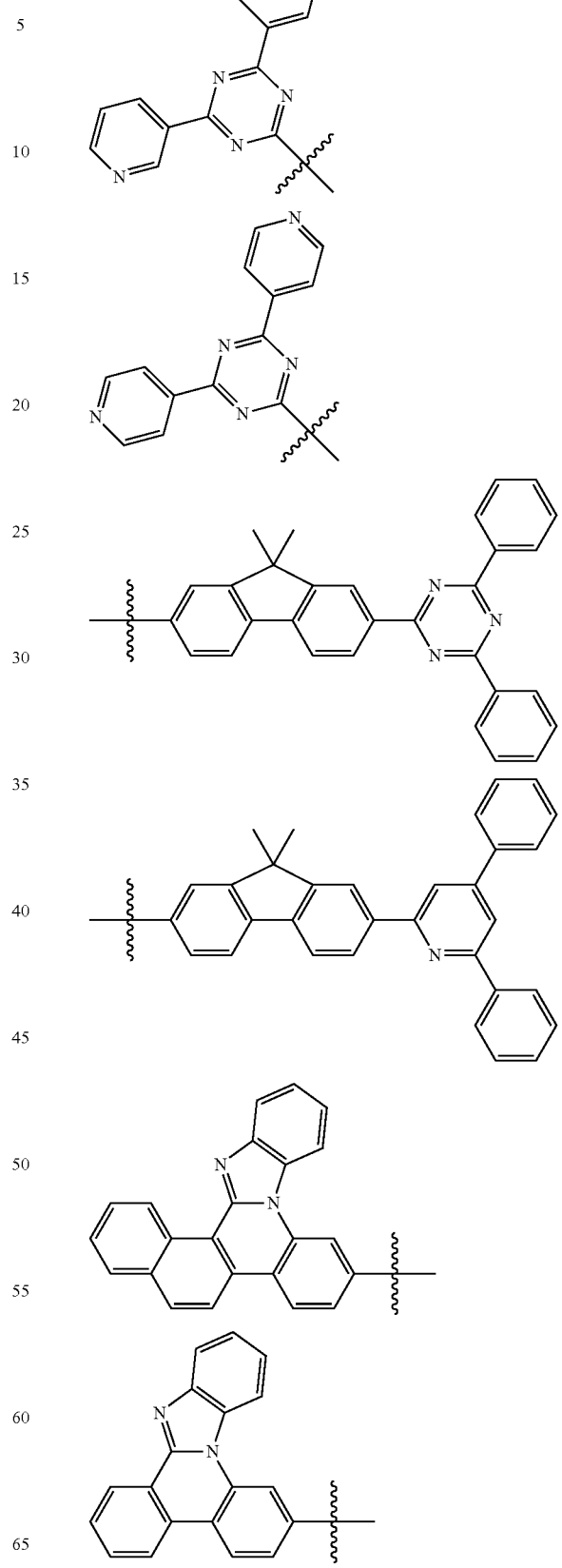

403
-continued
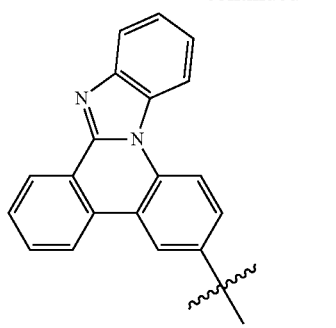
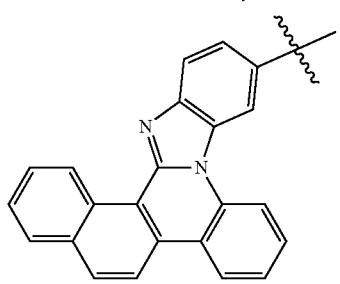
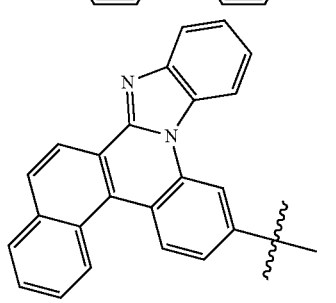
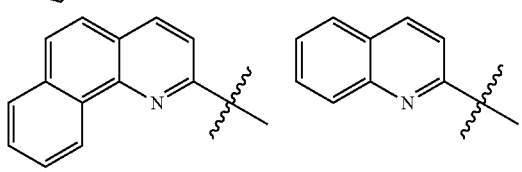
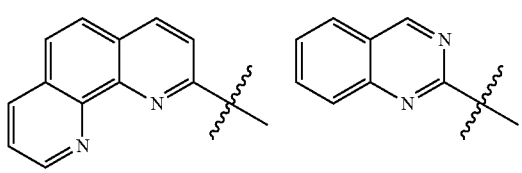
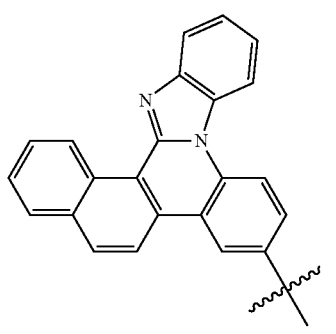
404
-continued
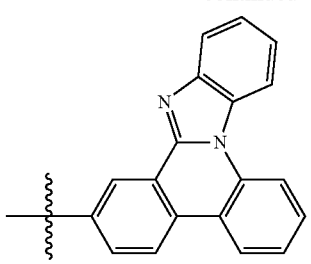
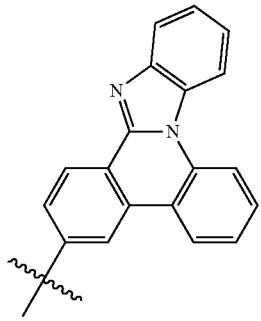
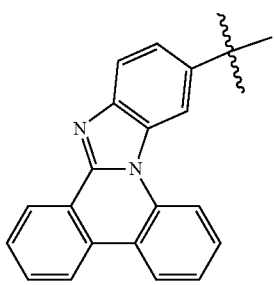
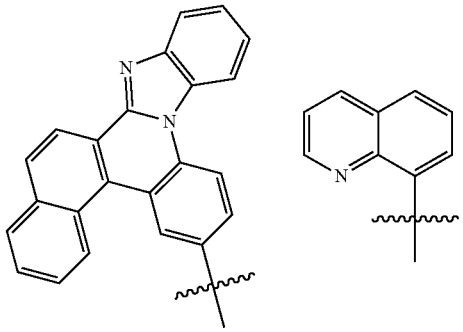
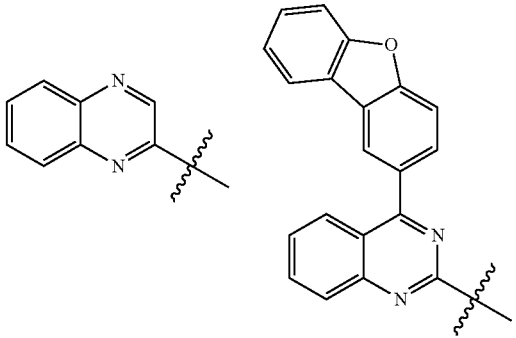

-continued
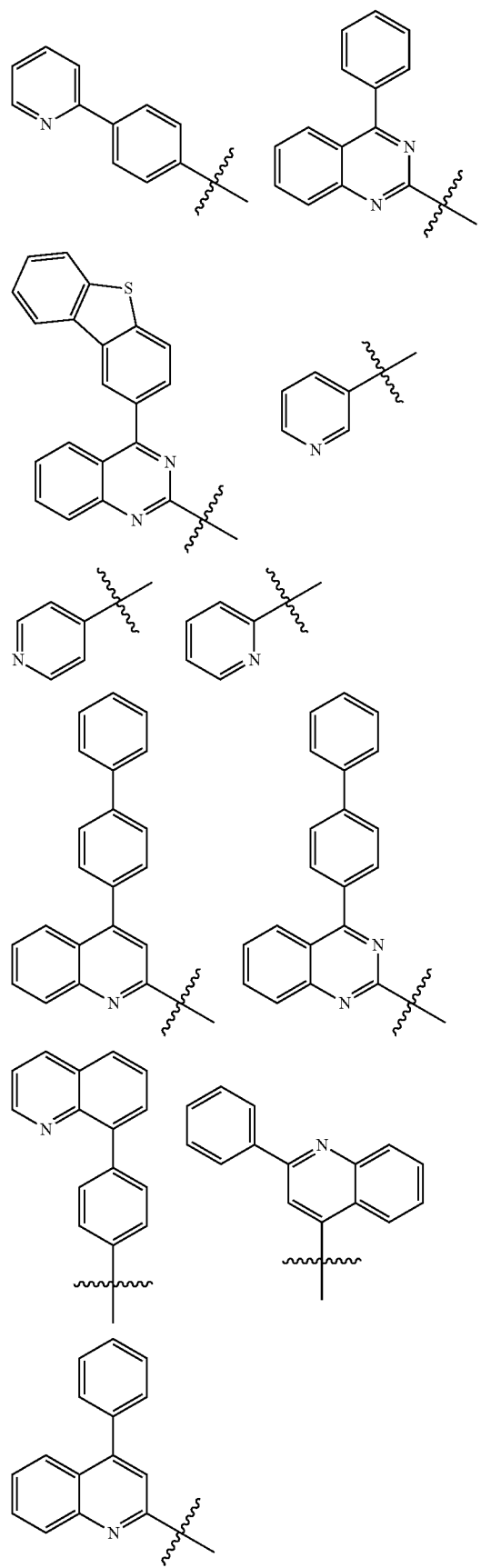
-continued
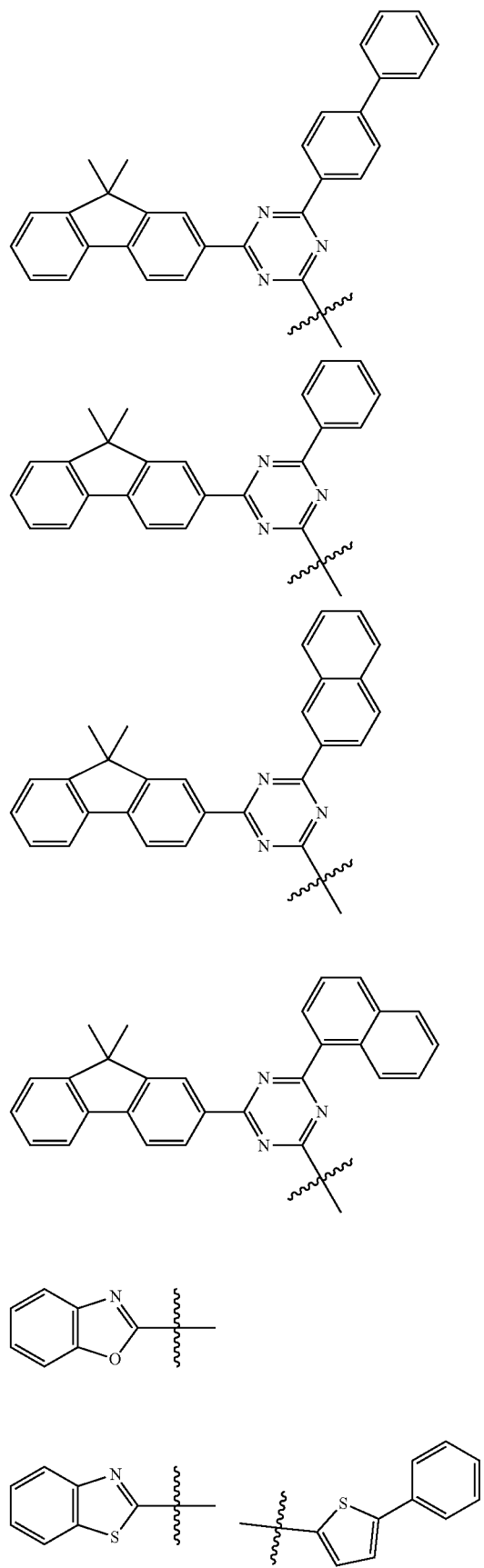

407
-continued
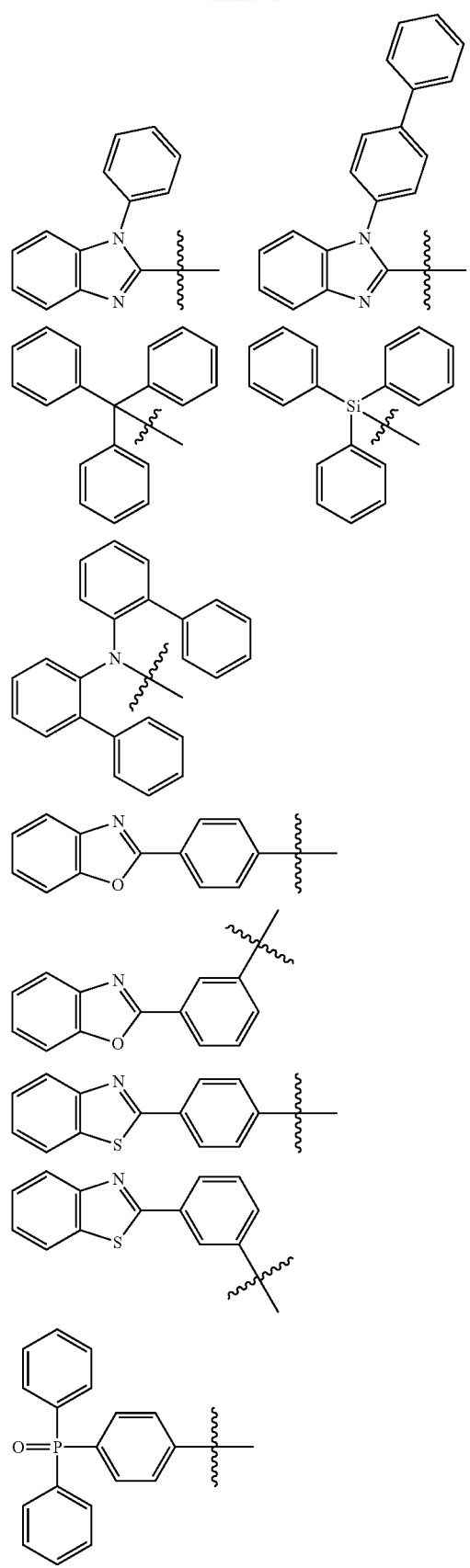
408
-continued
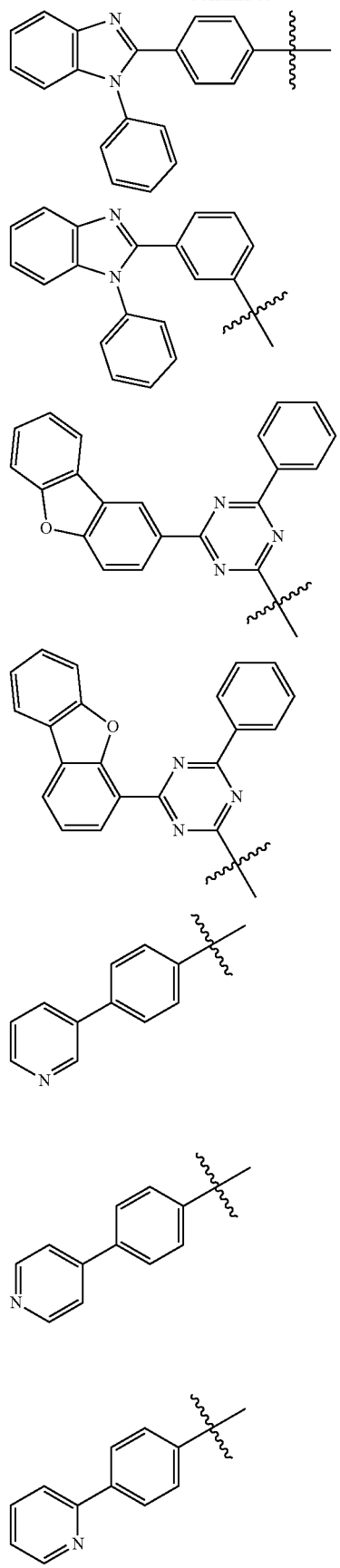

409
-continued
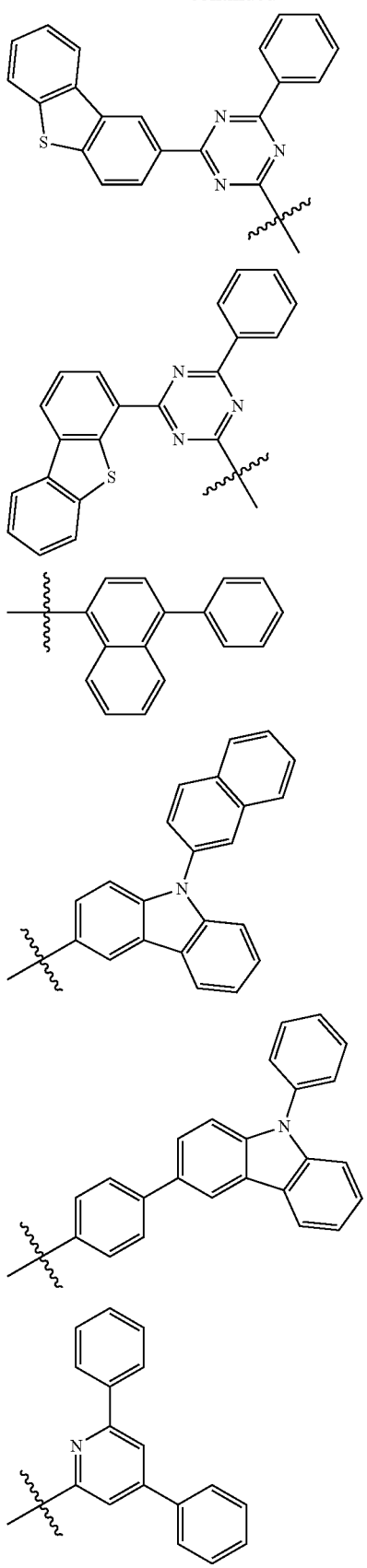
410
-continued
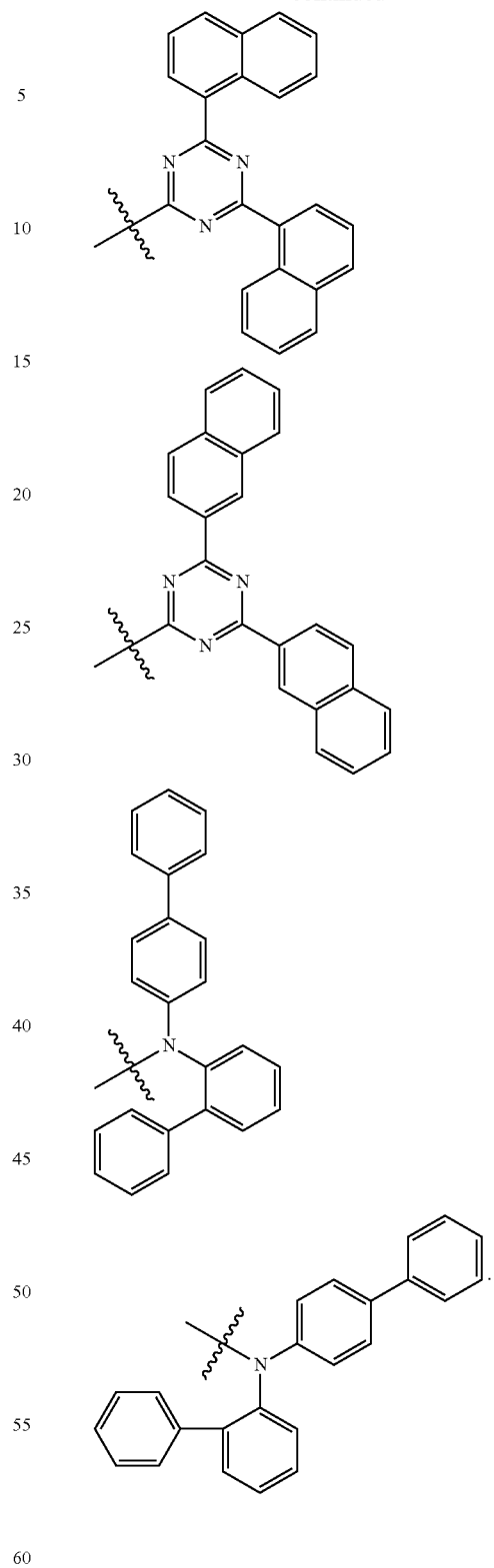
5. The organic light emitting device of claim 1, wherein the compound of Chemical Formula 1 is any one selected from the following structural formulae:

411
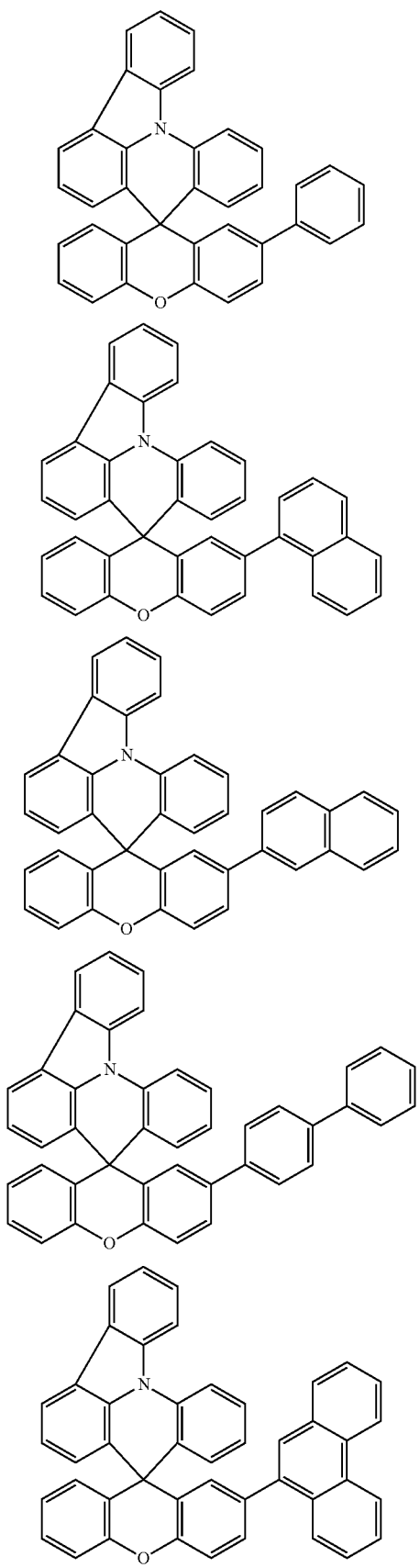
412
-continued
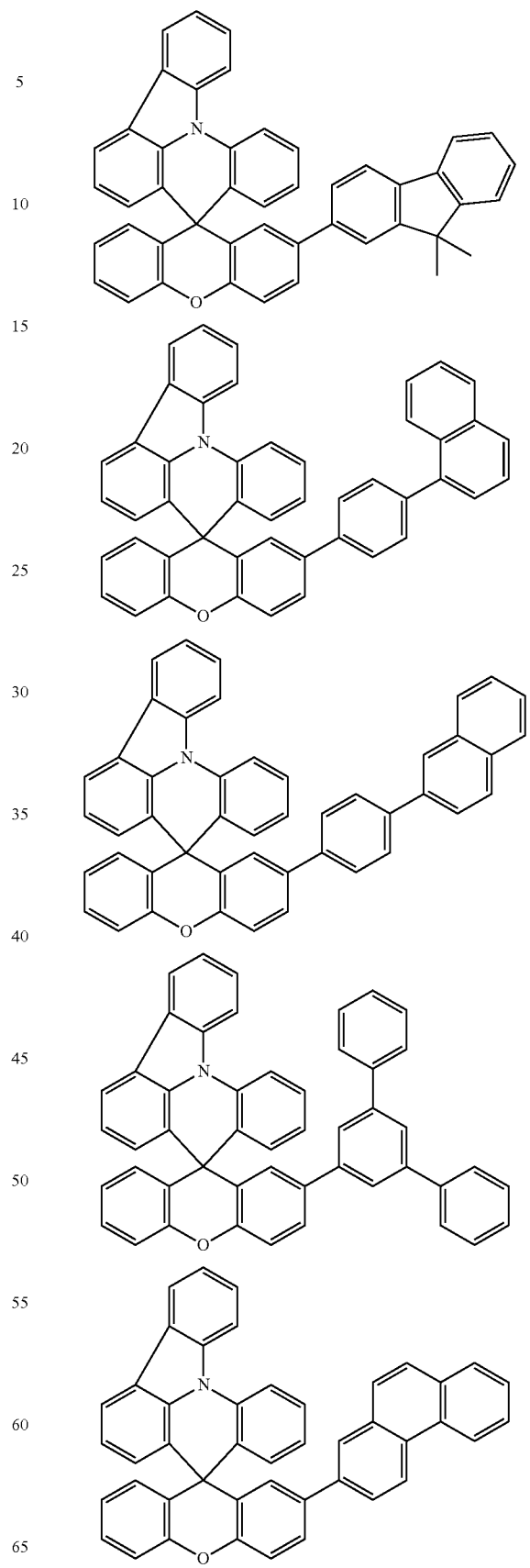

413
-continued
414
-continued
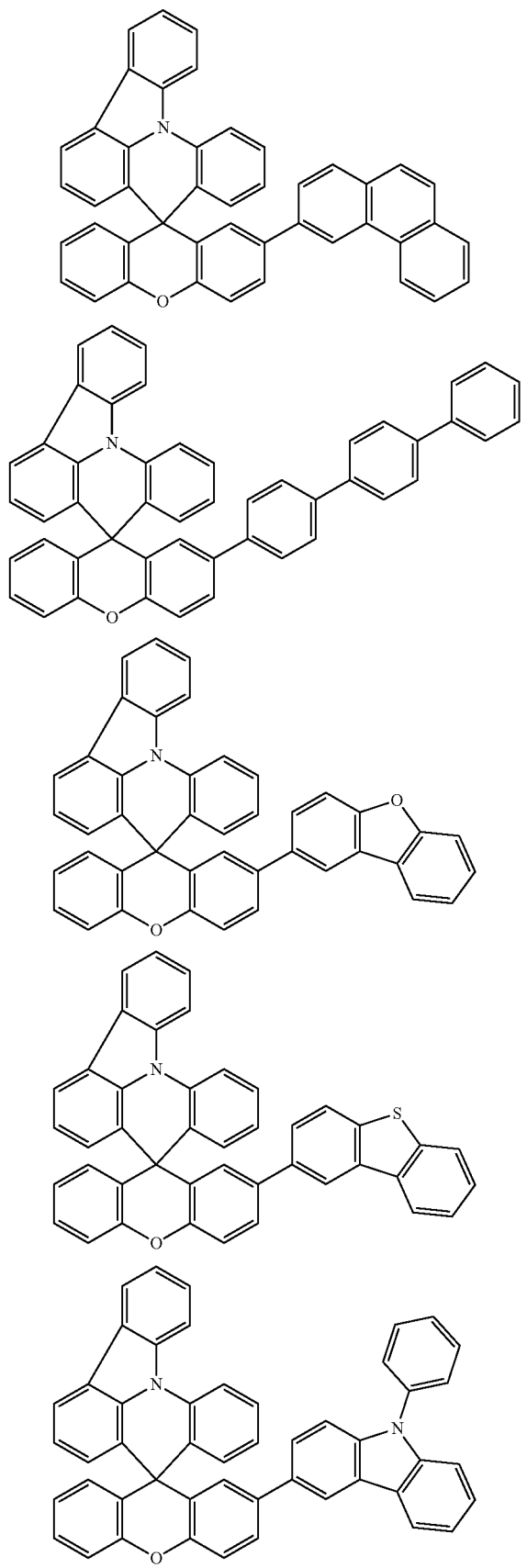
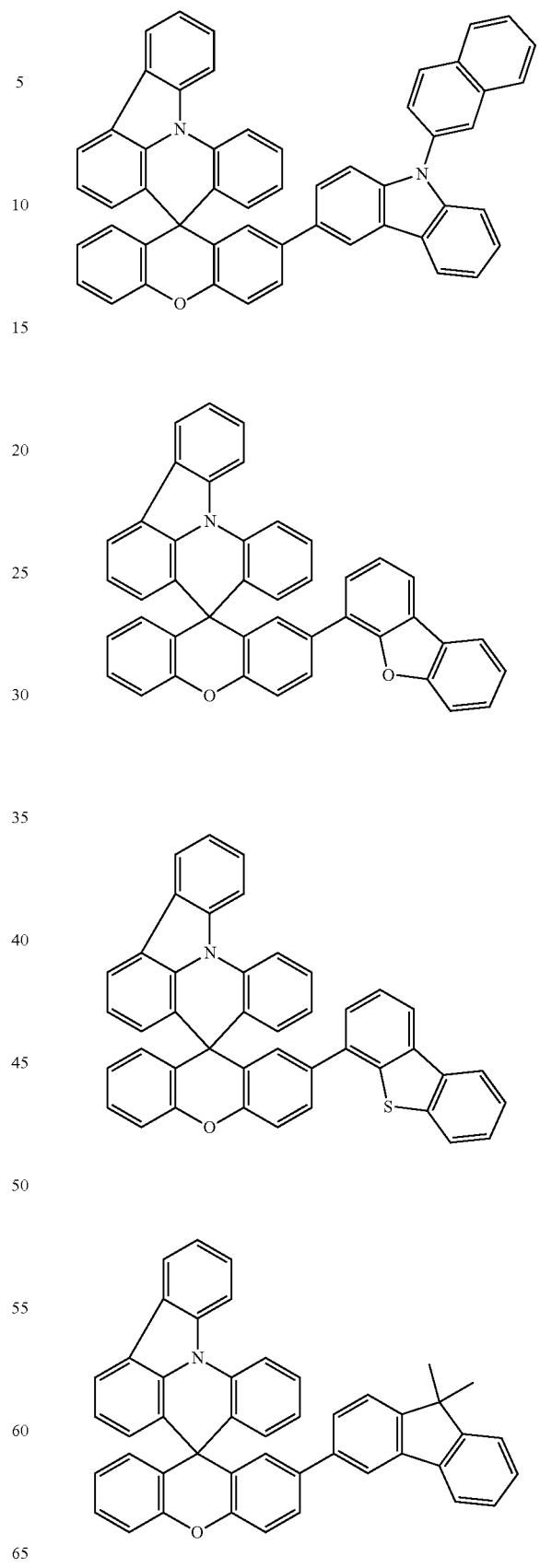

415
-continued
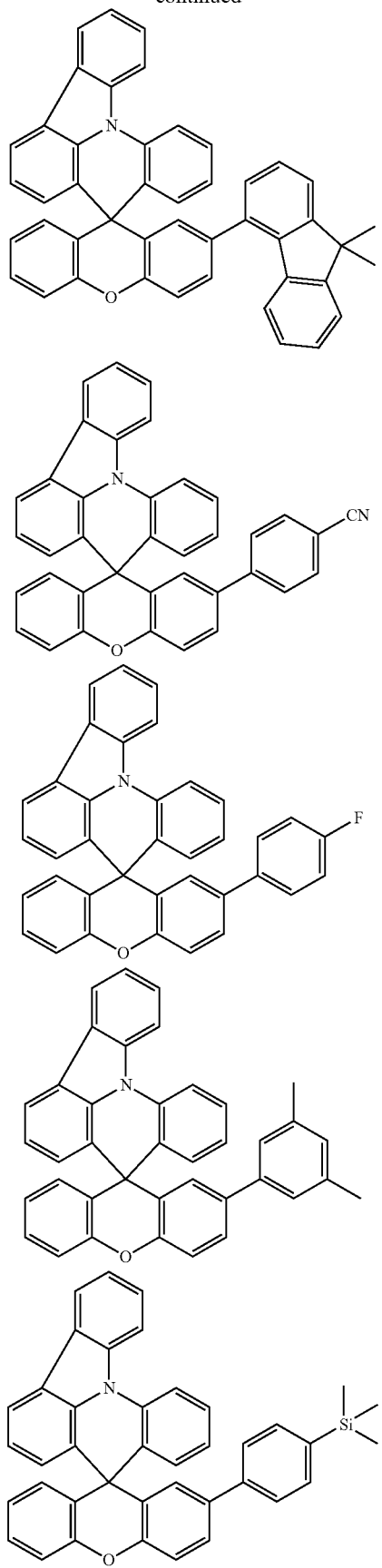
416
-continued
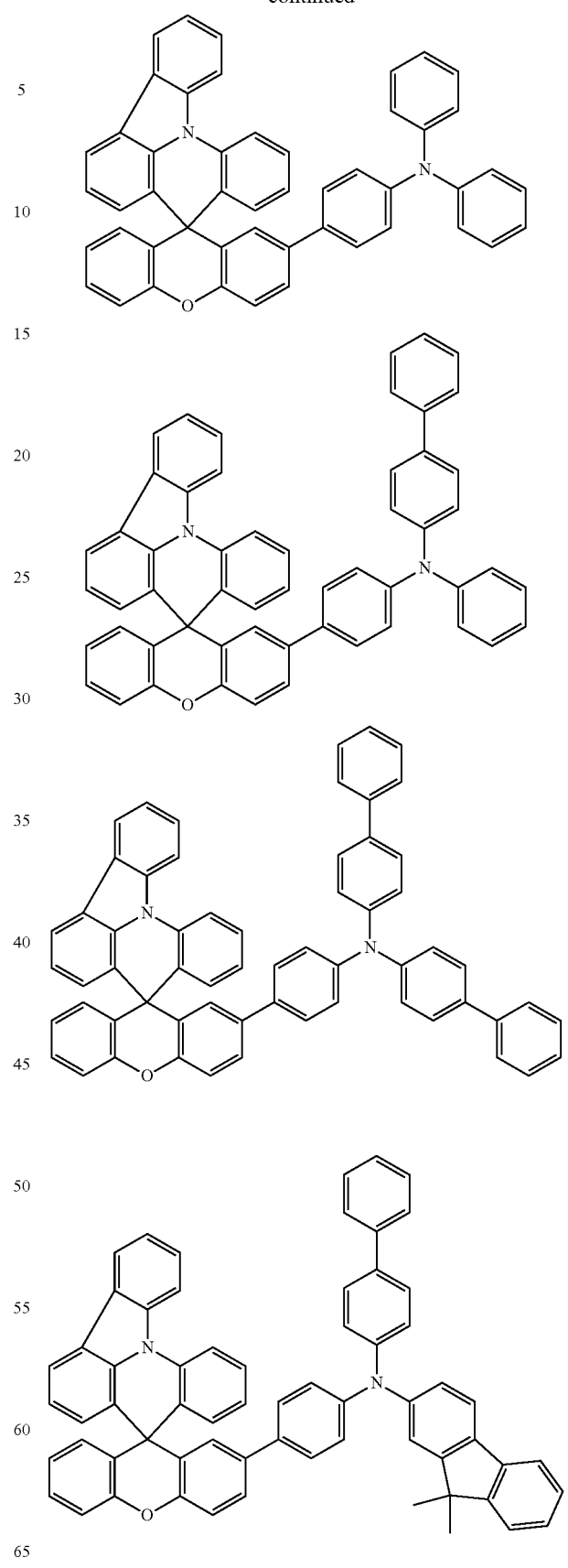

417
-continued
418
-continued
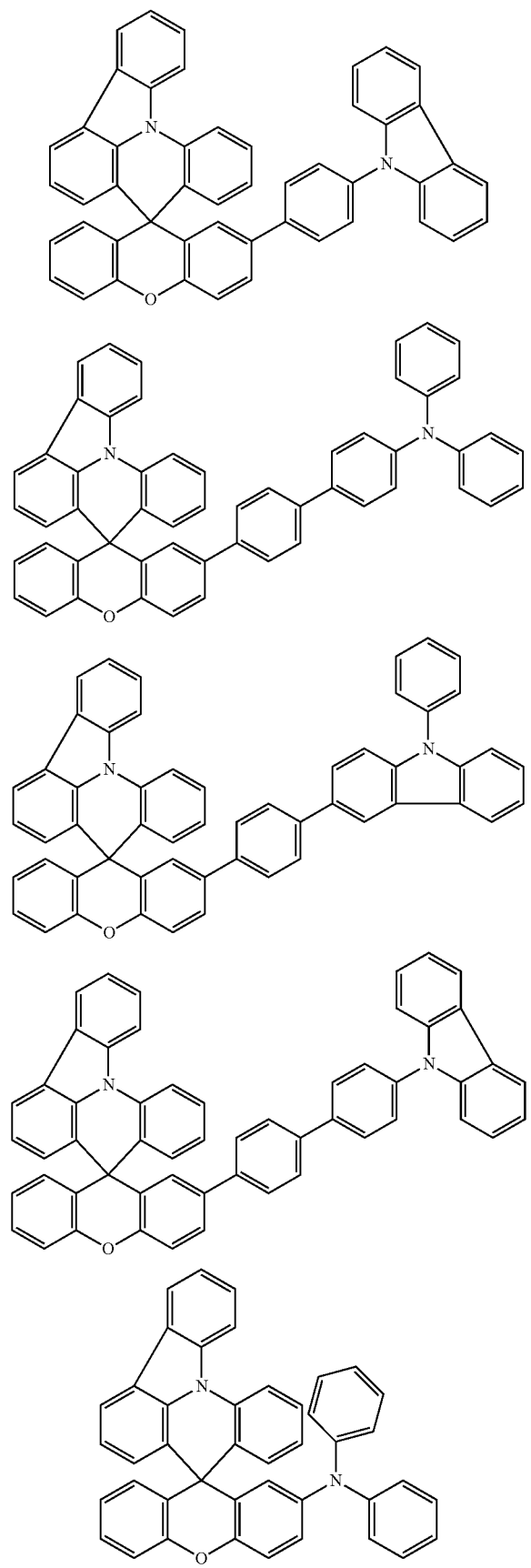
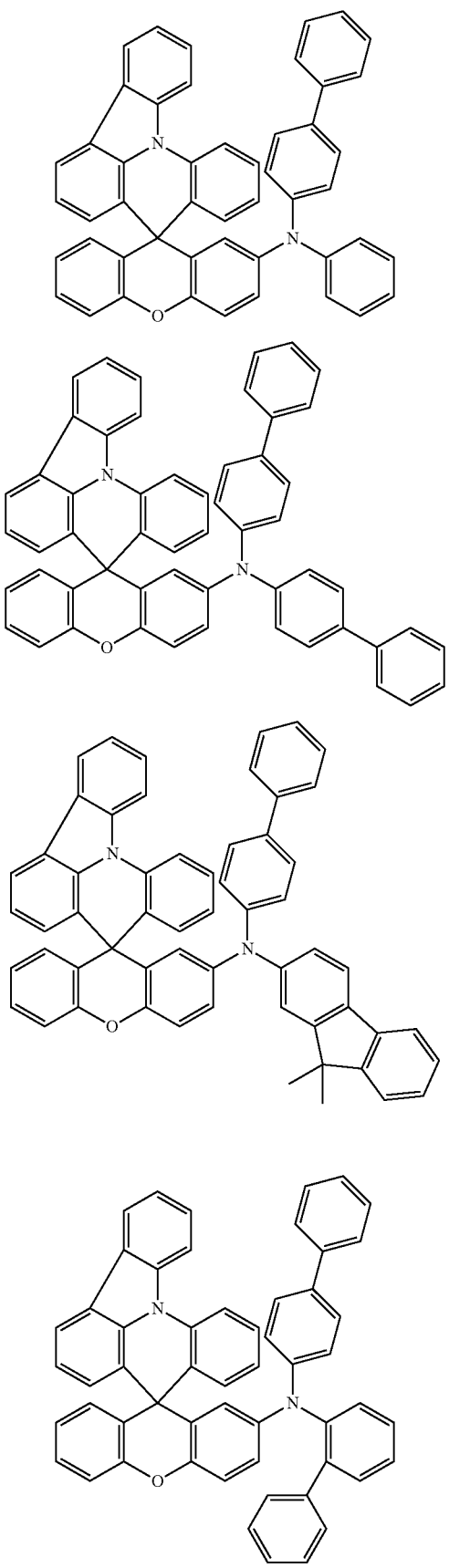

419
-continued
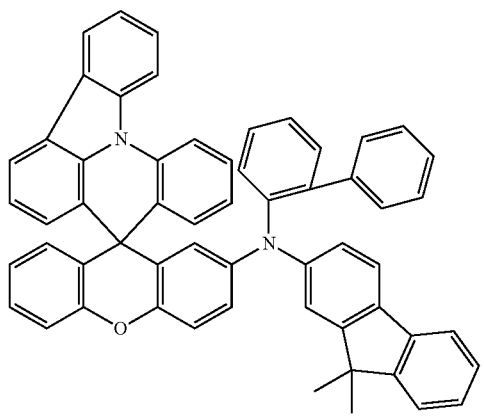
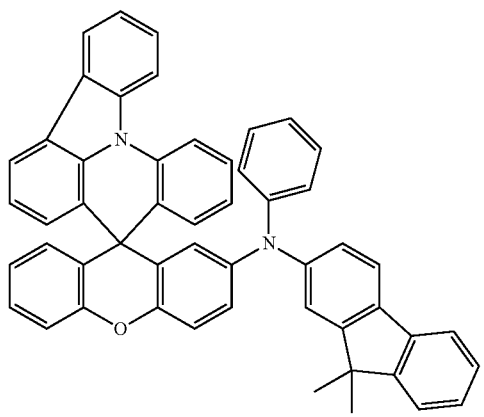
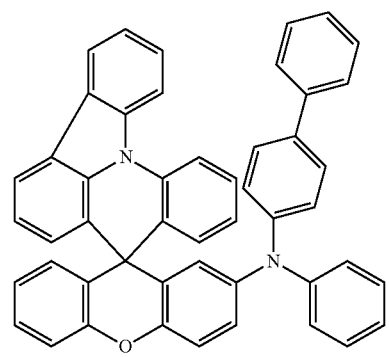
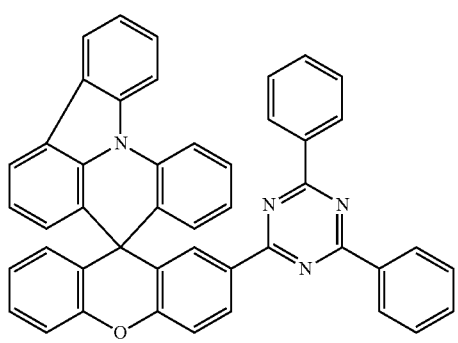
420
-continued
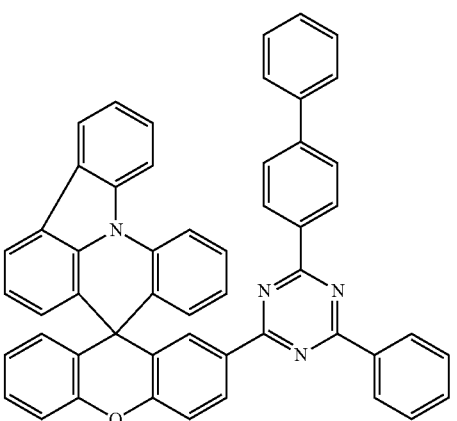
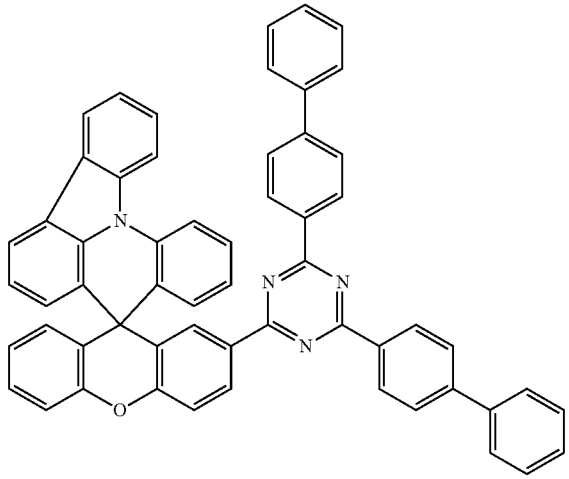
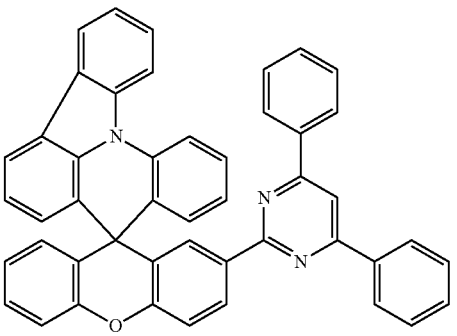
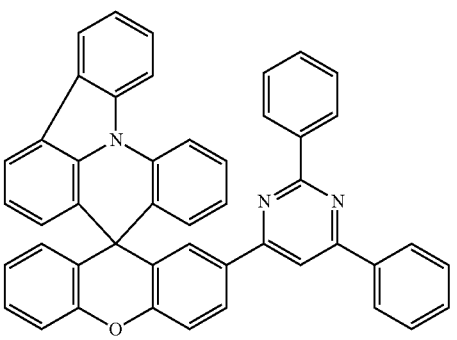

421
-continued
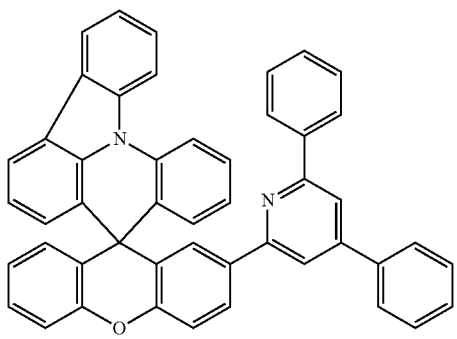
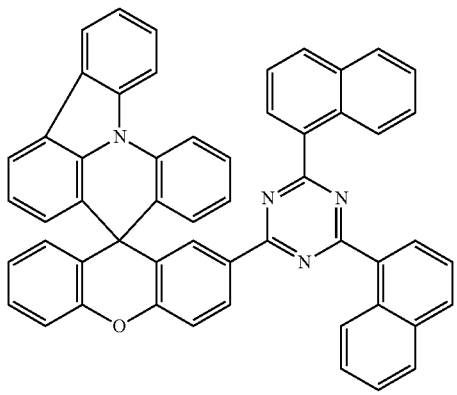
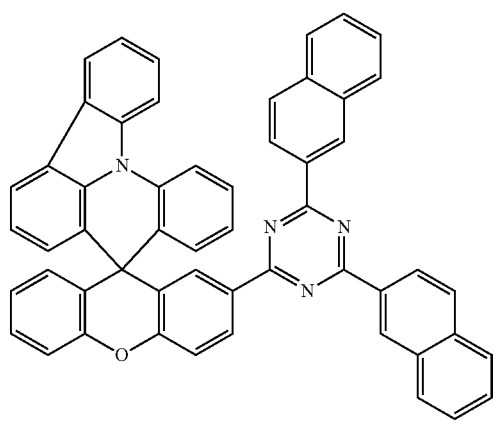
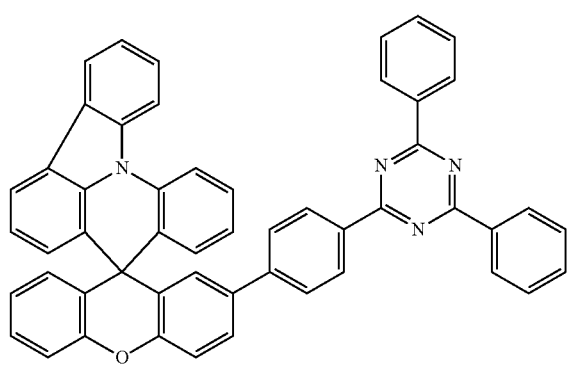
422
-continued
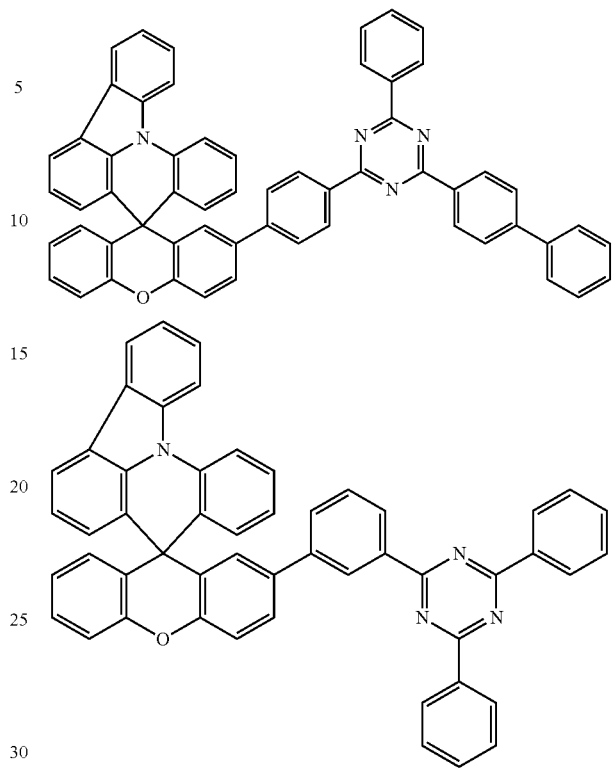
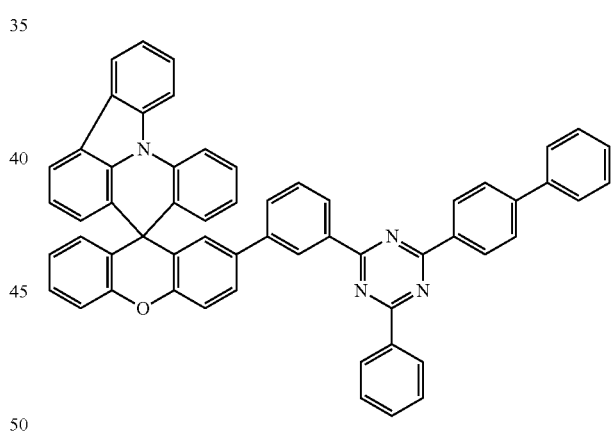
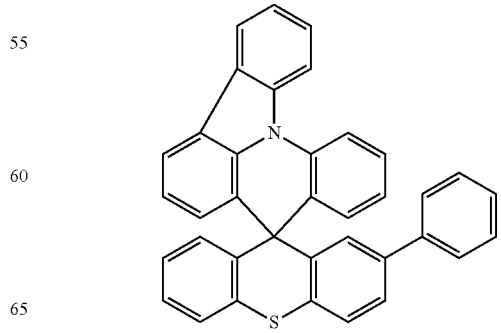

423
-continued
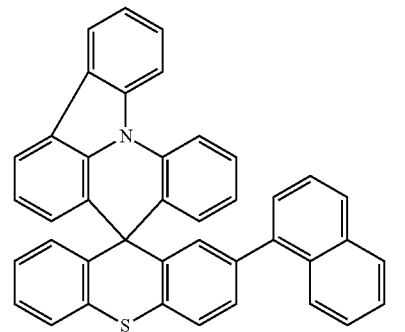
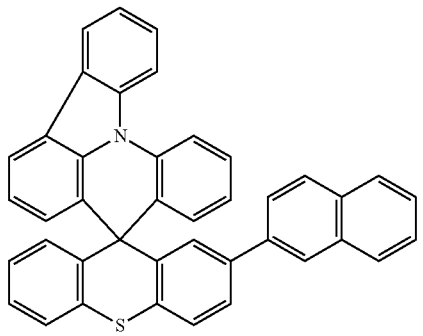
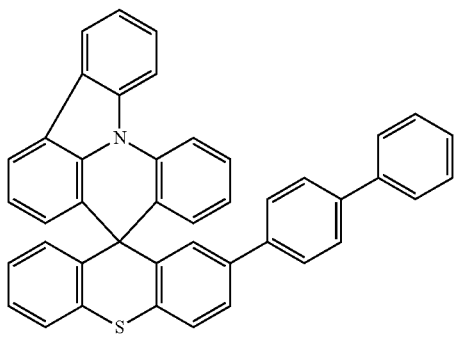
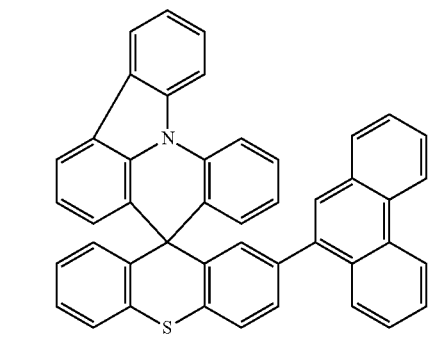
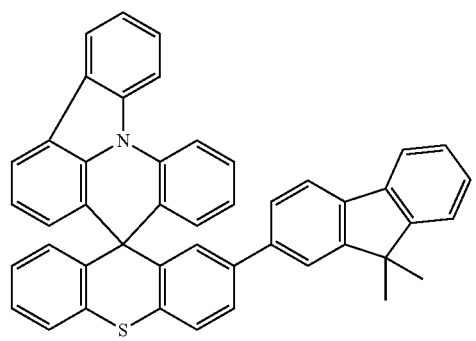
424
-continued
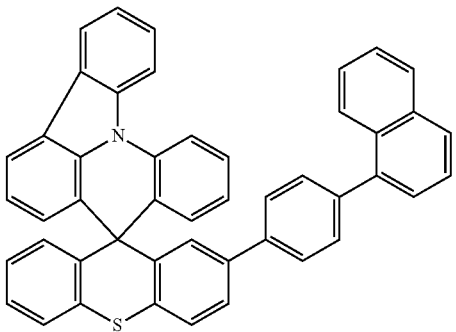
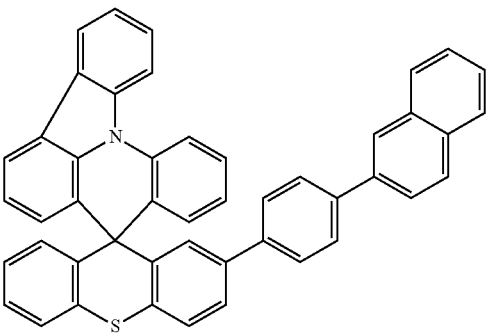
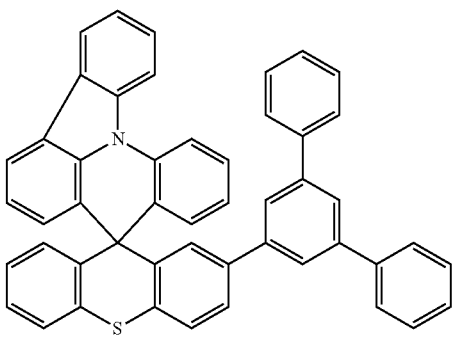
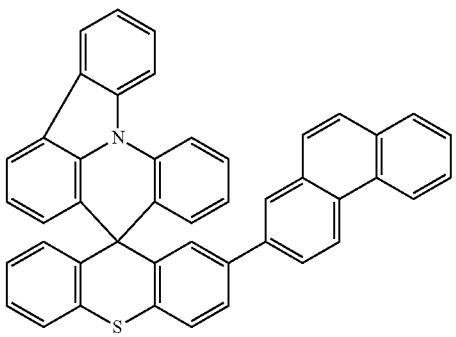
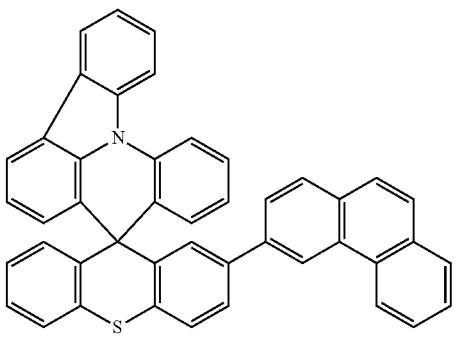

425
-continued
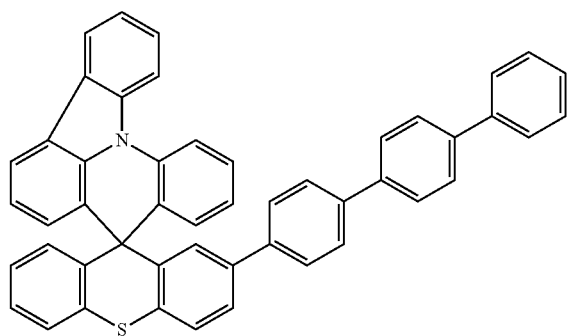
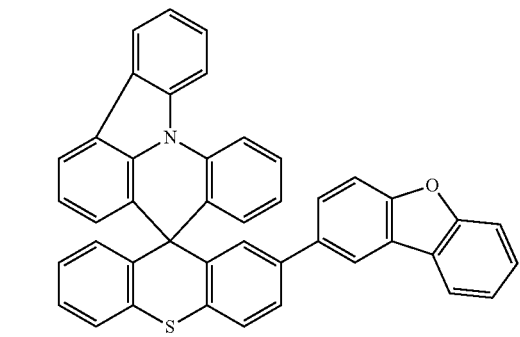
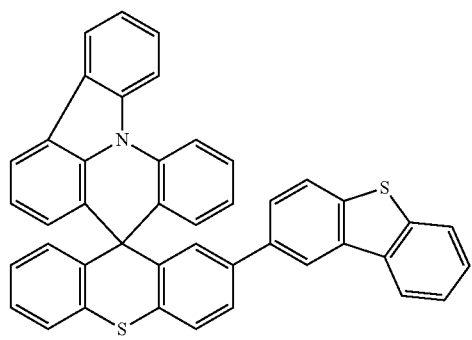
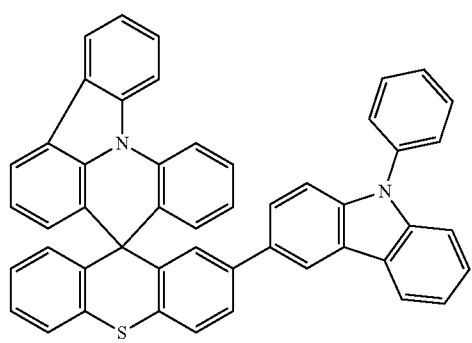
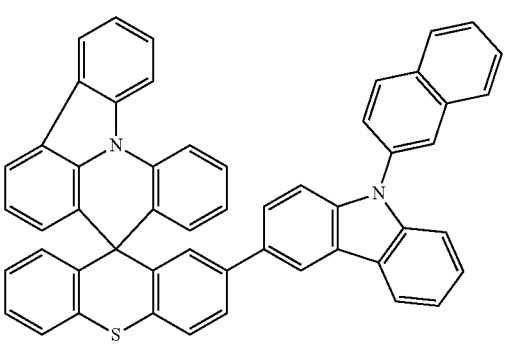
426
-continued
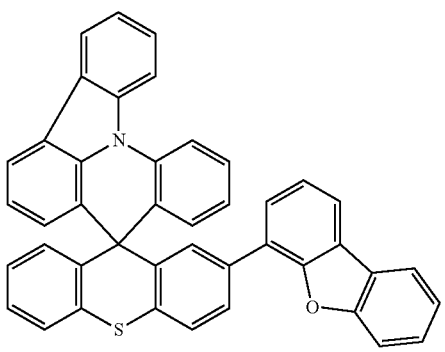
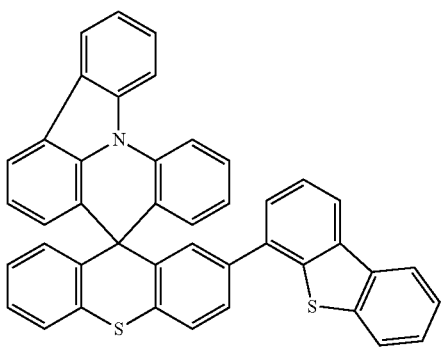
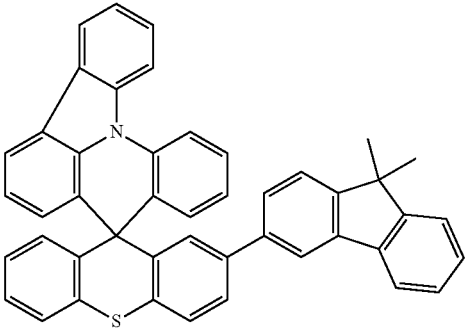
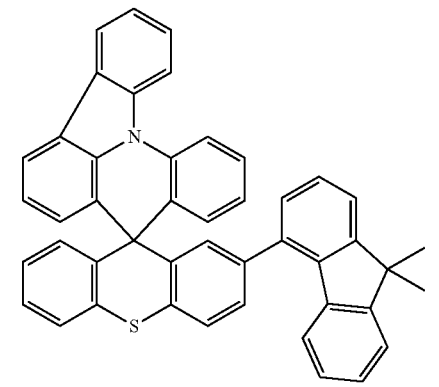

427
-continued
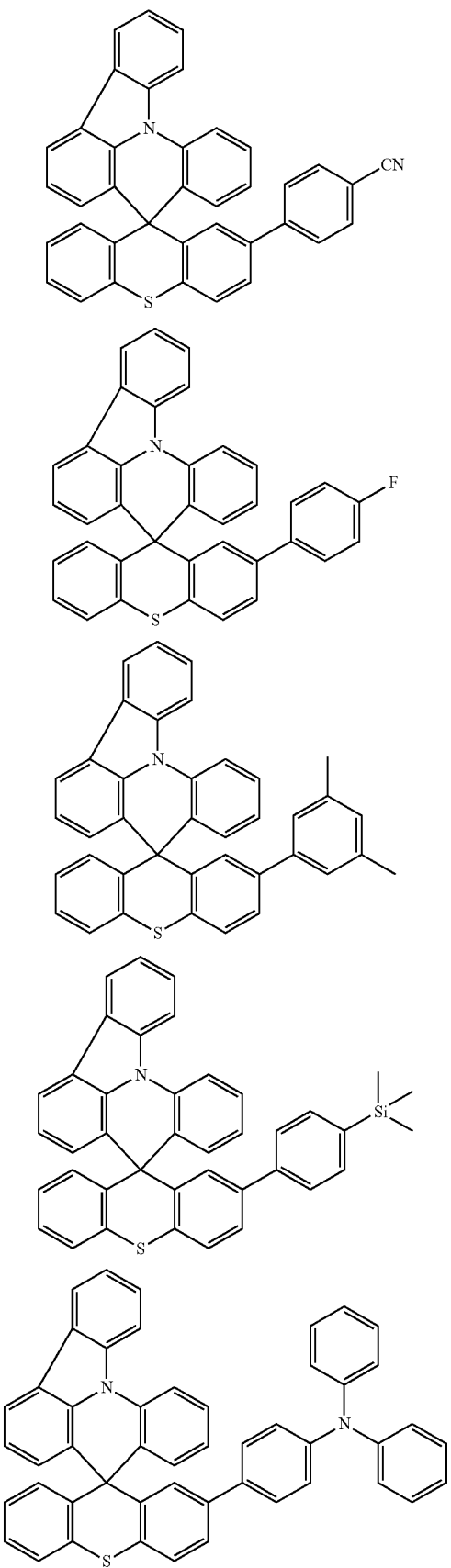
428
-continued
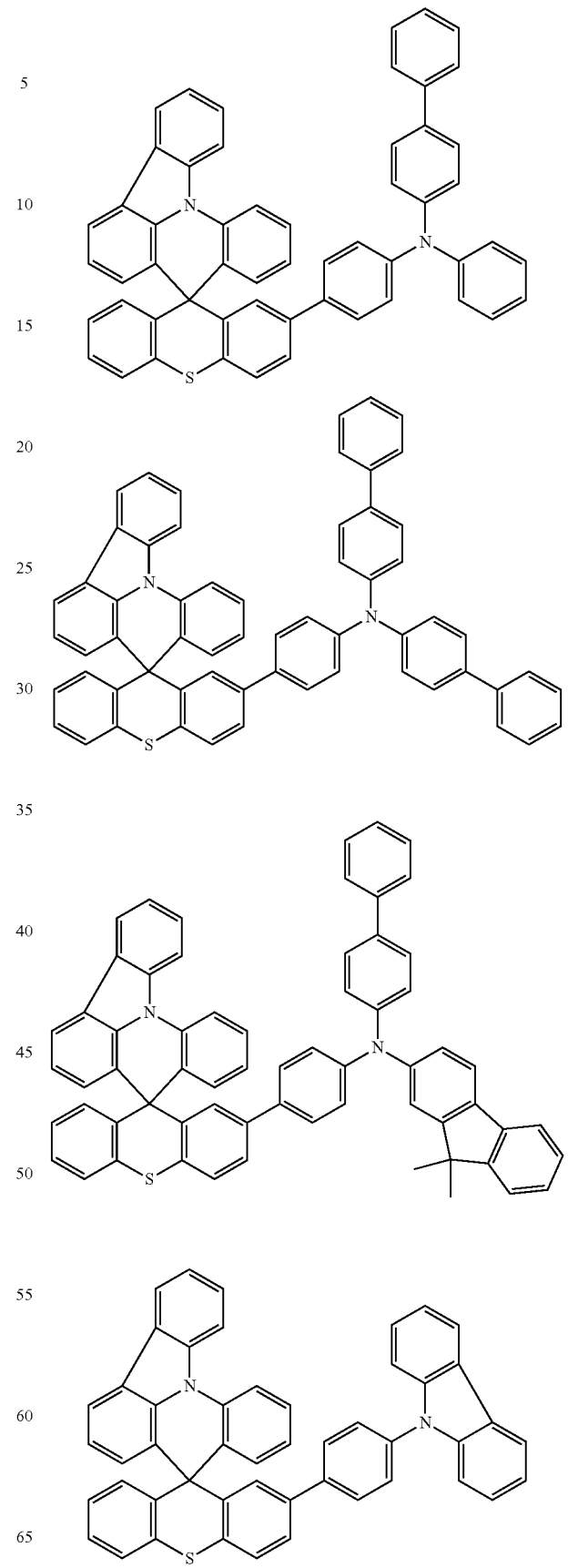

429
-continued
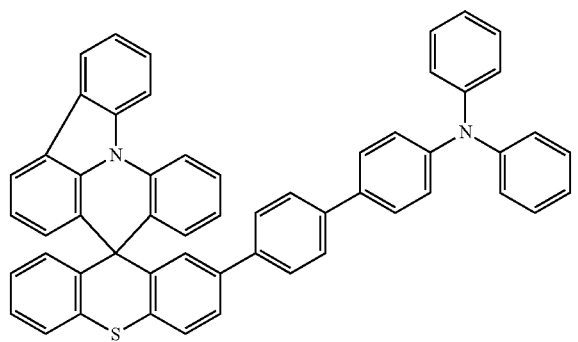
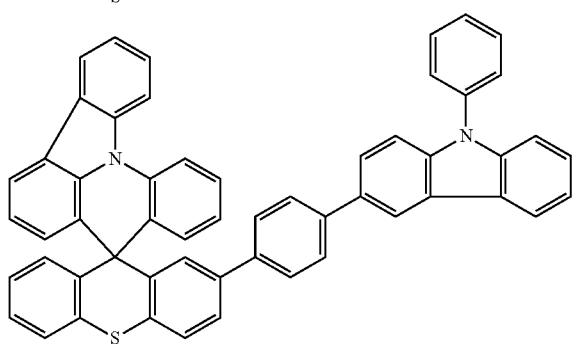
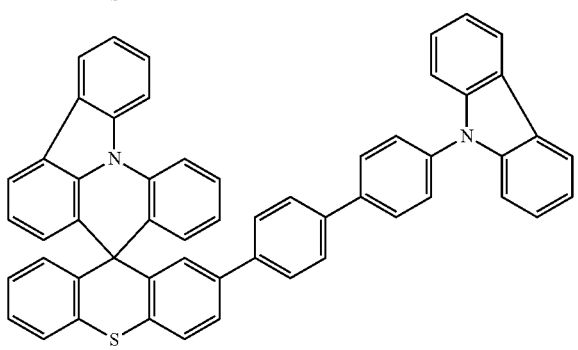
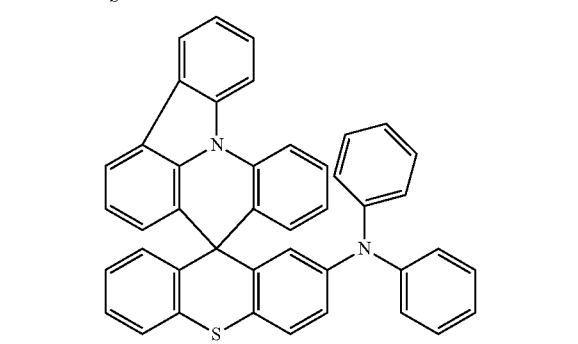
430
-continued
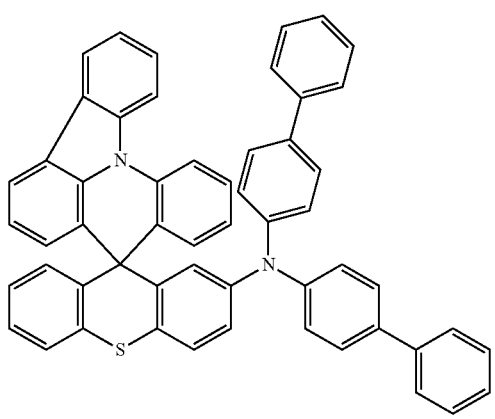
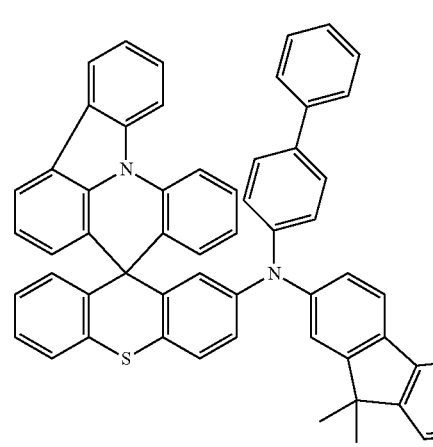
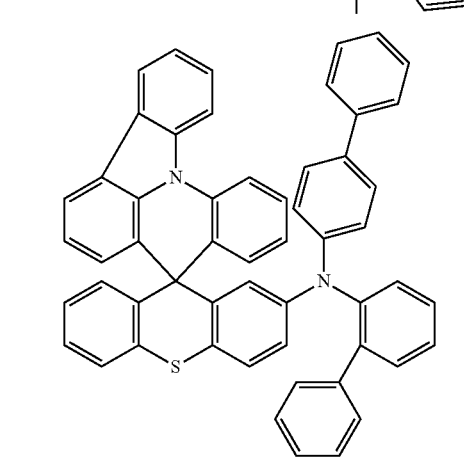
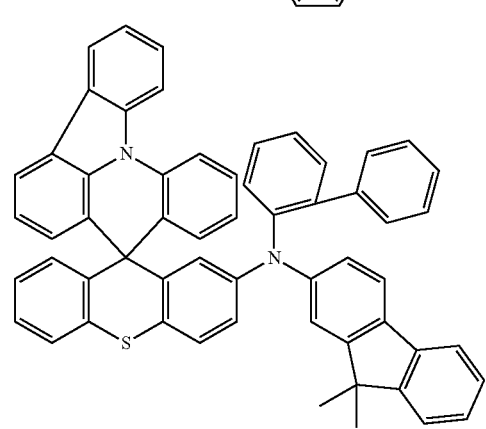

431
-continued
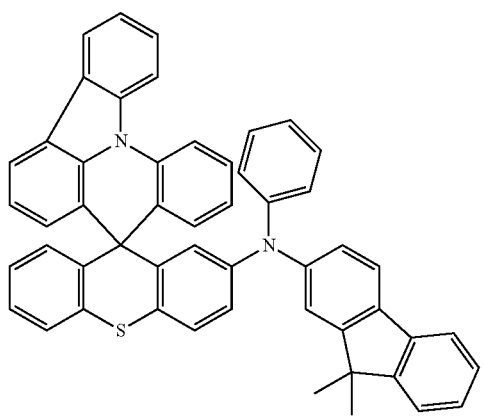
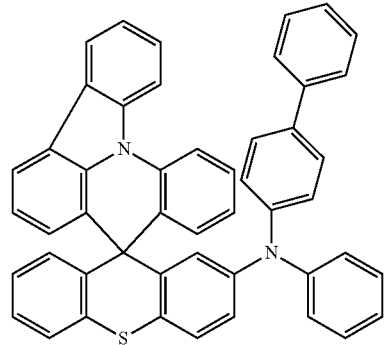
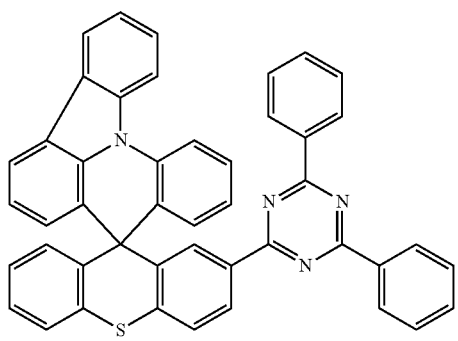
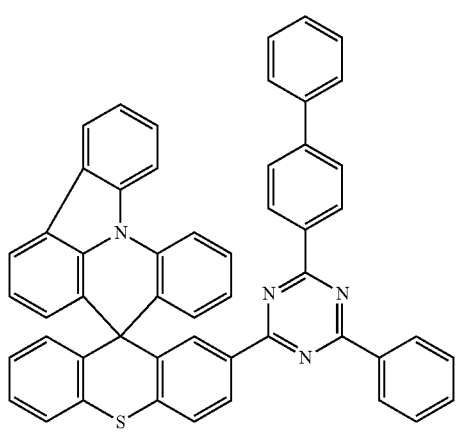
432
-continued
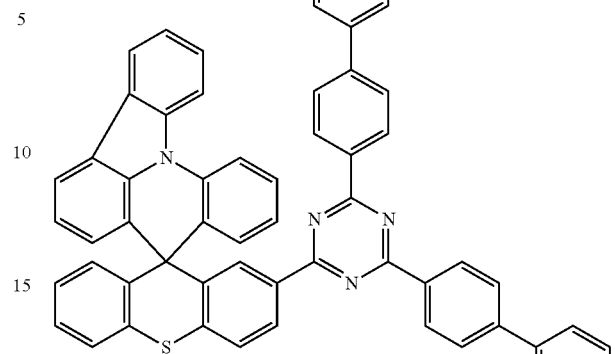
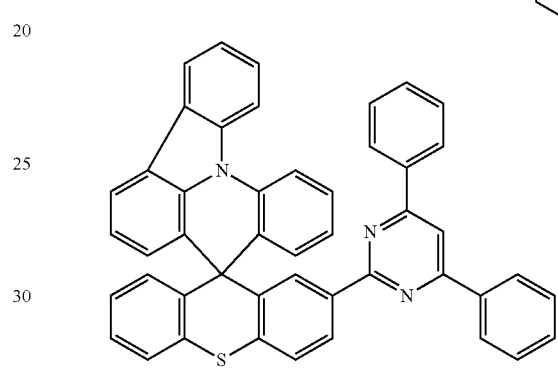
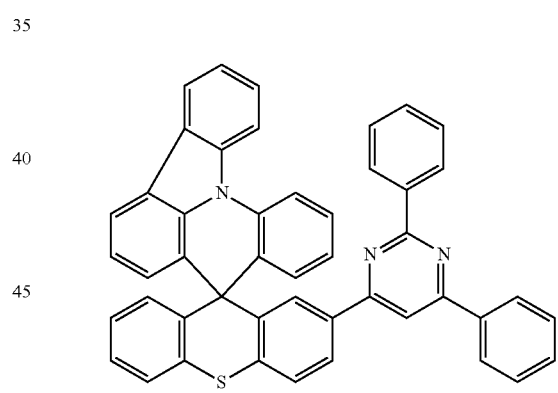
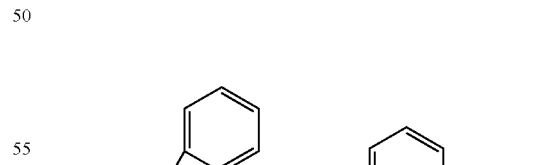
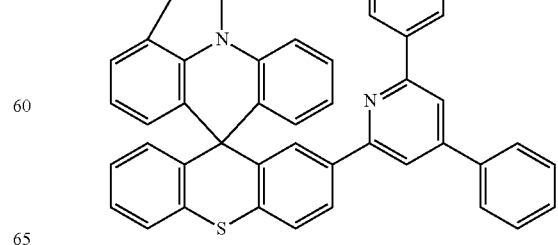

433
-continued
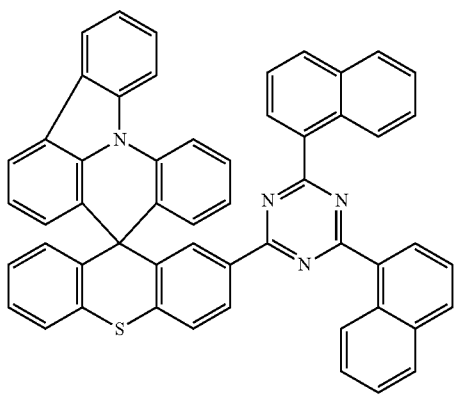
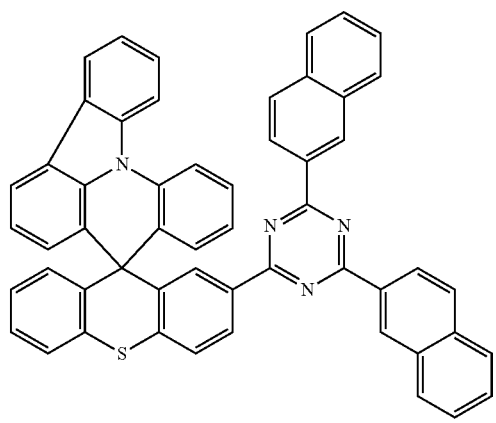
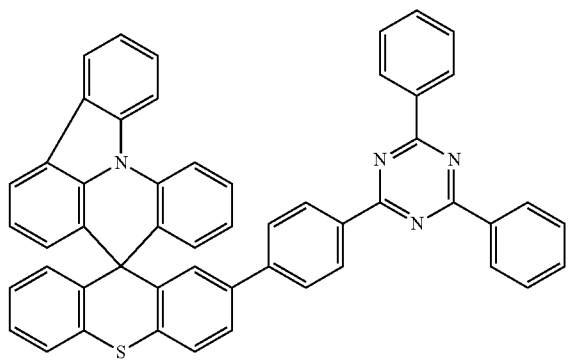
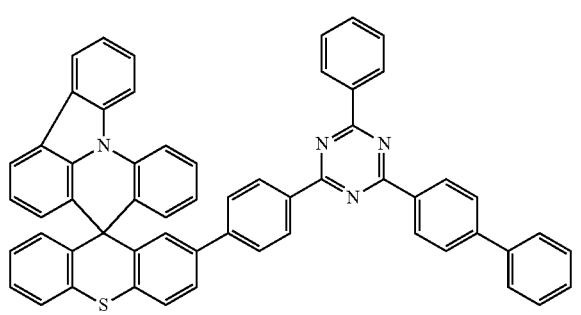
434
-continued
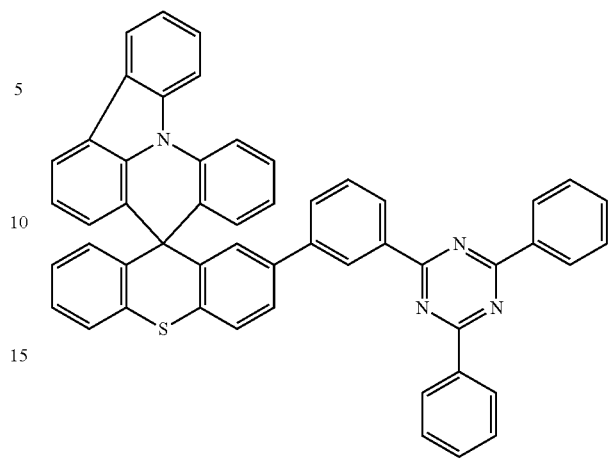
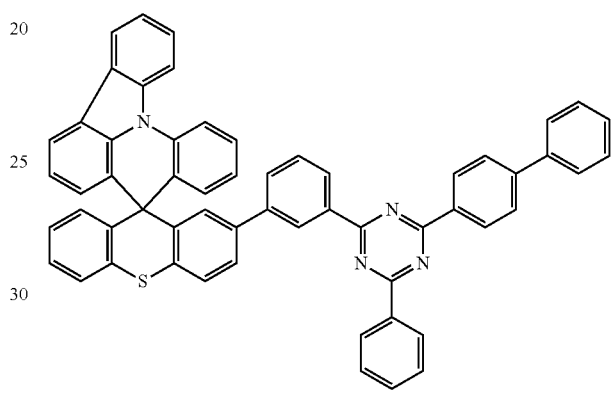
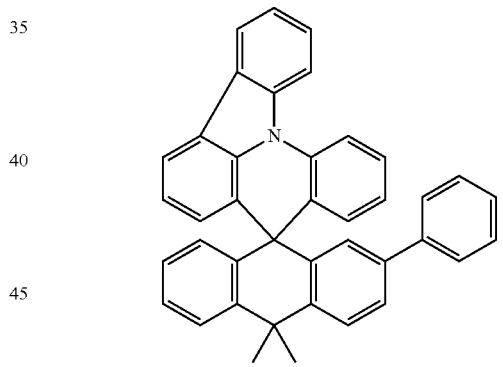
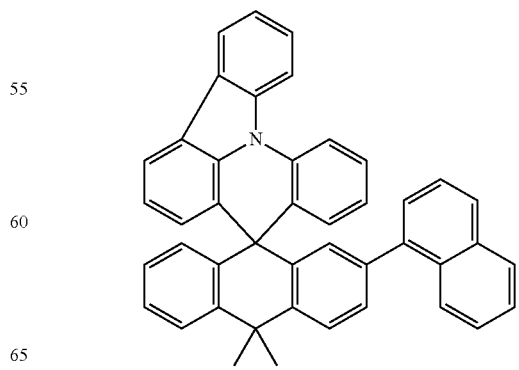

435
-continued
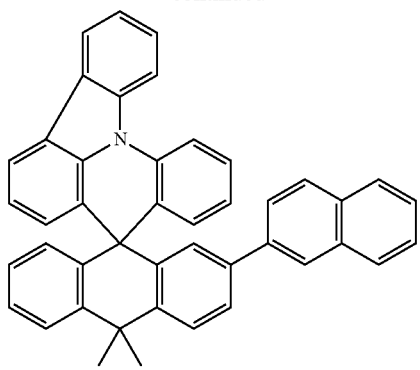
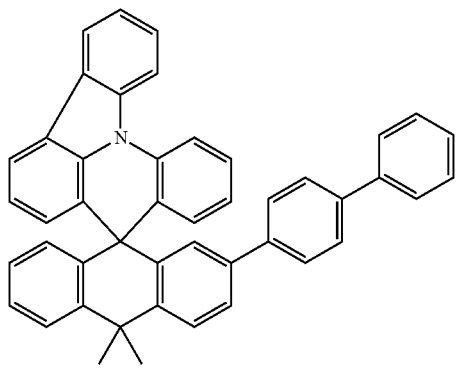
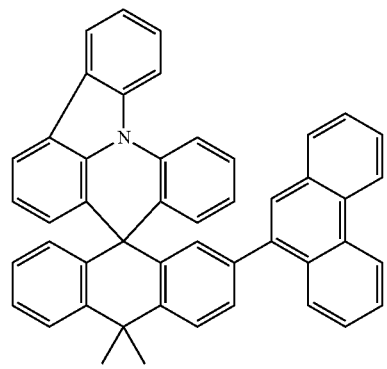
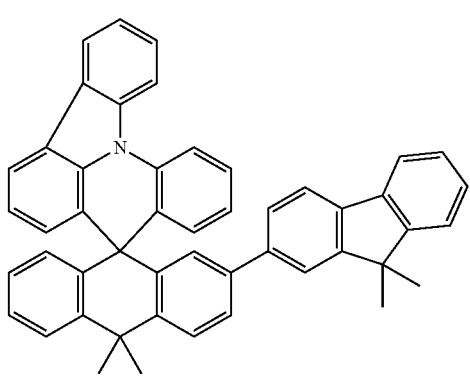
436
-continued
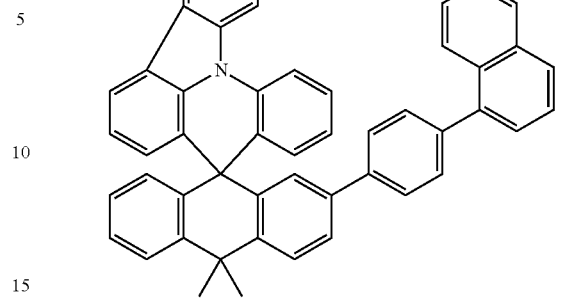
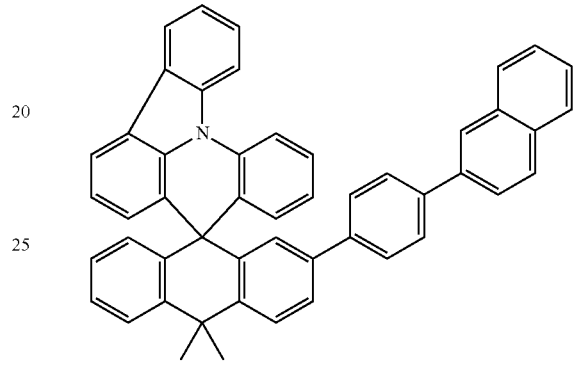
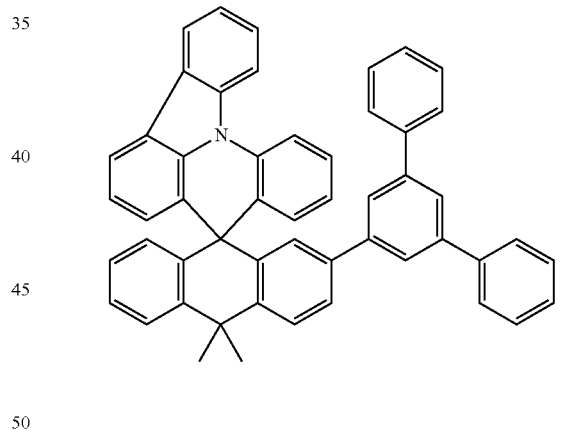
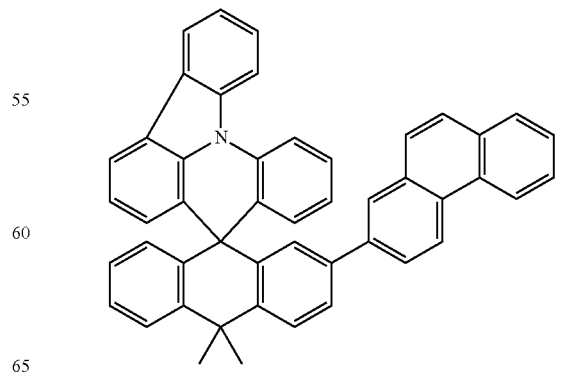

437
-continued
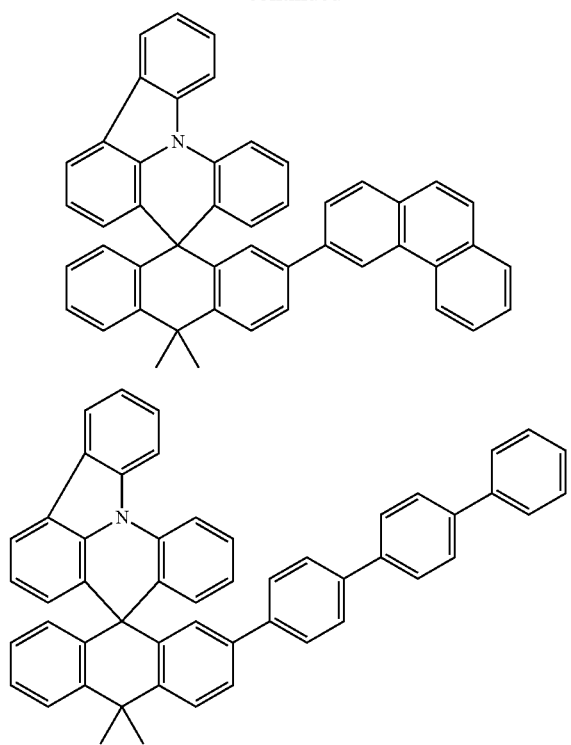
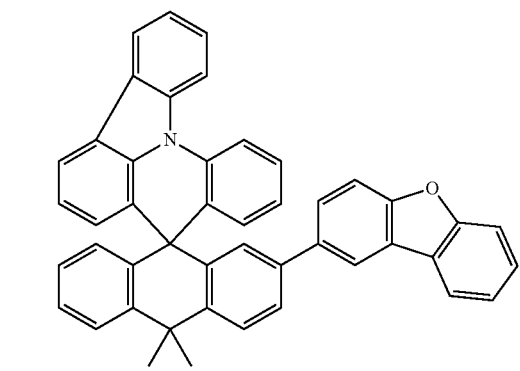
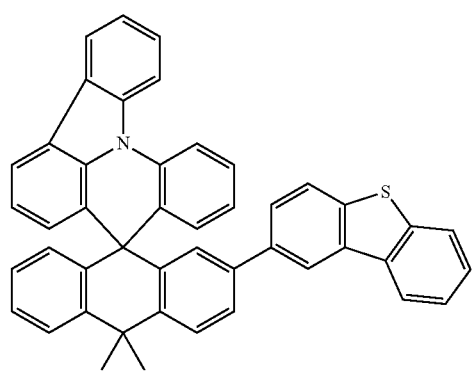
438
-continued
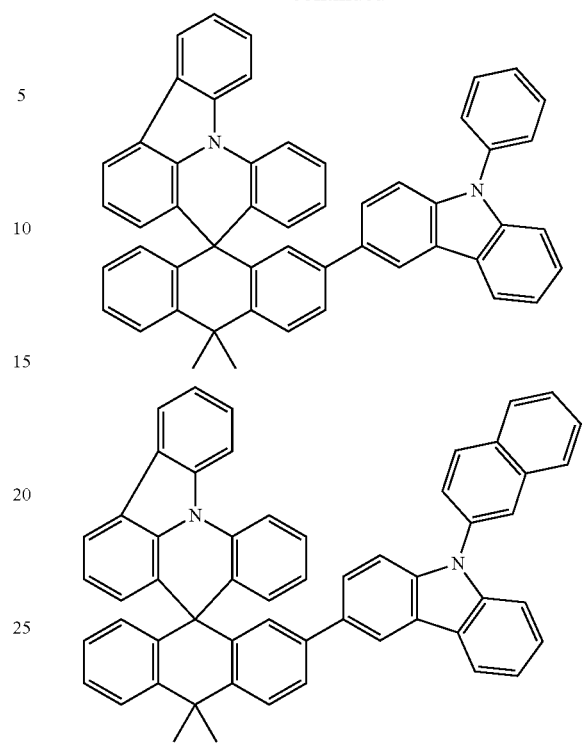
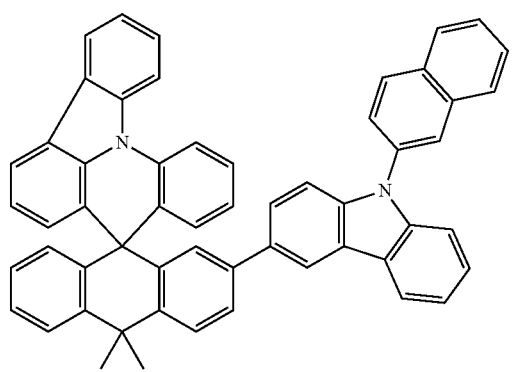
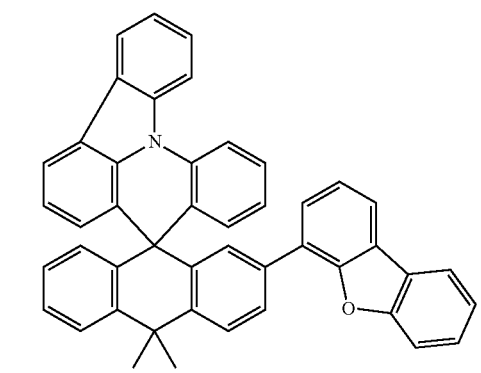
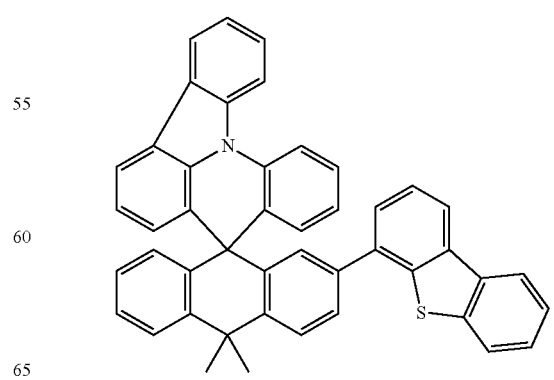

439
-continued
440
-continued
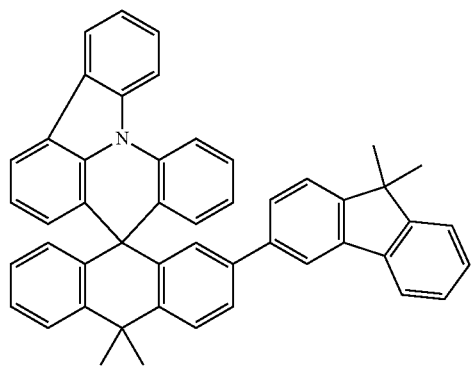
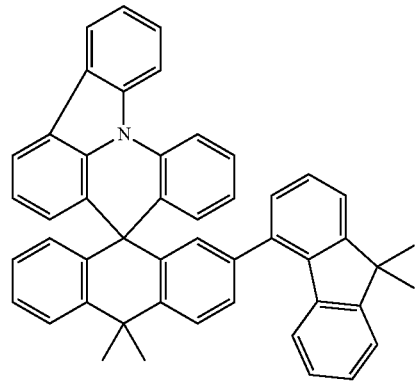
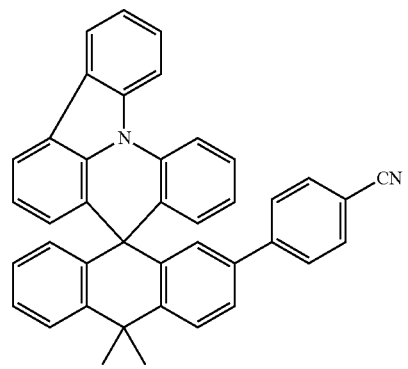
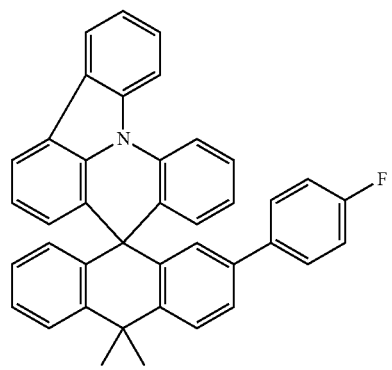
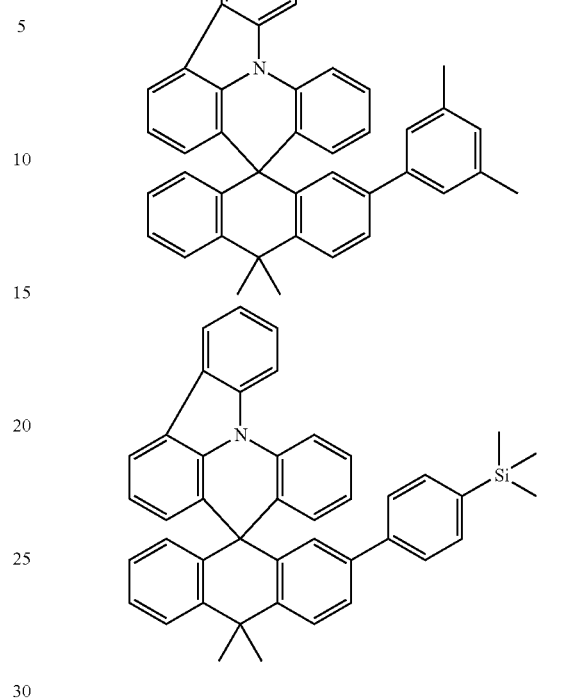
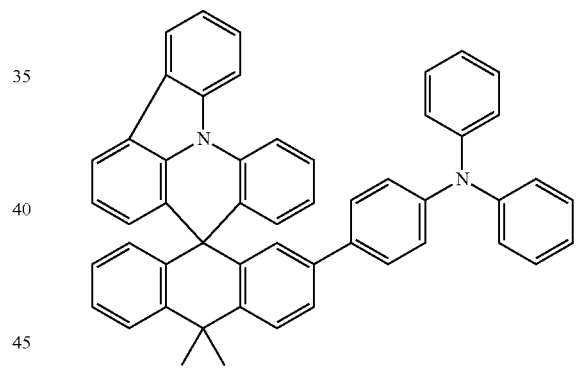
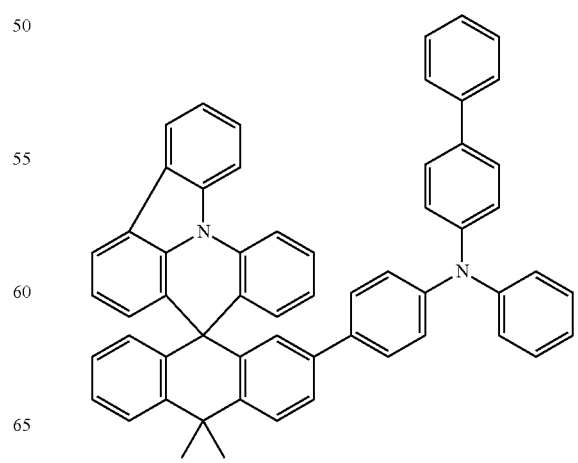

441
-continued
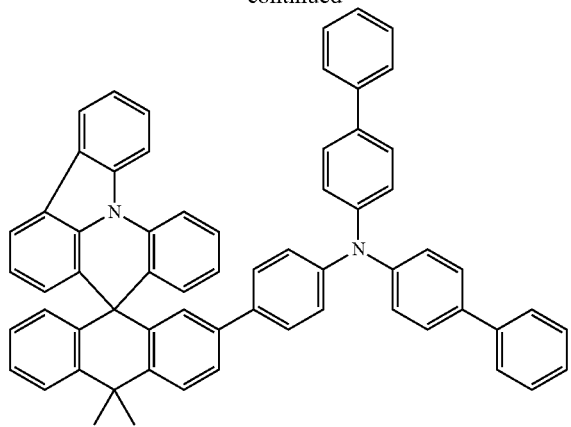
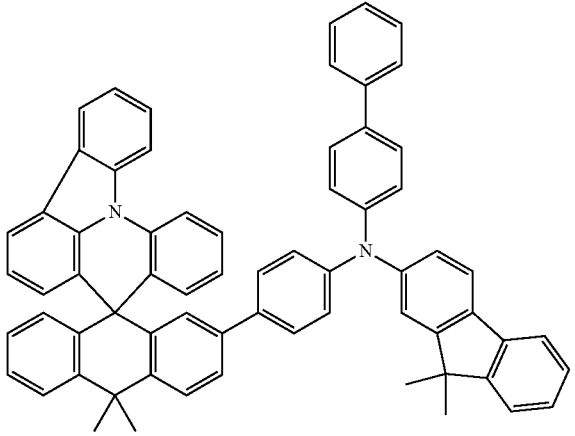
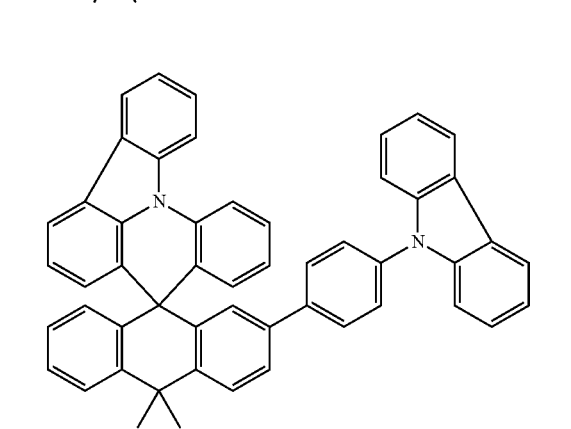
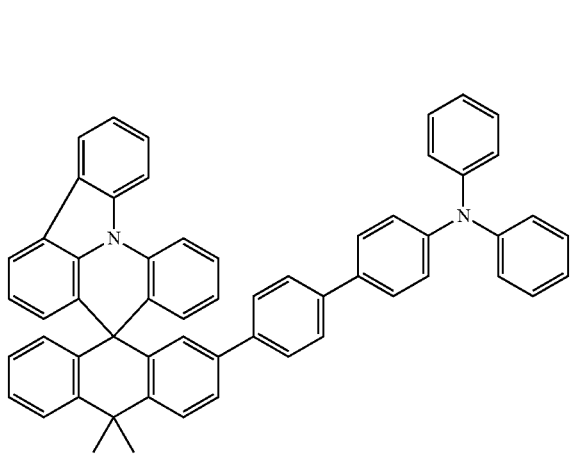
442
-continued
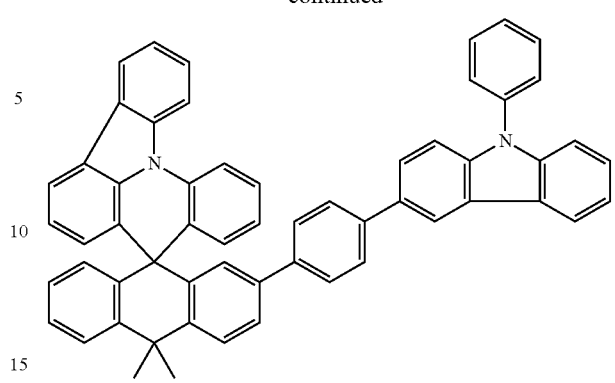
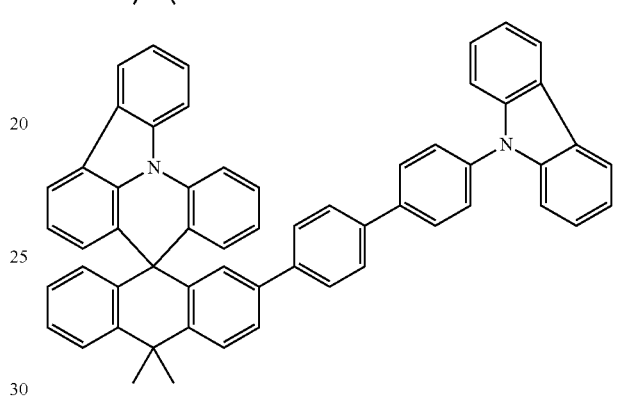
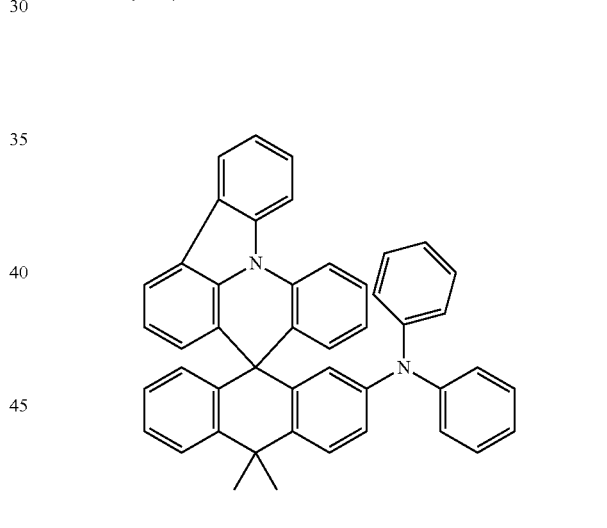
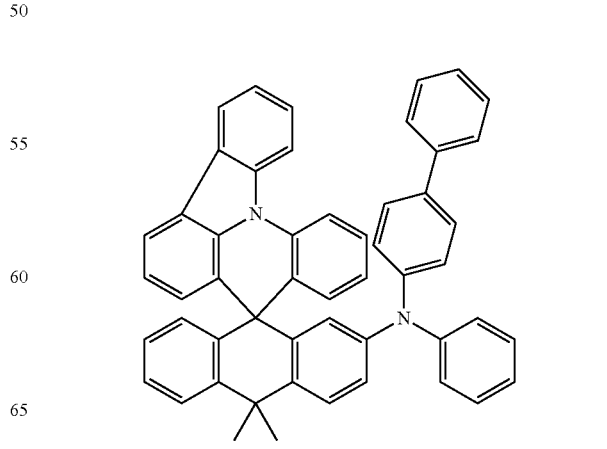

443
-continued
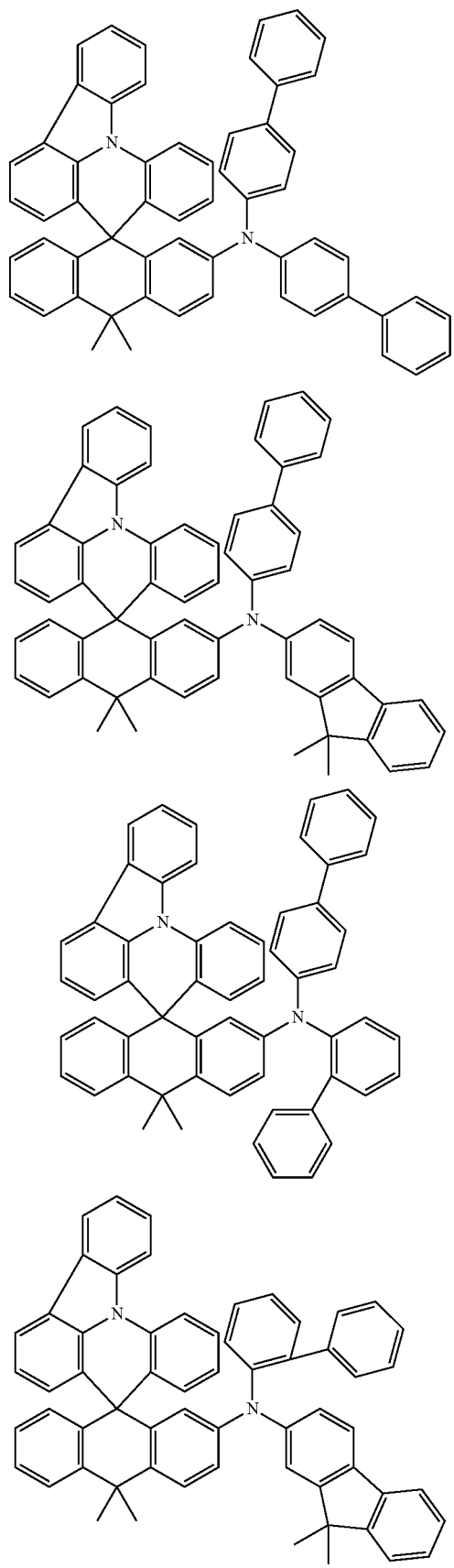
444
-continued
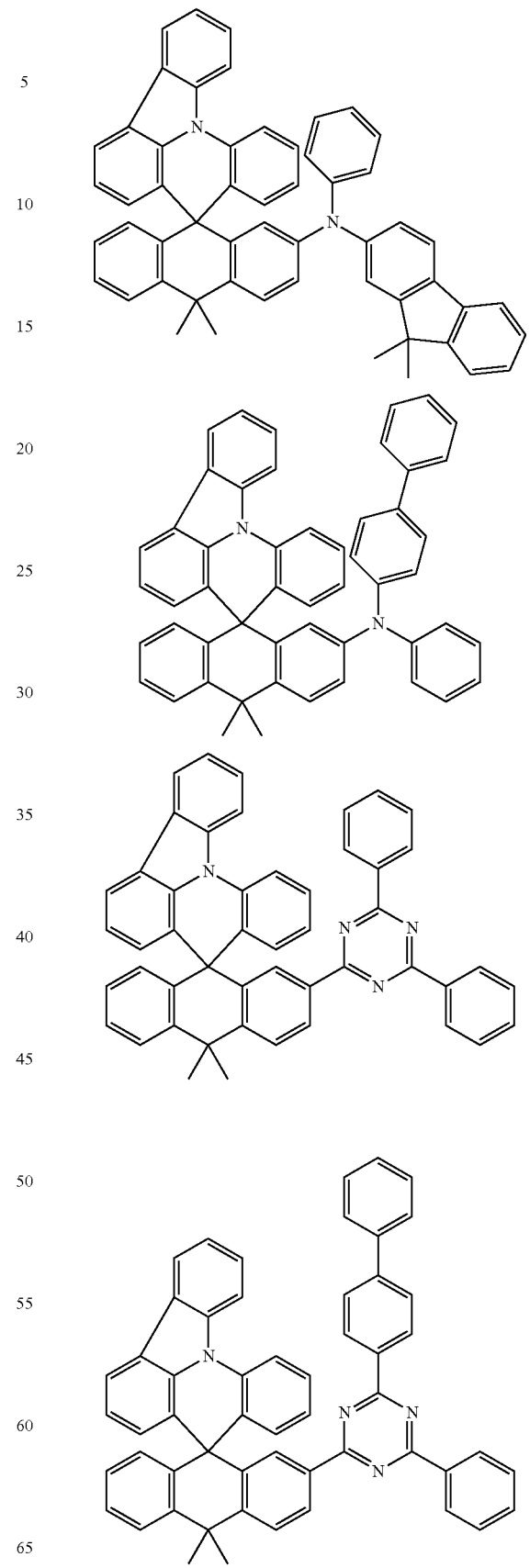

445
-continued
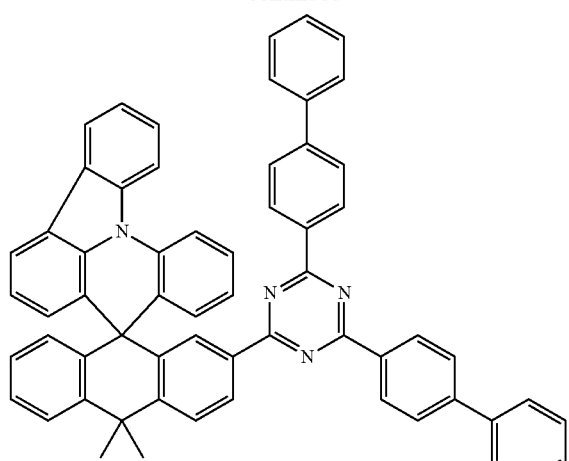
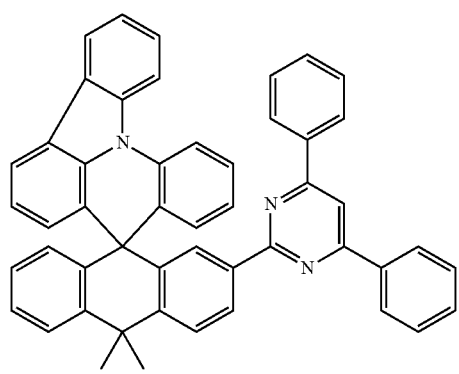
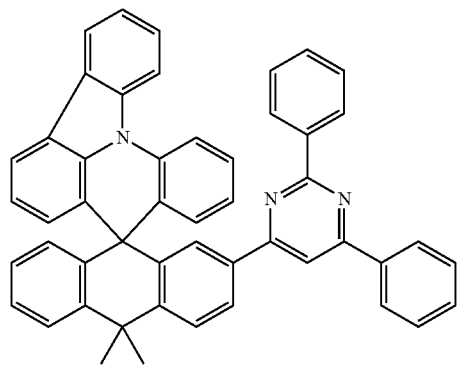
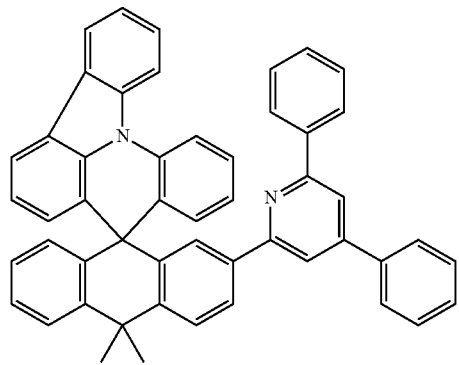
446
-continued
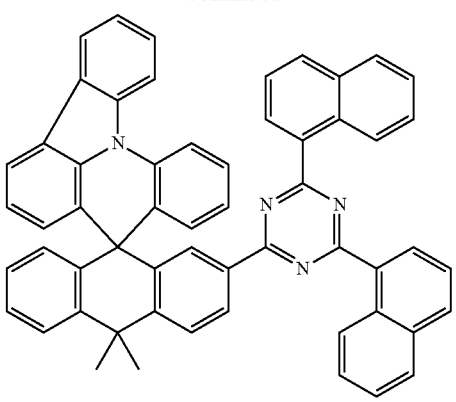
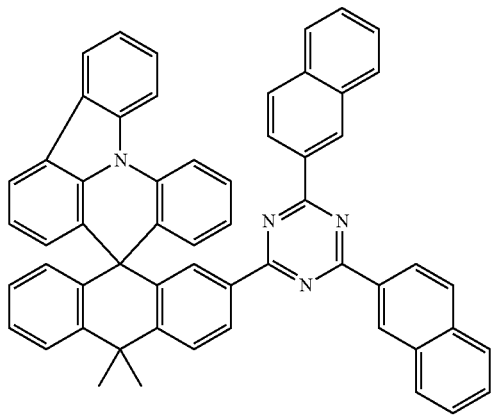
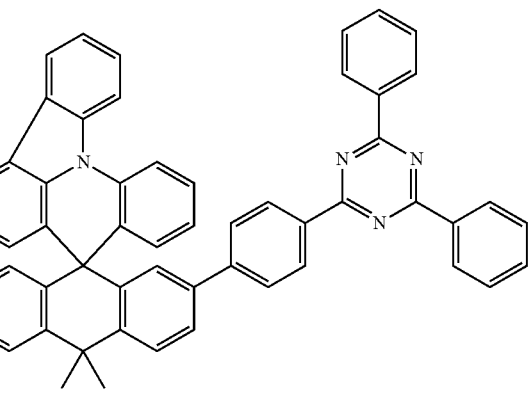
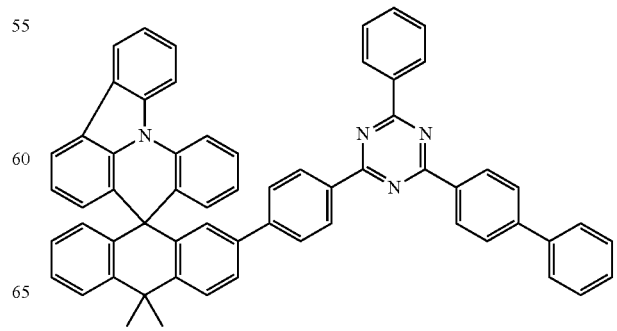

447
-continued
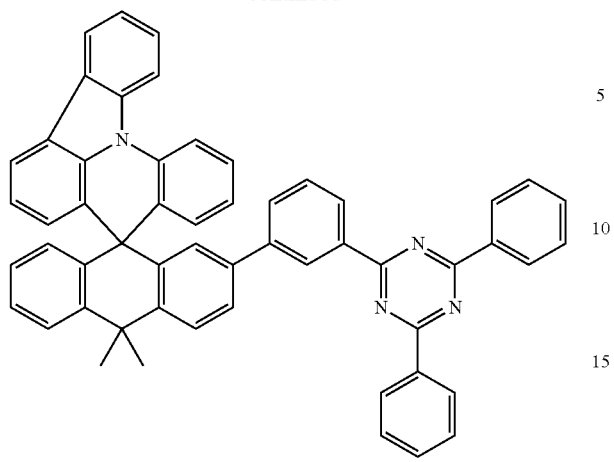
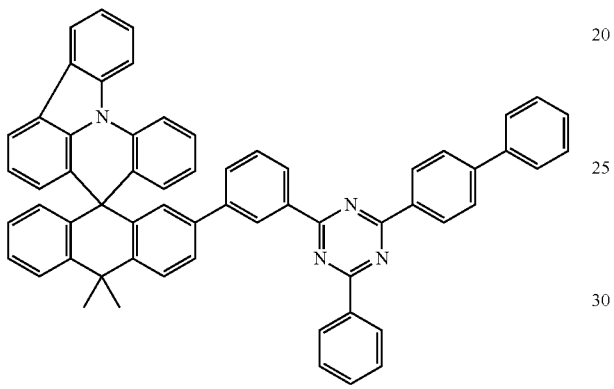
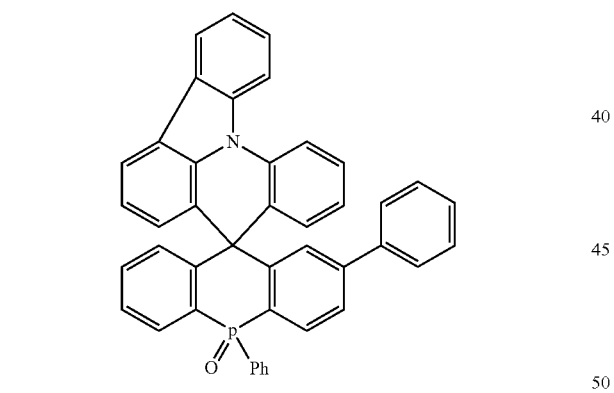
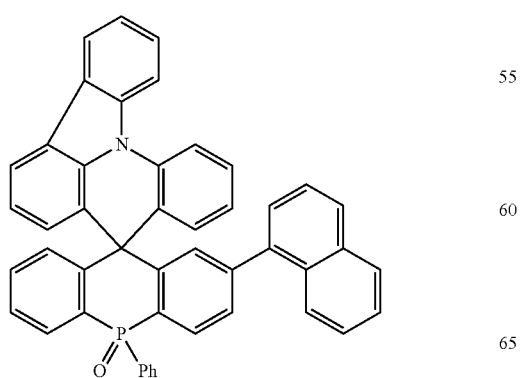
448
-continued
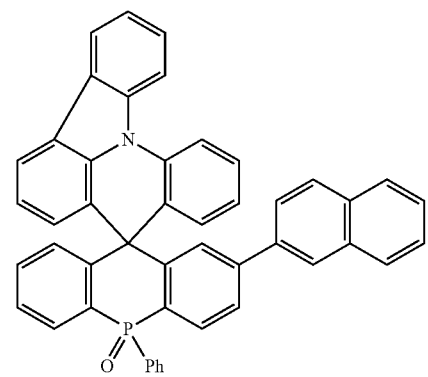
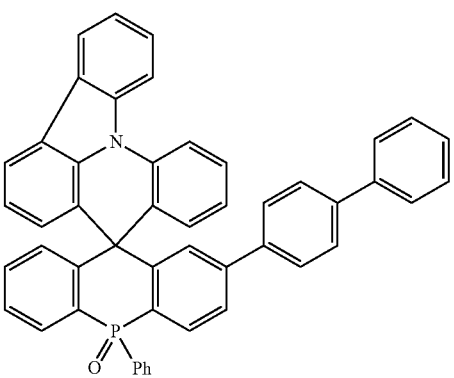
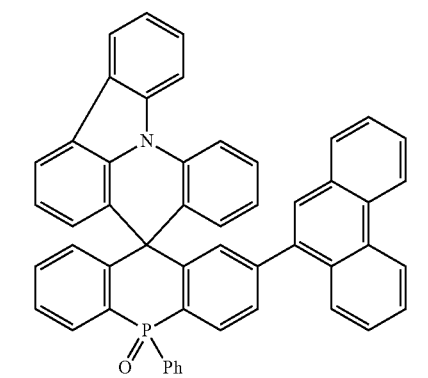
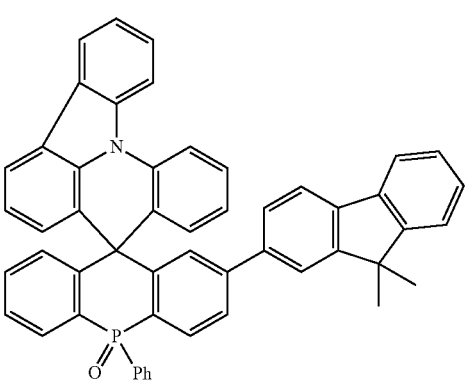

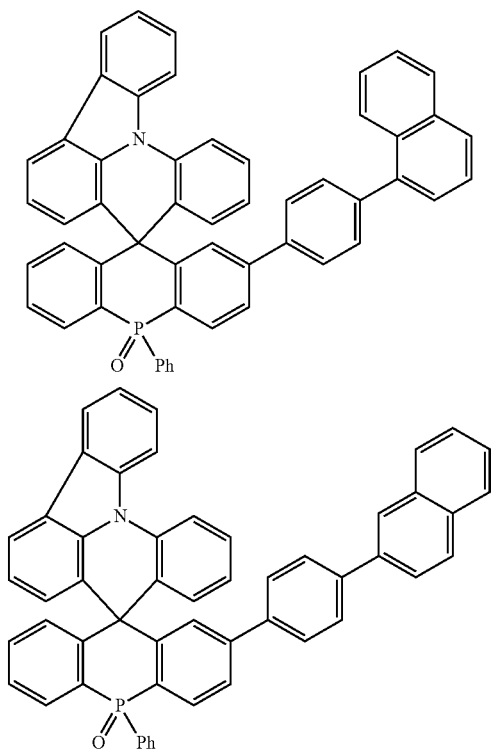
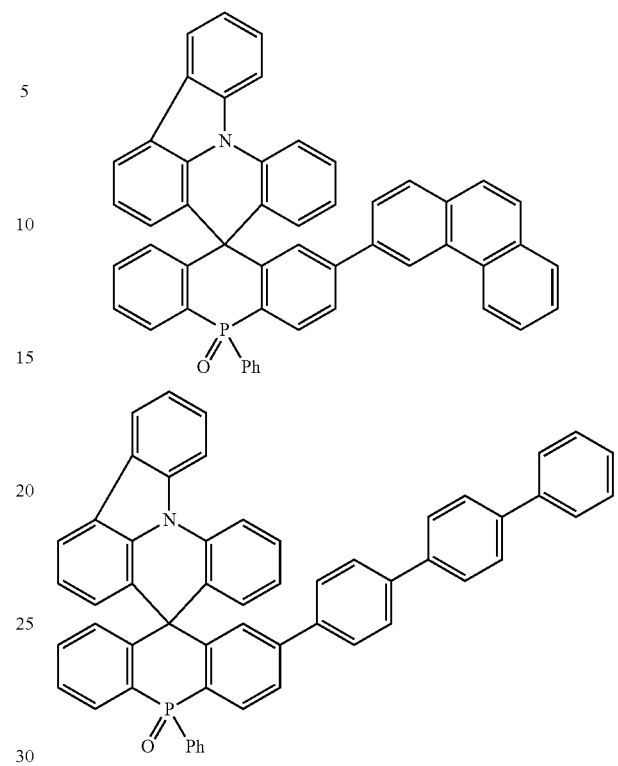
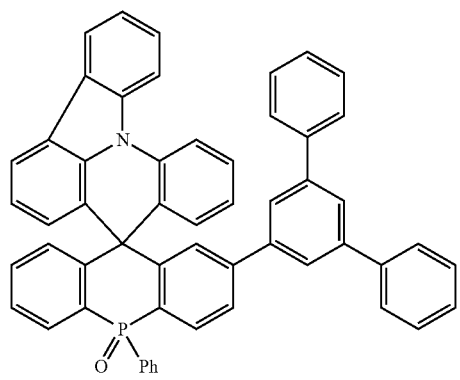
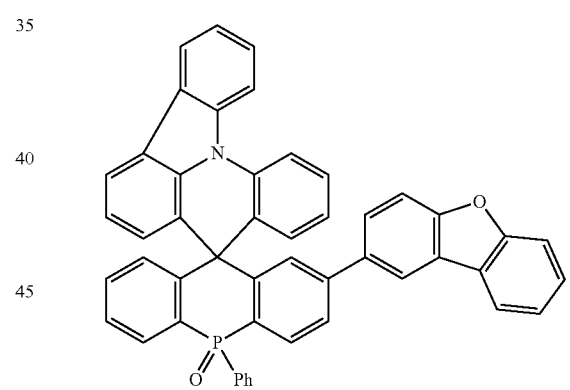
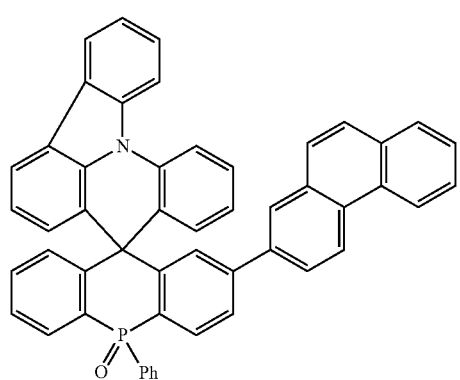
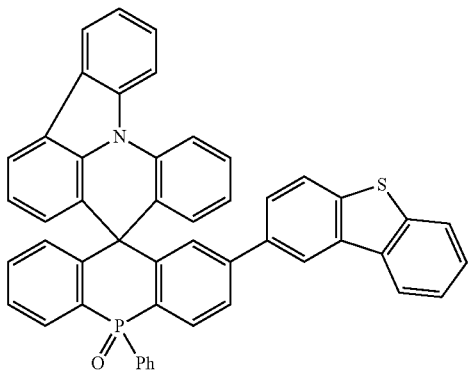

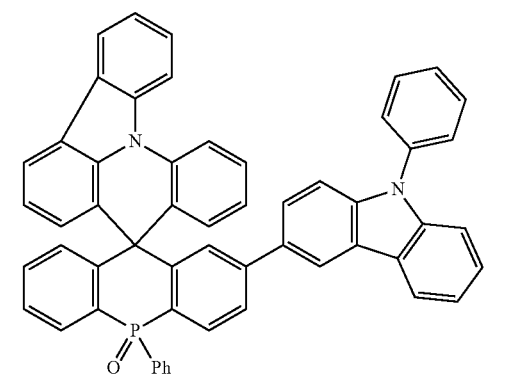
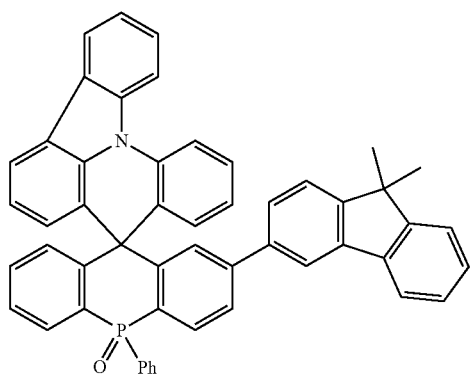
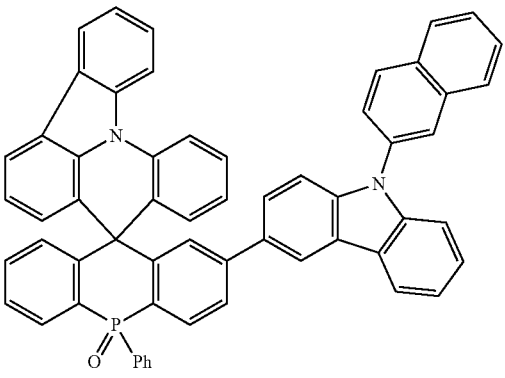
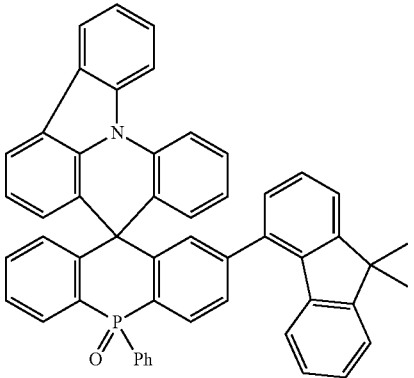
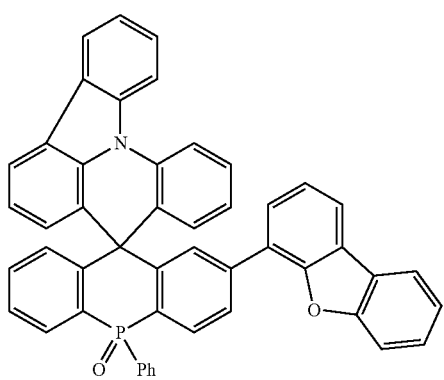
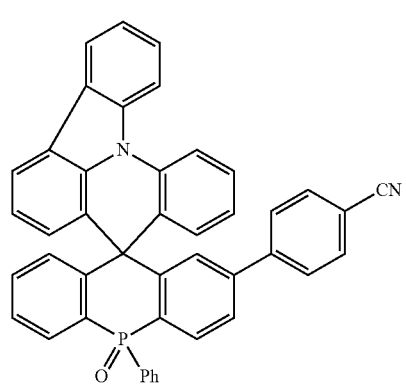
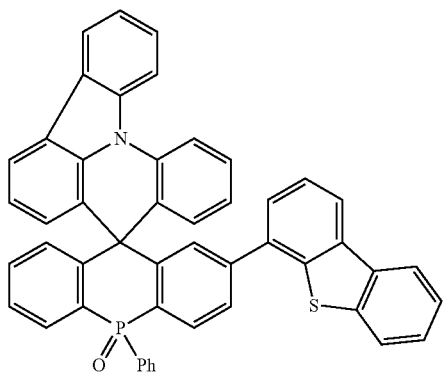
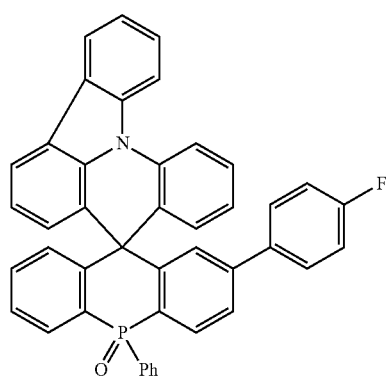

453
-continued
454
-continued
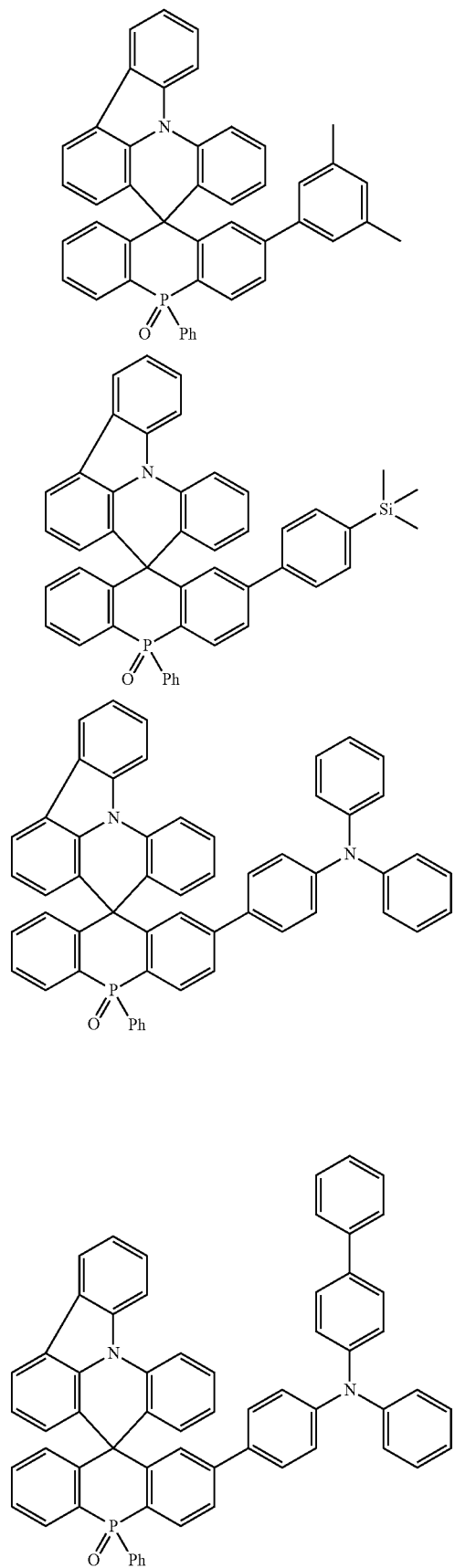
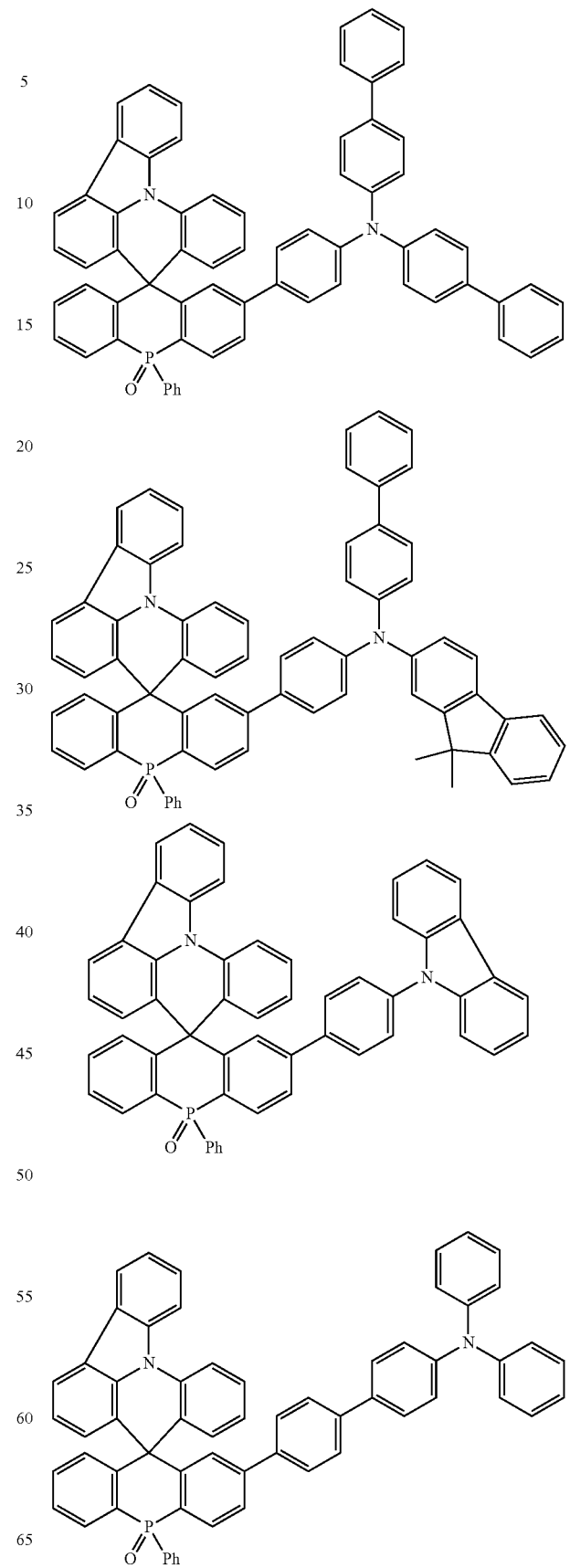

455
-continued
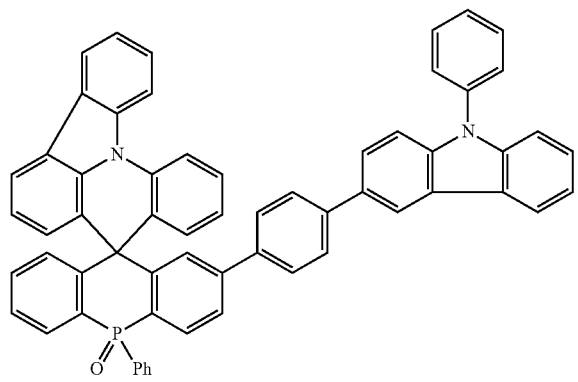
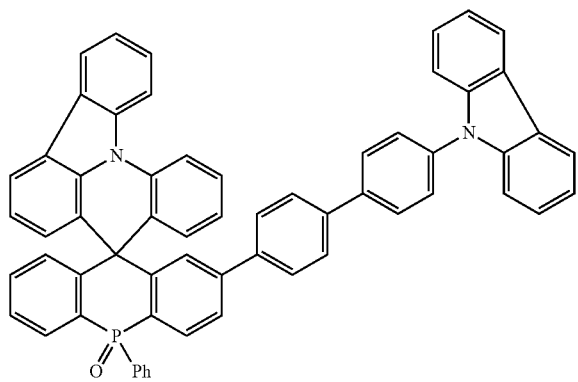
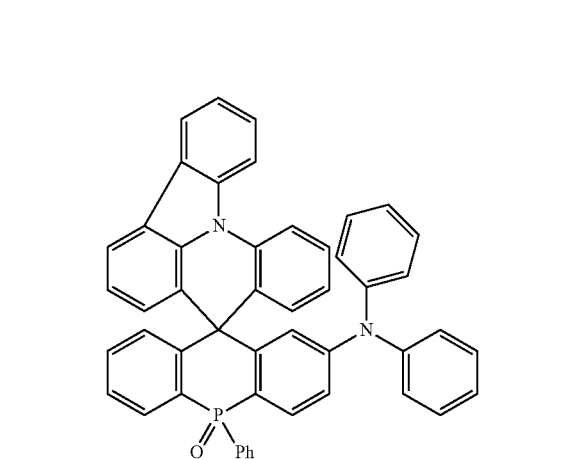
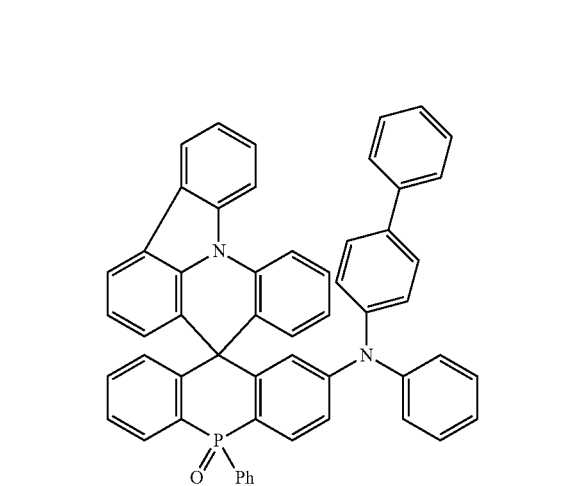
456
-continued
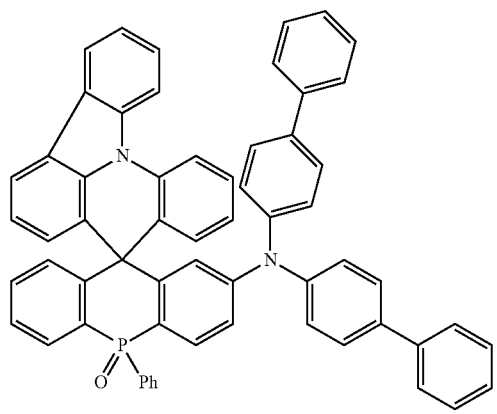
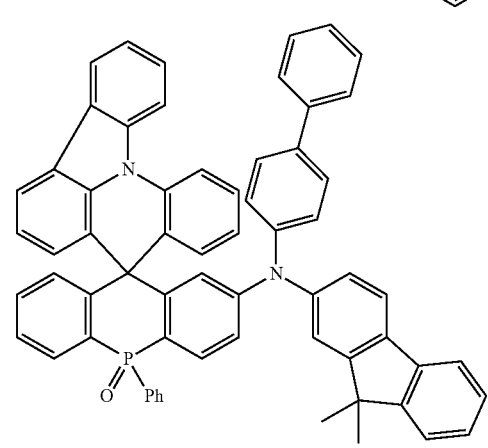
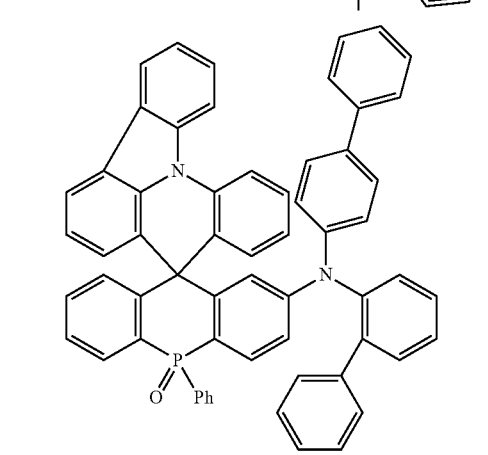
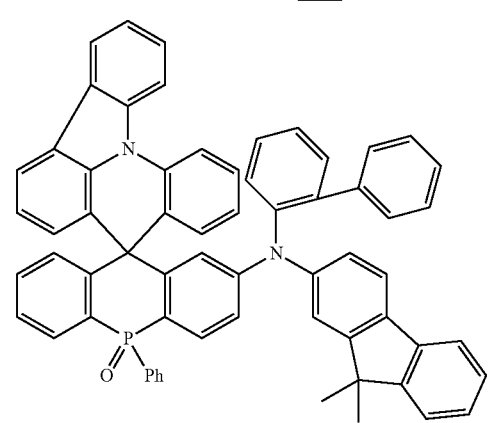

457
-continued
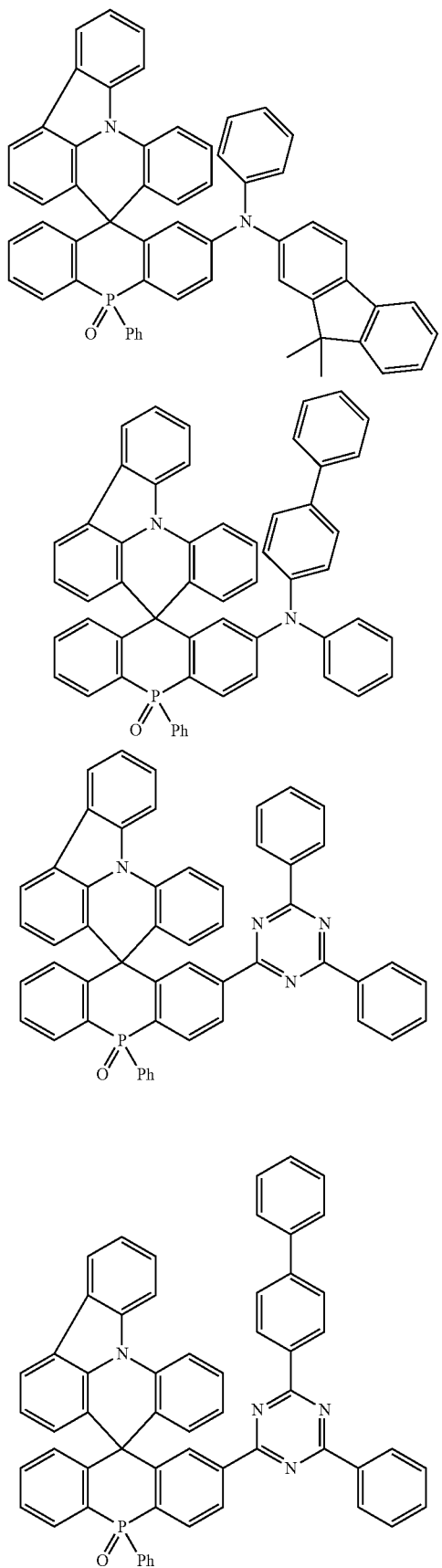
458
-continued
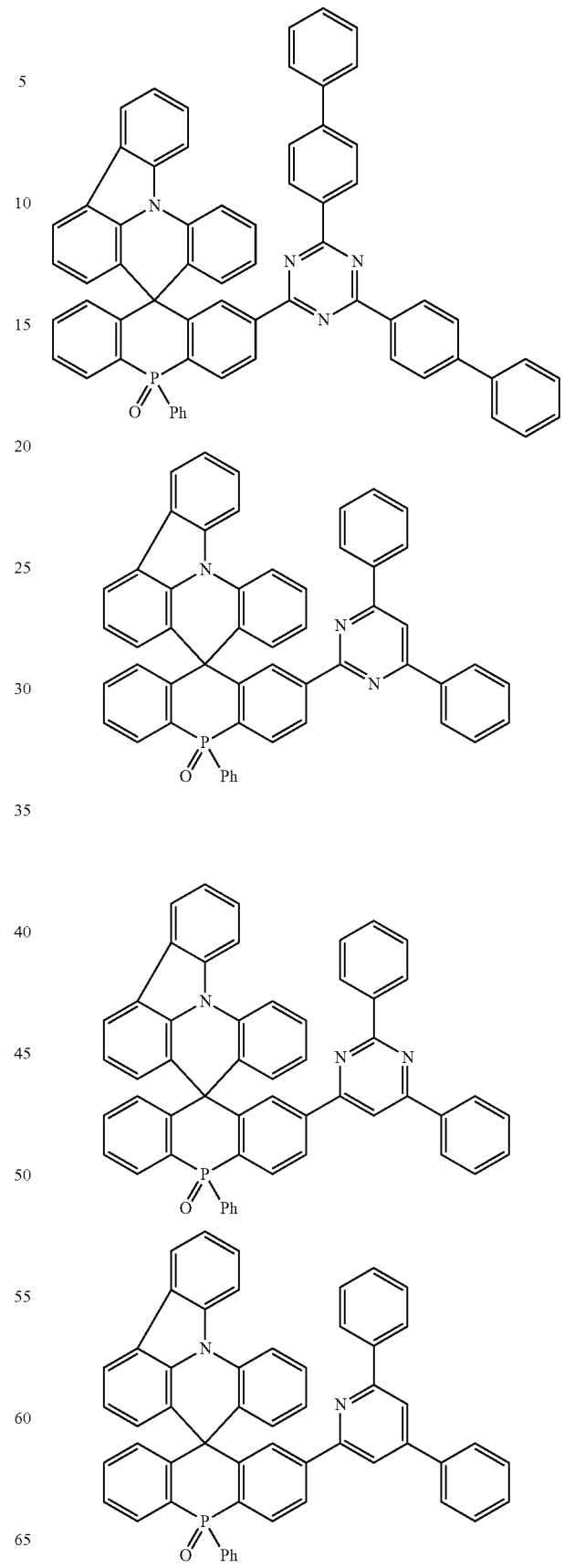

459
-continued
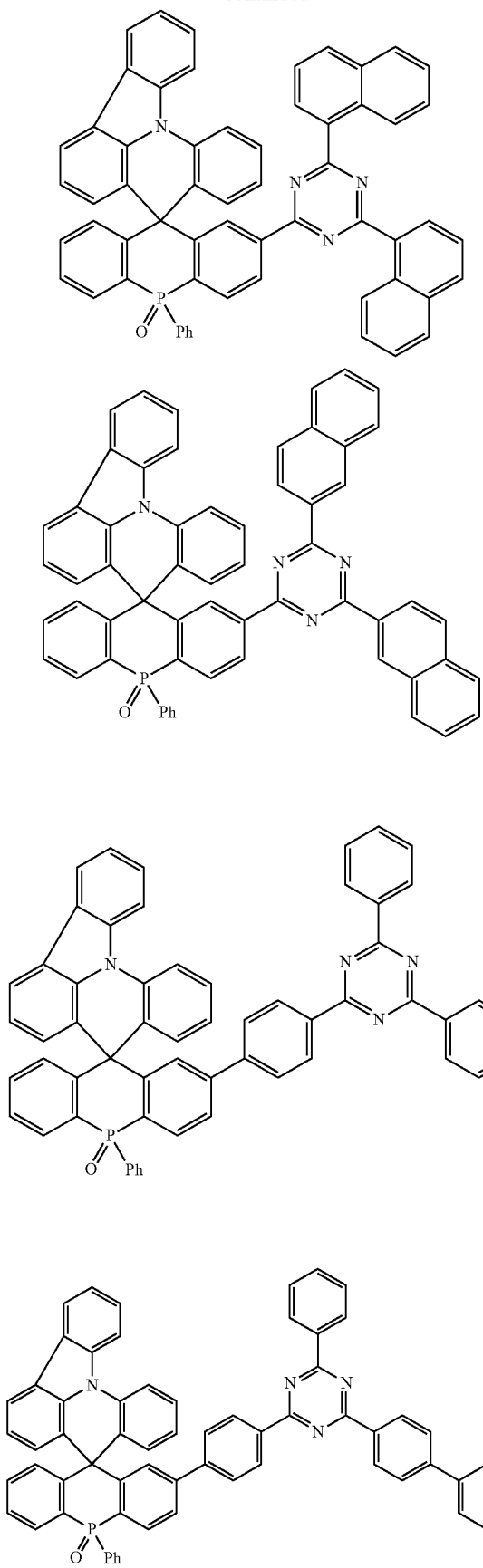
460
-continued
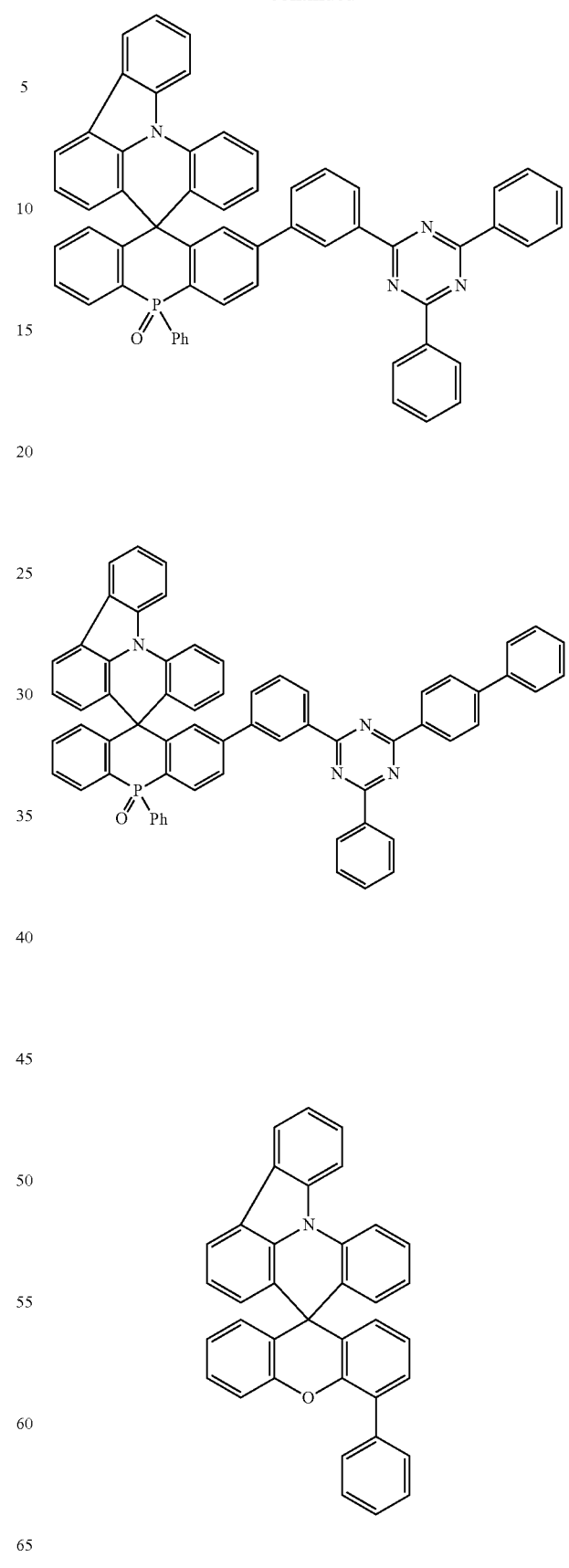

461
-continued
462
-continued
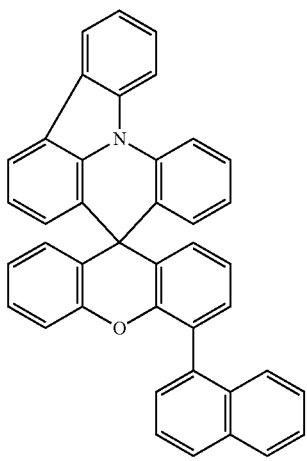
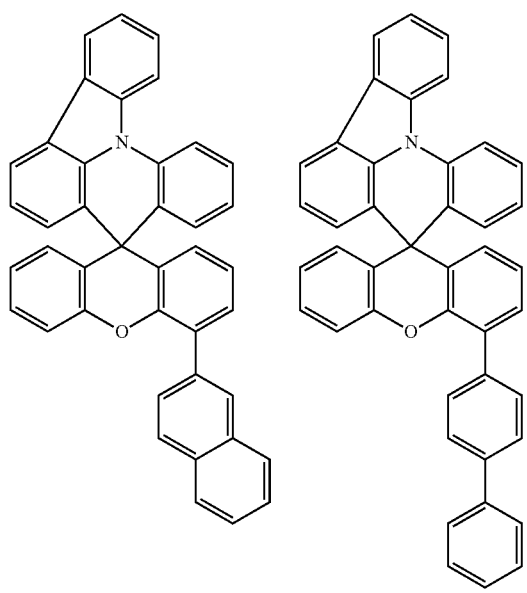
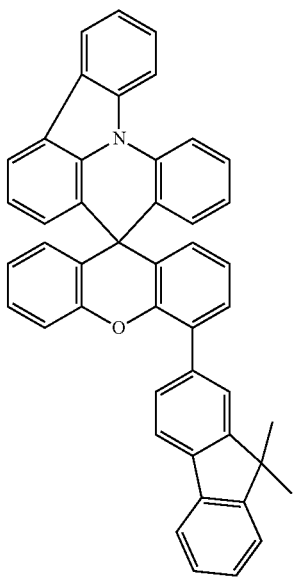
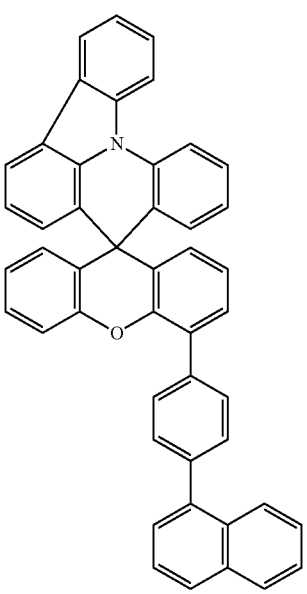

463
-continued
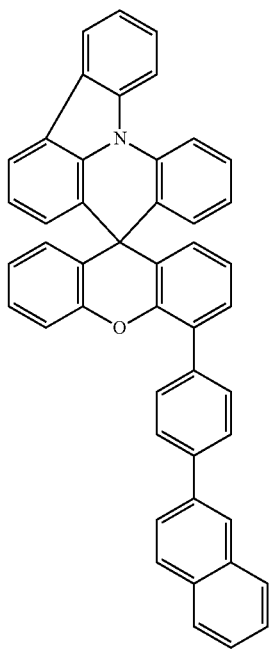
464
-continued
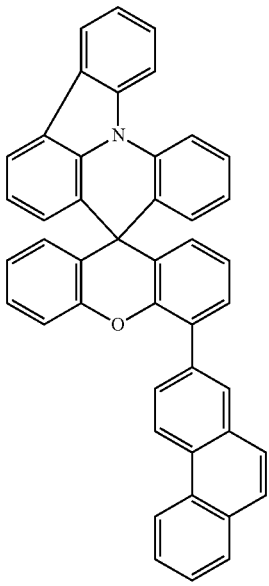
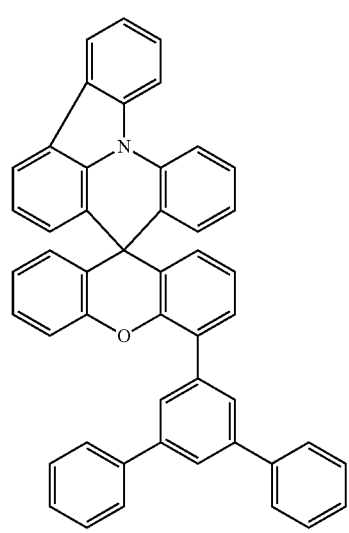
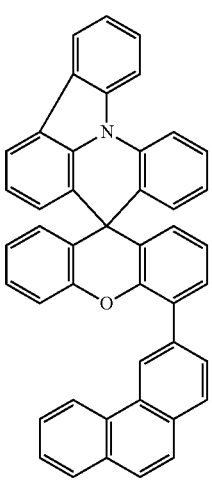 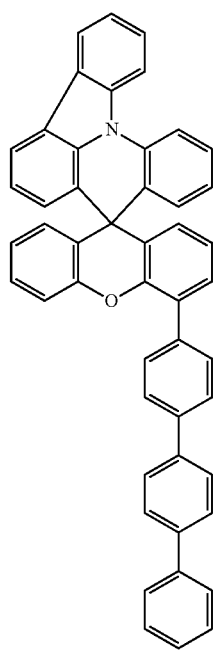

465
-continued
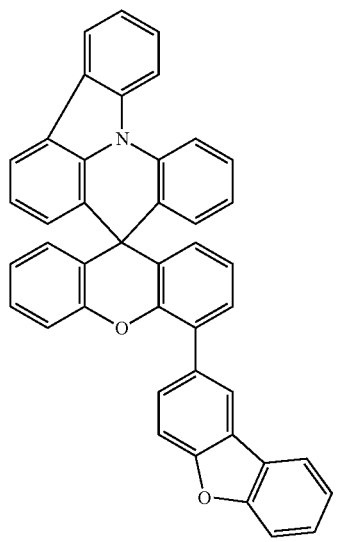
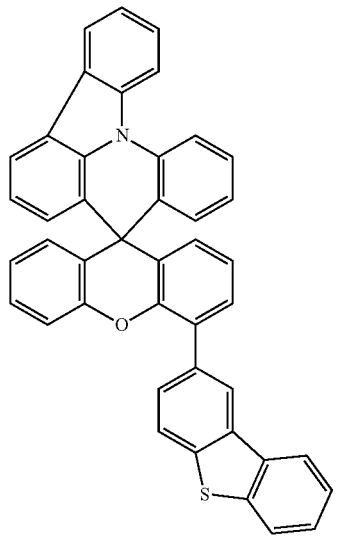
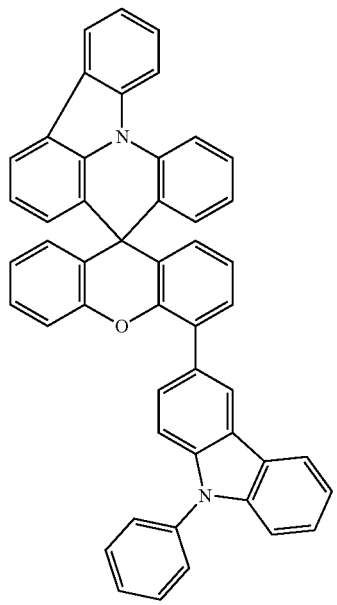
466
-continued
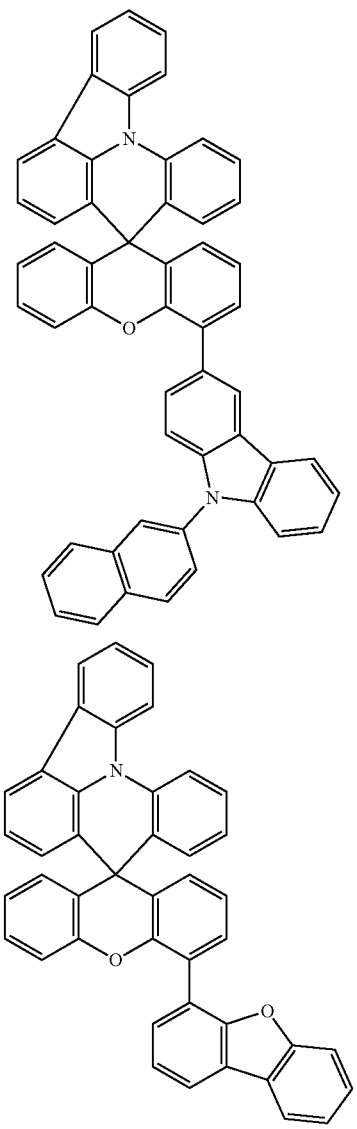
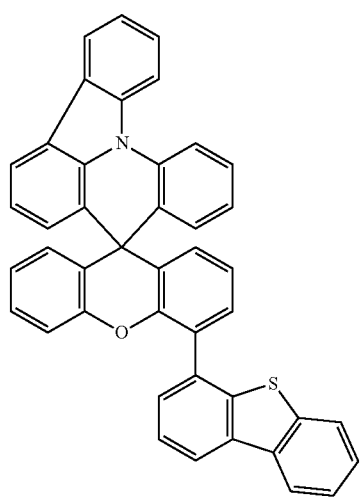

467
-continued
468
-continued
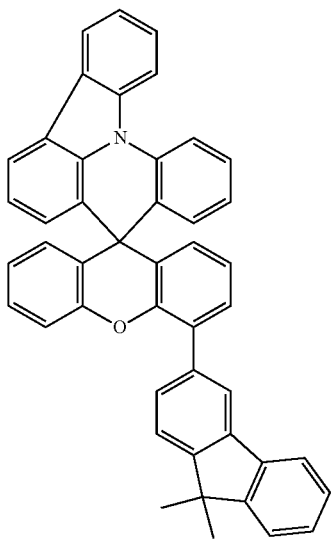
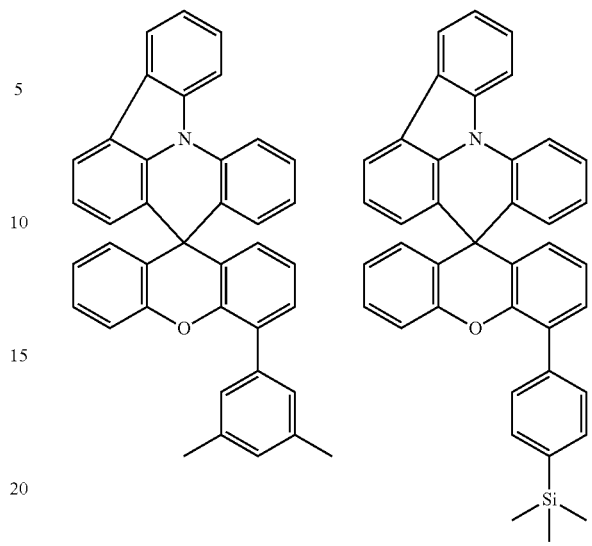
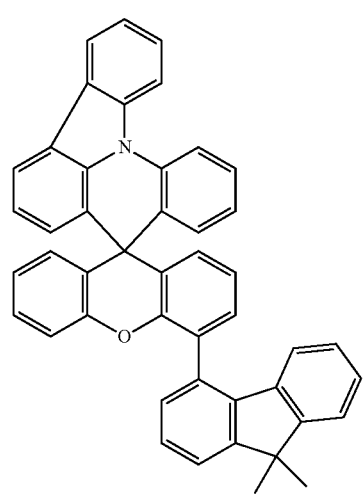
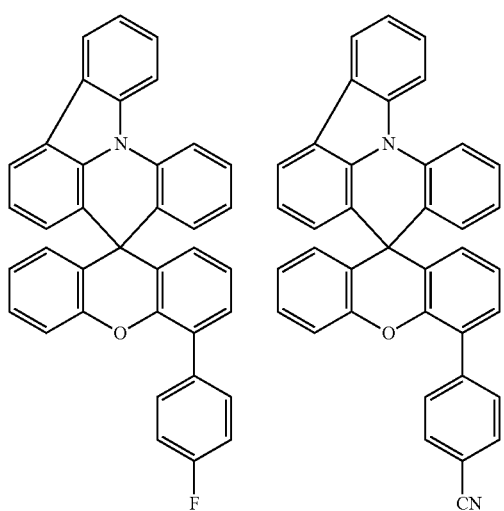
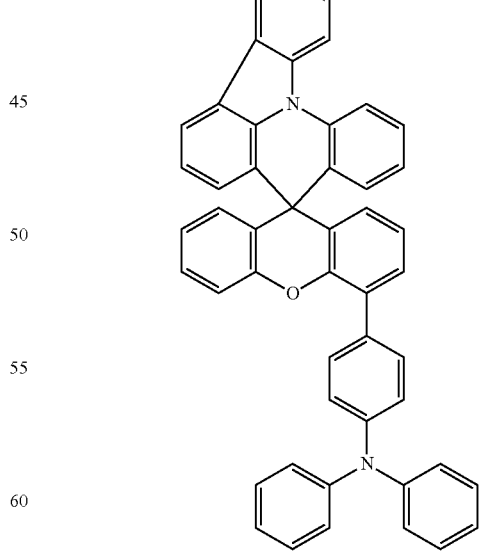

469
-continued
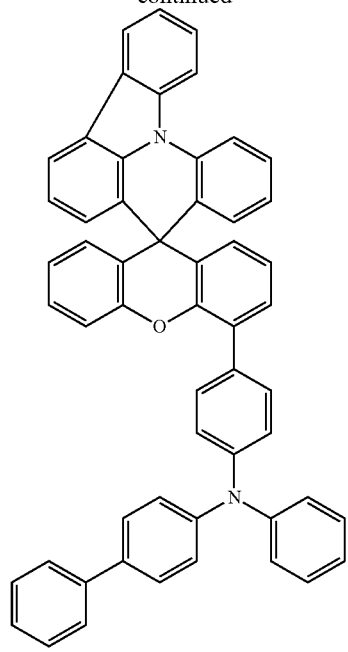
470
-continued
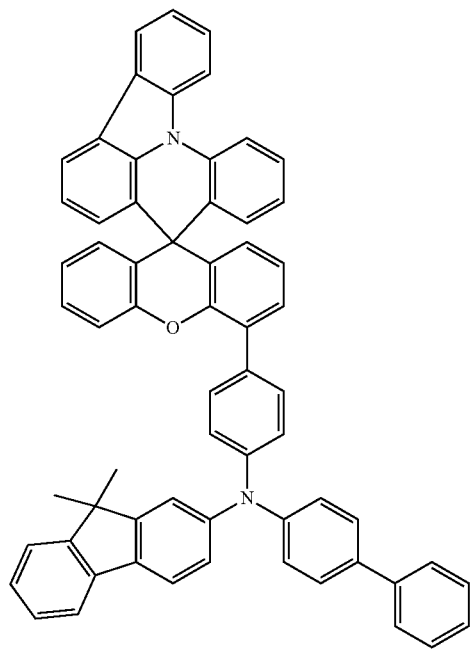
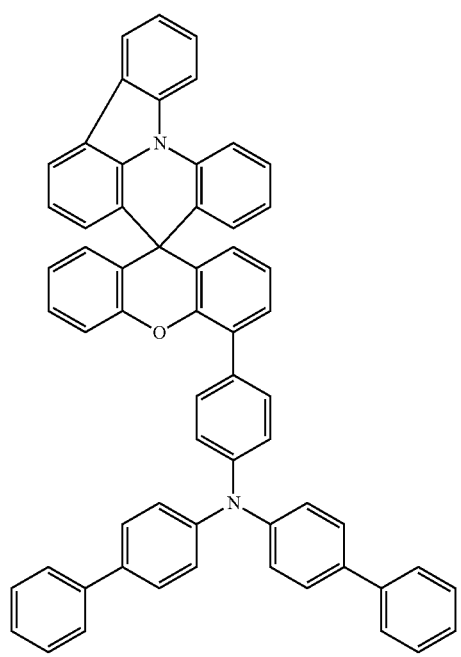
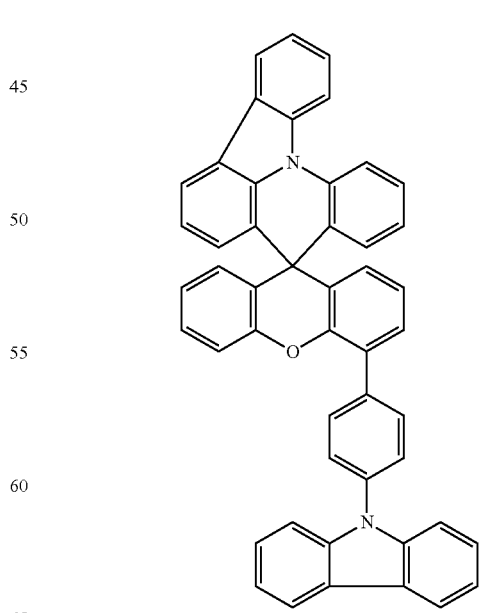

471
-continued
472
-continued
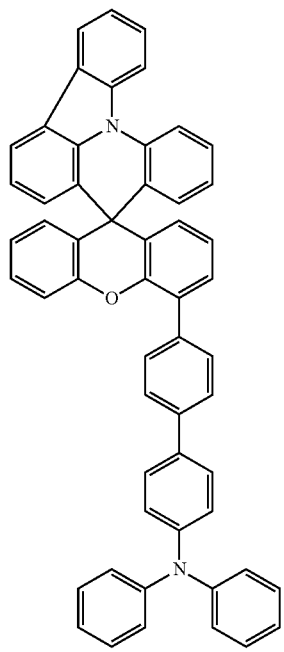
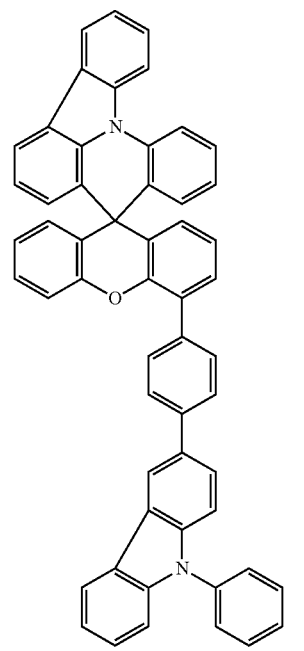
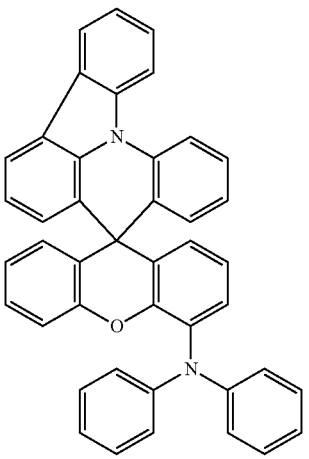
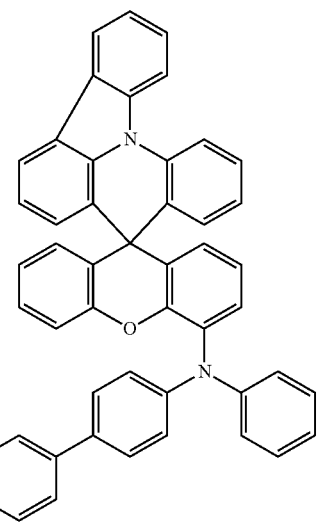

473
-continued
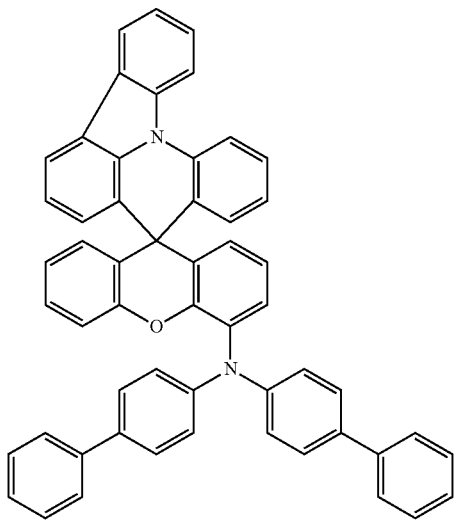
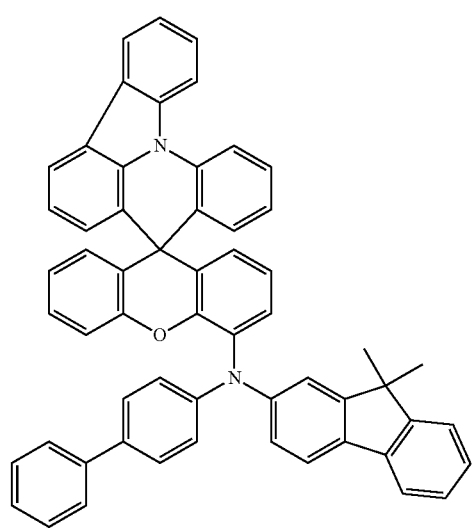
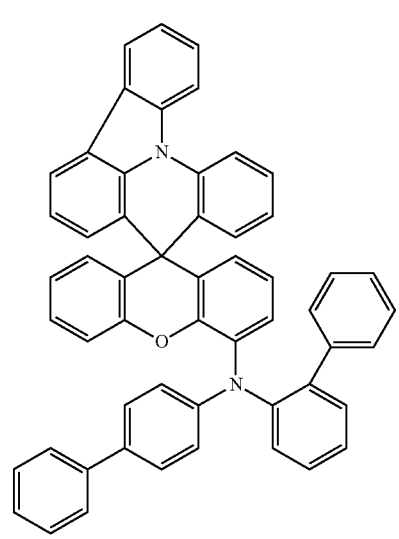
474
-continued
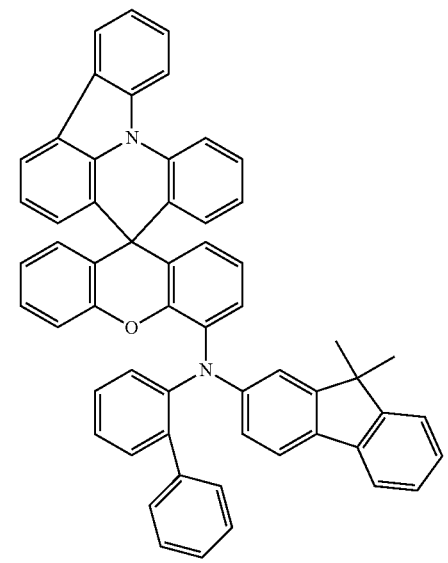
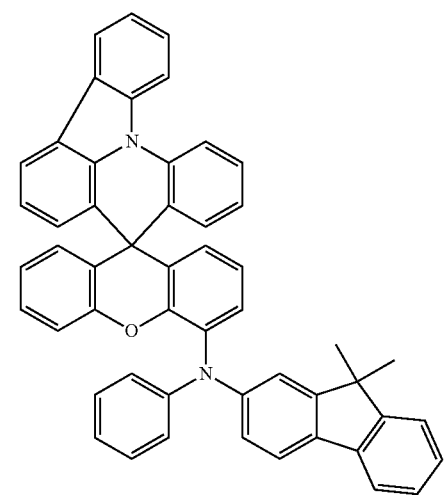
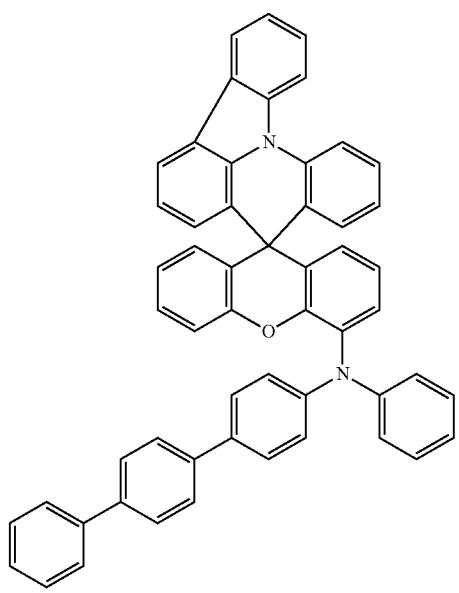

475
-continued
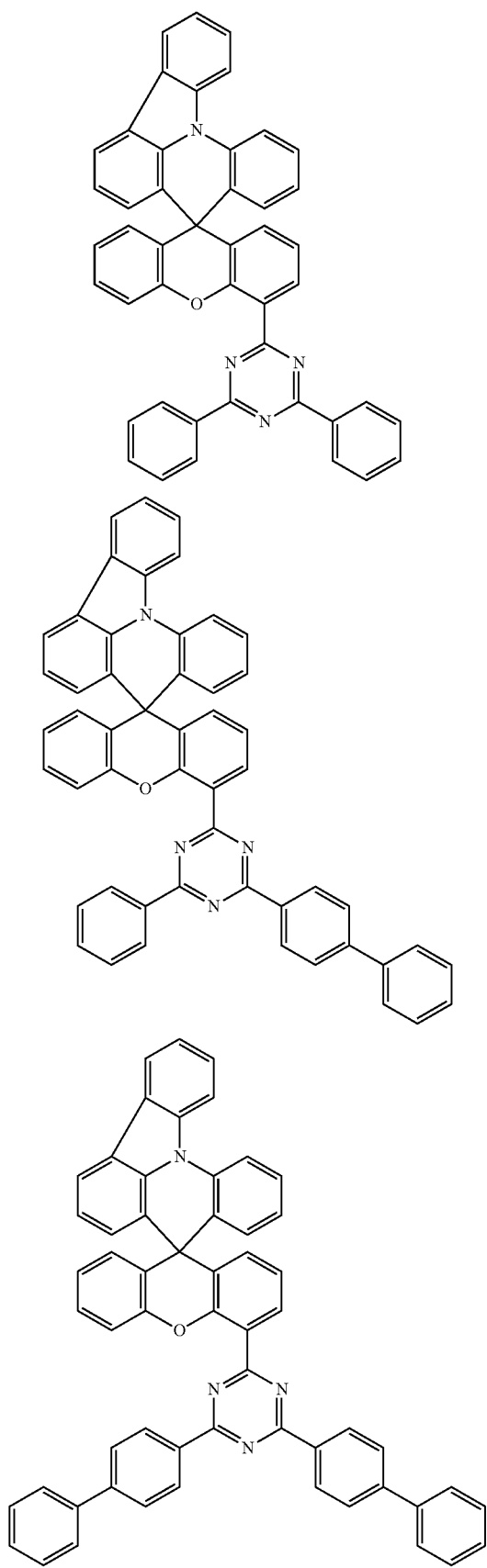
476
-continued
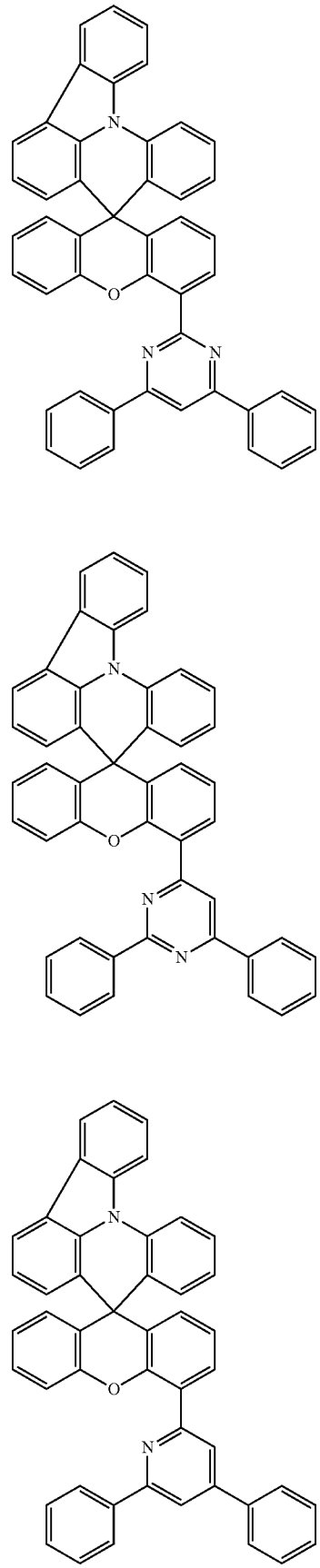

477
-continued
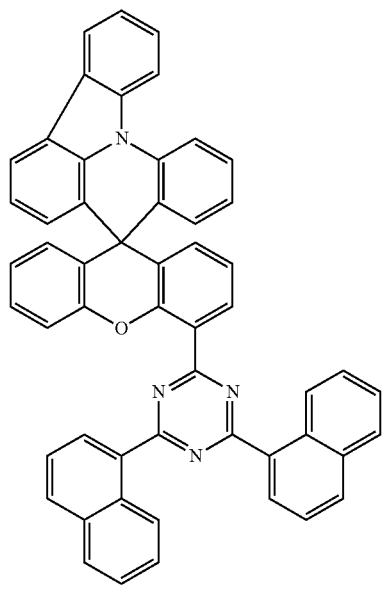
478
-continued
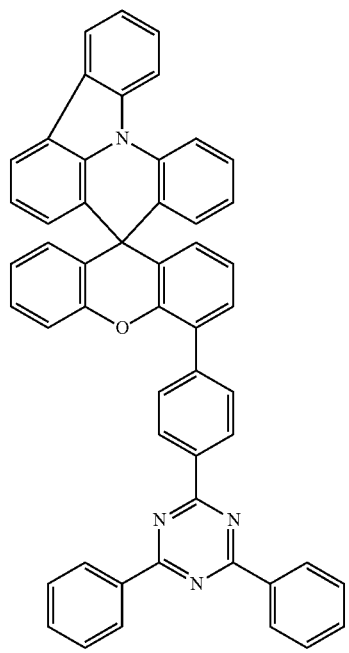
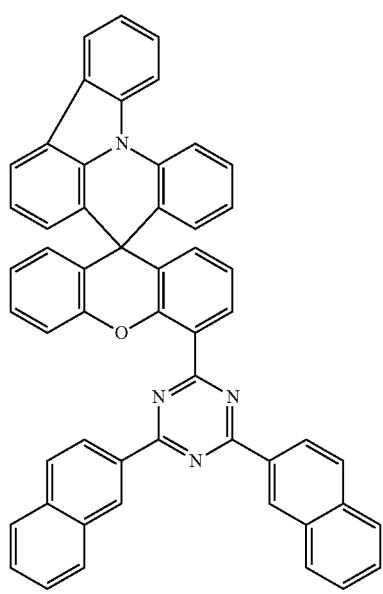
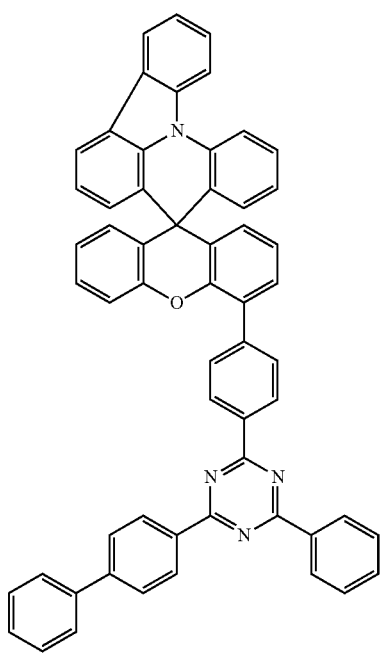

479
-continued
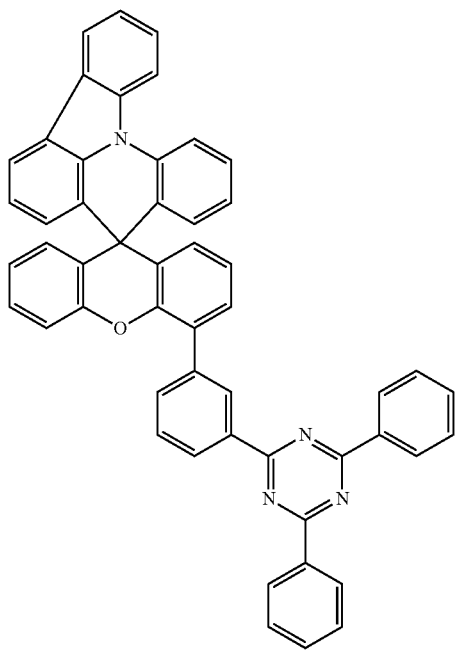
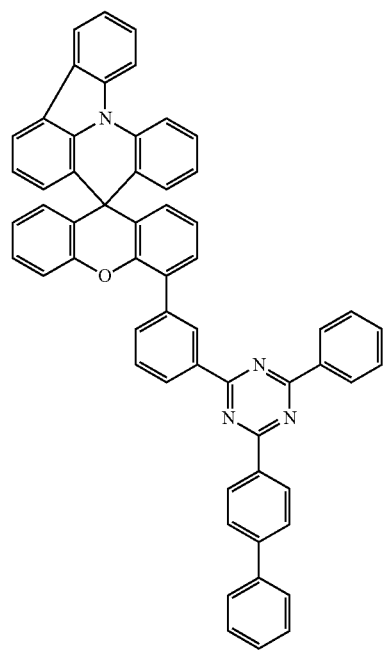
480
-continued
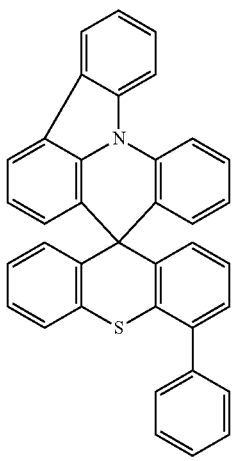
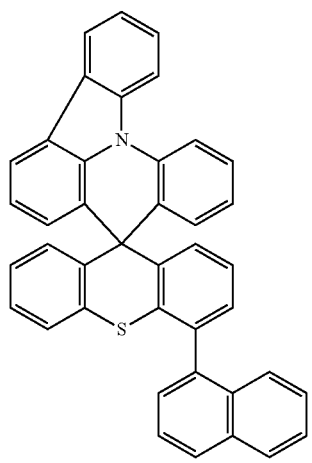
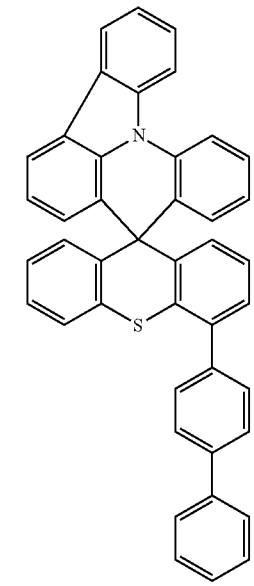

481
-continued
482
-continued
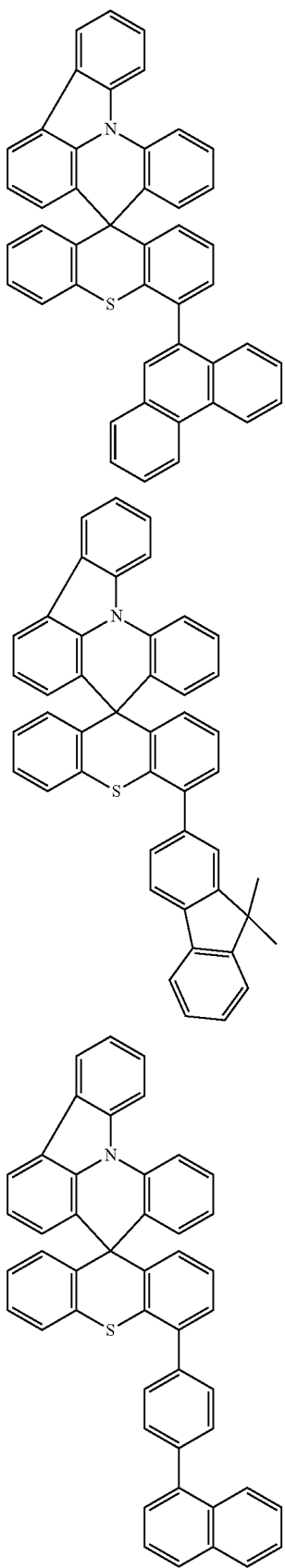
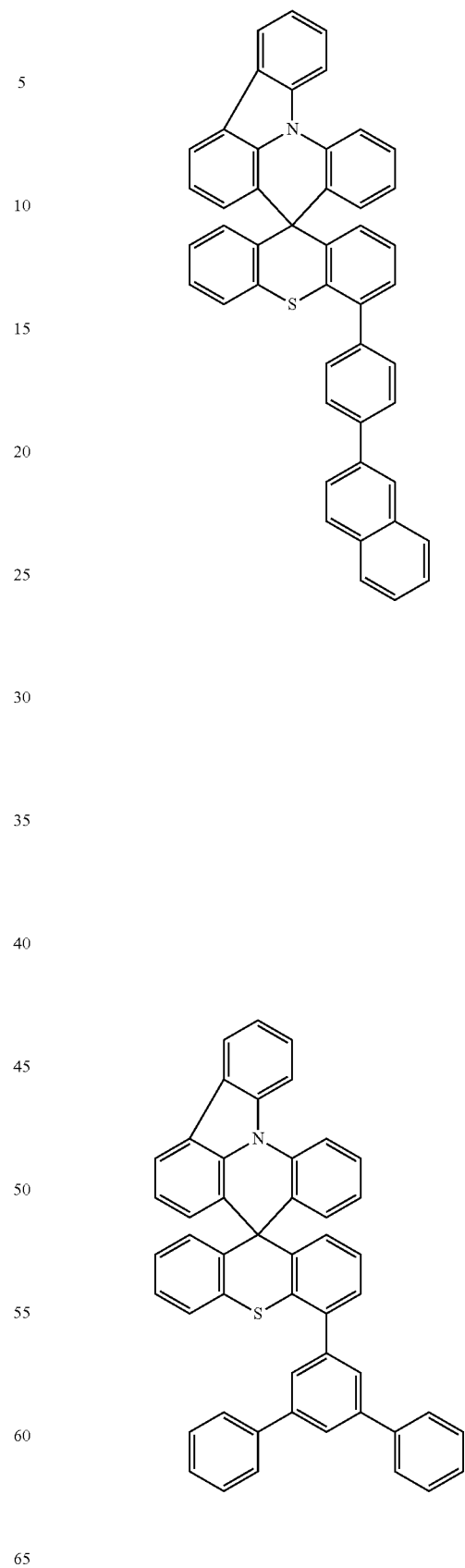

483
-continued
484
-continued
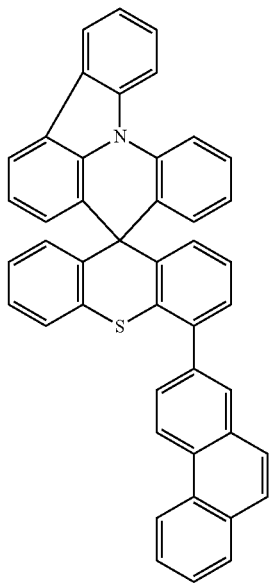
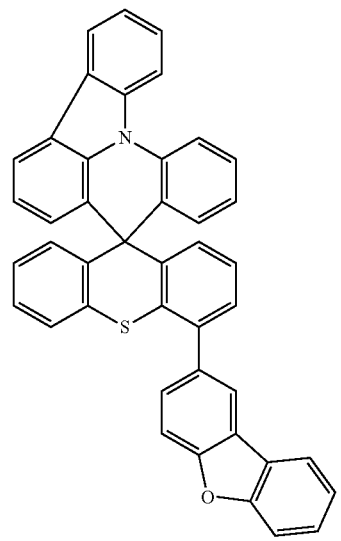
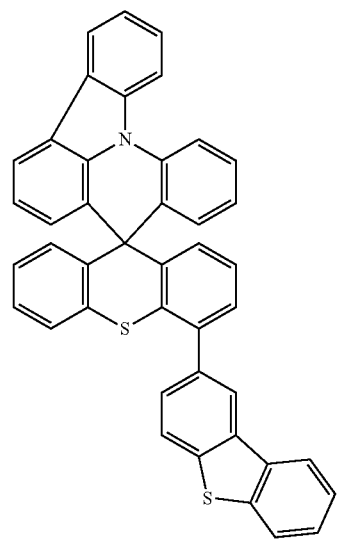
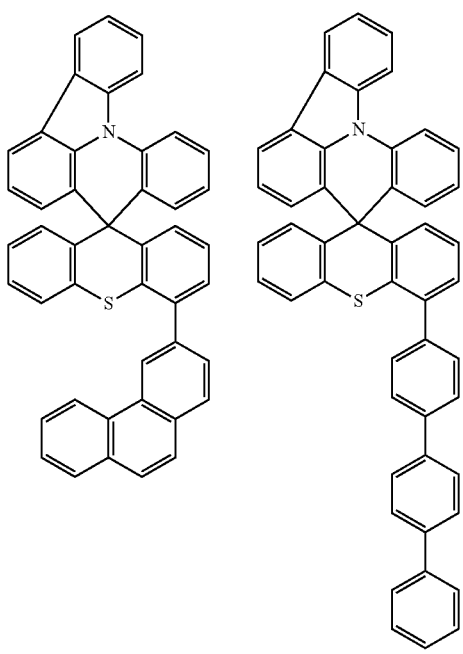

485
-continued
486
-continued
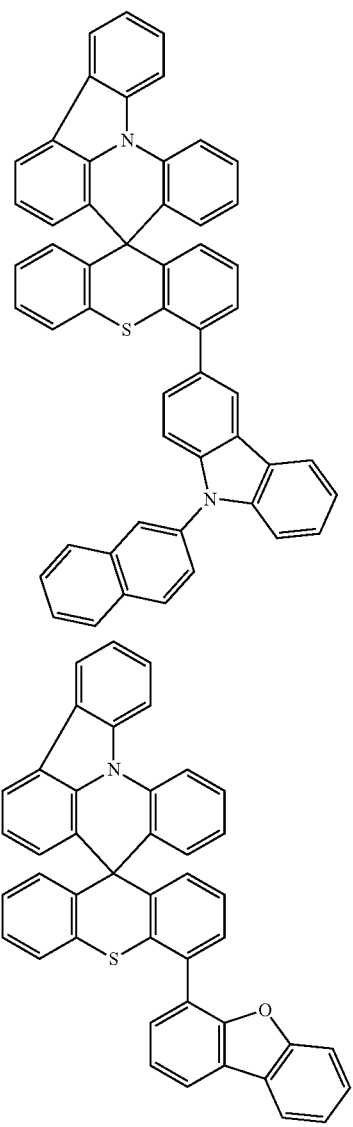
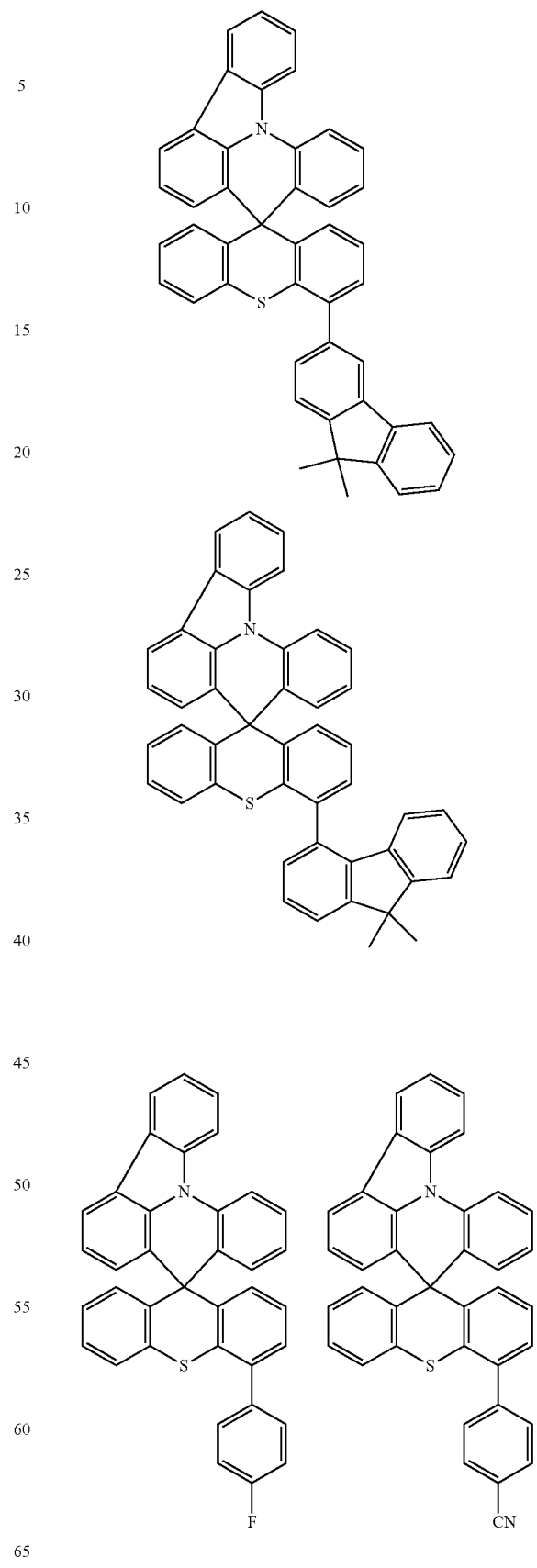

487
-continued
488
-continued
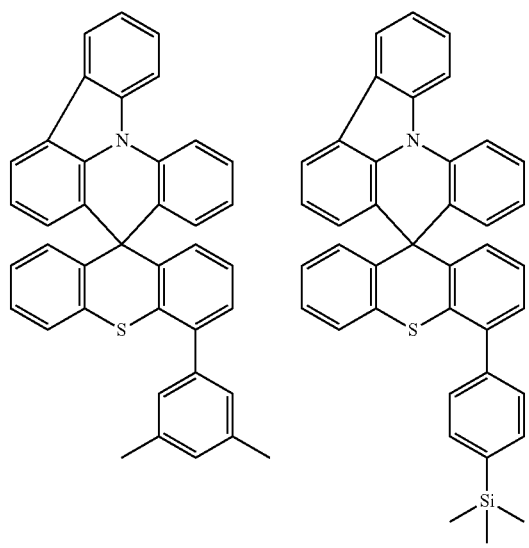
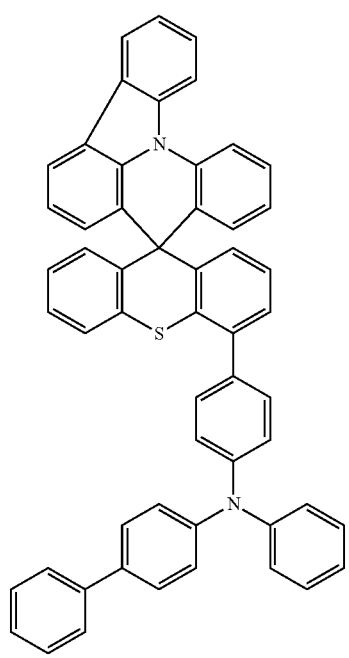
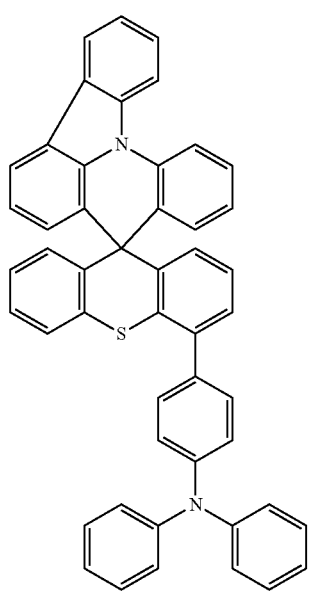
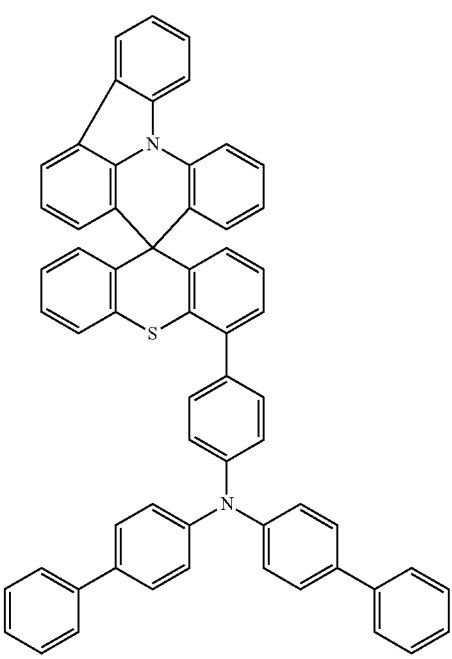

489
-continued
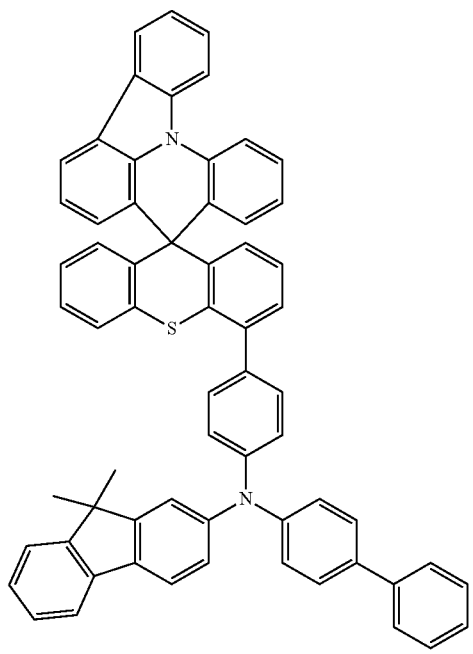
490
-continued
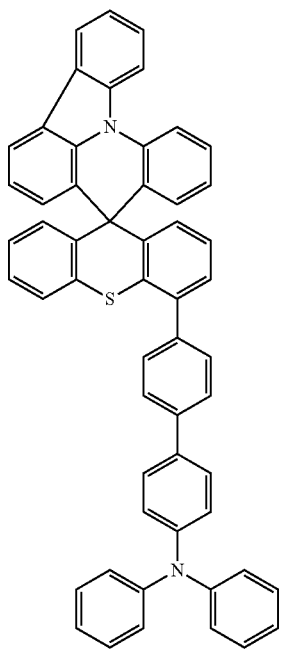
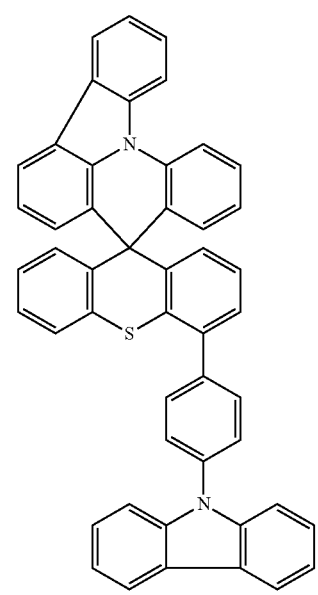
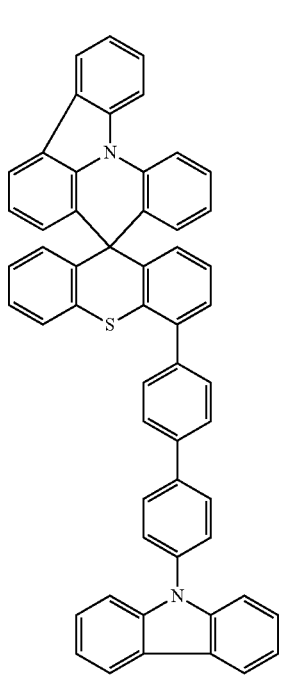

491
-continued
492
-continued
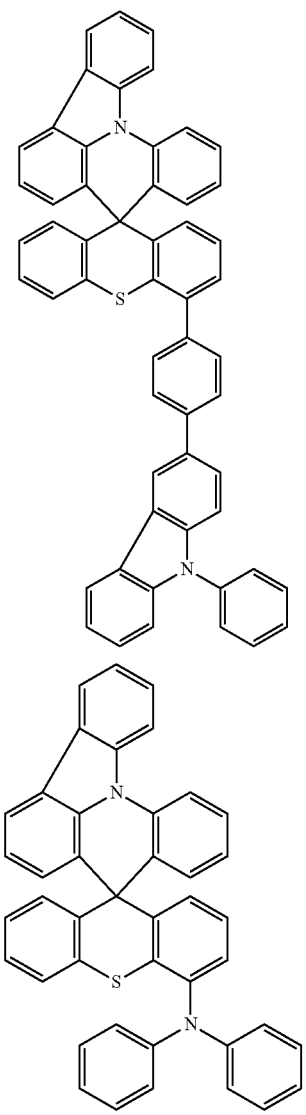
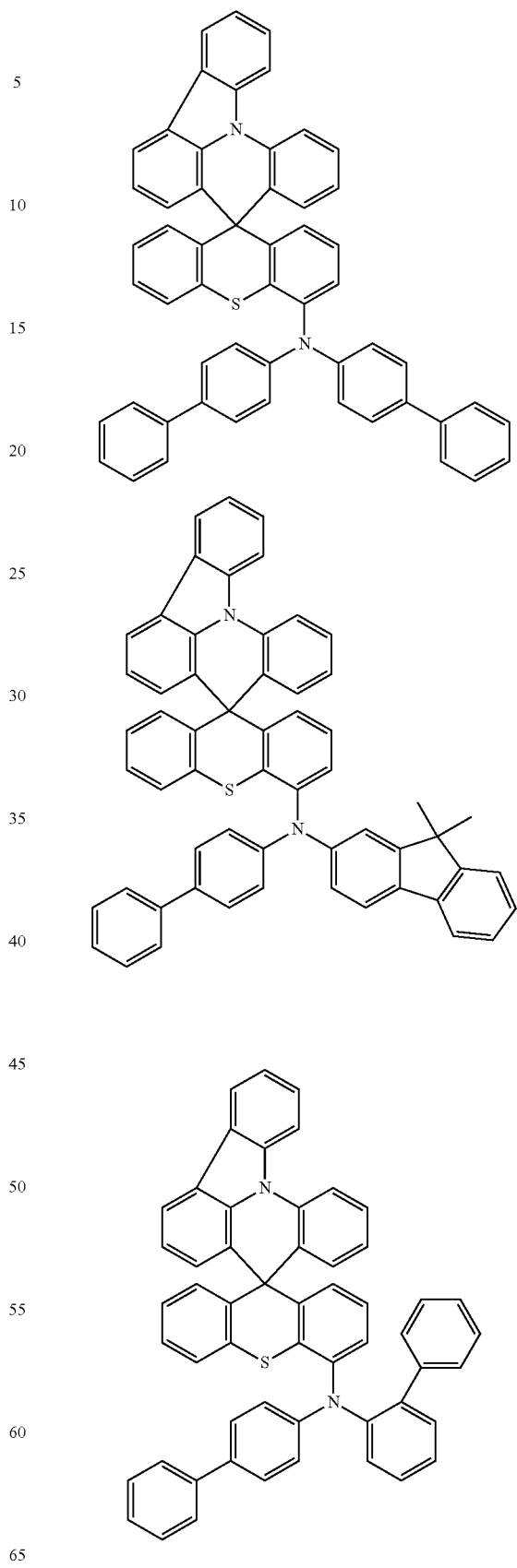

493
-continued
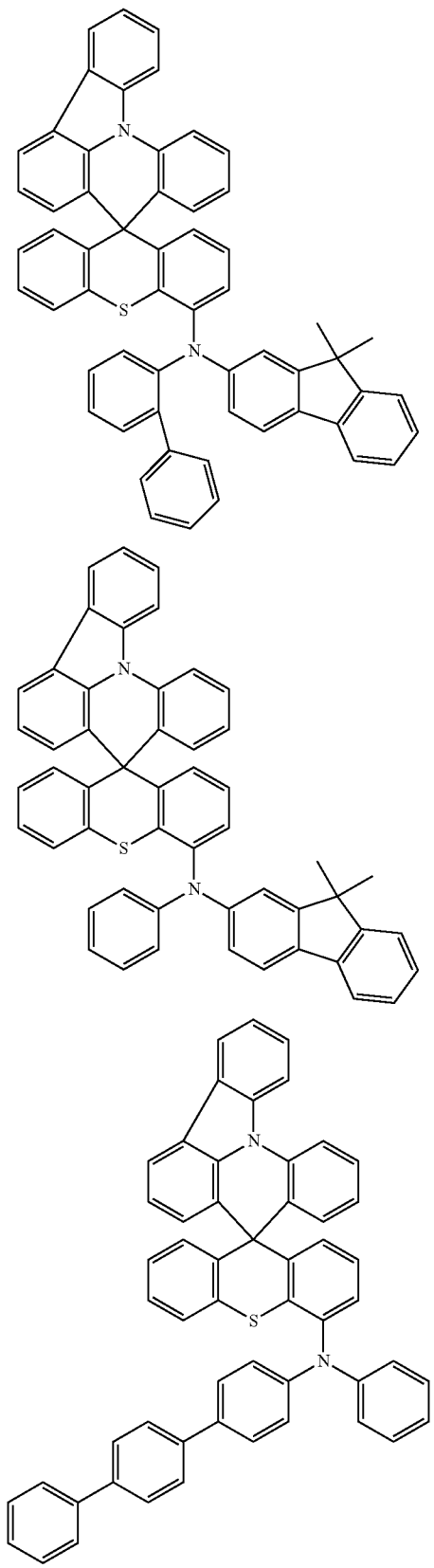
494
-continued
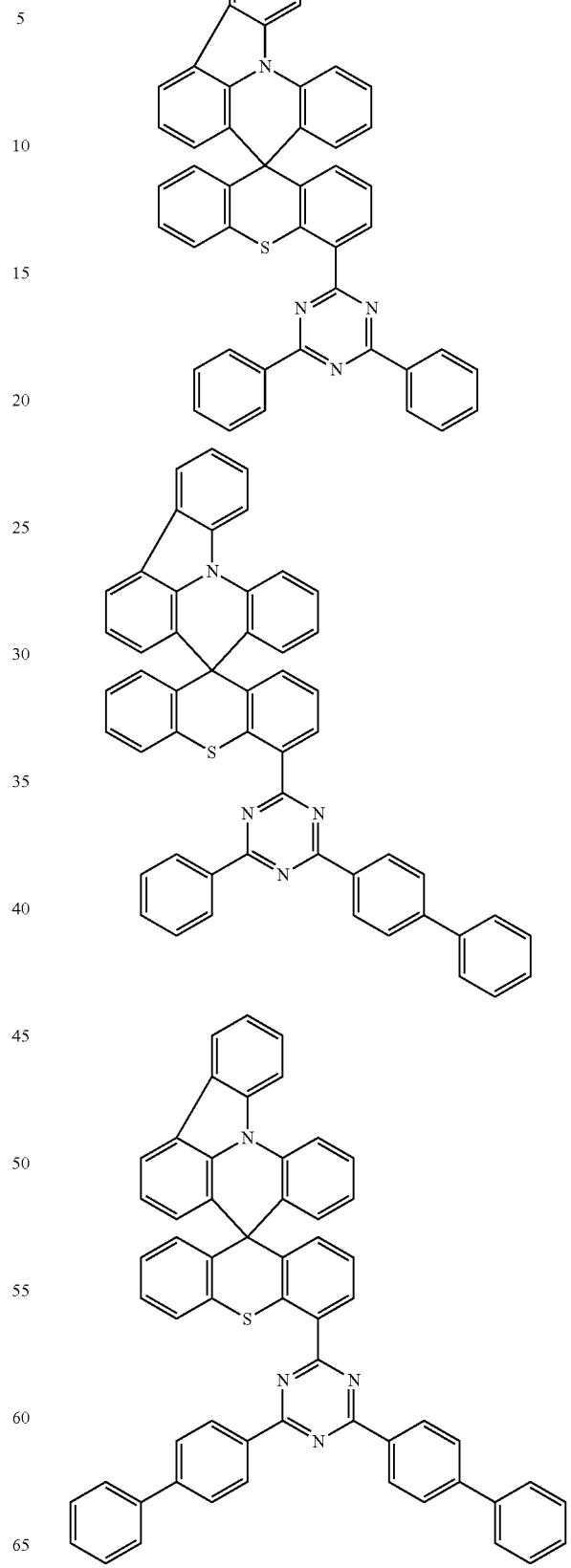

495
-continued
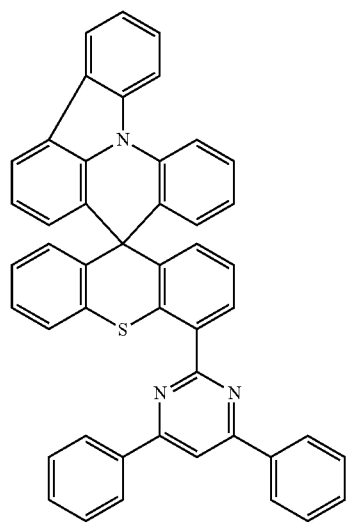
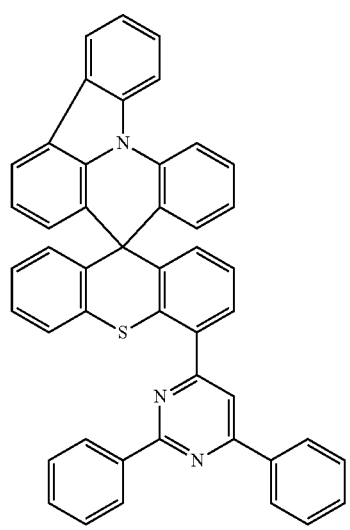
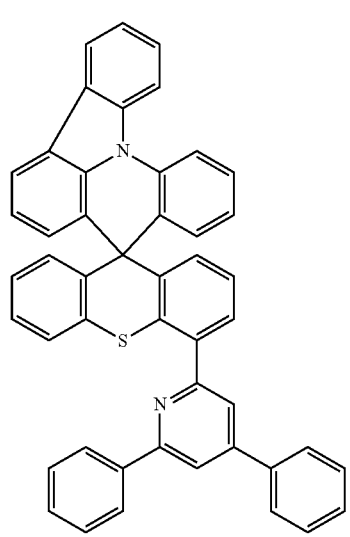
496
-continued
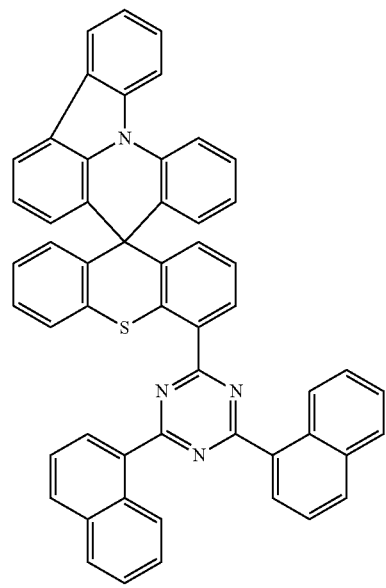
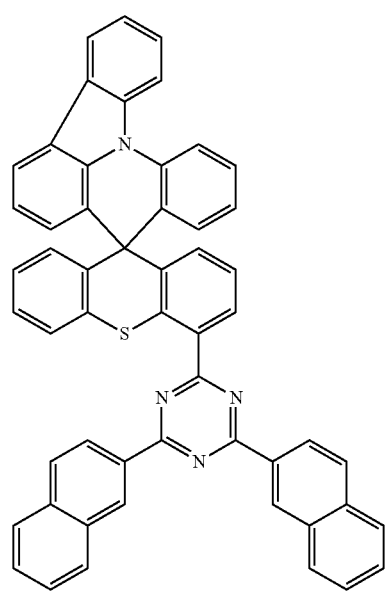

497
-continued
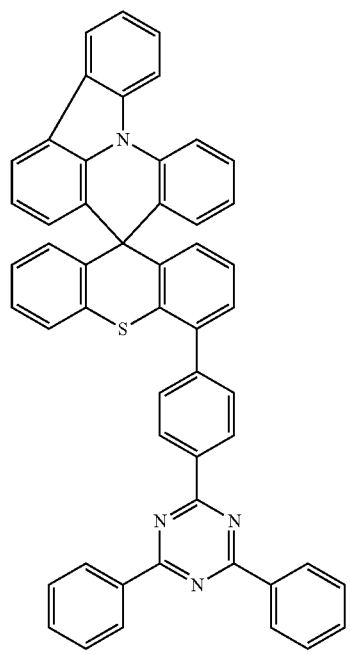
498
-continued
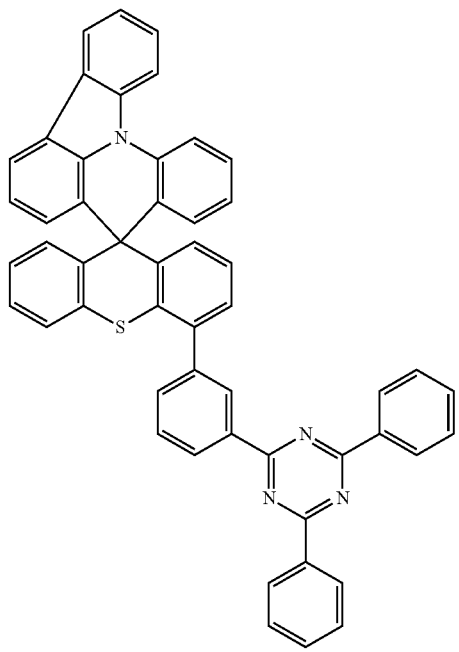
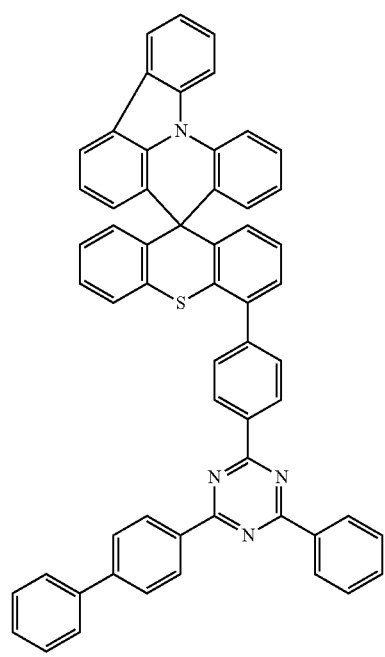
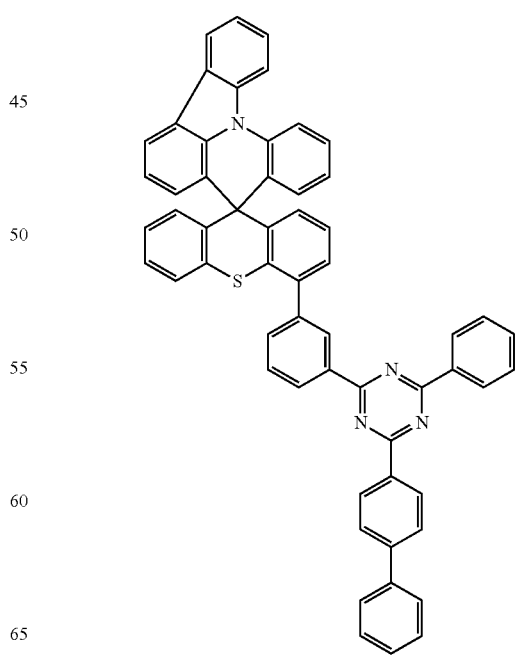

499
-continued
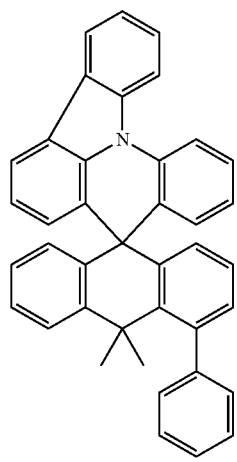
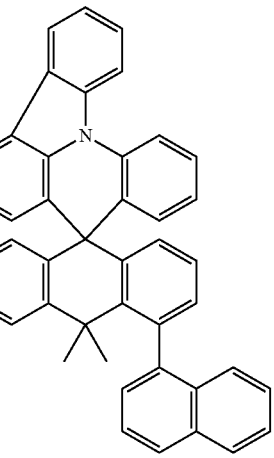
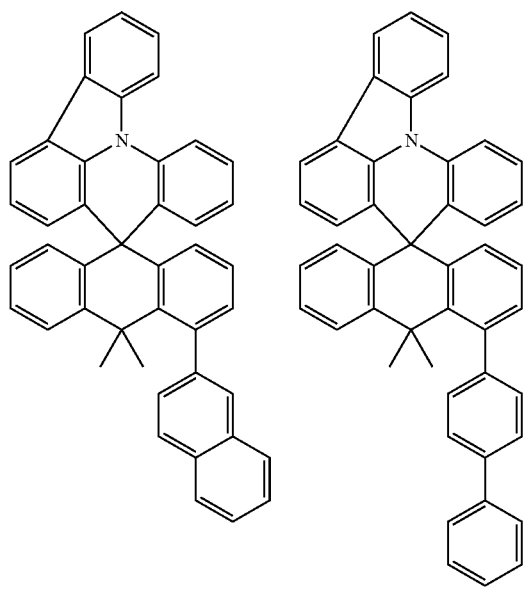
500
-continued
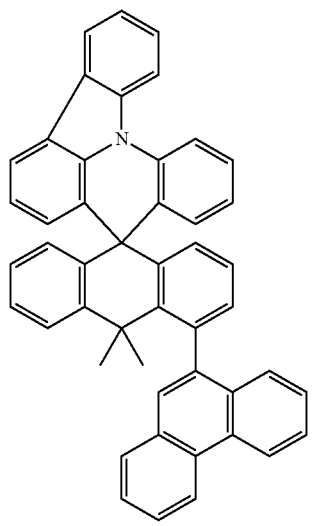
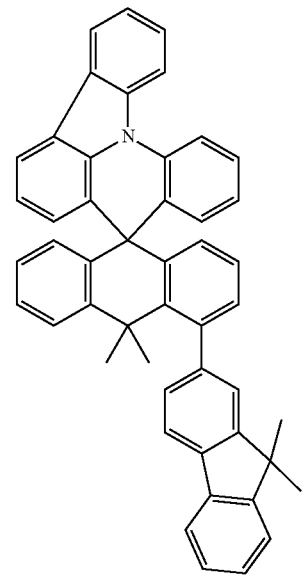
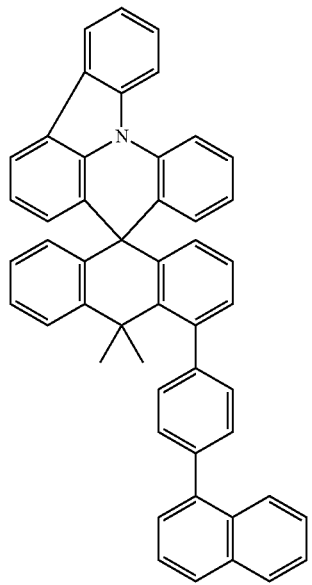

501
-continued
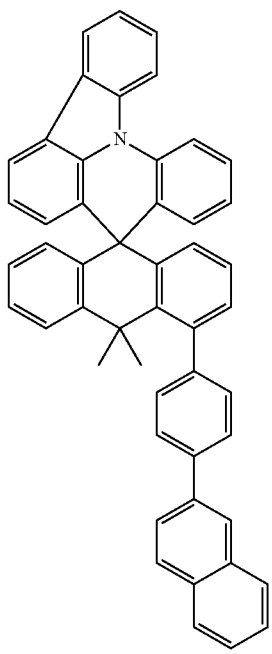
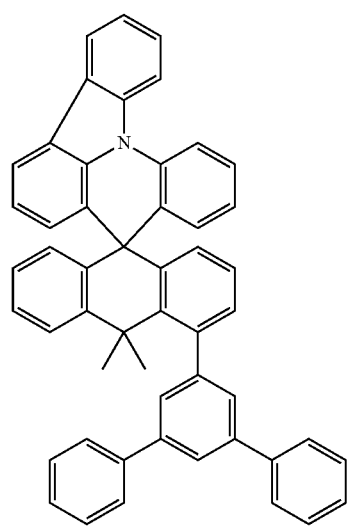
502
-continued
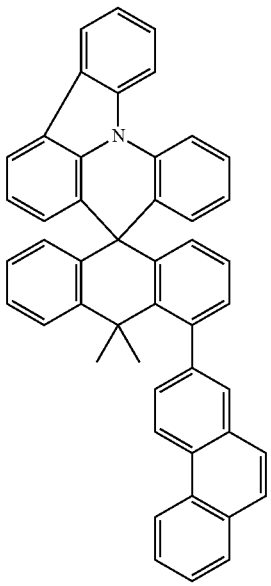
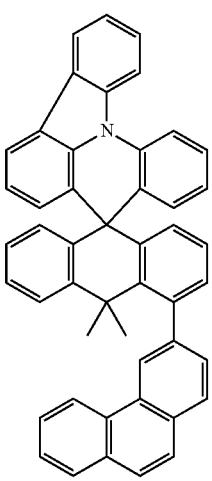 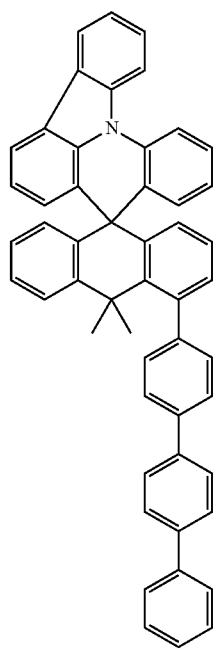

503
-continued
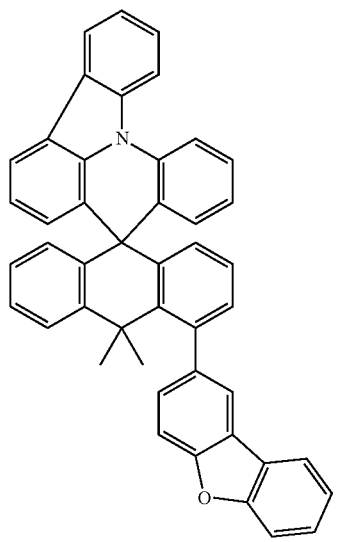
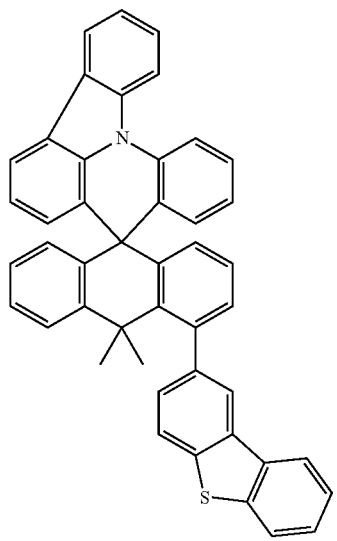
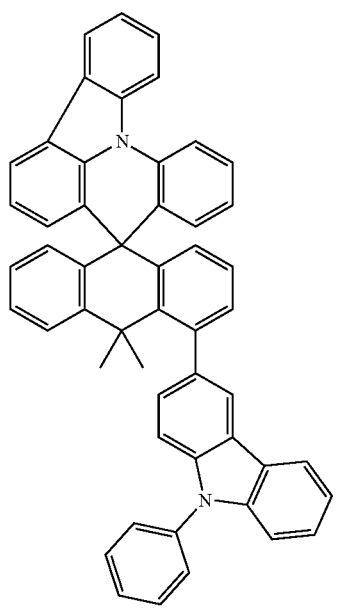
504
-continued
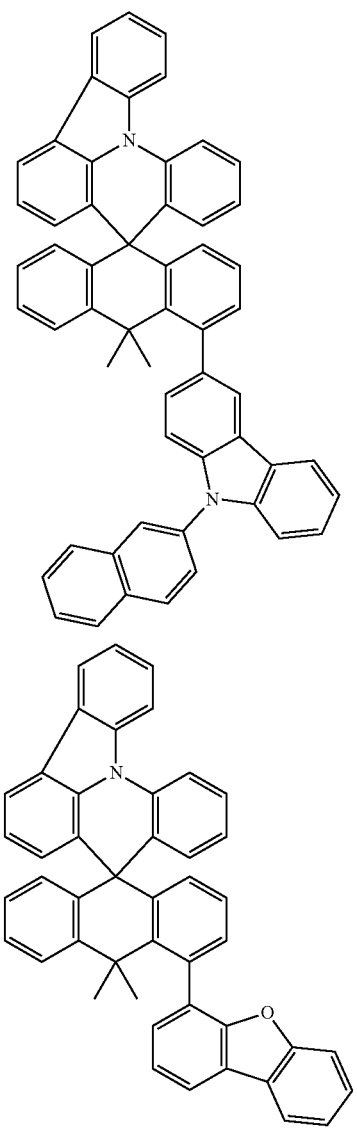
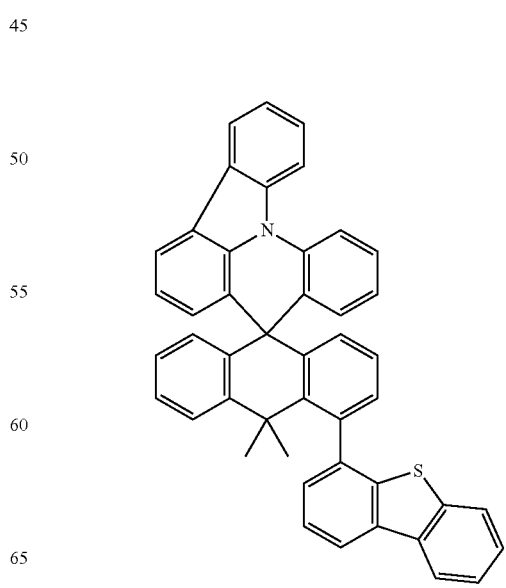

505
-continued
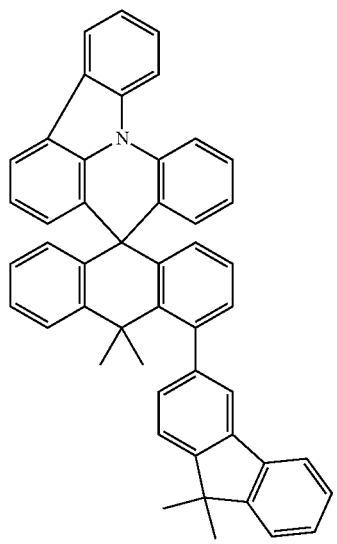
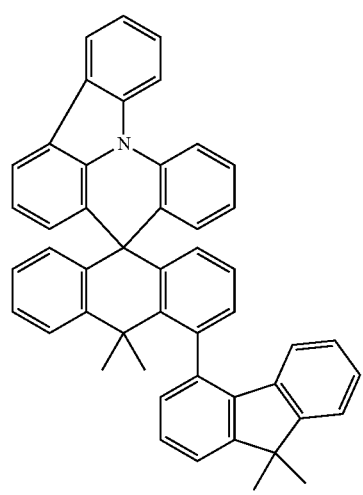
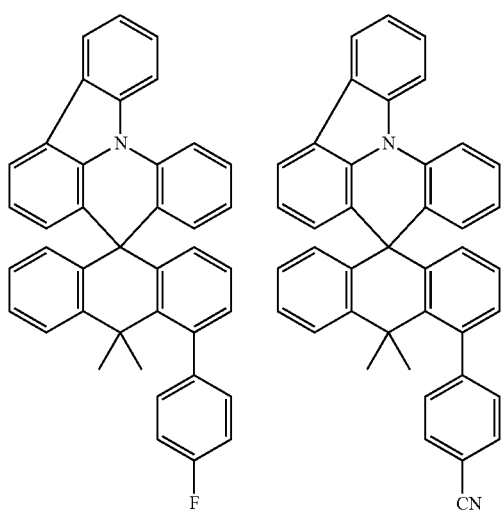
506
-continued
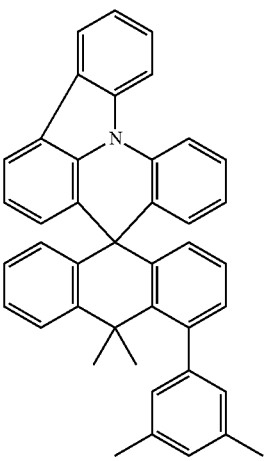
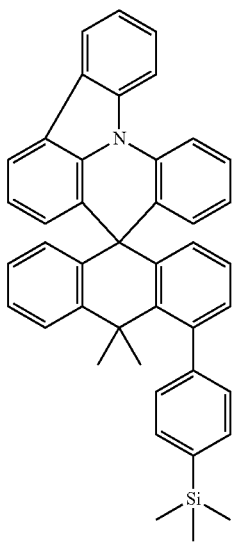
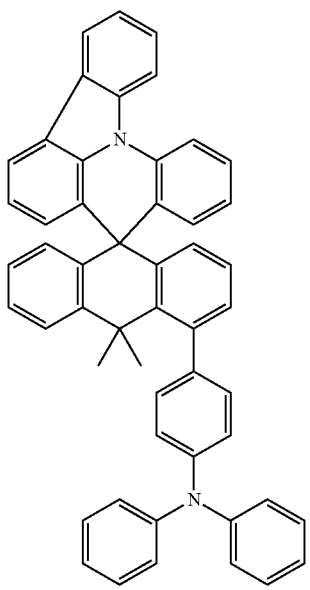

507
-continued
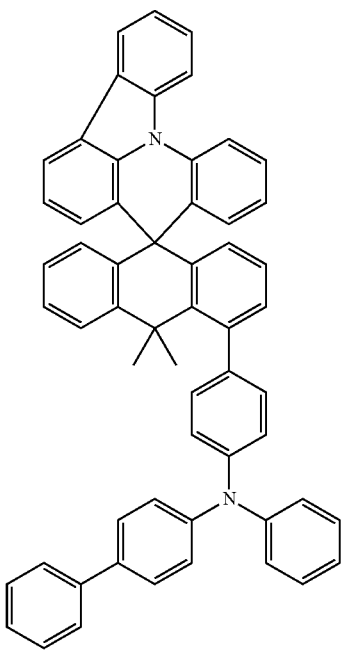
508
-continued
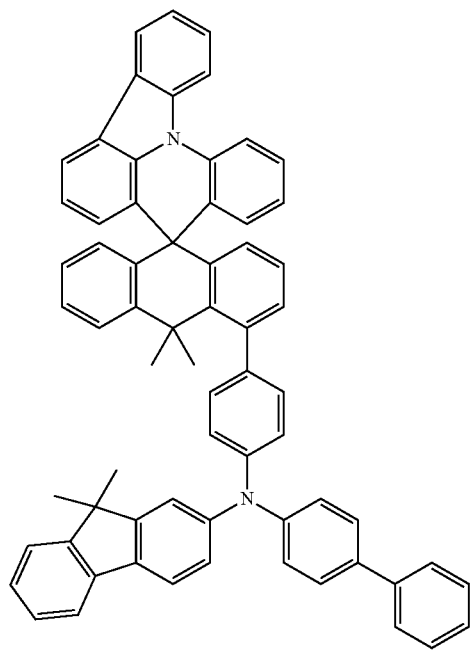
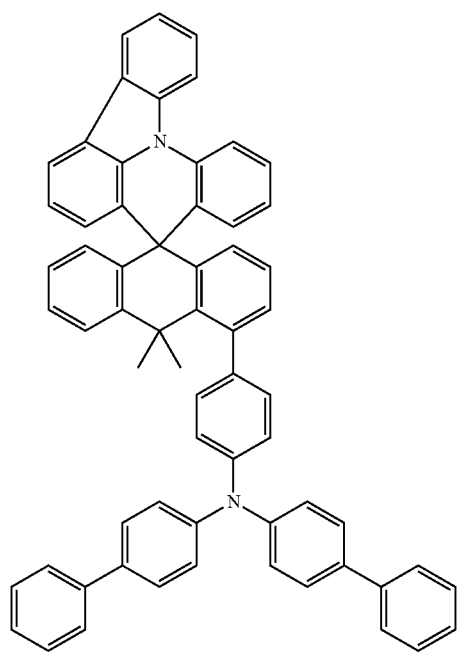
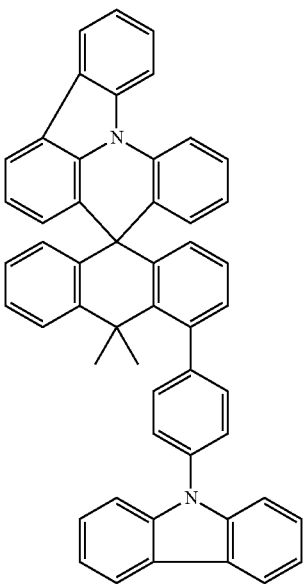

509
-continued
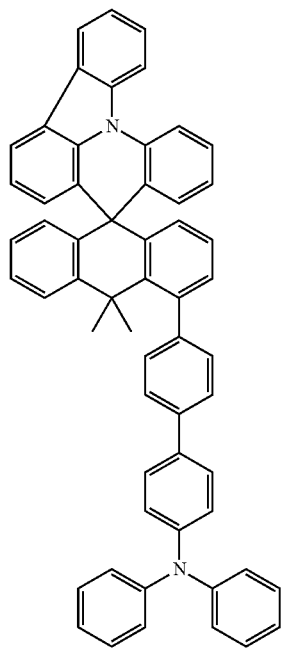
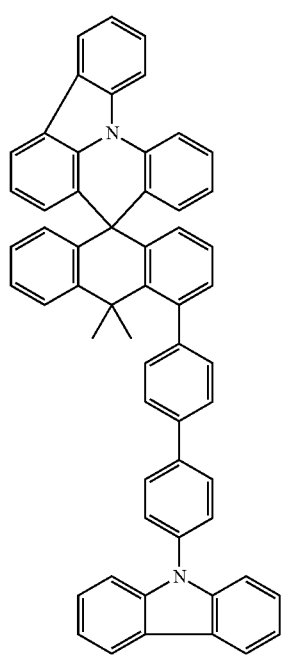
510
-continued
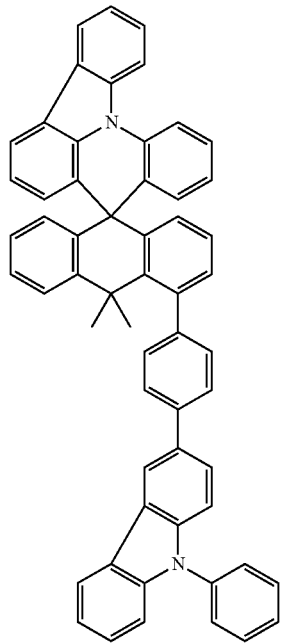
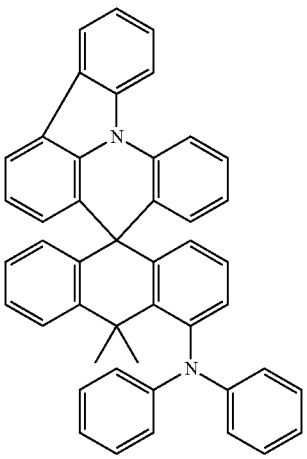
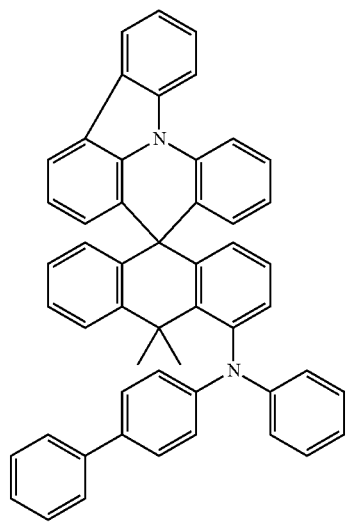

511
-continued
512
-continued
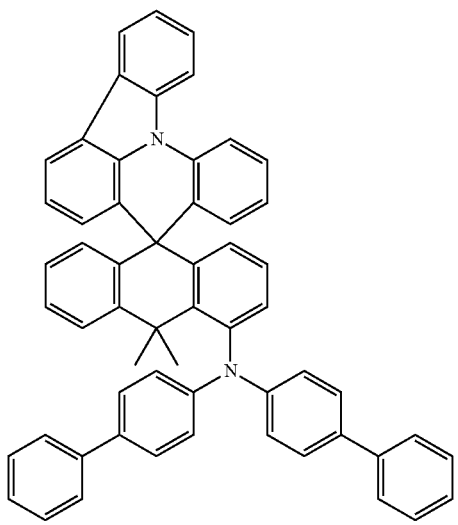
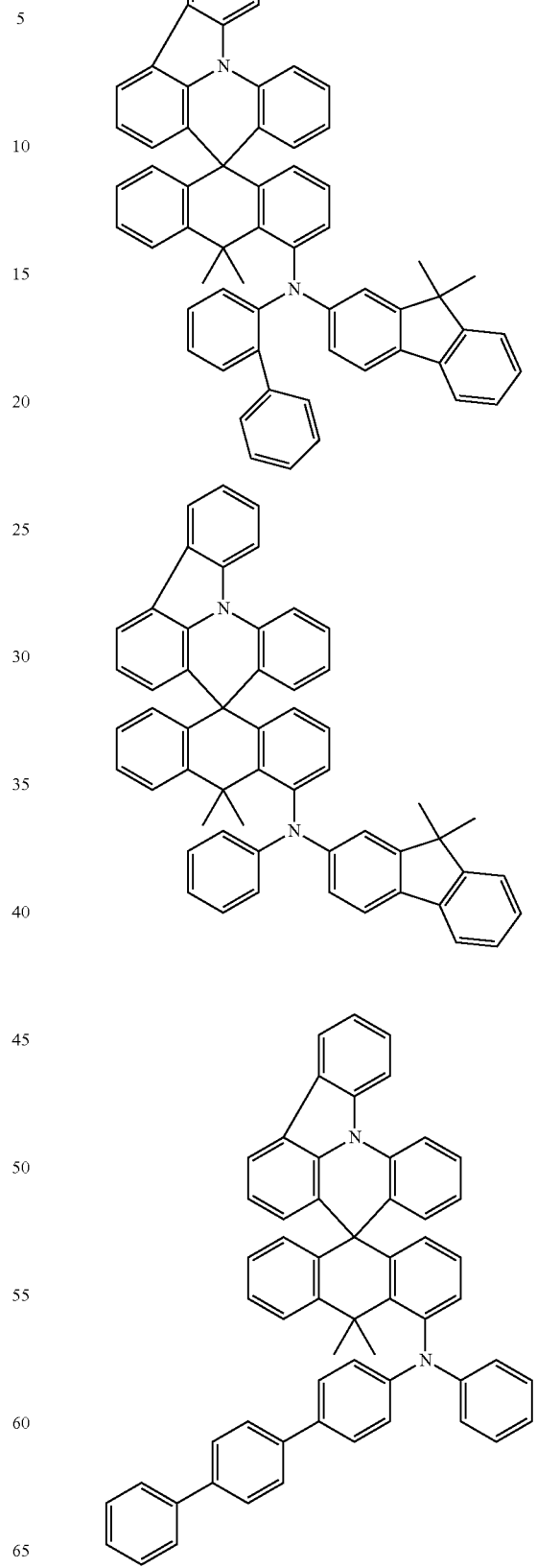

513
-continued
514
-continued
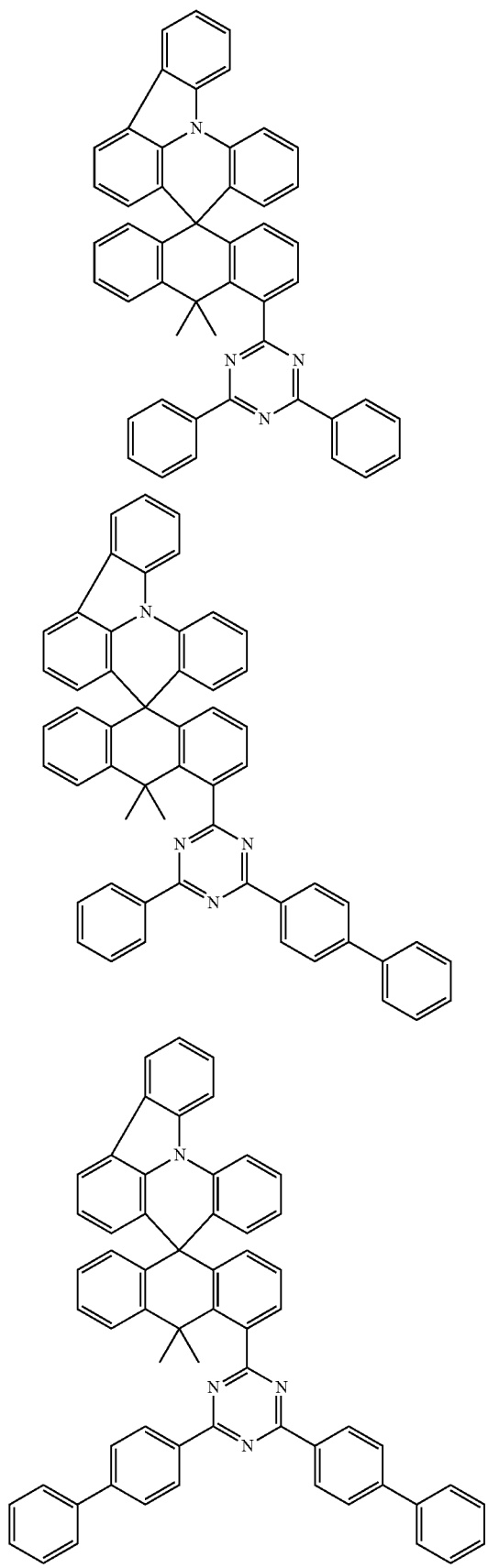
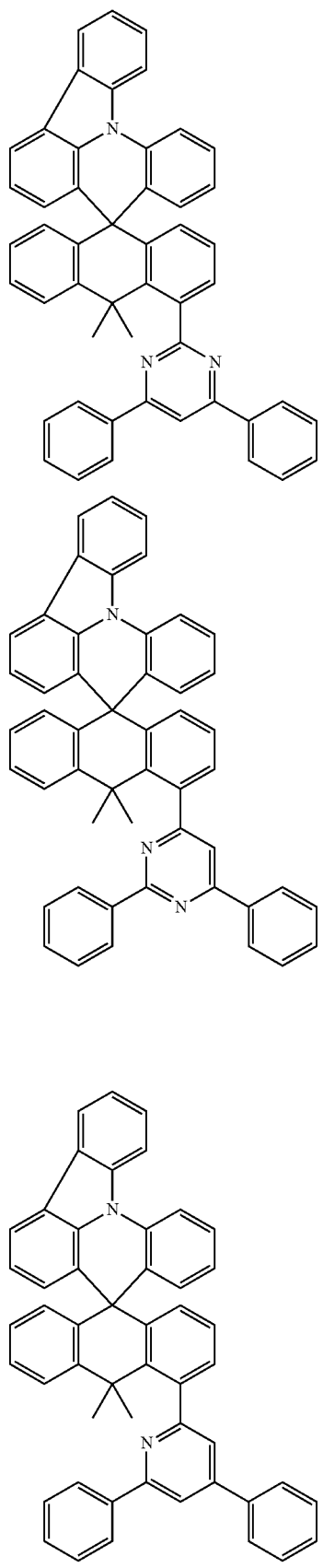

515
-continued
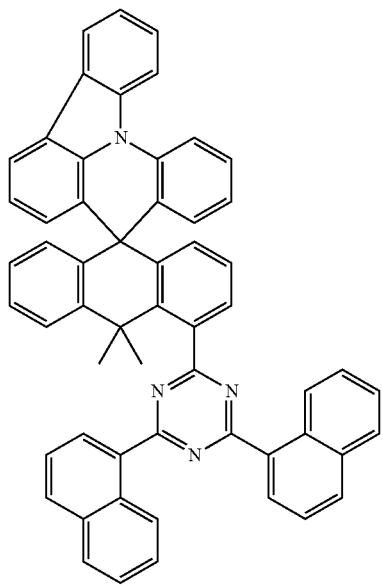
516
-continued
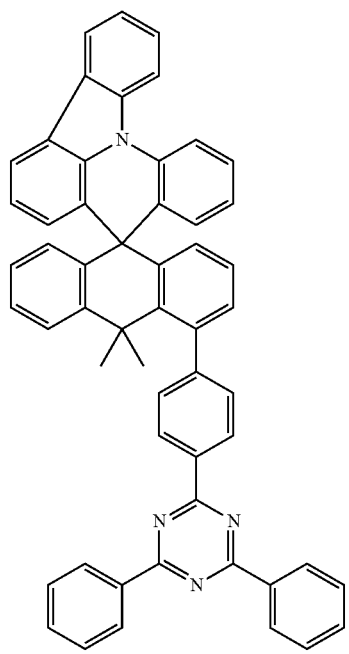
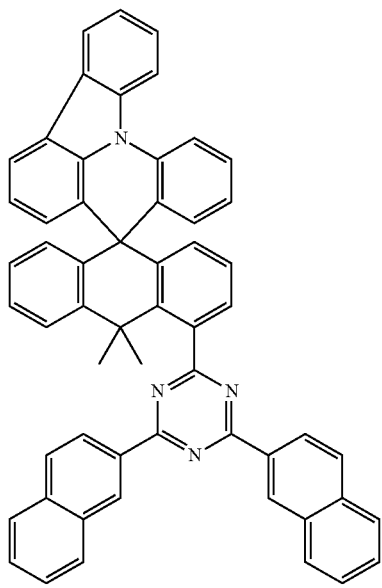
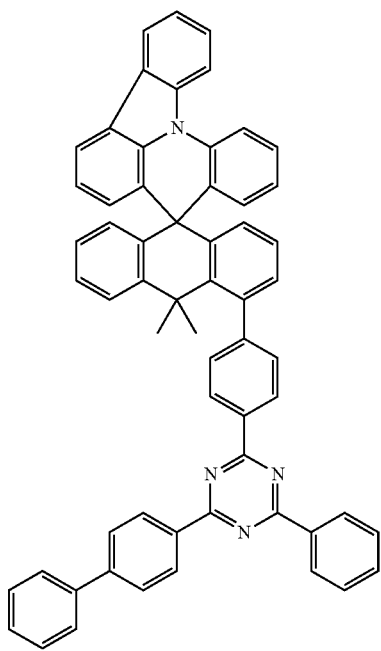

517
-continued
518
-continued
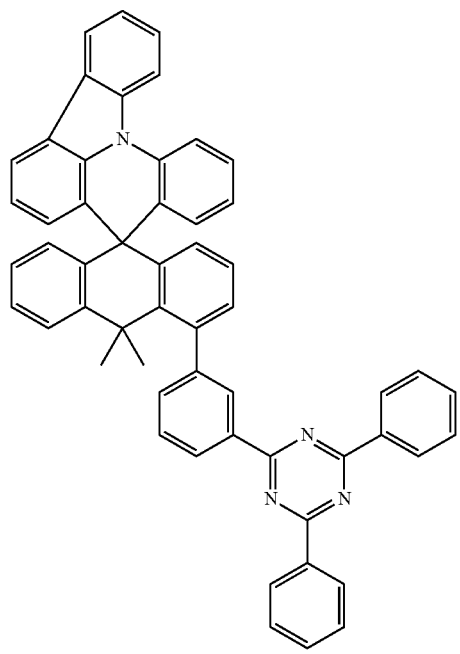
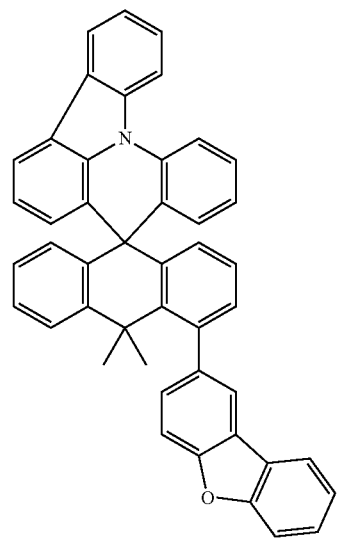
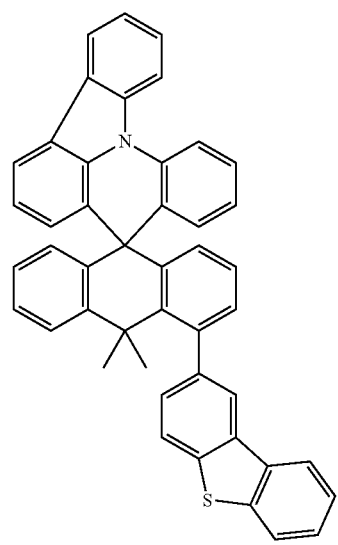
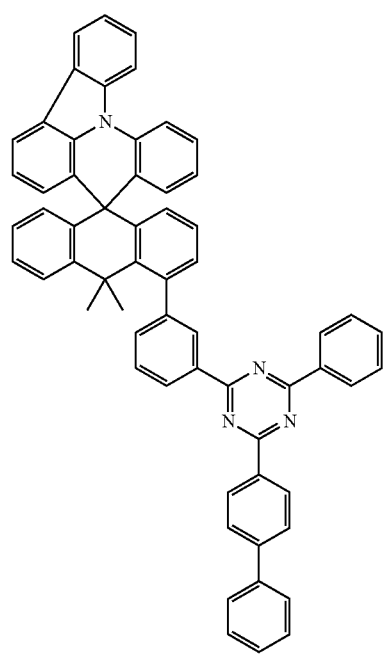

519
-continued
520
-continued
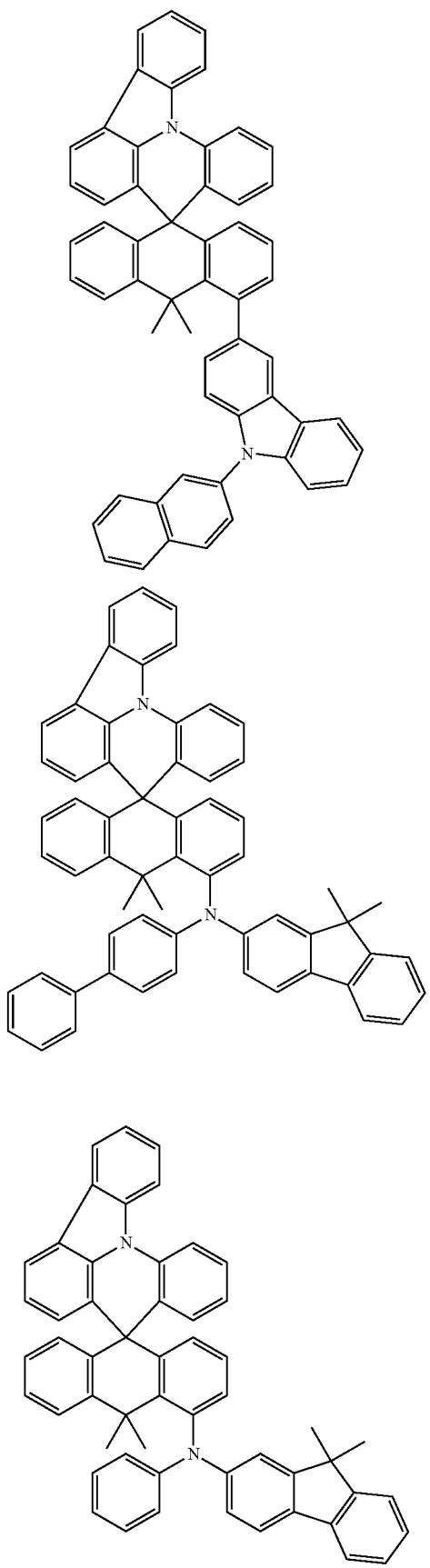
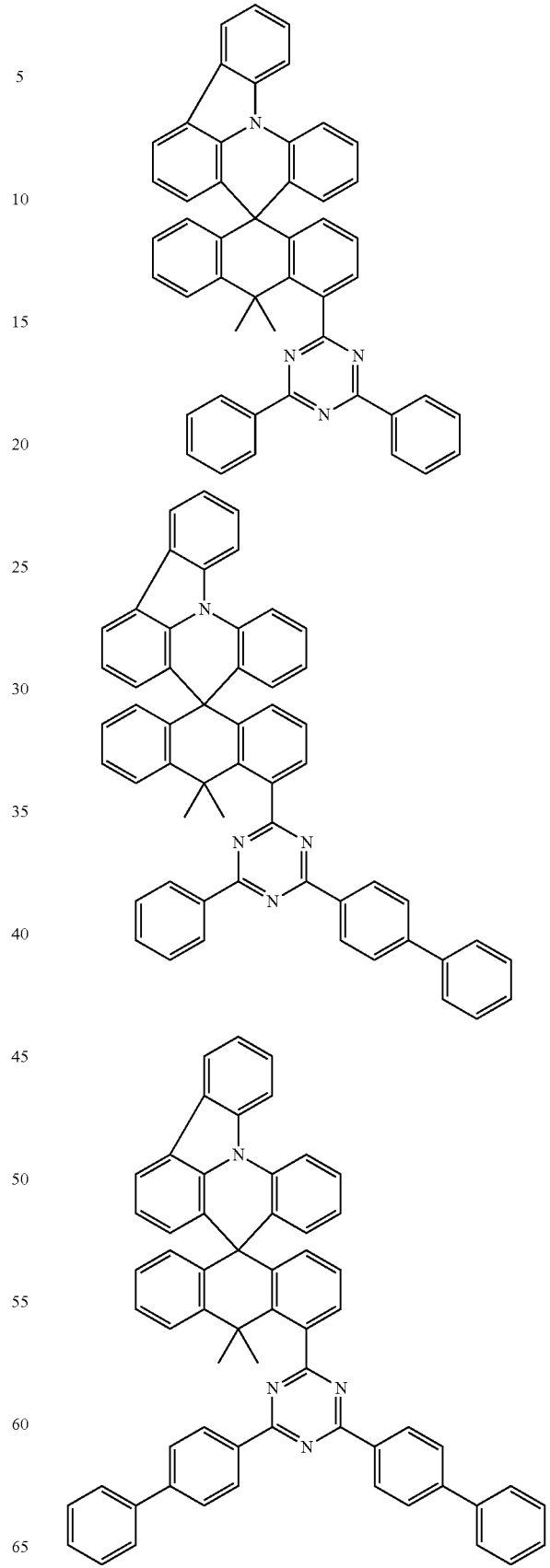

521
-continued
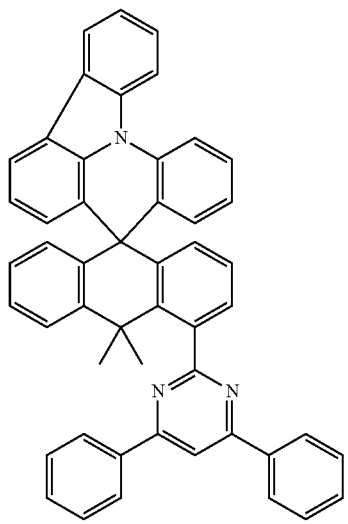 [SMILES: CC1(C)c2ccccc2C2(c3ccccc3-n3c4ccccc4c4cccc2c43)c2cccc(-c3nc(-c4ccccc4)cc(-c4ccccc4)n3)c21]
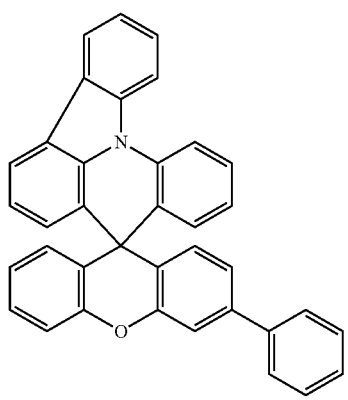
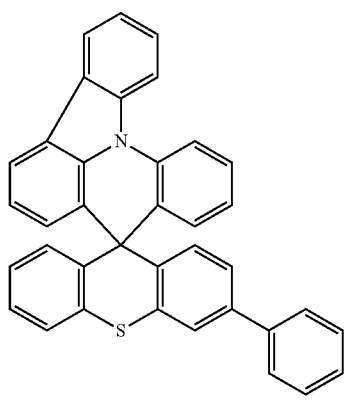
522
-continued
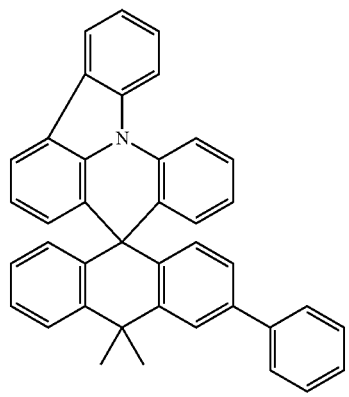
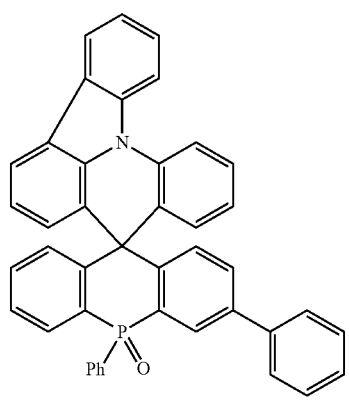
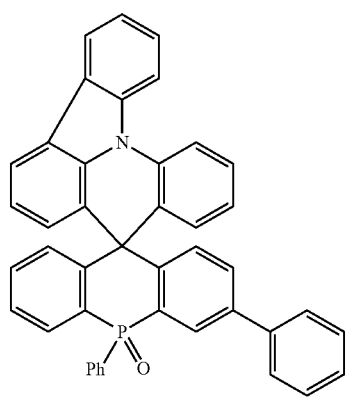
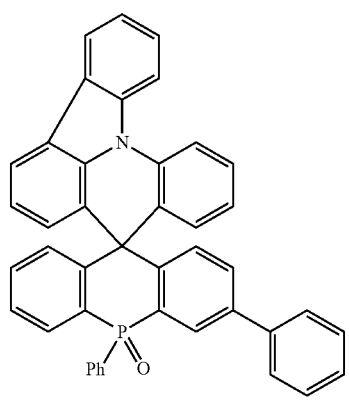

523
-continued
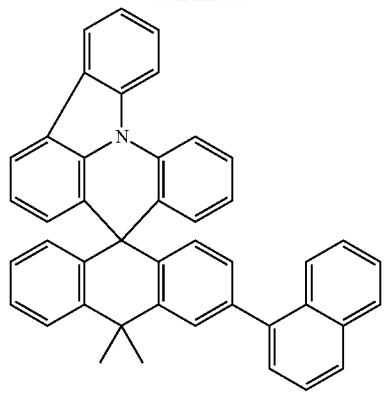
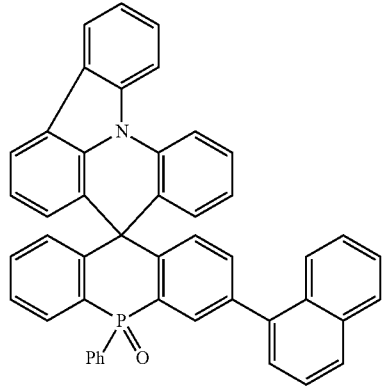
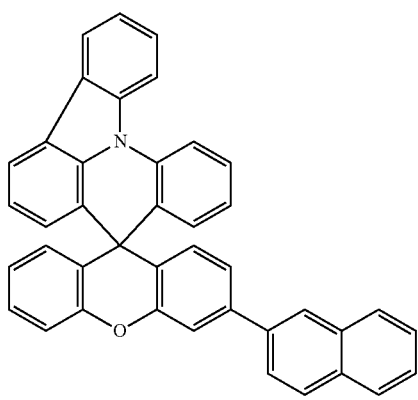
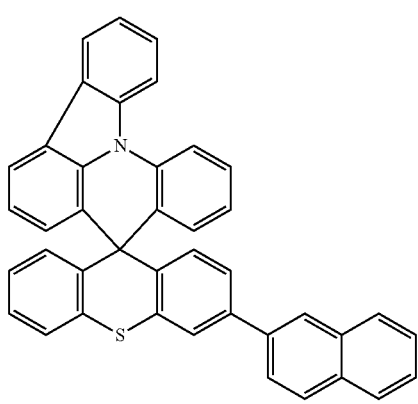
524
-continued
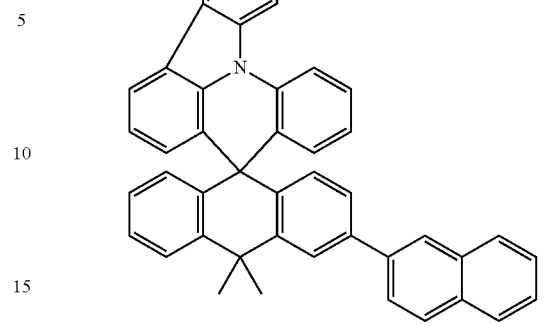
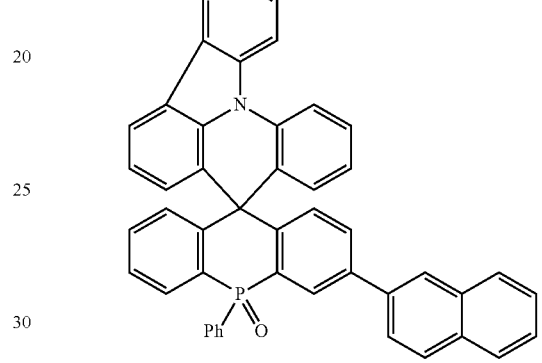
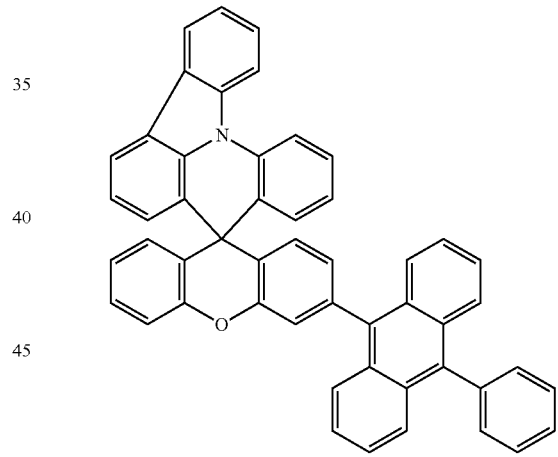
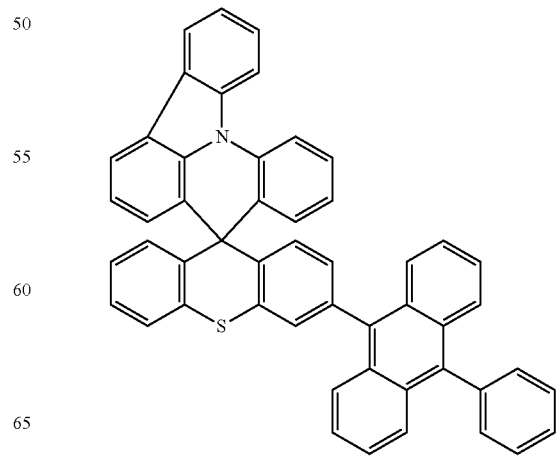

525
-continued
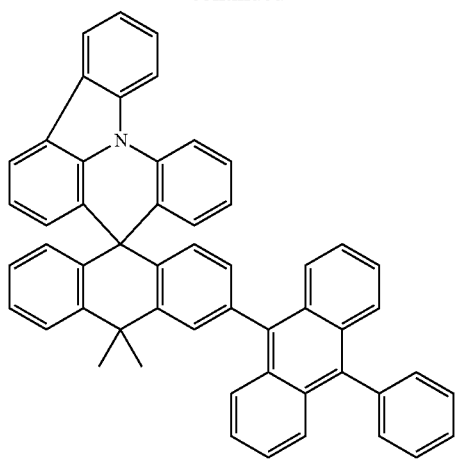
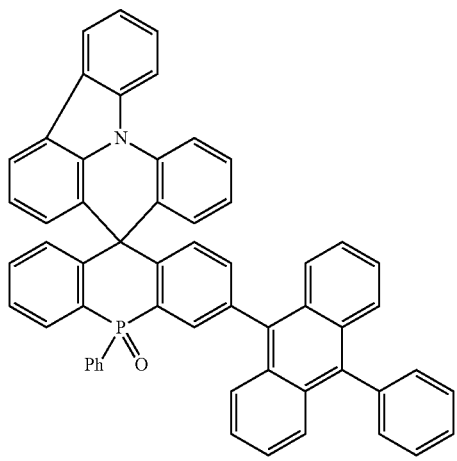
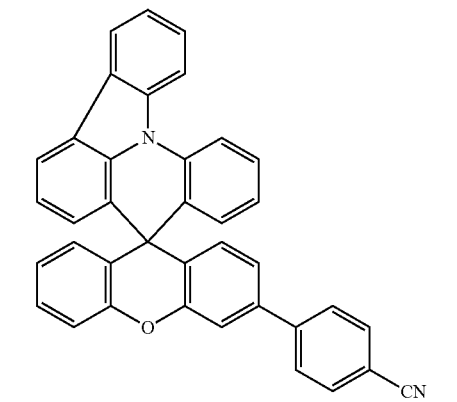
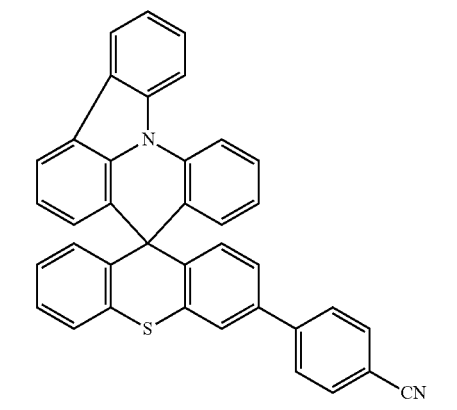
526
-continued
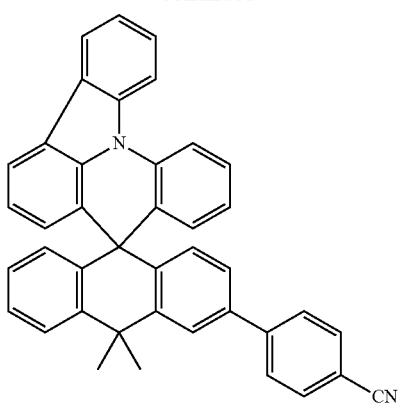
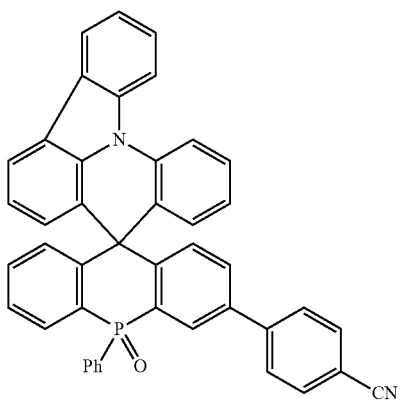
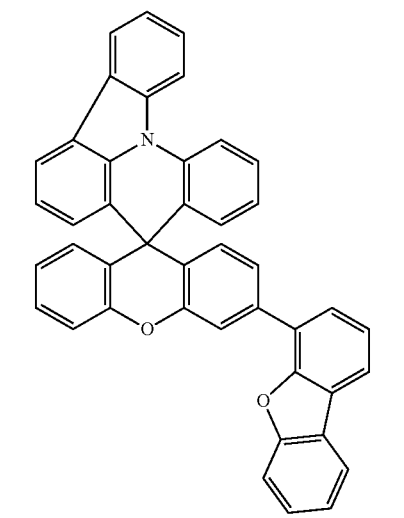

527
-continued
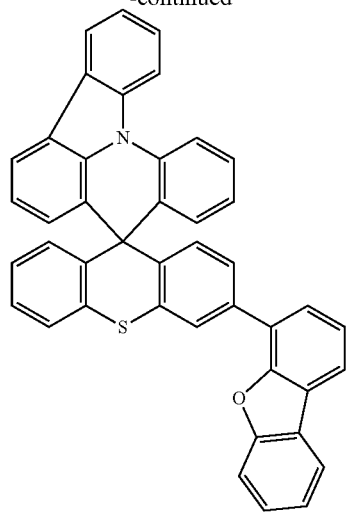
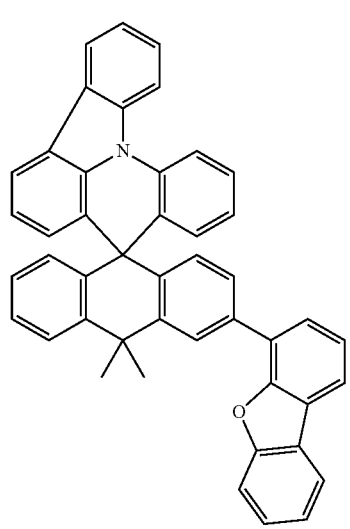
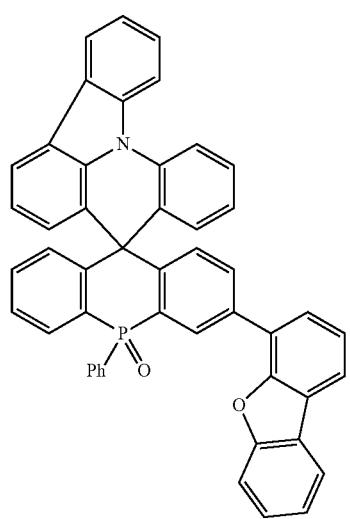
528
-continued
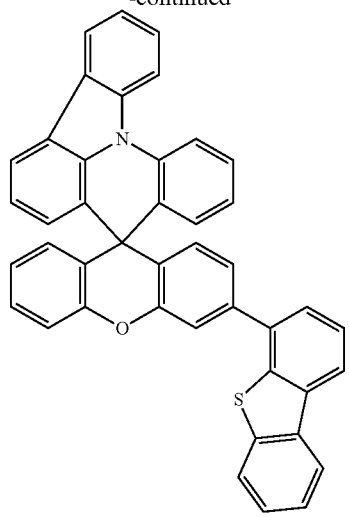
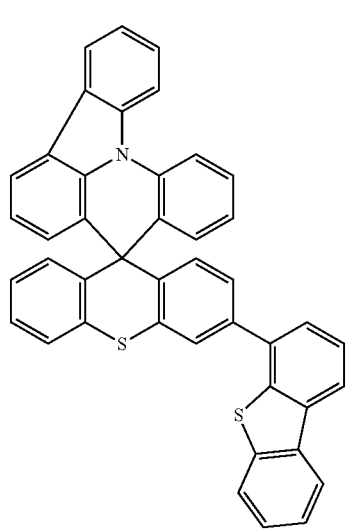
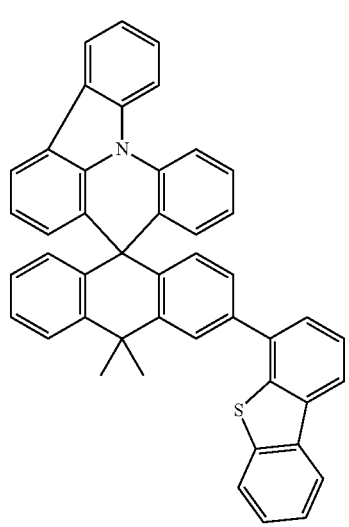

529
-continued
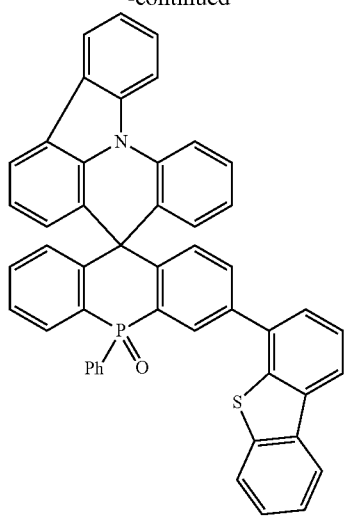
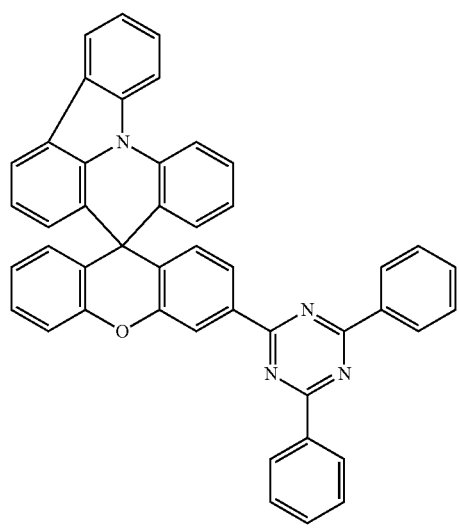
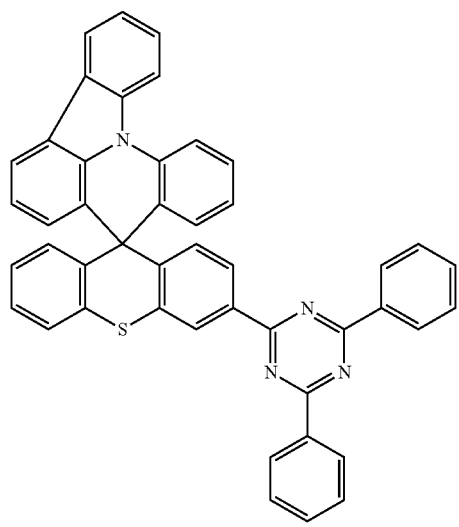
530
-continued
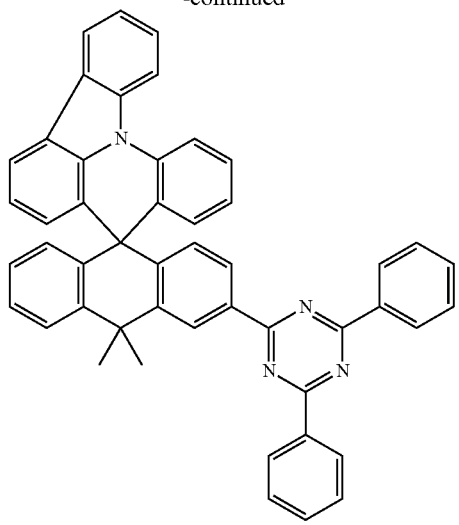
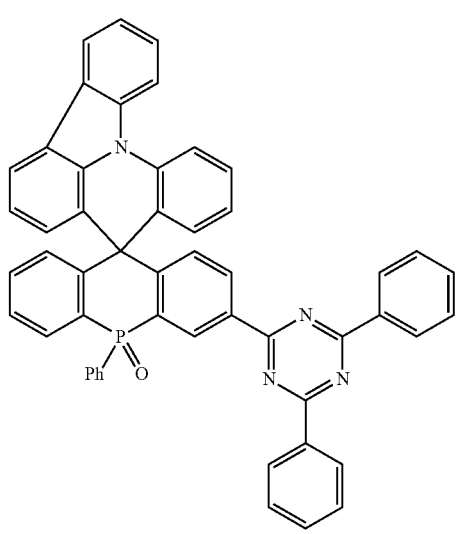
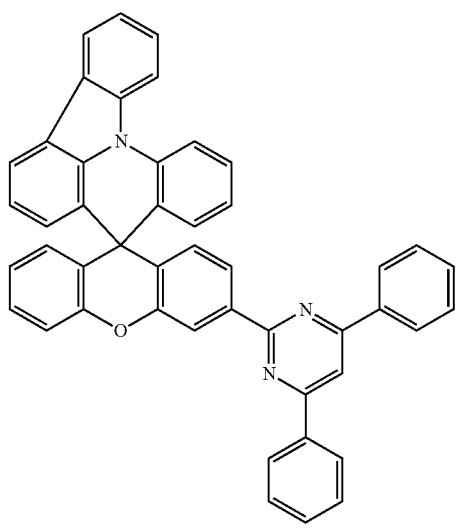

531
-continued
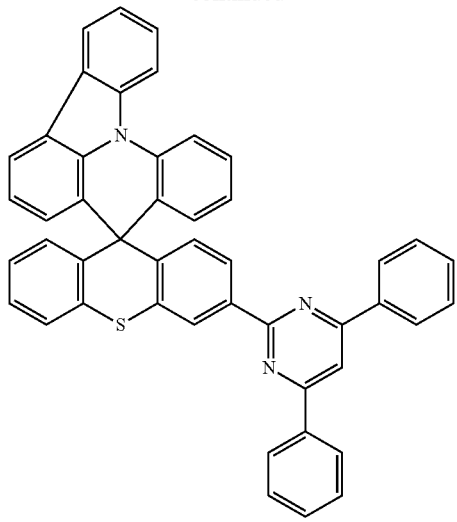
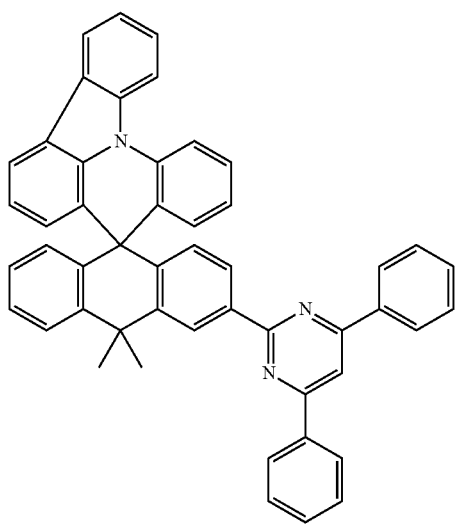
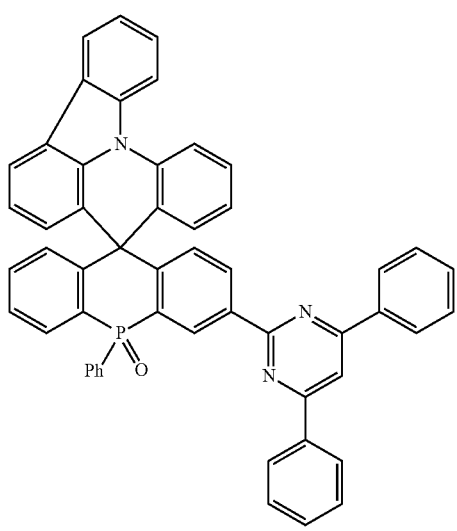
532
-continued
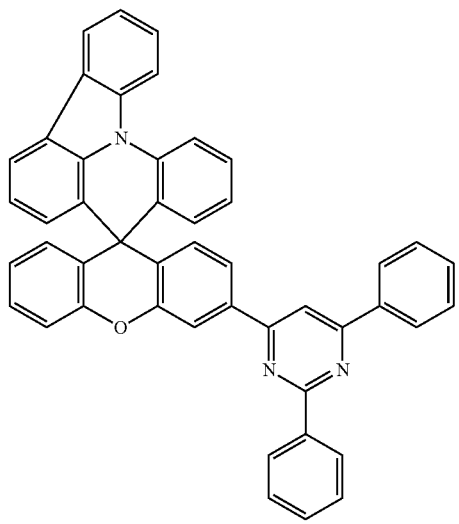
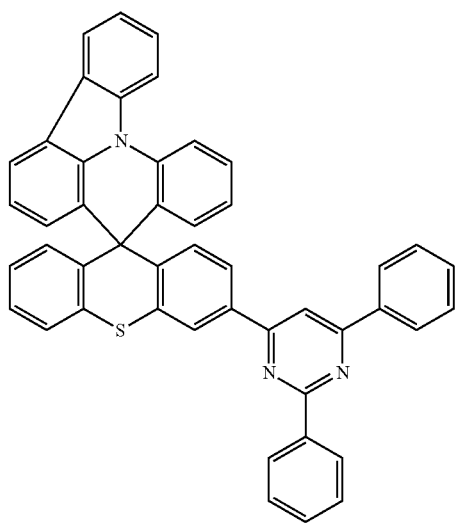
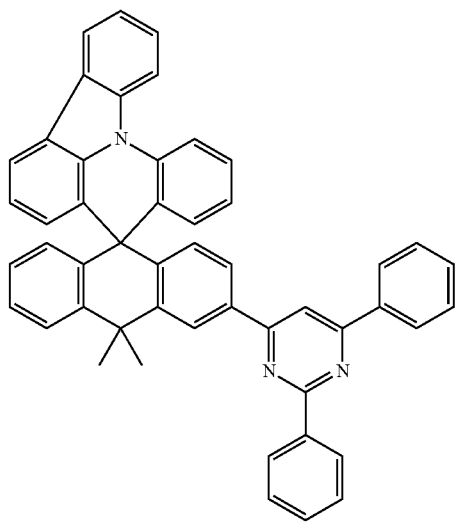

533
-continued
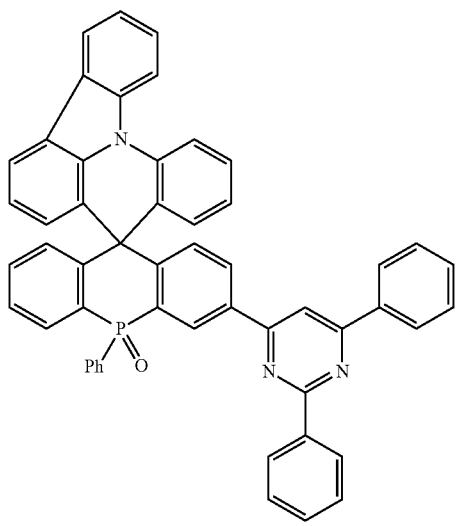
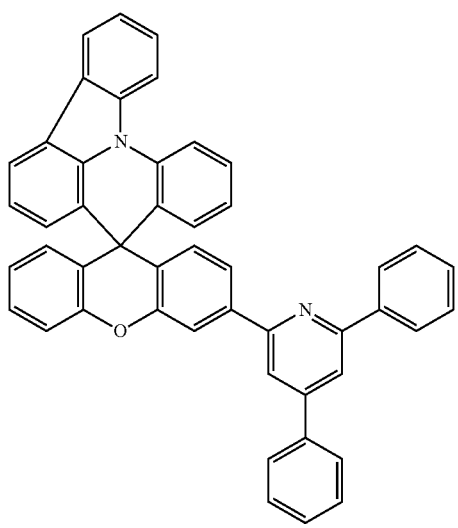
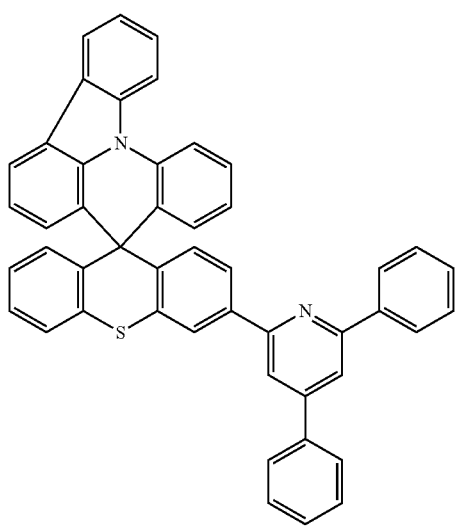
534
-continued
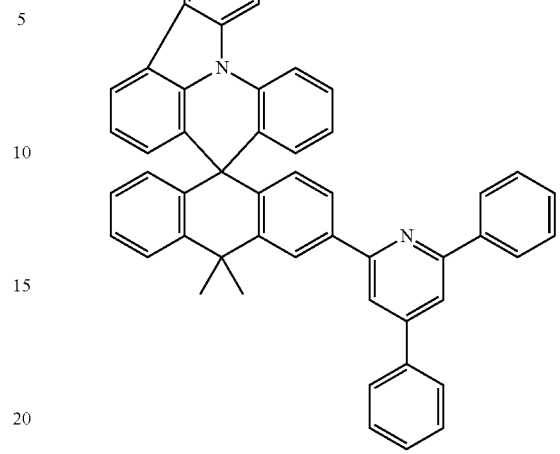
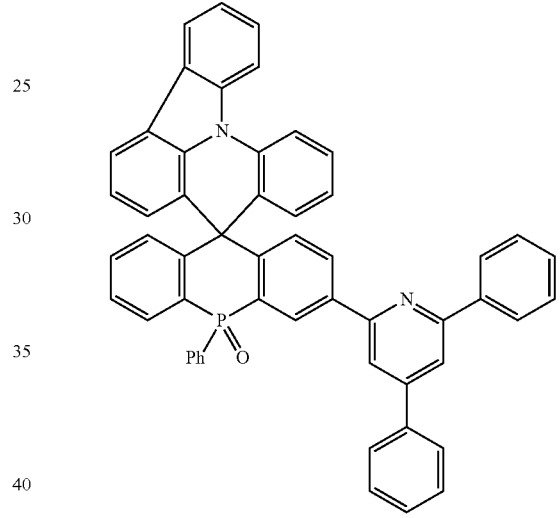
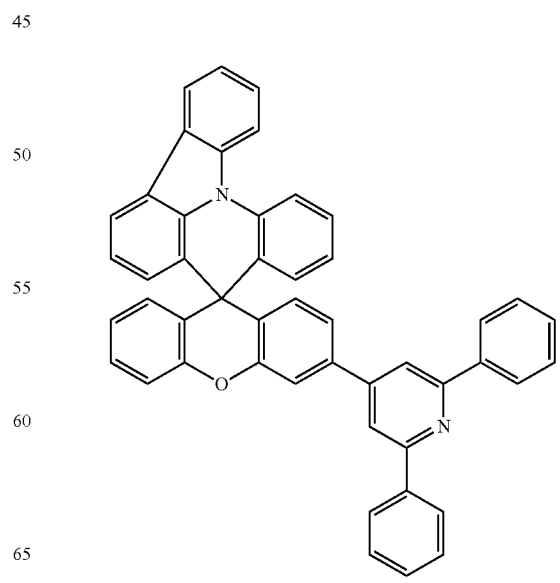

535
-continued
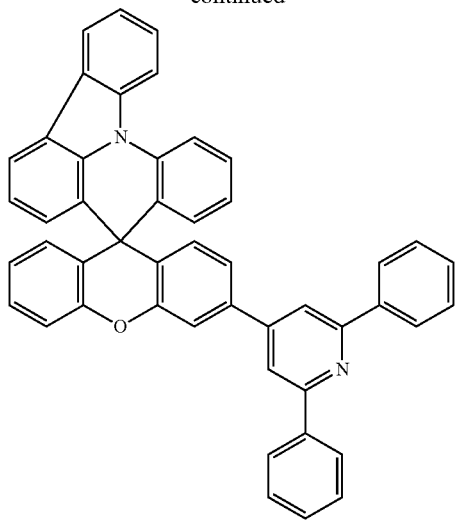
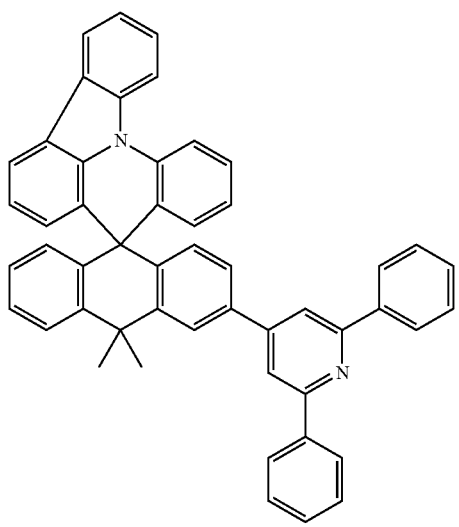
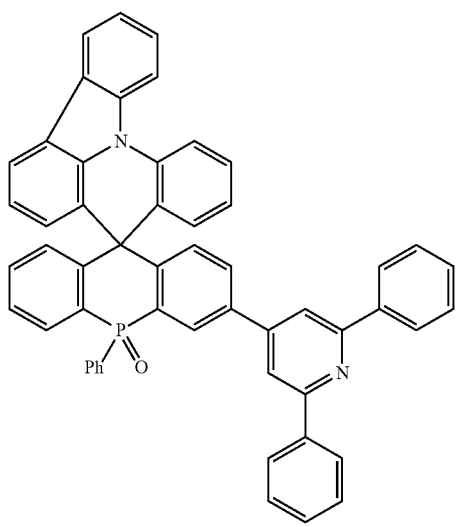
536
-continued
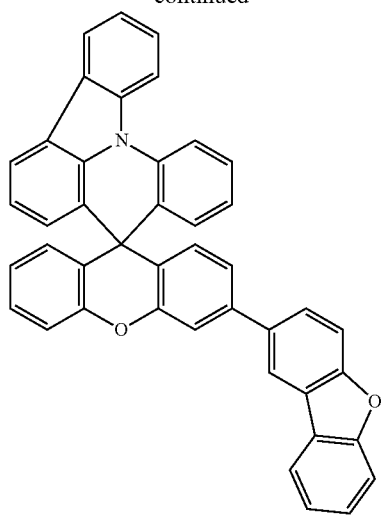
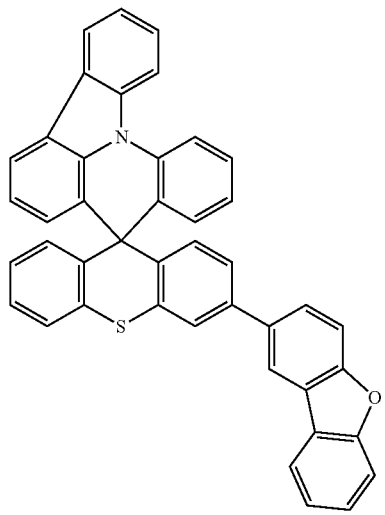
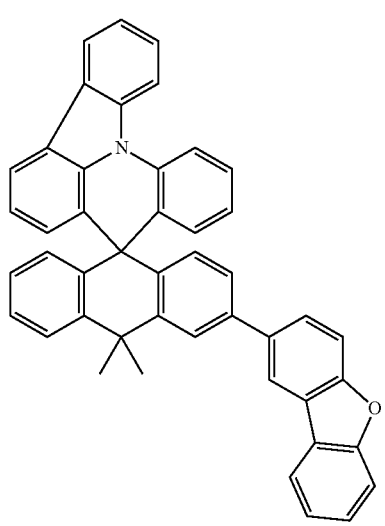

537
-continued
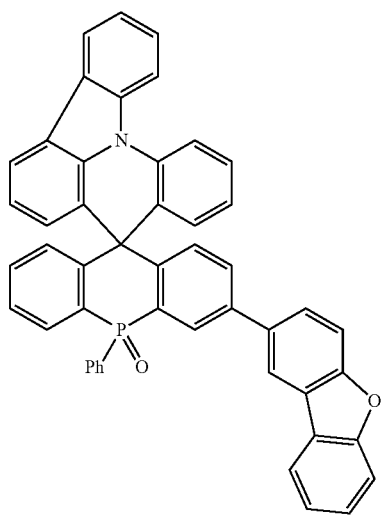
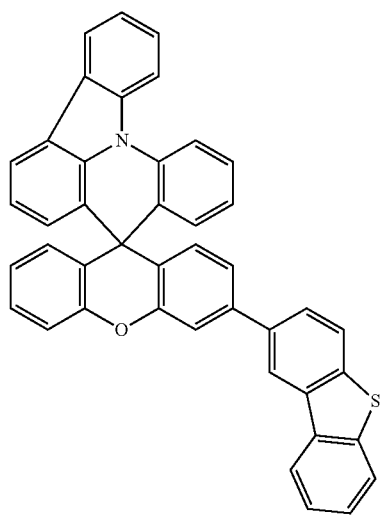
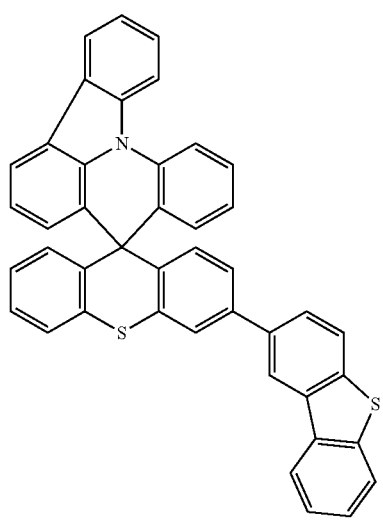
538
-continued
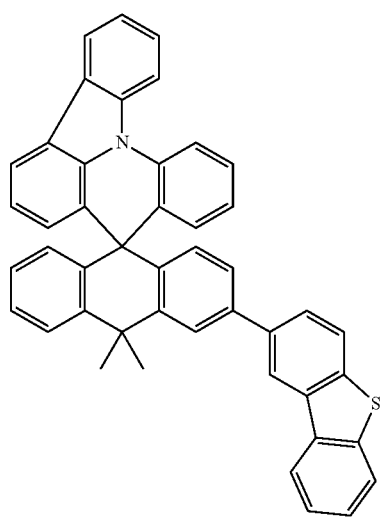
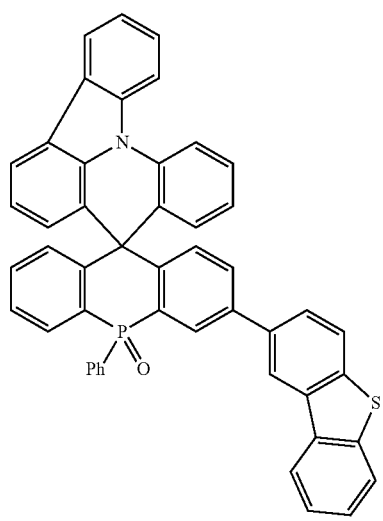
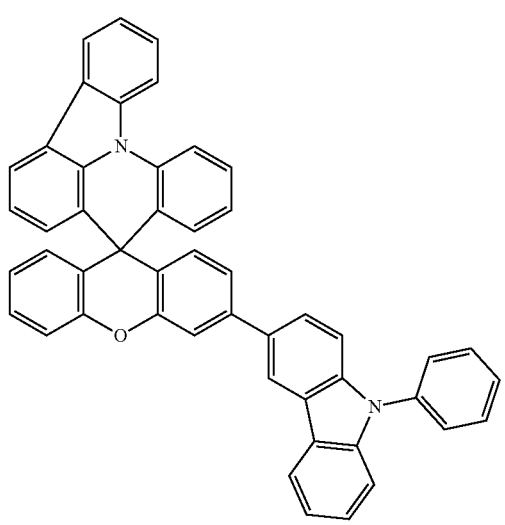

539
-continued
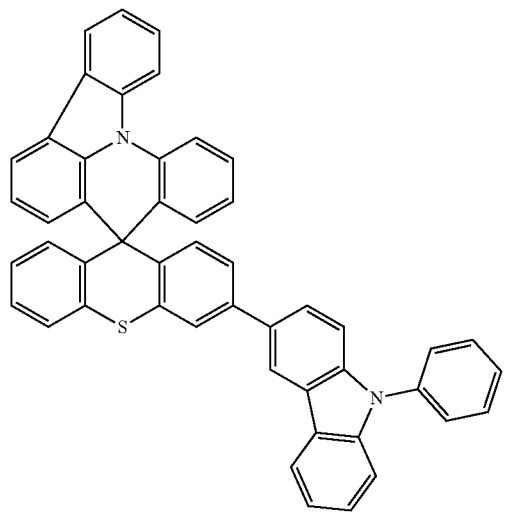
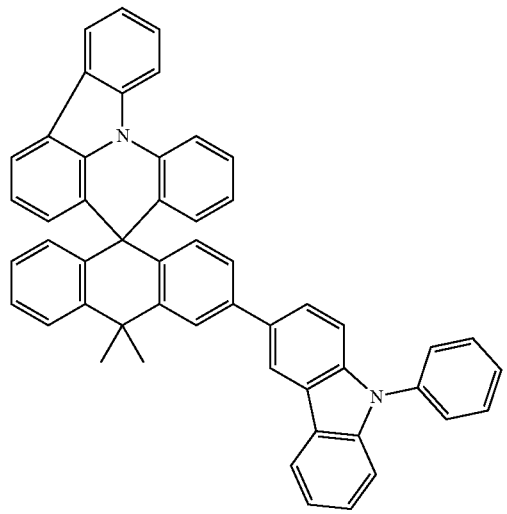
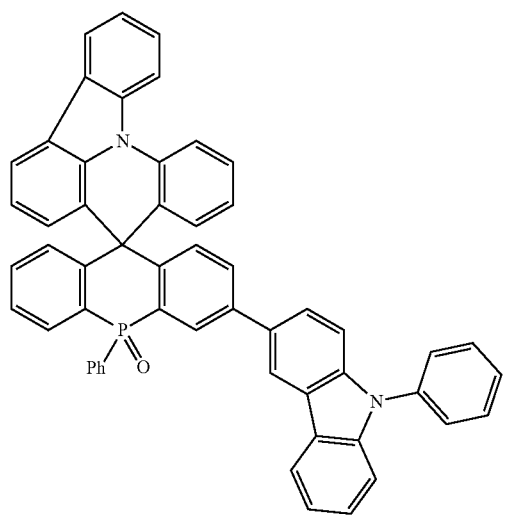
540
-continued
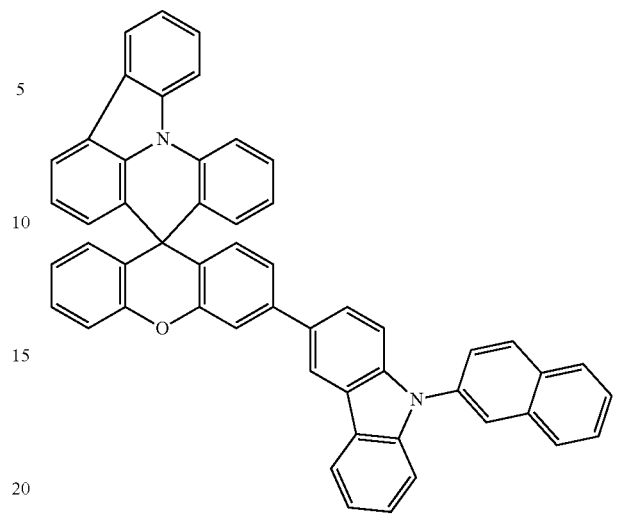
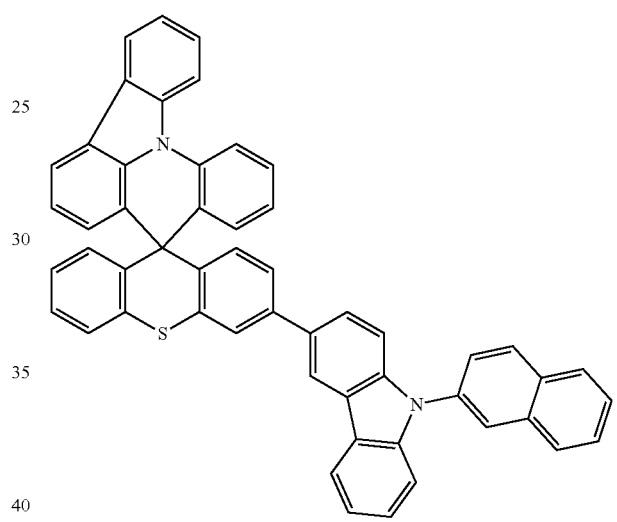
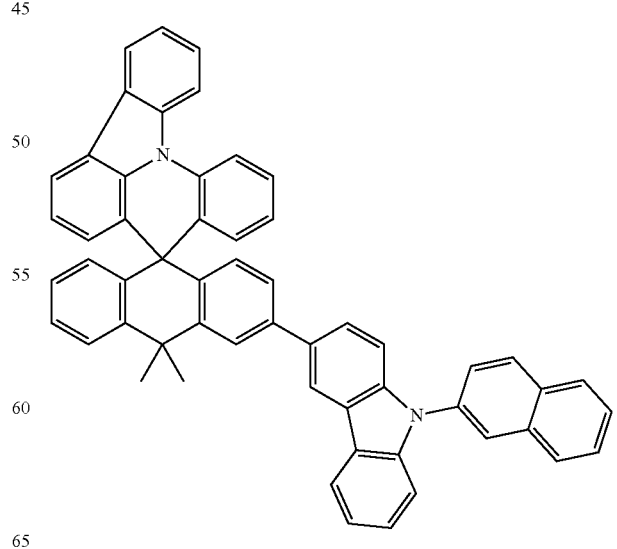

541
-continued
542
-continued
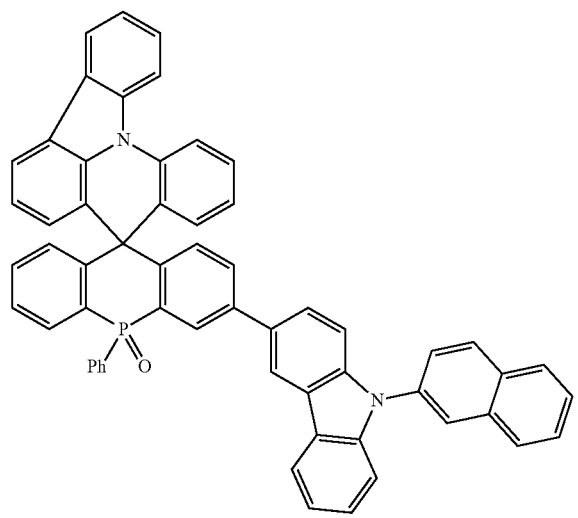
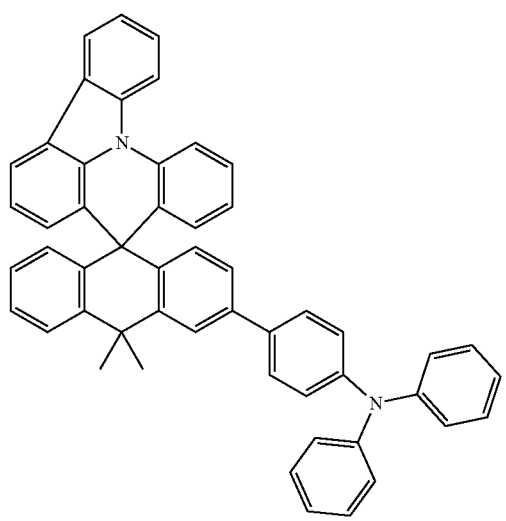
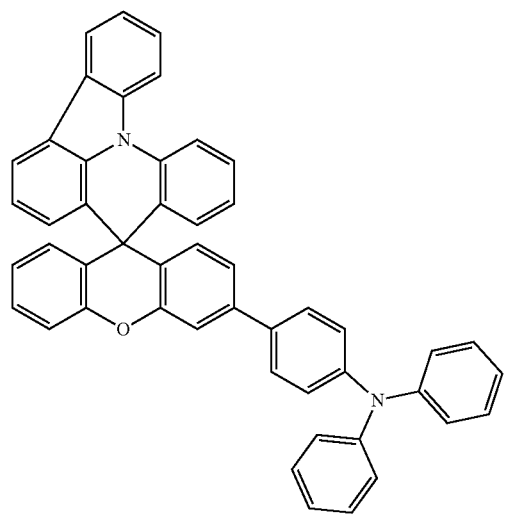
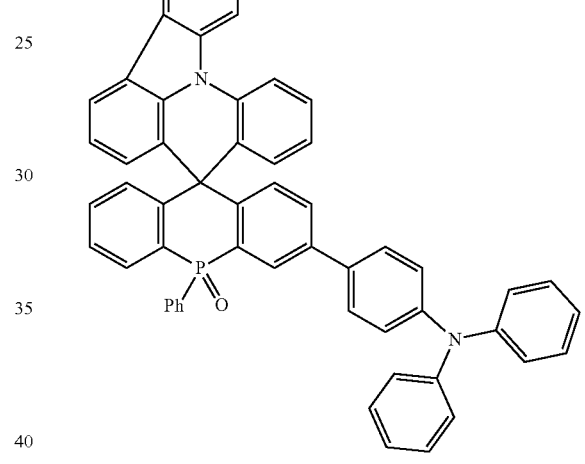
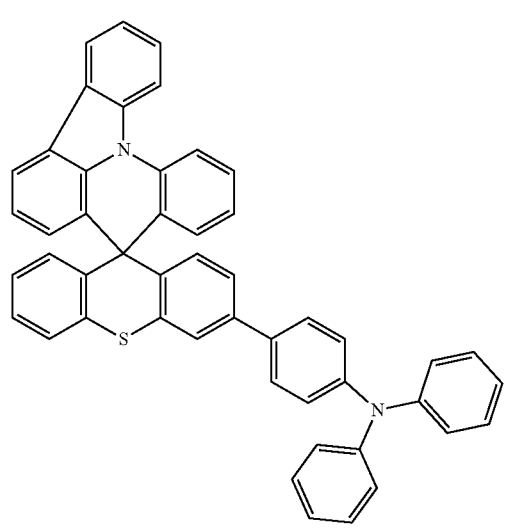
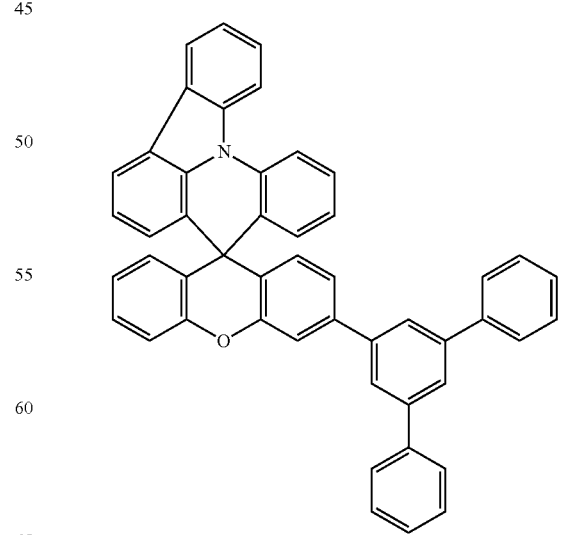

543
-continued
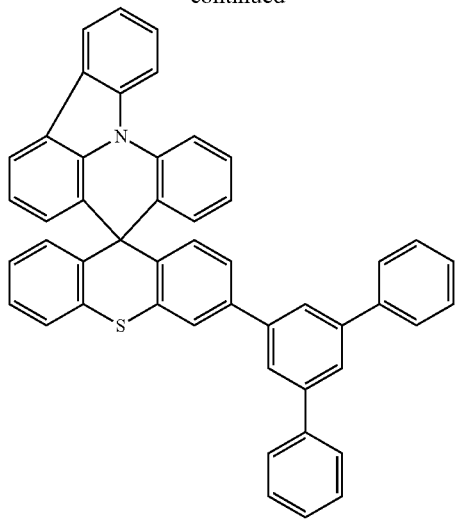
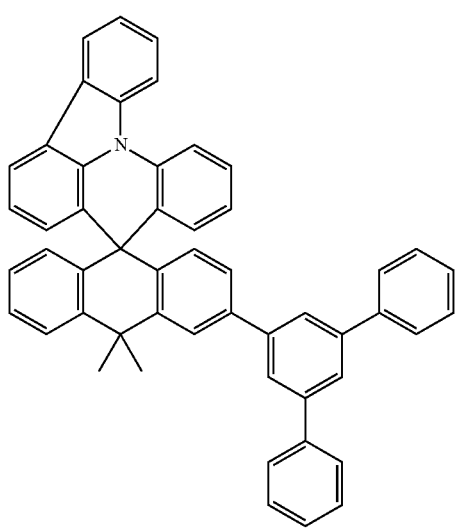
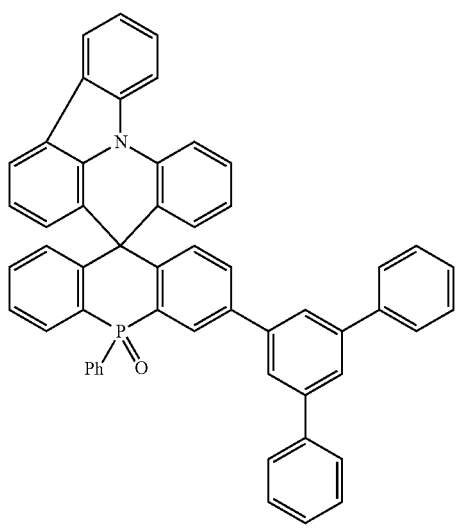
544
-continued
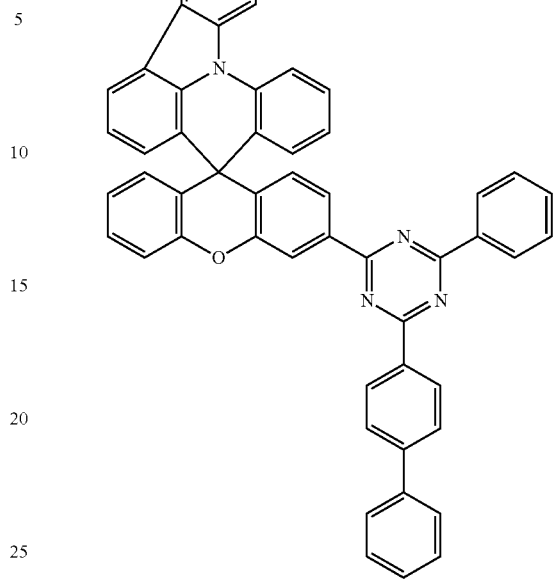
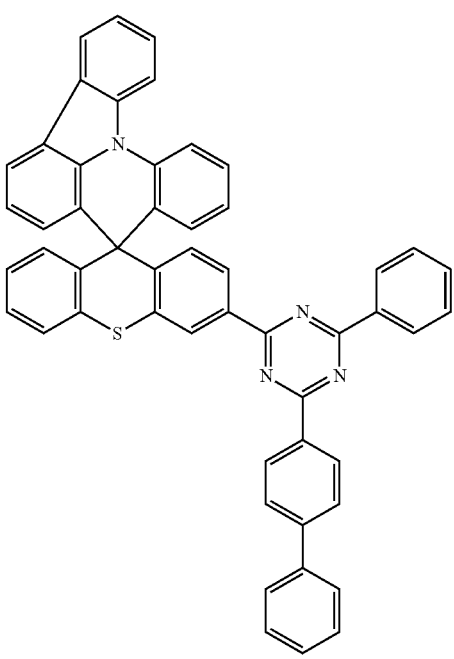

545
-continued
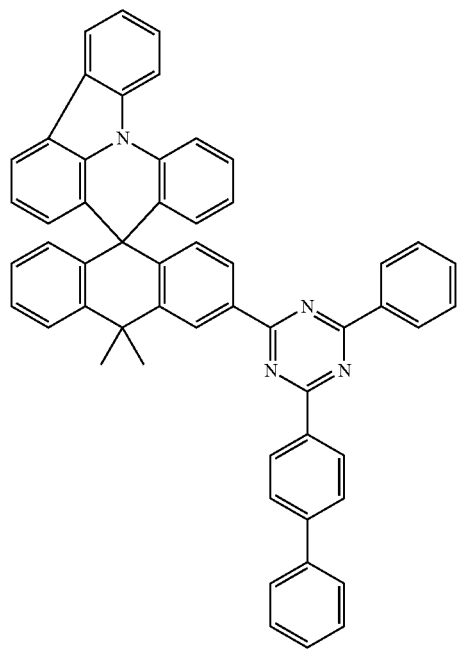
546
-continued
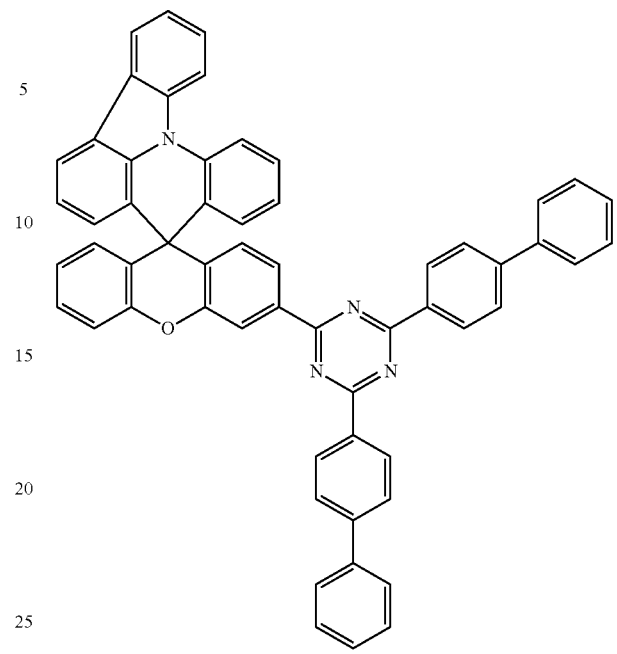
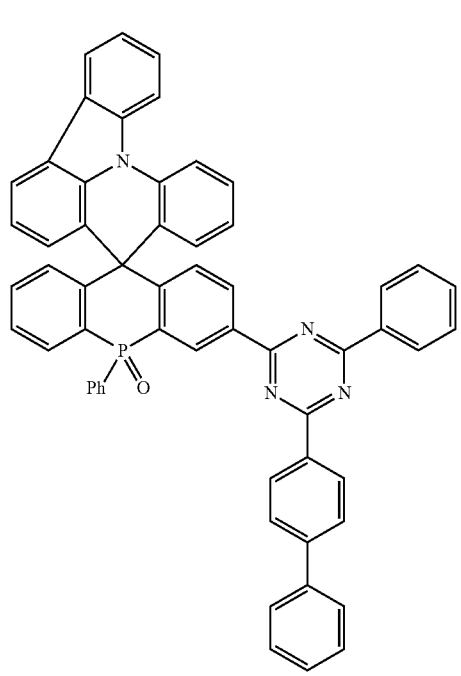
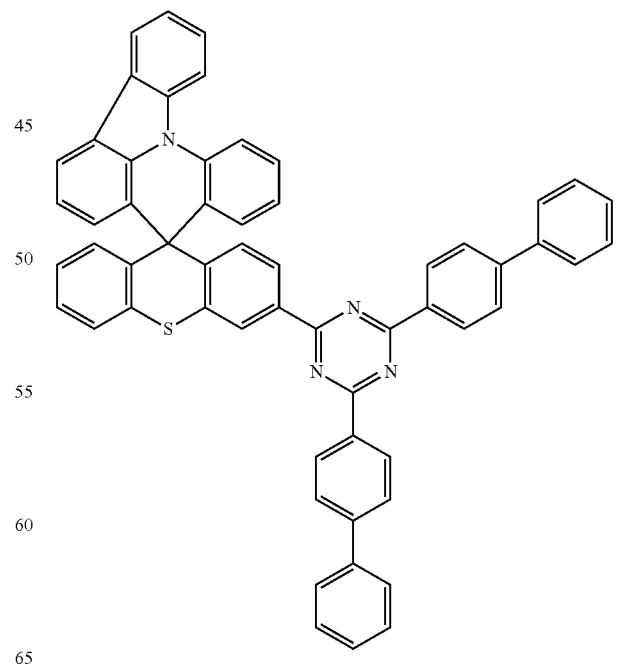

547
-continued
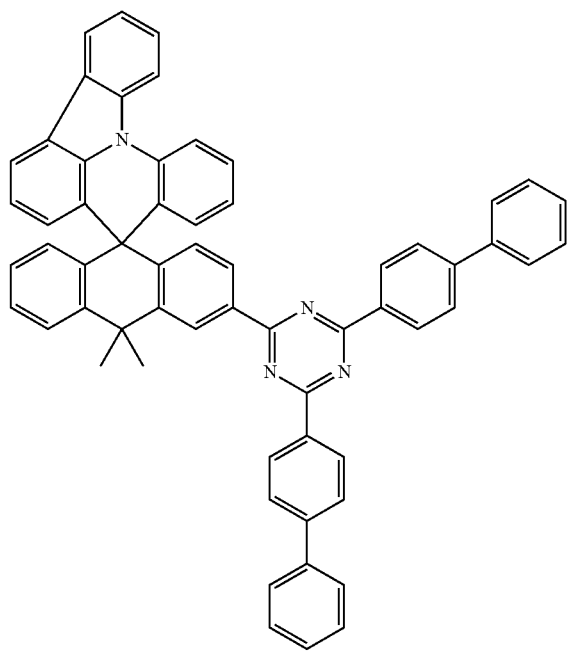
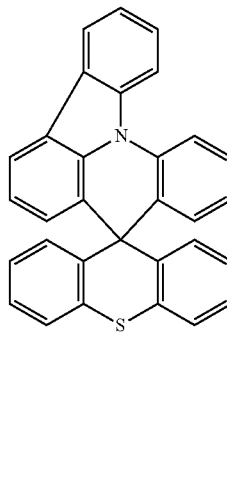
548
-continued
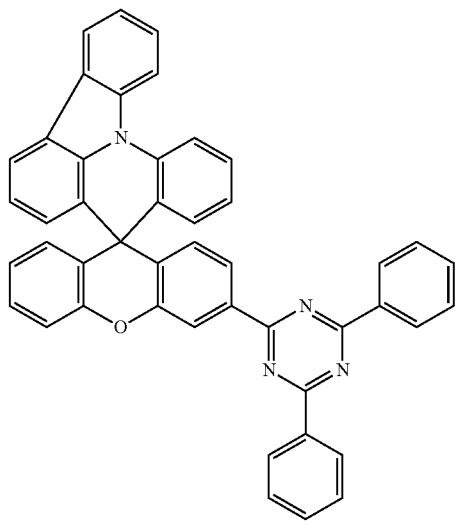
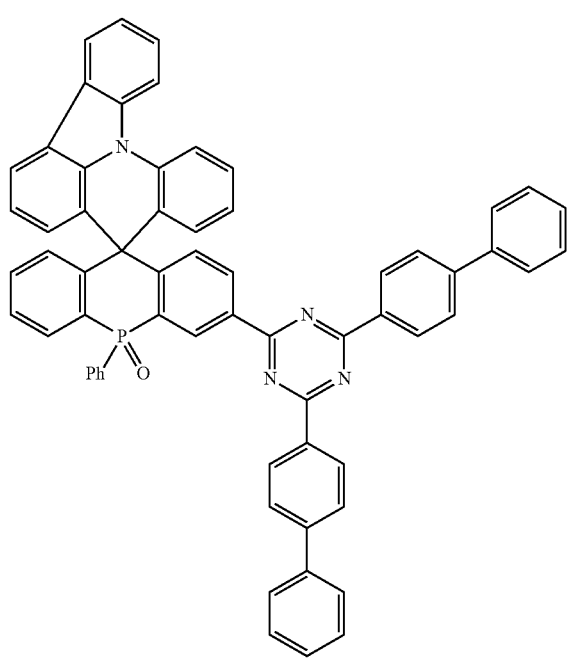
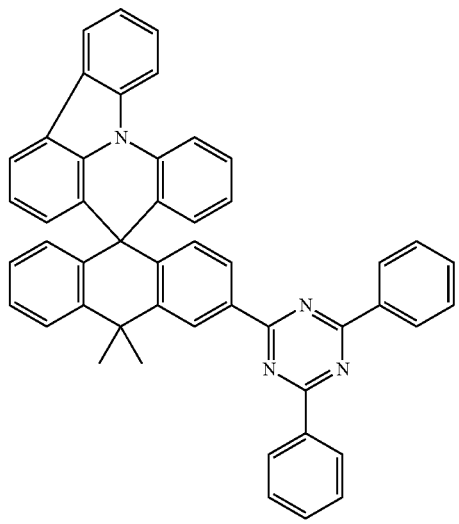

549
-continued
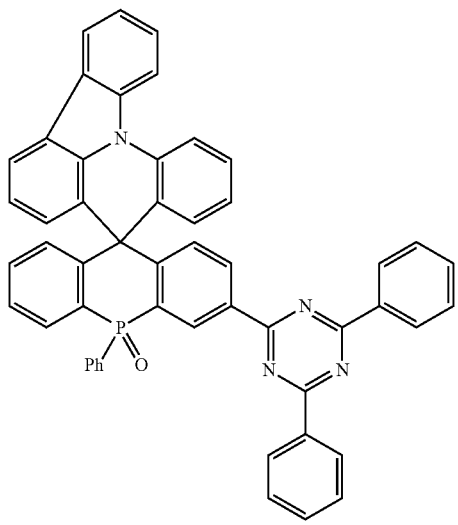
550
-continued
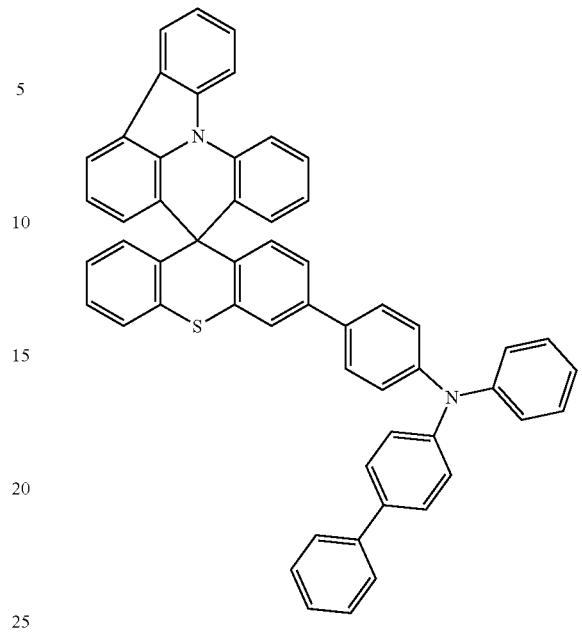
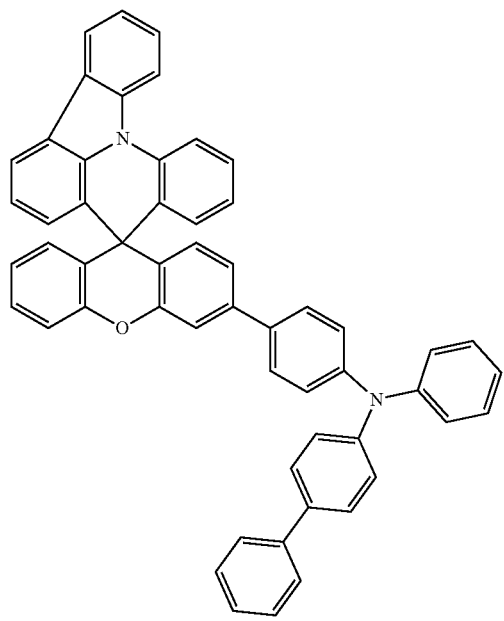
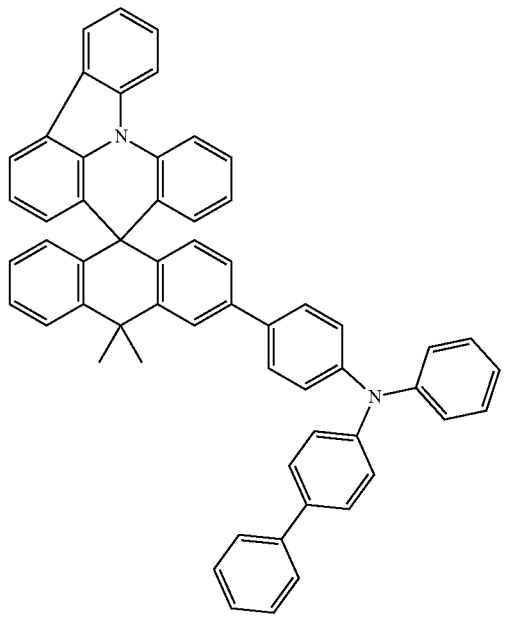

551
-continued
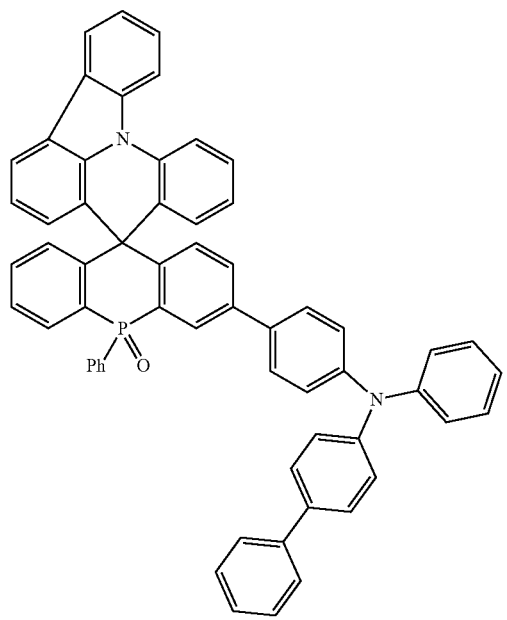
552
-continued
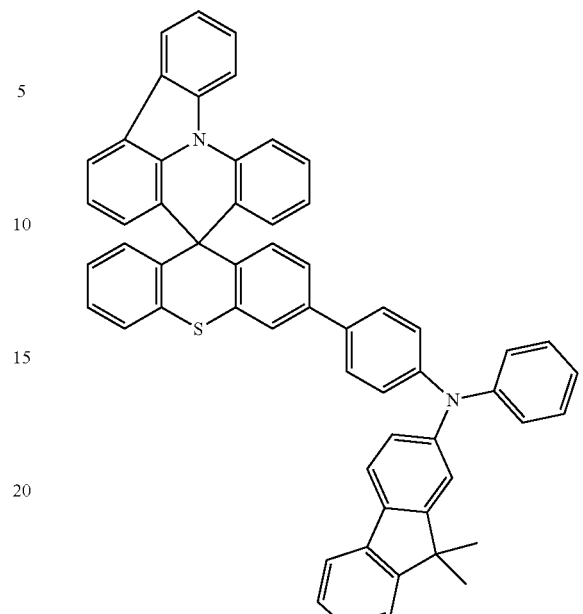
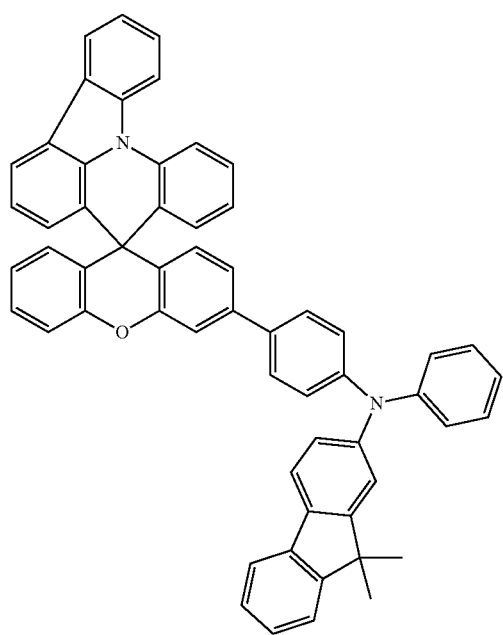
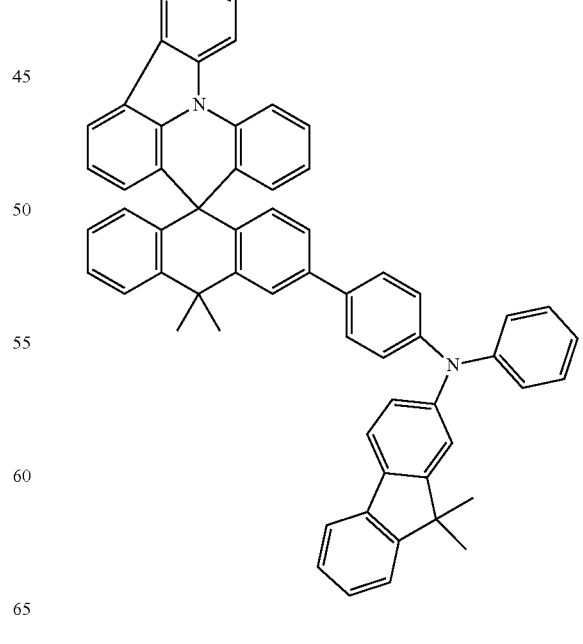

553
-continued
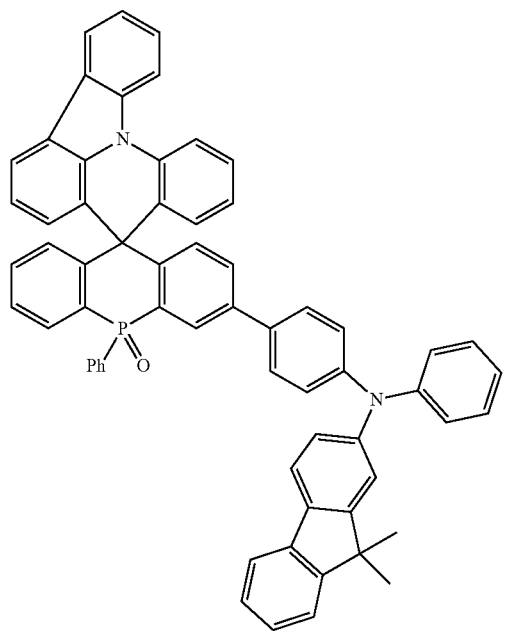
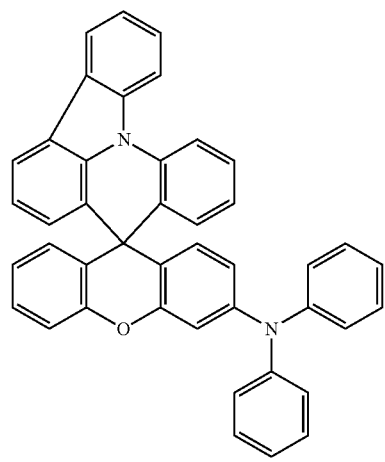
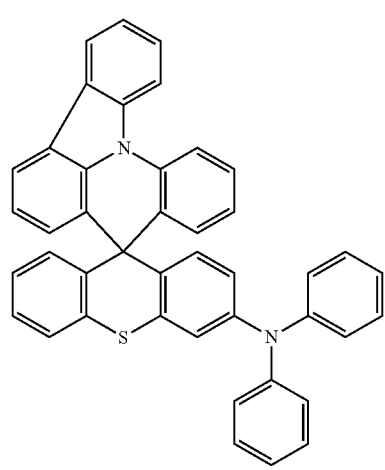
554
-continued
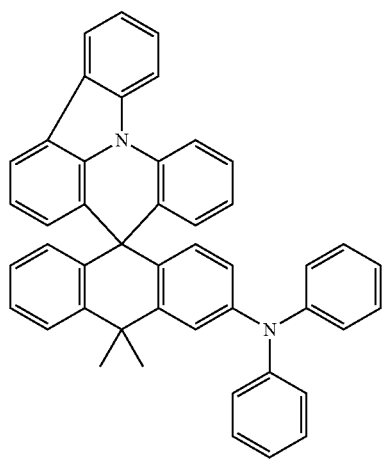
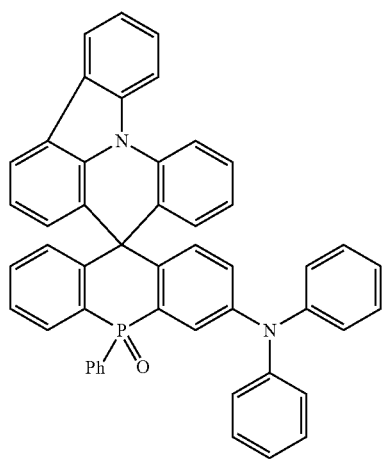
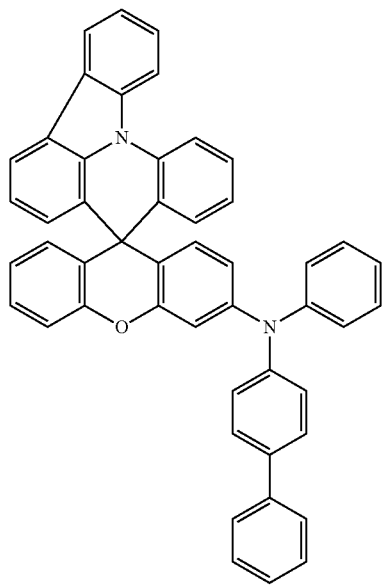

555
-continued
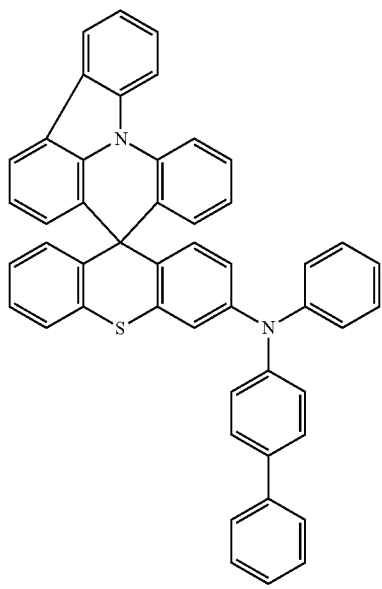
556
-continued
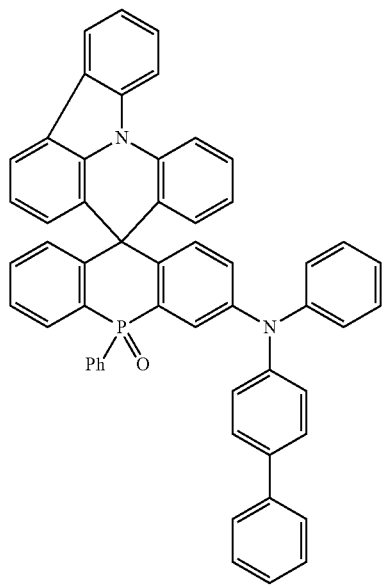
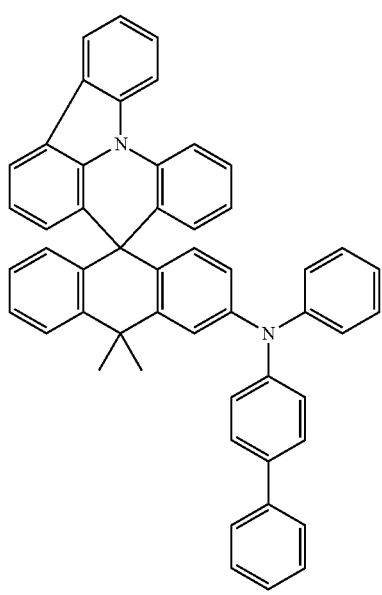
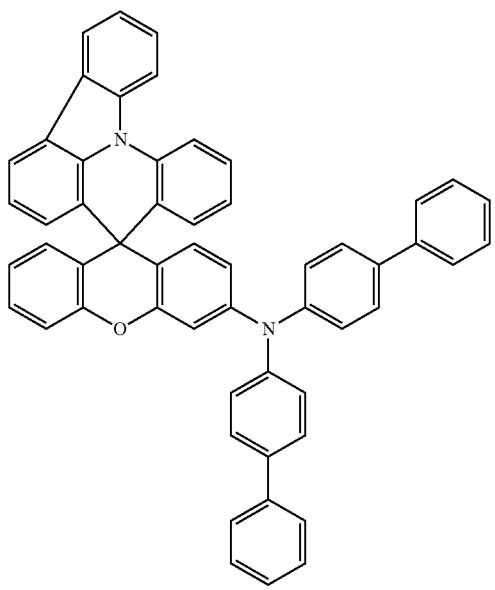

557
-continued
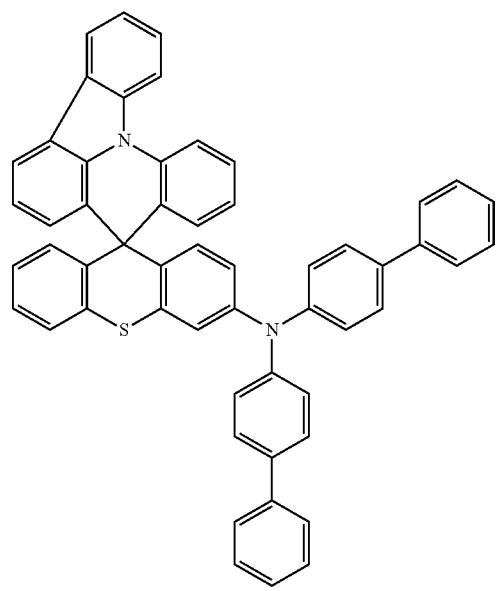
558
-continued
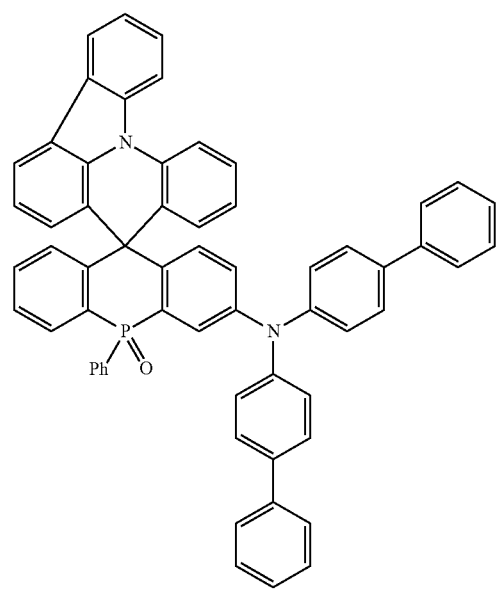
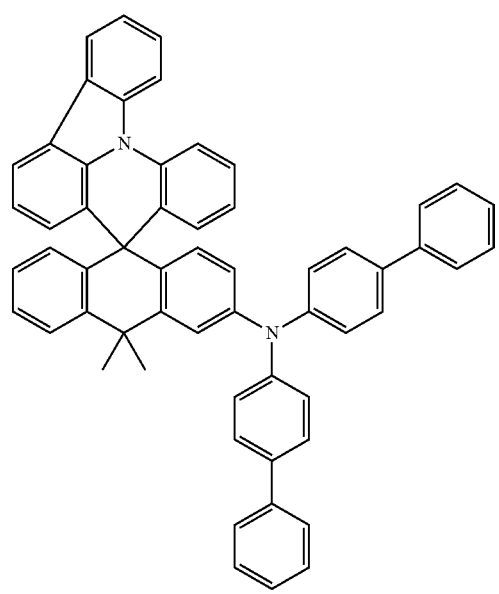
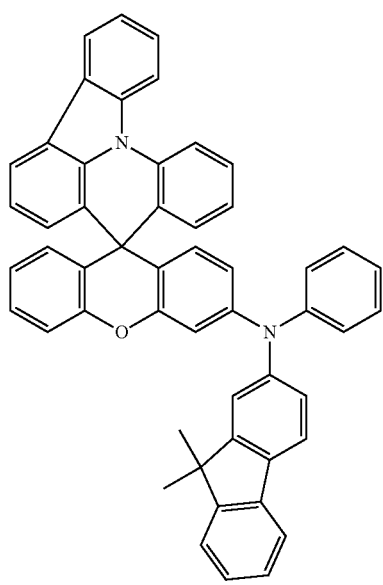

| 559 -continued | 560 -continued |
|---|---|
| 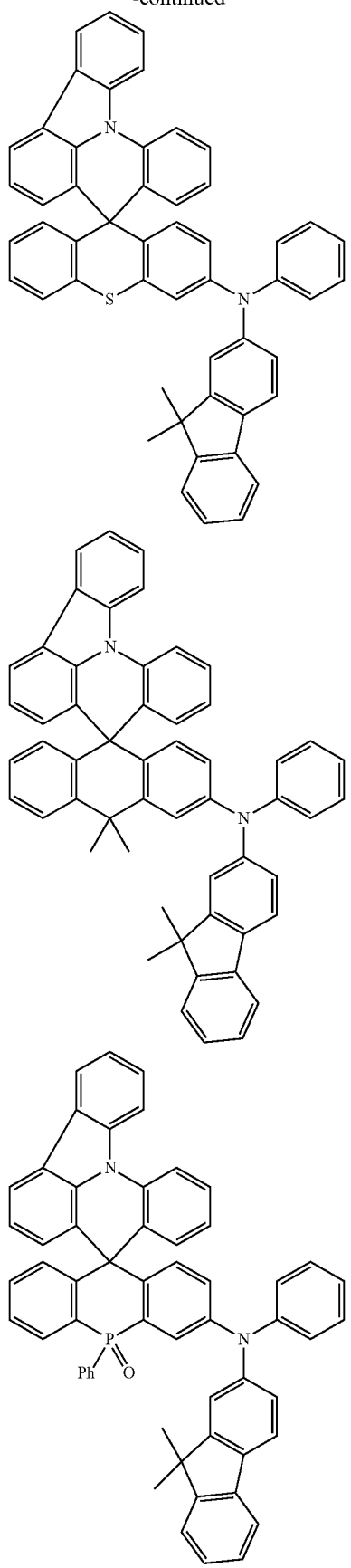 | 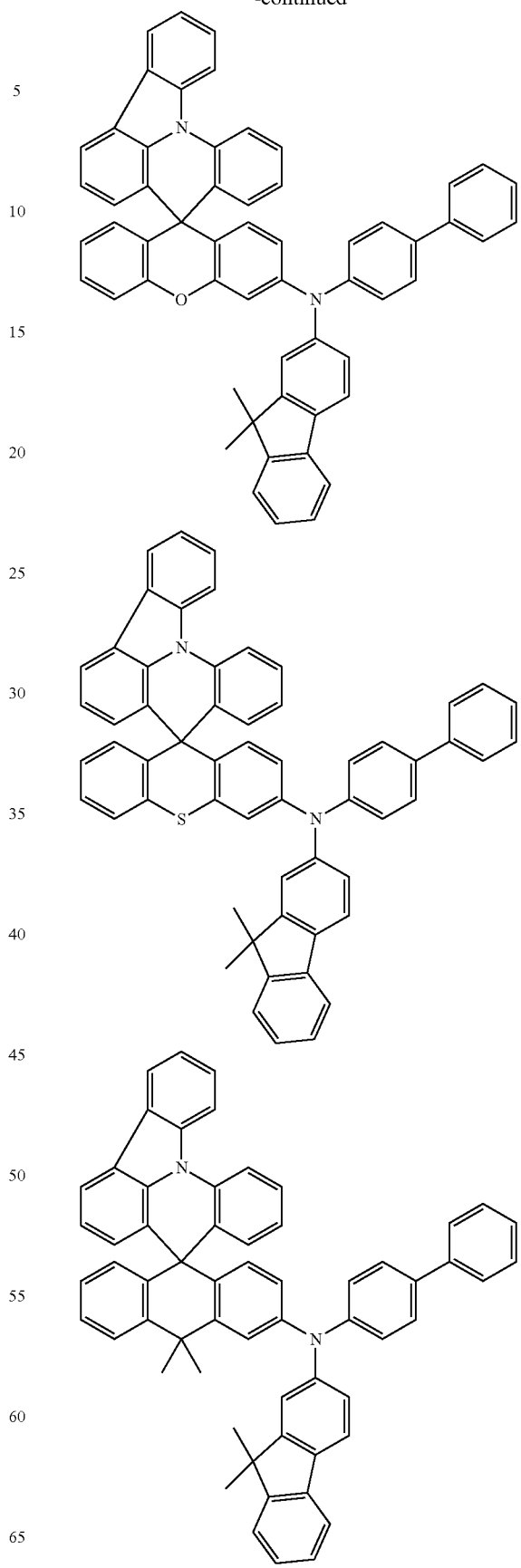 |

561
-continued
562
-continued
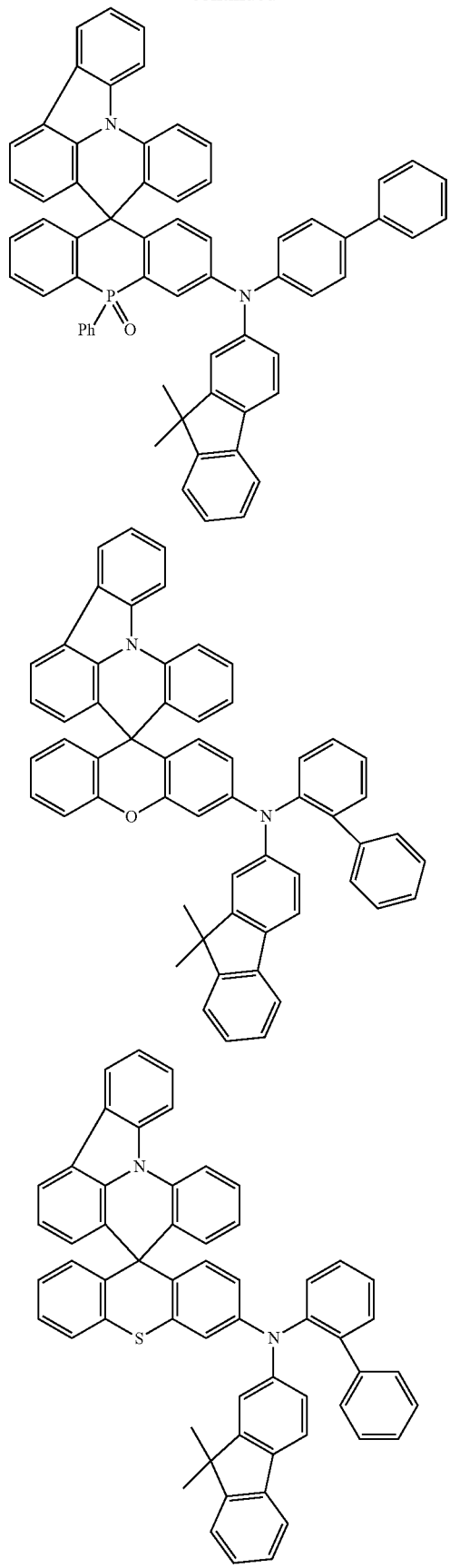 [SMILES: CC1(C)c2ccccc2-c2ccc(N(c3ccc(-c4ccccc4)cc3)c3ccc4c(c3)P(=O)(c3ccccc3)c3ccccc3C43c4ccccc4-n4c5ccccc5c5cccc3c54)cc21 ; CC1(C)c2ccccc2-c2ccc(N(c3ccc4c(c3)Oc3ccccc3C43c4ccccc4-n4c5ccccc5c5cccc3c54)c3ccccc3-c3ccccc3)cc21 ; CC1(C)c2ccccc2-c2ccc(N(c3ccc4c(c3)Sc3ccccc3C43c4ccccc4-n4c5ccccc5c5cccc3c54)c3ccccc3-c3ccccc3)cc21]

563
-continued
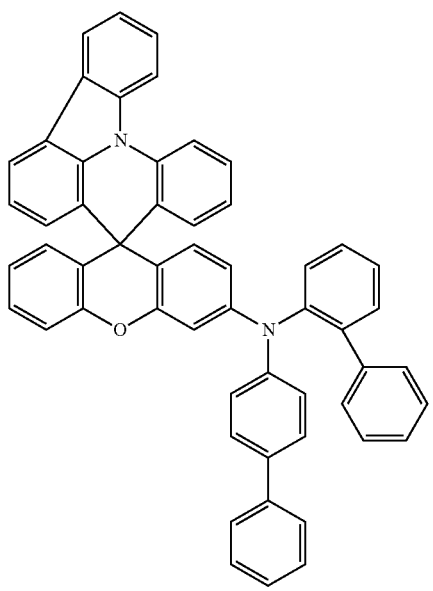
564
-continued
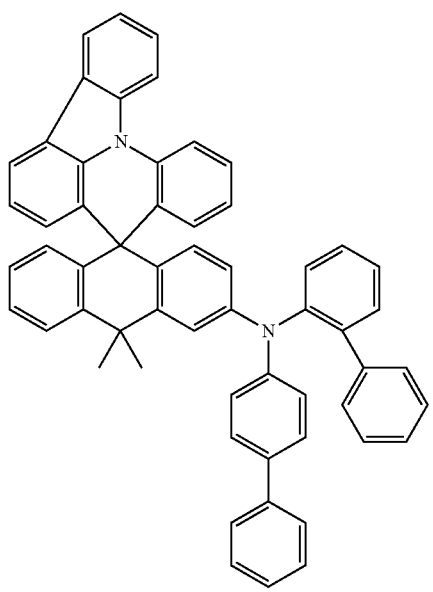
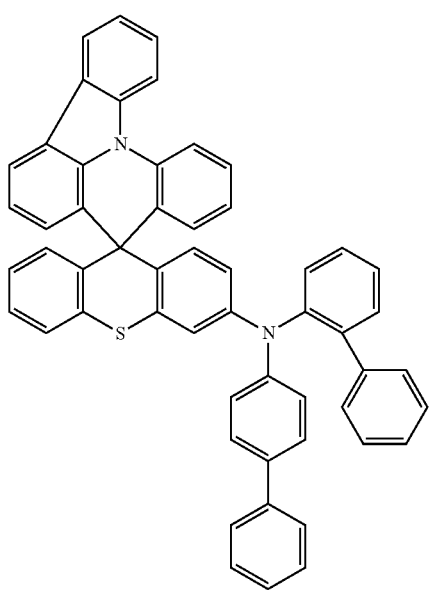
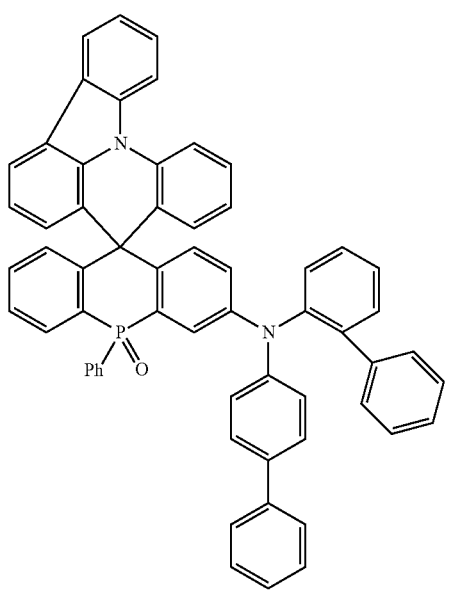

565
-continued
566
-continued
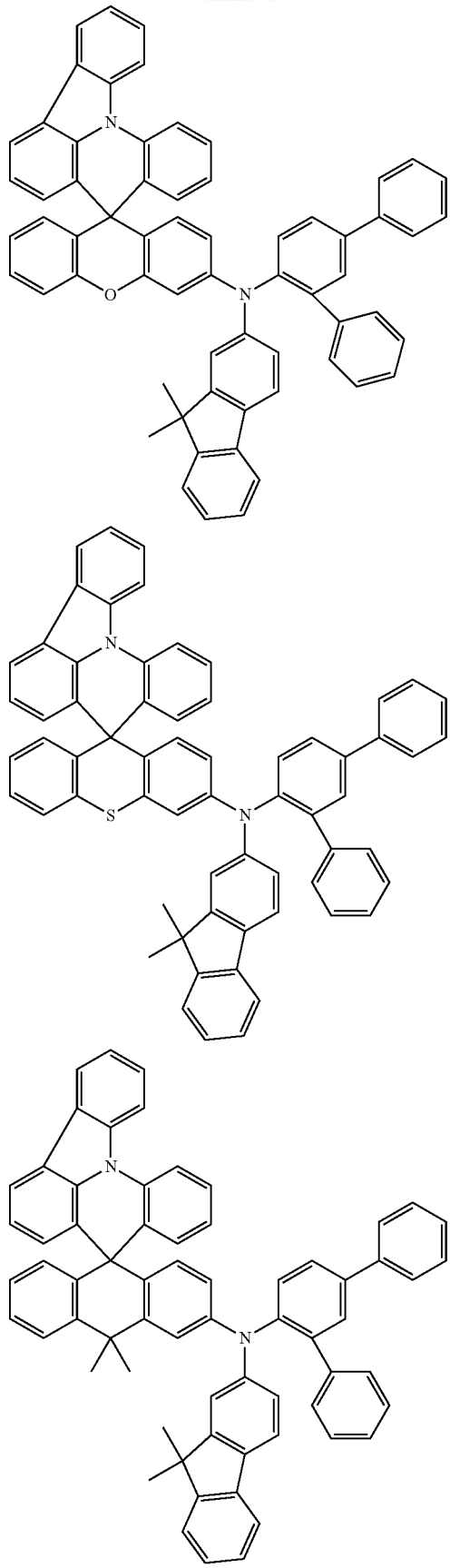 [SMILES: CC1(C)c2ccccc2-c2ccc(N(c3ccc4c(c3)Oc3ccccc3C43c4ccccc4-n4c5ccccc5c5cccc3c54)c3ccc(-c4ccccc4)cc3-c3ccccc3)cc21 ; CC1(C)c2ccccc2-c2ccc(N(c3ccc4c(c3)Sc3ccccc3C43c4ccccc4-n4c5ccccc5c5cccc3c54)c3ccc(-c4ccccc4)cc3-c3ccccc3)cc21 ; CC1(C)c2ccccc2-c2ccc(N(c3ccc4c(c3)C(C)(C)c3ccccc3C43c4ccccc4-n4c5ccccc5c5cccc3c54)c3ccc(-c4ccccc4)cc3-c3ccccc3)cc21]
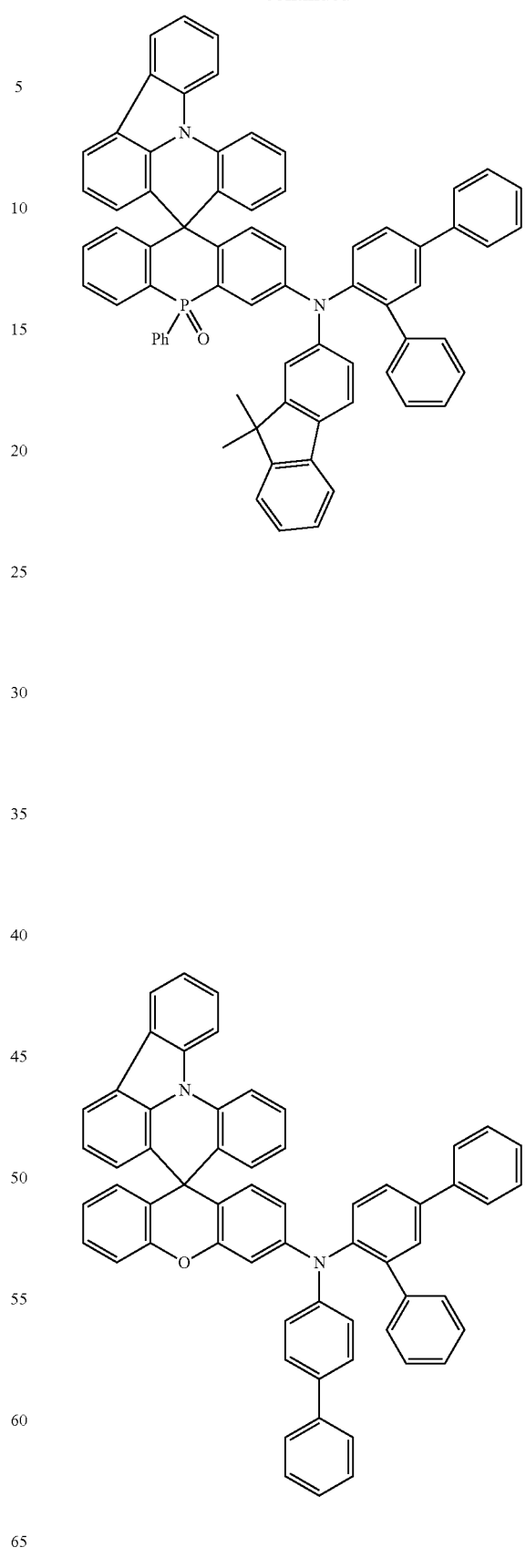

567
-continued
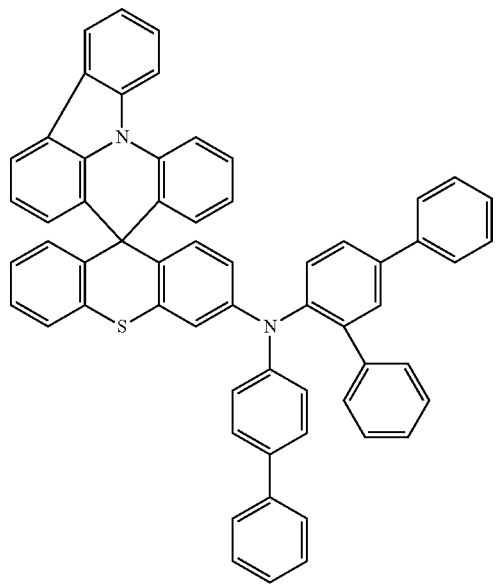
568
-continued
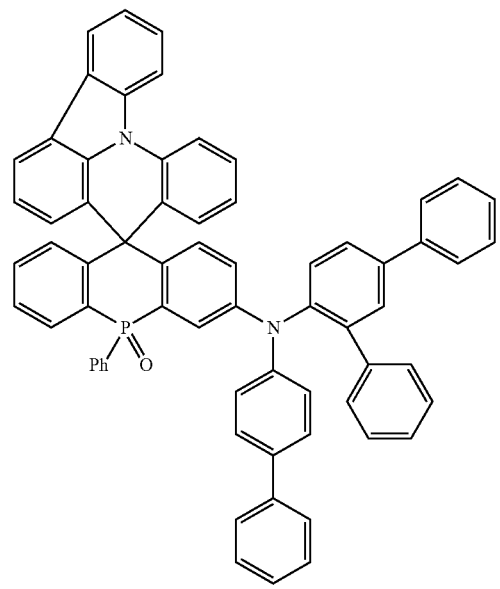
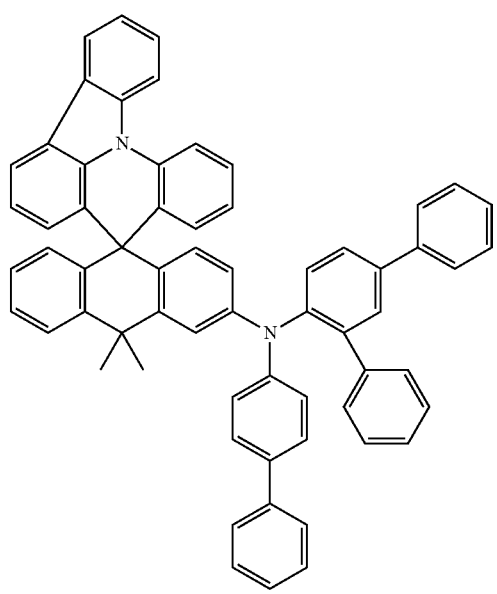
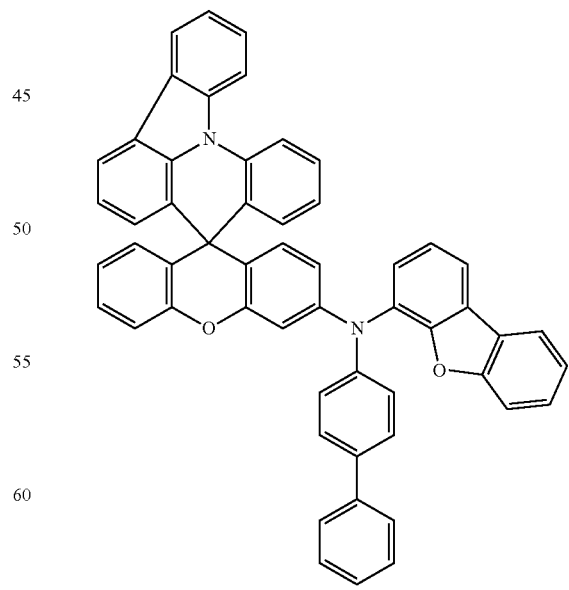

569
-continued
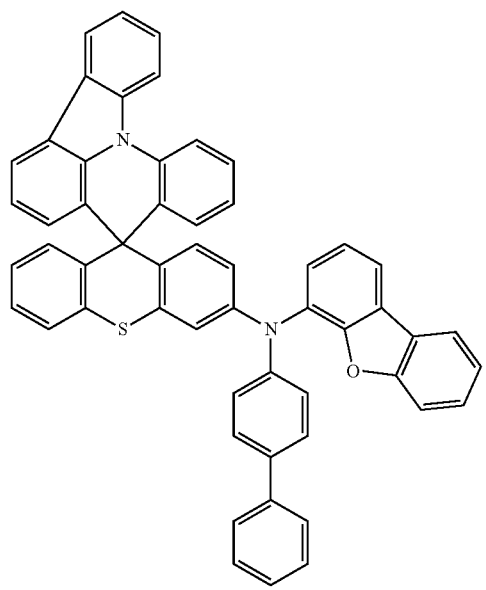
570
-continued
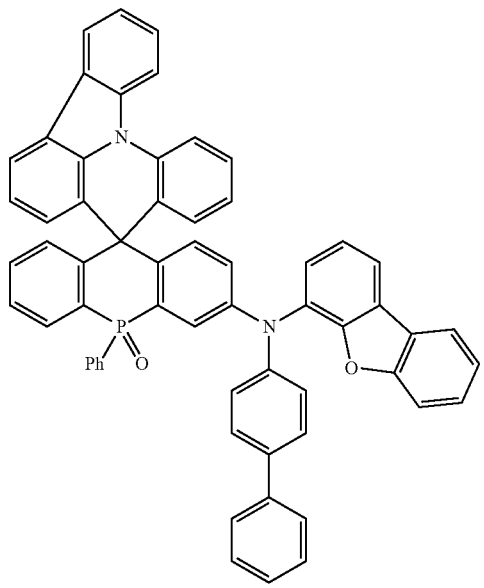
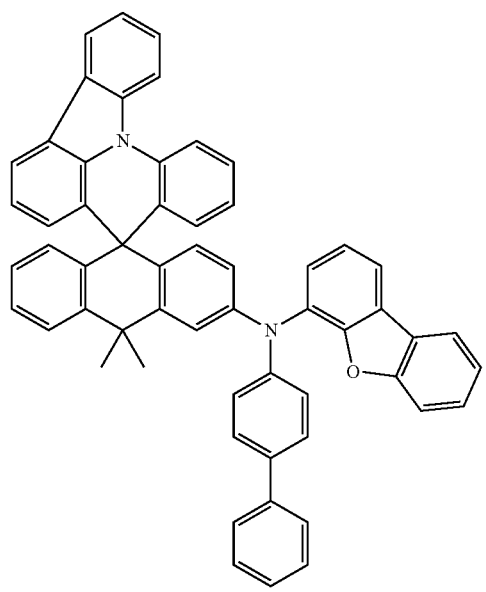
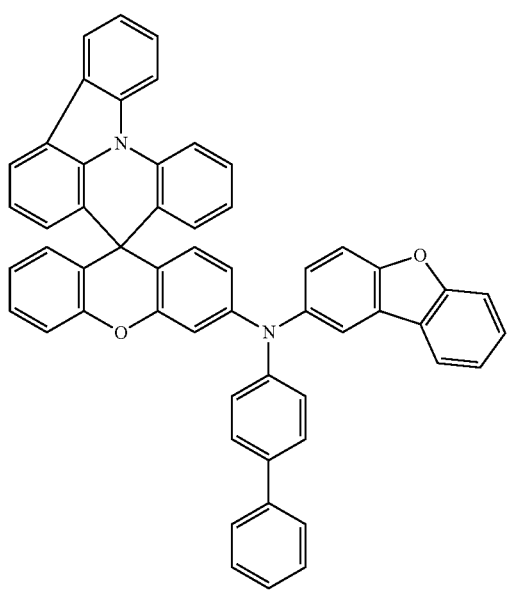

571
-continued
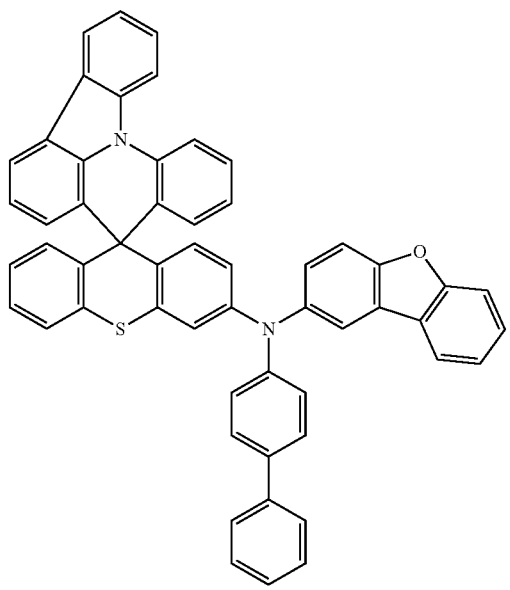
572
-continued
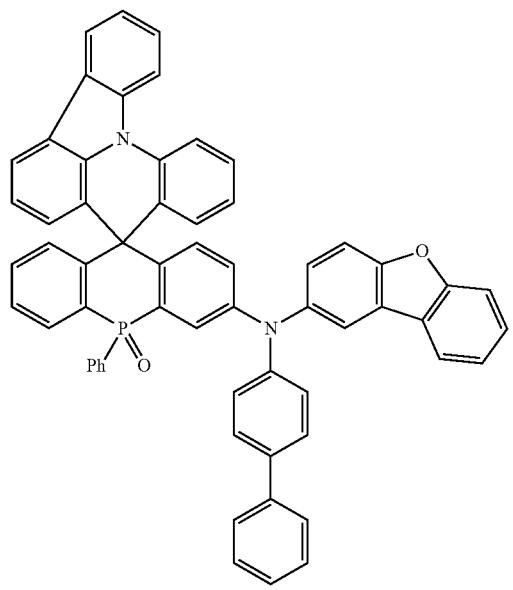
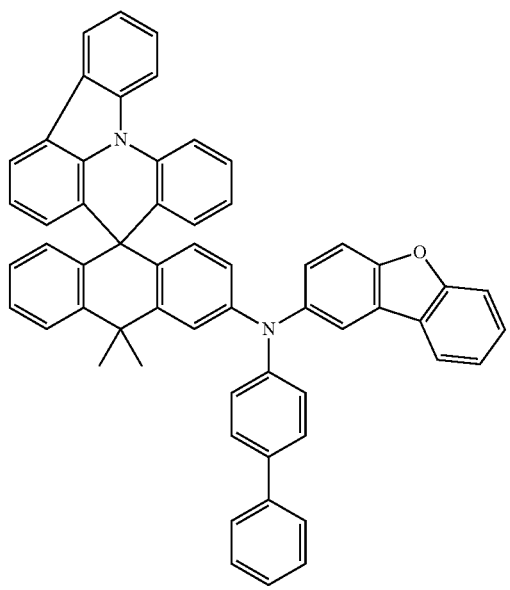
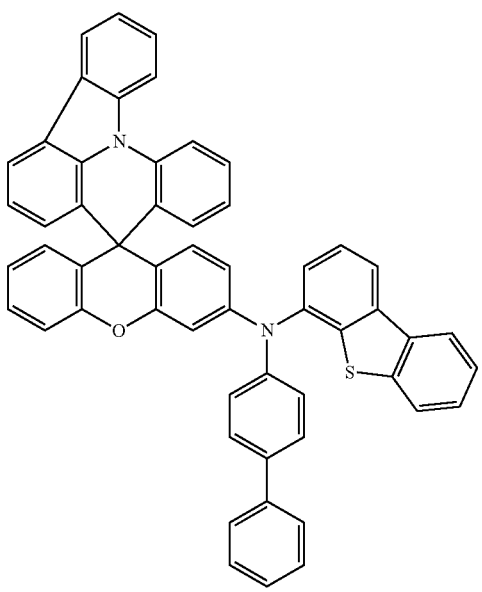

573
-continued
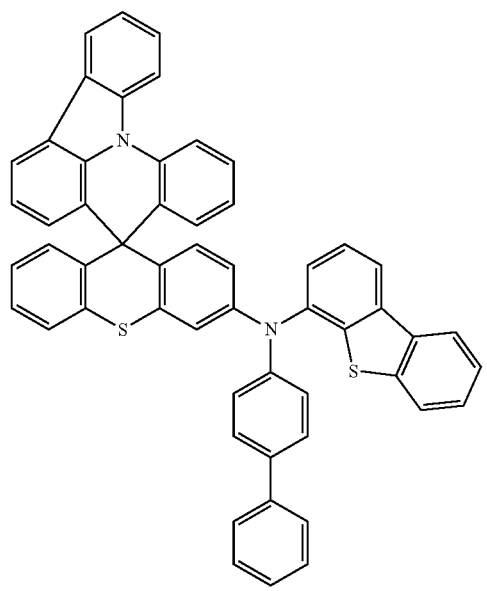
574
-continued
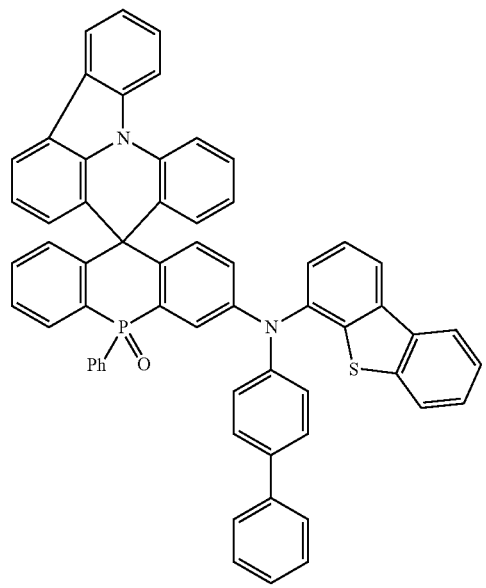
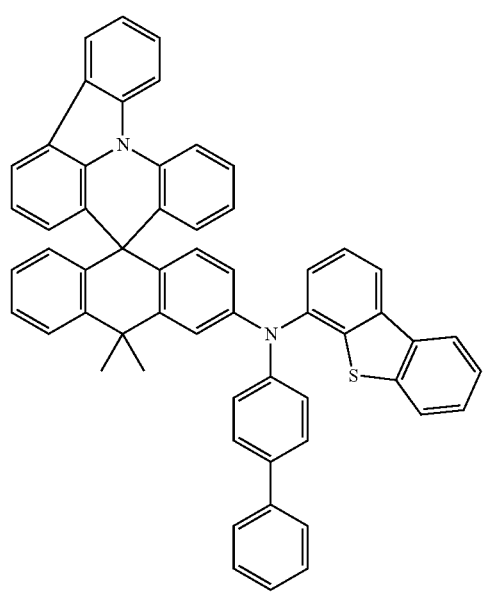
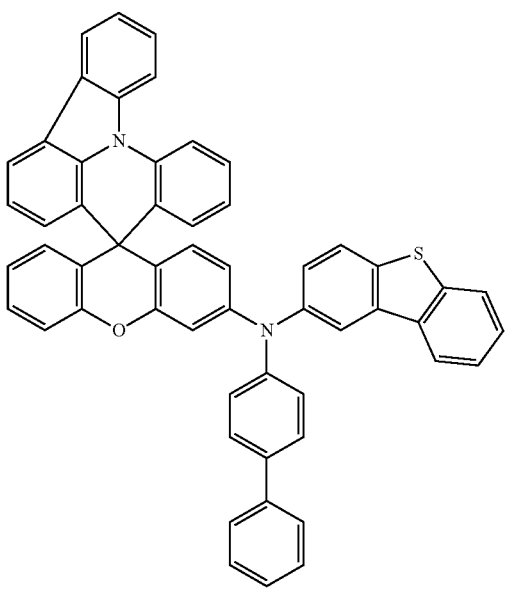

575
-continued
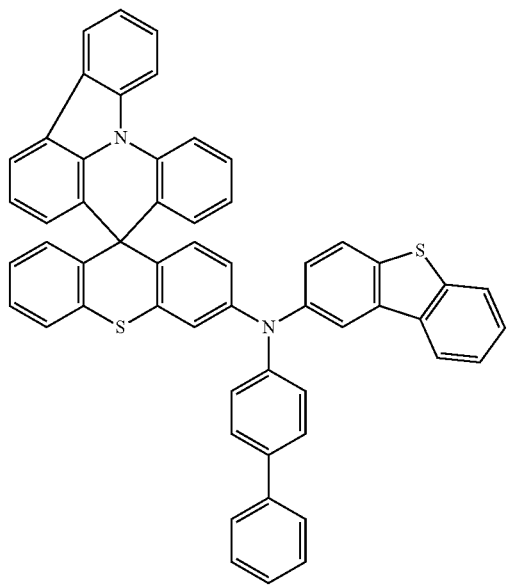
576
-continued
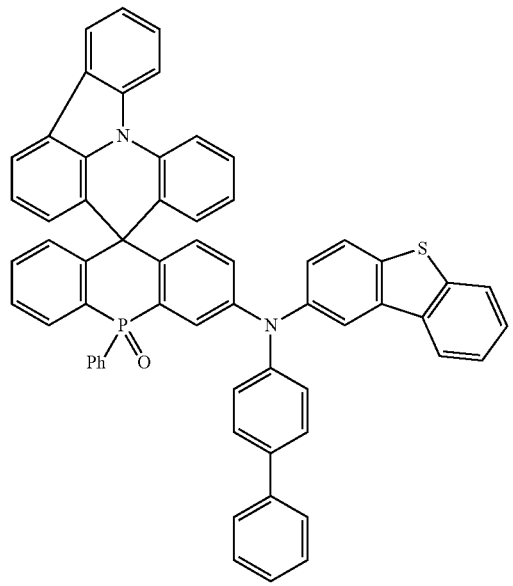
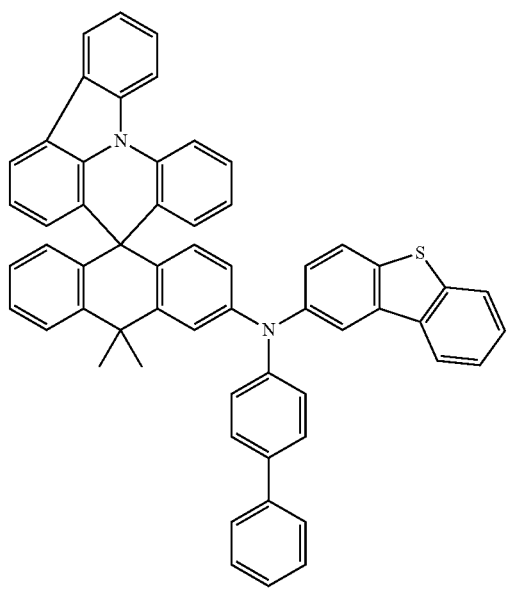
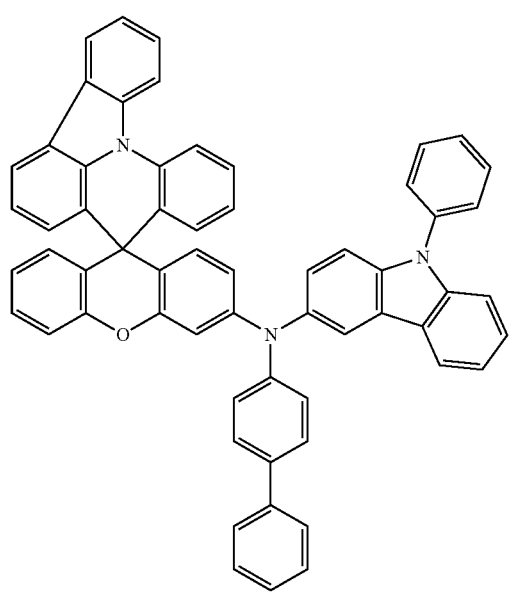

577
-continued
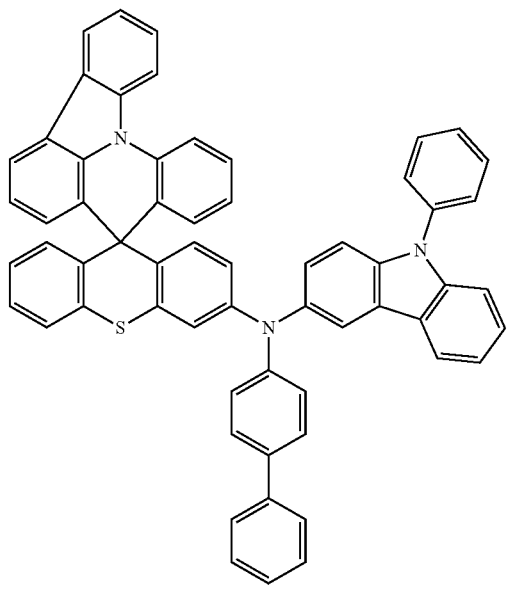
578
-continued
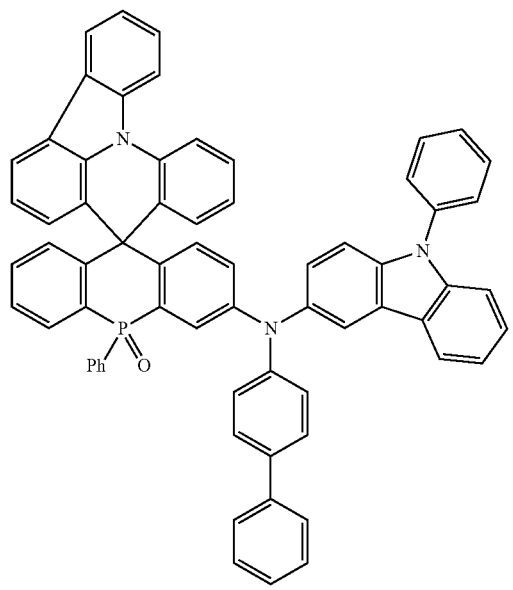
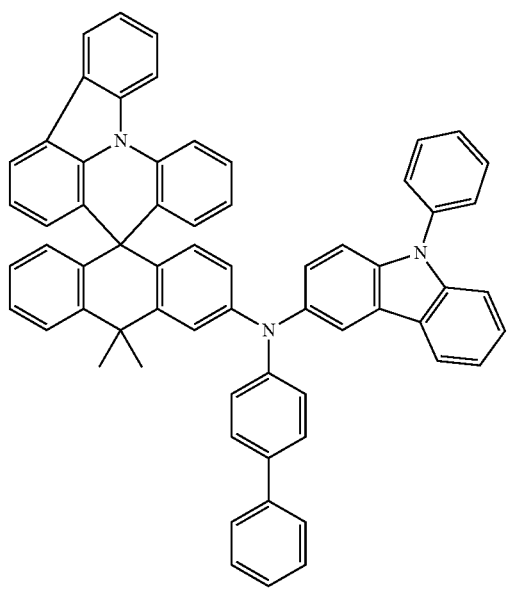
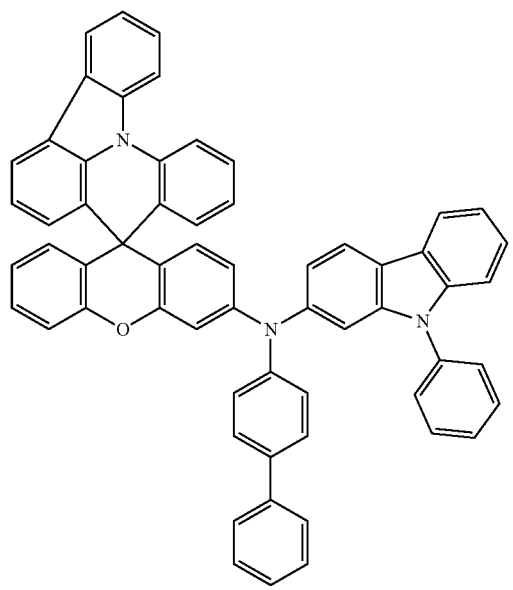

579
-continued
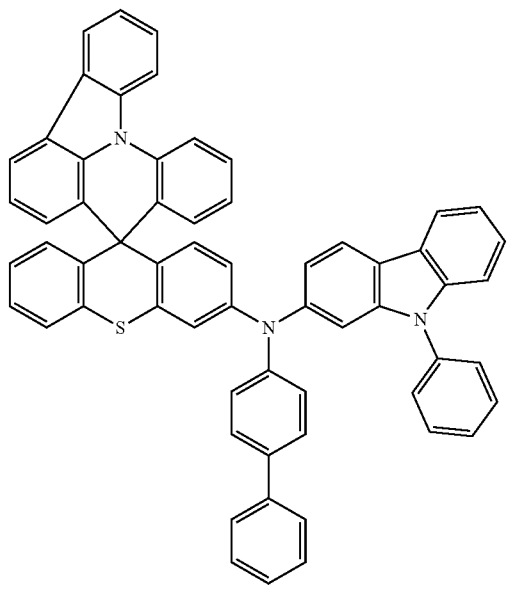
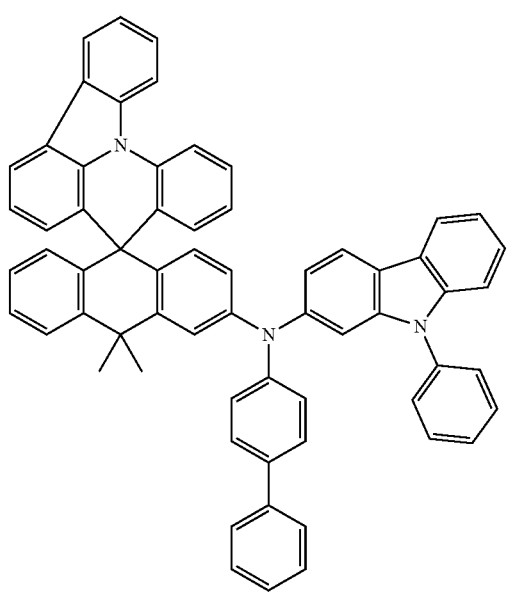
580
-continued
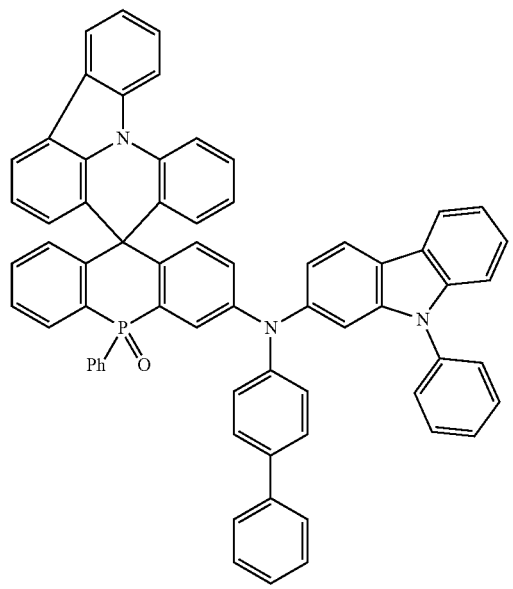
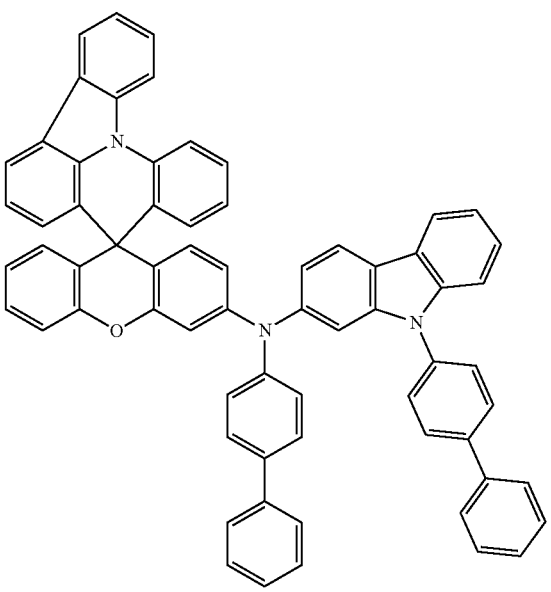

581
-continued
582
-continued
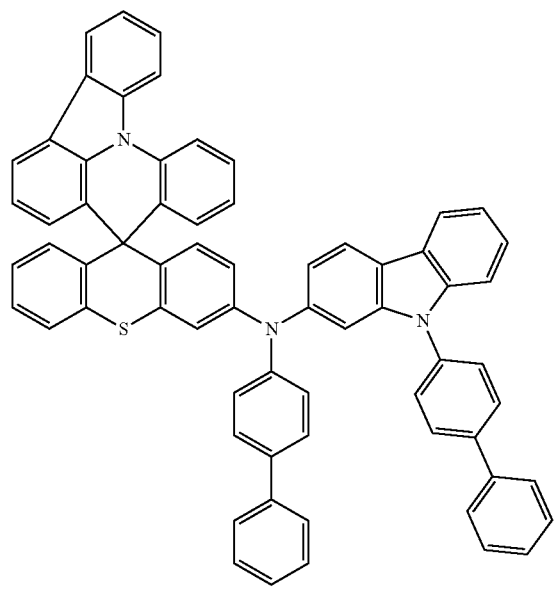
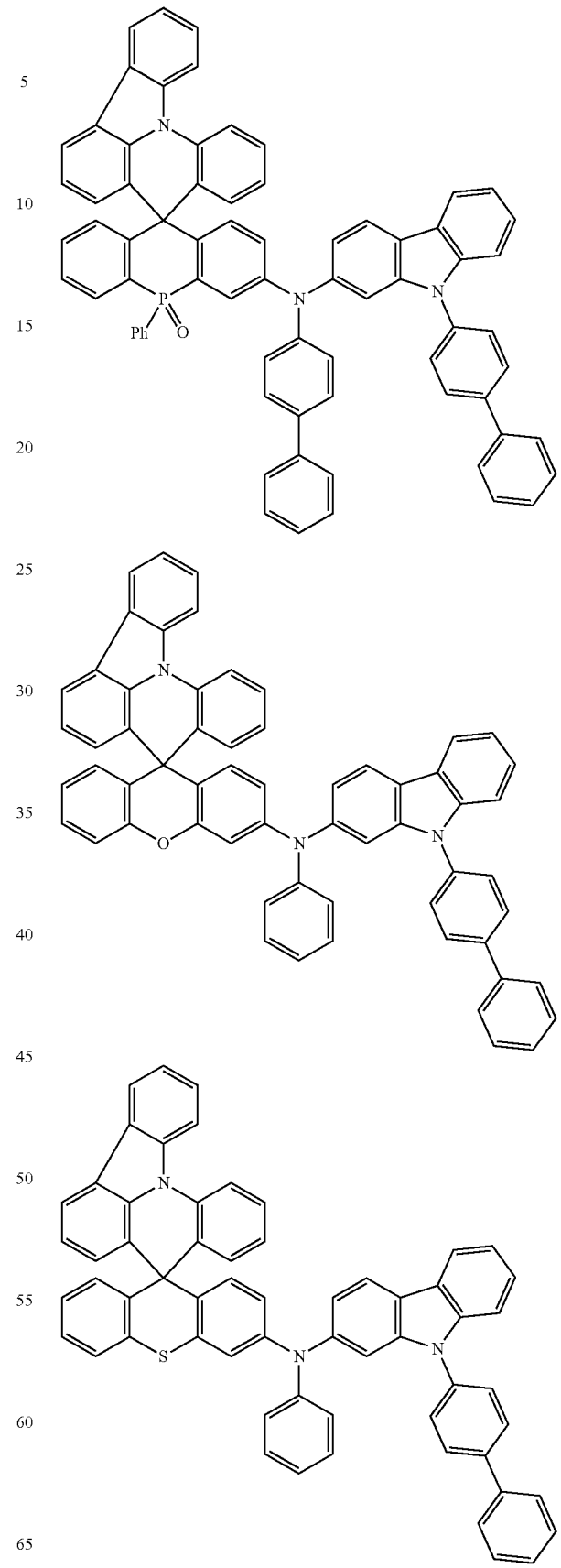

583
-continued
584
-continued
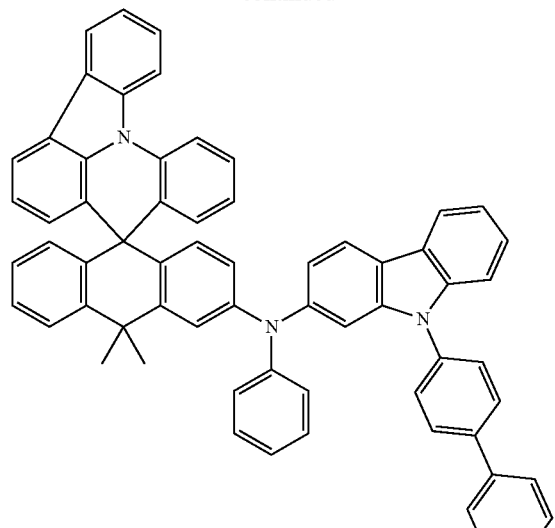
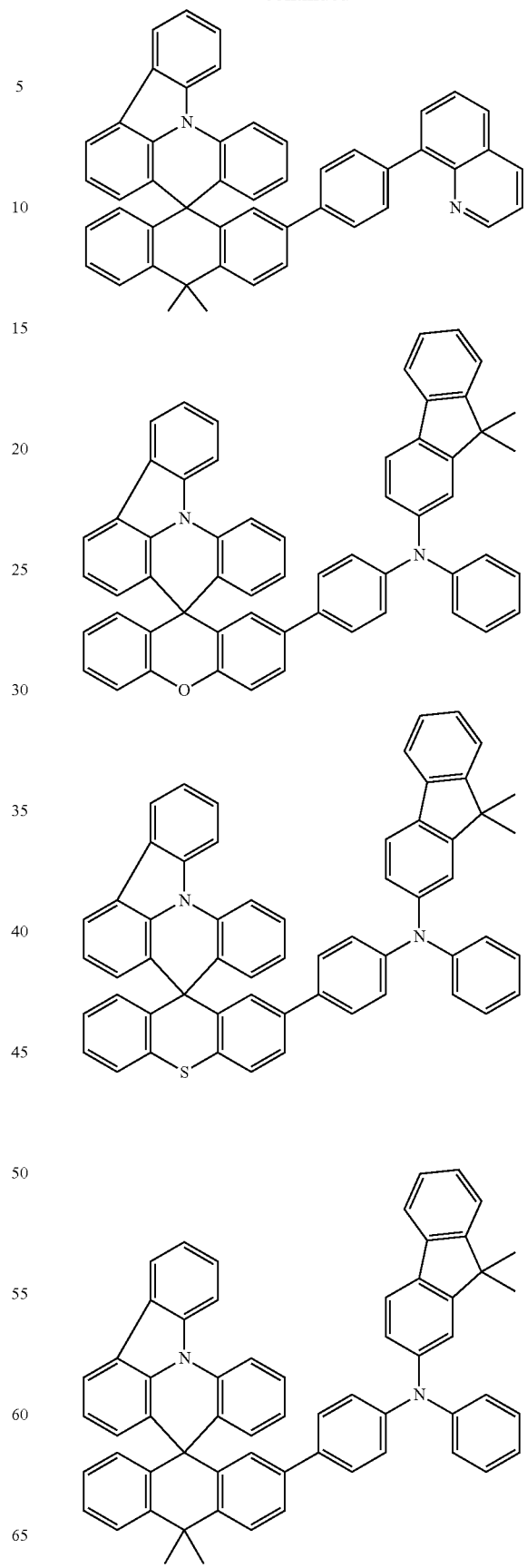

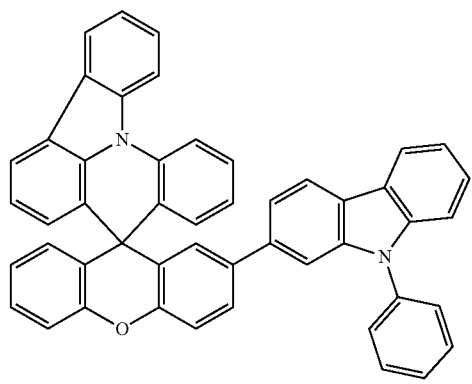

587
-continued
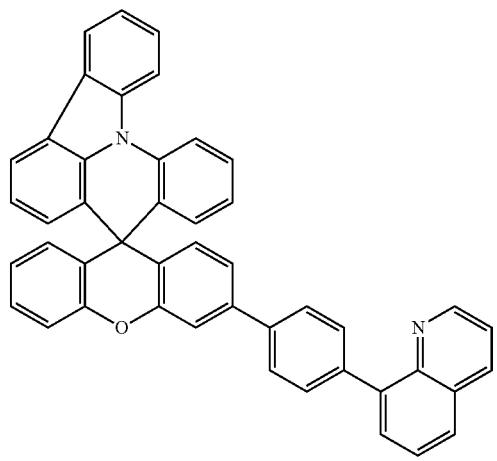
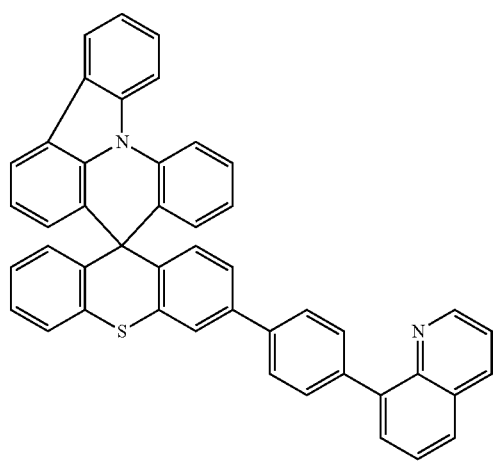
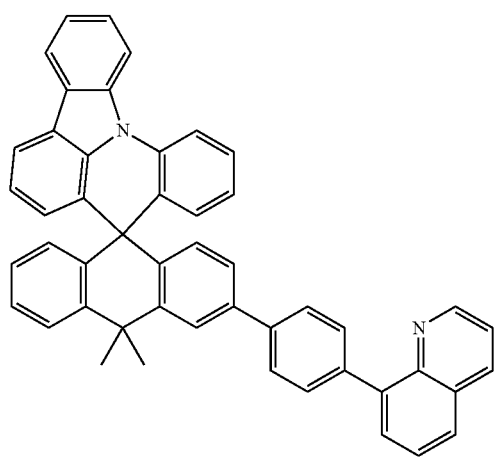
588
-continued
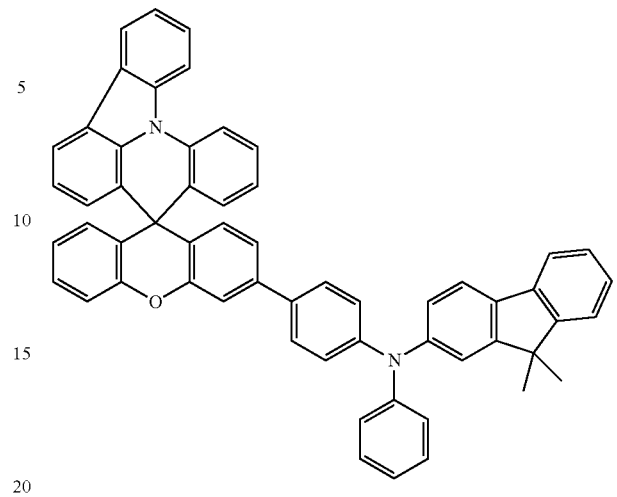
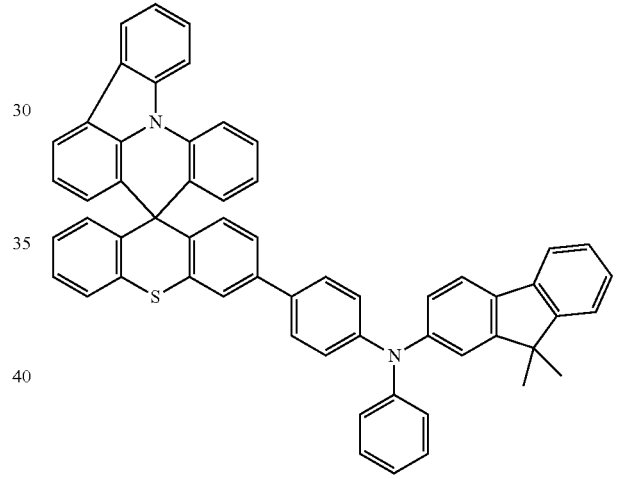
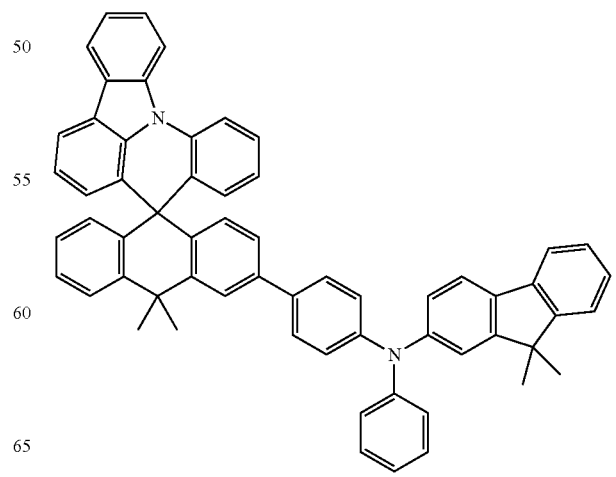

589
-continued
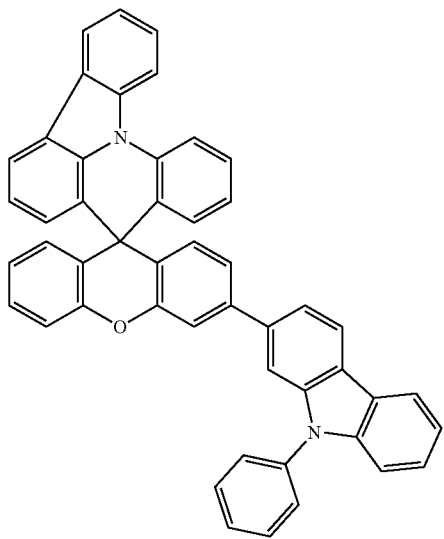
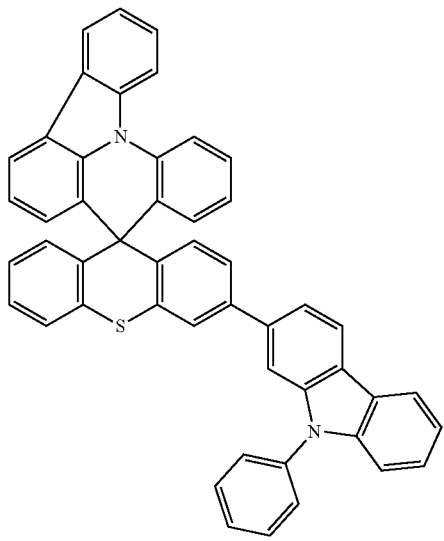
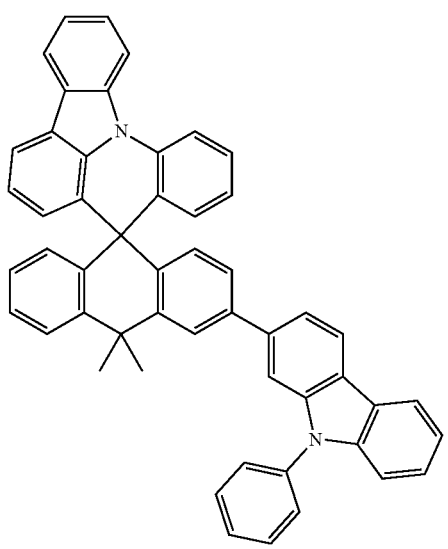
590
-continued
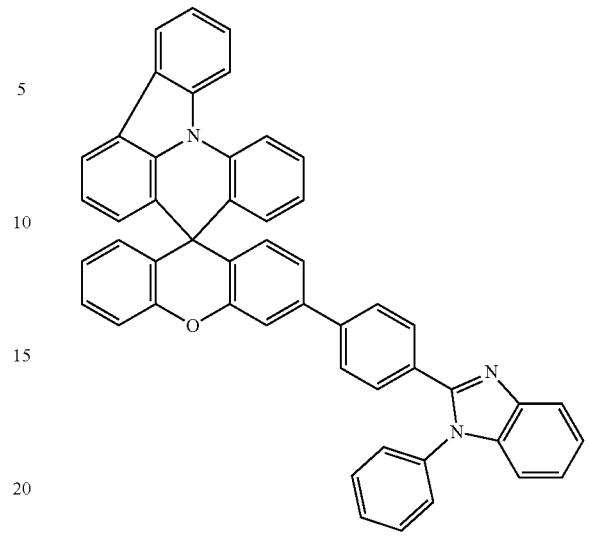
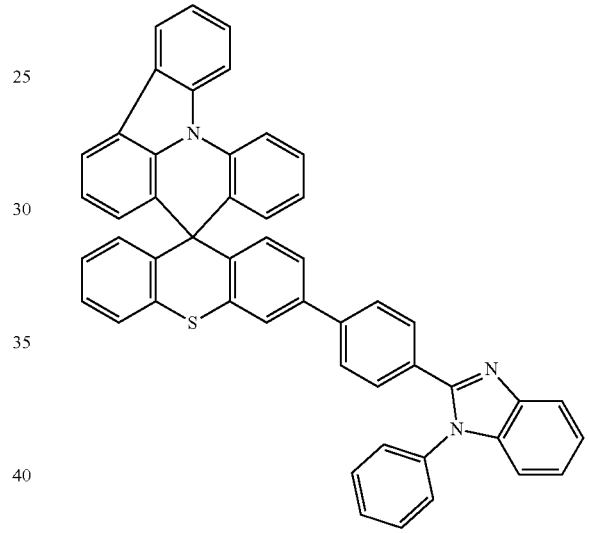
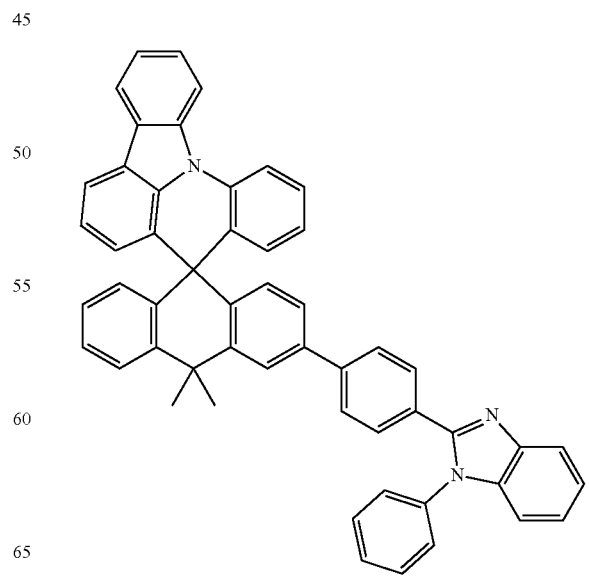

591
-continued
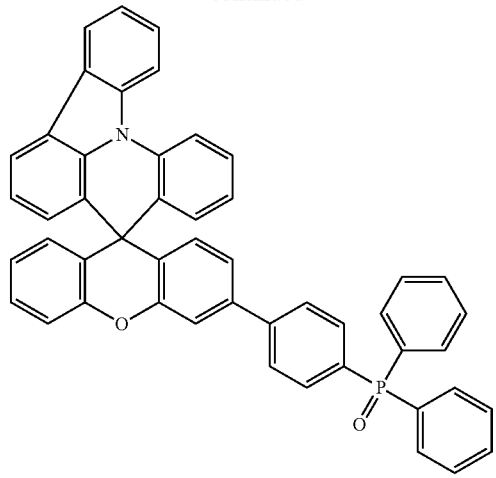
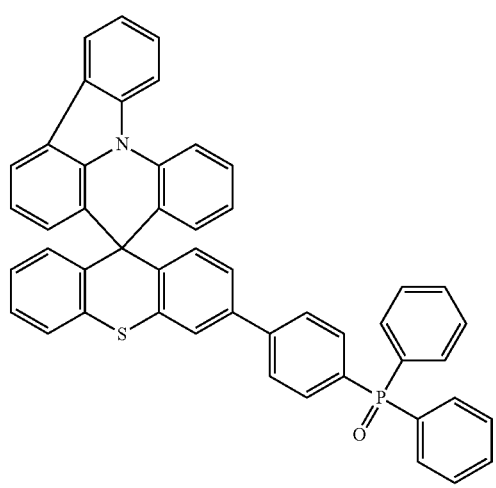
592
-continued
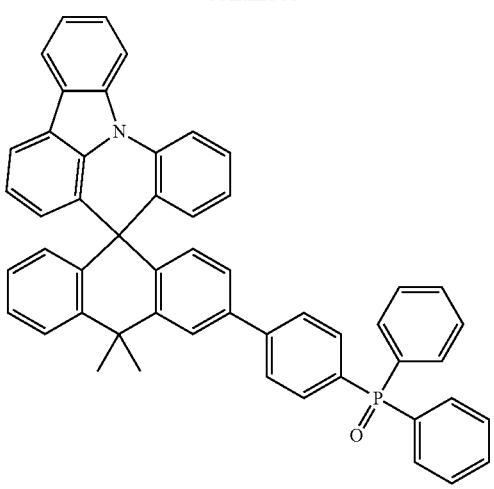 [SMILES: CC1(C)c2ccccc2C2(c3ccccc3-n3c4ccccc4c4cccc2c43)c2ccc(-c3ccc(P(=O)(c4ccccc4)c4ccccc4)cc3)cc21]
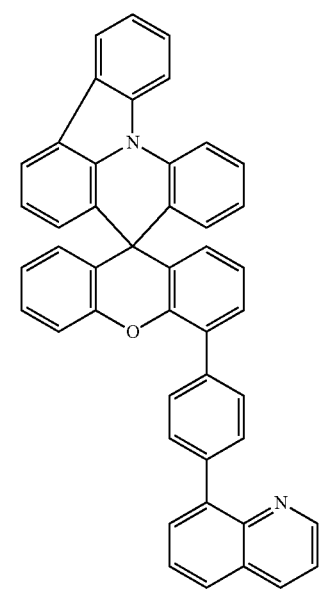
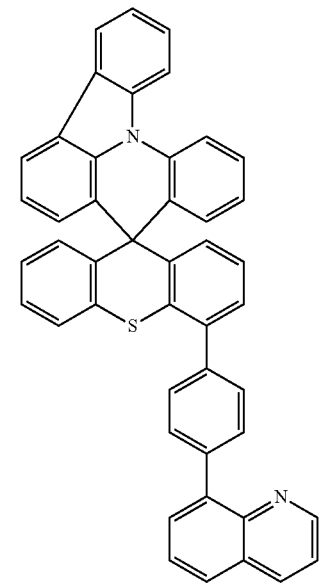

593
-continued
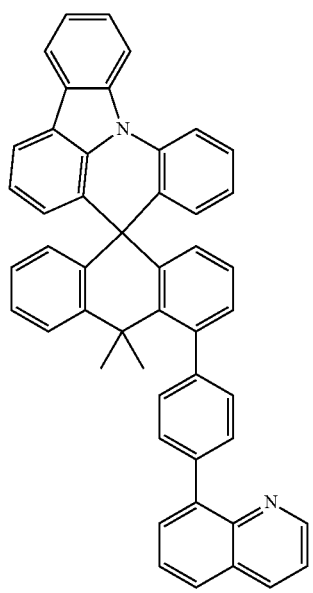 [SMILES: CC1(C)c2ccccc2C2(c3ccccc3-n3c4ccccc4c4cccc2c43)c2cccc(-c3ccc(-c4cccc5cccnc45)cc3)c21]
594
-continued
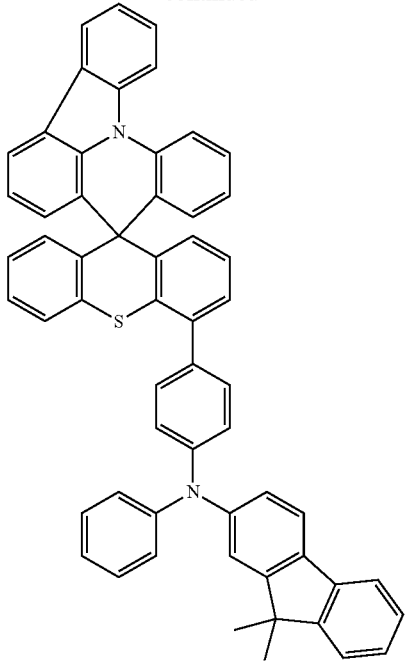
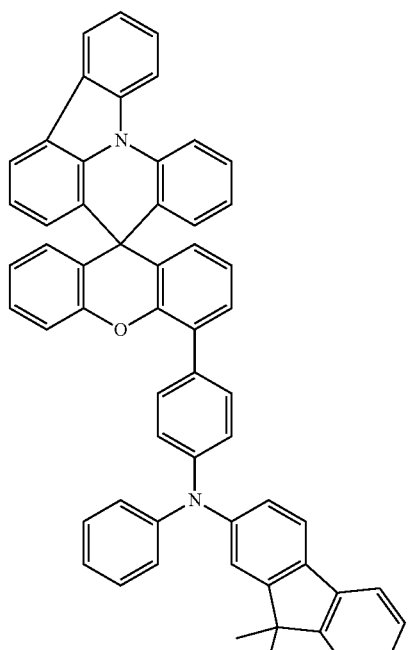
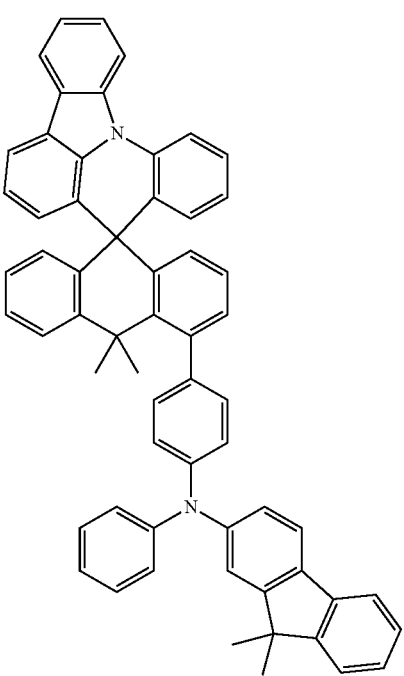 [SMILES: CC1(C)c2ccccc2-c2ccc(N(c3ccccc3)c3ccc(-c4cccc5c4C(C)(C)c4ccccc4C54c5ccccc5-n5c6ccccc6c6cccc4c65)cc3)cc21]

595
-continued
596
-continued
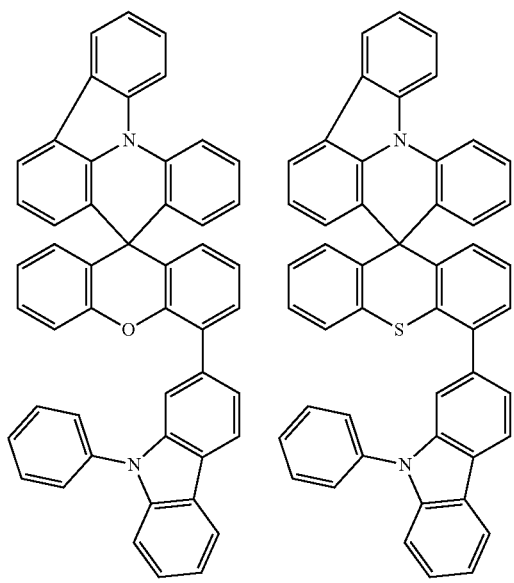
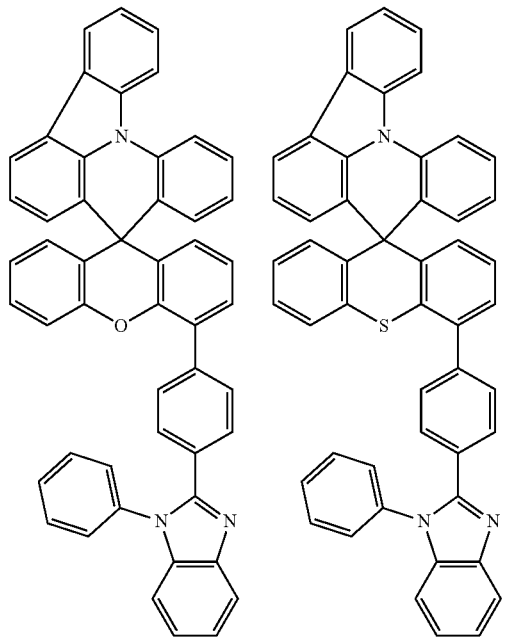
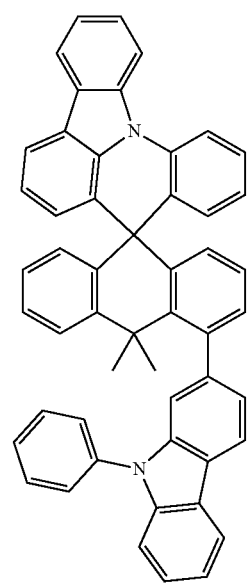
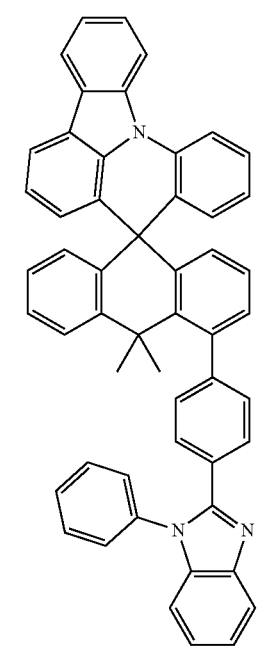

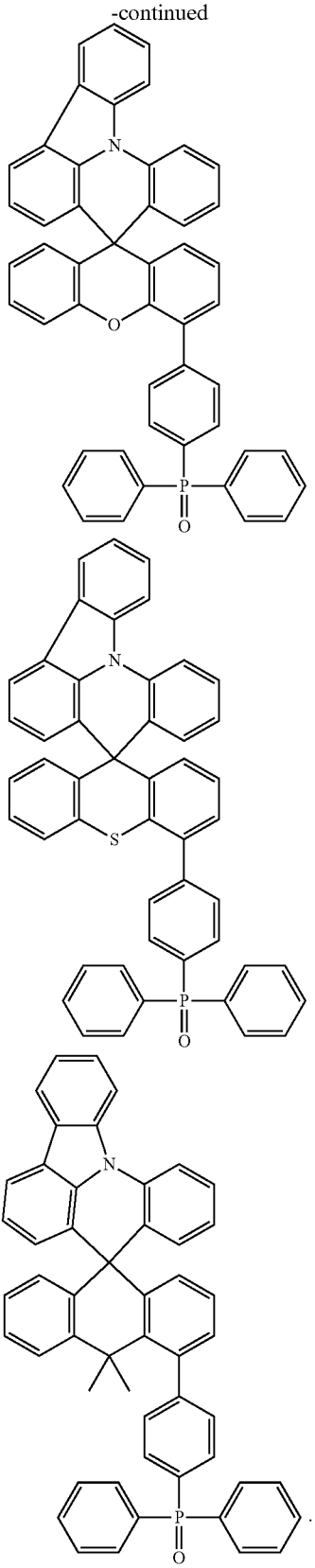

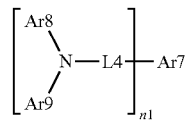
[Chemical Formula 1-A]

in Chemical Formula 1-A,
n1 is an integer of 1 or more,
Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L4 is a direct bond; a substituted or unsubstituted arylene group; or a substituted or unsubstituted heteroarylene group,
Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or are optionally bonded to each other to form a substituted or unsubstituted ring, and
when n1 is 2 or more, two or more structures in the parenthesis are the same as or different from each other.

7. The organic light emitting device of claim 6, wherein L4 is a direct bond, Ar7 is a divalent pyrene group, Ar8 and Ar9 are the same as or different from each other, and are each independently an aryl group having 6 to 30 carbon atoms, which is unsubstituted or substituted with an alkyl group having 1 to 30 carbon atoms, or a substituted or unsubstituted heteroaryl group having 2 to 30 carbon atoms, and n1 is 2.

8. The organic light emitting device of claim 1, wherein the organic material layer comprises a compound represented by the following Chemical Formula 2-A:

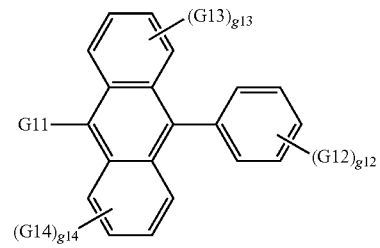
[Chemical Formula 2-A]

in Chemical Formula 2-A,
G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula 6. The organic light emitting device of claim 1, wherein the organic material layer comprises a compound represented by the following Chemical Formula 1-A:

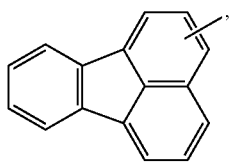

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer from 1 to 5, g13 and g14 are each an integer from 1 to 4, and when g12 to g14 are each 2 or more, two or more structures in the parenthesis are the same as or different from each other.

9. The organic light emitting device of claim 8, wherein G11 is a 1-naphthyl group, and G12 is a 2-naphthyl group.

10. The organic light emitting device of claim 6, wherein the organic material layer comprises a compound represented by the following Chemical Formula 2-A:

[Chemical Formula 2-A]

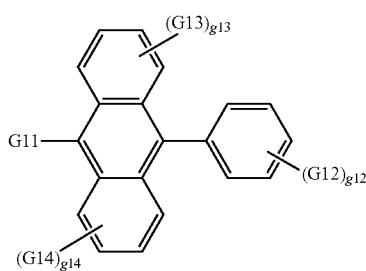

in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

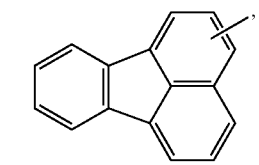

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer from 1 to 5, g13 and g14 are each an integer from 1 to 4, and when g12 to g14 are each 2 or more, two or more structures in the parenthesis are the same as or different from each other.

\* \* \* \* \*